US008501936B2

(12) United States Patent
Curry et al.

(10) Patent No.: US 8,501,936 B2
(45) Date of Patent: Aug. 6, 2013

(54) PREPARATION AND USES OF 1,2,4-TRIAZOLO [1,5A] PYRIDINE DERIVATIVES

(75) Inventors: Matthew A. Curry, Coatesville, PA (US); Bruce D. Dorsey, Ambler, PA (US); Benjamin J. Dugan, Glen Mills, PA (US); Diane E. Gingrich, Downingtown, PA (US); Eugen F. Mesaros, Wallingford, PA (US); Karen L. Milkiewicz, Exton, PA (US)

(73) Assignee: Cephalon, Inc., Frazer, PA (US)

( * ) Notice: Subject to any disclaimer, the term of this patent is extended or adjusted under 35 U.S.C. 154(b) by 118 days.

(21) Appl. No.: 12/793,984

(22) Filed: Jun. 4, 2010

(65) Prior Publication Data

US 2010/0311693 A1    Dec. 9, 2010

Related U.S. Application Data

(60) Provisional application No. 61/184,533, filed on Jun. 5, 2009.

(51) Int. Cl.
A61P 35/00 (2006.01)
C07D 471/04 (2006.01)

(52) U.S. Cl.
USPC ........... 544/58.2; 544/127; 544/362; 546/119

(58) Field of Classification Search
None
See application file for complete search history.

(56) References Cited

U.S. PATENT DOCUMENTS

| 5,858,924 A | 1/1999 | Johnson et al. |
| 6,514,989 B1 | 2/2003 | Nettekoven et al. |
| 2009/0163488 A1 | 6/2009 | Oguro et al. |
| 2010/0048557 A1* | 2/2010 | Zhu et al. ................. 514/233.2 |

FOREIGN PATENT DOCUMENTS

| JP | 2010-70503 | 4/2010 |
| WO | 01/17999 A2 | 3/2001 |
| WO | 02/38572 A1 | 5/2002 |
| WO | 02/060879 A2 | 8/2002 |
| WO | 03/010167 A1 | 2/2003 |
| WO | 03/031445 A1 | 4/2003 |
| WO | 2004/014908 A1 | 2/2004 |
| WO | 2005/097052 A1 | 10/2005 |
| WO | 2006/018718 A2 | 2/2006 |
| WO | 2006/038116 A2 | 4/2006 |
| WO | 2006/084184 A2 | 8/2006 |
| WO | 2007/077490 A2 | 7/2007 |
| WO | 2007/095588 A1 | 8/2007 |
| WO | 2007/129183 A2 | 11/2007 |
| WO | 2008/001182 A1 | 1/2008 |
| WO | 2008/006540 A1 | 1/2008 |
| WO | 2008/025821 A1 | 3/2008 |
| WO | 2008/045393 A2 | 4/2008 |
| WO | 2008/065198 A1 | 6/2008 |
| WO | 2008/124153 A1 | 10/2008 |
| WO | 2008/125111 A1 | 10/2008 |
| WO | 2008/129380 A1 | 10/2008 |
| WO | 2008/150015 A1 | 12/2008 |
| WO | 2009/010530 A1 | 1/2009 |
| WO | 2009/017954 A1 | 2/2009 |
| WO | 2009/023179 A2 | 2/2009 |
| WO | 2009/027283 A1 | 3/2009 |
| WO | 2009/027736 A2 | 3/2009 |
| WO | 2009/028629 A1 | 3/2009 |
| WO | 2009/047514 A1 | 4/2009 |
| WO | 2009/048474 A1 | 4/2009 |
| WO | 2009/068482 A1 | 6/2009 |
| WO | 2009/136663 A1 | 11/2009 |
| WO | 2009/155551 A1 | 12/2009 |
| WO | 2009/155565 A1 | 12/2009 |
| WO | 2010/007100 A1 | 1/2010 |
| WO | 2010/010184 A1 | 1/2010 |
| WO | 2010/010186 A1 | 1/2010 |
| WO | 2010/010187 A1 | 1/2010 |
| WO | 2010/010188 A1 | 1/2010 |
| WO | 2010/010189 A1 | 1/2010 |
| WO | 2010/010190 A1 | 1/2010 |
| WO | 2010/010191 A1 | 1/2010 |
| WO | 2010/018874 A1 | 2/2010 |
| WO | 2010/027500 A1 | 3/2010 |
| WO | 2010/057877 A1 | 5/2010 |
| WO | 2010/069322 A1 | 6/2010 |
| WO | 2010/092015 A1 | 8/2010 |
| WO | 2010/092041 A1 | 8/2010 |

OTHER PUBLICATIONS

Richard B. Silverman, The Organic Chemistry of Drug Design and Drug Action, Chapter 2: Drug Discovery, Design, and Development, Academic Press, p. 5-51 (1992).*
Alexander, "Suppressors of Cytokine Signalling (SOCS) in the Immune System", Nature Reviews Immunology (2002), vol. 2, pp. 1-7.
Antonysamy et al., "Fragment-Based Discovery of JAK-2 Inhibitors", Bioorg.& Med. Chem. Letters 19 (2009), pp. 279-282.
Bagi et al., "Dual Focal Adhesion Kinase/Pyk2 Inhibitor has Positive Effects on Bone Tumors", Cancer (2008), vol. 112(10); pp. 2313-2321.
Baker et al., "Hematopoietic Cytokine Receptor Signaling", Oncogene (2007), vol. 26, pp. 6724-6737.

(Continued)

Primary Examiner — Janet Andres
Assistant Examiner — Timothy R Rozof

(57) ABSTRACT

This application relates to compounds of the general Formula I

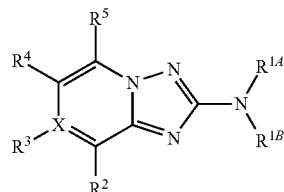

and salts thereof, wherein X, $R^{1A}$, $R^{1B}$, $R^2$, $R^3$, $R^4$, and $R^5$ are as defined herein. The application also relates to compositions and methods of treatment of hyperproliferative diseases or disorders.

9 Claims, No Drawings

OTHER PUBLICATIONS

Baxter et al., "Acquired Mutation of the Tyrosine Kinase JAK2 in Human Myeloproliferative Disorders", Lancet (2005), vol. 365, pp. 1054-1061.
Berishaj et al., "Stat3 is Tyrosine-Phosphorylated Through the Interleukin-6/Glycoprotein 130/Janus Kinase Pathway in Breast Cancer", Breast-Cancer Research (2007), 9(3), R32, pp. 1-8.
Bharadwaj et al., Elevated Interleukin-6 and G-CSF in Human Pancreatic Cancer Cell Conditioned Medium Suppress Dendritic Cell Differentiation and Activation, Cancer Res. (2007), vol. 67(11), pp. 5479-5488.
Blaskovich et al., "Discovery of JSI-124 (Cucurbitacin I), a Selective Janus Kinase/Signal Transducer and Activator of Transcription 3 Signaling Pathway Inhibitor with Potent Antitumor Activity against Human and Murine Cancer Cells in Mice", Cancer Research (2003), vol. 63, pp. 1270-1279.
Bromberg et al., "Stat3 as an Oncogene", Cell (1999), vol. 98, pp. 295-303.
Brunton et al., "Src and Focal Adhesion Kinase as Therapeutic Targets in Cancer", Current Opin. In Pharmacology (2008), vol. 8, pp. 427-432.
Buettner et al., "Activated STAT Signaling in Human Tumors Provides Novel Molecular Targets for Therapeutic Intervention," Clinical Cancer Res. (2002), vol. 8, pp. 945-954.
Chatzizacharias et al., "Focal Adhesion Kinase: a Promising Target for Anticancer Therapy", Expert Opin. Ther. Targets (2007), vol. 11(10), pp. 1315-1328.
Choy, "Inhibiting Interleukin-6 in Rheumatoid Arthritis", Current Rheumatology Reports (2008), vol. 10(5), pp. 413-417.
Constantinescu et al., "Mining for JAK-STAT Mutations in Cancer", Trends in Biochem. Sci. (2008), vol. 33(3), pp. 122-131.
Cronstein, "Interleukin-6: A Key Mediator of Systemic and Local Symptoms in Rheumatoid Arthritis," Bull. of the NYU Hosp.for joint Diseases (2007), vol. 65 (Suppl 1): S11-5.
Dagvadorj et al., "Autocrine Prolactin Promotes Prostate Cancer Cell Growth via Janus Kinase-2-Signal Transducer and Activator of Transcription-5a/b Signaling Pathway", Endocrinology (2007); vol. 148(7); pp. 3089-3101.
Ding et al., "Constitutively Activated STAT3 Promotes Cell Proliferation and Survival in the Activated B-cell Subtype of Diffuse Large B-cell Lymphomas," Blood (2008), vol. 111(3), pp. 1515-1523.
Ferrajoli et al., "The JAK-STAT Pathway: A Therapeutic Target in Hematological Malignancies," Current Cancer Drug Targets (2006), vol. 6, pp. 671-679.
Flex et al., "Somatically Acquired JAK1 Mutations in Adult Acute Lymphoblastic Leukemia," JEM (2008), vol. 205(4), pp. 751-758.
Galm et al., "SOCS-1, a Negative Regulator of Cytokine Signaling, is Frequently Silenced by Methylation in Multiple Myeloma," Blood (2003), vol. 101(7); pp. 2784-2788.
Gao et al., "Mutations in the EGFR Kinase Domain Mediate STAT3 Activation via IL-6 Production in Human Lung Adenocarcinomas," J. of Clin. Invest. (2007), vol. 117(12), pp. 3846-3856.
Grivennikov et al., "Autocrine IL-6 Signaling: A Key Event in Tumorigenesis?", Cancer Cell (2008), vol. 13, pp. 7-9.
Halder et al., "Therapeutic Efficacy of a Novel Focal Adhesion Kinase Inhibitor TAE226 in Ovarian Carcinoma," Cancer Res. (2007), vol. 67(22), pp. 10976-10983.
Halder et al., "Focal Adhesion Kinase Targeting Using In Vivo Short Interfering RNA Delivery in Neutral Liopsomes for Ovarian Carcinoma Therapy," Clin. Cancer Res. (2006), vol. 12(16), pp. 4916-4924.
Han et al., "Role of Focal Adhesion Kinase in Human Cancer: A Potential Target for Drug Discovery," Anti-Cancer Agents in Med. Chem. (2007), vol. 7, pp. 681-684.
Hexner et al., "Lestaurtinib (CEP701) is a JAK2 Inhibitor that Suppresses JAK2/STAT5 Signaling and the Proliferation of Primary Erythroid Cells from Patients with Myeloprolifreative Disorders," Blood (2008), vol. 111(12), pp. 5663-5671.
Igney et al., "Death and Anti-Death: Tumour Resistance to Apoptosis," Nature Reviews Cancer (2002), vol. 2, pp. 277-288.
Iwamaru et al., "A Novel Inhibitor of the STAT3 Pathway Induces Apoptosis in Malignant Glioma Cells Both in Vitro and In Vivo," Oncogene (2007), vol. 26, pp. 2435-2444.
James et al., "A Unique Clonal JAK2 Mutation Leading to Constitutive Signalling Causes Polycythaemia Vera," Nature (2005), vol. 434, pp. 1144-1148.
Jemal et al., "Cancer Statistics," CA Cancer J. Clin. (2008), vol. 58, pp. 71-96.
Johnson et al., "Focal Adhesion Kinase Controls Aggressive Phenotype of Androgen-Independent Prostate Cancer," Mol. Cancer Res. (2008), vol. 6(10), pp. 1639-1648.
Joos et al., "Genomic Imbalances Including Amplification of the Tyrosine Kinase Gene JAK2 in CD30+ Hodgkins Cells," Cancer Cancer Res. (2000), vol. 60, pp. 549-552.
Kaufmann et al., "Alterations in the Apoptotic Machinery and Their Potential Role in Anticancer Drug Resistance," Oncogene (2003), vol. 22, pp. 7414-7430.
Knoops et al., "JAK Kinases Overexpression Promotes In vitro Cell Transformation," Oncogene (2008), vol. 27, pp. 1511-1519.
Kohno et al., "CD151 Enhances Cell Motility and Metastasis of Cancer Cells in the Presence of Focal Adhesion Kinase," Int. J. Cancer (2002), vol. 97, pp. 336-343.
Kornberg et al., "Focal Adhesion Kinase Expression in Oral Cancers," Head & Neck (1998), vol. 20(7), pp. 634-639.
Kortylewski et al., "Inhibiting Stat3 Signaling in the Hematopoietic System Elicits Multicomponent Antitumor Immunity," Nature Medicine (2005), vol. 11(12), pp. 1314-1321.
Kralovics et al., "A Gain-of-Function Mutation of JAK2 in Myeloproliferatie Disorders," N. Engl. J. Med. (2005), vol. 352, pp. 1779-1790.
Lahlou et al., "Mammary Epithelial-Specific Disruption of the Focal Adhesion Kinase Blocks Mammary Tumor Progression," PNAS (2007), vol. 104(51), pp. 20302-20307.
Levine et al., "Activating Mutation in the Tyrosine Kinase JAK2 in Polycythemia Vera, Essential Thrombocythemia, and Myeloid Metaplasia with Myelofibrosis," Cancer Cell (2005), vol. 7, pp. 387-397.
Li et al., "Activation of Signal Transducer and Activator of Transcription 5 in Human Prostate Cancer is Associated with High Histological Grade," Cancer Res. (2004), vol. 64, pp. 4774-4782.
Li et al., "FAK Expression: Regulation and Therapeutic Potential," Advances in Cancer Res. (2008), vol. 101, pp. 45-61.
Lim et al., "Nuclear FAK Promotes Cell Proliferation and Survival Through FERM-Enhanced p53 Degradation," Molecular Cell (2008), vol. 29, pp. 9-22.
McLean et al., "The Role of Focal-Adhesion Kinase in Cancer—a New Therapeutic Opportunity," Nature Reviews Cancer (2005), vol. 5, pp. 505-515.
Melzner et al., "Biallelic Deletion Within 16p13.13 Including SOCS-1 in Karpas1106P Mediastinal B-cell Lymphoma Line is Associated with Delayed Degradation of JAK2 Protein," Int. J. Cancer (2006), vol. 118, pp. 1941-1944.
Melzner et al., "Biallelic Mutation of SOCS-1 Impairs JAK2 Degradation and Sustains Phospho-JAK2 Action in the MedB-1 Mediastinal Lymphoma Line," Blood (2005), vol. 105(6), pp. 2535-2542.
Mitra et al., "Focal Adhesion Kinase: in Command and Control of Cell Motility," Nature Reviews Molecular Cell Biology (2005), vol. 6(1), pp. 57-68.
Murati et al., "PCM1-JAK2 Fusion in Myeloproliferative Disorders and Acute Erythroid Leukemia with t(8;9) Translocation," Leukemia (2005), vol. 19, pp. 1692-1696.
Nefedova et al., "Regulation of Dendritic Cell Differentiation and Antitumor Immune Response in Cancer by Pharmacologic-Selective Inhibition of the Janus-Activated Kinase 2/Signal Transducers and Activators of Transcription 3 Pathway," Cancer Res. (2005), vol. 65(20), pp. 9525-9535.
Nefedova et al., "Targeting of JAK/STAT Pathway in Antigen Presenting Cells in Cancer," Current Cancer Drug Targets (2007), vol. 7, pp. 71-77.
Owens et al., "Focal Adhesion Kinase a a Marker of Invasive Potential in Differentiated Human Thyroid Cancer," Annals of Surgical Oncology (1996), vol. 3(1), pp. 100-105.
Owens et al. "Overexpression of the Focal Adhesion Kinase (p125 FAK) in Invasive Human Tumors," Cancer Res. (1995), vol. 55, pp. 2752-2755.

Pardanani, "JAK2 Inhibitor Therapy in Myeloproliferative Disorders: Rationale, Preclinical Studies and Ongoing Clinical Trials," Leukemia (2008), vol. 22, pp. 23-30.

Parsons et al., "Focal Adhesion Kinase: Targeting Adhesion Signaling Pathways for Therapeutic Intervention," Clin. Cancer Res. (2008), vol. 14(3), pp. 627-632.

Parsons, "Focal Adhesion Kinase: The First Ten Years," J. of Cell Sci. (2003), vol. 116, pp. 1409-1416.

Plushner, "Tocilizumab: An Interleukin-6 Receptor Inhibitor for the Treatment of Rheumatoid Arthritis," Annals of Pharmacotherapy (2008), vol. 42(11), pp. 1660-1668.

Pommier et al., "Apoptosis Defects and Chemotherapy Resistance: Molecular Interaction Maps and Networks," Oncogene (2004), vol. 23, pp. 2934-2949.

Pylayeva et al., "Ras- and PI3K-Dependent Breast Tumorigenesis in Mice and Humans Requires Focal Adhesion Kinase Signaling," J. Clin. Invest. (2009), vol. 119(2), pp. 252-266.

Rane et al., "JAKs, STATs and Src Kinases in Hematopoiesis," Oncogene (2002), vol. 21, pp. 3334-3358.

Reddy et al., "Differential Methylation of Genes that Regulate Cytokine Signaling in Lymphoid and Hematopoietic Tumors," Oncogene (2005), vol. 24, pp. 732-736.

Reed, "Apoptosis-Targeted Therapies for Cancer," Cancer Cell (2003), vol. 3, pp. 17-22.

Roberts et al., "Antitumor Activity and Pharmacology of a Selective Focal Adhesion Kinase Inhibitor, PF-562,271," Cancer Res. (2008), vol. 68(6), pp. 1935-1944.

Saudemont et al., "Dormant Tumor Cells Develop Cross-Resistance to Apoptosis Induced by CTLs or Imatinib Mesylate via Methylation of Suppressor of Cytokine Signaling 1," Cancer Res. (2007), vol. 67(9), pp. 4491-4498.

Scheeren et al., "IL-21 is Expressed in Hodgkin Lymphoma and Activates STAT5: Evidence that Activated STAT5 is Required for Hodgkin Lymphomagenesis," Blood (2008), vol. 111(9), pp. 4706-4715.

Shuai et al., "Regulation of JAK-STAT Signalling in the Immune System," Nature Reviews Immunology (2003), vol. 3 (11), pp. 900-910.

Tan et al., "Transcription Factor Stat5 Synergizes with Androgen Receptor in Prostate Cancer Cells," Cancer Res. (2008), vol. 68(1), pp. 236-248.

Tan et al., "Signal Transducer and Activator of Transcription 5A/B in Prostate and Breast Cancers," Endocrine-Related Cancer (2008), vol. 15, pp. 367-390.

Tefferi, "Chronic Myeloid Disorders: Classification and Treatment Overview," Seminars in Hematology (2001), vol. 38(1), Suppl 2, pp. 1-4.

Tefferi et al., "Polycythemia Vera: Scientific Advances and Current Practice," Semin Hematol. (2005), vol. 42, pp. 206-220.

Tremblay et al., "Focal Adhesion Kinase (pp12FAK) Expression, Activation and Association with Paxillin and p50CSK in Human Metastatic Prostate Carcinoma," Int. J. Cancer (1996), vol. 68, pp. 164-171.

Vannucchi et al., "Clinical Profile o Homozygous JAK2 617V>F Mutation in Patients with Polycythemia Vera or Essential Thrombocythemia," Blood (2007), vol. 110(3), pp. 840-846.

Wang et al., "Adaptive Secretion of Granulocyte-Macrophage Colony-Stimulating Factor (GM-CSF) Mediates Imatinib and Nilotinib Resistance in BCR/ABL+ Progenitors Via JAK-2/STAT-5 Pathway Activation", Blood (2007), vol. 109(5), pp. 2147-2155.

Weber et al., "SOCS-3 is Frequently Methylated in Head and Neck Squamous Cell Carcinoma and its Precursor Lesions and Causes Growth Inhibition", Oncogene (2003), vol. 24, pp. 6699-6708.

Weniger et al., "Mutations of the Tumor Suppressor Gene SOCS-1 in Classical Hodgkin Lymphoma are Frequent and Associated with Nuclear Phospho-STAT5 Accumulation", Oncogene (2006), vol. 25, pp. 2679-2684.

Yang et al., "The Nonreceptor Tyrosine Kinase ACK2, a Specific Target for Cdc42 and a Negative Regulator of Cell Growth and Focal Adhesion Complexes", J. Biol. Chem. (2001), vol. 276(47), pp. 43987-43993.

Yoshikawa et al., "SOCS-1, a Negative Regulator of the JAK/STAT Pathway, is Silenced by Methylation in Human Hepatocellular Carcinoma and Shows Growth-Suppression Activity", Nature Genetics (2001), vol. 28, pp. 29-35.

Yu et al., "That Stats of Cancer—New Molecular Targets Come of Age", Nature Reviews Cancer (2004), vol. 4, pp. 97-105.

Zhang et al., "STAT3- and DNA Methyltransferase 1-Mediated Epigenetic Silencing of SHP-1 Tyrosine Phosphatase Tumor Suppressor Gene in Malignant T Lymphocytes", PNAS (2005), vol. 102(19), pp. 6948-6953.

Zhao et al., "Signal Transduction by Focal Adhesion Kinase in Cancer", Cancer Metastasis Rev (2009), vol. 28, pp. 35-49.

Barber et al., "Selective Urokinae-Type Plasminogen Activator (uPA) Inhibitors. Part 2: (3-Substituted-5-halo-2pyridinyl)guanidines", Bioorg. & Med. Chem. Ltrs. (2002), vol. 12, pp. 185-187.

Borie et al., "JAK3 Inhibition as a New Concept for Immune Suppression", Current Opn. Investigational Drugs (2003), vol. 4(11), pp. 1297-1303.

Abdel-Monem, "Synthesis and Biological Evaluation of Some New Fused Heterobicyclic Derivatives Containing 1,2,4-Triazolo/1,2,4-Triazinopyridinone Moieties", Chem. Pap. (2004), vol. 58(4), pp. 276-285.

Kiss et al., Recent developments on JAK2 inhibitors: a patent review, Expert Opin. Ther. Patents (2010), vol. 20(4), pp. 471-495.

Molina et al., "Heterocyclization Reactions with Carbodiimides: Synthesis of Fused 1,2,4-Triazoles", Heterocycles (1986), vol. 24(12), pp. 3363-3368.

Pesu et al., "Therapeutic targeting of Janus kinases", Immunological Reviews (2008), vol. 223, pp. 132-142.

Molina et al., "Fused Mesoionic Heterocycles: Synthesis of 1,3,4-Triazolo[3,2-a]pyridine Derivatives", J. Chem. Soc. Perkin Trans. 1 (1984), pp. 1891-1897.

Yamazaki et al., "Cyclization of Isothiosemicarbazones. Part 10. A Novel Route to 2-Amino[1,2,4]triazolo[1,5-a]pyridine Derivatives", J. Chem. Soc. perkin Trans. 1 (1994), pp. 825-828.

Barsy et al., "Fused Pyridines by a Tandem Aza-Wittig/Heterocyclization Strategy: Synthesis of 1,2,4-Triazolo[1,5-a]pyridines and Pyrido[1,2-b][1,2,4]triazines", J. Heterocyclic Chem. (2008), vol. 45, pp. 773-778.

Potts et al., "1,2,4-Triazoles. XIV. Reactions of the s-Triazolo[4,3-a]pyridine Ring System", J. Org. Chem. (1966), vol. 31(1), pp. 265-273.

O'Shea et al., "A New Modality for Immunosuppression: Targeting the JAK/STAT Pathway", Nature Reviews/Drug Discovery (Jul. 2004), vol. 3, pp. 555-564.

Bell et al., "Application of the Tisler Triazolopyrimidine Cyclization to the Synthesis of a Crop Protection Agent and an Intermediate", Organic Process Res. & Dev. (2006), vol. 10, pp. 1167-1171.

El-Sayed et al., "Synthesis of Some New Heterocycles Derived from Arylmethylenemalononitriles", Synthetic Communications (1998), vol. 28(18), pp. 3331-3343.

Nettekoven et al., "Synthetic Access to 2-Amido-5-aryl-8-methoxy-triazolopyridine and 2-Amido-5-morpholino-8-methoxy-triazolopyridine Derivatives as Potential Inhibitors of the Adenosine Receptor Subtypes", Synthesis (2003), No. 11, pp. 1649-1652.

Molina et al., "Fused Mesoionic Heterocycles: Synthesis of 1,3,4-Triazolo(3,2-a)pyridine Derivatives", Tetrahedron Ltrs. (1983), vol. 24(33), pp. 3523-3526.

Hussein et al., "Studies with Arylhydrazono-3-Oxopropanals: A Novel Route to Synthesis of Substituted Pyrazoles, Oxoalkanonitrile and Glyoxalonitrile Containing Sulfa Drug Moieties", The British Library—The world's knowledge 37 (Sep.-Oct. 2008), pp. 386-392.

Hussein, "Pyridines as Building Blocks in Heterocyclic Synthesis. An Expeditious Synthesis of Triazolopyridines, Tetrazolopyridines, Pyridotriazines, Thienopyridines and Isoquinolines", Afinidad LVI (Nov.-Dec. 1999), The British Library—The world's knowledge, 484, pp. 377-382.

* cited by examiner

PREPARATION AND USES OF 1,2,4-TRIAZOLO [1,5A] PYRIDINE DERIVATIVES

SUMMARY

This application relates to compounds of the general Formula I wherein:

X is selected from C or N, provided that when X is N, $R^3$ is not present;

$R^{1A}$ and $R^{1B}$ are each independently selected from H and the group —W—$(CH_2)_n$—Y—$(CH_2)_m$—Z, wherein W is selected from a bond, —$CONR^6$—, or —$SO_2$—; and Y and Z are each independently selected from a bond, H, $(C_6$-$C_{10})$aryl, $(C_6$-$C_{10})$aryloxy, $(C_6$-$C_{10})$aryl$(C_1$-$C_4)$alkyl, $(C_6$-$C_{10})$aryl$(C_1$-$C_4)$alkoxy, $(C_3$-$C_{10})$cycloalkyl, $(C_3$-$C_{10})$cycloalkyloxy, $(C_3$-$C_{10})$cycloalkyl$(C_1$-$C_4)$alkyl, $(C_3$-$C_{14})$cycloalkyl$(C_1$-$C_4)$alkoxy, $(C_2$-$C_9)$heterocycloalkyl, $(C_2$-$C_9)$heterocycloalkyloxy, $(C_2$-$C_9)$heterocycloalkyl$(C_1$-$C_4)$alkyl, $(C_2$-$C_9)$heterocycloalkyl$(C_1$-$C_4)$alkoxy, $(C_2$-$C_9)$heteroaryl, $(C_2$-$C_9)$heteroaryloxy, $(C_2$-$C_9)$heteroaryl$(C_1$-$C_4)$alkyl, and $(C_2$-$C_9)$heteroaryl$(C_1$-$C_4)$alkoxy wherein each of the aforementioned groups, except for H, may be optionally substituted with between one to four substituents, provided that $R^{1A}$ and $R^{1B}$ are not both H; or $R^{1A}$ and $R^{1B}$ are taken together with the nitrogen atom to which they are attached to form a $(C_2$-$C_{14})$heterocycloalkyl group which may be optionally substituted with between one to four substituents;

one of $R^5$ and $R^2$ is the group -T-$(CH_2)_q$—U—$(CH_2)_r$—V wherein T is selected from a bond, —O—, —S—, —SO—, —$SO_2$—, —CO—, —$CONR^6$—, —COO—, —$CONR^6$—, —$NR^6CO$—, —$NR^6CONR^6$—, or —$NR^6$—, and U and V are each independently selected from a bond, H, $(C_3$-$C_{14})$cycloalkyl, $(C_3$-$C_{14})$cycloalkyloxy, $(C_3$-$C_{14})$cycloalkyl$(C_1$-$C_4)$alkyl, $(C_3$-$C_{14})$cycloalkyl$(C_1$-$C_4)$alkoxy, $(C_6$-$C_{10})$aryl, $(C_6$-$C_{10})$aryloxy, $(C_6$-$C_{10})$aryl$(C_1$-$C_4)$alkyl, $(C_6$-$C_{10})$aryl$(C_1$-$C_4)$alkoxy, $(C_2$-$C_{14})$heterocycloalkyl, $(C_2$-$C_{14})$heterocycloalkyloxy, $(C_2$-$C_{14})$heterocycloalkyl$(C_1$-$C_4)$alkyl, $(C_2$-$C_{14})$heterocycloalkyl$(C_1$-$C_4)$alkoxy, $(C_2$-$C_9)$heteroaryl, $(C_2$-$C_9)$heteroaryloxy, $(C_2$-$C_9)$heteroaryl$(C_1$-$C_4)$alkyl, and $(C_2$-$C_9)$heteroaryl$(C_1$-$C_4)$alkoxy wherein each of the aforementioned groups, except for H, may be optionally substituted with between one to four substituents; and the other is selected from H, —OH, —CN, —$NO_2$, halogen, —$NR^7R^7$, —$SO_2R^7$, —$OSO_2R^7$, $(C_1$-$C_8)$alkyl, $(C_1$-$C_8)$alkoxy, halo$(C_1$-$C_4)$alkyl, halo$(C_1$-$C_4)$alkoxy, $(C_3$-$C_{14})$cycloalkyl, $(C_3$-$C_{14})$cycloalkyloxy, $(C_3$-$C_{14})$cycloalkyl$(C_1$-$C_4)$alkyl, $(C_3$-$C_{14})$cycloalkyl$(C_1$-$C_4)$alkoxy, $(C_6$-$C_{10})$aryl, $(C_6$-$C_{10})$aryloxy, $(C_6$-$C_{10})$aryl$(C_1$-$C_4)$alkyl, $(C_6$-$C_{10})$aryl$(C_1$-$C_4)$alkoxy, $(C_2$-$C_{14})$heterocycloalkyl, $(C_2$-$C_{14})$heterocycloalkyloxy, $(C_2$-$C_{14})$heterocycloalkyl$(C_1$-$C_4)$alkyl, $(C_2$-$C_{14})$heterocycloalkyl$(C_1$-$C_4)$alkoxy, $(C_2$-$C_9)$heteroaryl, $(C_2$-$C_9)$heteroaryloxy, $(C_2$-$C_9)$heteroaryl$(C_1$-$C_4)$alkyl, and $(C_2$-$C_9)$heteroaryl$(C_1$-$C_4)$alkoxy, wherein any of the aforementioned groups with the exception of H, —OH, —CN, —$NO_2$, and halogen, may be optionally substituted with between one to four substituents;

$R^3$ and $R^4$ are each independently selected from H, —OH, —CN, —$NO_2$, halogen, —$NR^7R^7$, —$SO_2R^7$, $OSO_2R^7$, $(C_1$-$C_8)$alkyl, $(C_1$-$C_8)$alkoxy, halo$(C_1$-$C_4)$alkyl, halo$(C_1$-$C_4)$alkoxy, $(C_3$-$C_{14})$cycloalkyl, $(C_3$-$C_{14})$cycloalkyloxy, $(C_3$-$C_{14})$cycloalkyl$(C_1$-$C_4)$alkyl, $(C_3$-$C_{14})$cycloalkyl$(C_1$-$C_4)$alkoxy, $(C_6$-$C_{10})$aryl, $(C_6$-$C_{10})$aryloxy, $(C_6$-$C_{10})$aryl$(C_1$-$C_4)$alkyl, $(C_6$-$C_{10})$aryl$(C_1$-$C_4)$alkoxy, $(C_2$-$C_{14})$heterocycloalkyl, $(C_2$-$C_{14})$heterocycloalkyloxy, $(C_2$-$C_{14})$heterocycloalkyl$(C_1$-$C_4)$alkyl, $(C_2$-$C_{14})$heterocycloalkyl$(C_1$-$C_4)$alkoxy, $(C_2$-$C_9)$heteroaryl, $(C_2$-$C_9)$heteroaryloxy, $(C_2$-$C_9)$heteroaryl$(C_1$-$C_4)$alkyl, and $(C_2$-$C_9)$heteroaryl$(C_1$-$C_4)$alkoxy, wherein any of the aforementioned groups with the exception of H, —OH, —CN, —$NO_2$, and halogen, may be optionally substituted with between one to four substituents;

each $R^6$ is independently selected from H and $(C_1$-$C_8)$alkyl; each $R^7$ is independently selected from H, $(C_1$-$C_8)$alkyl, $(C_1$-$C_8)$alkoxy, halo$(C_1$-$C_4)$alkyl, halo$(C_1$-$C_4)$alkoxy, $(C_3$-$C_{14})$cycloalkyl, $(C_3$-$C_{14})$cycloalkyloxy, $(C_3$-$C_{14})$cycloalkyl$(C_1$-$C_4)$alkyl, $(C_3$-$C_{14})$cycloalkyl$(C_1$-$C_4)$alkoxy, $(C_6$-$C_{10})$aryl, $(C_6$-$C_{10})$aryloxy, $(C_6$-$C_{10})$aryl$(C_1$-$C_4)$alkyl, $(C_6$-$C_{10})$aryl$(C_1$-$C_4)$alkoxy, $(C_2$-$C_{14})$heterocycloalkyl, $(C_2$-$C_{14})$heterocycloalkyloxy, $(C_2$-$C_{14})$heterocycloalkyl$(C_1$-$C_4)$alkyl, $(C_2$-$C_{14})$heterocycloalkyl$(C_1$-$C_4)$alkoxy, $(C_2$-$C_9)$heteroaryl, $(C_2$-$C_9)$heteroaryloxy, $(C_2$-$C_9)$heteroaryl$(C_1$-$C_4)$alkyl, and $(C_2$-$C_9)$heteroaryl$(C_1$-$C_4)$alkoxy wherein any of the aforementioned groups, except for H, may be optionally substituted with between one to four substituents; n, m, q, and r are each independently selected from 0, 1, 2, or 3; and wherein said optional substituents are each independently selected from H, —OH, —CN, $NO_2$, oxo, halogen, $(C_1$-$C_8)$alkyl, $(C_1$-$C_8)$alkoxy, halo$(C_1$-$C_4)$alkyl, halo$(C_1$-$C_4)$alkoxy, $(C_3$-$C_{14})$cycloalkyl, $(C_3$-$C_{14})$cycloalkyl$(C_1$-$C_4)$alkyl, $(C_3$-$C_{14})$cycloalkyloxy, $(C_3$-$C_{14})$cycloalkyl$(C_1$-$C_4)$alkoxy, —$NR^6R^6$, $(C_6$-$C_{10})$aryl, $(C_6$-$C_{10})$aryl$(C_1$-$C_4)$alkyl, $(C_6$-$C_{10})$aryloxy, $(C_6$-$C_{10})$aryl$(C_1$-$C_4)$alkoxy, —$SO_2R^6$, —$C(O)NR^6R^6$, —$SO_2NR^6R^6$, $(C_2$-$C_{14})$heterocycloalkyl, $(C_2$-$C_{14})$heterocycloalkyloxy, $(C_2$-$C_{14})$heterocycloalkyl$(C_1$-$C_4)$alkyl, $(C_2$-$C_{14})$heterocycloalkyl$(C_1$-$C_4)$alkoxy, $(C_2$-$C_9)$heteroaryl, $(C_2$-$C_9)$heteroaryloxy, $(C_2$-$C_9)$heteroaryl$(C_1$-$C_4)$alkyl, $(C_2$-$C_9)$heteroaryl$(C_1$-$C_4)$alkoxy, —$COR^E$, —$NR^6COR^6$, —$NR^6SO_2R^6$, —$OSO_2R^6$, or —$CO_2R^6$.

This application also relates to salts of the compounds of general Formula I and compositions comprising compounds of general Formula I or salts thereof. The compounds of general Formula I and their pharmaceutically acceptable salts are useful for treating diseases or disorders mediated by one or more tyrosine kinases such as, for example, FAK (focal adhesion kinase) and JAK (Janus kinase).

BACKGROUND

Receptor protein tyrosine kinases (RPTKs) are enzymes which span the cell membrane and possess an extracellular ligand binding domain, a transmembrane domain, and a cytoplasmic (intracellular) tyrosine kinase domain (catalytic domain). The intracellular portion participates in cellular signal transduction by phosphorylating specific tyrosine residues in RPTK substrate proteins which in turn triggers other transduction events (signal propagation). As a result, tyrosine kinases influence a number of aspects of cellular responses, such as proliferation, growth, differentiation, migration, metabolism and programmed cell death (apoptosis). It has been shown that many of these tyrosine kinases are frequently mutated and/or aberrantly expressed in a number of human disease states such as, for example, breast cancer, gastrointestinal cancers (colon, rectal, and/or stomach cancers), leukemia, ovarian cancer, and pancreatic cancer.

Some examples of RPTKs that mediate various cellular responses associated with hyperproliferative disease states include c-erbB-2, c-met, tie-2, PDGRr, FGFr, and EGFR. As such, compounds that selectively inhibit or modulate the activity of one or more tyrosine kinases could provide significant therapeutic benefit in a variety of hyperproliferative disease states or disorders in mammals.

FAK (focal adhesion kinase) and JAK (Janus kinase), lck, src, abl or serine/threonine (e.g., cyclin dependent kinases) are examples of non-receptor (cytoplasmic) protein tyrosine kinases (NRPTKs). Initially, NRPTKs were identified in the context of cell growth and differentiation but subsequently the constitutive activation or aberrent expression of NRPTKs has been found to be associated with disease states characterized by abnormal cell growth, in particular cancer, in mammals.

The Janus kinase family (JAKs) consists of 4 members: JAK1, JAK2, JAK3 and TYK2. This family of kinases signal downstream from cytokine and some growth factor receptors. For example, the STAT (signal transduction and transcription) family of transcription factors is the principal, but not exclusive, target for JAKs. Constitutive JAK/STAT signaling is thought to play a critical role in oncogenesis and the progression of many different types of tumors by promoting multiple mechanisms of tumor pathogenesis, including cell proliferation, anti-apoptotic signaling, angiogenesis and tumor immune evasion (Yu et al. 2004). Moreover, constitutively activated JAK/STAT signaling is found in many tumor types, but not in normal tissues (Yu et al. 2004; Benekli et al. 2003). The ability of the JAK/STAT pathway to mediate resistance to apoptosis is particularly important, as most anticancer drugs affect tumors by inducing apoptosis.

Focal adhesion kinase (FAK) is an evolutionarily conserved non-receptor tyrosine kinase localized at focal adhesions, sites of cellular contact with the ECM (extra-cellular matrix) that functions as a critical transducer of signaling from integrin receptors and multiple receptor tyrosine kinases, including EGF-R, HER2, IGF-R1, PDGF-R and VEGF-R2 and TIE-2 (Parsons, 2003; Han and McGonigal, 2007). The integrin-activated FAK forms a binary complex with Src which can phosphorylate other substrates and trigger multiple signaling pathways. Given the central role of FAK binding and phosphorylation in mediating signal transduction with multiple SH2- and SH3-domain effector proteins (Mitra et al. 2005), activated FAK plays a central role in mediating cell adhesion, migration, morphogenesis, proliferation and survival in normal and malignant cells (Mitra et al. 2005; McClean et al. 2005; and Kyu-Ho Han and McGonigal, 2007). In tumors, FAK activation mediates anchorage-independent cell survival, one of the hallmarks of cancer cells. Moreover, FAK over expression and activation appear to be associated with an enhanced invasive and metastatic phenotype and tumor angiogenesis in these malignancies (Owens et al, 1995, 1996; Tremblay et al, 1996; Kornberg et al, 1998; Mc Clean et al 2005; Kyu-Ho Han and McGonigal, 2007) and correlated with poor prognosis and shorter metastasis-free survival.

DETAILED DESCRIPTION

The following provides additional non-limiting details of the compounds described or disclosed herein, including compounds of the general Formula I, subgenuses and various species and/or embodiments of compounds of the general Formula I, intermediates, and other compounds of interest. The section titles used herein are for indexing and search purposes only and should not be construed as limiting in any way.

In one aspect, this application provides and describes compounds of the general Formula I

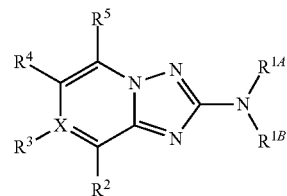

or salts thereof, wherein:

X is selected from C or N, provided that when X is N, $R^3$ is not present;

$R^{1A}$ and $R^{1B}$ are each independently selected from H and the group —W—$(CH_2)_n$—Y—$(CH_2)_m$—Z, wherein W is selected from a bond, —CONR$^6$—, or —SO$_2$—; and Y and Z are each independently selected from a bond, H, $(C_6\text{-}C_{10})$aryl, $(C_6\text{-}C_{10})$aryloxy, $(C_6\text{-}C_{10})$aryl$(C_1\text{-}C_4)$alkyl, $(C_6\text{-}C_{10})$aryl$(C_1\text{-}C_4)$alkoxy, $(C_3\text{-}C_{14})$cycloalkyl, $(C_3\text{-}C_{14})$cycloalkyloxy, $(C_3\text{-}C_{14})$cycloalkyl$(C_1\text{-}C_4)$alkyl, $(C_3\text{-}C_{14})$cycloalkyl$(C_1\text{-}C_4)$alkoxy, $(C_2\text{-}C_{14})$heterocycloalkyl, $(C_2\text{-}C_{14})$heterocycloalkyloxy, $(C_2\text{-}C_{14})$heterocycloalkyl$(C_1\text{-}C_4)$alkyl, $(C_2\text{-}C_{14})$heterocycloalkyl$(C_1\text{-}C_4)$alkoxy, $(C_2\text{-}C_9)$heteroaryl, $(C_2\text{-}C_9)$heteroaryloxy, $(C_2\text{-}C_9)$heteroaryl$(C_1\text{-}C_4)$alkyl, and $(C_2\text{-}C_9)$heteroaryl$(C_1\text{-}C_4)$alkoxy wherein each of the aforementioned groups, except for H, may be optionally substituted with between one to four substituents, provided that $R^{1A}$ and $R^{1B}$ are not both H; or $R^{1A}$ and $R^{1B}$ are taken together with the nitrogen atom to which they are attached to form a $(C_2\text{-}C_{14})$heterocycloalkyl group which may be optionally substituted with between one to four substituents;

one of $R^5$ and $R^2$ is the group -T-$(CH_2)_q$—U—$(CH_2)_r$—V wherein T is selected from a bond, —O—, —S—, —SO—, —CO—, —CONR$^6$—, —COO—, —CONR$^6$—, —NR$^6$CO—, —NR$^6$CONR$^6$—, or —NR$^6$—, and U and V are each independently selected from a bond, H, $(C_3\text{-}C_{14})$cycloalkyl, $(C_3\text{-}C_{14})$cycloalkyloxy, $(C_3\text{-}C_{14})$cycloalkyl$(C_1\text{-}C_4)$alkyl, $(C_3\text{-}C_{14})$cycloalkyl$(C_1\text{-}C_4)$alkoxy, $(C_6\text{-}C_{10})$aryl, $(C_6\text{-}C_{10})$aryloxy, $(C_6\text{-}C_{10})$aryl$(C_1\text{-}C_4)$alkyl, $(C_6\text{-}C_{10})$aryl$(C_1\text{-}C_4)$alkoxy, $(C_2\text{-}C_{14})$heterocycloalkyl, $(C_2\text{-}C_{14})$heterocycloalkyloxy, $(C_2\text{-}C_{14})$heterocycloalkyl$(C_1\text{-}C_4)$alkyl, $(C_2\text{-}C_{14})$heterocycloalkyl$(C_1\text{-}C_4)$alkoxy, $(C_2\text{-}C_9)$heteroaryl, $(C_2\text{-}C_9)$heteroaryloxy, $(C_2\text{-}C_9)$heteroaryl$(C_1\text{-}C_4)$alkyl, and $(C_2\text{-}C_9)$heteroaryl$(C_1\text{-}C_4)$alkoxy wherein each of the aforementioned groups, except for H, may be optionally substituted with between one to four substituents; and the other is selected from H, —OH, —CN, —NO$_2$, halogen, —NR$^7$R$^7$, —SO$_2$R$^7$, —OSO$_2$R$^7$, $(C_1\text{-}C_8)$alkyl, $(C_1\text{-}C_8)$alkoxy, halo$(C_1\text{-}C_4)$alkyl, halo$(C_1\text{-}C_4)$alkoxy, $(C_3\text{-}C_{14})$cycloalkyl, $(C_3\text{-}C_{14})$cycloalkyloxy, $(C_3\text{-}C_{14})$cycloalkyl$(C_1\text{-}C_4)$alkyl, $(C_3\text{-}C_{14})$cycloalkyl$(C_1\text{-}C_4)$alkoxy, $(C_6\text{-}C_{10})$aryl, $(C_6\text{-}C_{10})$aryloxy, $(C_6\text{-}C_{10})$aryl$(C_1\text{-}C_4)$alkyl, $(C_6\text{-}C_{10})$aryl$(C_1\text{-}C_4)$alkoxy, $(C_2\text{-}C_{14})$heterocycloalkyl, $(C_2\text{-}C_{14})$heterocycloalkyloxy, $(C_2\text{-}C_{14})$heterocycloalkyl$(C_1\text{-}C_4)$alkyl, $(C_2\text{-}C_{14})$heterocycloalkyl$(C_1\text{-}C_4)$alkoxy, $(C_2\text{-}C_9)$heteroaryl, ($C_2$-$C_9$)heteroaryloxy, ($C_2$-$C_9$)heteroaryl($C_1$-$C_4$)alkyl, and ($C_2$-$C_9$)heteroaryl($C_1$-$C_4$)alkoxy, wherein any of the aforementioned groups with the exception of H, —OH, —CN, —NO$_2$, and halogen, may be optionally substituted with between one to four substituents;

$R^3$ and $R^4$ are each independently selected from H, —OH, —CN, —NO$_2$, halogen, —NR$^7$R$^7$, —SO$_2$R$^7$, OSO$_2$R$^7$, ($C_1$-$C_8$)alkyl, ($C_1$-$C_8$)alkoxy, halo($C_1$-$C_4$)alkyl, halo($C_1$-$C_4$)alkoxy, ($C_3$-$C_{14}$)cycloalkyl, ($C_3$-$C_{14}$)cycloalkyloxy, ($C_3$-$C_{14}$)cycloalkyl($C_1$-$C_4$)alkyl, ($C_3$-$C_{14}$)cycloalkyl($C_1$-$C_4$)alkoxy, ($C_6$-$C_{10}$)aryl, ($C_6$-$C_{10}$)aryloxy, ($C_6$-$C_{10}$)aryl($C_1$-$C_4$)alkyl, ($C_6$-$C_{10}$)aryl($C_1$-$C_4$)alkoxy, ($C_2$-$C_{14}$)heterocycloalkyl, ($C_2$-$C_{14}$)heterocycloalkyloxy, ($C_2$-$C_{14}$)heterocycloalkyl($C_1$-$C_4$)alkyl, ($C_2$-$C_{14}$)heterocycloalkyl($C_1$-$C_4$)alkoxy, ($C_2$-$C_9$)heteroaryl, ($C_2$-$C_9$)heteroaryloxy, ($C_2$-$C_9$)heteroaryl($C_1$-$C_4$)alkyl, and ($C_2$-$C_9$)heteroaryl($C_1$-$C_4$)alkoxy, wherein any of the aforementioned groups with the exception of H, —OH, —CN, —NO$_2$, and halogen, may be optionally substituted with between one to four substituents;

each $R^6$ is independently selected from H and ($C_1$-$C_8$)alkyl; each $R^7$ is independently selected from H, ($C_1$-$C_8$)alkyl, ($C_1$-$C_8$)alkoxy, halo($C_1$-$C_4$)alkyl, halo($C_1$-$C_4$)alkoxy, ($C_3$-$C_{14}$)cycloalkyl, ($C_3$-$C_{14}$)cycloalkyloxy, ($C_3$-$C_{14}$)cycloalkyl($C_1$-$C_4$)alkyl, ($C_3$-$C_{14}$)cycloalkyl($C_1$-$C_4$)alkoxy, ($C_6$-$C_{10}$)aryl, ($C_6$-$C_{10}$)aryloxy, ($C_6$-$C_{10}$)aryl($C_1$-$C_4$)alkyl, ($C_6$-$C_{10}$)aryl($C_1$-$C_4$)alkoxy, ($C_2$-$C_{14}$)heterocycloalkyl, ($C_2$-$C_{14}$)heterocycloalkyloxy, ($C_2$-$C_{14}$)heterocycloalkyl($C_1$-$C_4$)alkyl, ($C_2$-$C_{14}$)heterocycloalkyl($C_1$-$C_4$)alkoxy, ($C_2$-$C_9$)heteroaryl, ($C_2$-$C_9$)heteroaryl($C_1$-$C_4$)alkyl, ($C_2$-$C_9$)heteroaryloxy, and ($C_2$-$C_9$)heteroaryl($C_1$-$C_4$)alkoxy wherein any of the aforementioned groups, except for H, may be optionally substituted with between one to four substituents; n, m, q, and r are each independently selected from 0, 1, 2, or 3; and wherein said optional substituents are each independently selected from H, —OH, —CN, oxo, NO$_2$, halogen, ($C_1$-$C_8$)alkyl, ($C_1$-$C_8$)alkoxy, halo($C_1$-$C_4$)alkyl, halo($C_1$-$C_4$)alkoxy, ($C_3$-$C_{14}$)cycloalkyl, ($C_3$-$C_{14}$)cycloalkyl($C_1$-$C_4$)alkyl, ($C_3$-$C_{14}$)cycloalkyloxy, ($C_3$-$C_{14}$)cycloalkyl($C_1$-$C_4$)alkoxy, —NR$^6$R$^6$, ($C_6$-$C_{10}$)aryl, ($C_6$-$C_{10}$)aryl($C_1$-$C_4$)alkyl, ($C_6$-$C_{10}$)aryloxy, ($C_6$-$C_{10}$)aryl($C_1$-$C_4$)alkoxy, —SO$_2$R$^6$, —C(O)NR$^6$R$^6$, —SO$_2$NR$^6$R$^6$, ($C_2$-$C_{14}$)heterocycloalkyl, ($C_2$-$C_{14}$)heterocycloalkyloxy, ($C_2$-$C_{14}$)heterocycloalkyl($C_1$-$C_4$)alkyl, ($C_2$-$C_{14}$)heterocycloalkyl($C_1$-$C_4$)alkoxy, ($C_2$-$C_9$)heteroaryl, ($C_2$-$C_9$)heteroaryloxy, ($C_2$-$C_9$)heteroaryl($C_1$-$C_4$)alkyl, ($C_2$-$C_9$)heteroaryl($C_1$-$C_4$)alkoxy, —COR$^E$, —NR$^6$COR$^6$, —NR$^6$SO$_2$R$^6$, —OSO$_2$R$^6$, or —CO$_2$R$^6$.

In another aspect, this application relates to compounds of the general Formula I, or salts thereof, wherein $R^5$ is the group -T-(CH$_2$)$_q$—U—(CH$_2$)$_r$—V where T is a bond, and U and V are each independently selected from ($C_6$-$C_{10}$)aryl, ($C_6$-$C_{10}$)aryloxy, ($C_6$-$C_{10}$)aryl($C_1$-$C_4$)alkyl, ($C_6$-$C_{10}$)aryl($C_1$-$C_4$)alkoxy, ($C_3$-$C_{14}$)cycloalkyl, ($C_3$-$C_{14}$)cycloalkyloxy, ($C_3$-$C_{14}$)cycloalkyl($C_1$-$C_4$)alkyl, ($C_3$-$C_{14}$)cycloalkyl($C_1$-$C_4$)alkoxy, ($C_2$-$C_{14}$)heterocycloalkyl, ($C_2$-$C_{14}$)heterocycloalkyloxy, ($C_2$-$C_{14}$)heterocycloalkyl($C_1$-$C_4$)alkyl, ($C_2$-$C_{14}$)heterocycloalkyl($C_1$-$C_4$)alkoxy, ($C_2$-$C_9$)heteroaryl, ($C_2$-$C_9$)heteroaryloxy, ($C_2$-$C_9$)heteroaryl($C_1$-$C_4$)alkyl, and ($C_2$-$C_9$)heteroaryl($C_1$-$C_4$)alkoxy, wherein any of the aforementioned groups may be optionally substituted with between one to four substituents. In some specific embodiments $R^2$ is H. In some specific embodiments, at least one of $R^3$ and $R^4$ is H. In still other specific embodiments, one or more of $R^2$, $R^3$ and $R^4$ are H. In further specific embodiments, none of $R^2$, $R^3$ and $R^4$ are H.

In another aspect, this application relates to compounds of the general Formula I, or salts thereof, wherein $R^5$ is the group -T-(CH$_2$)$_q$—U—(CH$_2$)$_r$—V wherein T is selected from —O—, —S—, —SO—, —NR$^6$CO—, —NR$^6$CONR$^6$—, or —NR$^6$— and at least one of U and V is selected from ($C_6$-$C_{10}$)aryl, ($C_6$-$C_{10}$)aryloxy, ($C_6$-$C_{10}$)aryl($C_1$-$C_4$)alkyl, ($C_6$-$C_{10}$)aryl($C_1$-$C_4$)alkoxy, ($C_3$-$C_{14}$)cycloalkyl, ($C_3$-$C_{14}$)cycloalkyloxy, ($C_3$-$C_{14}$)cycloalkyl($C_1$-$C_4$)alkyl, ($C_3$-$C_{14}$)cycloalkyl($C_1$-$C_4$)alkoxy, ($C_2$-$C_{14}$)heterocycloalkyl, ($C_2$-$C_{14}$)heterocycloalkyloxy, ($C_2$-$C_{14}$)heterocycloalkyl($C_1$-$C_4$)alkyl, ($C_2$-$C_{14}$)heterocycloalkyl($C_1$-$C_4$)alkoxy, ($C_2$-$C_9$)hetero aryl, ($C_2$-$C_9$)heteroaryloxy, ($C_2$-$C_9$)heteroaryl($C_1$-$C_4$)alkyl, and ($C_2$-$C_9$)heteroaryl($C_1$-$C_4$)alkoxy, wherein any of the aforementioned groups may be optionally substituted with between one to four substituents. In some specific embodiments, $R^2$ is H. In some specific embodiments, at least one of $R^3$ and $R^4$ is H. In still other specific embodiments, at least one of $R^4$, $R^3$, or $R^2$ is H. In further specific embodiments, none of $R^4$, $R^3$, or $R^2$ are H.

In another aspect, this application relates to compounds of the general Formula I, or salts thereof, wherein one of $R^{1A}$ and $R^{1B}$ is —W—(CH$_2$)$_n$—Y—(CH$_2$)$_m$—Z, wherein Y and Z are each independently selected from ($C_6$-$C_{10}$)aryl, ($C_6$-$C_{10}$)aryloxy, ($C_6$-$C_{10}$)aryl($C_1$-$C_4$)alkyl, ($C_6$-$C_{10}$)aryl($C_1$-$C_4$)alkoxy, ($C_3$-$C_{14}$)cycloalkyl, ($C_3$-$C_{14}$)cycloalkyloxy, ($C_3$-$C_{14}$)cycloalkyl($C_1$-$C_4$)alkyl, ($C_3$-$C_{14}$)cycloalkyl($C_1$-$C_4$)alkoxy, ($C_2$-$C_{14}$)heterocycloalkyl, ($C_2$-$C_{14}$)heterocycloalkyloxy, ($C_2$-$C_{14}$)heterocycloalkyl($C_1$-$C_4$)alkyl, ($C_2$-$C_{14}$)heterocycloalkyl($C_1$-$C_4$)alkoxy, ($C_2$-$C_9$)heteroaryl, ($C_2$-$C_9$)heteroaryloxy, ($C_2$-$C_9$)heteroaryl($C_1$-$C_4$)alkyl, and ($C_2$-$C_9$)heteroaryl($C_1$-$C_4$)alkoxy, wherein each of the aforementioned groups may be optionally substituted with between one to four substituents. In some specific embodiments, $R^2$ is H. In other specific embodiments, at least one of $R^3$ and $R^4$ is H. In still other specific embodiments, at least one of $R^4$, $R^3$, or $R^2$ is H. In further specific embodiments, none of $R^4$, $R^3$, or $R^2$ are H.

In another aspect, this application relates to compounds of the general Formula I, or salts thereof, wherein one of $R^{1A}$ and $R^{1B}$ is —W—(CH$_2$)$_n$—Y—(CH$_2$)$_m$—Z, and wherein Z is at least substituted with one of the following groups: ($C_6$-$C_{10}$)aryl, ($C_6$-$C_{10}$)aryloxy, ($C_6$-$C_{10}$)aryl($C_1$-$C_4$)alkyl, ($C_6$-$C_{10}$)aryl($C_1$-$C_4$)alkoxy, ($C_3$-$C_{14}$)cycloalkyl, ($C_3$-$C_{14}$)cycloalkyloxy, ($C_3$-$C_{14}$)cycloalkyl($C_1$-$C_4$)alkyl, ($C_3$-$C_{14}$)cycloalkyl($C_1$-$C_4$)alkoxy, ($C_2$-$C_{14}$)heterocycloalkyl, ($C_2$-$C_{14}$)heterocycloalkyloxy, ($C_2$-$C_{14}$)heterocycloalkyl($C_1$-$C_4$)alkyl, ($C_2$-$C_{14}$)heterocycloalkyl($C_1$-$C_4$)alkoxy, ($C_2$-$C_9$)heteroaryl, ($C_2$-$C_9$)heteroaryloxy, ($C_2$-$C_9$)heteroaryl($C_1$-$C_4$)alkyl, and ($C_2$-$C_9$)heteroaryl($C_1$-$C_4$)alkoxy, wherein each of the aforementioned groups may be optionally substituted with between one to four substituents. In some specific embodiments, $R^2$ is H. In other specific embodiments, at least one of $R^3$ and $R^4$ is H. In still other specific embodiments, at least one of $R^4$, $R^3$, or $R^2$ is H. In further specific embodiments, none of $R^4$, $R^3$, or $R^2$ are H.

In another aspect, this application relates to compounds of the general Formula I, or salts thereof, wherein $R^{1A}$ and $R^{1B}$ are taken together with the nitrogen atom to which they are attached to form a ($C_2$-$C_{14}$)heterocycloalkyl group which may be optionally substituted with between one to four substituents. In some specific embodiments, $R^2$ is H. In other specific embodiments, at least one of $R^3$ and $R^4$ is H. In still other specific embodiments, at least one of $R^4$, $R^3$, or $R^2$ is H. In yet other specific embodiments, $R^2$ is H, and one or both $R^4$ and $R^3$ is H. In further specific embodiments, none of $R^4$, $R^3$, or $R^2$ are H. In still other specific embodiments, $R^5$ is H. In still further specific embodiments, $R^5$ is H, and at least one of $R^3$ and $R^4$ is H.

In another aspect, this application relates to compounds of the general Formula Ia

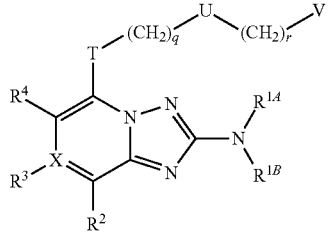

or salts thereof, wherein X, R⁴, R³, R¹ᴬ, R¹ᴮ, T, q, U, V, and r are as described in Formula I and wherein V is at least substituted with one of the following groups: $(C_6-C_{10})$aryl, $(C_6-C_{10})$aryloxy, $(C_6-C_{10})$aryl$(C_1-C_4)$alkyl, $(C_6-C_{10})$aryl$(C_1-C_4)$alkoxy, $(C_3-C_{14})$cycloalkyl, $(C_3-C_{14})$cycloalkyloxy, $(C_3-C_{14})$cycloalkyl$(C_1-C_4)$allyl, $(C_3-C_{14})$cycloalkyl$(C_1-C_4)$alkoxy, $(C_2-C_{14})$heterocycloalkyl, $(C_2-C_{14})$heterocycloalkyloxy, $(C_2-C_{14})$heterocycloalkyl$(C_1-C_4)$alkyl, $(C_2-C_{14})$heterocycloalkyl$(C_1-C_4)$alkoxy, $(C_2-C_9)$hetero aryl, $(C_2-C_9)$heteroaryloxy, $(C_2-C_9)$heteroaryl$(C_1-C_4)$alkyl, and $(C_2-C_9)$heteroaryl$(C_1-C_4)$alkoxy, wherein any of the aforementioned groups may be optionally substituted with between one to four substituents. Exemplary embodiments of compounds of the general Formula Ia include, but are not limited to, compounds such as:

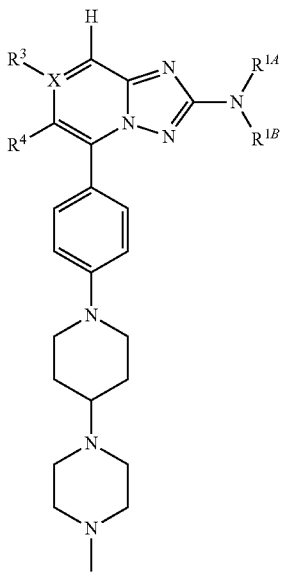

In other specific embodiments of compounds of Formula Ia, at least one of R³ and R⁴ is H. In still other specific embodiments, neither R³ and R⁴ are H.

In another aspect, this application relates to compounds of the general Formula Ib

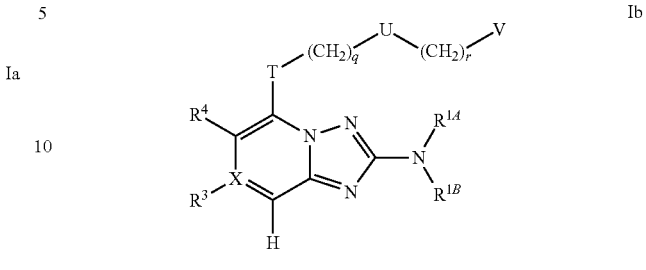

or salts thereof, wherein r is 0, V is H and X, R⁴, R³, R¹ᴬ, R¹ᴮ, T, and q are as described as for Formula I, and wherein U is selected from $(C_3-C_{14})$cycloalkyl, $(C_3-C_{14})$cycloalkyloxy, $(C_3-C_{14})$cycloalkyl$(C_1-C_4)$alkyl, $(C_3-C_{14})$cycloalkyl$(C_1-C_4)$alkoxy, $(C_2-C_{14})$heterocycloalkyl, $(C_2-C_{14})$heterocycloalkyloxy, $(C_2-C_{14})$heterocycloalkyl$(C_1-C_4)$alkyl, and $(C_2-C_{14})$heterocycloalkyl$(C_1-C_4)$alkoxy, wherein any of the aforementioned groups may be optionally substituted with between one to four substituents. Exemplary embodiments of compounds of the general Formula Ib include, but are not limited to, compounds such as:

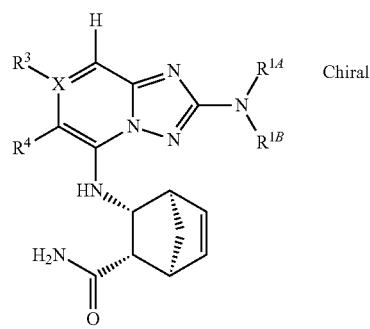

In other specific embodiments of compounds of Formula Ib, at least one of R³ and R⁴ is H. In still other specific embodiments, neither of R³ and R⁴ is H. In yet other embodiments, both of R³ and R⁴ are H.

In another aspect, this application relates to compounds of the general formula Ic

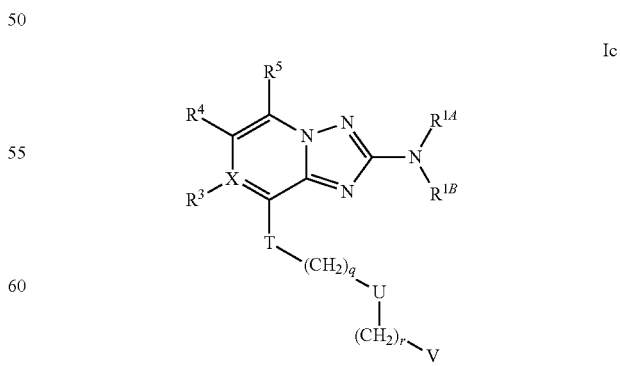

or salts thereof, wherein all of the variables are as defined as in Formula I. In some specific embodiments, R⁵ is H. In other specific embodiments, T is selected from —O—, —S—, —SO—, —NR$^6$CO—, —NR$^6$CONR$^6$—, or —NR$^6$— and at least one of U and V is selected from (C$_6$-C$_{10}$)aryl, (C$_6$-C$_{10}$) aryloxy, (C$_6$-C$_{10}$)aryl(C$_1$-C$_4$)alkyl, (C$_6$-C$_{10}$)aryl(C$_1$-C$_4$) alkoxy, (C$_3$-C$_{14}$)cycloalkyl, (C$_3$-C$_{14}$)cycloalkyloxy, (C$_3$-C$_{14}$)cycloalkyl(C$_1$-C$_4$)alkyl, (C$_3$-C$_{14}$)cycloalkyl(C$_1$-C$_4$) alkoxy, (C$_2$-C$_{14}$)heterocycloalkyl, (C$_2$-C$_{14}$) heterocycloalkyloxy, (C$_2$-C$_{14}$)heterocycloalkyl(C$_1$-C$_4$)alkyl, (C$_2$-C$_{14}$)heterocycloalkyl(C$_1$-C$_4$)alkoxy, (C$_2$-C$_9$)hetero aryl, (C$_2$-C$_9$)heteroaryloxy, (C$_2$-C$_9$)heteroaryl(C$_1$-C$_4$)alkyl, and (C$_2$-C$_9$)heteroaryl(C$_1$-C$_4$)alkoxy, wherein any of the aforementioned groups may be optionally substituted with between one to four substituents. In other specific embodiments of compounds of Formula Ic, at least one of R$^3$ and R$^4$ is H. In further specific embodiments, one or more of R$^3$, R$^4$, and R$^5$ are H. In yet further specific embodiments, none of R$^3$, R$^4$, and R$^5$ are H.

In another aspect, this application relates to compounds of the general Formula Id

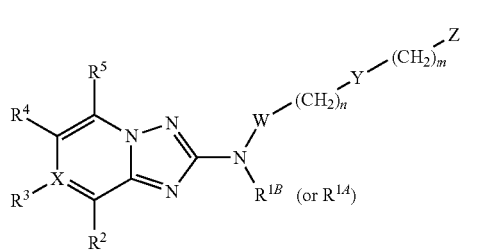

Id or salts thereof, wherein one of R$^{1A}$ or R$^{1B}$ is —W—(CH$_2$)$_n$—Y—(CH$_2$)$_m$—Z, and wherein Y and Z are each independently selected from (C$_6$-C$_{10}$)aryl, (C$_6$-C$_{10}$)aryloxy, (C$_6$-C$_{10}$)aryl(C$_1$-C$_4$)alkyl, (C$_6$-C$_{10}$)aryl(C$_1$-C$_4$)alkoxy, (C$_3$-C$_{14}$)cycloalkyl, (C$_3$-C$_{14}$)cycloalkyloxy, (C$_3$-C$_{14}$)cycloalkyl(C$_1$-C$_4$)alkyl, (C$_3$-C$_{14}$)cycloalkyl(C$_1$-C$_4$)alkoxy, (C$_2$-C$_{14}$)heterocycloalkyl, (C$_2$-C$_{14}$)heterocycloalkyloxy, (C$_2$-C$_{14}$)heterocycloalkyl(C$_1$-C$_4$)alkyl, (C$_2$-C$_{14}$)heterocycloalkyl(C$_1$-C$_4$)alkoxy, (C$_2$-C$_9$)heteroaryl, (C$_2$-C$_9$)heteroaryloxy, (C$_2$-C$_9$)heteroaryl(C$_1$-C$_4$)alkyl, and (C$_2$-C$_9$)heteroaryl(C$_1$-C$_4$)alkoxy, wherein each of the aforementioned groups may be optionally substituted with between one to four substituents, and X, W, R$^2$, R$^3$, R$^4$, R$^5$, n, m, and the other of R$^{1A}$ or R$^{1B}$ are as described in Formula I. In some specific embodiments, R$^2$ is H. In other specific embodiments, at least one of R$^2$, R$^3$, R$^4$, R$^5$ is H. In still other specific embodiments, one of R$^2$ and R$^5$ is H. In further specific embodiments, R$^2$ is H, one or both of R$^3$ and R$^4$ is H, and Z is substituted with at least one of (C$_6$-C$_{10}$)aryl, (C$_6$-C$_{10}$)aryloxy, (C$_6$-C$_{10}$)aryl(C$_1$-C$_4$)alkyl, (C$_6$-C$_{10}$)aryl(C$_1$-C$_4$)alkoxy, (C$_3$-C$_{14}$)cycloalkyl, (C$_3$-C$_{14}$)cycloalkyloxy, (C$_3$-C$_{14}$)cycloalkyl(C$_1$-C$_4$)alkyl, (C$_3$-C$_{14}$)cycloalkyl(C$_1$-C$_4$)alkoxy, (C$_2$-C$_{14}$)heterocycloalkyl, (C$_2$-C$_{14}$)heterocycloalkyloxy, (C$_2$-C$_{14}$)heterocycloalkyl(C$_1$-C$_4$)alkyl, (C$_2$-C$_{14}$)heterocycloalkyl(C$_1$-C$_4$)alkoxy, (C$_2$-C$_9$)heteroaryl, (C$_2$-C$_9$)heteroaryloxy, (C$_2$-C$_9$)heteroaryl(C$_1$-C$_4$)alkyl, and (C$_2$-C$_9$)heteroaryl(C$_1$-C$_4$)alkoxy, wherein each of the aforementioned groups may be optionally substituted with between one to four substituents.

In another aspect, this application relates to compounds of the general Formula Ie

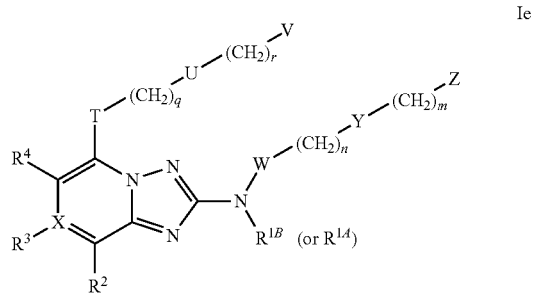

Ie or salts thereof, wherein one of R$^{1A}$ or R$^{1B}$ is —W—(CH$_2$)$_n$—Y—(CH$_2$)$_m$—Z, wherein Y and Z are each independently selected from (C$_6$-C$_{10}$)aryl, (C$_6$-C$_{10}$)aryloxy, (C$_6$-C$_{10}$) aryl(C$_1$-C$_4$)alkyl, (C$_6$-C$_{10}$)aryl(C$_1$-C$_4$)alkoxy, (C$_3$-C$_{14}$)cycloalkyl, (C$_3$-C$_{14}$)cycloalkyloxy, (C$_3$-C$_{14}$)cycloalkyl(C$_1$-C$_4$) alkyl, (C$_3$-C$_{14}$)cycloalkyl(C$_1$-C$_4$)alkoxy, (C$_2$-C$_{14}$) heterocycloalkyl, (C$_2$-C$_{14}$)heterocycloalkyloxy, (C$_2$-C$_{14}$) heterocycloalkyl(C$_1$-C$_4$)alkyl, (C$_2$-C$_{14}$)heterocycloalkyl(C$_1$-C$_4$)alkoxy, (C$_2$-C$_9$)heteroaryl, (C$_2$-C$_9$)heteroaryloxy, (C$_2$-C$_9$)heteroaryl(C$_1$-C$_4$)alkyl, and (C$_2$-C$_9$)heteroaryl(C$_1$-C$_4$) alkoxy, wherein each of the aforementioned groups may be optionally substituted with between one to four substituents; and both U and V are selected from (C$_6$-C$_{10}$)aryl, (C$_6$-C$_{10}$) aryloxy, (C$_6$-C$_{10}$)aryl(C$_1$-C$_4$)alkyl, (C$_6$-C$_{10}$)aryl(C$_1$-C$_4$) alkoxy, (C$_3$-C$_{14}$)cycloalkyl, (C$_3$-C$_{14}$)cycloalkyloxy, (C$_3$-C$_{14}$)cyclo alkyl(C$_1$-C$_4$)alkyl, (C$_3$-C$_{14}$)cycloakyl(C$_1$-C$_4$) alkoxy, (C$_2$-C$_{14}$)heterocycloalkyl, (C$_2$-C$_{14}$) heterocycloalkyloxy, (C$_2$-C$_{14}$)heterocycloalkyl(C$_1$-C$_4$)alkyl, (C$_2$-C$_{14}$)heterocycloalkyl(C$_1$-C$_4$)alkoxy, (C$_2$-C$_9$)heteroaryl, (C$_2$-C$_9$)heteroaryloxy, (C$_2$-C$_9$)heteroaryl(C$_1$-C$_4$)alkyl, and (C$_2$-C$_9$)heteroaryl(C$_1$-C$_4$)alkoxy, wherein each of the aforementioned groups may be optionally substituted with between one to four substituents; and X, W, T, R$^2$, R$^3$, R$^4$, n, m, r, q, and the other of R$^{1A}$ or R$^{1B}$ are as described as in Formula I. In some specific embodiments, R$^2$ is H. In other specific embodiments, at least one of R$^2$, R$^3$, and R$^4$ are H. In still other specific embodiments, R$^2$ is H, and one of R$^3$ and R$^4$ are H. In further specific embodiments, R$^2$ is H, and neither of R$^3$ and R$^4$ are H.

In another aspect, this application relates to compounds of the general Formula II:

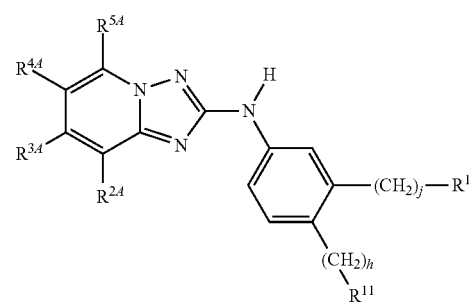

II or salts thereof, wherein:
R$^{2A}$ is the group -T$^A$-(CH$_2$)$_q$—U$^A$—(CH$_2$)$_r$—V$^A$, wherein T$^A$ is selected from a bond selected from a direct bond, —CH═CH—, or —C≡C—, —O—, —S—, or —NR$^{6A}$—, and $U^A$ is selected from $(C_3-C_{14})$cycloalkyl, $(C_3-C_{14})$cycloalkyloxy, $(C_3-C_{14})$cycloalkyl$(C_1-C_4)$alkyl, $(C_3-C_{14})$cycloalkyl$(C_1-C_4)$alkoxy, $(C_6-C_{10})$aryl, $(C_6-C_{10})$aryloxy, $(C_6-C_{10})$aryl$(C_1-C_4)$alkyl, $(C_6-C_{10})$aryl$(C_1-C_4)$alkoxy, $(C_2-C_{14})$heterocycloalkyl, $(C_2-C_{14})$heterocycloalkyloxy, $(C_2-C_{14})$heterocycloalkyl$(C_1-C_4)$alkyl, $(C_2-C_{14})$heterocycloalkyl$(C_1-C_4)$alkoxy, $(C_2-C_9)$heteroaryl, $(C_2-C_9)$heteroaryloxy, $(C_2-C_9)$heteroaryl$(C_1-C_4)$alkyl, and $(C_2-C_9)$heteroaryl$(C_1-C_4)$alkoxy, wherein each of the aforementioned groups, may be optionally substituted with between one to four substituents, and $V^A$ is selected from H, $(C_3-C_{14})$cycloalkyl, $(C_3-C_{14})$cycloalkyloxy, $(C_3-C_{14})$cycloalkyl$(C_1-C_4)$alkyl, $(C_3-C_{14})$cycloalkyl$(C_1-C_4)$alkoxy, $(C_6-C_{10})$aryl, $(C_6-C_{10})$aryloxy, $(C_6-C_{10})$aryl$(C_1-C_4)$alkyl, $(C_6-C_{10})$aryl$(C_1-C_4)$alkoxy, $(C_2-C_{14})$heterocycloalkyl, $(C_2-C_{14})$heterocycloalkyloxy, $(C_2-C_{14})$heterocycloalkyl$(C_1-C_4)$alkyl, $(C_2-C_{14})$heterocycloalkyl$(C_1-C_4)$alkoxy, $(C_2-C_9)$heteroaryl, $(C_2-C_9)$heteroaryloxy, $(C_2-C_9)$heteroaryl$(C_1-C_4)$alkyl, and $(C_2-C_9)$heteroaryl$(C_1-C_4)$alkoxy, wherein each of the aforementioned groups, except for H, may be optionally substituted with between one to four substituents;

$R^{3A}$, $R^{4A}$, and $R^{5A}$ are each independently selected from H, OH, CN, $NO_2$, halogen, $(C_1-C_8)$alkyl, $(C_1-C_8)$alkoxy, halo$(C_1-C_4)$alkyl, and halo$(C_1-C_4)$alkoxy;

$R^{6A}$ is selected from H and $(C_1-C_4)$alkyl;

$R^{7A}$ is each independently selected from H and $(C_1-C_8)$alkyl;

$R^{12}$ is H, j is 0, and $R^{11}$ is selected from $OSO_2$halo$(C_1-C_4)$alkyl, $(C_1-C_8)$alkoxy, $(C_4-C_{14})$cycloalkyl, $(C_3-C_{14})$cycloalkyloxy, $(C_3-C_{14})$cycloalkyl$(C_1-C_4)$alkyl, $(C_3-C_{14})$cycloalkyl$(C_1-C_4)$alkoxy, $(C_6-C_{10})$aryl, $(C_6-C_{10})$aryloxy, $(C_6-C_{10})$aryl$(C_1-C_4)$alkyl, $(C_6-C_{10})$aryl$(C_1-C_4)$alkoxy, $(C_2-C_{14})$heterocycloalkyl, $(C_2-C_{14})$heterocycloalkyloxy, $(C_2-C_{14})$heterocycloalkyl$(C_1-C_4)$alkyl, $(C_2-C_{14})$heterocycloalkyl$(C_1-C_4)$alkoxy, $(C_2-C_9)$heteroaryl, $(C_2-C_9)$heteroaryloxy, $(C_2-C_9)$heteroaryl$(C_1-C_4)$alkyl, and $(C_2-C_9)$heteroaryl$(C_1-C_4)$alkoxy, wherein each of the aforementioned groups, except for H, may be optionally substituted with between one to four substituents, provided that $(C_2-C_{14})$heterocycloalkyl is not unsubstituted N-isopropyl-piperazinyl or 3H-[1,3,4]oxadiazol-2-one-5-yl, $(C_2-C_9)$heteroaryl is not unsubstituted triazolyl or tetrazolyl, and $(C_2-C_9)$heteroaryl$(C_1-C_4)$alkyl is not unsubstituted $CH_2$-triazolyl or $CH_2$-imidazolyl; or $R^{11}$ is H, h is 0, and $R^{12}$ is selected from $SO_2(C_1-C_8)$alkyl, $(C_2-C_8)$alkyl, $(C_1-C_8)$alkoxy, halo$(C_2-C_4)$alkyl, halo$(C_1-C_4)$alkoxy, $(C_3-C_{14})$cycloalkyl, $(C_3-C_{14})$cycloalkyloxy, $(C_3-C_{14})$cycloalkyl$(C_1-C_4)$alkyl, $(C_3-C_{14})$cycloalkyl$(C_1-C_4)$alkoxy, $(C_6-C_{10})$aryl, $(C_6-C_{10})$aryloxy, $(C_6-C_{10})$aryl$(C_1-C_4)$alkyl, $(C_6-C_{10})$aryl$(C_1-C_4)$alkoxy, $(C_2-C_{14})$heterocycloalkyl, $(C_2-C_{14})$heterocycloalkyloxy, $(C_2-C_{14})$heterocycloalkyl$(C_1-C_4)$alkyl, $(C_2-C_{14})$heterocycloalkyl$(C_1-C_4)$alkoxy, $(C_2-C_9)$heteroaryl, $(C_2-C_9)$heteroaryloxy, $(C_2-C_9)$heteroaryl$(C_1-C_4)$alkyl, and $(C_2-C_9)$heteroaryl$(C_1-C_4)$alkoxy, wherein each of the aforementioned groups, except for H, may be optionally substituted with between one to four substituents; or $R^{11}$ and $R^{12}$ may be taken together to form a five to ten membered carbocyclic or heterocyclic ring or 6 membered heteroaromatic ring wherein any of the foregoing may be optionally substituted with between one to four substituents provided that when said heterocyclic ring is a 5 membered ring that contains one nitrogen atom said ring is not also substituted by oxo;

h, j, q and r are each independently selected from 0, 1, 2, or 3; and wherein said optional substituents are each independently selected from OH, CN, oxo, $NO_2$, halogen, $(C_1-C_8)$alkyl, $(C_1-C_8)$alkoxy, hydroxy$(C_1-C_4)$alkyl, halo$(C_1-C_4)$alkyl, halo$(C_1-C_4)$alkoxy, $(C_3-C_{14})$cycloalkyl, $(C_3-C_{14})$cycloalkyl$(C_1-C_4)$alkyl, $(C_3-C_{14})$cycloalkyloxy, $(C_3-C_{14})$cycloalkyl$(C_1-C_4)$alkoxy, $NR^{7A}R^{7A}$, $(C_1-C_4)$alkyl-$NR^{7A}R^{7A}$, $(C_6-C_{10})$aryl, $(C_6-C_{10})$aryl$(C_1-C_4)$alkyl, $(C_6-C_{10})$aryloxy, $(C_6-C_{10})$aryl$(C_1-C_4)$alkyl, $SO_2R^{7A}$, $(C_1-C_4)$alkyl-$SO_2R^{7A}$, $(C_1-C_4)$alkyl-$C(O)NR^{7A}R^{7A}$, $C(O)NR^{7A}R^{7A}$, $(C_1-C_4)$alkyl-$SO_2NR^{7A}R^{7A}$, $SO_2NR^{7A}R^{7A}$, $(C_2-C_{14})$heterocycloalkyl, $(C_2-C_{14})$heterocycloalkyloxy, $(C_2-C_{14})$heterocycloalkyl$(C_1-C_4)$alkyl, $(C_2-C_{14})$heterocyclo alkyl$(C_1-C_4)$alkoxy, $(C_2-C_9)$hetero aryl, $(C_2-C_9)$heteroaryloxy, $(C_2-C_9)$heteroaryl$(C_1-C_4)$alkyl, $(C_2-C_9)$hetero aryl$(C_1-C_4)$alkoxy, $COR^{7A}$, $(C_1-C_4)$alkyl-$COR^{7A}$, $NR^{7A}COR^{7A}$, $(C_1-C_4)$allyl-$NR^{7A}COR^{7A}$, $NR^{7A}SO_2R^{7A}$, $(C_1-C_4)$allyl-$NR^{7A}SO_2R^{7A}$, $OSO_2R^{7A}$, $(C_1-C_4)$allyl-$OSO_2R^{7A}$, $POR^{7A}R^{7A}$, $(C_1-C_4)$allyl-$POR^{7A}R^{7A}$, $CO_2R^{7A}$ or $(C_1-C_4)$alkyl-$CO_2R^{7A}$.

In another aspect, this application relates to compounds of the general Formula II, or salts thereof, wherein $R^{2A}$ is the group $-T^A-(CH_2)_q-U^A-(CH_2)_r-V^A$, and $U^A$ is selected from $(C_3-C_{14})$cycloalkyl, $(C_3-C_{14})$cycloalkyloxy, $(C_3-C_{14})$cycloalkyl$(C_1-C_4)$alkyl, $(C_3-C_{14})$cycloalkyl$(C_1-C_4)$alkoxy, $(C_6-C_{10})$aryl, $(C_6-C_{10})$aryloxy, $(C_6-C_{10})$aryl$(C_1-C_4)$alkyl, $(C_6-C_{10})$aryl$(C_1-C_4)$alkoxy, $(C_2-C_{14})$heterocycloalkyl, $(C_2-C_{14})$heterocycloalkyloxy, $(C_2-C_{14})$heterocycloalkyl$(C_1-C_4)$alkyl, $(C_2-C_{14})$heterocycloalkyl$(C_1-C_4)$alkoxy, $(C_2-C_9)$heteroaryl, $(C_2-C_9)$heteroaryloxy, $(C_2-C_9)$heteroaryl$(C_1-C_4)$alkyl, and $(C_2-C_9)$heteroaryl$(C_1-C_4)$alkoxy, wherein each of the aforementioned groups, may be optionally substituted with between one to four substituents. In some specific embodiments, $R^{5A}$, $R^{4A}$, $R^{3A}$ and $R^{12}$ are H, j is 0, and $U^A$ is $(C_6-C_{10})$aryl, which may be optionally substituted as described above. In other specific embodiments, $U^A$ is phenyl, which may be optionally substituted as described above. In other specific embodiments, $R^{5A}$, $R^{4A}$, $R^{3A}$ and $R^{12}$ are H, j is 0, and $U^A$ is $(C_2-C_9)$heteroaryl, which may be optionally substituted as described above. In still other specific embodiments, $U^A$ is pyridinyl, pyrazolyl, indazolyl, or pyrazinyl, all of which may be optionally substituted as described above. In other specific embodiments, $R^{5A}$, $R^{4A}$, $R^{3A}$ and $R^{12}$ are H, j is 0, and $U^A$ is $(C_2-C_{14})$heterocycloalkyl, which may be optionally substituted as described above. In some specific embodiments, $U^A$ is piperazinyl, thiomorpholinyl, piperidinyl, tetrahydropiperidinyl, pyrrolidinyl, azaphosphinanyl, or dihydropyridinyl, all of which may be optionally substituted as described above. In some additional specific embodiments, $U^A$ is benzo[1,3]dioxolyl, which may be optionally substituted as described above.

In another aspect, this application relates to compounds of the general Formula II, or salts thereof, wherein $R^{5A}$, $R^{4A}$, $R^{3A}$, and $R^{12}$ are H, j is 0, and $R^{11}$ is as defined above. In some specific embodiments, $T^A$ is a direct bond, $R^{5A}$, $R^{4A}$, $R^{3A}$, and $R^{12}$ are H, j is 0, and $R^{11}$ is a 6 membered heterocyclic ring which is optionally substituted with between one to four substituents. In other specific embodiments, $R^{11}$ is a 6 membered heterocyclic ring, in which at least one member is a nitrogen atom, optionally substituted as described above and $U^A$ is selected from $(C_6-C_{10})$aryl and $(C_2-C_9)$heteroaryl. In other specific embodiments, $R^{11}$ is selected from piperazinyl, piperidinyl, morpholinyl, azaphosphinanyl, and thiomorpholinyl, wherein any of the foregoing may be optionally substituted with between one to four substituents. In particular embodiments, a compound of the general Formula II, or a salt thereof, is selected from the following:

N-[4-(1-ethyl-4-oxido-1,4-azaphosphinan-4-yl)phenyl]-8-[4-(methylsulfonyl)phenyl][1,2,4]triazolo[1,5-a]pyridin-2-amine,

[8-(2-Methoxy-phenyl)-[1,2,4]triazolo[1,5-a]pyridin-2-yl]-(4-morpholin-4-yl-phenyl)-amine,

[8-(4-Methanesulfonyl-phenyl)-[1,2,4]triazolo[1,5-a]pyridin-2-yl]-(4-morpholin-4-yl-phenyl)-amine,
(4-Morpholin-4-yl-phenyl)-(8-pyridin-3-yl-[1,2,4]triazolo[1,5-a]pyridin-2-yl)-amine,
[8-(6-Methoxy-pyridin-3-yl)-[1,2,4]triazolo[1,5-a]pyridin-2-yl]-(4-morpholin-4-yl-phenyl)-amine,
(4-Morpholin-4-yl-phenyl)-(8-pyridin-4-yl-[1,2,4]triazolo[1,5-a]pyridin-2-yl)-amine,
[8-(3-Methanesulfonyl-phenyl)-[1,2,4]triazolo[1,5-a]pyridin-2-yl]-(4-morpholin-4-yl-phenyl)-amine,
[8-(4-Methanesulfonyl-phenyl)-[1,2,4]triazolo[1,5-a]pyridin-2-yl]-(4-piperidin-1-yl-phenyl)-amine,
[8-(4-Methanesulfonyl-phenyl)-[1,2,4]triazolo[1,5-a]pyridin-2-yl]-[4-(4-methyl-piperazin-1-yl)-phenyl]-amine,
[8-(4-Methanesulfonyl-phenyl)-[1,2,4]triazolo[1,5-a]pyridin-2-yl]-(4-morpholin-4-ylmethyl-phenyl)-amine,
[8-(4-Methanesulfonyl-phenyl)-[1,2,4]triazolo[1,5-a]pyridin-2-yl]-[4-(4-methyl-piperazin-1-ylmethyl)-phenyl]-amine,
[8-(4-Methanesulfonylmethyl-phenyl)-[1,2,4]triazolo[1,5-a]pyridin-2-yl]-[4-(4-methyl-piperazin-1-yl)-phenyl]-amine,
[8-(4-Methanesulfonyl-phenyl)-[1,2,4]triazolo[1,5-a]pyridin-2-yl]-[4-(4-morpholin-4-yl-piperidin-1-yl)-phenyl]-amine,
[8-(4-Methanesulfonyl-phenyl)-[1,2,4]triazolo[1,5-a]pyridin-2-yl]-[4-(1-methyl-piperidin-4-yl)-phenyl]-amine,
[8-(4-Methanesulfonyl-phenyl)-[1,2,4]triazolo[1,5-a]pyridin-2-yl]-{4-[4-(4-methyl-piperazin-1-yl)-piperidin-1-yl]-phenyl}-amine,
[4-(4-Methyl-piperazin-1-yl)-phenyl]-{8-[4-(propane-2-sulfonyl)-phenyl]-[1,2,4]triazolo[1,5-a]pyridin-2-yl}-amine,
N,N-Dimethyl-4-{2-[4-(4-methyl-piperazin-1-yl)-phenylamino]-[1,2,4]triazolo[1,5-a]pyridin-8-yl}-benzenesulfonamide,
[8-(2-Methoxy-phenyl)-[1,2,4]triazolo[1,5-a]pyridin-2-yl]-[4-(4-methyl-piperazin-1-yl)-phenyl]-amine,
[8-(3-Methanesulfonyl-phenyl)-[1,2,4]triazolo[1,5-a]pyridin-2-yl]-[4-(4-methyl-piperazin-1-yl)-phenyl]-amine,
N-Methyl-N-(4-{2-[4-(4-methyl-piperazin-1-yl)-phenylamino]-[1,2,4]triazolo[1,5-a]pyridin-8-yl}-phenyl)-methanesulfonamide,
[4-(4-Methyl-piperazin-1-yl)-phenyl]-[8-(4-trifluoromethyl-phenyl)-[1,2,4]triazolo[1,5-a]pyridin-2-yl]-amine,
[8-(2-Methanesulfonyl-phenyl)-[1,2,4]triazolo[1,5-a]pyridin-2-yl]-[4-(4-methyl-piperazin-1-yl)-phenyl]-amine,
N-{4[(1,1-dioxidothiomorpholin-4-yl)methyl]phenyl}-8-[4-(methylsulfonyl)phenyl][1,2,4]triazolo[1,5-a]pyridin-2-amine,
N-{4-[2-({4-[(1,1-dioxidothiomorpholin-4-yl)methyl]phenyl}amino)[1,2,4]triazolo[1,5-a]pyridin-8-yl]phenyl}-N-methylmethanesulfonamide,
N-Methyl-N-(3-{2-[4-(4-methyl-piperazin-1-yl)-phenylamino]-[1,2,4]triazolo[1,5-a]pyridin-8-yl}-phenyl)-methanesulfonamide,
N-Methyl-N-(3-{2-[4-(4-methyl-piperazin-1-yl)-phenylamino]-[1,2,4]triazolo[1,5-a]pyridin-8-yl}-benzyl)-methanesulfonamide,
N-Methyl-N-(3-{2-[4-(1-methyl-piperidin-4-yl)-phenylamino]-[1,2,4]triazolo[1,5-a]pyridin-8-yl}-benzyl)-methanesulfonamide,
[8-(2-Methoxy-5-trifluoromethyl-phenyl)-[1,2,4]triazolo[1,5-a]pyridin-2-yl]-[4-(4-methyl-piperazin-1-yl)-phenyl]-amine,
4-{4-[8-(2-Methoxy-pyridin-3-yl)-[1,2,4]triazolo[1,5-a]pyridin-2-ylamino]-phenyl}-piperidine-1-carboxylic acid tert-butyl ester,
[8-(2-Methoxy-pyridin-3-yl)-[1,2,4]triazolo[1,5-a]pyridin-2-yl]-(4-piperidin-4-yl-phenyl)-amine,
2-(4-{4-[8-(2-Methoxy-pyridin-3-yl)-[1,2,4]triazolo[1,5-a]pyridin-2-ylamino]-phenyl}-piperidin-1-yl)-N,N-dimethyl-acetamide,
N,N-Dimethyl-2-(4-{4-[8-(2-oxo-1,2-dihydro-pyridin-3-yl)-[1,2,4]triazolo[1,5-a]pyridin-2-ylamino]-phenyl}-piperidin-1-yl)-acetamide,
4-{4-[8-(2-Methoxy-5-trifluoromethyl-pyridin-3-yl)-[1,2,4]triazolo[1,5-a]pyridin-2-ylamino]-phenyl}-piperidine-1-carboxylic acid tert-butyl ester,
[8-(2-Methoxy-5-trifluoromethyl-pyridin-3-yl)-[1,2,4]triazolo[1,5-a]pyridin-2-yl]-(4-piperidin-4-yl-phenyl)-amine,
2-(4-{4-[8-(2-Methoxy-5-trifluoromethyl-pyridin-3-yl)-[1,2,4]triazolo[1,5-a]pyridin-2-ylamino]-phenyl}-piperidin-1-yl)-N,N-dimethyl-acetamide,
4-(4-{8-[1-(4-Fluoro-phenyl)-1H-pyrazol-4-yl]-[1,2,4]triazolo[1,5-a]pyridin-2-ylamino}-phenyl)-piperidine-1-carboxylic acid tert-butyl ester,
{8-[1-(4-Fluoro-phenyl)-1H-pyrazol-4-yl]-[1,2,4]triazolo[1,5-a]pyridin-2-yl}-(4-piperidin-4-yl-phenyl)-amine,
2-[4-(4-{8-[1-(4-Fluoro-phenyl)-1H-pyrazol-4-yl]-[1,2,4]triazolo[1,5-a]pyridin-2-ylamino}-phenyl)-piperidin-1-yl]-N,N-dimethyl-acetamide,
4-{4-[8-(5-Methoxy-pyrazin-2-yl)-[1,2,4]triazolo[1,5-a]pyridin-2-ylamino]-phenyl}-piperidine-1-carboxylic acid tert-butyl ester,
[8-(5-Methoxy-pyrazin-2-yl)-[1,2,4]triazolo[1,5-a]pyridin-2-yl]-(4-piperidin-4-yl-phenyl)-amine,
2-(4-{4-[8-(5-Methoxy-pyrazin-2-yl)-[1,2,4]triazolo[1,5-a]pyridin-2-ylamino]-phenyl}-piperidin-1-yl)-N,N-dimethyl-acetamide,
4-{4-[8-(1-p-Tolyl-1H-pyrazol-4-yl)-[1,2,4]triazolo[1,5-a]pyridin-2-ylamino]-phenyl}-piperidine-1-carboxylic acid tert-butyl ester,
(4-Piperidin-4-yl-phenyl)-[8-(1-p-tolyl-1H-pyrazol-4-yl)-[1,2,4]triazolo[1,5-a]pyridin-2-yl]-amine,
2-[4-(4-{8-[2-(2,2-Difluoro-ethoxy)-5-trifluoromethyl-phenyl]-[1,2,4]triazolo[1,5-a]pyridin-2-ylamino}-phenyl)-piperidin-1-yl]-N,N-dimethyl-acetamide,
2-(4-{4-[8-(4-Chloro-2-methoxy-phenyl)-[1,2,4]triazolo[1,5-a]pyridin-2-ylamino]-phenyl}-piperidin-1-yl)-N,N-dimethyl-acetamide,
4-{4-[8-(2-Methoxy-5-trifluoromethyl-phenyl)-[1,2,4]triazolo[1,5-a]pyridin-2-ylamino]-phenyl}-piperidine-1-carboxylic acid tert-butyl ester,
[8-(2-Methoxy-5-trifluoromethyl-phenyl)-[1,2,4]triazolo[1,5-a]pyridin-2-yl]-(4-piperidin-4-yl-phenyl)-amine,
2-(4-{4-[8-(2-Methoxy-5-trifluoromethyl-phenyl)-[1,2,4]triazolo[1,5-a]pyridin-2-ylamino]-phenyl}-piperidin-1-yl)-N,N-dimethyl-acetamide,
4-{4-[8-(4-Difluoromethyl-2-methoxy-phenyl)-[1,2,4]triazolo[1,5-a]pyridin-2-ylamino]-phenyl}-piperidine-1-carboxylic acid tert-butyl ester,
[8-(4-Difluoromethyl-2-methoxy-phenyl)-[1,2,4]triazolo[1,5-a]pyridin-2-yl]-(4-piperidin-4-yl-phenyl)-amine,
2-(4-{4-[8-(4-Difluoromethyl-2-methoxy-phenyl)-[1,2,4]triazolo[1,5-a]pyridin-2-ylamino]-phenyl}-piperidin-1-yl)-N,N-dimethyl-acetamide,
4-{4-[8-(4-Fluoro-phenyl)-[1,2,4]triazolo[1,5-a]pyridin-2-ylamino]-phenyl}-piperidine-1-carboxylic acid tert-butyl ester,
[8-(4-Fluoro-phenyl)-[1,2,4]triazolo[1,5-a]pyridin-2-yl]-(4-piperidin-4-yl-phenyl)-amine, 2-(4-{4-[8-(4-Fluoro-phenyl)-[1,2,4]triazolo[1,5-a]pyridin-2-ylamino]-phenyl}-piperidin-1-yl)-N,N-dimethyl-acetamide,
[8-(3-Methoxy-phenyl)-[1,2,4]triazolo[1,5-a]pyridin-2-yl]-(4-piperidin-4-yl-phenyl)-amine,
2-(4-{4-[8-(3-Methoxy-phenyl)-[1,2,4]triazolo[1,5-a]pyridin-2-ylamino]-phenyl}-piperidin-1-yl)-N,N-dimethyl-acetamide,
4-{4-[8-(2-Fluoro-3-methoxy-phenyl)-[1,2,4]triazolo[1,5-a]pyridin-2-ylamino]-phenyl}-piperidine-1-carboxylic acid tert-butyl ester,
[8-(2-Fluoro-3-methoxy-phenyl)-[1,2,4]triazolo[1,5-a]pyridin-2-yl]-(4-piperidin-4-yl-phenyl)-amine,
2-(4-{4-[8-(2-Fluoro-3-methoxy-phenyl)-[1,2,4]triazolo[1,5-a]pyridin-2-ylamino]-phenyl}-piperidin-1-yl)-N,N-dimethyl-acetamide,
4-{-4-[8-2,3-Dimethoxy-phenyl)-[1,2,4]triazolo[1,5-a]pyridin-2-ylamino]-phenyl}-piperidine-1-carboxylic acid tert-butyl ester,
[8-(2,3-Dimethoxy-phenyl)-[1,2,4]triazolo[1,5-a]pyridin-2-yl]-(4-piperidin-4-yl-phenyl)-amine,
2-(4-{4-[8-(2,3-Dimethoxy-phenyl)-[1,2,4]triazolo[1,5-a]pyridin-2-ylamino]-phenyl}-piperidin-1-yl)-N,N-dimethyl-acetamide,
4-{4-[8-(4-Cyano-phenyl)-[1,2,4]triazolo[1,5-a]pyridin-2-ylamino]-phenyl}-piperidine-1-carboxylic acid tert-butyl ester,
4-[2-(4-Piperidin-4-yl-phenylamino)-[1,2,4]triazolo[1,5-a]pyridin-8-yl]-benzonitrile,
2-(4-{4-[8-(4-Cyano-phenyl)-[1,2,4]triazolo[1,5-a]pyridin-2-ylamino]-phenyl}-piperidin-1-yl)-N,N-dimethyl-acetamide,
4-{4-[8-(2-Fluoro-4-methoxy-phenyl)-[1,2,4]triazolo[1,5-a]pyridin-2-ylamino]-phenyl}-piperidine-1-carboxylic acid tert-butyl ester,
[8-(2-Fluoro-4-methoxy-phenyl)-[1,2,4]triazolo[1,5-a]pyridin-2-yl]-(4-piperidin-4-yl-phenyl)-amine,
4-{4-[8-(3-Dimethylamino-phenyl)-[1,2,4]triazolo[1,5-a]pyridin-2-ylamino]-phenyl}-piperidine-1-carboxylic acid tert-butyl ester,
2-(4-{4-[8-(2-Fluoro-4-methoxy-phenyl)-[1,2,4]triazolo[1,5-a]pyridin-2-ylamino]-phenyl}-piperidin-1-yl)-N,N-dimethyl-acetamide,
[8-(3-Dimethylamino-phenyl)-[1,2,4]triazolo[1,5-a]pyridin-2-yl]-(4-piperidin-4-yl-phenyl)-amine,
N-Methyl-N-[2-(2-{2-[4-(4-methyl-piperazin-1-yl)-phenylamino]-[1,2,4]triazolo[1,5-a]pyridin-8-yl}-ethyl)-phenyl]-methanesulfonamide, and
2-(4-{4-[8-(3-Dimethylamino-phenyl)-[1,2,4]triazolo[1,5-a]pyridin-2-ylamino]-phenyl}-piperidin-1-yl)-N,N-dimethyl-acetamide.

In other specific embodiments, $T^4$ is $-NR^{6A}-$, $R^{5A}$, $R^{4A}$, $R^{3A}$, and $R^{12}$ are H, j is 0, and $R^{11}$ is a 6 membered heterocyclic ring which is optionally substituted with between one to four substituents. In some specific embodiments R11 is a 6 membered heterocyclic ring, in which at least one member is a nitrogen atom, optionally substituted as described above. In other specific embodiments, $R^{11}$ is selected from piperazinyl, piperidinyl, morpholinyl, and thiomorpholinyl, wherein any of the foregoing may be optionally substituted with between one to four substituents. In particular embodiments, a compound of the general Formula II, or a salt thereof, is selected from the following:

N(8)-(2-Methanesulfonyl-phenyl)-N(2)-[4-(4-methyl-piperazin-1-yl)-phenyl]-[1,2,4]triazolo[1,5-a]pyridine-2,8-diamine,
N(8)-(3-Methanesulfonyl-phenyl)-N(2)-[4-(4-methyl-piperazin-1-yl)-phenyl]-[1,2,4]triazolo[1,5-a]pyridine-2,8-diamine,
N(8)-(3-Methanesulfonyl-phenyl)-N(2)-[4-(4-methyl-piperazin-1-yl)-phenyl]-[1,2,4]triazolo[1,5-a]pyridine-2,8-diamine,
N-Methyl-N-[3-({2-[4-(4-methyl-piperazin-1-yl)-phenylamino]-[1,2,4]triazolo[1,5-a]pyridin-8-ylamino}-methyl)-pyridin-2-yl]-methanesulfonamide,
N-Methyl-N-[3-({2-[4-(1-methyl-piperidin-4-yl)-phenylamino]-[1,2,4]triazolo[1,5-a]pyridin-8-ylamino}-methyl)-pyridin-2-yl]-methanesulfonamide,
N(8)-(2-Methanesulfonyl-phenyl)-N(2)-[4-(1-methyl-piperidin-4-yl)-phenyl]-[1,2,4]triazolo[1,5-a]pyridine-2,8-diamine,
N-Methyl-N-(3-{2-[4-(4-methyl-piperazin-1-yl)-phenylamino]-[1,2,4]triazolo[1,5-a]pyridin-8-ylamino}-pyridin-2-yl)-methanesulfonamide,
N-Methyl-N-(3-{2-[4-(1-methyl-piperidin-4-yl)-phenylamino]-[1,2,4]triazolo[1,5-a]pyridin-8-ylamino}-pyridin-2-yl)-methanesulfonamide,
N(8)-(2-Methanesulfonyl-benzyl)-N(2)-[4-(4-methyl-piperazin-1-yl)-phenyl]-[1,2,4]triazolo[1,5-a]pyridine-2,8-diamine,
N(8)-(2-Methanesulfonyl-benzyl)-N(2)-[4-methyl-piperidin-4-yl)-phenyl]-[1,2,4]triazolo[1,5-a]pyridine-2,8-diamine,
N-Methyl-N-[2-({2-[4-(4-methyl-piperazin-1-yl)-phenylamino]-[1,2,4]triazolo[1,5-a]pyridin-8-ylamino}-methyl)-phenyl]-methanesulfonamide,
N-Methyl-N-[2-({2-[4-(1-methyl-piperidin-4-yl)-phenylamino]-[1,2,4]triazolo[1,5-a]pyridin-8-ylamino}-methyl)-phenyl]-methanesulfonamide,
N(2)-[4-(4-Methyl-piperazin-1-yl)-phenyl]-N(8)-pyridin-3-ylmethyl-[1,2,4]triazolo[1,5-a]pyridine-2,8-diamine,
N-{3-[(2-{4-[4-(2-Hydroxy-ethyl)-piperazin-1-yl]-phenylamino}-[1,2,4]triazolo[1,5-a]pyridin-8-ylamino)-methyl]-pyridin-2-yl}-N-methyl-methanesulfonamide,
N-Methyl-N-[2-({2-[4-(4-methyl-piperazin-1-yl)-phenylamino]-[1,2,4]triazolo[1,5-a]pyridin-8-ylamino}-methyl)-benzyl]-methanesulfonamide,
N-Methyl-N-[2-({2-[4-(1-methyl-piperidin-4-yl)-phenylamino]-[1,2,4]triazolo[1,5-a]pyridin-8-ylamino}-methyl)-benzyl]-methanesulfonamide,
N(8)-(3-Methanesulfonyl-benzyl)-N(2)-[4-(4-methyl-piperazin-1-yl)-phenyl]-[1,2,4]triazolo[1,5-a]pyridine-2,8-diamine,
N(8)-(3-Methanesulfonyl-benzyl)-N(2)-[4-(1-methyl-piperidin-4-yl)-phenyl]-[1,2,4]triazolo[1,5-a]pyridine-2,8-diamine,
3-({2-[4-(4-Methyl-piperazin-1-yl)-phenylamino]-[1,2,4]triazolo[1,5-a]pyridin-8-ylamino}-methyl)-pyrrolidine-1-carboxylic acid tert-butyl ester,
N(8)-(2-Methanesulfonylmethyl-phenyl)-N(2)-[4-(4-methyl-piperazin-1-yl)-phenyl]-[1,2,4]triazolo[1,5-a]pyridine-2,8-diamine,
N(8)-(2-Methanesulfonylmethyl-phenyl)-N(2)-[4-(1-methyl-piperidin-4-yl)-phenyl]-[1,2,4]triazolo[1,5-a]pyridine-2,8-diamine,
N-Methyl-N-[3-({2-[4-(4-methyl-piperazin-1-yl)-phenylamino]-[1,2,4]triazolo[1,5-a]pyridin-8-ylamino}-methyl)-phenyl]-methanesulfonamide,
N(8)-(1-Methanesulfonyl-pyrrolidin-2-ylmethyl)-N(2)-[4-(4-methyl-piperazin-1-yl)-phenyl]-[1,2,4]triazolo[1,5-a]pyridine-2,8-diamine, N-Methyl-N-(2-{2-[4-(4-methyl-piperazin-1-yl)-phenylamino]-[1,2,4]triazolo[1,5-a]pyridin-8-ylamino}-benzyl)-methanesulfonamide,
N-Methyl-N-(2-{2-[4-(1-methyl-piperidin-4-yl)-phenylamino]-[1,2,4]triazolo[1,5-a]pyridin-8-ylamino}-benzyl)-methanesulfonamide,
N-Methyl-N-{2-[(methyl-{2-[4-(4-methyl-piperazin-1-yl)-phenylamino]-[1,2,4]triazolo[1,5-a]pyridin-8-yl}-amino)-methyl]-phenyl}-methanesulfonamide,
N-Methyl-N-[2-(1-{2-[4-(4-methyl-piperazin-1-yl)-phenylamino]-[1,2,4]triazolo[1,5-a]pyridin-8-ylamino}-ethyl)-phenyl]-methanesulfonamide,
N(8)-(2-Methoxy-benzyl)-N(2)-[4-(4-methyl-piperazin-1-yl)-phenyl]-[1,2,4]triazolo[1,5-a]pyridine-2,8-diamine,
N(8)-(3-Methoxy-benzyl)-N(2)-[4-(4-methyl-piperazin-1-yl)-phenyl]-[1,2,4]triazolo[1,5-a]pyridine-2,8-diamine, and N(8)-(4-Methoxy-benzyl)-N(2)-[4-(4-methyl-piperazin-1-yl)-phenyl]-[1,2,4]triazolo[1,5-a]pyridine-2,8-diamine.

In other specific embodiments, $T^4$ is —O—, $R^{5A}$, $R^{4A}$, $R^{3A}$, and $R^{12}$ are H, j is 0, and $R^{11}$ is a 6 membered heterocyclic ring which is optionally substituted with between one to four substituents. In other specific embodiments, $R^{11}$ is a 6 membered heterocyclic ring, in which at least one member is a nitrogen atom, optionally substituted as described above. In particular embodiments, a compound of the general Formula II, or a salt thereof, is selected from the following:
N-Methyl-N-(2-{2-[4-(4-methyl-piperazin-1-yl)-phenylamino]-[1,2,4]triazolo[1,5-a]pyridin-8-yloxymethyl}-phenyl)-methanesulfonamide, [8-(3-Chloro-benzyloxy)-[1,2,4]triazolo[1,5-a]pyridin-2-yl]-[4-(4-methyl-piperazin-1-yl)-phenyl]-amine, and 2-{2-[4-(4-Methyl-piperazin-1-yl)-phenylamino]-[1,2,4]triazolo[1,5-a]pyridin-8-yloxymethyl}-benzonitrile.

In yet other specific embodiments, $T^4$ is —S—, $R^{5A}$, $R^{4A}$, $R^{3A}$, and $R^{12}$ are H, j is 0, and $R^{11}$ is selected from a 6 membered heterocyclic ring, in which at least one member is a nitrogen atom, optionally substituted with between one to four substituents. In particular embodiments, a compound of the general Formula II, or a salt thereof, is 4-{4-[8-(4-Acetylamino-phenylsulfanyl)-[1,2,4]triazolo[1,5-a]pyridin-2-ylamino]-phenyl}-piperidine-1-carboxylic acid tert-butyl ester.

In further specific embodiments, $T^4$ is —CH═CH—, $R^{5A}$, $R^{4A}$, $R^{3A}$, $R^{12}$ are H, j is 0, and $R^{11}$ is selected from a 6 membered heterocyclic ring, in which at least one member is a nitrogen atom, optionally substituted with between one to four substituents. In particular embodiments, a compound of the general Formula II, or a salt thereof, is N-Methyl-N-[2-((E)-2-{2-[4-(4-methyl-piperazin-1-yl)-phenylamino]-[1,2,4]triazolo[1,5-a]pyridin-8-yl}-vinyl)-phenyl]-methanesulfonamide.

In further specific embodiments, $T^4$ is —C≡C—, $R^{5A}$, $R^{4A}$, $R^{3A}$, and $R^{12}$ are H, j is 0, and $R^{11}$ is selected from a 6 membered heterocyclic ring, in which at least one member is a nitrogen atom, optionally substituted with between one to four substituents. In particular embodiments, a compound of the general Formula II, or a salt thereof, is N-Methyl-N-(2-{2-[4-(4-methyl-piperazin-1-yl)-phenylamino]-[1,2,4]triazolo[1,5-a]pyridin-8-ylethynyl}-phenyl)-methanesulfonamide.

In still other specific embodiments, $R^{11}$ is selected from a 6 membered heterocyclic ring, in which at least one member is a nitrogen atom, optionally substituted with between one to four substituents, $T^4$ is a direct bond, $R^{5A}$, $R^{3a}$, and $R^{12}$ are H, j is 0, and $R^{4A}$ is halo(C1-C4)alkyl. In particular embodiments, a compound of Formula II, or a salt thereof, is selected from: [8-(4-Methanesulfonyl-phenyl)-6-trifluoromethyl-[1,2,4]triazolo[1,5-a]pyridin-2-yl]-[4-(4-methyl-piperazin-1-yl)-phenyl]-amine and [6-Fluoro-8-(4-methanesulfonyl-phenyl)-[1,2,4]triazolo[1,5-a]pyridin-2-yl]-[4-(4-methyl-piperazin-1-yl)-phenyl]-amine.

In another aspect, this application relates to compounds of the general Formula II, or salts thereof, wherein $R^{5A}$, $R^{4A}$, $R^{3a}$, and $R^{12}$ are H, j is 0, and $R^{11}$ is $(C_2-C_{14})$heterocycloalkyl $(C_1-C_4)$alkoxy that may be optionally substituted with between one to four substituents. In some specific embodiments, $T^4$ is a direct bond and $R^{11}$ is a 5 or 6 membered heterocycloalkyl$(C_1-C_4)$alkoxy group, in which at least one member (of the heterocycloalkyl portion) is a nitrogen atom, optionally substituted as described above. In other specific embodiments, $R^{11}$ is pyrrolyl-$(C_1-C_4)$alkoxy and morpholinyl-$(C_1-C_4)$alkoxy, either of which may be optionally substituted as described above. In particular embodiments, a compound of Formula II, or a salt thereof, is selected from:
[8-(4-Methanesulfonyl-phenyl)-[1,2,4]triazolo[1,5-a]pyridin-2-yl]-[4-(2-pyrrolidin-1-yl-ethoxy)-phenyl]-amine,
[8-(3-Methanesulfonyl-phenyl)-[1,2,4]triazolo[1,5-a]pyridin-2-yl]-[4-(2-pyrrolidin-1-yl-ethoxy)-phenyl]-amine,
(8-Pyridin-4-yl-[1,2,4]triazolo[1,5-a]pyridin-2-yl)-[4-(2-pyrrolidin-1-yl-ethoxy)-phenyl]-amine,
[8-(4-Methanesulfonyl-phenyl)-[1,2,4]triazolo[1,5-a]pyridin-2-yl]-[4-(2-morpholin-4-yl-ethoxy)-phenyl]-amine,
N-Methyl-N-(3-{2-[4-(2-pyrrolidin-1-yl-ethoxy)-phenylamino]-[1,2,4]triazolo[1,5-a]pyridin-8-yl}-phenyl)-methanesulfonamide,
N-Methyl-N-(3-{2-[4-(2-pyrrolidin-1-yl-ethoxy)-phenylamino]-[1,2,4]triazolo[1,5-a]pyridin-8-yl}-benzyl)-methanesulfonamide,
[8-(2-Methoxy-5-trifluoromethyl-phenyl)-[1,2,4]triazolo[1,5-a]pyridin-2-yl]-[4-(2-morpholin-4-yl-ethoxy)-phenyl]-amine, and
[8-(2-Methoxy-5-trifluoromethyl-phenyl)-[1,2,4]triazolo[1,5-a]pyridin-2-yl]-[4-(2-pyrrolidin-1-yl-ethoxy)-phenyl]-amine.

In other specific embodiments, $T^4$ is —$NR^{6A}$— and $R^{11}$ is a 5 or 6 membered heterocycloalkyl$(C_1-C_4)$alkoxy group, in which at least one member (of the heterocycloalkyl portion) is a nitrogen atom, optionally substituted as described above. In other specific embodiments, $R^{11}$ is pyrrolyl-$(C_1-C_4)$alkoxy which may be optionally substituted as described above. In particular embodiments, a compound of Formula II, or a salt thereof, is selected from:
N-Methyl-N-[3-({2-[4-(2-pyrrolidin-1-yl-ethoxy)-phenylamino]-[1,2,4]triazolo[1,5-a]pyridin-8-ylamino}-methyl)-pyridin-2-yl]-methanesulfonamide,
N(8)-(2-Methanesulfonyl-phenyl)-N(2)-[4-(2-pyrrolidin-1-yl-ethoxy)-phenyl]-[1,2,4]triazolo[1,5-a]pyridine-2,8-diamine,
N-Methyl-N-(3-{2-[4-(2-pyrrolidin-1-yl-ethoxy)-phenylamino]-[1,2,4]triazolo[1,5-a]pyridin-8-ylamino}-pyridin-2-yl)-methanesulfonamide,
N(8)-(2-Methanesulfonyl-benzyl)-N(2)-[4-(2-pyrrolidin-1-yl-ethoxy)-phenyl]-[1,2,4]triazolo[1,5-a]pyridine-2,8-diamine,
N-Methyl-N-[2-({2-[4-(2-pyrrolidin-1-yl-ethoxy)-phenylamino]-[1,2,4]triazolo[1,5-a]pyridin-8-ylamino}-methyl)-phenyl]-methanesulfonamide,
N(8)-Pyridin-3-ylmethyl-N(2)-[4-(2-pyrrolidin-1-yl-ethoxy)-phenyl]-[1,2,4]triazolo[1,5-a]pyridine-2,8-diamine,
N-Methyl-N-[2-({2-[4-(2-pyrrolidin-1-yl-ethoxy)-phenylamino]-[1,2,4]triazolo[1,5-a]pyridin-8-ylamino}-methyl)-benzyl]-methanesulfonamide, and N-Methyl-N-(2-{2-[4-(2-pyrrolidin-1-yl-ethoxy)-phenylamino]-[1,2,4]triazolo[1,5-a]pyridin-8-ylamino}-benzyl)-methanesulfonamide.

In another aspect, this application relates to compounds of Formula II, or salts thereof, wherein $R^{5A}$, $R^{4A}$, $R^{3a}$, and $R^{12}$ are H, j is 0, and $R^{11}$ is $(C_1-C_8)$alkoxy. In some specific embodiments, $T^A$ is a direct bond. In other specific embodiments, $T^A$ is —$NR^{6A}$—.

In some particular embodiments, a compound of Formula II, or a salt thereof, is selected from the following:

[8-(4-Methanesulfonyl-phenyl)-[1,2,4]triazolo[1,5-a]pyridin-2-yl]-(4-methoxy-phenyl)-amine, (4-Methoxy-phenyl)-[8-(4-methyl-piperazin-1-yl)-[1,2,4]triazolo[1,5-a]pyridin-2-yl]-amine, 8-(1,1-dioxidothiomorpholin-4-yl)-N-(4-methoxyphenyl)[1,2,4]triazolo[1,5-a]pyridin-2-amine,

[8-(4-Methanesulfonyl-piperazin-1-yl)-[1,2,4]triazolo[1,5-a]pyridin-2-yl]-(4-methoxy-phenyl)-amine,

[8-(1-Methanesulfonyl-1,2,3,6-tetrahydro-pyridin-4-yl)-[1,2,4]triazolo[1,5-a]pyridin-2-yl]-(4-methoxy-phenyl)-amine, (4-Methoxy-phenyl)-[8-(1H-pyrazol-4-yl)-[1,2,4]triazolo[1,5-a]pyridin-2-yl]-amine, and

[8-(1-Methanesulfonyl-1H-pyrazol-4-yl)-[1,2,4]triazolo[1,5-a]pyridin-2-yl]-(4-methoxy-phenyl)-amine In other particular embodiments, a compound of Formula II, or a salt thereof, is selected from the following:

N(8)-(4-Methanesulfonyl-phenyl)-N(2)-(4-methoxy-phenyl)-[1,2,4]triazolo[1,5-a]pyridine-2,8-diamine, N(8)-(1-Methanesulfonyl-piperidin-4-yl)-N(2)-(4-methoxy-phenyl)-[1,2,4]triazolo[1,5-a]pyridine-2,8-diamine, and N(8)-(2-Methanesulfonyl-phenyl)-N(2)-(4-methoxy-phenyl)-[1,2,4]triazolo[1,5-a]pyridine-2,8-diamine In another aspect, this application relates to compounds of Formula II, or salts thereof, wherein $R^{5A}$, $R^{4A}$, and $R^{3A}$ are H, and $R^{11}$ and $R^{12}$ are taken together to form a five to ten membered heterocyclic ring optionally substituted with between one to four substituents. In some specific embodiments, $T^A$ is a direct bond, and $R^{11}$ and $R^{12}$ are taken together to form a five to seven membered heterocyclic ring, in which at least one member is a nitrogen atom, optionally substituted with between one to four substituents. In other specific embodiments, $T^A$ is —$NR^{6A}$— and $R^{11}$ and $R^{12}$ are taken together to form a five to seven membered heterocyclic ring, in which at least one member is a nitrogen atom, optionally substituted with between one to four substituents. In other specific embodiments, $T^A$ is —C≡C— and $R^{11}$ and $R^{12}$ are taken together to form a five to seven membered heterocyclic ring, in which at least one member is a nitrogen atom, optionally substituted with between one to four substituents. In further specific embodiments, $R^{11}$ and $R^{12}$ are taken together with the atoms to which they are attached to form dihydroisoindolyl, dihydro-isoquinolinyl, and tetrahydro-benzo[d]azepinyl moiety, any of which may be optionally substituted as described above. In particular embodiments, a compound of Formula II, or a salt thereof, is selected from:

[8-(4-Methanesulfonyl-phenyl)-[1,2,4]triazolo[1,5-a]pyridin-2-yl]-(2-methyl-2,3-dihydro-1H-isoindol-5-yl)-amine, 7-[8-(2-Methoxymethyl-phenyl)-[1,2,4]triazolo[1,5-a]pyridin-2-ylamino]-1,2,4,5-tetrahydro-benzo[d]azepine-3-carboxylic acid tert-butyl ester,

[8-(2-Methoxymethyl-phenyl)-[1,2,4]triazolo[1,5-a]pyridin-2-yl]-(2,3,4,5-tetrahydro-1H-benzo[d]azepin-7-yl)-amine, 7-[8-(2,2-Difluoro-benzo[1,3]dioxol-4-yl)-[1,2,4]triazolo[1,5-a]pyridin-2-ylamino]-1,2,4,5-tetrahydro-benzo[d]azepine-3-carboxylic acid tert-butyl ester,

[8-(2,2-Difluoro-benzo[1,3]dioxol-4-yl)-[1,2,4]triazolo[1,5-a]pyridin-2-yl]-(2,3,4,5-tetrahydro-1H-benzo[d]azepin-7-yl)-amine,

[3-(2-Methanesulfonyl-ethyl)-2,3,4,5-tetrahydro-1H-benzo[d]azepin-7-yl]-[8-(2-methoxymethyl-phenyl)-[1,2,4]triazolo[1,5-a]pyridin-2-yl]-amine, 2-{7-[8-(2-Methoxymethyl-phenyl)-[1,2,4]triazolo[1,5-a]pyridin-2-ylamino]-1,2,4,5-tetrahydro-benzo[d]azepin-3-yl}-N,N-dimethyl-acetamide,

[8-(2,2-Difluoro-benzo[1,3]dioxol-4-yl)-[1,2,4]triazolo[1,5-a]pyridin-2-yl]-[3-(2-methanesulfonyl-ethyl)-2,3,4,5-tetrahydro-1H-benzo[d]azepin-7-yl]-amine, 2-{7-[8-(2,2-Difluoro-benzo[1,3]dioxol-4-yl)-[1,2,4]triazolo[1,5-a]pyridin-2-ylamino]-1,2,4,5-tetrahydro-benzo[d]azepin-3-yl}-N,N-dimethyl-acetamide,

[8-(2-Chloro-5-trifluoromethyl-phenyl)-[1,2,4]triazolo[1,5-a]pyridin-2-yl]-[3-(2-methanesulfonyl-ethyl)-2,3,4,5-tetrahydro-1H-benzo[d]azepin-7-yl]-amine, 7-[8-(2-Fluoro-5-trifluoromethyl-phenyl)-[1,2,4]triazolo[1,5-a]pyridin-2-ylamino]-1,2,4,5-tetrahydro-benzo[d]azepine-3-carboxylic acid tert-butyl ester,

[8-(2-Fluoro-5-trifluoromethyl-phenyl)-[1,2,4]triazolo[1,5-a]pyridin-2-yl]-(2,3,4,5-tetrahydro-1H-benzo[d]azepin-7-yl)-amine, 7-[8-(2-Isobutoxy-phenyl)-[1,2,4]triazolo[1,5-a]pyridin-2-ylamino]-1,2,4,5-tetrahydro-benzo[d]azepine-3-carboxylic acid tert-butyl ester,

[8-(2-Isobutoxy-phenyl)-[1,2,4]triazolo[1,5-a]pyridin-2-yl]-(2,3,4,5-tetrahydro-1H-benzo[d]azepin-7-yl)-amine, 7-[8-(3-Isobutoxy-phenyl)-[1,2,4]triazolo[1,5-a]pyridin-2-ylamino]-1,2,4,5-tetrahydro-benzo[d]azepine-3-carboxylic acid tert-butyl ester,

[8-(3-Isobutoxy-phenyl)-[1,2,4]triazolo[1,5-a]pyridin-2-yl]-(2,3,4,5-tetrahydro-1H-benzo[d]azepin-7-yl)-amine, 7-[8-(2-Isobutoxy-4-methyl-phenyl)-[1,2,4]triazolo[1,5-a]pyridin-2-ylamino]-1,2,4,5-tetrahydro-benzo[d]azepine-3-carboxylic acid tert-butyl ester,

[8-(2-Isobutoxy-4-methyl-phenyl)-[1,2,4]triazolo[1,5-a]pyridin-2-yl]-(2,3,4,5-tetrahydro-1H-benzo[d]azepin-7-yl)-amine, 7-[8-(1-Methyl-1H-indazol-4-yl)-[1,2,4]triazolo[1,5-a]pyridin-2-ylamino]-1,2,4,5-tetrahydro-benzo[d]azepine-3-carboxylic acid tert-butyl ester,

[8-(1-Methyl-1H-indazol-4-yl)-[1,2,4]triazolo[1,5-a]pyridin-2-yl]-(2,3,4,5-tetrahydro-1H-benzo[d]azepin-7-yl)-amine,

[8-(2-Isopropoxy-phenyl)-[1,2,4]triazolo[1,5-a]pyridin-2-yl]-(2,3,4,5-tetrahydro-1H-benzo[d]azepin-7-yl)-amine,

[8-(2-Ethoxy-phenyl)-[1,2,4]triazolo[1,5-a]pyridin-2-yl]-(2,3,4,5-tetrahydro-1H-benzo[d]azepin-7-yl)-amine,

[8-(2-Cyclopropylmethoxy-phenyl)-[1,2,4]triazolo[1,5-a]pyridin-2-yl]-(2,3,4,5-tetrahydro-1H-benzo[d]azepin-7-yl)-amine, 7-[8-(2-Isopropoxy-phenyl)-[1,2,4]triazolo[1,5-a]pyridin-2-ylamino]-1,2,4,5-tetrahydro-benzo[d]azepine-3-carboxylic acid tert-butyl ester, 7-[8-(2-Ethoxy-phenyl)-[1,2,4]triazolo[1,5-a]pyridin-2-ylamino]-1,2,4,5-tetrahydro-benzo[d]azepine-3-carboxylic acid tert-butyl ester, 7-[8-(2-Cyclopropylmethoxy-phenyl)-[1,2,4]triazolo[1,5-a]pyridin-2-ylamino]-1,2,4,5-tetrahydro-benzo[d]azepine-3-carboxylic acid tert-butyl ester,

[8-(2-Isobutoxy-5-methyl-phenyl)-[1,2,4]triazolo[1,5-a]pyridin-2-yl]-(2,3,4,5-tetrahydro-1H-benzo[d]azepin-7-yl)-amine,
7-[8-(5-Chloro-2-propoxy-phenyl)-[1,2,4]triazolo[1,5-a]pyridin-2-ylamino]-1,2,4,5-tetrahydro-benzo[d]azepine-3-carboxylic acid tert-butyl ester,
[8-(5-Chloro-2-propoxy-phenyl)-[1,2,4]triazolo[1,5-a]pyridin-2-yl]-(2,3,4,5-tetrahydro-1H-benzo[d]azepin-7-yl)-amine,
2-{7-[8-(5-Chloro-2-propoxy-phenyl)-[1,2,4]triazolo[1,5-a]pyridin-2-ylamino]-1,2,4,5-tetrahydro-benzo[d]azepin-3-yl}-N,N-dimethyl-acetamide,
7-[8-(5-Chloro-2-ethoxy-phenyl)-[1,2,4]triazolo[1,5-a]pyridin-2-ylamino]-1,2,4,5-tetrahydro-benzo[d]azepine-3-carboxylic acid tert-butyl ester,
[8-(5-Chloro-2-ethoxy-phenyl)-[1,2,4]triazolo[1,5-a]pyridin-2-yl]-(2,3,4,5-tetrahydro-1H-benzo[d]azepin-7-yl)-amine,
7-[8-(2-Methoxy-phenyl)-[1,2,4]triazolo[1,5-a]pyridin-2-ylamino]-1,2,4,5-tetrahydro-benzo[d]azepine-3-carboxylic acid tert-butyl ester,
[8-(2-Methoxy-phenyl)-[1,2,4]triazolo[1,5-a]pyridin-2-yl]-(2,3,4,5-tetrahydro-1H-benzo[d]azepin-7-yl)-amine,
2-{7-[8-(2-Methoxy-phenyl)-[1,2,4]triazolo[1,5-a]pyridin-2-ylamino]-1,2,4,5-tetrahydro-benzo[d]azepin-3-yl}-N,N-dimethyl-acetamide,
[3-(2-Methanesulfonyl-ethyl)-2,3,4,5-tetrahydro-1H-benzo[d]azepin-7-yl]-[8-(2-methoxy-phenyl)-[1,2,4]triazolo[1,5-a]pyridin-2-yl]-amine,
7-[8-(2-Methoxy-5-trifluoromethyl-phenyl)-[1,2,4]triazolo[1,5-a]pyridin-2-ylamino]-1,2,4,5-tetrahydro-benzo[d]azepine-3-carboxylic acid tert-butyl ester,
[8-(2-Methoxy-5-trifluoromethyl-phenyl)-[1,2,4]triazolo[1,5-a]pyridin-2-yl]-(2,3,4,5-tetrahydro-1H-benzo[d]azepin-7-yl)-amine,
2-{7-[8-(2-Methoxy-5-trifluoromethyl-phenyl)-[1,2,4]triazolo[1,5-a]pyridin-2-ylamino]-1,2,4,5-tetrahydro-benzo[d]azepin-3-yl}-N,N-dimethyl-acetamide,
7-[8-(2-Ethoxy-5-trifluoromethyl-phenyl)-[1,2,4]triazolo[1,5-a]pyridin-2-ylamino]-1,2,4,5-tetrahydro-benzo[d]azepine-3-carboxylic acid tert-butyl ester,
[8-(2-Ethoxy-5-trifluoromethyl-phenyl)-[1,2,4]triazolo[1,5-a]pyridin-2-yl]-(2,3,4,5-tetrahydro-1H-benzo[d]azepin-7-yl)-amine,
[8-(2-Ethoxy-5-trifluoromethyl-phenyl)-[1,2,4]triazolo[1,5-a]pyridin-2-yl]-[3-(2-methanesulfonyl-ethyl)-2,3,4,5-tetrahydro-1H-benzo[d]azepin-7-yl]-amine,
2-{7-[8-(2-Ethoxy-5-trifluoromethyl-phenyl)-[1,2,4]triazolo[1,5-a]pyridin-2-ylamino]-1,2,4,5-tetrahydro-benzo[d]azepin-3-yl}-N,N-dimethyl-acetamide,
[3-(2-Methanesulfonyl-ethyl)-2,3,4,5-tetrahydro-1H-benzo[d]azepin-7-yl]-[8-(2-methoxy-5-trifluoromethyl-phenyl)-[1,2,4]triazolo[1,5-a]pyridin-2-yl]-amine,
2-{7-[8-(5-Fluoro-2-methoxy-phenyl)-[1,2,4]triazolo[1,5-a]pyridin-2-ylamino]-1,2,4,5-tetrahydro-benzo[d]azepin-3-yl}-N,N-dimethyl-acetamide,
2-{7-[8-(4-Fluoro-2-methoxy-phenyl)-[1,2,4]triazolo[1,5-a]pyridin-2-ylamino]-1,2,4,5-tetrahydro-benzo[d]azepin-3-yl}-N,N-dimethyl-acetamide,
2-{7-[8-(4-Chloro-2-methoxy-phenyl)-[1,2,4]triazolo[1,5-a]pyridin-2-ylamino]-1,2,4,5-tetrahydro-benzo[d]azepin-3-yl}-N,N-dimethyl-acetamide,
2-{7-[8-(2-Isopropoxy-5-trifluoromethyl-phenyl)-[1,2,4]triazolo[1,5-a]pyridin-2-ylamino]-1,2,4,5-tetrahydro-benzo[d]azepin-3-yl}-N,N-dimethyl-acetamide,
{8-[2-(2,2-Difluoro-ethoxy)-5-trifluoromethyl-phenyl]-[1,2,4]triazolo[1,5-a]pyridin-2-yl}-(2,3,4,5-tetrahydro-1H-benzo[d]azepin-7-yl)-amine,
2-(7-{8-[2-(2,2-Difluoro-ethoxy)-5-trifluoromethyl-phenyl]-[1,2,4]triazolo[1,5-a]pyridin-2-ylamino}-1,2,4,5-tetrahydro-benzo[d]azepin-3-yl)-N,N-dimethyl-acetamide,
6-[8-(2-Methoxy-5-trifluoromethyl-phenyl)-[1,2,4]triazolo[1,5-a]pyridin-2-ylamino]-3,4-dihydro-1H-isoquinoline-2-carboxylic acid tert-butyl ester,
[8-(2-Methoxy-5-trifluoromethyl-phenyl)-[1,2,4]triazolo[1,5-a]pyridin-2-yl]-(1,2,3,4-tetrahydro-isoquinolin-6-yl)-amine,
2-{6-[8-(2-Methoxy-5-trifluoromethyl-phenyl)-[1,2,4]triazolo[1,5-a]pyridin-2-ylamino]-3,4-dihydro-1H-isoquinolin-2-yl}-N,N-dimethyl-acetamide,
2-{6-[8-(4-Chloro-2-methoxy-phenyl)-[1,2,4]triazolo[1,5-a]pyridin-2-ylamino]-3,4-dihydro-1H-isoquinolin-2-yl}-N,N-dimethyl-acetamide,
(2,3-Dihydro-1H-isoindol-5-yl)-[8-(3-methoxy-phenyl)-[1,2,4]triazolo[1,5-a]pyridin-2-yl]-amine,
7-{8-[2-(2,2-Difluoro-ethoxy)-phenyl]-[1,2,4]triazolo[1,5-a]pyridin-2-ylamino}-1,2,4,5-tetrahydro-benzo[d]azepine-3-carboxylic acid tert-butyl ester,
{8-[2-(2,2-Difluoro-ethoxy)-phenyl]-[1,2,4]triazolo[1,5-a]pyridin-2-yl}-(2,3,4,5-tetrahydro-1H-benzo[d]azepin-7-yl)-amine,
2-(7-{8-[2-(2,2-Difluoro-ethoxy)-phenyl]-[1,2,4]triazolo[1,5-a]pyridin-2-ylamino}-1,2,4,5-tetrahydro-benzo[d]azepin-3-yl)-N,N-dimethyl-acetamide,
7-{8-[2-(2,2-Difluoro-ethoxy)-4-methanesulfonyl-phenyl]-2,3-dihydro-[1,2,4]triazolo[1,5-a]pyridin-2-ylamino}-1,2,4,5-tetrahydro-benzo[d]azepine-3-carboxylic acid tert-butyl ester,
{8-[2-(2,2-Difluoro-ethoxy)-4-methanesulfonyl-phenyl]-[1,2,4]triazolo[1,5-a]pyridin-2-yl}-(2,3,4,5-tetrahydro-1H-benzo[d]azepin-7-yl)-amine,
7-{8-[2-(2,2-Difluoro-ethoxy)-5-methanesulfonyl-phenyl]-[1,2,4]triazolo[1,5-a]pyridin-2-ylamino}-1,2,4,5-tetrahydro-benzo[d]azepine-3-carboxylic acid tert-butyl ester,
{8-[2-(2,2-Difluoro-ethoxy)-5-methanesulfonyl-phenyl]-[1,2,4]triazolo[1,5-a]pyridin-2-yl}-(2,3,4,5-tetrahydro-1H-benzo[d]azepin-7-yl)-amine,
2-(7-{8-[2-(2,2-Difluoro-ethoxy)-5-methanesulfonyl-phenyl]-[1,2,4]triazolo[1,5-a]pyridin-2-ylamino}-1,2,4,5-tetrahydro-benzo[d]azepin-3-yl)-N,N-dimethyl-acetamide,
7-[8-(3-Trifluoromethyl-phenyl)-[1,2,4]triazolo[1,5-a]pyridin-2-ylamino]-1,2,4,5-tetrahydro-benzo[d]azepine-3-carboxylic acid tert-butyl ester,
(2,3,4,5-Tetrahydro-1H-benzo[d]azepin-7-yl)-[8-(3-trifluoromethyl-phenyl)-[1,2,4]triazolo[1,5-a]pyridin-2-yl]-amine,
7-{8-[5-Chloro-2-(2,2-difluoro-ethoxy)-phenyl]-[1,2,4]triazolo[1,5-a]pyridin-2-ylamino}-1,2,4,5-tetrahydro-benzo[d]azepine-3-carboxylic acid tert-butyl ester,
{8-[5-Chloro-2-(2,2-difluoro-ethoxy)-phenyl]-[1,2,4]triazolo[1,5-a]pyridin-2-yl}-(2,3,4,5-tetrahydro-1H-benzo[d]azepin-7-yl)-amine,
2-(7-{8-[2-(2,2-Difluoro-ethoxy)-5-fluoro-phenyl]-[1,2,4]triazolo[1,5-a]pyridin-2-ylamino}-1,2,4,5-tetrahydro-benzo[d]azepin-3-yl)-N,N-dimethyl-acetamide,
[8-(2-Isobutoxy-5-trifluoromethyl-phenyl)-[1,2,4]triazolo[1,5-a]pyridin-2-yl]-(2,3,4,5-tetrahydro-1H-benzo[d]azepin-7-yl)-amine,
2-{7-[8-(2-Isobutoxy-5-trifluoromethyl-phenyl)-[1,2,4]triazolo[1,5-a]pyridin-2-ylamino]-1,2,4,5-tetrahydro-benzo[d]azepin-3-yl}-N,N-dimethyl-acetamide, 2-(7-{8-[5-Chloro-2-(2,2-difluoro-ethoxy)-phenyl]-[1,2,4]triazolo[1,5-a]pyridin-2-ylamino}-1,2,4,5-tetrahydro-benzo[d]azepin-3-yl)-N,N-dimethyl-acetamide, 7-{8-[5-Chloro-2-(2,2-difluoro-ethoxy)-phenyl]-[1,2,4]triazolo[1,5-a]pyridin-2-ylamino}-1,2,4,5-tetrahydro-benzo[d]azepine-3-carboxylic acid dimethylamide, 7-{8-[2-(2,2-Difluoro-ethoxy)-5-difluoromethyl-phenyl]-[1,2,4]triazolo[1,5-a]pyridin-2-ylamino}-1,2,4,5-tetrahydro-benzo[d]azepine-3-carboxylic acid tert-butyl ester, {8-[2-(2,2-Difluoro-ethoxy)-5-difluoromethyl-phenyl]-[1,2,4]triazolo[1,5-a]pyridin-2-yl}-(2,3,4,5-tetrahydro-1H-benzo[d]azepin-7-yl)-amine, and 2-(7-{8-[2-(2,2-Difluoro-ethoxy)-5-difluoromethyl-phenyl]-[1,2,4]triazolo[1,5-a]pyridin-2-ylamino}-1,2,4,5-tetrahydro-benzo[d]azepin-3-yl)-N,N-dimethyl-acetamide.

In other particular embodiments, a compound of Formula II, or a salt thereof, is selected from: N-Methyl-N-(3-{[2-(2-methyl-2,3-dihydro-1H-isoindol-5-ylamino)-[1,2,4]triazolo[1,5-a]pyridin-8-ylamino]-methyl}-pyridin-2-yl)-methanesulfonamide and N-Methyl-N-(2-{[2-(2-methyl-2,3-dihydro-1H-isoindol-5-ylamino)-[1,2,4]triazolo[1,5-a]pyridin-8-ylamino]-methyl}-phenyl)-methanesulfonamide.

In still other particular embodiments, compound of Formula II, or a salt thereof, is N-Methyl-N-{2-[2-(2-methyl-2,3-dihydro-1H-isoindol-5-ylamino)-[1,2,4]triazolo[1,5-a]pyridin-8-ylethynyl]-phenyl}-methanesulfonamide.

In another aspect, this application relates to compounds of Formula II, or salts thereof, wherein $R^{11}$ and $R^{12}$ are taken together to form a five to ten membered carbocyclic ring optionally substituted with between one to four substituents. In some specific embodiments, $R^{5A}$, $R^{4A}$, and $R^{3A}$ are H, and $R^{11}$ and $R^{12}$ are taken together to form a six or seven membered carbocyclic ring optionally substituted with between one to four substituents. In some specific embodiments, $T^A$ is a direct bond. In other specific embodiments, $T^A$ is $-NR^{6A}-$.

In some particular embodiments, a compound of Formula II, or a salt thereof, is selected from the following: [8-(4-Methanesulfonyl-phenyl)-[1,2,4]triazolo[1,5-a]pyridin-2-yl]-(5,5,8,8-tetramethyl-5,6,7,8-tetrahydro-naphthalen-2-yl)-amine and [8-(4-Methanesulfonyl-phenyl)-[1,2,4]triazolo[1,5-a]pyridin-2-yl]-(7-morpholin-4-yl-6,7,8,9-tetrahydro-5H-benzocyclohepten-2-yl)-amine In other particular embodiments, a compound of Formula II, or a salt thereof, is N-Methyl-N-(2-{[2-(7-morpholin-4-yl-6,7,8,9-tetrahydro-5H-benzocyclohepten-2-ylamino)-[1,2,4]triazolo[1,5-a]pyridin-8-ylamino]-methyl}-phenyl)-methanesulfonamide.

In another aspect, this application relates to compounds of Formula II, or salts thereof, wherein $R^{11}$ and $R^{12}$ are taken together to form a six membered heteroaromatic ring optionally substituted with between one to four substituents. In some specific embodiments, $R^{5A}$, $R^{4A}$, and $R^{3A}$ are H, and $R^{11}$ and $R^{12}$ are taken together to form a six membered heteroaromatic ring, in which at least member is a nitrogen atom, that may be optionally substituted as described above. In some specific embodiments, $R^{11}$ and $R^{12}$ are taken together with the atoms to which they are attached to form isoquinolinyl or quinolinyl, either of which may be optionally substituted as described above. In particular embodiments, a compound of Formula II, or a salt thereof, is selected from: N-(2-{[2-(Isoquinolin-6-ylamino)-[1,2,4]triazolo[1,5-a]pyridin-8-ylamino]-methyl}-phenyl)-N-methyl-methanesulfonamide, [8-(2-Methoxy-pyridin-3-yl)-[1,2,4]triazolo[1,5-a]pyridin-2-yl]-quinolin-6-yl-amine, and 3-[2-(Quinolin-6-ylamino)-[1,2,4]triazolo[1,5-a]pyridin-8-yl]-1H-pyridin-2-one.

In another aspect, this application relates to compounds of Formula II, or salts thereof, wherein $R^{11}$ is H, h is 0, and $R^{12}$ is selected from $SO_2(C_1-C_8)$alkyl, $(C_2-C_8)$alkyl, $(C_1-C_8)$alkoxy, halo$(C_2-C_4)$alkyl, halo$(C_1-C_4)$alkoxy, $(C_3-C_{14})$cycloalkyl, $(C_3-C_{14})$cycloalkyloxy, $(C_3-C_{14})$cycloalkyl$(C_1-C_4)$alkyl, $(C_3-C_{14})$cycloalkyl$(C_1-C_4)$alkoxy, $(C_6-C_{10})$aryl, $(C_6-C_{10})$aryloxy, $(C_6-C_{10})$aryl$(C_1-C_4)$alkyl, $(C_6-C_{10})$aryl$(C_1-C_4)$alkoxy, $(C_2-C_{14})$heterocycloalkyl, $(C_2-C_{14})$heterocycloalkyloxy, $(C_2-C_{14})$heterocycloalkyl$(C_1-C_4)$alkyl, $(C_2-C_{14})$heterocycloalkyl$(C_1-C_4)$alkoxy, $(C_2-C_9)$heteroaryl, $(C_2-C_9)$heteroaryloxy, $(C_2-C_9)$heteroaryl$(C_1-C_4)$alkyl, and $(C_2-C_9)$heteroaryl$(C_1-C_4)$alkoxy, wherein each of the aforementioned groups, except for H, may be optionally substituted with between one to four substituents.

In another aspect, this application relates to compounds of Formula II, or salts thereof, wherein, $R^{5A}$, $R^{4A}$, and $R^{3A}$ are H, $R^{11}$ is H, h is 0, and $R^{12}$ is as defined above. In some specific embodiments $R^{5A}$, $R^{4A}$, and $R^{3A}$ are H $R^{11}$ is H, h is 0, and $T^A$ is a direct bond. In further specific embodiments, $R^{5A}$, $R^{4A}$, and $R^{3A}$ are H, $R^{11}$ is H, h is 0, and $T^A$ is $-O-$. In still further specific embodiments, $R^{5A}$, $R^{4A}$, and $R^{3A}$ are H, $R^{11}$ is H, h is 0, and $T^A$ is $-NR^{6A}-$. In yet further specific embodiments, $R^{5A}$, $R^{4A}$, and $R^{3A}$ are H, $R^{11}$ is H, h is 0, and $T^A$ is $-C\equiv C-$. In still further specific embodiments, $T^A$ is a direct bond, $R^{5A}$ and $R^{3A}$ are H, $R^{11}$ is H, h is 0, and $R^{4A}$ is halo$(C_1-C_4)$alkyl.

In another aspect, this application relates to compounds of Formula II, or salts thereof, wherein $R^{5A}$, $R^{4A}$, and $R^{3A}$ are H, $R^{11}$ is H, h is 0, $T^A$ is a direct bond and $R^{12}$ is a 6 membered heterocycloalkyl, in which at least one member is a nitrogen atom, optionally substituted with between one to four substituents. In some specific embodiments, $R^{12}$ is selected from optionally substituted piperidinyl. In other specific embodiments $R^{12}$ is optionally substituted piperazinyl. In still other specific embodiments, $R^{12}$ is optionally substituted morpholinyl. In further specific embodiments, $R^{12}$ is optionally substituted thiomorpholinyl. In particular embodiments, a compound of Formula II, or a salt thereof, is selected from the following:

4-{3-[8-(4-Methanesulfonyl-phenyl)-[1,2,4]triazolo[1,5-a]pyridin-2-ylamino]-phenyl}-piperidine-1-carboxylic acid tert-butyl ester,

[8-(4-Methanesulfonyl-phenyl)-[1,2,4]triazolo[1,5-a]pyridin-2-yl]-[3-(4-morpholin-4-yl-piperidin-1-yl)-phenyl]-amine,

[8-(4-Methanesulfonyl-phenyl)-[1,2,4]triazolo[1,5-a]pyridin-2-yl]-(3-piperidin-4-yl-phenyl)-amine,

[8-(4-Methanesulfonyl-phenyl)-[1,2,4]triazolo[1,5-a]pyridin-2-yl]-[3-(1-methyl-piperidin-4-yl)-phenyl]-amine, {3-[1-(2-Methanesulfonyl-ethyl)-piperidin-4-yl]-phenyl}-[8-(4-methanesulfonyl-phenyl)-[1,2,4]triazolo[1,5-a]pyridin-2-yl]-amine,

[8-(4-Methanesulfonyl-phenyl)-[1,2,4]triazolo[1,5-a]pyridin-2-yl]-{3-[4-(4-methyl-piperazin-1-yl)-piperidin-1-yl]-phenyl}-amine, (±)-cis-3-Hydroxy-4-{3-[8-(4-methanesulfonyl-phenyl)-[1,2,4]triazolo[1,5-a]pyridin-2-ylamino]-phenyl}-piperidine-1-carboxylic acid tert-butyl ester, 2-(4-{3-[8-(4-Methanesulfonyl-phenyl)-[1,2,4]triazolo[1,5-a]pyridin-2-ylamino]-phenyl}-piperidin-1-yl)-acetamide, (±)-(cis)-4-{3-[8-(4-Methanesulfonyl-phenyl)-[1,2,4]triazolo[1,5-a]pyridin-2-ylamino]-phenyl}-piperidin-3-ol,

[8-(2-Methoxy-5-trifluoromethyl-phenyl)-[1,2,4]triazolo[1,5-a]pyridin-2-yl]-(3-piperidin-4-yl-phenyl)-amine, (±)-2-(cis)-3-Hydroxy-4-{3-[8-(4-methanesulfonyl-phenyl)-[1,2,4]triazolo[1,5-a]pyridin-2-ylamino]-phenyl}-piperidin-1-yl)-acetamide, N-Methyl-N-(3-{2-[3-(1-methyl-piperidin-4-yl)-phenylamino]-[1,2,4]triazolo[1,5-a]pyridin-8-yl}-phenyl)-methanesulfonamide,
2-(4-{3-[8-(2-Methoxy-5-trifluoromethyl-phenyl)-[1,2,4]triazolo[1,5-a]pyridin-2-ylamino]-phenyl}-piperidin-1-yl)-N,N-dimethyl-acetamide,
2-(4-{3-[8-(4-Chloro-2-methoxy-phenyl)-[1,2,4]triazolo[1,5-a]pyridin-2-ylamino]-phenyl}-piperidin-1-yl)-N,N-dimethyl-acetamide,
4-{3-[8-(2-Methoxy-5-trifluoromethyl-phenyl)-[1,2,4]triazolo[1,5-a]pyridin-2-ylamino]-phenyl}-piperidine-1-carboxylic acid tert-butyl ester,
N-Methyl-N-(2-{2-[3-(1-methyl-piperidin-4-yl)-phenylamino]-[1,2,4]triazolo[1,5-a]pyridin-8-yl}-phenyl)-methanesulfonamide, and
{8-[4-(Dimethyl-phosphinoyl)-phenyl]-[1,2,4]triazolo[1,5-a]pyridin-2-yl}-{3-[1-(2-methanesulfonyl-ethyl)-piperidin-4-yl]-phenyl}-amine In other particular embodiments, a compound of Formula II, or a salt thereof, is selected from the following:
{8-[4-(Dimethyl-phosphinoyl)-phenyl]-[1,2,4]triazolo[1,5-a]pyridin-2-yl}-[3-(4-methyl-piperazin-1-yl)-phenyl]-amine,
(S)-1-(4-{3-[8-(4-Methanesulfonyl-phenyl)-[1,2,4]triazolo[1,5-a]pyridin-2-ylamino]-phenyl}-piperazin-1-yl)-propan-2-ol,
[8-(4-Methanesulfonyl-phenyl)-[1,2,4]triazolo[1,5-a]pyridin-2-yl]-[3-(4-methyl-piperazin-1-yl)-phenyl]-amine,
4-{3-[8-(4-Methanesulfonyl-phenyl)-[1,2,4]triazolo[1,5-a]pyridin-2-ylamino]-phenyl}-piperazine-1-carboxylic acid tert-butyl ester,
2-(4-{3-[8-(4-Methanesulfonyl-phenyl)-[1,2,4]triazolo[1,5-a]pyridin-2-ylamino]-phenyl}-piperazin-1-yl)-ethanol,
[3-(4-Methyl-piperazin-1-yl)-phenyl]-[8-(4-trifluoromethyl-phenyl)-[1,2,4]triazolo[1,5-a]pyridin-2-yl]-amine,
[8-(4-Methanesulfonyl-phenyl)-[1,2,4]triazolo[1,5-a]pyridin-2-yl]-(3-piperazin-1-yl-phenyl)-amine,
[8-(4-Methanesulfonyl-phenyl)-[1,2,4]triazolo[1,5-a]pyridin-2-yl]-[3-(4-methyl-piperazin-1-ylmethyl)-phenyl]-amine,
(R)-1-(4-{3-[8-(4-Methanesulfonyl-phenyl)-[1,2,4]triazolo[1,5-a]pyridin-2-ylamino]-phenyl}-piperazin-1-yl)-propan-2-ol,
2-(4-{3-[8-(4-Methanesulfonyl-phenyl)-[1,2,4]triazolo[1,5-a]pyridin-2-ylamino]-phenyl}-piperazin-1-yl)-acetamide,
1-(4-{3-[8-(4-Methanesulfonyl-phenyl)-[1,2,4]triazolo[1,5-a]pyridin-2-ylamino]-phenyl}-piperazin-1-yl)-2-methyl-propan-2-ol,
N-Methyl-N-(3-{2-[3-(4-methyl-piperazin-1-yl)-phenylamino]-[1,2,4]triazolo[1,5-a]pyridin-8-yl}-benzyl)-methanesulfonamide,
N-Methyl-N-(4-{2-[3-(4-methyl-piperazin-1-yl)-phenylamino]-[1,2,4]triazolo[1,5-a]pyridin-8-yl}-phenyl)-methanesulfonamide,
{3-[4-(3-Fluoro-propyl)-piperazin-1-yl]-phenyl}-[8-(4-methanesulfonyl-phenyl)-[1,2,4]triazolo[1,5-a]pyridin-2-yl]-amine,
[8-(3-Methanesulfonyl-phenyl)-[1,2,4]triazolo[1,5-a]pyridin-2-yl]-[3-(4-methyl-piperazin-1-yl)-phenyl]-amine,
[3-(4-Methyl-piperazin-1-yl)-phenyl]-{8-[4-(propane-2-sulfonyl)-phenyl]-[1,2,4]triazolo[1,5-a]pyridin-2-yl]-amine,
[8-(2-Methoxy-5-trifluoromethyl-phenyl)-[1,2,4]triazolo[1,5-a]pyridin-2-yl]-[3-(4-methyl-piperazin-1-yl)-phenyl]-amine,
[8-(4-Fluoro-phenyl)-[1,2,4]triazolo[1,5-a]pyridin-2-yl]-[3-(4-methyl-piperazin-1-yl)-phenyl]-amine,
[8-(2-Methoxy-phenyl)-[1,2,4]triazolo[1,5-a]pyridin-2-yl]-[3-(4-methyl-piperazin-1-yl)-phenyl]-amine,
[8-(2-Methanesulfonyl-phenyl)-[1,2,4]triazolo[1,5-a]pyridin-2-yl]-[3-(4-methyl-piperazin-1-yl)-phenyl]-amine,
1-{3-[8-(4-Methanesulfonyl-phenyl)-[1,2,4]triazolo[1,5-a]pyridin-2-ylamino]-phenyl}-4-methyl-piperazin-2-one,
4-Ethyl-1-{3-[8-(4-methanesulfonyl-phenyl)-[1,2,4]triazolo[1,5-a]pyridin-2-ylamino]-phenyl}-piperazin-2-one,
[3-(4-Methyl-piperazin-1-yl)-phenyl]-(8-{4-[4-(4-methyl-piperazin-1-yl)-piperidin-1-yl]-phenyl}-[1,2,4]triazolo[1,5-a]pyridin-2-yl)-amine,
1-(3-{8-[4-(Dimethyl-phosphinoyl)-phenyl]-[1,2,4]triazolo[1,5-a]pyridin-2-ylamino}-phenyl)-4-methyl-piperazin-2-one, and
1-(3-{8-[4-(Dimethyl-phosphinoyl)-phenyl]-[1,2,4]triazolo[1,5-a]pyridin-2-ylamino}-phenyl)-4-ethyl-piperazin-2-one.

In other particular embodiments, a compound of Formula II, or a salt thereof, is selected from N-{3-[(1,1-dioxidothiomorpholin-4-yl)methyl]phenyl}-8-[4-(methylsulfonyl)phenyl][1,2,4]triazolo[1,5-a]pyridin-2-amine In still other particular embodiments, a compound of Formula II, or a salt thereof, is selected from:
[8-(4-Methanesulfonyl-phenyl)-[1,2,4]triazolo[1,5-a]pyridin-2-yl]-(3-morpholin-4-yl-phenyl)-amine,
[8-(3-Methanesulfonyl-phenyl)-[1,2,4]triazolo[1,5-a]pyridin-2-yl]-(3-morpholin-4-yl-phenyl)-amine, and
[8-(4-Methanesulfonyl-phenyl)-[1,2,4]triazolo[1,5-a]pyridin-2-yl]-(3-morpholin-4-ylmethyl-phenyl)-amine In another aspect, this application relates to compounds of Formula II, or salts thereof, wherein $R^{5A}$, $R^{4A}$, and $R^{3A}$ are H, $R^{11}$ is H, h is 0, and $R^{12}$ is $SO_2(C_1-C_4)$alkyl. In some specific embodiments, $T^4$ is a direct bond. In other specific embodiments, $T^4$ is $—NR^{6A}—$. In particular embodiments, a compound of Formula II, or a salt thereof, is (3-Methanesulfonyl-phenyl)-[8-(4-methanesulfonyl-phenyl)-[1,2,4]triazolo[1,5-a]pyridin-2-yl]-amine. In other particular embodiments, a compound of Formula II, or a salt thereof, is N-(3-{[2-(3-Methanesulfonyl-phenylamino)-[1,2,4]triazolo[1,5-a]pyridin-8-ylamino]-methyl}-pyridin-2-yl)-N-methyl-methanesulfonamide.

In another aspect, this application relates to compounds of Formula II, or salts thereof, wherein $R^{5A}$, $R^{4A}$, and $R^{3A}$ are H, $R^{11}$ is H, h is 0, $T^4$ is a direct bond and $R^{12}$ is $(C_1-C_8)$alkoxy. In particular embodiments, a compound of Formula II, or a salt thereof, is [8-(4-Methanesulfonyl-phenyl)-[1,2,4]triazolo[1,5-a]pyridin-2-yl]-(3-methoxy-phenyl)-amine.

In another aspect, this application relates to compounds of Formula II, or salts thereof, wherein $R^{5A}$, $R^{4A}$, and $R^{3A}$ are H, $R^{11}$ is H, h is 0, $T^4$ is $—O—$ and $R^{12}$ is a 6 membered heterocycloalkyl group, in which at least one member is a nitrogen atom, optionally substituted with between one to four substituents. In some specific embodiments, $R^{12}$ is piperazinyl which may be optionally substituted as described above. In particular embodiments, a compound of Formula II, or a salt thereof, is selected from:
2-{2-[3-(4-Methyl-piperazin-1-yl)-phenylamino]-[1,2,4]triazolo[1,5-a]pyridin-8-yloxymethyl}-benzonitrile,
[8-(3-Chloro-benzyloxy)-[1,2,4]triazolo[1,5-a]pyridin-2-yl]-[3-(4-methyl-piperazin-1-yl)-phenyl]-amine,
2-{2-[3-(4-Methyl-piperazin-1-yl)-phenylamino]-[1,2,4]triazolo[1,5-a]pyridin-8-yloxymethyl}-benzamide, and
[8-(4-Methanesulfonyl-phenoxy)-[1,2,4]triazolo[1,5-a]pyridin-2-yl]-[3-(4-methyl-piperazin-1-yl)-phenyl]-amine.

In another aspect, this application relates to compounds of Formula II, or salts thereof, wherein $R^{5A}$, $R^{4A}$, $R^{3A}$, and $R^{6A}$ are H, $R^{11}$ is H, h is 0, $T^4$ is $—NR^{6A}—$ and $R^{12}$ is a 6 membered heterocycloalkyl group, in which at least one member is a nitrogen atom, optionally substituted with between one and four substituents. In some specific embodiments, $R^{12}$ is piperazinyl which may be optionally substituted as described above. In other specific embodiments, $R^{12}$ is piperazinyl which may be optionally substituted as described above and $U^4$ is phenyl which may be optionally substituted with between one to four substituents. In further specific embodiments, $R^{12}$ is piperazinyl which may be optionally substituted as described above and $U^4$ is pyridinyl which may be optionally substituted with between one to four substituents.

In particular embodiments, a compound of Formula II, or a salt thereof, is selected from the following:

N-Methyl-N-(3-{2-[3-(4-methyl-piperazin-1-yl)-phenylamino]-[1,2,4]triazolo[1,5-a]pyridin-8-ylamino}-pyridin-2-yl)-methanesulfonamide, N-Methyl-N-[3-({2-[3-(4-methyl-piperazin-1-yl)-phenylamino]-[1,2,4]triazolo[1,5-a]pyridin-8-ylamino]-methyl)-pyridin-2-yl]-methanesulfonamide, and N(2)-[3-(4-Methyl-piperazin-1-yl)-phenyl]-N(8)-pyridin-3-ylmethyl-[1,2,4]triazolo[1,5-a]pyridine-2,8-diamine.

In other particular embodiments, a compound of Formula II, or a salt thereof, is selected from the following:

N(8)-(2-Methanesulfonyl-phenyl)-N(2)-[3-(4-methyl-piperazin-1-yl)-phenyl]-[1,2,4]triazolo[1,5-a]pyridine-2,8-diamine, N(8)-(3-Methanesulfonyl-benzyl)-N(2)-[3-(4-methyl-piperazin-1-yl)-phenyl]-[1,2,4]triazolo[1,5-a]pyridine-2,8-diamine, N-Methyl-N-[2-({2-[3-(4-methyl-piperazin-1-yl)-phenylamino]-[1,2,4]triazolo[1,5-a]pyridin-8-ylamino}-methyl)-benzyl]-methanesulfonamide, N-Methyl-N-[2-({2-[3-(4-methyl-piperazin-1-yl)-phenylamino]-[1,2,4]triazolo[1,5-a]pyridin-8-ylamino}-methyl)-phenyl]-methanesulfonamide, N(8)-(2-Methanesulfonyl-benzyl)-N(2)-[3-(4-methyl-piperazin-1-yl)-phenyl]-[1,2,4]triazolo[1,5-a]pyridine-2,8-diamine, N-Methyl-N-(2-{2-[3-(4-methyl-piperazin-1-yl)-phenylamino]-[1,2,4]triazolo[1,5-a]pyridin-8-ylamino}-benzyl)-methanesulfonamide, N(8)-(3-Methanesulfonyl-phenyl)-N(2)-[3-(4-methyl-piperazin-1-yl)-phenyl]-[1,2,4]triazolo[1,5-a]pyridine-2,8-diamine, N(8)-(2-Methoxy-5-trifluoromethyl-phenyl)-N*2*-[3-(4-methyl-piperazin-1-yl)-phenyl]-[1,2,4]triazolo[1,5-a]pyridine-2,8-diamine, N(8)-(2-Methoxy-benzyl)-N(2)-[3-(4-methyl-piperazin-1-yl)-phenyl]-[1,2,4]triazolo[1,5-a]pyridine-2,8-diamine, N(8)-(3-Methoxy-benzyl)-N(2)-[3-(4-methyl-piperazin-1-yl)-phenyl]-[1,2,4]triazolo[1,5-a]pyridine-2,8-diamine, N(8)-(4-Methoxy-benzyl)-N(2)-[3-(4-methyl-piperazin-1-yl)-phenyl]-[1,2,4]triazolo[1,5-a]pyridine-2,8-diamine, N(8)-(2-Fluoro-benzyl)-N(2)-[3-(4-methyl-piperazin-1-yl)-phenyl]-[1,2,4]triazolo[1,5-a]pyridine-2,8-diamine, and N(8)-(4-Fluoro-benzyl)-N(2)-[3-(4-methyl-piperazin-1-yl)-phenyl]-[1,2,4]triazolo[1,5-a]pyridine-2,8-diamine In another aspect, this application relates to compounds of Formula II, or salts thereof, wherein $R^{5A}$, $R^{4A}$, $R^{3A}$, and $R^{6A}$ are H, $R^{11}$ is H, h is 0, $T^4$ is a direct bond and $R^{12}$ is a 6 membered heterocycloalkyl group, in which at least one member is a nitrogen atom, optionally substituted with between one to four substituents and $U^4$ is $(C_2-C_9)$heteroaryl, in which at least one member is a nitrogen atom, optionally substituted with between one to four substituents. In some specific embodiments, $R^{12}$ is piperazinyl which may be optionally substituted as described above and $U^4$ is a 5 membered heteroaryl which may be optionally substituted as described above. In other specific embodiments, $R^{12}$ is piperazinyl which may be optionally substituted as described above and $U^4$ is pyrazolyl, which may be optionally substituted as described above. In a particular embodiment, a compound of Formula II, or a salt thereof, is {8-[1-(4-Fluorophenyl)-1H-pyrazol-4-yl]-[1,2,4]triazolo[1,5-a]pyridin-2-yl}-[3-(4-methyl-piperazin-1-yl)-phenyl]-amine In another aspect, this application relates to compounds of Formula II, or salts thereof, wherein $R^{5A}$, $R^{4A}$, $R^{3A}$, and $R^{6A}$ are H, $R^{11}$ is H, h is 0, $T^4$ is —C≡C—, and $R^{12}$ is a 6 membered heterocycloalkyl group, in which at least one member is a nitrogen atom, optionally substituted with between one to four substituents. In some specific embodiments, $R^{12}$ is piperazinyl which may be optionally substituted as described above and $U^4$ is phenyl which may be optionally substituted with between one to four substituents. In a particular embodiment, a compound of Formula II, or a salt thereof, is N-Methyl-N-(2-{2-[3-(4-methyl-piperazin-1-yl)-phenylamino]-[1,2,4]triazolo[1,5-a]pyridin-8-ylethynyl}-phenyl)-methanesulfonamide.

In another aspect, this application relates to compounds of Formul III:

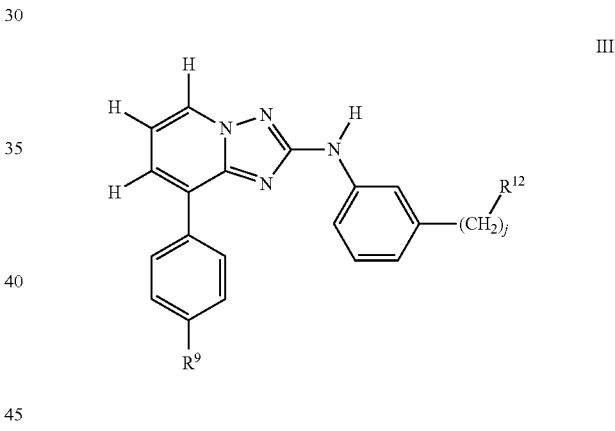

III wherein $R^{12}$ is selected from $SO_2R^{7A}$, $(C_2-C_8)$alkyl, $(C_1-C_8)$alkoxy, halo$(C_2-C_4)$alkyl, halo$(C_1-C_4)$alkoxy, $(C_3-C_{14})$cycloalkyl, $(C_3-C_{14})$cycloalkyloxy, $(C_3-C_{14})$cycloalkyl$(C_1-C_4)$alkyl, $(C_3-C_{14})$cycloalkyl$(C_1-C_4)$alkoxy, $(C_6-C_{10})$aryl, $(C_6-C_{10})$aryloxy, $(C_6-C_{10})$aryl$(C_1-C_4)$alkyl, $(C_6-C_{10})$aryl$(C_1-C_4)$alkoxy, $(C_2-C_{14})$heterocycloalkyl, $(C_2-C_{14})$heterocycloalkyloxy, $(C_2-C_{14})$heterocycloalkyl$(C_1-C_4)$alkyl, $(C_2-C_{14})$heterocycloalkyl$(C_1-C_4)$alkoxy, $(C_2-C_9)$heteroaryl, $(C_2-C_9)$heteroaryloxy, $(C_2-C_6)$heteroaryl$(C_1-C_4)$alkyl, and $(C_2-C_6)$heteroaryl$(C_1-C_4)$alkoxy, wherein each of the aforementioned groups may be optionally substituted with between one to four substituents;

$R^9$ is selected from $SO_2R^{7A}$, $POR^{7A}R^{7A}$, $NR^{7A}SO_2R^{7A}$, halo$(C_1-C_4)$alkyl, halogen, or $(C_2-C_{14})$heterocycloalkyl optionally substituted with between one to four substituents;

j is selected from 0, 1, 2, or 3; and wherein said optional substituents are each independently selected from OH, CN, oxo, $NO_2$, halogen, $(C_1-C_8)$alkyl, $(C_1-C_8)$alkoxy, hydroxy$(C_1-C_4)$alkyl, halo$(C_1-C_4)$alkyl, halo ($C_1$-$C_4$)alkoxy, ($C_3$-$C_{14}$)cycloalkyl, ($C_3$-$C_{14}$)cycloalkyl($C_1$-$C_4$)alkyl, ($C_3$-$C_{14}$)cycloalkyloxy, ($C_3$-$C_{14}$)cycloalkyl($C_1$-$C_4$)alkoxy, $NR^{74}R^{74}$, ($C_1$-$C_4$)alkyl-$NR^{74}R^{74}$, ($C_6$-$C_{10}$)aryl, ($C_6$-$C_{10}$)aryl($C_1$-$C_4$)alkyl, ($C_6$-$C_{10}$)aryloxy, ($C_6$-$C_{10}$)aryl($C_1$-$C_4$)alkoxy, $SO_2R^{74}$, ($C_1$-$C_4$)alkyl-$SO_2R^{74}$, ($C_1$-$C_4$)alkyl-$C(O)NR^{74}R^{74}$, $C(O)NR^{74}R^{74}$, ($C_1$-$C_4$)alkyl-$SO_2NR^{74}R^{74}$, $SO_2NR^{74}R^{74}$, ($C_2$-$C_{14}$)heterocycloalkyl, ($C_2$-$C_{14}$)heterocycloalkyloxy, ($C_2$-$C_{14}$)heterocycloalkyl($C_1$-$C_4$)alkyl, ($C_2$-$C_{14}$)heterocyclo alkyl($C_1$-$C_4$)alkoxy, ($C_2$-$C_9$)hetero aryl, ($C_2$-$C_9$)heteroaryloxy, ($C_2$-$C_9$)heteroaryl($C_1$-$C_4$)alkyl, ($C_2$-$C_9$)heteroaryl($C_1$-$C_4$)alkoxy, $COR^{74}$, ($C_1$-$C_4$)alkyl-$COR^{74}$, $NR^{74}COR^{74}$, ($C_1$-$C_4$)alkyl-$NR^{74}COR^{74}$, $NR^{74}SO_2R^{74}$, ($C_1$-$C_4$)alkyl-$NR^{74}SO_2R^{74}$, $OSO_2R^{74}$, ($C_1$-$C_4$)alkyl-$OSO_2R^{74}$, $POR^{74}R^{74}$, ($C_1$-$C_4$)alkyl-$POR^{74}R^{74}$, $CO_2R^{74}$ or ($C_1$-$C_4$)alkyl-$CO_2R^{74}$.

In another aspect, this application relates to compounds of the general Formula III, or salts thereof, wherein $R^{12}$ is $SO_2$($C_1$-$C_8$)alkyl. In particular embodiments, a compound of Formula III, or a salt thereof, is (3-Methanesulfonyl-phenyl)-[8-(4-methanesulfonyl-phenyl)-[1,2,4]triazolo[1,5-a]pyridin-2-yl]-amine In another aspect, this application relates to compounds of the general Formula III, or salts thereof, wherein $R^{12}$ is ($C_1$-$C_8$)alkoxy. In particular embodiments, a compound of Formula III, or a salt thereof, is [8-(4-Methanesulfonyl-phenyl)-[1,2,4]triazolo[1,5-a]pyridin-2-yl]-(3-methoxy-phenyl)-amine.

In another aspect, this application relates to compounds of the general Formula III, or salts thereof, wherein $R^{12}$ is a 6 membered heterocycloalkyl group, in which at least one member is a nitrogen atom, optionally substituted with between one to four substituents. In some specific embodiments, $R^{12}$ is piperizinyl, piperadinyl, thiomorpholinyl, and morpholinyl, any of which may be optionally substituted as described above. In particular embodiments, a compound of Formula III, or a salt thereof, is selected from the following:

4-{3-[8-(4-Methanesulfonyl-phenyl)-[1,2,4]triazolo[1,5-a]pyridin-2-ylamino]-phenyl}-piperidine-1-carboxylic acid tert-butyl ester, {8-[4-(Dimethyl-phosphinoyl)-phenyl]-[1,2,4]triazolo[1,5-a]pyridin-2-yl}-[3-(4-methyl-piperazin-1-yl)-phenyl]-amine, (S)-1-(4-{3-[8-(4-Methanesulfonyl-phenyl)-[1,2,4]triazolo[1,5-a]pyridin-2-ylamino]-phenyl}-piperazin-1-yl)-propan-2-ol,

[8-(4-Methanesulfonyl-phenyl)-[1,2,4]triazolo[1,5-a]pyridin-2-yl]-[3-(4-morpholin-4-yl-piperidin-1-yl)-phenyl]-amine,

[8-(4-Methanesulfonyl-phenyl)-[1,2,4]triazolo[1,5-a]pyridin-2-yl]-[3-(4-methyl-piperazin-1-yl)-phenyl]-amine,

[8-(4-Methanesulfonyl-phenyl)-[1,2,4]triazolo[1,5-a]pyridin-2-yl]-(3-morpholin-4-yl-phenyl)-amine, 4-{3-[8-(4-Methanesulfonyl-phenyl)-[1,2,4]triazolo[1,5-a]pyridin-2-ylamino]-phenyl}-piperazine-1-carboxylic acid tert-butyl ester,

[8-(4-Methanesulfonyl-phenyl)-[1,2,4]triazolo[1,5-a]pyridin-2-yl]-(3-piperidin-4-yl-phenyl)-amine,

[8-(4-Methanesulfonyl-phenyl)-[1,2,4]triazolo[1,5-a]pyridin-2-yl]-[3-(1-methyl-piperidin-4-yl)-phenyl]-amine, 2-(4-{3-[8-(4-Methanesulfonyl-phenyl)-[1,2,4]triazolo[1,5-a]pyridin-2-ylamino]-phenyl}-piperazin-1-yl)-ethanol, {3-[1-(2-Methanesulfonyl-ethyl)-piperidin-4-yl]-phenyl}-[8-(4-methanesulfonyl-phenyl)-[1,2,4]triazolo[1,5-a]pyridin-2-yl]-amine, N-{3-[(1,1-dioxidothiomorpholin-4-yl)methyl]phenyl}-8-[4-(methylsulfonyl)phenyl][1,2,4]triazolo[1,5-a]pyridin-2-amine,

[3-(4-Methyl-piperazin-1-yl)-phenyl]-[8-(4-trifluoromethyl-phenyl)-[1,2,4]triazolo[1,5-a]pyridin-2-yl]-amine,

[8-(4-Methanesulfonyl-phenyl)-[1,2,4]triazolo[1,5-a]pyridin-2-yl]-{3-[4-(4-methyl-piperazin-1-yl)-piperidin-1-yl]-phenyl}-amine,

[8-(4-Methanesulfonyl-phenyl)-[1,2,4]triazolo[1,5-a]pyridin-2-yl]-(3-piperazin-1-yl-phenyl)-amine, (±)-cis-3-Hydroxy-4-{3-[8-(4-methanesulfonyl-phenyl)-[1,2,4]triazolo[1,5-a]pyridin-2-ylamino]-phenyl}-piperidine-1-carboxylic acid tert-butyl ester, 2-(4-{3-[8-(4-Methanesulfonyl-phenyl)-[1,2,4]triazolo[1,5-a]pyridin-2-ylamino]-phenyl}-piperidin-1-yl)-acetamide,

[8-(4-Methanesulfonyl-phenyl)-[1,2,4]triazolo[1,5-a]pyridin-2-yl]-[3-(4-methyl-piperazin-1-ylmethyl)-phenyl]-amine, (R)-1-(4-{3-[8-(4-Methanesulfonyl-phenyl)-[1,2,4]triazolo[1,5-a]pyridin-2-ylamino]-phenyl}-piperazin-1-yl)-propan-2-ol, 2-(4-{3-[8-(4-Methanesulfonyl-phenyl)-[1,2,4]triazolo[1,5-a]pyridin-2-ylamino]-phenyl}-piperazin-1-yl)-acetamide, 1-(4-{3-[8-(4-Methanesulfonyl-phenyl)-[1,2,4]triazolo[1,5-a]pyridin-2-ylamino]-phenyl}-piperazin-1-yl)-2-methyl-propan-2-ol, (±)-(cis)-4-{3-[8-(4-Methanesulfonyl-phenyl)-[1,2,4]triazolo[1,5-a]pyridin-2-ylamino]-phenyl}-piperidin-3-ol, N-Methyl-N-(4-{2-[3-(4-methyl-piperazin-1-yl)-phenylamino]-[1,2,4]triazolo[1,5-a]pyridin-8-yl}-phenyl)-methanesulfonamide, {3-[4-(3-Fluoro-propyl)-piperazin-1-yl]-phenyl}-[8-(4-methanesulfonyl-phenyl)-[1,2,4]triazolo[1,5-a]pyridin-2-yl]-amine,

[3-(4-Methyl-piperazin-1-yl)-phenyl]-{8-[4-(propane-2-sulfonyl)-phenyl]-[1,2,4]triazolo[1,5-a]pyridin-2-yl}-amine,

[8-(4-Methanesulfonyl-phenyl)-[1,2,4]triazolo[1,5-a]pyridin-2-yl]-(3-morpholin-4-ylmethyl-phenyl)-amine, (±)-2-(cis)-3-Hydroxy-4-{3-[8-(4-methanesulfonyl-phenyl)-[1,2,4]triazolo[1,5-a]pyridin-2-ylamino]-phenyl}-piperidin-1-yl)-acetamide,

[8-(4-Fluoro-phenyl)-[1,2,4]triazolo[1,5-a]pyridin-2-yl]-[3-(4-methyl-piperazin-1-yl)-phenyl]-amine, {8-[4-(Dimethyl-phosphinoyl)-phenyl]-[1,2,4]triazolo[1,5-a]pyridin-2-yl}-{3-[1-(2-methanesulfonyl-ethyl)-piperidin-4-yl]-phenyl}-amine, 1-{3-[8-(4-Methanesulfonyl-phenyl)-[1,2,4]triazolo[1,5-a]pyridin-2-ylamino]-phenyl}-4-methyl-piperazin-2-one, 4-Ethyl-1-{3-[8-(4-methanesulfonyl-phenyl)-[1,2,4]triazolo[1,5-a]pyridin-2-ylamino]-phenyl}-piperazin-2-one,

[3-(4-Methyl-piperazin-1-yl)-phenyl]-(8-{4-[4-(4-methyl-piperazin-1-yl)-piperidin-1-yl]-phenyl}-[1,2,4]triazolo[1,5-a]pyridin-2-yl)-amine, 1-(3-{8-[4-(Dimethyl-phosphinoyl)-phenyl]-[1,2,4]triazolo[1,5-a]pyridin-2-ylamino}-phenyl)-4-methyl-piperazin-2-one, and 1-(3-{8-[4-(Dimethyl-phosphinoyl)-phenyl]-[1,2,4]triazolo[1,5-a]pyridin-2-ylamino}-phenyl)-4-ethyl-piperazin-2-one.

In another aspect, this application relates to compounds of the general Formula IV:

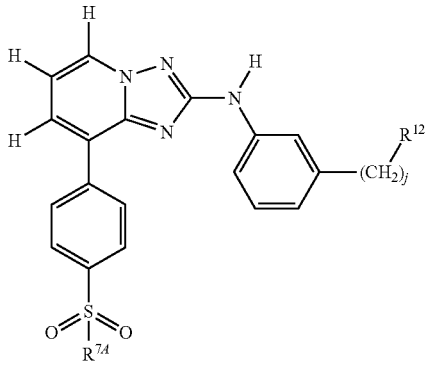

or salts thereof, wherein j, $R^{7A}$ and $R^{12}$ are as defined above.

In some specific embodiments, $R^{7A}$ is $(C_1-C_8)$alkyl and $R^{12}$ is $SO_2(C_1-C_8)$alkyl. In other specific embodiments, $R^{7A}$ is $(C_1-C_8)$alkyl and $R^{12}$ is $(C_1-C_8)$alkoxy. In still other specific embodiments, $R^{7A}$ is $(C_1-C_8)$alkyl and $R^{12}$ is a 6 membered heterocycloalkyl, in which at least one member is a nitrogen atom, optionally substituted with between one to four substituents. In still other specific embodiments, $R^{7A}$ is $(C_1-C_8)$ alkyl and $R^{12}$ is selected from piperazinyl, piperidinyl, thiomorpholinyl, and morpholinyl, any of which may be optionally substituted with between one to four substituents.

In particular embodiments, a compound of Formula IV, or a salt thereof, is (3-Methanesulfonyl-phenyl)-[8-(4-methanesulfonyl-phenyl)-[1,2,4]triazolo[1,5-a]pyridin-2-yl]-amine In other particular embodiments, a compound of Formula IV, or a salt thereof, is [8-(4-Methanesulfonyl-phenyl)-[1,2,4]triazolo[1,5-a]pyridin-2-yl]-(3-methoxy-phenyl)-amine.

In still other particular embodiments, a compound of Formula IV, or a salt thereof, is selected from the following:
4-{3-[8-(4-Methanesulfonyl-phenyl)-[1,2,4]triazolo[1,5-a]pyridin-2-ylamino]-phenyl}-piperidine-1-carboxylic acid tert-butyl ester,
(S)-1-(4-{3-[8-(4-Methanesulfonyl-phenyl)-[1,2,4]triazolo[1,5-a]pyridin-2-ylamino]-phenyl}-piperazin-1-yl)-propan-2-ol,
[8-(4-Methanesulfonyl-phenyl)-[1,2,4]triazolo[1,5-a]pyridin-2-yl]-[3-(4-morpholin-4-yl-piperidin-1-yl)-phenyl]-amine,
[8-(4-Methanesulfonyl-phenyl)-[1,2,4]triazolo[1,5-a]pyridin-2-yl]-[3-(4-methyl-piperazin-1-yl)-phenyl]-amine,
[8-(4-Methanesulfonyl-phenyl)-[1,2,4]triazolo[1,5-a]pyridin-2-yl]-(3-morpholin-4-yl-phenyl)-amine,
4-{3-[8-(4-Methanesulfonyl-phenyl)-[1,2,4]triazolo[1,5-a]pyridin-2-ylamino]-phenyl}-piperazine-1-carboxylic acid tert-butyl ester,
[8-(4-Methanesulfonyl-phenyl)-[1,2,4]triazolo[1,5-a]pyridin-2-yl]-(3-piperidin-4-yl-phenyl)-amine,
[8-(4-Methanesulfonyl-phenyl)-[1,2,4]triazolo[1,5-a]pyridin-2-yl]-[3-(1-methyl-piperidin-4-yl)-phenyl]-amine,
2-(4-{3-[8-(4-Methanesulfonyl-phenyl)-[1,2,4]triazolo[1,5-a]pyridin-2-ylamino]-phenyl}-piperazin-1-yl)-ethanol,
{3-[1-(2-Methanesulfonyl-ethyl)-piperidin-4-yl]-phenyl}-[8-(4-methanesulfonyl-phenyl)-[1,2,4]triazolo[1,5-a]pyridin-2-yl]-amine,
N-{3-[(1,1-dioxidothiomorpholin-4-yl)methyl]phenyl}-8-[4-(methylsulfonyl)phenyl][1,2,4]triazolo[1,5-a]pyridin-2-amine,
[8-(4-Methanesulfonyl-phenyl)-[1,2,4]triazolo[1,5-a]pyridin-2-yl]-{3-[4-(4-methyl-piperazin-1-yl)-piperidin-1-yl]-phenyl}-amine,
[8-(4-Methanesulfonyl-phenyl)-[1,2,4]triazolo[1,5-a]pyridin-2-yl]-(3-piperazin-1-yl-phenyl)-amine,
(±)-cis-3-Hydroxy-4-{3-[8-(4-methanesulfonyl-phenyl)-[1,2,4]triazolo[1,5-a]pyridin-2-ylamino]-phenyl}-piperidine-1-carboxylic acid tert-butyl ester,
2-(4-{3-[8-(4-Methanesulfonyl-phenyl)-[1,2,4]triazolo[1,5-a]pyridin-2-ylamino]-phenyl}-piperidin-1-yl)-acetamide,
[8-(4-Methanesulfonyl-phenyl)-[1,2,4]triazolo[1,5-a]pyridin-2-yl]-[3-(4-methyl-piperazin-1-ylmethyl)-phenyl]-amine,
(R)-1-(4-{3-[8-(4-Methanesulfonyl-phenyl)-[1,2,4]triazolo[1,5-a]pyridin-2-ylamino]-phenyl}-piperazin-1-yl)-propan-2-ol,
2-(4-{3-[8-(4-Methanesulfonyl-phenyl)-[1,2,4]triazolo[1,5-a]pyridin-2-ylamino]-phenyl}-piperazin-1-yl)-acetamide,
1-(4-{3-[8-(4-Methanesulfonyl-phenyl)-[1,2,4]triazolo[1,5-a]pyridin-2-ylamino]-phenyl}-piperazin-1-yl)-2-methyl-propan-2-ol,
(±)-(cis)-4-{3-[8-(4-Methanesulfonyl-phenyl)-[1,2,4]triazolo[1,5-a]pyridin-2-ylamino]-phenyl}-piperidin-3-ol,
{3-[4-(3-Fluoro-propyl)-piperazin-1-yl]-phenyl}-[8-(4-methanesulfonyl-phenyl)-[1,2,4]triazolo[1,5-a]pyridin-2-yl]-amine,
[3-(4-Methyl-piperazin-1-yl)-phenyl]-{8-[4-(propane-2-sulfonyl)-phenyl]-[1,2,4]triazolo[1,5-a]pyridin-2-yl}-amine,
[8-(4-Methanesulfonyl-phenyl)-[1,2,4]triazolo[1,5-a]pyridin-2-yl]-(3-morpholin-4-ylmethyl-phenyl)-amine,
(±)-2-(cis)-3-Hydroxy-4-{3-[8-(4-methanesulfonyl-phenyl)-[1,2,4]triazolo[1,5-a]pyridin-2-ylamino]-phenyl}-piperidin-1-yl)-acetamide,
1-{3-[8-(4-Methanesulfonyl-phenyl)-[1,2,4]triazolo[1,5-a]pyridin-2-ylamino]-phenyl}-4-methyl-piperazin-2-one, and 4-Ethyl-1-{3-[8-(4-methanesulfonyl-phenyl)-[1,2,4]triazolo[1,5-a]pyridin-2-ylamino]-phenyl}-piperazin-2-one.

In another aspect, this application relates to compounds of the general Formula V ![Formula V structure]

or salts thereof, wherein:
$R^{3A}$, $R^{4A}$, and $R^{5A}$ are each independently selected from H, OH, CN, $NO_2$, halogen, $(C_1-C_8)$alkyl, $(C_1-C_8)$alkoxy, halo$(C_1-C_4)$alkyl, and halo$(C_1-C_4)$alkoxy;
$R^{7A}$ is selected from H and $(C_1-C_8)$alkyl;
$R^8$ is selected from $SO_2R^{7A}$, $NR^{7A}COR^{7A}$, $(C_2-C_8)$alkyl, $(C_1-C_8)$alkoxy, halo$(C_2-C_4)$alkyl, halo$(C_1-C_4)$alkoxy, $(C_3-C_{14})$ cycloalkyl, $(C_3-C_{14})$cycloalkyloxy, $(C_3-C_{14})$cycloalkyl$(C_1-C_4)$alkyl, $(C_3-C_{14})$cycloalkyl$(C_1-C_4)$alkoxy, $(C_6-C_{10})$aryl, $(C_6-C_{10})$aryloxy, $(C_6-C_{10})$aryl$(C_1-C_4)$alkyl, $(C_6-C_{10})$aryl ($C_1$-$C_4$)alkoxy, ($C_2$-$C_{14}$)heterocycloalkyl, ($C_2$-$C_{14}$)heterocycloalkyloxy, ($C_2$-$C_{14}$)heterocycloalkyl($C_1$-$C_4$)alkyl, ($C_2$-$C_{14}$)heterocycloalkyl($C_1$-$C_4$)alkoxy, ($C_2$-$C_9$)heteroaryl, ($C_2$-$C_9$)heteroaryloxy, ($C_2$-$C_9$)heteroaryl($C_1$-$C_4$)alkyl, and ($C_2$-$C_9$)heteroaryl($C_1$-$C_4$)alkoxy, wherein each of the aforementioned groups may be optionally substituted with between one to four substituents;

$R^9$ is selected from $SO_2R^{7A}$, $POR^{7A}R^{7A}$, $NR^{7A}SO_2R^{7A}$, halo ($C_1$-$C_4$)alkyl, halogen, or ($C_2$-$C_{14}$)heterocycloalkyl optionally substituted with between one to four substituents;

$R^{10}$ is selected from H and ($C_1$-$C_4$)alkyl optionally substituted with $SO_2$($C_1$-$C_4$)alkyl;

g is selected from 0, 1, 2, or 3; and wherein said optional substituents are each independently selected from OH, CN, oxo, $NO_2$, halogen, ($C_1$-$C_8$)alkyl, ($C_1$-$C_8$)alkoxy, hydroxy($C_1$-$C_4$)alkyl, halo($C_1$-$C_4$)alkyl, halo ($C_1$-$C_4$)alkoxy, ($C_3$-$C_{14}$)cycloalkyl, ($C_3$-$C_{14}$)cycloalkyl($C_1$-$C_4$)alkyl, ($C_3$-$C_{14}$)cycloalkyloxy, ($C_3$-$C_{14}$)cycloalkyl($C_1$-$C_4$)alkoxy, $NR^{7A}R^{7A}$, ($C_1$-$C_4$)alkyl-$NR^{7A}R^{7A}$, ($C_6$-$C_{10}$)aryl, ($C_6$-$C_{10}$)aryl($C_1$-$C_4$)alkyl, ($C_6$-$C_{10}$)aryloxy, ($C_6$-$C_{10}$)aryl ($C_1$-$C_4$)alkoxy, $SO_2R^{7A}$, ($C_1$-$C_4$)alkyl-$SO_2R^{7A}$, ($C_1$-$C_4$)alkyl-C(O)$NR^{7A}R^{7A}$, C(O)$NR^{7A}R^{7A}$, ($C_1$-$C_4$)alkyl-$SO_2NR^{7A}R^{7A}$, $SO_2NR^{7A}R^{7A}$, ($C_2$-$C_{14}$)heterocycloalkyl, ($C_2$-$C_{14}$)heterocycloalkyloxy, ($C_2$-$C_{14}$)heterocycloalkyl($C_1$-$C_4$) alkyl, ($C_2$-$C_{14}$)heterocycloalkyl($C_1$-$C_4$)alkoxy, ($C_2$-$C_9$) heteroaryl, ($C_2$-$C_9$)heteroaryloxy, ($C_2$-$C_9$)heteroaryl($C_1$-$C_4$) alkyl, ($C_2$-$C_9$)heteroaryl($C_1$-$C_4$)alkoxy, $COR^{7A}$, ($C_1$-$C_4$) alkyl-$COR^{7A}$, $NR^{7A}COR^{7A}$, ($C_1$-$C_4$)alkyl-$NR^{7A}COR^{7A}$, $NR^{7A}SO_2R^{7A}$, ($C_1$-$C_4$)alkyl-$NR^{7A}SO_2R^{7A}$, $OSO_2R^{7A}$, ($C_1$-$C_4$)alkyl-$OSO_2R^{7A}$, $POR^{7A}R^{7A}$, ($C_1$-$C_4$)alkyl-$POR^{7A}R^{7A}$, $CO_2R^{7A}$ or ($C_1$-$C_4$)alkyl-$CO_2R^{7A}$.

In another aspect, this application relates to compounds of the general Formula V, or salts thereof, wherein $R^{3A}$, $R^{4A}$, $R^{5A}$, and $R^{10}$ are H.

In another aspect, this application relates to compounds of the general Formula V, or salts thereof, wherein $R^{3A}$, $R^{4A}$, $R^{5A}$, and $R^{10}$ are H and $R^9$ is selected from $SO_2$($C_1$-$C_8$)alkyl.

In another aspect, this application relates to compounds of the general Formula V, or salts thereof, wherein $R^{3A}$, $R^{4A}$, $R^{5A}$, and $R^{10}$ are H and $R^8$ is a 6 membered heterocycloalkyl, in which at least one member is a nitrogen atom, optionally substituted with between one to four substituents. In some specific embodiments, $R^8$ is selected from piperazinyl, piperidinyl, morpholinyl, and thiomorpholinyl, any of which may be optionally substituted as described above. In some specific embodiments, $R^9$ is $SO_2$($C_1$-$C_8$)alkyl and $R^8$ is selected from piperazinyl, piperidinyl, morpholinyl, and thiomorpholinyl, any of which may be optionally substituted as described above.

In another aspect, this application relates to compounds of the general Formula V, or salts thereof, wherein $R^{3A}$, $R^{4A}$, $R^{5A}$, and $R^{10}$ are H and $R^8$ is $SO_2$($C_1$-$C_4$)alkyl.

In another aspect, this application relates to compounds of the general Formula V, or salts thereof, wherein $R^{3A}$, $R^{4A}$, $R^{5A}$, and $R^{10}$ are H and $R^8$ is ($C_1$-$C_4$)alkoxy.

In another aspect, this application relates to compounds of the general Formula V, or salts thereof, wherein $R^{3A}$, $R^{4A}$, $R^{5A}$, and $R^{10}$ are H and $R^8$ is $NHCO$($C_1$-$C_4$)alkyl.

In another aspect, this application relates to pharmaceutically acceptable salts of the compounds described herein.

In another aspect, this application relates to compositions comprising one or more compounds of the general Formula I or a salt thereof. In some specific embodiments, the salt is a pharmaceutically acceptable salt. In some specific embodiments, the composition comprises at least one pharmaceutically acceptable excipient. In other specific embodiments, the composition further comprises at least one additional therapeutically active agent.

In another aspect, this application relates to methods of treating diseases or disorders mediated by at least one of FAK (focal adhesion kinase) or JAK (Janus kinase). In some embodiments, the disease or disorder is mediated by at least one of FAK and JAK2. In some specific embodiments, the disease or disorder is cancer.

In another aspect, this application relates to methods of treating diseases or disorders mediated by FAK (focal adhesion kinase) comprising administering a therapeutically effective amount of a compound of the general Formula I or a pharmaceutically acceptable salt thereof.

In another aspect, this application relates to methods of treating diseases or disorders mediated by JAK2 (Janus kinase 2) comprising administering a therapeutically effective amount of a compound of the general Formula I or a pharmaceutically acceptable salt thereof. In some specific embodiments, the method further comprises administration of at least one additional therapeutically active agent.

In another aspect, this application relates to methods for treating a hyperproliferative disease or disorder for which inhibition of at least one of FAK or JAK2 is indicated comprising administering a therapeutically effective amount of a compound of the general Formula I or a pharmaceutically acceptable salt thereof. In some specific embodiments, the method further comprises administration of at least one additional therapeutically active agent.

In another aspect, this application relates to methods for treating a hyperproliferative disease or disorder for which inhibition of at least JAK2 is indicated comprising administering a therapeutically effective amount of a compound of the general Formula III or a pharmaceutically acceptable salt thereof. In some specific embodiments, a compound of Formula III preferentially inhibits the JAK2 enzyme in vitro. In other specific embodiments, the compound of Formula III is at least about 20 fold more selective for the JAK2 enzyme over the JAK3 enzyme in vitro.

In another aspect, this application relates to methods for treating a hyperproliferative disease or disorder for which inhibition of at least JAK2 is indicated comprising administering a therapeutically effective amount of a compound of the general Formula IV or a pharmaceutically acceptable salt thereof. In some specific embodiments, a compound of Formula IV preferentially inhibits the JAK2 enzyme in vitro. In other specific embodiments, the compound of Formula IV is at least about 20 fold more selective for the JAK2 enzyme over the JAK3 enzyme in vitro.

In another aspect, this application relates to methods for treating a hyperproliferative disease or disorder for which inhibition of at least JAK2 is indicated comprising administering a therapeutically effective amount of a compound of the general Formula V or a pharmaceutically acceptable salt thereof. In some specific embodiments, a compound of Formula V preferentially inhibits the JAK2 enzyme in vitro. In other specific embodiments, the compound of Formula V is at least about 20 fold more selective for the JAK2 enzyme over the JAK3 enzyme in vitro.

DEFINITIONS

The compounds and intermediates described herein may be named according to either the IUPAC (International Union for Pure and Applied Chemistry) or CAS (Chemical Abstracts Service) nomenclature systems. It should be understood that unless expressly stated to the contrary, "compounds of the general Formula I" and "compounds of Formula I" refers to and includes any and all compounds described by and/or with reference to Formula I, as well as Formulae Ia through Ie, and Formulae II through Formula V, inclusive, and all salts thereof.

The various hydrocarbon-containing moieties described herein may be described using a prefix designating the minimum and maximum number of carbon atoms in the moiety, i.e. "$(C_a\text{-}C_b)$". For example, $(C_a\text{-}C_b)$alkyl indicates an alkyl moiety of the integer "a" to the integer "b" carbon atoms, inclusive. Certain moieties may also be described according to the minimum and maximum number of members with or without specific reference to a particular atom or overall structure. For example, the terms "a to b-membered" or "having between a to b members" refer to a moiety having the integer "a" to the integer "b" number of atoms, inclusive.

As used herein by themselves or in conjunction with another term or terms, "alkyl" and "$(C_1\text{-}C_8)$alkyl" refer to straight or branched hydrocarbon groups containing the requisite number of carbon atoms as described above. As used herein, alkyl groups may be optionally substituted with between one to four substituents. Representative examples of alkyl groups include, but are not limited to, e.g., methyl, ethyl, n-propyl, isopropyl, n-butyl, isobutyl, sec-butyl, t-butyl, etc.

As used herein by themselves or in conjunction with another term or terms, "alkoxy", "alkyloxy" and "$(C_1\text{-}C_8)$ alkoxy" refer to straight or branched hydrocarbon groups containing the requisite number of carbon atoms as described above, bonded to an oxygen atom. As used herein, alkoxy groups may be optionally substituted with between one to four substituents. Representative examples of alkoxy groups include, but are not limited to, e.g. methoxy, ethoxy, tert-butoxy, etc.

As used herein by themselves or in conjunction with another term or terms, "alkenyl" and "$(C_1\text{-}C_8)$alkenyl" refer to straight or branched hydrocarbon groups containing the requisite number of carbon atoms as described above, and at least one double bond. As used herein, alkenyl groups may be optionally substituted with between one to four substituents. Representative examples of alkenyl groups include, but are not limited to, e.g. ethenyl, 2-propenyl (allyl), iso-propenyl, 2-methyl-1-propenyl, etc.

As used herein by themselves or in conjunction with another term or terms, "alkynyl" and "$(C_1\text{-}C_8)$alkynyl" refer to straight or branched hydrocarbon groups containing the requisite number of carbon atoms as described above, and one triple bond. As used herein, alkynyl groups may be optionally substituted with between one to four substituents. Representative examples of alkynyl groups include, but are not limited to, e.g. ethynyl, propynyl, butynyl, etc.

As used herein by itself or in conjunction with another term or terms, "aromatic" refers to monocyclic and polycyclic ring systems containing 4 n+2 pi electrons, where n is an integer. As used herein, aromatic refers to and includes ring systems that contain only carbon atoms (i.e. "aryl") as well as ring systems that contain at least one heteroatom selected from N, O or S (i.e. "heteroaromatic" or "heteroaryl"). As used herein, an aromatic ring system may be optionally substituted with between one to four substituents.

As used herein by itself or in conjunction with another term or terms, "non-aromatic" refers to a monocyclic or polycyclic ring system having at least one isolated double bond, i.e. a double bond that is not part of a conjugated pi system. As used herein, non-aromatic refers to and includes ring systems that contain only carbon atoms as well as ring systems that contain at least one heteroatom selected from N, O or S. A non-aromatic ring system may be optionally substituted with between one to four substituents.

As used herein by themselves or in conjunction with another term or terms, "aryl" and "$(C_6\text{-}C_{10})$aryl" refer to monocyclic and polycyclic aromatic hydrocarbon ring systems containing the requisite number of carbon atoms as described above, which may be optionally substituted with between one to four substituents at any position. Representative examples include phenyl and napthyl, either of which may be optionally substituted with between one to four substituents.

As used herein by themselves or in conjunction with another term or terms, "arylalkyl" and "$(C_6\text{-}C_{10})$aryl$(C_1\text{-}C_4)$ alkyl" refer to alkyl groups, as defined above, having an aryl group, as defined above, as a substituent. Arylalkyl groups may be optionally substituted with between one to four substituents. Representative examples include, but are not limited to, e.g., benzyl, phenylethyl, etc.

As used herein by themselves or in conjunction with another term or terms, "aryloxy", "$(C_6\text{-}C_{10})$aryloxy", "arylalkyloxy", "arylalkoxy", and "$(C_6\text{-}C_{10})$aryl$(C_1\text{-}C_4)$alkoxy" refer to aryl groups, as defined above, that are bonded directly to an oxygen atom or to an alkoxy group, as defined above, respectively. These groups may be optionally substituted with between one to four substituents. Representative examples include, but are not limited to, e.g., phenoxy, benzyloxy, phenylethoxy, etc.

As used herein by themselves or in conjunction with another term or terms, "carbocyclic" and "carbocycle" refer to monocyclic and polycyclic ring systems that contain only carbon atoms in the ring(s), i.e., hydrocarbon ring systems, without regard or reference to aromaticity. Thus, carbocyclic and carbocycle refer to and include ring systems that are saturated or unsaturated, aromatic or non-aromatic, as well as ring systems having fully saturated, aromatic and/or non-aromatic portions. The terms carbocyclic and carbocycle further include bridged, fused, and spirocyclic ring systems. Carbocycles may be optionally substituted with between one to four substituents. Representative examples include, but are not limited to, e.g., cyclopropyl, cyclobutyl, 1,3-dimethylcyclopentyl, cyclohexyl, phenyl, napthyl, cyclohexenyl, 2,3-dihydro-indenyl, 1,2,3,4-tetrahydro-naphthalene, spiro[3.4] octanyl, bicycle[2.2.1]hept-5-enyl, adamantanyl, norbornanyl, bicyclo[2.2.1]heptanyl, etc.

As used herein by themselves or in conjunction with another term or terms, "halo" and "halogen" include fluorine, chlorine, bromine, and iodine atoms and substituents.

As used herein by themselves or in conjunction with another term or terms, "haloalkyl" and "halo$(C_1\text{-}C_4)$alkyl" refer to alkyl groups, as defined above, having one or more hydrogen atoms replaced by halogen atoms, as defined above. It should be understood that where there is more than one halogen atom present in a haloalkyl group, the halogen atoms may be the same or different and/or may be located on the same carbon atom or on different carbon atoms. Representative examples of haloalkyl groups include, but are not limited to, e.g., difluoromethyl, trifluoromethyl, chloromethyl, 3-bromo-2-chloro-propyl, 2,2-dibromoethyl, 2-bromo-2-chloro-ethyl, 1,1,2,2,3,3,4,4-octafluoro-butyl, etc.

As used herein by themselves or in conjunction with another term or terms, "haloalkoxy" and "halo$(C_1\text{-}C_4)$ alkoxy" refer to haloalkyl groups, as defined above, bonded to an oxygen atom. Representative examples of haloalkoxy groups include, but are not limited to, e.g., difluoromethoxy, trifluoromethoxy, chloromethoxy, 2,2-dibromoethoxy, 3-bromo-2-chloro-propoxy, 1,1,2,2,3,3,4,4-octafluoro-butoxy, etc.

As used herein by themselves or in conjunction with another term or terms, "cycloalkyl" and "$(C_3\text{-}C_{14})$cycloalkyl" refer to monocyclic and polycyclic hydrocarbon ring systems containing the requisite number of carbon atoms as described above, which may be optionally substituted with between one to four substituents. These terms refer to and include ring systems that are fully saturated or contain at least one double bond, as well as ring systems with fully saturated, aromatic or non-aromatic portions, such as, for example, 1,2,3,4-tetrahydro-naphthalenyl. It should be understood that these terms further refer to and include bridged and/or fused polycyclic structures such as, for example, tetrahydro-5H-benzocycloheptenyl, bicyclo[3.2.1]octanyl, bicyclo[5.2.0] nonanyl, bicyclo[2.2.1]hept-5-enyl and the like, as well as spirocyclic ring systems such as, for example, spiro[3.4]octanyl, spiro[3.5]nonyl and the like. Other representative examples of cycloalkyl groups include, but are not limited to, e.g., cyclopropyl, methylcyclopropyl, cyclobutyl, cyclobutenyl, isopropylcyclobutyl, cyclopentyl, 1,3-dimethylcyclopentyl, cyclohexyl, cyclohexenyl, cycloheptyl, 2,3-dihydro-1H-inden-2-yl, norbornyl, decahydronaphthalenyl, etc.

As used herein by themselves or in conjunction with another term or terms, "cycloalkyloxy" and "$(C_3-C_{14})$cycloalkyl$(C_1-C_4)$alkoxy" refer to a cycloalkyl group having the requisite number of carbon atoms as described above, bonded directly to an oxygen atom or an alkoxy group, respectively. As used herein, these groups may be optionally substituted with between one to four substituents. Representative examples include, but are not limited to, e.g., cyclopropyloxy, cyclobutyloxy, cyclopentyloxy, 2-cyclopentylethoxy, cyclohexyl-methoxy, cyclohex-3-yloxy, etc.

As used herein by themselves or in conjunction with another term or terms, "heterocycloalkyl", "$(C_2-C_{14})$heterocycloalkyl", "heterocycle", and "heterocyclic" refer to monocyclic and polycyclic ring systems containing the requisite number of carbon atoms as described above and at least one heteroatom selected from P, N, O, or S. These groups may be optionally substituted with between one to four substituents. These terms further refer to and include ring systems that are fully saturated or contain at least one double bond, as well as ring systems with fully saturated, aromatic and/or non-aromatic portions, such as for example, 1,2,3,4-tetrahydroquinolinyl. It should be understood that polycyclic heterocycloalkyl groups further include fused, bridged and spirocyclic ring systems and ring systems in which the P, N or S is oxidized, such as for example, i.e., 1,1-dioxide-thiomorpholinyl (1,1-dioxidothiomorpholinyl), 1-oxo-piperidinyl or 4-oxo-azaphosphinanyl Representative examples of heterocycloalkyl groups include, but are not limited to, e.g., oxiranyl, thiaranyl, aziridinyl, oxetanyl, thiatanyl, azetidinyl, tetrahydrofuranyl, tetrahydrothiophenyl, pyrrolidinyl, dihydrofuranyl, tetrahydropyranyl, pyranyl, tetrahydrothiopyranyl, thiopyranyl, piperidinyl, 1,4-dioxanyl, 1,4-oxathianyl, morpholinyl, thiomorpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-azaphosphinanyl, 1,4-diazepanyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, chromanyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, 7-oxa-1-azaspiro[4.4]nonanyl, 3-azabicyclo[3.1.0]hexanyl, indolinyl, octahydro-1H-indolyl, octahydro-2H-pyrido[1,2-a]pyrazinyl, 3-azabicyclo[4.1.0]heptanyl, 3,4-dihydro-2H-pyranyl, 1,2,3,4-tetrahydropyridinyl, 1,2,5,6-tetrahydropyridinyl, tetrahydro-1H-benzo[d]azepinyl, dihydro-1H-isoindolyl, etc.

As used herein by themselves or in conjunction with another term or terms, "heterocycloalkylalkyl" and "$(C_2-C_{14})$ heterocycloalkyl$(C_1-C_4)$alkyl" refer to alkyl groups, as defined above, having a heterocycloalkyl group, as defined above, as a substituent. Heterocycloalkylalkyl groups may be optionally substituted with between one to four substituents. Representative examples include, but are not limited to, e.g., piperidinylmethyl, pyrrolidinylethyl, etc.

As used herein by themselves or in conjunction with another term or terms, "heterocycloalkyloxy", "$(C_2-C_{14})$heterocycloalkyloxy", "heterocycloalkylalkoxy" and "$(C_2-C_{14})$ heterocycloalkoxy" and "$(C_2-C_{14})$heterocycloalkyl$(C_1-C_4)$ alkoxy" respectively refer to a heterocycloalkyl or a heterocycloalkylalkyl group, as defined above, bonded to an oxygen atom, which may be optionally substituted with between one to four substituents. Representative examples include, but are not limited to, e.g., pyrrolidin-3-yloxy, piperidin-4-yloxy, azepan-4-yloxy, pyrrolidin-1-yl-ethoxy, pyrrolidin-2-ylmethoxy, etc.

As used herein by themselves or in conjunction with another term or terms, "heteroaryl", "$(C_2-C_9)$heteroaryl", and "heteroaromatic", refer to monocyclic and polycyclic aromatic ring systems containing the requisite number of carbon atoms, as described above, and at least one heteroatom selected from N, O, or S. As used herein, a heteroaromatic ring system refers to and includes polycyclic ring systems that contain aromatic portions, while other portions of the ring system may be fully saturated or non-aromatic. Heteroaromatic rings may be optionally substituted with between one to four substituents. Representative examples include, but are not limited to, e.g., pyrrolyl, furanyl, thiophenyl, thienyl, pyrazolyl, imidazolyl, isoxazolyl, oxazolyl, isothiazolyl, thiazolyl, 1,2,3-triazolyl, 1,2,4-triazolyl, tetrazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridinyl (pyridyl), pyridazinyl, pyrimidinyl, pyrazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b] thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolinyl, quinolinyl, phthalazinyl, quinoxalinyl, quinazolinyl, benzoxazinyl, 1,2,3,4-tetrahydro-isoquinolinyl, 2,3-dihydro-1H-isoindolyl, 1,3,4,5-tetrahydro-benzo[b] azepin-2-one, 1,3,4,5-Tetrahydro-benzo[d]azepin-2-one, 2,3,4,5-Tetrahydro-benzo[c]azepin-1-one, 1,2,4,5-Tetrahydro-benzo[c]azepin-3-one, 2,3,4,5-Tetrahydro-1H-benzo[b] azepinyl, 2,3,4,5-Tetrahydro-1H-benzo[d]azepinyl, 2,3,4,5-Tetrahydro-1H-benzo[c]azepinyl, etc.

As used herein, "~~~" indicates a point of attachment.

As used herein by itself of in conjunction with another term or terms, "a bond", refers to and includes, a direct bond, a double bond (which may be denoted as —CH=CH—) or a triple bond (which may be denoted as —C≡C—) unless expressly stated otherwise.

As used herein by itself or in conjunction with another term or terms, "pharmaceutically acceptable" indicates that the designated entity such as for example, e.g. carrier, vehicle, diluent, excipient, salt or prodrug, is generally chemically and/or physically compatible with the other ingredients comprising a formulation, and/or is generally physiologically compatible with the recipient thereof.

As used herein by themselves or in conjunction with another term or terms, "subject(s)" and "patient(s)", refer to mammals, including humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s) when used in conjunction with the phrase " . . . optionally substituted by between one to four . . . " unless otherwise specified.

As used herein, representative examples of substituents include, but are not limited to, e.g., hydrogen (may be denoted as H), halogen, $(C_1-C_8)$alkyl, $(C_1-C_8)$alkoxy, $(C_1-C_8)$alkoxy ($C_1$-$C_4$)alkyl, carboxyl (may be denoted as —COOH), formyl, ($C_1$-$C_6$)acyl, halo($C_1$-$C_4$)alkyl, halo($C_1$-$C_4$)alkoxy, hydroxyl (may be denoted as —OH), nitro (may be denoted as —$NO_2$), cyano (may be denoted as —CN), amino (may be denoted as —$NH_2$), mono- or di-($C_1$-$C_4$)alkylamino (may be denoted as —NHR, —NRR or —N(R)$_2$), oxo (may be denoted as >=O or carbonyl), ($C_6$-$C_{10}$)aryl, ($C_6$-$C_{10}$)aryloxy, ($C_6$-$C_{10}$)aryl($C_1$-$C_4$)alkyl, ($C_6$-$C_{10}$)aryl($C_1$-$C_4$)alkoxy, ($C_2$-$C_9$)heteroaryl, ($C_2$-$C_9$)heteroaryloxy, ($C_2$-$C_9$)heteroaryl($C_1$-$C_4$)alkyl, ($C_2$-$C_9$)heteroaryl($C_1$-$C_4$)alkoxy, ($C_1$-$C_6$) alkoxycarbonyl (may be denoted as —COOR), ($C_3$-$C_{14}$)cycloalkyl, ($C_3$-$C_{14}$)cycloalkyl($C_1$-$C_4$)alkyl, ($C_3$-$C_{14}$) cycloalkyloxy, ($C_3$-$C_{14}$)cycloalkyl($C_1$-$C_4$)alkoxy, ($C_2$-$C_{14}$) heterocycloalkyl, ($C_3$-$C_{14}$)heterocycloalkyl($C_1$-$C_4$)alkyl, ($C_2$-$C_{14}$)heterocycloalkyloxy, ($C_2$-$C_{14}$)heterocycloalkyl($C_1$-$C_4$)alkoxy, ($C_1$-$C_8$)alkoxycarbonyl($C_1$-$C_4$)alkyl, ($C_1$-$C_8$) alkoxycarbonyl, ($C_1$-$C_4$)alkylsulfinyl (may be denoted —SOR), ($C_1$-$C_4$)alkylsulfonyl (may be denoted as —$SO_2$R), ($C_1$-$C_4$)alkylsulfide (may be denoted as —SR), mono- and di-($C_1$-$C_4$)alkylaminocarbonyl (may be denoted as $NH_2$CO—, —NHCO—, —NRCO—, $NR_2$CO—), ($C_1$-$C_8$) acylthio, ($C_1$-$C_6$)acyloxy, PO(($C_1$-$C_4$)alkyl)$_2$, etc.

As used herein, "treating", "treated", and "treatment", whether used alone or in conjunction with another term or terms, include preventative (e.g., prophylactic), ameliorative, palliative, and curative uses and results, or any combination thereof. It should be understood that the terms "preventing" and "preventative" and "prophylactic" are not absolute but rather refer to uses and results where the administration of a compound or composition diminishes the likelihood or seriousness of a condition, symptom, or disease state, and/or delays the onset of a condition, symptom, or disease state for a period of time. In some embodiments, the terms "treating", "treated", and "treatment" refer to curative uses and results as well as uses and results that diminish or reduce the severity of a particular condition, symptom, disorder, or disease described herein.

As used herein, the terms "therapeutic" and "therapeutically effective amount", whether used alone or in conjunction with another term or terms, denote an amount of a compound, composition or medicament that (a) treats or prevents a particular disease, condition or disorder; (b) attenuates, ameliorates or eliminates one or more symptoms of a particular disease, condition or disorder; (c) prevents or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c).

As used herein, a "therapeutically active agent", whether used alone or in conjunction with another term or terms, refers to any compound, i.e. a drug, that has been found to be useful in the treatment of a disease or disorder and is not described by Formula I.

The compounds (including final products and intermediates) described herein may be isolated and used per se or may be isolated in the form of a salt. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more. Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved (by a regulatory authority such as FDA) for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of Formula I may have two or more asymmetric centers and therefore can exist in a number of stereoisomeric configurations. Consequently, such compounds can be synthesized and/or isolated as mixtures of enantiomers and/or as individual (pure) enantiomers, as well as diastereomers and mixtures of different diastereomers. It should be understood that the present application includes all such enantiomers and diastereomers and mixtures thereof in all ratios.

In practice, resolution and isolation of pure enantiomers can be achieved using methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation or inversion.

For those compounds of the general Formula I that contain one or more additional stereogenic centers, those skilled in the art will appreciate that all diastereoisomers and diastereoisomeric mixtures of the compounds illustrated and discussed herein are within the scope of the present application. Compounds of Formula I that exist as diastereoisomers may be isolated by methods known to those skilled in the art, for example, by crystallization, gas-liquid or liquid chromatography. Alternatively, intermediates in the course of a synthesis that exist as racemic mixtures may be subjected to resolution by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers may be synthesized by asymmetric synthesis using optically active reagents, substrates, catalysts or solvents, or by converting one stereoisomer into the other by asymmetric transformation or inversion.

It should be understood that reference to "compounds of Formula I", "compounds of the general Formula I" or simply "compounds", whether used by themselves or in combination with another term or terms, encompasses all stereoisomers, i.e. cis and trans isomers, as well as optical isomers, i.e. R and S enantiomers, of such compounds and all salts thereof, in substantially pure form and/or any mixtures of the foregoing isomers in any ratio. This understanding extends to pharmaceutical compositions and methods of treatment that employ or comprise one or more compounds of the general Formula I, either by themselves or in combination with additional agents. It should be further understood that any reference to compounds of Formula I includes compounds described by Formula I as well as Formula Ia through Formula Ie, and Formulae II through V, inclusive.

Compounds of the application may be administered as prodrugs. The term "prodrug" refers to a compound that is transformed in vivo to yield a compound of Formula I. The in vivo transformation may occur by various mechanisms, such as hydrolysis, in the blood or other biological fluids.

A prodrug of a compound of Formula I may be formed in a conventional manner with one or more functional groups in the compound, such as an amino, hydroxyl or carboxyl group. For example, if a compound of Formula I contains a carboxylic acid functional group, a prodrug can comprise: (1) an ester formed by the replacement of a hydrogen of the acid group with a group such as $(C_1-C_6)$alkyl or $(C_6-C_{10})$ aryl; (2) an activated ester formed by the replacement of the hydrogen of the acid group with groups such as —$(CR_2)COOR'$, where $CR_2$ is a spacer and R can be groups such as H or methyl and R' can be groups such as $(C_1-C_6)$alkyl or $(C_6-C_{10})$ aryl; and/or (3) a carbonate formed by the replacement of the hydrogen of the acid with groups such as CHROCOOR' where R can be groups such as H or methyl and R' can be groups such as $(C_1-C_6)$alkyl or $(C_6-C_{10})$aryl. Similarly, if a compound of Formula I contains an alcohol functional group, a prodrug can be formed via the replacement of the hydrogen of the alcohol with groups such as $(C_1-C_6)$ alkanoyloxymethyl or $(C_1-C_6)$alkanoyloxyaryl or by forming an ester via condensation with, for example, an amino acid. Where a compound of Formula I contains a primary or secondary amino group, a prodrug may comprise, for example, an amide formed by the replacement of one or both of the hydrogens of the amino group with $(C_1-C_{10})$alkanoyl or $(C_6-C_{10})$aroyl. Other prodrugs of amines are well known to those skilled in the art. Alternatively, certain compounds of Formula I may themselves act as prodrugs of other compounds of Formula I.

Discussions regarding prodrugs and their the use can be found in, for example, "Prodrugs as Novel Delivery Systems," T. Higuchi and W. Stella, Vol. 14 of the ACS Symposium Series, and *Bioreversible Carriers in Drug Design*, Pergamon Press, 1987 (ed. E B Roche, American Pharmaceutical Association). Further examples of replacement groups may be found in the aforementioned references.

Preparations and Examples

In general, compounds of the general Formula I may be prepared by the methods described in the Preparations, Schemes, and Experimental sections of the present application and/or by additional or alternative processes and procedures known in the chemical arts in combination with the knowledge of the skilled practitioner. It should be understood that the methods set forth in the following descriptions, reaction Schemes, Preparations and Experimentals are intended for illustrative purposes and are not to be construed as limiting the scope of the disclosure.

Alternative reagents, intermediates, starting materials, synthetic routes and methods can be used or adapted in practice, particularly in light of the scope of the present disclosure in combination with the knowledge of one of ordinary skill in the art. Such alternatives and modifications should be understood as being within the spirit and scope of the present application and the claims.

Unless otherwise indicated, the variables X, $R^{1A}$, $R^{1B}$, $R^2$, $R^3$, $R^4$, and $R^5$ shown or referenced in the Preparations and Schemes are defined as above or as defined in the Claims. In the reaction schemes below, it should be understood that for compounds where X is N, the variable $R^3$ is absent.

Although specific embodiments or individual compounds will be described with reference to particular Schemes, Preparations, and/or Examples, it should be understood that these embodiments or compounds are illustrative of a small number (i.e. a subset) of the more general descriptions, genera, formulae, species, embodiments and compounds that fall within the scope and spirit of the present application. Accordingly, these specific embodiments and compounds should not be interpreted as limiting the scope of the disclosure in any way.

General Synthesis

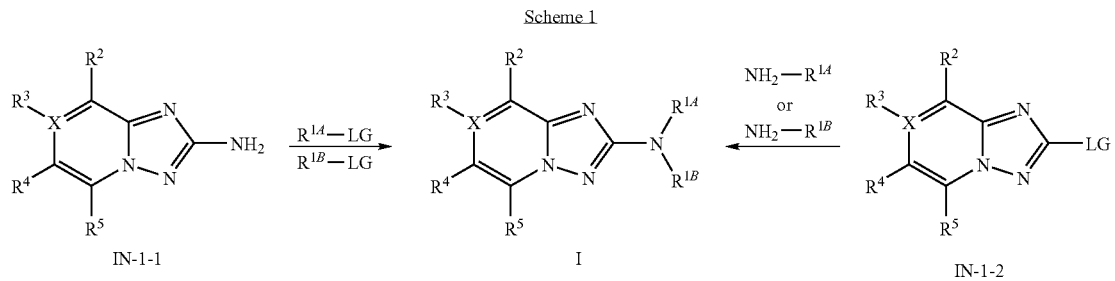

As shown in Scheme 1, various compounds of Formula I may be prepared by introducing the corresponding substituent, where LG denotes a leaving group such as halogen or triflate (—O—SO$_2$—CF$_3$) to the appropriately substituted amine, IN-1-1, or the appropriately substituted heterocycle, IN-1-2, in a Buchwald-type cross coupling reaction. The coupling reaction may be carried out under a variety of conditions well known in the art, such as, for example using palladium acetate (Pd(OAc)$_2$) in the presence of 2,2'-Bis(dicyclohexylphosphino)-1,1'-biphenyl or 4,5-Bis(diphenylphosphino)-9,9-dimethylxanthene and a base such as, for example, sodium carbonate, sodium tert-butoxide, cesium carbonate, potassium phosphate, in an appropriate solvent or mixture of solvents, such as, for example, dimethylformamide (DMF), toluene, and dioxane. The reaction proceeds for a suitable period of time, such as between 8 to 48 hours, at an appropriate temperature, such as, for example, between about 50° C. to about 180° C. Variations of cross coupling reactions are also well-known in the art and may be applied and/or adapted to the procedures described herein as necessary.

Various compounds of Formula I may also be prepared via nucleophilic displacement.

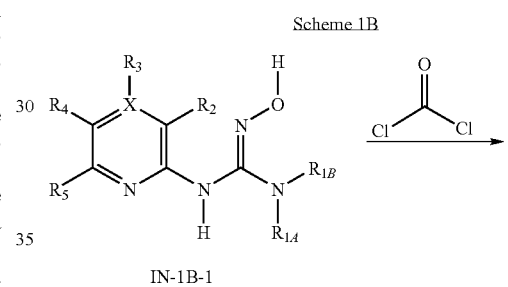

As shown in Scheme 1A, an appropriately functionalized intermediate, IN-1-2, where LG denotes a halogen such as chlorine, may be reacted with a desired amine, where R$^{1A}$ and R$^{1B}$ are not aryl or heteroaryl. In practice the desired amine may be used as a solvent for the reaction. This reaction typically proceeds at elevated temperatures (thermal or microwave) such as, for example, between 80° and 200° C. for a suitable period of time, such as, for example, between about 1 hour to about 4 hours. Displacement reactions are well known in the art and alternative conditions and/or starting materials may be readily applied to afford a variety of compounds of Formula I.

Another alternative preparation is shown in Scheme 1B.

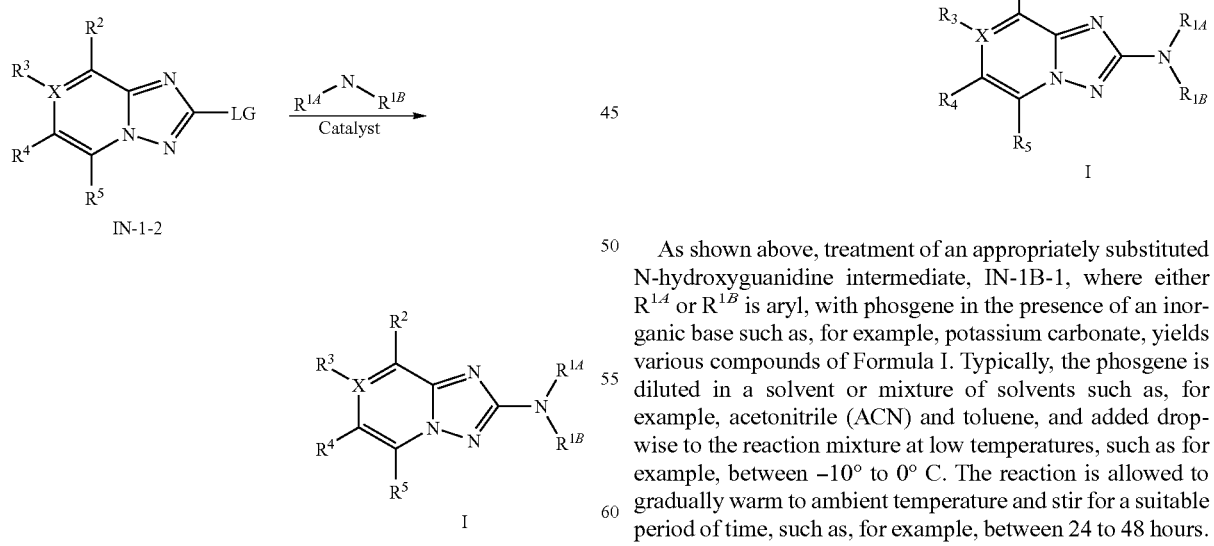

As shown above, treatment of an appropriately substituted N-hydroxyguanidine intermediate, IN-1B-1, where either R$^{1A}$ or R$^{1B}$ is aryl, with phosgene in the presence of an inorganic base such as, for example, potassium carbonate, yields various compounds of Formula I. Typically, the phosgene is diluted in a solvent or mixture of solvents such as, for example, acetonitrile (ACN) and toluene, and added dropwise to the reaction mixture at low temperatures, such as for example, between −10° to 0° C. The reaction is allowed to gradually warm to ambient temperature and stir for a suitable period of time, such as, for example, between 24 to 48 hours. This transformation is well known in the art and alternative conditions and/or starting materials may be readily applied to provide a variety of compounds of Formula I. See for example, Org. Proc. Res. Dev., 2006, 10(6), 1167-1171.

Suzuki-type cross coupling reactions may also be used to prepare various compounds of Formula I.

Scheme 1C

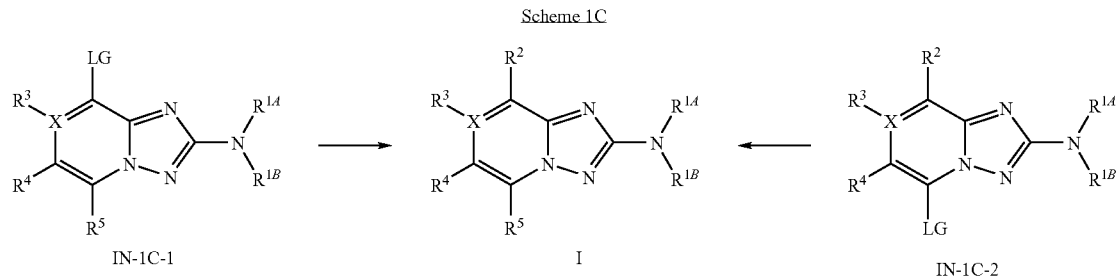

As shown in Scheme 1C, various substituents, such as $R^2$ and $R^5$, may be introduced to the appropriate heterocyclic intermediate, IN-1C-1 and IN-1C-2, where LG denotes a halogen or triflate, via a suitable boron reagent such as an arylboronic acid or ester. Also, various substituents, such as $R^2$ and $R^5$, may be introduced to the appropriate heterocyclic intermediate, IN-1C-1 and IN-1C-2, where LG denotes a boronic acid or boronic ester, via a suitable reagent such as an aryl halide or aryl triflate. Typically, the reaction proceeds in the presence of a palladium catalyst, such as, for example, tetrakis(triphenylphosphine)palladium ($Pd(PPh_3)_4$), and a base such as triethyl amine (TEA), sodium carbonate and cesium carbonate, in a solvent or mixture of solvents such as dioxane, DMF, tetrahydrofuran (THF) and water. The reaction proceeds for a suitable period of time, such as between 8 to 48 hours, at an appropriate temperature, such as, for example, between about 50° C. to about 180° C. Alternative cross coupling conditions, reagents, and starting materials are well-known in the art and may be readily applied to affect the transformation described herein.

Alternatively, for compounds where LG is a halogen such as bromine and the $R^5$ substituent is, for example, 'O' linked, introduction of the substituent may be accomplished using copper sulphate ($CuSO_4$) and a strong base such as potassium hydroxide (KOH) in a high boiling solvent such as 1,2-dimethoxyethane (DME). Similar transformations are known in the art. See, for example, *Bioorg. Med. Chem. Lett.*, 12 (2002), 185-187.

Various intermediates of the general formulae IN-1-1 may be prepared as shown in Scheme 2.

Scheme 2

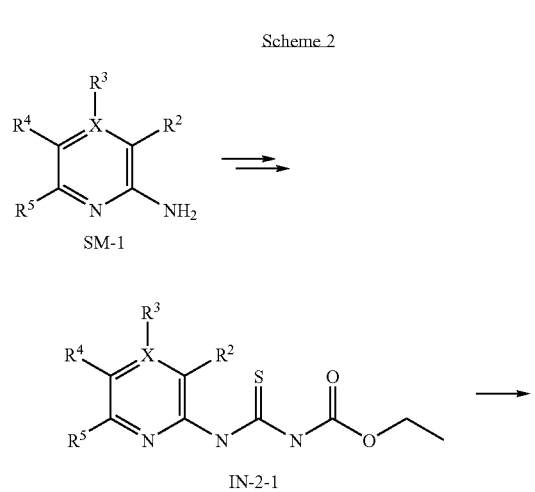

-continued

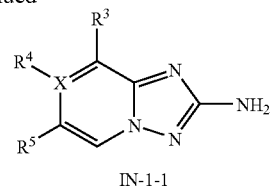

As shown above, various intermediates of the general formula IN-1-1 may be prepared via cyclization of the corresponding thiourea IN-2-1. Typically, for compounds where, for example, X is carbon and/or $R^4$ and $R^3$ are substituents such as, for example, halogen, or haloalkyl, treatment of IN-2-1 with hydroxyl amine and an amine base such as diisopropyl ethyl amine (DIEA) or DMAP in a protic solvent or mixture of solvents, such as, for example methanol (MeOH), and ethanol (EtOH) yields the desired cyclized product. The reaction proceeds at a suitable temperature, such as for example ambient temperature to about 60° C., for an appropriate period of time, such as, for example, between about 2 to about 8 hours. This transformation is well known in the art and alternative conditions and/or starting materials may be readily applied to provide a variety of intermediates of the general formula IN-1-1. See for example, *Synthesis*, 2003, 11, 1649-1652.

Various intermediates of the general formula IN-1A-1 may be prepared as shown in Scheme 2A.

Scheme 2A

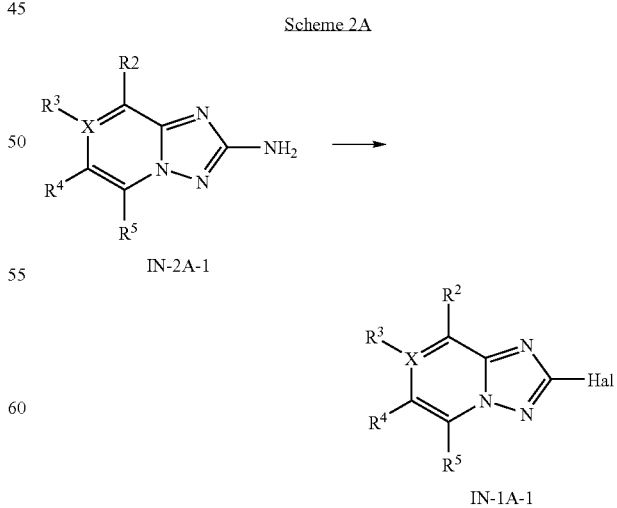

As shown above, various intermediates of the general formula IN-1A-1 where Hal denotes a halogen, such as, for example, chlorine may be prepared from the corresponding amino derivative, IN-2A-1. Treatment of the appropriate amine, IN-2A-1, with sodium nitrite in the presence of a catalytic amount of a copper (II) halide such as CuCl$_2$ affords the desired halogenated product IN-1A-1. Typically, this transformation is conducted at low temperatures such as between 0° C. to about ambient temperature, in a solution of the corresponding mineral acid, i.e. HCl. Halogenation reactions are well known in the art and alternative conditions and/or starting materials may be readily applied to provide a variety of intermediates of the general formula IN-1A-1.

Alternatively, various intermediates of the general formula IN-1A-1 may be prepared as shown in Scheme 2B.

-continued

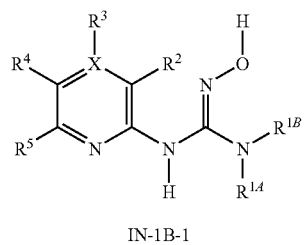

IN-1B-1

Scheme 2B

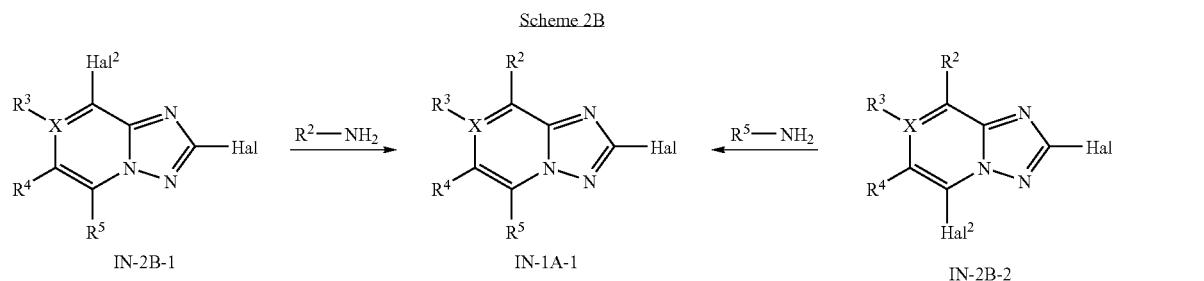

As shown above, an appropriately substituted dihalo derivative, IN-2B-1 or IN-2B-2, where Hal and Hal$^2$ are different halogen atoms, may undergo a Buchwald-type cross coupling reaction with the appropriate substituent, such as for example, R$^5$ or R$^2$, to afford the corresponding intermediate of the general formula IN-1A-1. Typically, for compounds where Hal is a chlorine atom and Hal$^2$ is a bromine atom, the reaction proceeds under conditions similar to those described in Scheme 1. Various dihalo derivatives of formulas IN-2B-1 and IN-2B-2 may be prepared using procedures known in or adapted from the chemical literature or as described herein.

Intermediates of the general formula IN-1B-1 may be prepared as shown in Scheme 2C.

As shown above, intermediates of the formula IN-1B-1 may be prepared from the corresponding methylated thioimidate IN-2B-1, after treatment with hydroxyl amine hydrochloride (NH$_2$OH.HCl) in the presence of an amine base such as diisopropyl ethyl amine (DIEA). Typically the reaction proceeds in an appropriate solvent, such as dioxane, at elevated temperatures, such as for example, between about 80° C. to about 100° C. The methyl thioimidate intermediate, IN-2B-1, may be prepared from the corresponding amino heterocycle SM-1 using procedures known or adapted from the chemical literature or as described herein. See for example, Org. Proc. Res. Dev., 2006, 10(6), 1167-1171.

Various intermediates of the general formula IN-2-1 may be prepared as shown in Scheme 2D.

Scheme 2C

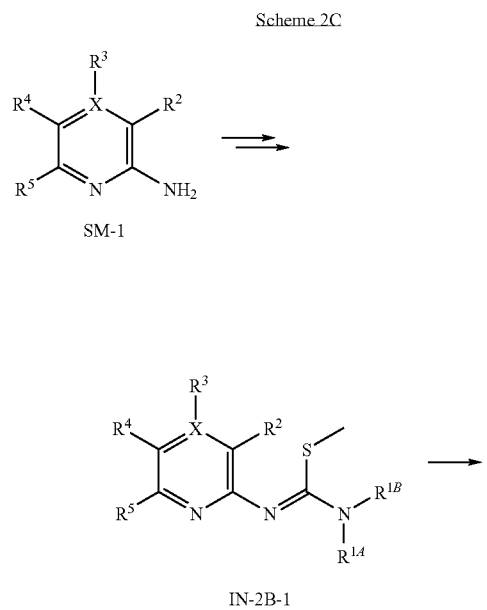

Scheme 2D

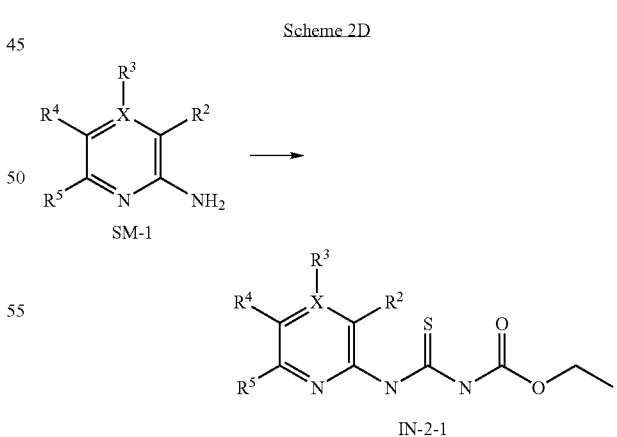

Various thioureas of the general formula IN-2-1 may be prepared from an appropriately substituted amino heterocycle, SM-1. For example, for compounds where R$^2$ is hydroxyl (OH), treatment of SM-1 with N-carboethoxyisothiocyanate in an appropriate solvent, such as, for example, acetonitrile or dioxane, provides the corresponding hydroxyl-thiourea of general formula IN-2-1. Typically, this reaction proceeds at ambient temperature for suitable period of time, such as, for example, between about 12 hours to about 24 hours. Other intermediates of formula IN-2-1 may be prepared as described herein or via standard or modified procedures described in the chemical literature. See, for example, *Synthesis*, 2003, 11, 1649-1652. Starting materials of the general formula SM-1 may be purchased or likewise prepared using procedures known in the art or as described herein.

Other useful intermediates and derivatives not specifically described herein generally may be prepared from appropriately substituted materials using transformations and/or reaction sequences known in the art in combination with the knowledge of one of skill in the art. Such procedures are described in reference books such as, for example, *Compendium of Organic Synthetic Methods*, Vols. I-VI (Wiley-Interscience).

One of skill in the art will appreciate that in some cases protecting groups may be required during a multi-step or single-step reaction sequence. In practice, a protecting group is used to mask or block a particular site/functional group in preparation for a chemical transformation at a different site/functional group in a molecule. After a particular target or transformation is complete or at some specific step later in a synthetic route, the protecting group can be removed using methods well know to those of ordinary skill in the art. The introduction, use and removal of protecting groups is thoroughly described in *Protective Groups in Organic Synthesis*, ($3^{rd}$ Ed., John Wiley & Sons, 1999).

Compositions

The compounds of the general Formula I and the pharmaceutically acceptable salts of such compounds may be administered as crystalline or amorphous materials, and may be administered alone or in combination with one or more of the other compounds described herein. In addition, compounds of the general Formula I and the pharmaceutically acceptable salts of such compounds may be administered in combination with one or more other therapeutically active agents. Generally, the compound(s) will be administered as a formulation, i.e. pharmaceutical composition, in association with one or more pharmaceutically acceptable excipients. The term "excipient" as used herein refers to any ingredient in the formulation other than the compound(s) of the general Formula I and any additional therapeutically active agent(s) as described above that may be present. Accordingly, excipient refers to and includes ingredients such as, for example: carriers, vehicles, solvents, adjuvants, lubricants, surfactants, binders, buffers, diluents, flavorings, coloring agents/dyes, disintegrants, emulsifying agents, suspending agents, plasticizers, solubilizers, fillers, bulking agents, and the like. The choice of excipient(s) will largely depend on factors such as: the particular mode of administration, the effect of the excipient(s) on solubility, stability, and release profile, and the nature of the dosage form. One skilled in the art will readily appreciate that this list of factors is not exhaustive. The compound(s) of the general Formula I and any additional therapeutically active agents (if present) may be generally referred to as the active ingredient(s) in a formulation or pharmaceutical composition.

Pharmaceutical compositions suitable for the delivery of compounds of the general Formula I and methods for their preparation will be readily apparent to those skilled in the art. Such compositions and methods for their preparation may be found, for example, in *Remington's Pharmaceutical Sciences*, 19th Edition (Mack Publishing Company, 1995).

The pharmaceutical composition may, for example, be in a form suitable for oral administration as a tablet, capsule (hard or soft filled), pill, powder, sustained or immediate release formulations, solution, suspension; for parenteral injection as a sterile solution, suspension or emulsion; or for topical administration as an ointment or cream. Additional dosage forms not specifically mentioned herein would be readily appreciated by one of ordinary skill in the art as being within the scope of the present application.

The relative amounts of the active ingredient(s) and the excipient(s) in a formulation or pharmaceutical composition will vary, depending upon the identity, size, and condition of the subject treated and further depending upon the route by which the composition is to be administered. By way of example, the composition may comprise between 0.1% and 100% (w/w) of active ingredient.

A pharmaceutical composition comprising one or more compounds of the general Formula I may be prepared, packaged, distributed, or sold in bulk, as a single unit dose, or as a plurality of single unit doses. As used herein, a "unit dose" is a discrete amount of a pharmaceutical composition comprising a predetermined amount of the active ingredient(s). The amount of the active ingredient(s) is generally equal to the dosage of the active ingredient(s) which would be administered to a subject or a convenient fraction of such a dosage such as, for example, one-half or one-third of such a dosage.

Dosing

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate pharmaceutical compositions in a unit dosage form for ease of administration and uniformity of treatment/therapeutic effect. As used herein, "unit dosage form" or "unit dose", by themselves or in combination with another term or terms, refer to the physically discreet amount(s) of medication, i.e. the active ingredient(s) in a pharmaceutical formulation, suitable for a one-time administration to the patient or subject to be treated; each unit dose containing a predetermined quantity of active compound(s) calculated to produce the desired therapeutic effect in association with the required pharmaceutical carrier. The more specific composition of the unit dosage forms comprising compounds of the general Formula I is dictated by and directly dependent on a number of variables, such as, for example: (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the skilled artisan. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

Indications

Various compounds of the general Formula I are useful in inhibiting the activity of one or more tyrosine kinases or in inhibiting the downstream events resulting from or mediated by the activation of one or more tryosine kinases. By inhibiting the activity of more than one tyrosine kinase, various compounds of Formula I can potentially suppress multiple mechanisms underlying disease states such as tumor formation and progression.

In one embodiment, various compounds of the general Formula I are useful in inhibiting or suppressing uncontrolled cell proliferation, anti-apoptotic signalling, tumor immune evasion, metastasis, angiogenesis, tumorigenesis, and/or tumor growth in mammalian (including human) cancers. Examples of such cancers include: solid tumors, hematopoietic cancer, prostate cancer, breast cancer, colon cancer, lung carcinomas, ovarian cancer, thyroid cancer, gliomas, leukemias and lymphomas.

Focal Adhesion Kinase (FAK)

Compared to normal quiescent cells, FAK over expression and activation is a hallmark of multiple solid tumors, particularly those with a propensity for bone metastasis, specifically breast, ovarian, thyroid, prostate, and HNSCC carcinomas (Zhao et al., 2009). Moreover, FAK over expression and activation are associated with an enhanced invasive and metastatic phenotype and tumor angiogenesis in these malignancies (Owens et al, 1995, 1996; Tremblay et al, 1996; Kornberg et al, 1998; Mc Clean et al 2005; Kyu-Ho Han and McGonigal, 2007) and correlated with poor prognosis and shorter metastasis-free survival. Elevated FAK levels in tumors are often caused by amplification of the FAK locus i.e. in breast carcinomas (Pylayeva et al., 2009). Increased FAK gene dosage occurs during transition from noninvasive to invasive carcinoma in a colon cancer model (Agochiya et al., 1999). FAK activation also protected tumor cells from chemotherapy-induced apoptosis, contributing further to tumor survival and resistance (Kyu-Ho Han and McGonigal, 2007; Halder et al, 2007). FAK activation can also promote tumor cell survival in a kinase-independent manner via its interaction with p53 which suppresses transcriptional activation of multiple p53 target genes (p21, Bax) and also promotes proteasome-mediated degradation of p53 (Lim et al., 2008; Cance et al., 2008).

Multiple proof-of-concept studies conducted in various solid tumors using si-RNA (Halder et al, 2006), dominant-negative FAK (Kohno et al, 2002), and small molecule FAK inhibitors (Halder et al, 2007; Roberts et al, 2008) have provided pre-clinical support for the therapeutic utility of FAK inhibition as an anti-tumor/anti-angiogenic strategy specifically for androgen-independent prostate cancers, breast cancers, and HNSCCs. The utility of FAK inhibition may be particularly useful in the management of breast and androgen-independent prostate cancers that have a high propensity for bone metastatic spread. In preclinical models of human breast cancer (MDA-MB-231) in nude rats, administration of a small molecule FAK inhibitor (PF-562,271) inhibited primary tumor growth and intra-tibial tumor spread, and restored tumor-induced bone loss (Bagi et al, 2008). Roberts et al (2008) showed that PF-562,271 inhibited bone metastases, prevented bone resorption, and increased osteogenesis in breast and androgen-independent prostate cancer patients with and without bone metastases, supporting an additional benefit of FAK inhibition in these specific malignancies.

JAK2

Most tumors, in particular solid ones, are characterized by constitutive JAK2 activation. There is a large body of preclinical evidence demonstrating tumor-promoting activities of JAK2 signaling, such as antitumor activity of JAK2 inhibitors in animal models. JAK2 contributes to tumor growth and progression through multiple mechanisms including increased tumor cell proliferation and survival, increased tumor angiogenesis and immune evasion. Not surprisingly, JAK2/STAT activation correlates with more malignant and metastatic phenotype, and is often associated with a refractory and relapsing disease. In contrast, JAK3 activation is not well documented in human tumors, and does not seem to play a critical role in tumorigenesis (except in some hematopoietic tumors). Various studies suggest that JAK3 inhibition offers no obvious additional benefits for antitumor activity of JAK2 inhibitors (Pesu, 2008). Thus, preferential or selective inhibition of JAK2 is a more critical target for antitumor therapies.

JAK3

JAK3 expression is generally limited to hematopoietic cells where it specifically associates with so called common gamma chain (c receptor, a subunit of receptors for IL-2, IL-4, IL-7, IL-15, IL-21 and others. These receptors are critical for proper functioning of immune system and genetic ablation of JAK3 (or gamma receptor) in mice resulted in a severe combined immunodeficiency (SCID). SCID mice have small thymuses, absence of lymph nodes and reduced numbers of thymocytes, CD8+ and NK cells; also, development of B cells is severely impaired. Importantly, mutations in JAK3 and gamma chain in human result in a very similar phenotype and account for most clinical cases of SCID. Thus, inhibition of JAK3 can result in a suppression of immune responses and severe immunodeficiency (Bone, 2003 and O'Shea, 2004). Consequently, JAK3 inhibitors have been developed as a novel class of immunosuppressant to treat transplant rejection and autoimmune diseases. The most advanced inhibitor, CP-690,550, prevented graft rejection in multiple animal models, including in cynomolgus monkey and its activity was associated with decrease in CD8 and NK cells. In Phase I and Phase II clinical studies, CYP-690,550 showed clinical efficacy in de novo kidney allograft recipients; however, increased incidence of infections was also observed. By 6 months post-transplant, significantly more patients developed infections and cytomegalovirus disease in a treated group. Additionally, 20% of subjects receiving CP-690,550 at 30 mg BID developed polyoma-associated nephropathy. These observations indicate that JAK3 inhibition results in immunodeficiency, which in cancer patients, can accelerate disease progression and complicate treatments due to additional toxicities. In particular, cancer patients undergoing multiple rounds of various and toxic therapies are often immunocompromised and additional toxicities in this area are highly undesirable.

In view of the above, compounds that preferentially inhibit JAK2 over JAK3 should exhibit antitumor activity while avoiding immunosuppressive effects associated with JAK3 inhibition. The potential immunosuppressant toxicities related to non-preferential JAK2 inhibitors, i.e., dual JAK2/JAK3 inhibitors, might be dose limiting and could decrease the therapeutic window.

JAK2/STAT

The JAK/STAT pathway is the major signaling cascade downstream from cytokine and growth factor receptors including growth hormone, prolactin and leptin (Rane et al. 2002; Levy et al. 2002; Baker et al. 2007). The signaling cascade consists of the family of non-receptor tyrosine kinases, Janus kinases (JAK) and transcription factors, STATs (signal transduction and transcription). Activated JAKs phosphorylate and activate STATs, allowing formation of homo- and heterodimers that translocate to the nucleus to regulate the transcription of STAT-dependent genes. In addition, STATs can be directly phosphorylated by non-receptor tyrosine kinases like Src or Abl. Under normal physiological conditions ligand-dependent activation of JAK/STAT signaling is transient and tightly regulated (Alexander 2002; Shuai et al. 2003).

JAK/STAT Signaling in Tumors

Constitutive activation of JAKs and STATs occurs in a wide spectrum of human cancers, both solid and hematopoietic, and is often correlated with a more malignant and metastatic phenotype and refractory tumors (Ferrajoli et al. 2006; Yu et al. 2004). In most tumors JAK2/STAT activation is mediated by constitutive expression of cytokines (IL-6, IL-4, GM-CSF) and/or by inactivation of endogenous repressors of the JAK/STAT pathway, including members of the suppressor of cytokine signaling (SOCS) family or phosphatase SHP-1. In some tumors, activating mutations in JAK1 (Flex et al. 2008), JAK2, JAK3 or JAK2 chimeric molecules are directly implicated in tumorigenesis. In addition, amplification of the JAK2 locus occurred in 35% of Hodgkin's lymphoma (HL) and 50% of primary mediastinal B-cell lymphoma (PMBL) cases (Melzner et al. 2005). Among hematological cancers, ABC-DLBCL accounts for the majority of non-Hodgkin's lymphoma (NHL) mortality with these tumors expressing high levels of activated STAT3 and showing resistance to conventional cytotoxic therapies. ABC-DLBCL cells are dependent on JAK2/STAT signaling and the inactivation of STAT3 by siRNA or small molecule JAK2 inhibition suppressed proliferation and induced apoptosis in these tumor cell lines (Ding et al. 2008).

The ectopic expression of JAK1, JAK2 and JAK3, as well as STAT3 and STAT5 results in oncogenic transformation in recipient cells, demonstrating that the activated JAK2/STAT pathway was sufficient to mediate oncogenesis in various solid and hematological tumors (Bromberg et al. 1999; Knoops et al. 2008; Scheeren et al. 2008). Inhibition of JAK2/STAT signaling in various tumor cells, including prostate, breast, colon, lung carcinomas, gliomas, and leukemias and lymphomas resulted in inhibition of growth, induction of apoptosis and suppression of tumor growth in vivo (Yu et al. 2004; Li et al. 2004; Iwamaru et al. 2007; Gao et al. 2007; Ding et al. 2008). Constitutively activated JAK2/STAT signaling in tumor cells not only promoted uncontrolled cell proliferation and anti-apoptotic signaling, but also mediated tumor immune evasion and angiogenesis (Kortylewski et al. 2005; Nefedova et al. 2007). Therefore, inhibitors of JAK/STAT signaling offer the potential to suppress multiple mechanisms underlying tumor formation and progression.

Molecular Mechanisms: JAK/STAT-Mediated Tumor Cell Survival

Activation of the JAK2/STAT pathway mediates increased survival of tumor cells by up regulating expression of multiple antiapoptotic proteins, including Bcl-2, Bcl-$X_L$, Mcl-1, survivin and others (Yu et al. 2004). Increased anti-apoptotic signaling protects tumor cells from therapy-induced cell death, a major factor contributing to drug resistance. In many tumor models inhibitors of JAK2/STAT signaling suppressed expression of anti-apoptotic proteins, decreased the apoptotic threshold and induced chemo-sensitization. Administration of non-selective JAK inhibitors like AG490 chemosensitized various tumor cell lines to multiple targeting drugs including cisplatin, fludarabine, adriamycin and doxorubicin (Alas et al. 2003). Constitutive JAK2 activation is often triggered by cytokines expressed in para- or auto-crine fashion. Elevated tumor and circulating cytokine levels are frequently detected in cancer patients and are associated with increased metastasis, drug resistance and disease relapse. High levels of IL-6 were found in 50% of patients with breast, pancreatic and lung carcinomas, HNSCC and various lymphomas (Grivennikov et al. 2008).

Acquired drug resistance can be mediated by a cytokine-driven adaptive activation of the JAK2/STAT pathway and could be overcome by the administration of JAK2 inhibitors (Wang et al. 2008), providing additional support for the role of activated JAK2/STAT signaling in cell survival and drug resistance in a variety of tumors.

Molecular Mechanisms: JAK/STAT-Mediated Tumor Immune Evasion

Constitutive activation of the JAK2/STAT pathway in tumor cells suppresses tumor immunosurveillance and dendritic cell (DC) maturation and promotes proliferation of T regulatory cells. Abnormal differentiation and accumulation of DCs in the tumor environment is the major contributor to immune evasion and is mediated by tumor-derived cytokines whose expression is driven by constitutive JAK2/STAT signaling (Nefedova et al. 2007). Pharmacological inhibition of JAK2 by JCI-124 overcame DC maturation block and promoted anti-tumor immune responses in cell culture and animal models (Nefedova et al. 2005). In this context, JAK2 inhibitors could be used against multiple tumors as immunostimulants in a maintenance phase of therapy. Immunosuppression mediated by IL-6-driven JAK2/STAT signaling in DCs could be reversed by inhibition of JAK2 activation (Bharaduwaj et al. 2007).

Constitutive Activation of JAK2/STAT Signaling: Inactivation of Endogenous Repressors:

Activation of the JAK/STAT pathway in normal cells is transient and is negatively regulated by endogenous suppressors, members of the SOCS family and phosphatases, which can directly inhibit activity of JAKs. In addition, SOCS proteins facilitate proteosomal degradation of activated JAKs. In tumors, SOCS proteins and/or phosphatase SHP-1 are frequently inactivated by promoter methylation or specific deletions (Yoshikava et al. 2001; Weber at al. 2005; Melzner et al. 2006; Weniger et al. 2006).

Clinical Implications:

The widespread inactivation of endogenous suppressors of JAK2/STAT signaling indicates a genetically-driven selective pressure suggesting that constitutive activation of the JAK2/STAT pathway is critical for growth/survival advantage of tumor cells. A frequent inactivation of endogenous repressors of the JAK2/STAT pathway combined with high levels of cytokines present in multiple tumors provides a molecular rationale for the constitutive activation of JAK2/STAT signaling observed in numerous human tumors. Thus, tumors with constitutive JAK2 signaling can readily identified via their JAK2 mutational status, STAT activation (pSTAT levels) or promoter methylation profiles using conventional diagnostic techniques and would be predicted to be sensitive to JAK2 inhibitors.

Potential Advantages of Dual FAK-JAK2 Inhibitors:

Given the considerations above, simultaneous inhibition of FAK and JAK2 signaling represents an attractive therapeutic strategy for cancer treatment and management of a variety of solid tumors (Kyu-Ho Han and McGonigal, 2007). FAK and JAK2 are constitutively activated in a wide spectrum of human tumors and their activation correlates with a relapsed, refractory and more metastatic disease. However, both kinases promote tumorigenesis through different mechanisms. FAK contributes to tumorigenesis mostly by promoting tumor cells motility, invasiveness and metastasis, and also by promoting tumor-associated angiogenesis. In contrast, JAK2/STAT signaling plays a critical role in tumor cell proliferation and anti-apoptotic signaling. The latter has been shown to mediate chemoresistance to multiple therapies. In addition, JAK/STAT signaling mediates tumor immune evasion. Thus, a dual FAK/JAK2 inhibitor can potentially suppress all major mechanisms underlying tumor growth and progression resulting in a superior antitumor efficacy.

At a molecular level, FAK signaling often operates "in parallel" to other oncogenic pathways. Although FAK activation has been shown to initiate multiple signaling cascades, including MAPK and AKT pathways, the critical pathway mediating FAK-dependent cell invasiveness and metastasis involves p130CAS/Crk/Rack pathway and the Rho family of small GTPases (Mitra et al., 2005; Zhao et al., 2009). Thus, inhibition of FAK should complement suppression of JAK/STAT and AKT pathways mediated by JAK2 inhibitors, providing a molecular framework for synergistic antitumor activity. It is important to note that in genetic mouse models of breast cancer, the loss of FAK did not affect the ability of normal cell types such as fibroblasts, keratinocytes and mammary epithelial cells to proliferate, but exerted striking inhibitory effects on mammary tumor cells carrying oncogenic mutations in Ras or PI3K (Pylayeva et al., 2009). These data suggest that these and other tumor cells exhibiting activation of both FAK and JAK/STAT signaling pathways are dependent upon these dual signaling pathways relative to normal cells. Simultaneous inhibition of both FAK and JAK2 could thus provide a "double strike" against pathways critical for tumor cell survival and malignant progression.

In addition, a dual FAK/JAK2 inhibitor should be very well suited for combinatorial therapies with conventional cytotoxic agents. Constitutive JAK2/STAT signaling contributes to chemoresistance by driving expression of antiapoptotic proteins, specifically Bcl2-family members, survivin and IAP proteins. Multiple studies demonstrate that ablation of FAK signaling (by SiRNA or dominant negative approaches) potentiated the antitumor efficacy of various agents including doxorubicin, docetaxel and gemcitabine in pre-clinical tumor animal models (Chatzizacharias et al., 2007). Pharmacological inhibition of FAK by TAE226 in combination with docetaxel achieved a strong synergistic efficacy and tumor regression in an ovarian carcinoma model (Halder et al., 2007).

A dual FAK/JAK2 inhibitor offers the potential for improved therapeutic and/or clinical efficacy in those specific cancers dependent upon activated FAK and JAK2/STAT signaling pathways (e.g. hormone-independent prostate cancers, breast cancers, colon carcinomas and HNSSCs).

Exemplary Therapeutic Applications

Several types of solid tumors are potential therapeutic and/or clinical targets for dual FAK/JAK2 inhibitors, although additional tumor types might also be of interest (Mahajan et al. 2005; Constantinescu et al. 2007; Kyu-Ho Han and McGonigal, 2007). Three selected examples of solid tumors are highlighted below.

Androgen Independent Prostate Carcinoma

JAK2/STAT5 is a major signaling pathway downstream from the prolactin receptor. Prolactin is a mitogen and survival factor for prostate cells and its expression is associated with high grade carcinomas and contributed to androgen-independent tumorigenesis (Dagvadorj et al. 2008). JAK2 inhibition suppressed prolactin-mediated signaling (Li et al. 2004). Activated STAT5 was found in 50-60% of prostate tumor specimen and in 95% of recurrent, androgen-independent prostate carcinomas. STAT5 phosphorylation correlated with high grade tumors and was predictive of an early disease reoccurrence (Li et al. 2004; Tan et al. 2008). Pre-clinically, inactivation of JAK2 or STAT5 in prostate tumor cell lines was sufficient to inhibit cell growth and induce apoptosis. It has also been demonstrated that STAT5 and the androgen receptor form stable complexes; this interaction resulted in a functional synergy and increased activity of both transcription factors, providing another molecular mechanism for androgen-independent cell proliferation linked to JAK2/STAT5 signaling (Tan et al. 2008). It is well documented that constitutive FAK activation and overexpression are frequently associated with aggressive and metastatic prostate carcinomas and that FAK controls the invasive phenotype of androgen-independent prostate cancer cells. Given the biologic and mechanistic bases for the role of both FAK and JAK2, in the invasive and metastatic phenotype of androgen-independent prostate cancer, (and in particular, the role of FAK in osteolytic metastases in this malignancy, there is a compelling rationale for the utility of a FAK/JAK2 inhibitor to address this growing unmet medical need. At present, no acceptable treatment exists for hormone-refractory prostate cancer.

EGFR-Dependent Breast Carcinomas

Constitutive EGFR signaling in breast carcinomas up regulates expression of IL-6, activating the JAK2/STAT pathway (Grivennikov et al 2008) and inducing expression of anti-apoptotic proteins. JAK2 inhibition suppressed the growth and induced apoptosis of breast tumor cell lines carrying mutated EGFR (Berishaj et al. 2007; Gao et al. 2007). Fifty percent of patients with breast carcinoma evaluated had high levels of tumor IL-6 expression and activation of STAT3 (Grivennikov et al. 2008) suggesting that these tumors would be responsive to JAK2 inhibitors. Elevated expression of IL-6 and pSTAT3 in primary tumors correlated with a poor prognosis and resistance to therapies. The role of FAK in breast tumors has been well established. The FAK gene locus is amplified in more than 50% of human breast tumors and the increased copy number correlated with significantly increased FAK expression (Pylayeva et al., 2009). High levels of FAK expression strongly correlated with metastatic breast tumors and shorter metastasis-free survival. In addition, the multivariate analysis demonstrated that elevated FAK is an independent predictor of poor outcome and it outperforms many clinically used parameters such as lymph node involvement, ER negativity or poor differentiation. These data indicate that FAK overexpression contributes to tumorigenesis of breast carcinoma. In mouse genetic models of breast cancer, Ras- and PI3K-dependent tumorigenesis required FAK signaling for initiation, maintenance and metastasis of tumors (Pylayeva et al., 2009; Lahlou et al., 2007).

Head and Neck Squamous Cell Carcinomas (HNSCC)

The widespread inactivation (>90% incidence) of the SOCS3 suppressor of JAK2/STAT signaling is indicative of activated JAK2/STAT signaling in a high percentage of human HNSCC. The role and functions of FAK in HNSCC has been studied extensively (Kornberg 1998; Mitra et al, 2005; McClean et al 2005; and Kyu-Ho Han and McGonigal, 2007) Immunohistochemical analyses of more than 200 human HNSCC clinical specimens revealed FAK over expression in the majority of primary HNSCC samples, including benign hyperplastic, pre-invasive dysplastic lesions and 100% of lymph node metastases. Pre-clinically, the deletion of FAK prior to carcinogen-induction induction of skin tumors inhibited benign papilloma formation, and the conditional ablation of FAK after benign tumors had formed inhibited their malignant progression to metastatic HNSCC (Mc Clean et al 2005; Kyu-Ho Han and McGonigal, 2007) supporting a direct association of FAK activation with the malignant progression of HNSCC.

REFERENCES

A number of scientific papers were referenced above so as to more fully describe the state of the art to which this application pertains. Full citations for these references are provided below.

Alexander W S., "Suppressors of cytokine signaling (SOCS) in the immune system", *Nature Reviews Immunology,* 2: 1-7, 2002.

Antonysamy, Stephen; Hirst, Gavin; Park, Frances; Sprengeler, Paul; Stappenbeck, Frank; Steensma, Ruo; Wilson, Mark; Wong, Melissa, "Fragment-based discovery of JAK-2 inhibitors", *Bioorg. Med. Chem. Lett.*, (2009), 19: 279-282, 2009.

Bagi C M, Roberts G W and Andresen C J, "Dual focal adhesion kinse/Pyk2 inhibitor has positive effects on bone tumors—implications for bone metastases'", *Cancer,* 2008, 112(10), 2313-2321.

Baker S J. et al., "Hematopoietic cytokine receptor signaling", *Oncogene,* 26: 6724-37, 2007.

Baxter E. et al., "Acquired mutation of the tyrosine kinase JAK2 in human myeloproliferative disorders", *Lancet:* 1054-61, 2005.

Berishaj M. et al., "Stat3 is tyrosine-phosphorylated through the interleukin-6/glycoprotein 130/Janus kinase pathway in breast cancer", *Breast Cancer Res.,* 9: R32, 2007.

Bharadwaj U. et al., "Elevated interleukin-6 and G-CSF in human pancreatic cancer cell conditioned medium suppress dendritic cell differentiation and activation", *Cancer Res.,* 67:5479-88, 2007.

Blaskovich M. et al., "Discovery of JSI-124 (cucurbitacin I), a selective Janus kinase/signal transducer and activator of transcription 3 signaling pathway inhibitor with potent antitumor activity against human and murine cancer cells in mice", *Cancer Research,* 63: 1270-1279, 2003.

Bone D. et al., "JAK3 Inhibition as a new concept for immune suppression", *Curr Opin Invest Drugs,* 2003, 4(11): 1297-1303.

Bromberg J. et al., "Stat3 as an oncogene", *Cell:* 295-303, 1999.

Buettner R. et al., "Activated STAT signaling in human tumors provides novel molecular targets for therapeutic intervention", *Clinical Cancer Research,* 8: 945-954, 2002.

Brunton, Valerie G.; Frame, Margaret C., "Src and focal adhesion kinase as therapeutic targets in cancer", *Current Opinion in Pharmacology,* 8: 427-432, 2008.

Cance W G, and Golubovskaya V M., "Focal adhesion kinase versus p53: apoptosis or survival?", *Sci Signal.,* 20; 1(20), 2008.

Chatzizacharias N et al., "Focal adhesion kinase: a promising target for anticancer therapy", *Expert Opin Ther Targets,* 11:1315-28, 2007.

Choy E., "Inhibiting interleukin-6 in rheumatoid arthritis", *Curr Rheumatol Rep:* 10, 413-7, 2008.

Constantinescu S F, Girardot M and Pecquet C., "Mining for JAK-STAT mutations in cancer", *Trends Biochem. Sci.,* 33: 122-31, 2008.

Cronstein B N, "Interleukin-6-a key mediator of systemic and local symptoms in rheumatoid arthritis", *Bull NYU Hosp Jt Dis:* 65, S11-5, 2007.

Dagvadorj A. et al., "Autocrine prolactin promotes prostate cancer cell growth via Janus kinase-2-signal transducer and activator of transcription-5a/b signaling pathway", *Endocrinology,* 148:3089-101, 2007.

Ding B. et al., "Constitutively activated STAT3 promotes cell proliferation and survival in the activated B-cell subtype of diffuse large B-cell lymphomas", *Blood,* 111:1515-23, 2008.

Ferrajoli A. et al., "The JAK-STAT pathway: a therapeutic target in hematological malignancies", *Curr Cancer Drug Targets,* 6: 671-9, 2006.

Flex E. et al., "Somatically acquired JAK1 mutations in adult acute lymphoblastic leukemia", *J Exp Med.,* 2008, 205(4), 751-758.

Galm O. et al., "SOCS-1, a negative regulator of cytokine signaling, is frequently silenced by methylation in multiple myeloma", *Blood,* 101: 2784-2788, 2003.

Gao S. Et al., "Mutations in the EGFR kinase domain mediate STAT3 activation via IL-6 production in human lung adenocarcinomas", *J Clin Invest.,* 117:3846-56, 2007.

Grivennikov S. et al., "Autocrine IL-6 signaling: a key event in tumorigenesis?", *Cancer Cell,* 13:7-9, 2008.

Halder J, Kamat A A, et al., "Focal adhesion kinase targeting using in vivo short interfering RNA delivery in neutral liposomes for ovarian carcinoma therapy", *Clin Cancer Res,* 12: 4916-24, 2006.

Halder J, Lin Y G, et al., "Therapeutic efficacy of a novel focal adhesion kinase inhibitor TAE226 in ovarian carcinoma", *Cancer Res,* 67: 10976-83, 2007.

Hexner E. et al., "Lestaurtinib (CEP701) is a JAK2 inhibitor that suppresses JAK2/STAT5 signaling and the proliferation of primary erythroid cells from patients with myeloproliferative disorders", *Blood,* 2008, 111, 5663-5671.

Igney F H. et al., "Death and anti-death: tumor resistance to apoptosis", *Nature Reviews Cancer,* 2: 277-288, 2002.

Iwamaru A. et al., "A novel inhibitor of the STAT3 pathway induces apoptosis in malignant glioma cells both in vitro and in vivo", *Oncogene,* 26:2435-44, 2007.

James et al., "A unique clonal JAK2 mutation leading to constitutive signaling causes polycythemia vera", *Nature,* 434: 1144-1148, 2005.

Jemal A, Siegel R, Ward E, Hao Y, Xu J, Murray T, Thun M J., "Cancer Statistics, 2008", *CA Cancer J Clin* 58; 71-96, (2008).

Johnson T et al., "Focal adhesion kinase controls aggressive phenotype of androgen-independent prostate cancer", *Mol Cancer Res,* 6:1639-48, 2008.

Joos S. et al., "Genomic imbalances including amplification of JAK2 in CD30+ Hodgkin cells", *Cancer Research:* 60, 549-552, 2000.

Kaufmann S H. et al., "Alterations in the apoptotic machinery and their potential role in anticancer drug resistance", *Oncogene,* 22: 7414-7430, 2003.

Kohno M, Hasegawa H, et al., "CD151 enhances cell motility and metastasis of cancer cells in the presence of focal adhesion kinase", *Int J Cancer,* 97: 336-43, 2002.

Kornberg I J., "Focal adhesion kinase in oral cancers", *Head and Neck,* 20: 634-9, 1998.

Kortylewski M. et al., "Inhibiting Stat3 signaling in the hematopoietic system elicits multicomponent antitumor immunity", *Nat. Med.,* 11:1314-21, 2005.

Knoops L. et al., "JAK kinases overexpression promotes in vitro cell transformation", *Oncogene,* 27:1511-9, 2008.

Kralovics R. et al., "A gain-of-function mutation of JAK2 in myeloproliferative disorders", *N. Eng. J. Med.,* 352, 1779-90, 2005.

Kyu-Ho Han E and McGonigal T., "Role of focal adhesion kinase in human cancer: a potential target for drug discovery", *Anti-cancer Agents in Med Chem,* 7: 681-84, 2007.

Lahlou et al., "Mammmary epithelial-specific disruption of the focal adhesion kinase blocks mammary tumor progression", *PNAS,* 104: 20302-20307, 2007.

Levine R. et al., "Activating mutation in the tyrosine kinase JAK2 in polycythemia vera", *Cancer Cell,* 7, 387-397, 2005.

Li H. et al., "Activation of signal transducer and activator of transcription 5 in human prostate cancer is associated with high histological grade", *Cancer Res.,* 64:4774-82, 2004.

Li Shufeng; Hua Zi-Chun, "FAK expression regulation and therapeutic potential", *Advances in cancer research,* 101: 45-61, 2008.

Lim S T et al., "Nuclear FAK promotes cell proliferation and survival through FERM-enhanced p53 degradation", *Mol. Cell.,* 18:9-22, 2008.

Lipka Daniel; Heidel Florian; Huber Christoph; Fischer Thomas, "Development of tyrosine kinase inhibitors for hematologic neoplasms. FLT3 and JAK2 as therapeutic targets", *Pharmazie in unserer Zeit,* 37: 394-403, 2008.

McLean G W, Carragher N O et al., "The role of focal adhesion kinase in cancer—a new therapeutic opportunity", *Nat Rev Cancer,* 5: 505-15, 2005.

Melzner et al., "Biallelic mutation in SOCS-1 impairs JAK2 degradation and sustains phosphor-JAK2 action in the MedB-1 mediastinal lymphoma line", *Blood:* 2535-2542, 2005.

Melzner et al., "Biallelic deletion within 16p13.13 including SOCS-1 in Karpas1106P mediastinal B-cell lymphoma line is associated with delayed degradation of JAK2 protein", *Int J Cancer,* 118:1941-4, 2006.

Mitra S K, Hanson D A, et al., "Focal adhesion kinase—in command and control of cell motility", *Nat Rev Mol Cell Biol,* 6: 56-68, 2005.

Murati A. et al., "PCM1-JAK2 fusion in myeloproliferative disorders and acute erythroid leukemia with t(8; 9) translocation", *Leukemia,* 19, 1692-1696, 2005.

Nefedova Y. et al., "Regulation of dendritic cell differentiation and antitumor immune response in cancer by pharmacologic-selective inhibition of the Janus-activated kinase 2/signal transducers and activators of transcription 3 pathway", *Cancer Res.,* 65: 9525-35, 2005.

Nefedova Y et al., "Targeting of Jak/STAT pathway in antigen presenting cells in cancer", *Curr Cancer Drug Targets,* 7:71-7, 2007.

O'Shea J. et al., "A New Modality for Immunosuppression: Targeting the JAK/STAT Pathway", *Nature Reviews Drug Discovery,* 2004, 3, 555-564.

Owens L V, Xu L, et al., "Over expression of the focal adhesion kinase (p125 FAK) in invasive human tumors", *Cancer Res,* 55: 2752-55, 1995.

Owens L V, Xu L, et al., "Focal adhesion kinase as a marker of invasive potential in differentiated human thyroid cancer", *Ann Surg Oncol,* 3: 100-5, 1996.

Pardanani, A., "JAK2 inhibitor therapy in myeloproliferative disorders: rationale, preclinical studies and ongoing clinical trials", *Leukemia:* 22: 23-30, 2008.

Parsons J T., "Focal adhesion kinase: the first ten years", *J Cell Sci,* 116: 1409-16, 2003.

Parsons, J. Thomas; Slack-Davis, Jill; Tilghman, Robert; Roberts, W. Gregory, "Focal Adhesion Kinase: Targeting Adhesion Signaling Pathways for Therapeutic Intervention", *Clinical Cancer Research:* 14: 627-632, 2008.

Pesu M et al., "Therapeutic targeting of Janus Kinases", *Immunological Reviews,* 2008, 223: 132-142.

Plushner S., "Tocilizumab: An interleukin-6 receptor inhibitor for the treatment of rheumatoid arthritis", *Annal of Pharmacotherapy:* 42, 1660-8, 2008.

Pommier Y. et al., "Apoptosis defects and chemotherapy resistance: molecular interaction maps and networks", *Oncogene,* 23: 2934-2949, 2004.

Pyleyeva Y. et al., "Ras- and PI3K-dependent breast tumorigenesis in mice and humans requires focal adhesion kinase signaling", *J. Clin Invest.,* 119: 252-66, 2009.

Rane S G. et al., "JAKs, STATs and Src kinases in hematopoiesis", *Oncogene,* 21: 3334-3358, 2002.

Reed J C., "Apoptosis-targeted therapies for cancer", *Cancer Cell,* 3: 17-22, 2003.

Reddy J. et al., "Differential methylation of genes that regulate cytokine signaling in lymphoid and hematopoietic tumors", *Oncogene,* 24, 732-736, 2005.

Roberts W G, Ung E, et al., "Antitumor activity and pharmacology of a selective focal adhesion kinase inhibitor, PF-562,271", *Cancer Res.,* 68: 1935-44, 2008.

Saudemont A. et al., "Dormant tumor cells develop cross-resistance to apoptosis induced by CTLs or imatinib mesylate via methylation of suppressor of cytokine signaling 1", *Cancer Res.,* 67:4491-8, 2007.

Scheeren F A. et al., "IL-21 is expressed in Hodgkin Lymphoma and activates STAT5; evidence that activated STAT5 is required for Hodgkin Lymphomagenesis", *Blood,* 2008, 111, 4706-4715.

Shuai K. et al., "Regulation of JAK-STAT signalling in the immune system", *Nature Reviews Immunology,* 3: 900-910, 2003.

Tan S H. Et al., "Transcription factor Stat5 synergizes with androgen receptor in prostate cancer cells", *Cancer Res.,* 68:236-48, 2008.

Tan, Shyh-Han; Nevalainen, Marja T., "Signal transducer and activator of transcription 5A/B in prostate and breast cancers", *Endocrine-Related Cancer,* 15: 367-390, 2008.

Tefferi A. and Spivak J., "Polycythemia vera: scientific advance and current practice", *Sem. Hematology:* 42: 206-220, 2005.

Tefferi A., "Chronic myeloid disorders: Classification and treatment overview", *Semin Hematol.,* 38 (1) Suppl 2:1-4, 2001.

Tremblay L, Hauck W, et al., "Focal adhesion kinase (pp 125FAK) expression, activation and association with paxillin and p50CSK in human metastatic prostate carcinoma", *Int J Cancer,* 68: 164-71, 1996.

Vannucchi A. et al., "Clinical profile of homozygous JAK2V617F mutation in patients with polycythemia vera or essential thrombocythemia", *Blood,* 110: 840-46, 2007.

Wang Y. et al., "Adaptive secretion of granulocyte-macrophage colony-stimulating factor (GM-CSF) mediates imatinib and nilotinib resistance in BCR/ABL+ progenitors via JAK-2/STAT-5 pathway activation", *Blood,* 109:2147-55, 2007.

Weber A. et al., "SOCS-3 is frequently methylated in head and neck squamous cell carcinoma and its precursor lesions and causes growth inhibition", *Oncogene*, 24: 6699-708, 2005.

Weniger M. et al., "Mutations of the tumor suppressor gene SOCS-1 in classical Hodgkin lymphoma are frequent and associated with nuclear phospho-STAT5 accumulation", *Oncogene*, 25: 2679-84, 2006.

Yang W, Lin Q, et al., "The nonreceptor tyrosine kinase ACK, a specific target for Cdc42 and a negative regulator of cell growth and focal adhesion complexes", *J Biol Chem*, 276: 43987-93, 2001.

Yoshikawa H. et al., "SOCS-1, a negative regulator of the JAK/STAT pathway, is silenced by methylation in human hepatocellular carcinoma and shows growth-suppression activity", *Nature Genetics*, 28: 29-35, 2001.

Yu H. et al., "The STATs of cancer-new molecular targets come of age", *Nature Reviews Cancer*, 4: 97-105, 2004.

Zhang Q. et al., "STAT3- and DNA methyltransferase-mediated epigenetic silencing of SHP-1 tyrosine phosphatase tumor suppressor gene in malignant T lymphocytes", *PNAS*, 102, 6948-6953, 2005.

Zhao J and Guan J L., "Signal transduction by focal adhesion kinase in cancer", *Cancer Metastasis Rev.*, 2009, 28, 35-49.

Assays and Model Systems and Methods

The compounds described herein were tested for their ability to inhibit the activity of a number of different kinases as described below. In general, the compounds of Formula I were found to effectively inhibit the activity of at least one or more of the kinases tested.

In one aspect, various compounds of the general Formula I may inhibit one of the kinases tested. Such compounds may be referred to as selectively inhibiting or preferentially inhibiting a particular kinase. For example, particular compounds of the general Formula I may selectively or preferentially inhibit FAK. Alternatively, particular compounds of the general Formula I may selectively or preferentially inhibit JAK2.

In another aspect, various compounds of the general Formula I may inhibit two of the kinases tested. Such compounds may be referred to as dual inhibitors. For example, particular compounds of the general Formula I may inhibit both JAK2 and FAK. Alternatively, compounds of the general Formula I may inhibit either FAK or JAK2 in addition to one of the other kinases tested.

In yet another aspect, various compounds of the general Formula III may preferentially inhibit the JAK2 enzyme in vitro. In some specific embodiments, various compounds of the general Formula III may be at least 20 fold more selective for the JAK2 enzyme over the JAK3 enzyme in vitro. In other specific embodiments, various compounds of the general Formula III may be between about 25 fold to about 200 fold more selective for the JAK2 enzyme in vitro. In still other specific embodiments, various compounds of the general Formula III may be between at least 30 fold to about 150 fold more selective for the JAK2 enzyme in vitro.

In still another aspect, various compounds of the general Formula IV may preferentially inhibit the JAK2 enzyme in vitro. In some specific embodiments, various compounds of the general Formula IV may be at least 20 fold more selective for the JAK2 enzyme over the JAK3 enzyme in vitro. In other specific embodiments, various compounds of the general Formula IV may be between about 25 fold to about 200 fold more selective for the JAK2 enzyme in vitro. In still other specific embodiments, various compounds of the general Formula IV may be between at least 30 fold to about 150 fold more selective for the JAK2 enzyme in vitro. In still other specific embodiments, In a further aspect, various compounds of the general Formula V may preferentially inhibit the JAK2 enzyme in vitro. In some specific embodiments, various compounds of the general Formula V may be at least 20 fold more selective for the JAK2 enzyme over the JAK3 enzyme in vitro. In other specific embodiments, various compounds of the general Formula V may be between about 25 fold to about 200 fold more selective for the JAK2 enzyme in vitro. In still other specific embodiments, various compounds of the general Formula V may be between at least 30 fold to about 150 fold more selective for the JAK2 enzyme in vitro. In still other specific embodiments, In a still further aspect, various compounds of the general Formulae III through V may be at least 40 fold more selective for the JAK2 enzyme over the JAK3 enzyme in vitro. In some specific embodiments, various compounds of the general Formulae III through V may be at least 50 fold more selective for the JAK2 enzyme in vitro. In other specific embodiments, various compounds of the general Formulae III through V may be at least 70 fold more selective for the JAK2 enzyme in vitro. In further specific embodiments, various compounds of the general Formulae III through V may be at least 90 fold more selective for the JAK2 enzyme in vitro.

In Vitro Assays:

Enzyme Assays for JAK Kinases:

Compounds were tested for their ability to inhibit the kinase activity of baculovirus-expressed human JAK kinases (JAK1, JAK2, JAK3 or TYK2) using the time-resolved fluorescence (TRF) detection system. The JAK1, JAK2, and JAK3 assays were run in 96-well Costar high binding plates (Cat#3922) while the TYK2 assays were performed in 96-well PerkinElmer yellow high binding plates (Cat# AAAND-0001). Both plate types were coated with 100 µL/well of 10 µg/mL Neutravidin (Pierce #31000) in TBS at 37° C. for 2 h, followed by 100 µL/well of 1 µg/mL 15-mer peptide substrate (biotinyl-amino-hexanoyl-EQEDE-PEGDYFEWLE-amide, Infinity Biotech Research and Resource) at 37° C. for 1 h. The kinase assay mixture (total volume=100 µL/well) consisting of 20 mM HEPES (pH 7.2), ATP ($K_m$ level for each kinase), 1 mM $MnCl_2$, 0.1% BSA, and test compound (diluted in DMSO; 2.5% DMSO final in assay) was added to the assay plate. The concentrations of ATP used were as follows: 0.2 µM for JAK1, JAK2 and TYK2; 0.1 µM for JAK3. Enzyme (15 ng/mL $JAK2_{C318}$ Lot#JA2-2.1; 100 ng/mL $JAK1_{C300}$ Lot# JA1-4.1; 20 ng/mL $JAK3_{C341}$ Lot# JK3-2.1; or 50 ng/mL $TYK2_{C311}$ Lot# TY2-4.1) was added and the reaction was allowed to proceed at room temperature for 20 min. Detection of the phosphorylated product was performed by adding 100 µL/well of Eu—N1 labeled PY100 antibody diluted 1:5000 or 1:10000 in 0.25% BSA in TBS-T (PerkinElmer #AD0041). Samples were incubated at room temperature for 1 h, followed by addition of 100 µL enhancement solution (PerkinElmer #1244-105). Plates were agitated for 10 min and the fluorescence of the resulting solution measured using the PerkinElmer EnVision® 2102 or 2104 multi-label plate reader. Inhibition data were analyzed using ActivityBase and $IC_{50}$ curves generated using XLFit.

Enzyme Assays for FAK and PYK2:

The ability of compounds to inhibit the kinase activity of baculovirus-expressed human FAK and PYK2 was measured using the 96-well plate TRF assay system described above for JAK2. Recombinant human full-length GST-tagged FAK (activated in vitro by His-tagged src) was obtained from Invitrogen (Cat# PV3832 Lot#493284A) while PYK2 (Lot# PKg-1.1) was generated in-house. For the FAK kinase assay, the reaction mixture (total volume=100 µL/well) contained 20 mM HEPES (pH 7.2), 10 µM ATP, 5 mM MgCl$_2$, 0.5 mM DTT, 0.1% BSA, and test compound (diluted in DMSO; 2.5% DMSO final in assay). For PYK2, the 100 µL assay solution consisted of 20 mM HEPES (pH 7.2), 3 µM ATP, 5 mM MnCl$_2$, 0.1% BSA, and test compound (diluted in DMSO; 2.5% DMSO final in assay). Enzyme (10 ng/mL FAK or 25 ng/mL PYK2) was added and the reaction was allowed to proceed at room temperature for 30 min. Detection of the phosphorylated product was performed by adding 100 µL/well of Eu—N1 labeled PY100 antibody diluted 1:75000 in 0.25% BSA in TBS-T (PerkinElmer #AD0041). Samples were incubated at room temperature for 1 h, followed by addition of 100 µL enhancement solution (PerkinElmer #1244-105). Plates were agitated for 10 min and fluorescence of the resulting solution measured using the PerkinElmer EnVision® 2102 or 2104 multi-label plate reader. Inhibition data were analyzed using ActivityBase and IC$_{50}$ curves generated using XLFit.

Insulin Receptor Counterscreen:

Inhibition of the kinase activity of baculovirus-expressed human βIR$_{CD}$ (Lot# hIRK-2.1) was measured in a TRF assay system using 96-well plates (Greiner #655074). Briefly, each plate was coated with 100 µL/well of 20 mg/mL substrate solution (recombinant GST-PLCγ Lot # P5.1A) in TBS. The IR assay mixture (total volume=100 µL/well) consisting of 20 mM HEPES (pH 7.2), 20 µM ATP, 5 mM MnCl$_2$, 0.1% BSA, and test compound (diluted in DMSO; 2.5% DMSO final) was added to the assay plates. Enzyme (20 ng/mL βIR$_{CD}$) was added and the reaction was allowed to proceed at room temperature for 20 min. Detection of the phosphorylated product was performed by adding 100 µL/well of Eu—N1 labeled PY100 antibody (PerkinElmer#AD0160; 1:10,000 in 0.25% BSA in TBS-T). Incubation at 37° C. for 1 h was followed by addition of 50 µL enhancement solution (PerkinElmer #1244-105). Plates were agitated for 10 min and the fluorescence of the resulting solution was measured using the PerkinElmer EnVision® 2102 or 2104 multi-label plate reader Inhibition data were analyzed using ActivityBase and IC$_{50}$ curves were generated using XLFit.

Cellular Wild-Type JAK2 Assay:

Banked irf-bla TF-1 cells were quickly thawed and diluted 1:20 into assay media containing modified DMEM/F12 (Gibco Cat#12634), 0.5% FBS (Invitrogen Cat#26400-044), 2 mM glutamine (Gibco Cat#35050), 100 U/mL penicillin, 100 µg/mL streptomycin (Mediatech Cat#30-002-CI). The suspension was spun at 1500 rpm for 3 min and resuspended at 1.25×10$^6$ cells/mL. Aliquots (40 µL/well) were transferred into black 384-well clear bottom plates (Corning Cat#3712); 40 µL media substituted for background wells. The assay plate was incubated overnight at 5% CO$_2$, 37° C. Compound serial dilutions (½-log, ten-point concentrations) in DMSO at 400× final assay concentration were made in 384-well polypropylene plates (NUNC Cat#264573) utilizing the Biomek NX Span-8 liquid handler.

Compound or DMSO (100 nL) was added to assay plates utilizing the pintool attachment of the Biomek FX-384. The assay plate was incubated for 1 h prior to adding 5 µL/well of GM-CSF (Invitrogen Cat#PHC2015) diluted in assay media (1 ng/mL final concentration in assay). The plate was incubated for another 5 h. Development was initiated by addition of 8 µL LiveBLAzer FRET β-lactamase loading solution per well (Invitrogen #K1095), and the plate incubated for 4 h at room temperature. Detection was performed on the PerkinElmer Envision® plate reader [bottom read, general dual mirror, excitation filter 405 nm (8 nm bandwidth) emission filters 535 nm (25 nm bandwidth) and 460 nm (25 nm bandwidth)]. Controls included on each assay plate were as follows: no cell background (n=16); positive control/DMSO only (n=24) and negative control/CEP-0100501 at 2 µM (n=24). The average emission of no cell control wells was subtracted from the emission of each cell-containing well for both the 460 nm and the 530 nm measurements. The 460/530 ratios of the background-subtracted wells were determined and the percent inhibition calculated using the 460/530 ratio Inhibition data were analyzed by nonlinear regression using the sigmoidal dose-response (variable slope) equation in XLFit (ActivityBase) to determine IC$_{50}$ values. The values for bottom and top were fixed at 0 and 100, respectively. For each compound, the mean IC$_{50}$ value was reported as the average of at least 3 independent determinations.

Cellular JAK2 V617F Assay:

Banked irf-bla HEL cells were quickly thawed and diluted 1:20 into assay media containing Advanced-RPMI 1640 media, 2 mM glutamine, 100 U/mL penicillin and 100 µg/mL streptomycin. The suspension was spun at 1500 rpm for 3 min. and resuspended in assay media at 7.5×10$^5$ cells/mL. Cells were dispensed into assay plates, incubated and inhibitor added as described for the wild-type assay. After inhibitor addition, the assay plates were incubated for 6 h before the addition of the β-lactamase loading solution. FRET measurement was done using the PerkinElmer Envision® plate reader. Data analysis was performed as described for wild-type JAK2.

Cellular pFAK and FAK Assays:

Selected human tumor cell lines were plated in a full medium 14-16 h before a treatment with inhibitors. Cells (50-60% confluent) were rinsed with PBS and incubated for 2 h in a serum-free medium containing inhibitor at indicated concentrations. Cells were lysed in a Triton-based lysis buffer supplemented with proteases and phosphatases inhibitors (for western blot) or in an ELISA lysis buffer (BioSource). For western blots, 30-40 µg extract per lane was separated by PAGE and specific antibodies were used to evaluate pFAK (BioSource, #44-624G) and FAK (Cell Signaling, #3285) expression. Precoated ELISA kits for pFAK and FAK were purchased from BioSource and analysis was performed according to manufacturer's recommendations. Expression of phoshoFAK was normalized to the total FAK and controls were designated as 100%.

The compounds described herein were tested according to procedures described above. The results of these tests are set forth below in Table 1:

| Ex. # | FAK IC50 (nM) | JAK2 IC50 (nM) | JAK3 IC50 (nM) | Name |
|---|---|---|---|---|
| 1 | | 1089.1 | 2999 | Phenyl-[1,2,4]triazolo[1,5-a]pyridin-2-yl-amine |
| 2 | 6499 | 20.0 | 88.3 | [8-(2-Methoxy-phenyl)-[1,2,4]triazolo[1,5-a]pyridin-2-yl]-(4-morpholin-4-yl-phenyl)-amine |

-continued

| Ex. # | FAK IC50 (nM) | JAK2 IC50 (nM) | JAK3 IC50 (nM) | Name |
|---|---|---|---|---|
| 3 | | 96.9 | 509.6 | [8-(2-Methoxy-phenyl)-[1,2,4]triazolo[1,5-a]pyridin-2-yl]-phenyl-amine |
| 4 | 461.2 | 0.9 | 22.5 | [8-(4-Methanesulfonyl-phenyl)-[1,2,4]triazolo[1,5-a]pyridin-2-yl]-(4-morpholin-4-yl-phenyl)-amine |
| 5 | | 1.5 | 41 | [8-(4-Methanesulfonyl-phenyl)-[1,2,4]triazolo[1,5-a]pyridin-2-yl]-phenyl-amine |
| 6 | 2999 | 25.9 | 1223.2 | (4-Morpholin-4-yl-phenyl)-(8-pyridin-3-yl-[1,2,4]triazolo[1,5-a]pyridin-2-yl)-amine |
| 7 | | 149.1 | 3752.5 | Phenyl-(8-pyridin-3-yl-[1,2,4]triazolo[1,5-a]pyridin-2-yl)-amine |
| 8 | 1477.4 | 13.4 | 517.9 | [8-(6-Methoxy-pyridin-3-yl)-[1,2,4]triazolo[1,5-a]pyridin-2-yl]-(4-morpholin-4-yl-phenyl)-amine |
| 9 | | 50.2 | 1901.1 | [8-(6-Methoxy-pyridin-3-yl)-[1,2,4]triazolo[1,5-a]pyridin-2-yl]-phenyl-amine |
| 10 | 205.8 | 1.0 | 40.3 | [8-(4-Methanesulfonyl-phenyl)-[1,2,4]triazolo[1,5-a]pyridin-2-yl]-[4-(2-pyrrolidin-1-yl-ethoxy)-phenyl]-amine |
| 11 | 6499 | 5.5 | 174.3 | (4-Morpholin-4-yl-phenyl)-(8-pyridin-4-yl-[1,2,4]triazolo[1,5-a]pyridin-2-yl)-amine |
| 12 | 434 | 0.7 | 17.7 | [5-(4-Methanesulfonyl-phenyl)-[1,2,4]triazolo[1,5-a]pyridin-2-yl]-(4-morpholin-4-yl-phenyl)-amine |
| 13 | 523.7 | 3.0 | 111.5 | [8-(3-Methanesulfonyl-phenyl)-[1,2,4]triazolo[1,5-a]pyridin-2-yl]-[4-(2-pyrrolidin-1-yl-ethoxy)-phenyl]-amine |
| 14 | 9999 | 53.4 | 1891.4 | (8-Pyridin-4-yl-[1,2,4]triazolo[1,5-a]pyridin-2-yl)-[4-(2-pyrrolidin-1-yl-ethoxy)-phenyl]-amine |
| 15 | | 2999.0 | 9999 | Phenyl-(8-pyridin-4-yl-[1,2,4]triazolo[1,5-a]pyridin-2-yl)-[4-(2-pyrrolidin-1-yl-ethoxy)-phenyl]-amine |
| 16 | 3123.7 | 2.6 | 87.6 | [8-(3-Methanesulfonyl-phenyl)-[1,2,4]triazolo[1,5-a]pyridin-2-yl]-(4-morpholin-4-yl-phenyl)-amine |
| 17 | | 8.5 | 415.2 | [8-(3-Methanesulfonyl-phenyl)-[1,2,4]triazolo[1,5-a]pyridin-2-yl]-phenyl-amine |
| 18 | | 0.6 | 26.8 | [8-(4-Methanesulfonyl-phenyl)-[1,2,4]triazolo[1,5-a]pyridin-2-yl]-(4-piperidin-1-yl-phenyl)-amine |
| 19 | 1580.8 | 1.0 | 41.3 | [8-(4-Methanesulfonyl-phenyl)-[1,2,4]triazolo[1,5-a]pyridin-2-yl]-(4-methoxy-phenyl)-amine |
| 20 | | 9999.0 | 9999 | (2-Methoxy-phenyl)-[8-(4-trifluoromethyl-phenyl)-[1,2,4]triazolo[1,5-a]pyridin-2-yl]-amine |
| 21 | | 2999.0 | 9999 | (2-Methoxy-phenyl)-[8-(3-trifluoromethyl-phenyl)-[1,2,4]triazolo[1,5-a]pyridin-2-yl]-amine |
| 22 | | 9999.0 | 9999 | (2-Methoxy-phenyl)-(8-phenyl-[1,2,4]triazolo[1,5-a]pyridin-2-yl)-amine |
| 23 | | 9999.0 | 9999 | 3-[2-(2-Methoxy-phenylamino)-[1,2,4]triazolo[1,5-a]pyridin-8-yl]-N-methyl-benzamide |
| 24 | | 9999.0 | 9999 | 4-[2-(2-Methoxy-phenylamino)-[1,2,4]triazolo[1,5-a]pyridin-8-yl]-N-methyl-benzamide |
| 25 | | 1321.1 | 9999 | [8-(4-Methanesulfonyl-phenyl)-[1,2,4]triazolo[1,5-a]pyridin-2-yl]-(2-methoxy-phenyl)-amine |
| 26 | 584.9 | 1.3 | 38.5 | [8-(4-Methanesulfonyl-phenyl)-[1,2,4]triazolo[1,5-a]pyridin-2-yl]- |

-continued

| Ex. # | FAK IC50 (nM) | JAK2 IC50 (nM) | JAK3 IC50 (nM) | Name |
|---|---|---|---|---|
| 27 | 2022.2 | 0.4 | 31 | [4-(2-morpholin-4-yl-ethoxy)-phenyl]-amine [8-(4-Methanesulfonyl-phenyl)-[1,2,4]triazolo[1,5-a]pyridin-2-yl]-(3-morpholin-4-yl-phenyl)-amine |
| 28 | | 27.7 | 9999 | [8-(4-Methanesulfonyl-phenyl)-[1,2,4]triazolo[1,5-a]pyridin-2-yl]-(5,5,8,8-tetramethyl-5,6,7,8-tetrahydro-naphthalen-2-yl)-amine |
| 29 | 1348.9 | 5.6 | 183 | [8-(3-Methanesulfonyl-phenyl)-[1,2,4]triazolo[1,5-a]pyridin-2-yl]-(3-morpholin-4-yl-phenyl)-amine |
| 30 | | 440.6 | 9999 | (4-Methoxy-phenyl)-[8-(4-methyl-piperazin-1-yl)-[1,2,4]triazolo[1,5-a]pyridin-2-yl]-amine |
| 31 | | 568.0 | 6499 | 8-(1,1-dioxidothiomorphotin-4-yl)-N-(4-methoxyphenyl)[1,2,4]triazolo[1,5-a]pyridin-2-amine |
| 32 | 410.2 | 2.4 | 30.7 | [8-(4-Methanesulfonyl-phenyl)-[1,2,4]triazolo[1,5-a]pyridin-2-yl]-[4-(4-methyl-piperazin-1-yl)-phenyl]-amine |
| 33 | | 60.4 | 1506.5 | [8-(4-Methanesulfonyl-piperazin-1-yl)-[1,2,4]triazolo[1,5-a]pyridin-2-yl]-(4-methoxy-phenyl)-amine |
| 34 | | 1.0 | 68 | [8-(1-Methanesulfonyl-1,2,3,6-tetrahydro-pyridin-4-yl)-[1,2,4]triazolo[1,5-a]pyridin-2-yl]-(4-methoxy-phenyl)-amine |
| 35 | 1056.3 | 1.3 | 84.7 | [8-(4-Methanesulfonyl-phenyl)-[1,2,4]triazolo[1,5-a]pyridin-2-yl]-[3-(4-methyl-piperazin-1-yl)-phenyl]-amine |
| 36 | 9999 | 9999.0 | 9999 | [6-(4-Methanesulfonyl-phenyl)-[1,2,4]triazolo[1,5-a]pyridin-2-yl]-(4-morpholin-4-yl-phenyl)-amine |
| 37 | 9999 | 2973.1 | 9999 | [6-(4-Methanesulfonyl-phenyl)-[1,2,4]triazolo[1,5-a]pyridin-2-yl]-[4-(4-methyl-piperazin-1-yl)-phenyl]-amine |
| 38 | 9999 | 470.2 | 6499 | N(8)-(4-Methanesulfonyl-phenyl)-N(2)-(4-methoxy-phenyl)-[1,2,4]triazolo[1,5-a]pyridine-2,8-diamine |
| 39 | 2357.8 | 32.6 | 510.3 | (4-Methoxy-phenyl)-[8-(1H-pyrazol-4-yl)-[1,2,4]triazolo[1,5-a]pyridin-2-yl]-amine |
| 40 | 1355 | 1.0 | 60.8 | [8-(4-Methanesulfonyl-phenyl)-[1,2,4]triazolo[1,5-a]pyridin-2-yl]-(3-methoxy-phenyl)-amine |
| 41 | 9999 | 374.9 | 9999 | N(8)-(1-Methanesulfonyl-piperidin-4-yl)-N(2)-(4-methoxy-phenyl)-[1,2,4]triazolo[1,5-a]pyridine-2,8-diamine |
| 42 | 507.4 | 3.0 | 56.3 | [8-(1-Methanesulfonyl-1H-pyrazol-4-yl)-[1,2,4]triazolo[1,5-a]pyridin-2-yl]-(4-methoxy-phenyl)-amine |
| 43 | 1170.8 | 2.2 | 67.6 | [8-(4-Methanesulfonyl-phenyl)-[1,2,4]triazolo[1,5-a]pyridin-2-yl]-(4-morpholin-4-ylmethyl-phenyl)-amine |
| 44 | 1126.1 | 2.4 | 58.6 | [8-(4-Methanesulfonyl-phenyl)-[1,2,4]triazolo[1,5-a]pyridin-2-yl]-[4-(4-methyl-piperazin-1-ylmethyl)-phenyl]-amine |
| 45 | 9999 | 106.1 | 9999 | 1,1,2,2,3,3,4,4,4-Nonafluoro-butane-1-sulfonic acid 4-[8-(4-methanesulfonyl-phenyl)-[1,2,4]triazolo[1,5-a]pyridin-2-ylamino]-phenyl ester |
| 46 | 953.3 | 0.6 | 14.8 | [8-(4-Methanesulfonyl-phenyl)-[1,2,4]triazolo[1,5-a]pyridin-2-yl]-(3-morpholin-4-ylmethyl-phenyl)-amine |
| 47 | 2999 | 12.8 | 111.7 | N(8)-(2-Methanesulfonyl-phenyl)-N(2)-(4-methoxy-phenyl)- |

-continued

| Ex. # | FAK IC50 (nM) | JAK2 IC50 (nM) | JAK3 IC50 (nM) | Name |
|---|---|---|---|---|
| | | | | [1,2,4]triazolo[1,5-a]pyridine-2,8-diamine |
| 48 | 1718.5 | 0.7 | 1.5 | [8-(4-Methanesulfonylmethyl-phenyl)-[1,2,4]triazolo[1,5-a]pyridin-2-yl]-[4-(4-methyl-piperazin-1-yl)-phenyl]-amine |
| 49 | 250.7 | | 59.5 | [8-(4-Methanesulfonyl-phenyl)-[1,2,4]triazolo[1,5-a]pyridin-2-yl]-[4-(4-morpholin-4-yl-piperidin-1-yl)-phenyl]-amine |
| 50 | 568.8 | 1.1 | 34.6 | [8-(4-Methanesulfonyl-phenyl)-[1,2,4]triazolo[1,5-a]pyridin-2-yl]-[4-(1-methyl-piperidin-4-yl)-phenyl]-amine |
| 51 | 168.3 | 1.8 | 31.2 | [8-(4-Methanesulfonyl-phenyl)-[1,2,4]triazolo[1,5-a]pyridin-2-yl]-{4-[4-(4-methyl-piperazin-1-yl)-piperidin-1-yl]-phenyl}-amine |
| 52 | 306.4 | 2.1 | 42.4 | [4-(4-Methyl-piperazin-1-yl)-phenyl]-{8-[4-(propane-2-sulfonyl)-phenyl]-[1,2,4]triazolo[1,5-a]pyridin-2-yl}-amine |
| 53 | 865 | 1.3 | 37.8 | [3-(4-Methyl-piperazin-1-yl)-phenyl]-{8-[4-(propane-2-sulfonyl)-phenyl]-[1,2,4]triazolo[1,5-a]pyridin-2-yl}-amine |
| 54 | 787.3 | 1.7 | 33.3 | N,N-Dimethyl-4-{2-[4-(4-methyl-piperazin-1-yl)-phenylamino]-[1,2,4]triazolo[1,5-a]pyridin-8-yl}-benzenesulfonamide |
| 55 | 2999 | 38.4 | 100.5 | [8-(2-Methoxy-phenyl)-[1,2,4]triazolo[1,5-a]pyridin-2-yl]-[4-(4-methyl-piperazin-1-yl)-phenyl]-amine |
| 56 | 2999 | 26.8 | 219.7 | [8-(2-Methoxy-phenyl)-[1,2,4]triazolo[1,5-a]pyridin-2-yl]-[3-(4-methyl-piperazin-1-yl)-phenyl]-amine |
| 57 | 1178.1 | 0.5 | 47.6 | [8-(4-Methanesulfonyl-phenyl)-[1,2,4]triazolo[1,5-a]pyridin-2-yl]-[3-(4-morpholin-4-yl-piperidin-1-yl)-phenyl]-amine |
| 58 | 2385.2 | 1.5 | 81.3 | [8-(4-Methanesulfonyl-phenyl)-[1,2,4]triazolo[1,5-a]pyridin-2-yl]-{3-[4-(4-methyl-piperazin-1-yl)-piperidin-1-yl]-phenyl}-amine |
| 59 | 2586 | 3.3 | 89.4 | [8-(3-Methanesulfonyl-phenyl)-[1,2,4]triazolo[1,5-a]pyridin-2-yl]-[4-(4-methyl-piperazin-1-yl)-phenyl]-amine |
| 60 | 1255.1 | 6.4 | 206.7 | [8-(3-Methanesulfonyl-phenyl)-[1,2,4]triazolo[1,5-a]pyridin-2-yl]-[3-(4-methyl-piperazin-1-yl)-phenyl]-amine |
| 61 | 265.1 | 0.7 | 52.1 | [8-(4-Methanesulfonyl-phenyl)-[1,2,4]triazolo[1,5-a]pyridin-2-yl]-[3-(1-methyl-piperidin-4-yl)-phenyl]-amine |
| 62 | 999 | 0.6 | 11.9 | N-Methyl-N-(4-{2-[4-(4-methyl-piperazin-1-yl)-phenylamino]-[1,2,4]triazolo[1,5-a]pyridin-8-yl}-phenyl)-methanesulfonamide |
| 63 | 1350.1 | 0.6 | 26 | N-Methyl-N-(4-{2-[3-(4-methyl-piperazin-1-yl)-phenylamino]-[1,2,4]triazolo[1,5-a]pyridin-8-yl}-phenyl)-methanesulfonamide |
| 64 | 1247.9 | 3.1 | 69.9 | [4-(4-Methyl-piperazin-1-yl)-phenyl]-[8-(4-trifluoromethyl-phenyl)-[1,2,4]triazolo[1,5-a]pyridin-2-yl]-amine |
| 65 | 999 | 3.7 | 208.1 | [3-(4-Methyl-piperazin-1-yl)-phenyl]-[8-(4-trifluoromethyl-phenyl)-[1,2,4]triazolo[1,5-a]pyridin-2-yl]-amine |

-continued

| Ex. # | FAK IC50 (nM) | JAK2 IC50 (nM) | JAK3 IC50 (nM) | Name |
|---|---|---|---|---|
| 66 | 9999 | 1326.3 | 6499 | [8-(2-Methanesulfonyl-phenyl)-[1,2,4]triazolo[1,5-a]pyridin-2-yl]-[4-(4-methyl-piperazin-1-yl)-phenyl]-amine |
| 67 | 9999 | 2496.3 | 9999 | [8-(2-Methanesulfonyl-phenyl)-[1,2,4]triazolo[1,5-a]pyridin-2-yl]-[3-(4-methyl-piperazin-1-yl)-phenyl]-amine |
| 68 | 608.4 | 29.0 | 612 | N(8)-(2-Methanesulfonyl-phenyl)-N(2)-[3-(4-methyl-piperazin-1-yl)-phenyl]-[1,2,4]triazolo[1,5-a]pyridine-2,8-diamine |
| 69 | 6499 | 9999.0 | 9999 | N(2),N(8)-Bis-(2-methanesulfonyl-phenyl)-[1,2,4]triazolo[1,5-a]pyridine-2,8-diamine |
| 70 | 291 | 1.1 | 14.7 | 5-{4-[(1,1-dioxidothiomorpholin-4-yl)methyl]phenyl}-N-[4-(4-methylpiperazin-1-yl)phenyl][1,2,4]triazolo[1,5-a]pyridin-2-amine |
| 71 | 502.4 | 0.8 | 37.8 | 5-{4-[(1,1-dioxidothiomorpholin-4-yl)methyl]phenyl}-N-[3-(4-methylpiperazin-1-yl)phenyl][1,2,4]triazolo[1,5-a]pyridin-2-amine |
| 72 | 379.8 | 8.3 | 160 | N(8)-(2-Methanesulfonyl-phenyl)-N(2)-[4-(4-methyl-piperazin-1-yl)-phenyl]-[1,2,4]triazolo[1,5-a]pyridine-2,8-diamine |
| 73 | 226.9 | 2.1 | 71 | [5-(4-Methanesulfonyl-phenyl)-[1,2,4]triazolo[1,5-a]pyridin-2-yl]-[4-(2-pyrrolidin-1-yl-ethoxy)-phenyl]-amine |
| 74 |  | 2.1 | 92.7 | [5-(4-Methanesulfonyl-phenyl)-[1,2,4]triazolo[1,5-a]pyridin-2-yl]-phenyl-amine |
| 75 | 359.4 | 1.3 | 50.2 | 4-{4-[5-(4-Methanesulfonyl-phenyl)-[1,2,4]triazolo[1,5-a]pyridin-2-ylamino]-phenyl}-piperazine-1-carboxylic acid tert-butyl ester |
| 76 | 9999 | 9999.0 | 9999 | (5-Phenyl-[1,2,4]triazolo[1,5-a]pyridin-2-yl)-[4-(2-pyrrolidin-1-yl-ethoxy)-phenyl]-amine |
| 77 |  | 6.6 | 100.9 | 4-[4-(5-Phenyl-[1,2,4]triazolo[1,5-a]pyridin-2-ylamino)-phenyl]-piperazine-1-carboxylic acid tert-butyl ester |
| 78 | 1531 | 3.2 | 52.6 | [5-(3-Methanesulfonyl-phenyl)-[1,2,4]triazolo[1,5-a]pyridin-2-yl]-(4-morpholin-4-yl-phenyl)-amine |
| 79 |  | 15.1 | 197 | [5-(3-Methanesulfonyl-phenyl)-[1,2,4]triazolo[1,5-a]pyridin-2-yl]-(3-methoxy-phenyl)-amine |
| 80 |  | 1210.9 | 9999 | [5-(3-Methanesulfonyl-phenyl)-[1,2,4]triazolo[1,5-a]pyridin-2-yl]-(2-methoxy-phenyl)-amine |
| 81 | 421.2 | 6.9 | 99.2 | [5-(4-Methanesulfonyl-phenyl)-[1,2,4]triazolo[1,5-a]pyridin-2-yl]-[4-(4-methyl-piperazin-1-yl)-phenyl]-amine |
| 82 | 584 | 9.2 | 137.9 | [5-(3-Methanesulfonyl-phenyl)-[1,2,4]triazolo[1,5-a]pyridin-2-yl]-[4-(4-methyl-piperazin-1-yl)-phenyl]-amine |
| 83 | 552.7 | 19.0 | 497.5 | N-(3-{2-[4-(4-Methyl-piperazin-1-yl)-phenylamino]-[1,2,4]triazolo[1,5-a]pyridin-5-yl}-phenyl)-methanesulfonamide |
| 84 | 2284.1 | 2.8 | 67.6 | N-(4-{2-[4-(4-Methyl-piperazin-1-yl)-phenylamino]-[1,2,4]triazolo[1,5-a]pyridin-5-yl}-phenyl)-methanesulfonamide |
| 85 | 173 | 1.1 | 36.8 | [5-(4-Methanesulfonyl-phenyl)-[1,2,4]triazolo[1,5-a]pyridin-2-yl]-(4-morpholin-4-ylmethyl-phenyl)-amine |

-continued

| Ex. # | FAK IC50 (nM) | JAK2 IC50 (nM) | JAK3 IC50 (nM) | Name |
|---|---|---|---|---|
| 86 | 263.5 | 1.7 | 76.1 | [5-(4-Methanesulfonyl-phenyl)-[1,2,4]triazolo[1,5-a]pyridin-2-yl]-[4-(4-methyl-piperazin-1-ylmethyl)-phenyl]-amine |
| 87 | 341.2 | 4.9 | 105.6 | [5-(3-Methanesulfonyl-phenyl)-[1,2,4]triazolo[1,5-a]pyridin-2-yl]-(4-morpholin-4-ylmethyl-phenyl)-amine |
| 88 | 1031.3 | 11.7 | 219.6 | [5-(3-Methanesulfonyl-phenyl)-[1,2,4]triazolo[1,5-a]pyridin-2-yl]-[4-(4-methyl-piperazin-1-ylmethyl)-phenyl]-amine |
| 89 | 8832.3 | 229.5 | 2353.8 | 1-[5-(3-Methanesulfonyl-phenyl)-[1,2,4]triazolo[1,5-a]pyridin-2-yl]-3-[4-(4-methyl-piperazin-1-yl)-phenyl]-urea |
| 90 | 9999 | 1531.9 | 9999 | 1-[5-(4-Methanesulfonyl-phenyl)-[1,2,4]triazolo[1,5-a]pyridin-2-yl]-3-[4-(4-methyl-piperazin-1-yl)-phenyl]-urea |
| 91 | 2599.8 | 1.9 | 63.9 | [5-(4-Methanesulfonyl-phenyl)-[1,2,4]triazolo[1,5-a]pyridin-2-yl]-(4-methoxy-phenyl)-amine |
| 92 | 1268.1 | 2.8 | 121.9 | [5-(4-Methanesulfonyl-phenyl)-[1,2,4]triazolo[1,5-a]pyridin-2-yl]-[3-(4-methyl-piperazin-1-yl)-phenyl]-amine |
| 93 | 531.5 | 1.4 | 69.9 | (4-Methanesulfonyl-phenyl)-[5-(4-methanesulfonyl-phenyl)-[1,2,4]triazolo[1,5-a]pyridin-2-yl]-amine |
| 94 | 2999 | 9.3 | 718.9 | (3-Methanesulfonyl-phenyl)-[5-(4-methanesulfonyl-phenyl)-[1,2,4]triazolo[1,5-a]pyridin-2-yl]-amine |
| 95 | 1999 | 1.0 | 25.3 | 5-{4-[(1,1-dioxidothiomorpholin-4-yl)methyl]phenyl}-N-(4-methoxyphenyl)[1,2,4]triazolo[1,5-a]pyridin-2-amine |
| 96 | 9999 | 9999.0 | 9999 | [2-(4-Methyl-piperazin-1-yl)-[1,2,4]triazolo[1,5-a]pyridin-8-yl]-(3-nitro-benzyl)-amine |
| 97 | 9999 | 9999.0 | 9999 | (3-Amino-benzyl)-[2-(4-methyl-piperazin-1-yl)-[1,2,4]triazolo[1,5-a]pyridin-8-yl]-amine |
| 98 | 9999 | 9999.0 | 9999 | (2-Morpholin-4-yl-[1,2,4]triazolo[1,5-a]pyridin-8-yl)-(3-nitro-benzyl)-amine |
| 99 | 9999 | 9999.0 | 9999 | [2-(4-Amino-piperidin-1-yl)-[1,2,4]triazolo[1,5-a]pyridin-8-yl]-pyridin-3-ylmethyl-amine |
| 101 | 9999 | 9999.0 | 9999 | N*2*-(2-Morpholin-4-yl-ethyl)-N*8*-pyridin-3-ylmethyl-[1,2,4]triazolo[1,5-a]pyridine-2,8-diamine |
| 102 | 9999 | 9999.0 | 9999 | [8-(4-Methanesulfonyl-phenyl)-6-trifluoromethyl-[1,2,4]triazolo[1,5-a]pyridin-2-yl]-[3-(4-methyl-piperazin-1-yl)-phenyl]-amine |
| 103 | 9999 | 9999.0 | 9999 | [8-(4-Methanesulfonyl-phenyl)-6-trifluoromethyl-[1,2,4]triazolo[1,5-a]pyridin-2-yl]-[4-(4-methyl-piperazin-1-yl)-phenyl]-amine |
| 104 | 669.3 | 927.5 | 3440.6 | [8-(4-Methanesulfonyl-phenyl)-6-trifluoromethyl-[1,2,4]triazolo[1,5-a]pyridin-2-yl]-[6-(4-methyl-piperazin-1-yl)-pyridin-3-yl]-amine |
| 105 | 1053 | 324.1 | 2138.4 | [6-Fluoro-8-(4-methanesulfonyl-phenyl)-[1,2,4]triazolo[1,5-a]pyridin-2-yl]-bis-[3-(4-methyl-piperazin-1-yl)-phenyl]-amine |
| 106 | 2999 | 31.6 | 932.9 | [6-Fluoro-8-(4-methanesulfonyl-phenyl)-[1,2,4]triazolo[1,5-a]pyridin-2-yl]-[4-(4-methyl-piperazin-1-yl)-phenyl]-amine |
| 107 | 854.6 | 307.1 | 9999 | [5-(4-Methanesulfonyl-phenyl)-[1,2,4]triazolo[1,5-a]pyrazin-2-yl]- |

-continued

| Ex. # | FAK IC50 (nM) | JAK2 IC50 (nM) | JAK3 IC50 (nM) | Name |
|---|---|---|---|---|
| 108 | 3374.2 | 927.1 | 9999 | [3-(4-methyl-piperazin-1-yl)-phenyl]-amine [5-(4-Methanesulfonyl-phenyl)-[1,2,4]triazolo[1,5-a]pyrazin-2-yl]-[5-(4-methyl-piperazin-1-yl)-pyridin-3-yl]-amine |
| 109 | 9999 | 326.56 | 3049.69 | N(8)-(3-Methanesulfonyl-phenyl)-N(2)-[4-(4-methyl-piperazin-1-yl)-phenyl]-[1,2,4]triazolo[1,5-a]pyridine-2,8-diamine |
| 110 | 2999 | 1312.24 | 8249 | N(8)-(3-Methanesulfonyl-phenyl)-N(2)-[3-(4-methyl-piperazin-1-yl)-phenyl]-[1,2,4]triazolo[1,5-a]pyridine-2,8-diamine |
| 111 | 1999 | 60.26 | 1036.1 | N-Methyl-N-(3-{2-[3-(4-methyl-piperazin-1-yl)-phenylamino]-[1,2,4]triazolo[1,5-a]pyridin-8-ylamino}-pyridin-2-yl)-methanesulfonamide |
| 112 | 531.12 | 1.30 | 81.28 | (4-Methanesulfonyl-phenyl)-[8-(4-methanesulfonyl-phenyl)-[1,2,4]triazolo[1,5-a]pyridin-2-yl]-amine |
| 113 | 693.36 | 5.57 | 607.13 | (3-Methanesulfonyl-phenyl)-[8-(4-methanesulfonyl-phenyl)-[1,2,4]triazolo[1,5-a]pyridin-2-yl]-amine |
| 114 | 1477.99 | 0.75 | 30.27 | N-{4-[(1,1-dioxidothiomorpholin-4-yl)methyl]phenyl}-8-[4-(methylsulfonyl)phenyl][1,2,4]triazolo[1,5-a]pyridin-2-amine |
| 115 | 1053.01 | 0.66 | 26.08 | N-{4-[(1,1-dioxidothiomorpholin-4-yl)methyl]phenyl}-5-[4-(methylsulfonyl)phenyl][1,2,4]triazolo[1,5-a]pyridin-2-amine |
| 116 | 2999 | 3.07 | 149.68 | [8-(4-Methanesulfonyl-phenyl)-[1,2,4]triazolo[1,5-a]pyridin-2-yl]-[3-(4-methyl-piperazin-1-ylmethyl)-phenyl]-amine |
| 117 | 1468.32 | 0.95 | 52.26 | [5-(4-Methanesulfonyl-phenyl)-[1,2,4]triazolo[1,5-a]pyridin-2-yl]-(3-morpholin-4-ylmethyl-phenyl)-amine |
| 118 | 2862.98 | 1.43 | 66.86 | [5-(4-Methanesulfonyl-phenyl)-[1,2,4]triazolo[1,5-a]pyridin-2-yl]-[3-(4-methyl-piperazin-1-ylmethyl)-phenyl]-amine |
| 119 | 9999 | 0.27 | 11.01 | N-{4-[2-({4-[(1,1-dioxidothiomorpholin-4-yl)methyl]phenyl}amino)[1,2,4]triazolo[1,5-a]pyridin-8-yl]phenyl}-N-methylmethanesulfonamide |
| 120 | 1999 | 0.67 | 38.78 | N-{3-[(1,1-dioxidothiomorpholin-4-yl)methyl]phenyl}-8-[4-(methylsulfonyl)phenyl][1,2,4]triazolo[1,5-a]pyridin-2-amine |
| 121 | 999 | 0.55 | 42.12 | N-{3-[(1,1-dioxidothiomorpholin-4-yl)methyl]phenyl}-5-[4-(methylsulfonyl)phenyl][1,2,4]triazolo[1,5-a]pyridin-2-amine |
| 122 | 29.99 | 20.73 | 514.95 | N-Methyl-N-[3-({2-[4-(4-methyl-piperazin-1-yl)-phenylamino]-[1,2,4]triazolo[1,5-a]pyridin-8-ylamino}-methyl)-pyridin-2-yl]-methanesulfonamide |
| 123 | 77.33 | 40.28 | 835.51 | N-Methyl-N-[3-({2-[4-(1-methyl-piperidin-4-yl)-phenylamino]-[1,2,4]triazolo[1,5-a]pyridin-8-ylamino}-methyl)-pyridin-2-yl]-methanesulfonamide |
| 124 | 59.73 | 41.18 | 838.05 | N-Methyl-N-[3-({2-[4-(2-pyrrolidin-1-yl-ethoxy)-phenylamino]-[1,2,4]triazolo[1,5-a]pyridin-8-ylamino}-methyl)-pyridin-2-yl]-methanesulfonamide |
| 125 | 2048.76 | 6.60 | 140.87 | N(8)-(2-Methanesulfonyl-phenyl)-N(2)-[4-(1-methyl-piperidin-4-yl)- |

-continued

| Ex. # | FAK IC50 (nM) | JAK2 IC50 (nM) | JAK3 IC50 (nM) | Name |
|---|---|---|---|---|
| | | | | phenyl]-[1,2,4]triazolo[1,5-a]pyridine-2,8-diamine |
| 126 | 1297.82 | 14.35 | 239.34 | N(8)-(2-Methanesulfonyl-phenyl)-N(2)-[4-(2-pyrrolidin-1-yl-ethoxy)-phenyl]-[1,2,4]triazolo[1,5-a]pyridine-2,8-diamine |
| 127 | 3134.71 | 18.68 | 173.06 | N-Methyl-N-(3-{2-[4-(4-methyl-piperazin-1-yl)-phenylamino]-[1,2,4]triazolo[1,5-a]pyridin-8-yl}-phenyl)-methanesulfonamide |
| 128 | 2306.66 | 33.95 | 320.76 | N-Methyl-N-(3-{2-[4-(2-pyrrolidin-1-yl-ethoxy)-phenylamino]-[1,2,4]triazolo[1,5-a]pyridin-8-yl}-phenyl)-methanesulfonamide |
| 129 | 759.22 | 8.88 | 211.35 | N-Methyl-N-(3-{2-[3-(1-methyl-piperidin-4-yl)-phenylamino]-[1,2,4]triazolo[1,5-a]pyridin-8-yl}-phenyl)-methanesulfonamide |
| 130 | 2999 | 1197.86 | 830.05 | N-Methyl-N-(2-{2-[3-(1-methyl-piperidin-4-yl)-phenylamino]-[1,2,4]triazolo[1,5-a]pyridin-8-yl}-phenyl)-methanesulfonamide |
| 131 | 1367.36 | 11.41 | 78.92 | N-Methyl-N-(3-{2-[4-(4-methyl-piperazin-1-yl)-phenylamino]-[1,2,4]triazolo[1,5-a]pyridin-8-ylamino}-pyridin-2-yl)-methanesulfonamide |
| 132 | 2999 | 33.07 | 266.92 | N-Methyl-N-(3-{2-[4-(2-pyrrolidin-1-yl-ethoxy)-phenylamino]-[1,2,4]triazolo[1,5-a]pyridin-8-ylamino}-pyridin-2-yl)-methanesulfonamide |
| 133 | 2065.53 | 17.42 | 166.83 | N-Methyl-N-(3-{2-[4-(1-methyl-piperidin-4-yl)-phenylamino]-[1,2,4]triazolo[1,5-a]pyridin-8-ylamino}-pyridin-2-yl)-methanesulfonamide |
| 134 | 751.66 | 17.32 | 273.97 | N-(3-{[2-(4-Methanesulfonyl-phenylamino)-[1,2,4]triazolo[1,5-a]pyridin-8-ylamino]-methyl}-pyridin-2-yl)-N-methyl-methanesulfonamide |
| 135 | 215.11 | 77.84 | 919.83 | N-(3-{[2-(3-Methanesulfonyl-phenylamino)-[1,2,4]triazolo[1,5-a]pyridin-8-ylamino]-methyl}-pyridin-2-yl)-N-methyl-methanesulfonamide |
| 136 | 71.08 | 77.18 | 646.76 | N-Methyl-N-[3-({2-[3-(4-methyl-piperazin-1-yl)-phenylamino]-[1,2,4]triazolo[1,5-a]pyridin-8-ylamino}-methyl)-pyridin-2-yl]-methanesulfonamide |
| 137 | 39.71 | 2999.00 | 9999 | N-[3-({2-[2-Methoxy-4-(4-methyl-piperazin-1-yl)-phenylamino]-[1,2,4]triazolo[1,5-a]pyridin-8-ylamino}-methyl)-pyridin-2-yl]-N-methyl-methanesulfonamide |
| 138 | 199.46 | 13.24 | 97.39 | N(8)-(2-Methanesulfonyl-benzyl)-N(2)-[4-(4-methyl-piperazin-1-yl)-phenyl]-[1,2,4]triazolo[1,5-a]pyridine-2,8-diamine |
| 139 | 200.46 | 26.32 | 184.7 | N(8)-(2-Methanesulfonyl-benzyl)-N(2)-[3-(4-methyl-piperazin-1-yl)-phenyl]-[1,2,4]triazolo[1,5-a]pyridine-2,8-diamine |
| 140 | 123.79 | 22.59 | 244.39 | N(8)-(2-Methanesulfonyl-benzyl)-N(2)-[4-(1-methyl-piperidin-4-yl)-phenyl]-[1,2,4]triazolo[1,5-a]pyridine-2,8-diamine |
| 141 | 98.78 | 15.09 | 193.78 | N(8)-(2-Methanesulfonyl-benzyl)-N(2)-[4-(2-pyrrolidin-1-yl-ethoxy)-phenyl]-[1,2,4]triazolo[1,5-a]pyridine-2,8-diamine |
| 142 | 935.28 | 0.75 | 77.87 | (S)-1-(4-{3-[8-(4-Methanesulfonyl-phenyl)-[1,2,4]triazolo[1,5-a]pyridin-2-ylamino]-phenyl}-piperazin-1-yl)-propan-2-ol |

-continued

| Ex. # | FAK IC50 (nM) | JAK2 IC50 (nM) | JAK3 IC50 (nM) | Name |
|---|---|---|---|---|
| 143 | 1986.16 | 1.13 | 53.19 | (R)-1-(4-{3-[8-(4-Methanesulfonyl-phenyl)-[1,2,4]triazolo[1,5-a]pyridin-2-ylamino]-phenyl}-piperazin-1-yl)-propan-2-ol |
| 144 | 2049.42 | 2.61 | 110.46 | 1-(4-{3-[8-(4-Methanesulfonyl-phenyl)-[1,2,4]triazolo[1,5-a]pyridin-2-ylamino]-phenyl}-piperazin-1-yl)-2-methyl-propan-2-ol |
| 145 | 670.93 | 1.55 | 43.02 | [8-(4-Methanesulfonyl-phenyl)-[1,2,4]triazolo[1,5-a]pyridin-2-yl]-(7-morpholin-4-yl-6,7,8,9-tetrahydro-5H-benzocyclohepten-2-yl)-amine |
| 146 | 105.75 | 27.42 | 286.66 | N-Methyl-N-(3-{[2-(1-methyl-2-oxo-2,3-dihydro-1H-indol-5-ylamino)-[1,2,4]triazolo[1,5-a]pyridin-8-ylamino]-methyl}-pyridin-2-yl)-methanesulfonamide |
| 147 | 11.39 | 29.10 | 224.57 | N-Methyl-N-[2-({2-[4-(4-methyl-piperazin-1-yl)-phenylamino]-[1,2,4]triazolo[1,5-a]pyridin-8-ylamino}-methyl)-phenyl]-methanesulfonamide |
| 148 | 14.63 | 66.38 | 527.19 | N-Methyl-N-[2-({2-[3-(4-methyl-piperazin-1-yl)-phenylamino]-[1,2,4]triazolo[1,5-a]pyridin-8-ylamino}-methyl)-phenyl]-methanesulfonamide |
| 149 | 13.58 | 38.50 | 268.58 | N-Methyl-N-[2-({2-[4-(1-methyl-piperidin-4-yl)-phenylamino]-[1,2,4]triazolo[1,5-a]pyridin-8-ylamino}-methyl)-phenyl]-methanesulfonamide |
| 150 | 12.96 | 43.74 | 345.16 | N-Methyl-N-[2-({2-[4-(2-pyrrolidin-1-yl-ethoxy)-phenylamino]-[1,2,4]triazolo[1,5-a]pyridin-8-ylamino}-methyl)-phenyl]-methanesulfonamide |
| 151 | 6499 | 487.83 | 4197.95 | N(2)-[4-(4-Methyl-piperazin-1-yl)-phenyl]-N(8)-pyridin-3-ylmethyl-[1,2,4]triazolo[1,5-a]pyridine-2,8-diamine |
| 152 | 999 | 2.37 | 168.37 | 2-(4-{3-[8-(4-Methanesulfonyl-phenyl)-[1,2,4]triazolo[1,5-a]pyridin-2-ylamino]-phenyl}-piperazin-1-yl)-ethanol |
| 153 | 6499 | 646.78 | 2999 | N(2)-[3-(4-Methyl-piperazin-1-yl)-phenyl]-N(8)-pyridin-3-ylmethyl-[1,2,4]triazolo[1,5-a]pyridine-2,8-diamine |
| 154 | 9999 | 570.68 | 2793.21 | N(8)-Pyridin-3-ylmethyl-N(2)-[4-(2-pyrrolidin-1-yl-ethoxy)-phenyl]-[1,2,4]triazolo[1,5-a]pyridine-2,8-diamine |
| 155 | 379.27 | 36.05 | 406.91 | N-{3-[(2-{4-[4-(2-Hydroxy-ethyl)-piperazin-1-yl]-phenylamino}-[1,2,4]triazolo[1,5-a]pyridin-8-ylamino)-methyl]-pyridin-2-yl}-N-methyl-methanesulfonamide |
| 156 | 178.99 | 35.44 | 576.56 | N-Methyl-N-[2-({2-[4-(4-methyl-piperazin-1-yl)-phenylamino]-[1,2,4]triazolo[1,5-a]pyridin-8-ylamino}-methyl)-benzyl]-methanesulfonamide |
| 157 | 299.53 | 219.62 | 2575.04 | N-Methyl-N-[2-({2-[3-(4-methyl-piperazin-1-yl)-phenylamino]-[1,2,4]triazolo[1,5-a]pyridin-8-ylamino}-methyl)-benzyl]-methanesulfonamide |
| 158 | 276.37 | 97.47 | 1782.92 | N-Methyl-N-[2-({2-[4-(2-pyrrolidin-1-yl-ethoxy)-phenylamino]-[1,2,4]triazolo[1,5-a]pyridin-8-ylamino}-methyl)-benzyl]-methanesulfonamide |
| 159 | 537.99 | 115.68 | 1445.13 | N-Methyl-N-[2-({2-[4-(1-methyl-piperidin-4-yl)-phenylamino]- |

-continued

| Ex. # | FAK IC50 (nM) | JAK2 IC50 (nM) | JAK3 IC50 (nM) | Name |
|---|---|---|---|---|
| | | | | [1,2,4]triazolo[1,5-a]pyridin-8-ylamino}-methyl)-benzyl]-methanesulfonamide |
| 160 | 9999 | 262.42 | 2999 | N(8)-(3-Methanesulfonyl-benzyl)-N(2)-[4-(4-methyl-piperazin-1-yl)-phenyl]-[1,2,4]triazolo[1,5-a]pyridine-2,8-diamine |
| 161 | 9999 | 398.69 | 6499 | N(8)-(3-Methanesulfonyl-benzyl)-N(2)-[3-(4-methyl-piperazin-1-yl)-phenyl]-[1,2,4]triazolo[1,5-a]pyridine-2,8-diamine |
| 162 | 9999 | 327.52 | 2999 | N(8)-(3-Methanesulfonyl-benzyl)-N(2)-[4-(1-methyl-piperidin-4-yl)-phenyl]-[1,2,4]triazolo[1,5-a]pyridine-2,8-diamine |
| 163 | 9999 | 98.01 | 3256.6 | 3-({2-[4-(4-Methyl-piperazin-1-yl)-phenylamino]-[1,2,4]triazolo[1,5-a]pyridin-8-ylamino}-methyl)-pyrrolidine-1-carboxylic acid tert-butyl ester |
| 164 | 1281.18 | 22.10 | 452.9 | N(8)-(2-Methanesulfonylmethyl-phenyl)-N(2)-[4-(4-methyl-piperazin-1-yl)-phenyl]-[1,2,4]triazolo[1,5-a]pyridine-2,8-diamine |
| 165 | 1999 | 39.89 | 820.91 | N(8)-(2-Methanesulfonylmethyl-phenyl)-N(2)-[4-(1-methyl-piperidin-4-yl)-phenyl]-[1,2,4]triazolo[1,5-a]pyridine-2,8-diamine |
| 166 | 48.13 | 12.82 | 306.37 | N-Methyl-N-(3-{[2-(2-methyl-2,3-dihydro-1H-isoindol-5-ylamino)-[1,2,4]triazolo[1,5-a]pyridin-8-ylamino]-methyl}-pyridin-2-yl)-methanesulfonamide |
| 167 | 17.76 | 9.19 | 109.77 | N-Methyl-N-(2-{[2-(2-methyl-2,3-dihydro-1H-isoindol-5-ylamino)-[1,2,4]triazolo[1,5-a]pyridin-8-ylamino]-methyl}-phenyl)-methanesulfonamide |
| 168 | 816.14 | 0.73 | 77.56 | [8-(4-Methanesulfonyl-phenyl)-[1,2,4]triazolo[1,5-a]pyridin-2-yl]-(2-methyl-2,3-dihydro-1H-isoindol-5-yl)-amine |
| 169 | 6499 | 144.80 | 3238.72 | N-Methyl-N-[3-({2-[4-(4-methyl-piperazin-1-yl)-phenylamino]-[1,2,4]triazolo[1,5-a]pyridin-8-ylamino}-methyl)-phenyl]-methanesulfonamide |
| 170 | 872.25 | 11.63 | 160.34 | N(8)-(1-Methanesulfonyl-pyrrolidin-2-ylmethyl)-N(2)-[4-(4-methyl-piperazin-1-yl)-phenyl]-[1,2,4]triazolo[1,5-a]pyridine-2,8-diamine |
| 171 | 999 | 70.80 | 541.65 | N-Methyl-N-(2-{2-[4-(4-methyl-piperazin-1-yl)-phenylamino]-[1,2,4]triazolo[1,5-a]pyridin-8-ylamino}-benzyl)-methanesulfonamide |
| 172 | 2999 | 453.17 | 3180.14 | N-Methyl-N-(2-{2-[3-(4-methyl-piperazin-1-yl)-phenylamino]-[1,2,4]triazolo[1,5-a]pyridin-8-ylamino}-benzyl)-methanesulfonamide |
| 173 | 1999 | 143.05 | 1171.33 | N-Methyl-N-(2-{2-[4-(2-pyrrolidin-1-yl-ethoxy)-phenylamino]-[1,2,4]triazolo[1,5-a]pyridin-8-ylamino}-benzyl)-methanesulfonamide |
| 174 | 9999 | 111.13 | 679.34 | N-Methyl-N-(2-{2-[4-(1-methyl-piperidin-4-yl)-phenylamino]-[1,2,4]triazolo[1,5-a]pyridin-8-ylamino}-benzyl)-methanesulfonamide |
| 175 | 2999 | 7.95 | 126.92 | N-Methyl-N-(3-{2-[4-(4-methyl-piperazin-1-yl)-phenylamino]- |

-continued

| Ex. # | FAK IC50 (nM) | JAK2 IC50 (nM) | JAK3 IC50 (nM) | Name |
|---|---|---|---|---|
| 176 | 2999 | 5.94 | 247.06 | [1,2,4]triazolo[1,5-a]pyridin-8-yl)-benzyl)-methanesulfonamide N-Methyl-N-(3-{2-[3-(4-methyl-piperazin-1-yl)-phenylamino]-[1,2,4]triazolo[1,5-a]pyridin-8-yl}-benzyl)-methanesulfonamide |
| 177 | 2999 | 7.34 | 287.19 | N-Methyl-N-(3-{2-[4-(2-pyrrolidin-1-yl-ethoxy)-phenylamino]-[1,2,4]triazolo[1,5-a]pyridin-8-yl}-benzyl)-methanesulfonamide |
| 178 | 999 | 7.21 | 215.49 | N-Methyl-N-(3-{2-[4-(1-methyl-piperidin-4-yl)-phenylamino]-[1,2,4]triazolo[1,5-a]pyridin-8-yl}-benzyl)-methanesulfonamide |
| 179 | 9999 | 3.72 | 297.04 | 4-{3-[8-(4-Methanesulfonyl-phenyl)-[1,2,4]triazolo[1,5-a]pyridin-2-ylamino]-phenyl}-piperazine-1-carboxylic acid tert-butyl ester |
| 180 | 9999 | 1.90 | 216.19 | 4-{3-[8-(4-Methanesulfonyl-phenyl)-[1,2,4]triazolo[1,5-a]pyridin-2-ylamino]-phenyl}-piperidine-1-carboxylic acid tert-butyl ester |
| 181 | 1127.21 | 0.97 | 52.56 | [8-(4-Methanesulfonyl-phenyl)-[1,2,4]triazolo[1,5-a]pyridin-2-yl]-(3-piperazin-1-yl-phenyl)-amine |
| 182 | 1002.53 | 0.53 | 37.93 | [8-(4-Methanesulfonyl-phenyl)-[1,2,4]triazolo[1,5-a]pyridin-2-yl]-(3-piperidin-4-yl-phenyl)-amine |
| 183 | 6499 | 0.65 | 28.6 | 2-(4-{3-[8-(4-Methanesulfonyl-phenyl)-[1,2,4]triazolo[1,5-a]pyridin-2-ylamino]-phenyl}-piperazin-1-yl)-acetamide |
| 184 | 384.26 | 0.41 | 20.2 | 2-(4-{3-[8-(4-Methanesulfonyl-phenyl)-[1,2,4]triazolo[1,5-a]pyridin-2-ylamino]-phenyl}-piperidin-1-yl)-acetamide |
| 185 | 62.53 | 51.06 | 432.96 | N-Methyl-N-{2-[(methyl-{2-[4-(4-methyl-piperazin-1-yl)-phenylamino]-[1,2,4]triazolo[1,5-a]pyridin-8-yl}-amino)-methyl]-phenyl}-methanesulfonamide |
| 186 | 2992.43 | 1.35 | 71.14 | (±)-cis-3-Hydroxy-4-{3-[8-(4-methanesulfonyl-phenyl)-[1,2,4]triazolo[1,5-a]pyridin-2-ylamino]-phenyl}-piperidine-1-carboxylic acid tert-butyl ester |
| 187 | 2437.14 | 4.93 | 164.57 | {3-[4-(3-Fluoro-propyl)-piperazin-1-yl]-phenyl}-[8-(4-methanesulfonyl-phenyl)-[1,2,4]triazolo[1,5-a]pyridin-2-yl]-amine |
| 188 | 1940.37 | 1.43 | 59.54 | (±)-(cis)-4-{3-[8-(4-Methanesulfonyl-phenyl)-[1,2,4]triazolo[1,5-a]pyridin-2-ylamino]-phenyl}-piperidin-3-ol |
| 189 | 521.75 | 2.61 | 69.6 | N-Methyl-N-(2-{2-[4-(4-methyl-piperazin-1-yl)-phenylamino]-[1,2,4]triazolo[1,5-a]pyridin-8-ylethynyl}-phenyl)-methanesulfonamide |
| 190 | 580.33 | 0.46 | 27.33 | {3-[1-(2-Methanesulfonyl-ethyl)-piperidin-4-yl]-phenyl}-[8-(4-methanesulfonyl-phenyl)-[1,2,4]triazolo[1,5-a]pyridin-2-yl]-amine |
| 191 | 999 | 0.55 | 13.23 | (±)2-(cis)-3-Hydroxy-4-{3-[8-(4-methanesulfonyl-phenyl)-[1,2,4]triazolo[1,5-a]pyridin-2-ylamino]-phenyl}-piperidin-1-yl)-acetamide |
| 192 | 2423.72 | 23.89 | 548.03 | N-Methyl-N-(2-{2-[3-(4-methyl-piperazin-1-yl)-phenylamino]-[1,2,4]triazolo[1,5-a]pyridin-8-ylethynyl}-phenyl)-methanesulfonamide |

-continued

| Ex. # | FAK IC50 (nM) | JAK2 IC50 (nM) | JAK3 IC50 (nM) | Name |
|---|---|---|---|---|
| 193 | 2999 | 11.53 | 398.3 | N-Methyl-N-{2-[2-(2-methyl-2,3-dihydro-1H-isoindol-5-ylamino)-[1,2,4]triazolo[1,5-a]pyridin-8-ylethynyl]-phenyl}-methanesulfonamide |
| 194 | 41.73 | 218.02 | 655.75 | N-Methyl-N-[2-(2-{2-[4-(4-methyl-piperazin-1-yl)-phenylamino]-[1,2,4]triazolo[1,5-a]pyridin-8-yl}-ethyl)-phenyl]-methanesulfonamide |
| 195 | 21.81 | 15.01 | 134.76 | N-Methyl-N-(2-{2-[4-(4-methyl-piperazin-1-yl)-phenylamino]-[1,2,4]triazolo[1,5-a]pyridin-8-yloxymethyl}-phenyl)-methanesulfonamide |
| 196 | 999 | 32.09 | | N-Methyl-N-[2-((E)-2-{2-[4-(4-methyl-piperazin-1-yl)-phenylamino]-[1,2,4]triazolo[1,5-a]pyridin-8-yl}-vinyl)-phenyl]-methanesulfonamide |
| 197 | 999 | 418.16 | | N-Methyl-N-[2-(1-{2-[4-(4-methyl-piperazin-1-yl)-phenylamino]-[1,2,4]triazolo[1,5-a]pyridin-8-ylamino}-ethyl)-phenyl]-methanesulfonamide |
| 198 | 9999 | 1.73 | 191.96 | {8-[4-(Dimethyl-phosphinoyl)-phenyl]-[1,2,4]triazolo[1,5-a]pyridin-2-yl}-[3-(4-methyl-piperazin-1-yl)-phenyl]-amine |
| 199 | 9999 | 95.79 | | {8-[4-(Dimethyl-phosphinoyl)-phenyl]-[1,2,4]triazolo[1,5-a]pyridin-2-yl}-(2-methanesulfonyl-ethyl)-{3-[1-(2-methanesulfonyl-ethyl)-piperidin-4-yl]-phenyl}-amine |
| 200 | 18.18 | 134.47 | | N-Methyl-N-(2-{[2-(7-morpholin-4-yl-6,7,8,9-tetrahydro-5H-benzocyclohepten-2-ylamino)-[1,2,4]triazolo[1,5-a]pyridin-8-ylamino]-methyl}-phenyl)-methanesulfonamide |
| 201 | 167.28 | 116.17 | | N-(2-{[2-(Isoquinolin-6-ylamino)-[1,2,4]triazolo[1,5-a]pyridin-8-ylamino]-methyl}-phenyl)-N-methyl-methanesulfonamide |
| 202 | 189.47 | 571.33 | | N-Methyl-N-{2-[(2-phenylamino-[1,2,4]triazolo[1,5-a]pyridin-8-ylamino)-methyl]-phenyl}-methanesulfonamide |
| 203 | 9999 | 165.79 | | {8-[4-(Dimethyl-phosphinoyl)-phenyl]-[1,2,4]triazolo[1,5-a]pyridin-2-yl}-{3-[1-(2-methanesulfonyl-ethyl)-piperidin-4-yl]-phenyl}-amine |
| 204 | 9999 | 1.63 | 138.13 | 1-{3-[8-(4-Methanesulfonyl-phenyl)-[1,2,4]triazolo[1,5-a]pyridin-2-ylamino]-phenyl}-4-methyl-piperazin-2-one |
| 205 | 9999 | 1.88 | 147.29 | 4-Ethyl-1-{3-[8-(4-methanesulfonyl-phenyl)-[1,2,4]triazolo[1,5-a]pyridin-2-ylamino]-phenyl}-piperazin-2-one |
| 206 | 2999 | 45.02 | | [3-(4-Methyl-piperazin-1-yl)-phenyl]-(8-{4-[4-(4-methyl-piperazin-1-yl)-piperidin-1-yl]-phenyl}-[1,2,4]triazolo[1,5-a]pyridin-2-yl)-amine |
| 207 | 9999 | 10.47 | 2999 | 1-(3-{8-[4-(Dimethyl-phosphinoyl)-phenyl]-[1,2,4]triazolo[1,5-a]pyridin-2-ylamino}-phenyl)-4-methyl-piperazin-2-one |
| 208 | 9999 | 13.19 | | 1-(3-{8-[4-(Dimethyl-phosphinoyl)-phenyl]-[1,2,4]triazolo[1,5-a]pyridin-2-ylamino}-phenyl)-4-ethyl-piperazin-2-one |

-continued

| Ex. # | FAK IC50 (nM) | JAK2 IC50 (nM) | JAK3 IC50 (nM) | Name |
|---|---|---|---|---|
| 209 | 9999 | 1.88 | 99.92 | (1-Ethyl-1H-pyrazol-4-yl)-[8-(4-methanesulfonyl-phenyl)-[1,2,4]triazolo[1,5-a]pyridin-2-yl]-amine |
| 210 | 9999 | 2999.00 | 9999 | [8-(4-Methanesulfonyl-phenyl)-[1,2,4]triazolo[1,5-a]pyridin-2-yl]-(1,3,5-trimethyl-1H-pyrazol-4-yl)-amine |
| 211 | 9999 | 1156.98 | 2999 | (1-Ethyl-1H-pyrazol-4-yl)-[8-(4-methanesulfonyl-phenoxy)-[1,2,4]triazolo[1,5-a]pyridin-2-yl]-amine |
| 212 | 2999 | 0.50 | 20.92 | 4-{4-[8-(4-Methanesulfonyl-phenyl)-[1,2,4]triazolo[1,5-a]pyridin-2-ylamino]-pyrazol-1-yl}-piperidine-1-carboxylic acid tert-butyl ester |
| 213 | 2999 | 0.71 | 59.57 | [8-(4-Methanesulfonyl-phenyl)-[1,2,4]triazolo[1,5-a]pyridin-2-yl]-(1-piperidin-4-yl-1H-pyrazol-4-yl)-amine |
| 214 | 9999 | 1646.77 | 9999 | [8-(4-Methanesulfonyl-phenoxy)-[1,2,4]triazolo[1,5-a]pyridin-2-yl]-[3-(4-methyl-piperazin-1-yl)-phenyl]-amine |
| 215 | 9999 | 2.84 | 70.19 | (1-Ethyl-1H-pyrazol-4-yl)-[8-(4-trifluoromethyl-phenyl)-[1,2,4]triazolo[1,5-a]pyridin-2-yl]-amine |
| 216 | 9999 | 9.10 | 193.88 | [1-(2-Pyrrolidin-1-yl-ethyl)-1H-pyrazol-4-yl]-[8-(4-trifluoromethyl-phenyl)-[1,2,4]triazolo[1,5-a]pyridin-2-yl]-amine |
| 217 | 1223.29 | 2999.00 | 9999 | [8-(4-Methanesulfonyl-phenoxy)-[1,2,4]triazolo[1,5-a]pyridin-2-yl]-[1-(2-pyrrolidin-1-yl-ethyl)-1H-pyrazol-4-yl]-amine |
| 219 | 9999 | 13.90 | 475.64 | [8-(4-Methanesulfonyl-phenyl)-[1,2,4]triazolo[1,5-a]pyridin-2-yl]-[1-(2-pyrrolidin-1-yl-ethyl)-1H-pyrazol-4-yl]-amine |
| 223 | 9999 | 2999.00 | 9999 | 2-(4-Trifluoromethyl-phenylamino)-[1,2,4]triazolo[1,5-a]pyridin-8-ol |
| 226 | 9999 | 650.29 | 2540.53 | 7-[5-(2-Methoxymethyl-phenyl)-[1,2,4]triazolo[1,5-a]pyridin-2-ylamino]-1,2,4,5-tetrahydro-benzo[d]azepine-3-carboxylic acid tert-butyl ester |
| 227 | 9999 | 9999.00 | 9999 | 1,1'-[1,2,4]triazolo[1,5-a]pyridine-2,5-diyldi-1,2,3,4-tetrahydroquinoline |
| 228 | 9999 | 9999.00 | 9999 | [5-(2-Methoxymethyl-phenyl)-[1,2,4]triazolo[1,5-a]pyridin-2-yl]-(2,3,4,5-tetrahydro-1H-benzo[d]azepin-7-yl)-amine |
| 229 | 2999 | 47.41 | 166.82 | 2-{7-[5-(2-Methoxymethyl-phenyl)-[1,2,4]triazolo[1,5-a]pyridin-2-ylamino]-1,2,4,5-tetrahydro-benzo[d]azepin-3-yl}-N,N-dimethyl-acetamide |
| 230 | 1999 | 27.55 | 133.32 | [3-(2-Methanesulfonyl-ethyl)-2,3,4,5-tetrahydro-1H-benzo[d]azepin-7-yl]-[5-(2-methoxymethyl-phenyl)-[1,2,4]triazolo[1,5-a]pyridin-2-yl]-amine |
| 234 | 547.04 | 23.38 | 351.41 | [5-(2-Methoxy-5-trifluoromethyl-phenyl)-[1,2,4]triazolo[1,5-a]pyridin-2-yl]-(2,3,4,5-tetrahydro-1H-benzo[d]azepin-7-yl)-amine |
| 235 | 135.43 | 26.69 | 410.53 | [5-(2-Methoxy-5-trifluoromethyl-phenyl)-[1,2,4]triazolo[1,5-a]pyridin-2-yl]-[3-(2-methylsulfanyl-ethyl)-2,3,4,5-tetrahydro-1H-benzo[d]azepin-7-yl]-amine |

-continued

| Ex. # | FAK IC50 (nM) | JAK2 IC50 (nM) | JAK3 IC50 (nM) | Name |
|---|---|---|---|---|
| 236 | 1013.31 | 7.40 | 52.76 | [5-(2-Methoxy-4-trifluoromethyl-phenyl)-[1,2,4]triazolo[1,5-a]pyridin-2-yl]-(2,3,4,5-tetrahydro-1H-benzo[d]azepin-7-yl)-amine |
| 237 | 714.14 | 53.86 | 342.23 | N-[8-(2-Methoxy-5-trifluoromethyl-phenyl)-[1,2,4]triazolo[1,5-a]pyridin-2-yl]-acetamide |
| 238 | 1947.44 | 7.01 | 43.74 | [3-(2-Methanesulfonyl-ethyl)-2,3,4,5-tetrahydro-1H-benzo[d]azepin-7-yl]-[5-(2-methoxy-4-trifluoromethyl-phenyl)-[1,2,4]triazolo[1,5-a]pyridin-2-yl]-amine |
| 241 | 9999 | 1103.03 | 2388.36 | 7-[8-(2-Methoxymethyl-phenyl)-[1,2,4]triazolo[1,5-a]pyridin-2-ylamino]-1,2,4,5-tetrahydro-benzo[d]azepine-3-carboxylic acid tert-butyl ester |
| 242 | 9999 | 130.71 | 628.38 | [8-(2-Methoxymethyl-phenyl)-[1,2,4]triazolo[1,5-a]pyridin-2-yl]-(2,3,4,5-tetrahydro-1H-benzo[d]azepin-7-yl)-amine |
| 243 | 9999 | 2114.62 | 9999 | 7-[8-(2,2-Difluoro-benzo[1,3]dioxol-4-yl)-[1,2,4]triazolo[1,5-a]pyridin-2-ylamino]-1,2,4,5-tetrahydro-benzo[d]azepine-3-carboxylic acid tert-butyl ester |
| 244 | 6499 | 43.61 | 657.36 | [8-(2,2-Difluoro-benzo[1,3]dioxol-4-yl)-[1,2,4]triazolo[1,5-a]pyridin-2-yl]-(2,3,4,5-tetrahydro-1H-benzo[d]azepin-7-yl)-amine |
| 245 | 9999 | 70.04 | 249.52 | [3-(2-Methanesulfonyl-ethyl)-2,3,4,5-tetrahydro-1H-benzo[d]azepin-7-yl]-[8-(2-methoxymethyl-phenyl)-[1,2,4]triazolo[1,5-a]pyridin-2-yl]-amine |
| 246 | 9999 | 212.47 | 556.95 | 2-{7-[8-(2-Methoxymethyl-phenyl)-[1,2,4]triazolo[1,5-a]pyridin-2-ylamino]-1,2,4,5-tetrahydro-benzo[d]azepin-3-yl}-N,N-dimethyl-acetamide |
| 247 | 1999 | 24.83 | 222.96 | [8-(2,2-Difluoro-benzo[1,3]dioxol-4-yl)-[1,2,4]triazolo[1,5-a]pyridin-2-yl]-[3-(2-methanesulfonyl-ethyl)-2,3,4,5-tetrahydro-1H-benzo[d]azepin-7-yl]-amine |
| 248 | 1697.77 | 30.41 | 350.32 | 2-{7-[8-(2,2-Difluoro-benzo[1,3]dioxol-4-yl)-[1,2,4]triazolo[1,5-a]pyridin-2-ylamino]-1,2,4,5-tetrahydro-benzo[d]azepin-3-yl}-N,N-dimethyl-acetamide |
| 254 | 1081.89 | 31.33 | 420.74 | [8-(2-Methoxy-5-trifluoromethyl-phenyl)-[1,2,4]triazolo[1,5-a]pyridin-2-yl]-[4-(4-methyl-piperazin-1-yl)-phenyl]-amine |
| 255 | 1215.18 | 158.30 | 2827.84 | [8-(2-Methoxy-5-trifluoromethyl-phenyl)-[1,2,4]triazolo[1,5-a]pyridin-2-yl]-[3-(4-methyl-piperazin-1-yl)-phenyl]-amine |
| 256 | 9999 | 9999.00 | 9999 | 4-{3-[8-(2-Methoxy-5-trifluoromethyl-phenyl)-[1,2,4]triazolo[1,5-a]pyridin-2-ylamino]-phenyl}-piperidine-1-carboxylic acid tert-butyl ester |
| 257 | 481.21 | 28.92 | 705.92 | [8-(2-Methoxy-5-trifluoromethyl-phenyl)-[1,2,4]triazolo[1,5-a]pyridin-2-yl]-(3-piperidin-4-yl-phenyl)-amine |
| 258 | 6499 | 84.50 | 1041.68 | [8-(2-Methoxy-5-trifluoromethyl-phenyl)-[1,2,4]triazolo[1,5-a]pyridin-2-yl]-[4-(2-morpholin-4-yl-ethoxy)-phenyl]-amine |

-continued

| Ex. # | FAK IC50 (nM) | JAK2 IC50 (nM) | JAK3 IC50 (nM) | Name |
|---|---|---|---|---|
| 259 | 3392.26 | 73.74 | 805.87 | [8-(2-Methoxy-5-trifluoromethyl-phenyl)-[1,2,4]triazolo[1,5-a]pyridin-2-yl]-[4-(2-pyrrolidin-1-yl-ethoxy)-phenyl]-amine |
| 260 | 1104.46 | 43.55 | 796.85 | [8-(3-Chloro-benzyloxy)-[1,2,4]triazolo[1,5-a]pyridin-2-yl]-[4-(4-methyl-piperazin-1-yl)-phenyl]-amine |
| 261 | 1592.16 | 99.52 | 1677.38 | [8-(3-Chloro-benzyloxy)-[1,2,4]triazolo[1,5-a]pyridin-2-yl]-[3-(4-methyl-piperazin-1-yl)-phenyl]-amine |
| 262 | 2562.89 | 15.10 | 323.81 | 2-{2-[4-(4-Methyl-piperazin-1-yl)-phenylamino]-[1,2,4]triazolo[1,5-a]pyridin-8-yloxymethyl}-benzonitrile |
| 263 | 2999 | 26.89 | 1758.94 | 2-{2-[3-(4-Methyl-piperazin-1-yl)-phenylamino]-[1,2,4]triazolo[1,5-a]pyridin-8-yloxymethyl}-benzonitrile |
| 264 | 9999 | 566.68 | 9999 | 2-[4-(4-Methyl-piperazin-1-yl)-phenylamino]-[1,2,4]triazolo[1,5-a]pyridin-8-ol |
| 265 | 9999 | 2623.32 | 9999 | (4-Methanesulfonyl-phenyl)-(8-methyl-[1,2,4]triazolo[1,5-a]pyridin-2-yl)-amine |
| 266 | 1665.67 | 142.78 | 2359.82 | 2-{2-[3-(4-Methyl-piperazin-1-yl)-phenylamino]-[1,2,4]triazolo[1,5-a]pyridin-8-yloxymethyl}-benzamide |
| 267 | 9999 | 3.43 | 162.03 | N-{3-[8-(4-Methanesulfonyl-phenyl)-[1,2,4]triazolo[1,5-a]pyridin-2-ylamino]-phenyl}-acetamide |
| 268 | 999 | 16.84 | 359.53 | [8-(2-Chloro-5-trifluoromethyl-phenyl)-[1,2,4]triazolo[1,5-a]pyridin-2-yl]-[3-(2-methanesulfonyl-ethyl)-2,3,4,5-tetrahydro-1H-benzo[d]azepin-7-yl]-amine |
| 269 | 9999 | 586.02 | 9999 | 7-[8-(2-Fluoro-5-trifluoromethyl-phenyl)-[1,2,4]triazolo[1,5-a]pyridin-2-ylamino]-1,2,4,5-tetrahydro-benzo[d]azepine-3-carboxylic acid tert-butyl ester |
| 270 | 6499 | 7.64 | 137.2 | [8-(2-Fluoro-5-trifluoromethyl-phenyl)-[1,2,4]triazolo[1,5-a]pyridin-2-yl]-(2,3,4,5-tetrahydro-1H-benzo[d]azepin-7-yl)-amine |
| 271 | 9999 | 674.80 | 2999 | 4-{4-[8-(2-Methoxy-pyridin-3-yl)-[1,2,4]triazolo[1,5-a]pyridin-2-ylamino]-phenyl}-piperidine-1-carboxylic acid tert-butyl ester |
| 272 | 9999 | 377.05 | 2351.49 | [8-(2-Methoxy-pyridin-3-yl)-[1,2,4]triazolo[1,5-a]pyridin-2-yl]-(4-piperidin-4-yl-phenyl)-amine |
| 273 | 999 | 251.31 | 1685.1 | 2-(4-{4-[8-(2-Methoxy-pyridin-3-yl)-[1,2,4]triazolo[1,5-a]pyridin-2-ylamino]-phenyl}-piperidin-1-yl)-N,N-dimethyl-acetamide |
| 274 | 9999 | 191.93 | 1346.05 | [8-(2-Methoxy-pyridin-3-yl)-[1,2,4]triazolo[1,5-a]pyridin-2-yl]-quinolin-6-yl-amine |
| 275 | 1999 | 270.24 | 344.88 | N,N-Dimethyl-2-(4-{4-[8-(2-oxo-1,2-dihydro-pyridin-3-yl)-[1,2,4]triazolo[1,5-a]pyridin-2-ylamino]-phenyl}-piperidin-1-yl)-acetamide |
| 276 | 9999 | 224.04 | 434.11 | 3-[2-(Quinolin-6-ylamino)-[1,2,4]triazolo[1,5-a]pyridin-8-yl]-1H-pyridin-2-one |
| 277 | 9999 | | 9999 | 4-{4-[8-(2-Methoxy-5-trifluoromethyl-pyridin-3-yl)-[1,2,4]triazolo[1,5-a]pyridin-2-ylamino]-phenyl}-piperidine-1-carboxylic acid tert-butyl ester |

-continued

| Ex. # | FAK IC50 (nM) | JAK2 IC50 (nM) | JAK3 IC50 (nM) | Name |
|---|---|---|---|---|
| 278 | 9999 | 132.71 | 574.34 | [8-(2-Methoxy-5-trifluoromethyl-pyridin-3-yl)-[1,2,4]triazolo[1,5-a]pyridin-2-yl]-(4-piperidin-4-yl-phenyl)-amine |
| 279 | 9999 | 74.59 | 2243.29 | 2-(4-{4-[8-(2-Methoxy-5-trifluoromethyl-pyridin-3-yl)-[1,2,4]triazolo[1,5-a]pyridin-2-ylamino]-phenyl}-piperidin-1-yl)-N,N-dimethyl-acetamide |
| 280 | 9999 | 1108.85 | 9999 | 4-(4-{8-[1-(4-Fluoro-phenyl)-1H-pyrazol-4-yl]-[1,2,4]triazolo[1,5-a]pyridin-2-ylamino}-phenyl)-piperidine-1-carboxylic acid tert-butyl ester |
| 281 | 9999 | 9999.00 | 9999 | 4-{4-[8-(4-Acetylamino-phenylsulfanyl)-[1,2,4]triazolo[1,5-a]pyridin-2-ylamino]-phenyl}-piperidine-1-carboxylic acid tert-butyl ester |
| 282 | 999 | 2.12 | 119.79 | {8-[1-(4-Fluoro-phenyl)-1H-pyrazol-4-yl]-[1,2,4]triazolo[1,5-a]pyridin-2-yl}-(4-piperidin-4-yl-phenyl)-amine |
| 283 | 1374.28 | 1.06 | 46.05 | 2-[4-(4-{8-[1-(4-Fluoro-phenyl)-1H-pyrazol-4-yl]-[1,2,4]triazolo[1,5-a]pyridin-2-ylamino}-phenyl)-piperidin-1-yl]-N,N-dimethyl-acetamide |
| 284 | 9999 | 1491.53 | 9999 | 4-{4-[8-(5-Methoxy-pyrazin-2-yl)-[1,2,4]triazolo[1,5-a]pyridin-2-ylamino]-phenyl}-piperidine-1-carboxylic acid tert-butyl ester |
| 285 | 2467.32 | 73.75 | 391.68 | [8-(5-Methoxy-pyrazin-2-yl)-[1,2,4]triazolo[1,5-a]pyridin-2-yl]-(4-piperidin-4-yl-phenyl)-amine |
| 286 | 2999 | 134.39 | 449.05 | 2-(4-{4-[8-(5-Methoxy-pyrazin-2-yl)-[1,2,4]triazolo[1,5-a]pyridin-2-ylamino]-phenyl}-piperidin-1-yl)-N,N-dimethyl-acetamide |
| 287 | 9999 | 1690.16 | 9999 | 4-{4-[8-(1-p-Tolyl-1H-pyrazol-4-yl)-[1,2,4]triazolo[1,5-a]pyridin-2-ylamino]-phenyl}-piperidine-1-carboxylic acid tert-butyl ester |
| 288 | 2999 | 5.64 | 152.93 | {8-[1-(4-Fluoro-phenyl)-1H-pyrazol-4-yl]-[1,2,4]triazolo[1,5-a]pyridin-2-yl}-[3-(4-methyl-piperazin-1-yl)-phenyl]-amine |
| 289 | 2415.34 | 4.04 | 82.56 | (4-Piperidin-4-yl-phenyl)-[8-(1-p-tolyl-1H-pyrazol-4-yl)-[1,2,4]triazolo[1,5-a]pyridin-2-yl]-amine |
| 290 | 9999 | 2999.00 | 9999 | N*8*-(2-Methoxy-5-trifluoromethyl-phenyl)-N*2*-[3-(4-methyl-piperazin-1-yl)-phenyl]-[1,2,4]triazolo[1,5-a]pyridine-2,8-diamine |
| 291 | | | | 7-[8-(2-Isobutoxy-phenyl)-[1,2,4]triazolo[1,5-a]pyridin-2-ylamino]-1,2,4,5-tetrahydro-benzo[d]azepine-3-carboxylic acid tert-butyl ester |
| 292 | 1999 | 1792.10 | 9999 | [8-(2-Isobutoxy-phenyl)-[1,2,4]triazolo[1,5-a]pyridin-2-yl]-(2,3,4,5-tetrahydro-1H-benzo[d]azepin-7-yl)-amine |
| 293 | | | | 7-[8-(3-Isobutoxy-phenyl)-[1,2,4]triazolo[1,5-a]pyridin-2-ylamino]-1,2,4,5-tetrahydro-benzo[d]azepine-3-carboxylic acid tert-butyl ester |
| 294 | 2999 | 32.64 | 342.21 | [8-(3-Isobutoxy-phenyl)-[1,2,4]triazolo[1,5-a]pyridin-2-yl]-(2,3,4,5-tetrahydro-1H-benzo[d]azepin-7-yl)-amine |
| 295 | | | | 7-[8-(2-Isobutoxy-4-methyl-phenyl)-[1,2,4]triazolo[1,5-a]pyridin-2-ylamino]-1,2,4,5- |

-continued

| Ex. # | FAK IC50 (nM) | JAK2 IC50 (nM) | JAK3 IC50 (nM) | Name |
|---|---|---|---|---|
| 296 | 2999 | 2795.86 | 9999 | tetrahydro-benzo[d]azepine-3-carboxylic acid tert-butyl ester [8-(2-Isobutoxy-4-methyl-phenyl)-[1,2,4]triazolo[1,5-a]pyridin-2-yl]-(2,3,4,5-tetrahydro-1H-benzo[d]azepin-7-yl)-amine |
| 297 | | | | 7-[8-(1-Methyl-1H-indazol-4-yl)-[1,2,4]triazolo[1,5-a]pyridin-2-ylamino]-1,2,4,5-tetrahydro-benzo[d]azepine-3-carboxylic acid tert-butyl ester |
| 298 | 1033.14 | 16.54 | 226.9 | [8-(1-Methyl-1H-indazol-4-yl)-[1,2,4]triazolo[1,5-a]pyridin-2-yl]-(2,3,4,5-tetrahydro-1H-benzo[d]azepin-7-yl)-amine |
| 299 | 999 | 56.24 | | [8-(2-Isopropoxy-phenyl)-[1,2,4]triazolo[1,5-a]pyridin-2-yl]-(2,3,4,5-tetrahydro-1H-benzo[d]azepin-7-yl)-amine |
| 300 | 2999 | 16.51 | | [8-(2-Ethoxy-phenyl)-[1,2,4]triazolo[1,5-a]pyridin-2-yl]-(2,3,4,5-tetrahydro-1H-benzo[d]azepin-7-yl)-amine |
| 301 | 2789.04 | 111.81 | | [8-(2-Cyclopropylmethoxy-phenyl)-[1,2,4]triazolo[1,5-a]pyridin-2-yl]-(2,3,4,5-tetrahydro-1H-benzo[d]azepin-7-yl)-amine |
| 302 | | | | 7-[8-(2-Isopropoxy-phenyl)-[1,2,4]triazolo[1,5-a]pyridin-2-ylamino]-1,2,4,5-tetrahydro-benzo[d]azepine-3-carboxylic acid tert-butyl ester |
| 303 | | | | 7-[8-(2-Ethoxy-phenyl)-[1,2,4]triazolo[1,5-a]pyridin-2-ylamino]-1,2,4,5-tetrahydro-benzo[d]azepine-3-carboxylic acid tert-butyl ester |
| 304 | | | | 7-[8-(2-Cyclopropylmethoxy-phenyl)-[1,2,4]triazolo[1,5-a]pyridin-2-ylamino]-1,2,4,5-tetrahydro-benzo[d]azepine-3-carboxylic acid tert-butyl ester |
| 305 | 9999 | 3084.02 | | [8-(2-Isobutoxy-5-methyl-phenyl)-[1,2,4]triazolo[1,5-a]pyridin-2-yl]-(2,3,4,5-tetrahydro-1H-benzo[d]azepin-7-yl)-amine |
| 306 | | | | 7-[8-(5-Chloro-2-propoxy-phenyl)-[1,2,4]triazolo[1,5-a]pyridin-2-ylamino]-1,2,4,5-tetrahydro-benzo[d]azepine-3-carboxylic acid tert-butyl ester |
| 307 | 1047.75 | 827.82 | | [8-(5-Chloro-2-propoxy-phenyl)-[1,2,4]triazolo[1,5-a]pyridin-2-yl]-(2,3,4,5-tetrahydro-1H-benzo[d]azepin-7-yl)-amine |
| 308 | 946.14 | 365.41 | | 2-{7-[8-(5-Chloro-2-propoxy-phenyl)-[1,2,4]triazolo[1,5-a]pyridin-2-ylamino]-1,2,4,5-tetrahydro-benzo[d]azepin-3-yl}-N,N-dimethyl-acetamide |
| 309 | | | | 7-[8-(5-Chloro-2-ethoxy-phenyl)-[1,2,4]triazolo[1,5-a]pyridin-2-ylamino]-1,2,4,5-tetrahydro-benzo[d]azepine-3-carboxylic acid tert-butyl ester |
| 310 | 1228.96 | 33.44 | | [8-(5-Chloro-2-ethoxy-phenyl)-[1,2,4]triazolo[1,5-a]pyridin-2-yl]-(2,3,4,5-tetrahydro-1H-benzo[d]azepin-7-yl)-amine |
| 311 | | | | 7-[8-(2-Methoxy-phenyl)-[1,2,4]triazolo[1,5-a]pyridin-2-ylamino]-1,2,4,5-tetrahydro-benzo[d]azepine-3-carboxylic acid tert-butyl ester |
| 312 | | | | [8-(2-Methoxy-phenyl)-[1,2,4]triazolo[1,5-a]pyridin-2-yl]- |

-continued

| Ex. # | FAK IC50 (nM) | JAK2 IC50 (nM) | JAK3 IC50 (nM) | Name |
|---|---|---|---|---|
| 313 | 9999 | 39.21 | 173.78 | (2,3,4,5-tetrahydro-1H-benzo[d]azepin-7-yl)-amine<br>2-{7-[8-(2-Methoxy-phenyl)-[1,2,4]triazolo[1,5-a]pyridin-2-ylamino]-1,2,4,5-tetrahydro-benzo[d]azepin-3-yl}-N,N-dimethyl-acetamide |
| 314 | 9999 | 17.76 | 189.05 | [3-(2-Methanesulfonyl-ethyl)-2,3,4,5-tetrahydro-1H-benzo[d]azepin-7-yl]-[8-(2-methoxy-phenyl)-[1,2,4]triazolo[1,5-a]pyridin-2-yl]-amine |
| 315 | | | | 7-[8-(2-Methoxy-5-trifluoromethyl-phenyl)-[1,2,4]triazolo[1,5-a]pyridin-2-ylamino]-1,2,4,5-tetrahydro-benzo[d]azepine-3-carboxylic acid tert-butyl ester |
| 316 | | | | [8-(2-Methoxy-5-trifluoromethyl-phenyl)-[1,2,4]triazolo[1,5-a]pyridin-2-yl]-(2,3,4,5-tetrahydro-1H-benzo[d]azepin-7-yl)-amine |
| 317 | 1999 | 54.48 | 749.57 | 2-{7-[8-(2-Methoxy-5-trifluoromethyl-phenyl)-[1,2,4]triazolo[1,5-a]pyridin-2-ylamino]-1,2,4,5-tetrahydro-benzo[d]azepin-3-yl}-N,N-dimethyl-acetamide |
| 318 | | | | 7-[8-(2-Ethoxy-5-trifluoromethyl-phenyl)-[1,2,4]triazolo[1,5-a]pyridin-2-ylamino]-1,2,4,5-tetrahydro-benzo[d]azepine-3-carboxylic acid tert-butyl ester |
| 319 | 1311.53 | 136.55 | 1114.57 | [8-(2-Ethoxy-5-trifluoromethyl-phenyl)-[1,2,4]triazolo[1,5-a]pyridin-2-yl]-(2,3,4,5-tetrahydro-1H-benzo[d]azepin-7-yl)-amine |
| 320 | 2999 | 159.91 | 3384.89 | [8-(2-Ethoxy-5-trifluoromethyl-phenyl)-[1,2,4]triazolo[1,5-a]pyridin-2-yl]-[3-(2-methanesulfonyl-ethyl)-2,3,4,5-tetrahydro-1H-benzo[d]azepin-7-yl]-amine |
| 321 | 1783.16 | 223.03 | 1435.57 | 2-{7-[8-(2-Ethoxy-5-trifluoromethyl-phenyl)-[1,2,4]triazolo[1,5-a]pyridin-2-ylamino]-1,2,4,5-tetrahydro-benzo[d]azepin-3-yl}-N,N-dimethyl-acetamide |
| 322 | 572.16 | 12.74 | 133.14 | [3-(2-Methanesulfonyl-ethyl)-2,3,4,5-tetrahydro-1H-benzo[d]azepin-7-yl]-[8-(2-methoxy-5-trifluoromethyl-phenyl)-[1,2,4]triazolo[1,5-a]pyridin-2-yl]-amine |
| 323 | 690.79 | 11.29 | 150.09 | 2-{7-[8-(5-Fluoro-2-methoxy-phenyl)-[1,2,4]triazolo[1,5-a]pyridin-2-ylamino]-1,2,4,5-tetrahydro-benzo[d]azepin-3-yl}-N,N-dimethyl-acetamide |
| 324 | 2999 | 46.97 | 292.28 | 2-{7-[8-(4-Fluoro-2-methoxy-phenyl)-[1,2,4]triazolo[1,5-a]pyridin-2-ylamino]-1,2,4,5-tetrahydro-benzo[d]azepin-3-yl}-N,N-dimethyl-acetamide |
| 325 | 1999 | 8.48 | 31.82 | 2-{7-[8-(4-Chloro-2-methoxy-phenyl)-[1,2,4]triazolo[1,5-a]pyridin-2-ylamino]-1,2,4,5-tetrahydro-benzo[d]azepin-3-yl}-N,N-dimethyl-acetamide |
| 326 | 5499 | 1205.98 | 3248.21 | 2-{7-[8-(2-Isopropoxy-5-trifluoromethyl-phenyl)-[1,2,4]triazolo[1,5-a]pyridin-2-ylamino]-1,2,4,5-tetrahydro-benzo[d]azepin-3-yl}-N,N-dimethyl-acetamide |

-continued

| Ex. # | FAK IC50 (nM) | JAK2 IC50 (nM) | JAK3 IC50 (nM) | Name |
|---|---|---|---|---|
| 327 | 2999 | 524.30 | 1622.78 | 2-[4-(4-{8-[2-(2,2-Difluoro-ethoxy)-5-trifluoromethyl-phenyl]-[1,2,4]triazolo[1,5-a]pyridin-2-ylamino}-phenyl)-piperidin-1-yl]-N,N-dimethyl-acetamide |
| 328 | 999 | 257.43 | 2870.92 | {8-[2-(2,2-Difluoro-ethoxy)-5-trifluoromethyl-phenyl]-[1,2,4]triazolo[1,5-a]pyridin-2-yl}-(2,3,4,5-tetrahydro-1H-benzo[d]azepin-7-yl)-amine |
| 329 | 999 | 316.51 | 1667.36 | 2-(7-{8-[2-(2,2-Difluoro-ethoxy)-5-trifluoromethyl-phenyl]-[1,2,4]triazolo[1,5-a]pyridin-2-ylamino}-1,2,4,5-tetrahydro-benzo[d]azepin-3-yl)-N,N-dimethyl-acetamide |
| 330 | 2999 | 37.11 | 104.39 | 2-(4-{4-[8-(4-Chloro-2-methoxy-phenyl)-[1,2,4]triazolo[1,5-a]pyridin-2-ylamino]-phenyl}-piperidin-1-yl)-N,N-dimethyl-acetamide |
| 331 | 6499 | 21.25 | 93 | 2-{6-[8-(4-Chloro-2-methoxy-phenyl)-[1,2,4]triazolo[1,5-a]pyridin-2-ylamino]-3,4-dihydro-1H-isoquinolin-2-yl}-N,N-dimethyl-acetamide |
| 332 | 1999 | 15.23 | 128.16 | 2-(4-{3-[8-(4-Chloro-2-methoxy-phenyl)-[1,2,4]triazolo[1,5-a]pyridin-2-ylamino]-phenyl}-piperidin-1-yl)-N,N-dimethyl-acetamide |
| 333 | 9999 | 6499.00 | 9999 | 4-{4-[8-(2-Methoxy-5-trifluoromethyl-phenyl)-[1,2,4]triazolo[1,5-a]pyridin-2-ylamino]-phenyl}-piperidine-1-carboxylic acid tert-butyl ester |
| 334 | 2999 | 79.87 | 740.39 | [8-(2-Methoxy-5-trifluoromethyl-phenyl)-[1,2,4]triazolo[1,5-a]pyridin-2-yl]-(4-piperidin-4-yl-phenyl)-amine |
| 335 | 999 | 59.74 | 415.06 | 2-(4-{4-[8-(2-Methoxy-5-trifluoromethyl-phenyl)-[1,2,4]triazolo[1,5-a]pyridin-2-ylamino]-phenyl}-piperidin-1-yl)-N,N-dimethyl-acetamide |
| 336 | 9999 | 1148.54 | 6499 | 6-[8-(2-Methoxy-5-trifluoromethyl-phenyl)-[1,2,4]triazolo[1,5-a]pyridin-2-ylamino]-3,4-dihydro-1H-isoquinoline-2-carboxylic acid tert-butyl ester |
| 337 | 778.47 | 41.87 | 674.98 | [8-(2-Methoxy-5-trifluoromethyl-phenyl)-[1,2,4]triazolo[1,5-a]pyridin-2-yl]-(1,2,3,4-tetrahydro-isoquinolin-6-yl)-amine |
| 338 | 1365.43 | 41.40 | 533.77 | 2-{6-[8-(2-Methoxy-5-trifluoromethyl-phenyl)-[1,2,4]triazolo[1,5-a]pyridin-2-ylamino]-3,4-dihydro-1H-isoquinolin-2-yl}-N,N-dimethyl-acetamide |
| 339 | 9999 | 1411.38 | 2999 | 4-{4-[8-(4-Difluoromethyl-2-methoxy-phenyl)-[1,2,4]triazolo[1,5-a]pyridin-2-ylamino]-phenyl}-piperidine-1-carboxylic acid tert-butyl ester |
| 340 | 1999 | 65.86 | 201.78 | [8-(4-Difluoromethyl-2-methoxy-phenyl)-[1,2,4]triazolo[1,5-a]pyridin-2-yl]-(4-piperidin-4-yl-phenyl)-amine |
| 341 | 2999 | 33.69 | 91.06 | 2-(4-{4-[8-(4-Difluoromethyl-2-methoxy-phenyl)-[1,2,4]triazolo[1,5-a]pyridin-2-ylamino]-phenyl}-piperidin-1-yl)-N,N-dimethyl-acetamide |
| 342 | 9999 | 360.56 | 9999 | 4-{4-[8-(4-Fluoro-phenyl)-[1,2,4]triazolo[1,5-a]pyridin-2- |

-continued

| Ex. # | FAK IC50 (nM) | JAK2 IC50 (nM) | JAK3 IC50 (nM) | Name |
|---|---|---|---|---|
| | | | | ylamino]-phenyl}-piperidine-1-carboxylic acid tert-butyl ester |
| 345 | 1344.62 | 8.12 | 252.09 | [8-(4-Fluoro-phenyl)-[1,2,4]triazolo[1,5-a]pyridin-2-yl]-(4-piperidin-4-yl-phenyl)-amine |
| 346 | 999 | 6.63 | 159.62 | (2,3-Dihydro-1H-isoindol-5-yl)-[8-(3-methoxy-phenyl)-[1,2,4]triazolo[1,5-a]pyridin-2-yl]-amine |
| 347 | 1477.52 | 10.36 | 245.31 | 2-(4-{4-[8-(4-Fluoro-phenyl)-[1,2,4]triazolo[1,5-a]pyridin-2-ylamino]-phenyl}-piperidin-1-yl)-N,N-dimethyl-acetamide |
| 348 | 999 | 7.60 | 218.66 | [8-(3-Methoxy-phenyl)-[1,2,4]triazolo[1,5-a]pyridin-2-yl]-(4-piperidin-4-yl-phenyl)-amine |
| 349 | 999 | 10.69 | 180.27 | 2-(4-{4-[8-(3-Methoxy-phenyl)-[1,2,4]triazolo[1,5-a]pyridin-2-ylamino]-phenyl}-piperidin-1-yl)-N,N-dimethyl-acetamide |
| 350 | 9999 | 529.59 | 1649.49 | 4-{4-[8-(2-Fluoro-3-methoxy-phenyl)-[1,2,4]triazolo[1,5-a]pyridin-2-ylamino]-phenyl}-piperidine-1-carboxylic acid tert-butyl ester |
| 351 | 2999 | 30.45 | 183.25 | [8-(2-Fluoro-3-methoxy-phenyl)-[1,2,4]triazolo[1,5-a]pyridin-2-yl]-(4-piperidin-4-yl-phenyl)-amine |
| 352 | 2999 | 18.73 | 96.1 | 2-(4-{4-[8-(2-Fluoro-3-methoxy-phenyl)-[1,2,4]triazolo[1,5-a]pyridin-2-ylamino]-phenyl}-piperidin-1-yl)-N,N-dimethyl-acetamide |
| 353 | 9999 | 326.43 | 1105.66 | 4-{4-[8-(2,3-Dimethoxy-phenyl)-[1,2,4]triazolo[1,5-a]pyridin-2-ylamino]-phenyl}-piperidine-1-carboxylic acid tert-butyl ester |
| 354 | 1906.62 | 58.04 | 184.67 | [8-(2,3-Dimethoxy-phenyl)-[1,2,4]triazolo[1,5-a]pyridin-2-yl]-(4-piperidin-4-yl-phenyl)-amine |
| 355 | 1606.68 | 45.65 | 123.71 | 2-(4-{4-[8-(2,3-Dimethoxy-phenyl)-[1,2,4]triazolo[1,5-a]pyridin-2-ylamino]-phenyl}-piperidin-1-yl)-N,N-dimethyl-acetamide |
| 356 | 9999 | 61.59 | 2999 | 4-{4-[8-(4-Cyano-phenyl)-[1,2,4]triazolo[1,5-a]pyridin-2-ylamino]-phenyl}-piperidine-1-carboxylic acid tert-butyl ester |
| 357 | 2999 | 5.81 | 249.4 | 4-[2-(4-Piperidin-4-yl-phenylamino)-[1,2,4]triazolo[1,5-a]pyridin-8-yl]-benzonitrile |
| 358 | 2999 | 3.88 | 143.36 | 2-(4-{4-[8-(4-Cyano-phenyl)-[1,2,4]triazolo[1,5-a]pyridin-2-ylamino]-phenyl}-piperidin-1-yl)-N,N-dimethyl-acetamide |
| 359 | 9999 | 163.75 | 999 | 4-{4-[8-(2-Fluoro-4-methoxy-phenyl)-[1,2,4]triazolo[1,5-a]pyridin-2-ylamino]-phenyl}-piperidine-1-carboxylic acid tert-butyl ester |
| 360 | 2999 | 9.04 | 58.06 | [8-(2-Fluoro-4-methoxy-phenyl)-[1,2,4]triazolo[1,5-a]pyridin-2-yl]-(4-piperidin-4-yl-phenyl)-amine |
| 361 | 9999 | 193.08 | 9999 | 4-{4-[8-(3-Dimethylamino-phenyl)-[1,2,4]triazolo[1,5-a]pyridin-2-ylamino]-phenyl}-piperidine-1-carboxylic acid tert-butyl ester |
| 362 | 2999 | 4.41 | 36.42 | 2-(4-{4-[8-(2-Fluoro-4-methoxy-phenyl)-[1,2,4]triazolo[1,5-a]pyridin-2-ylamino]-phenyl}-piperidin-1-yl)-N,N-dimethyl-acetamide |
| 363 | 1748.45 | 3.93 | 82.16 | [8-(3-Dimethylamino-phenyl)-[1,2,4]triazolo[1,5-a]pyridin-2-yl]-(4-piperidin-4-yl-phenyl)-amine |

-continued

| Ex. # | FAK IC50 (nM) | JAK2 IC50 (nM) | JAK3 IC50 (nM) | Name |
|---|---|---|---|---|
| 364 | 862.75 | 4.99 | 89.07 | 2-(4-{4-[8-(3-Dimethylamino-phenyl)-[1,2,4]triazolo[1,5-a]pyridin-2-ylamino]-phenyl}-piperidin-1-yl)-N,N-dimethyl-acetamide |
| 365 | 999 | 29.07 | 494.04 | [8-(4-Fluoro-phenyl)-[1,2,4]triazolo[1,5-a]pyridin-2-yl]-[3-(4-methyl-piperazin-1-yl)-phenyl]-amine |
| 366 | | | | 7-{8-[2-(2,2-Difluoro-ethoxy)-phenyl]-[1,2,4]triazolo[1,5-a]pyridin-2-ylamino}-1,2,4,5-tetrahydro-benzo[d]azepine-3-carboxylic acid tert-butyl ester |
| 367 | 1905.36 | 129.80 | 832.18 | {8-[2-(2,2-Difluoro-ethoxy)-phenyl]-[1,2,4]triazolo[1,5-a]pyridin-2-yl}-(2,3,4,5-tetrahydro-1H-benzo[d]azepin-7-yl)-amine |
| 368 | 2432.11 | 196.66 | 1094.94 | 2-(7-{8-[2-(2,2-Difluoro-ethoxy)-phenyl]-[1,2,4]triazolo[1,5-a]pyridin-2-ylamino}-1,2,4,5-tetrahydro-benzo[d]azepin-3-yl)-N,N-dimethyl-acetamide |
| 369 | | | | 7-{8-[2-(2,2-Difluoro-ethoxy)-4-methanesulfonyl-phenyl]-2,3-dihydro-[1,2,4]triazolo[1,5-a]pyridin-2-ylamino}-1,2,4,5-tetrahydro-benzo[d]azepine-3-carboxylic acid tert-butyl ester |
| 370 | 999 | 61.87 | | {8-[2-(2,2-Difluoro-ethoxy)-4-methanesulfonyl-phenyl]-[1,2,4]triazolo[1,5-a]pyridin-2-yl}-(2,3,4,5-tetrahydro-1H-benzo[d]azepin-7-yl)-amine |
| 371 | | | | 7-{8-[2-(2,2-Difluoro-ethoxy)-5-methanesulfonyl-phenyl]-[1,2,4-triazolo[1,5-a]pyridin-2-ylamino}-1,2,4,5-tetrahydro-benzo[d]azepine-3-carboxylic acid tert-butyl ester |
| 372 | 9999 | 600.24 | | {8-[2-(2,2-Difluoro-ethoxy)-5-methanesulfonyl-phenyl]-[1,2,4]triazolo[1,5-a]pyridin-2-yl}-(2,3,4,5-tetrahydro-1H-benzo[d]azepin-7-yl)-amine |
| 373 | 9999 | 504.69 | | 2-(7-{8-[2-(2,2-Difluoro-ethoxy)-5-methanesulfonyl-phenyl]-[1,2,4]triazolo[1,5-a]pyridin-2-ylamino}-1,2,4,5-tetrahydro-benzo[d]azepin-3-yl)-N,N-dimethyl-acetamide |
| 374 | | | | 7-[8-(3-Trifluoromethyl-phenyl)-[1,2,4]triazolo[1,5-a]pyridin-2-ylamino]-1,2,4,5-tetrahydro-benzo[d]azepine-3-carboxylic acid tert-butyl ester |
| 375 | 422.01 | 42.52 | | (2,3,4,5-Tetrahydro-1H-benzo[d]azepin-7-yl)-[8-(3-trifluoromethyl-phenyl)-[1,2,4]triazolo[1,5-a]pyridin-2-yl]-amine |
| 376 | | | | 7-{8-[5-Chloro-2-(2,2-difluoro-ethoxy)-phenyl]-[1,2,4]triazolo[1,5-a]pyridin-2-ylamino}-1,2,4,5-tetrahydro-benzo[d]azepine-3-carboxylic acid tert-butyl ester |
| 377 | 442.65 | 43.97 | | {8-[5-Chloro-2-(2,2-difluoro-ethoxy)-phenyl]-[1,2,4]triazolo[1,5-a]pyridin-2-yl}-(2,3,4,5-tetrahydro-1H-benzo[d]azepin-7-yl)-amine |
| 378 | 1249.7 | 519.79 | | 2-(7-{8-[2-(2,2-Difluoro-ethoxy)-5-fluoro-phenyl]-[1,2,4]triazolo[1,5-a]pyridin-2-ylamino}-1,2,4,5-tetrahydro-benzo[d]azepin-3-yl)-N,N-dimethyl-acetamide |
| 379 | 2999 | 1078.21 | | [8-(2-Isobutoxy-5-trifluoromethyl-phenyl)-[1,2,4]triazolo[1,5- |

-continued

| Ex. # | FAK IC50 (nM) | JAK2 IC50 (nM) | JAK3 IC50 (nM) | Name |
|---|---|---|---|---|
| 380 | 2999 | 2999.00 | | a]pyridin-2-yl)-(2,3,4,5-tetrahydro-1H-benzo[d]azepin-7-yl)-amine<br>2-{7-[8-(2-Isobutoxy-5-trifluoromethyl-phenyl)-[1,2,4]triazolo[1,5-a]pyridin-2-ylamino]-1,2,4,5-tetrahydro-benzo[d]azepin-3-yl}-N,N-dimethyl-acetamide |
| 381 | 434.28 | 115.82 | 1024.27 | 2-(7-{8-[5-Chloro-2-(2,2-difluoro-ethoxy)-phenyl]-[1,2,4]triazolo[1,5-a]pyridin-2-ylamino}-1,2,4,5-tetrahydro-benzo[d]azepin-3-yl)-N,N-dimethyl-acetamide |
| 382 | 1999 | 198.22 | | 7-{8-[5-Chloro-2-(2,2-difluoro-ethoxy)-phenyl]-[1,2,4]triazolo[1,5-a]pyridin-2-ylamino}-1,2,4,5-tetrahydro-benzo[d]azepine-3-carboxylic acid dimethylamide |
| 383 | | | | 7-{8-[2-(2,2-Difluoro-ethoxy)-5-difluoromethyl-phenyl]-[1,2,4]triazolo[1,5-a]pyridin-2-ylamino}-1,2,4,5-tetrahydro-benzo[d]azepine-3-carboxylic acid tert-butyl ester |
| 384 | 1076.57 | 203.10 | 9999 | {8-[2-(2,2-Difluoro-ethoxy)-5-difluoromethyl-phenyl]-[1,2,4]triazolo[1,5-a]pyridin-2-yl}-(2,3,4,5-tetrahydro-1H-benzo[d]azepin-7-yl)-amine |
| 385 | 1120.97 | 269.87 | 9999 | 2-(7-{8-[2-(2,2-Difluoro-ethoxy)-5-difluoromethyl-phenyl]-[1,2,4]triazolo[1,5-a]pyridin-2-ylamino}-1,2,4,5-tetrahydro-benzo[d]azepin-3-yl)-N,N-dimethyl-acetamide |
| 386 | 9999 | 29.92 | | [8-(4-Methanesulfonyl-phenyl)-[1,2,4]triazolo[1,5-a]pyridin-2-yl]-(4-methyl-3,4,5,6-tetrahydro-2H-[1,2']bipyrazinyl-6'-yl)-amine |
| 387 | 552.58 | 12.26 | 154.54 | N(8)-(2-Methoxy-benzyl)-N(2)-[4-(4-methyl-piperazin-1-yl)-phenyl]-[1,2,4]triazolo[1,5-a]pyridine-2,8-diamine |
| 388 | 951.19 | 45.95 | | N(8)-(2-Methoxy-benzyl)-N(2)-[3-(4-methyl-piperazin-1-yl)-phenyl]-[1,2,4]triazolo[1,5-a]pyridine-2,8-diamine |
| 389 | 1058.8 | 6499.00 | | N-Methyl-N-(2-{[2-(4-methyl-3,4,5,6-tetrahydro-2H-[1,2']bipyrazinyl-6'-ylamino)-[1,2,4]triazolo[1,5-a]pyridin-8-ylamino]-methyl}-phenyl)-methanesulfonamide |
| 390 | 9999 | 1339.32 | | N(8)-(3-Methoxy-benzyl)-N(2)-[4-(4-methyl-piperazin-1-yl)-phenyl]-[1,2,4]triazolo[1,5-a]pyridine-2,8-diamine |
| 391 | 9999 | 3021.96 | | N(8)-(4-Methoxy-benzyl)-N(2)-[4-(4-methyl-piperazin-1-yl)-phenyl]-[1,2,4]triazolo[1,5-a]pyridine-2,8-diamine |
| 392 | 9999 | 2999.00 | | N(8)-(3-Methoxy-benzyl)-N(2)-[3-(4-methyl-piperazin-1-yl)-phenyl]-[1,2,4]triazolo[1,5-a]pyridine-2,8-diamine |
| 393 | 9999 | 9999.00 | | N(8)-(4-Methoxy-benzyl)-N(2)-[3-(4-methyl-piperazin-1-yl)-phenyl]-[1,2,4]triazolo[1,5-a]pyridine-2,8-diamine |
| 394 | 9999 | 9999.00 | | N(8)-(3-Methoxy-benzyl)-N(2)-(6-methoxy-pyridin-3-yl)-[1,2,4]triazolo[1,5-a]pyridine-2,8-diamine |
| 395 | 1482.18 | 180.36 | | N(8)-(2-Fluoro-benzyl)-N(2)-[3-(4-methyl-piperazin-1-yl)-phenyl]-[1,2,4]triazolo[1,5-a]pyridine-2,8-diamine |

-continued

| Ex. # | FAK IC50 (nM) | JAK2 IC50 (nM) | JAK3 IC50 (nM) | Name |
|---|---|---|---|---|
| 396 | 9999 | 1434.69 | | N(8)-(4-Fluoro-benzyl)-N(2)-[3-(4-methyl-piperazin-1-yl)-phenyl]-[1,2,4]triazolo[1,5-a]pyridine-2,8-diamine |
| 397 | 9999 | 591.96 | | N(8)-(3-Methoxy-benzyl)-N(2)-(2-methyl-pyridin-4-yl)-[1,2,4]triazolo[1,5-a]pyridine-2,8-diamine |
| 398 | 9999 | 816.37 | | N(8-(3-Methoxy-benzyl)-N(2)-pyridin-3-yl-[1,2,4]triazolo[1,5-a]pyridine-2,8-diamine |
| 399 | 9999 | 998.92 | | N(8)-(3-Methoxy-benzyl)-N(2)-pyridin-4-yl-[1,2,4]triazolo[1,5-a]pyridine-2,8-diamine |
| 400 | 3115.79 | 32.27 | | N(8)-(2-Methoxy-benzyl)-N(2)-pyridin-3-yl-[1,2,4]triazolo[1,5-a]pyridine-2,8-diamine |
| 401 | 6499 | 54.84 | | N(8)-(2-Methoxy-benzyl)-N(2)-pyridin-4-yl-[1,2,4]triazolo[1,5-a]pyridine-2,8-diamine |
| 402 | 2999 | 42.66 | | N(8)-(2-Methoxy-benzyl)-N(2)-(6-methoxy-pyridin-3-yl)-[1,2,4]triazolo[1,5-a]pyridine-2,8-diamine |
| 403 | 1882.86 | 27.56 | | N(8)-(2-Methoxy-benzyl)-N(2)-(6-methyl-pyridin-3-yl)-[1,2,4]triazolo[1,5-a]pyridine-2,8-diamine |
| 404 | 2584.52 | 24.70 | | N(8)-(2-Methoxy-benzyl)-N(2)-(2-methyl-pyridin-4-yl)-[1,2,4]triazolo[1,5-a]pyridine-2,8-diamine |
| 405 | 9999 | 1018.22 | | N(8)-(3-Methoxy-benzyl)-N(2)-(6-methyl-pyridin-3-yl)-[1,2,4]triazolo[1,5-a]pyridine-2,8-diamine |
| 406 | 9999 | 9999.00 | | [8-(4-Methanesulfonyl-phenyl)-[1,2,4]triazolo[1,5-a]pyridin-2-yl]-(2-pyridin-2-yl-ethyl)-amine |
| 407 | 9999 | 1977.01 | | [8-(4-Methanesulfonyl-phenyl)-[1,2,4]triazolo[1,5-a]pyridin-2-yl]-(2-pyridin-3-yl-ethyl)-amine |
| 408 | 9999 | 2757.82 | | [8-(4-Methanesulfonyl-phenyl)-[1,2,4]triazolo[1,5-a]pyridin-2-yl]-pyridin-3-ylmethyl-amine |
| 409 | 9999 | 6499.00 | | 8-(4-Methanesulfonyl-phenyl)-[1,2,4]triazolo[1,5-a]pyridin-2-yl]-pyridin-2-ylmethyl-amine |
| 410 | 658.33 | 75.48 | 1118.93 | 2-(4-{3-[8-(2-Methoxy-5-trifluoromethyl-phenyl)-[1,2,4]triazolo[1,5-a]pyridin-2-ylamino]-phenyl}-piperidin-1-yl)-N,N-dimethyl-acetamide |
| 411 | 1862.67 | 1.62 | 57.86 | N-[4-(1-ethyl-4-oxido-1,4-azaphosphinan-4-yl)phenyl]-8-[4-(methylsulfonyl)phenyl][1,2,4]triazolo[1,5-a]pyridin-2-amine |

PREPARATIVE EXAMPLES

The compounds described below or in Table 1 above are non-limiting examples of compounds encompassed by the general Formula I that were prepared and characterized according to one or more of the procedures outlined below. The preparation of various intermediates and starting materials are also described below.

$^1$H NMR (Nuclear Magnetic Resonance) spectra were in all cases consistent with the proposed structures. Characteristic chemical shifts (δ) are given in parts per million (ppm) using conventional abbreviations for the designation of major peaks: s=singlet, d=doublet, t=triplet, m=multiplet, dd=doublet of doublets, ddd=doublet of doublet of doublets, q=quartet, b=broad.

Final compounds and intermediates were also characterized by mass spectrometry (MS) and reported as (MH)+, i.e. the molecular ion plus hydrogen, and/or melting point ranges.

Example 1

Phenyl-[1,2,4]triazolo[1,5-a]pyridin-2-yl-amine

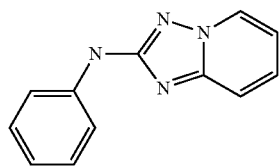 [SMILES: c1ccc(Nc2nc3ccccn3n2)cc1]

1a) A suspension of 1-phenyl-3-pyridin-2-yl-thiourea (1.0 g, 4.4 mmol) and dimethyl sulfate (0.45 mL, 4.8 mmol) in acetonitrile (6 mL) was heated at reflux for 4 hours. The mixture was cooled to room temperature and the volatiles were evaporated.

1b) To the residue was added hydroxylamine hydrochloride (0.67 g, 9.6 mmol), N,N-diisopropylethylamine (3.3 mL, 19 mmol) and dichloromethane (8 mL). The mixture was stirred at room temperature for 18 hours. Water (10 mL) was added. A nitrogen sparge tube connected to a bleach scrubber was fitted to the reaction flask. The mixture was sparged with nitrogen. The resulting oily liquid was partitioned between ethyl acetate (100 mL) and water. The organic layer was washed with water (3×20 mL), dried over magnesium sulfate and filtered. The solvent was evaporated under reduced pressure.

1c) To the residue in acetonitrile (10 mL) at −5° C. was added potassium carbonate (1.5 g, 11 mmol) followed by dropwise addition of 20% phosgene in toluene (1:4, phosgene:toluene, 2.6 mL, 4.9 mmol). The mixture was stirred for 1 hour at −5° C. then warmed to room temperature. Additional 20% phosgene in toluene (1.0 mL) and potassium carbonate (1.0 g) was added to the mixture and stirred for 48 hours. The volatiles were evaporated and the residue was partitioned between ethyl acetate (100 mL) and water. The organic layer was washed with water (3×20 mL), dried over magnesium sulfate and filtered. The solvent was evaporated under reduced pressure and the product was purified via flash chromatography utilizing an ISCO automated purification apparatus (silica gel column, elution gradient of 5%→100% ethyl acetate in heptane). Phenyl-[1,2,4]triazolo[1,5-a]pyridin-2-yl-amine was isolated as a yellow solid (0.17 g, 18%). MP=180-184° C. $^1$H NMR (400 MHz, CDCl$_3$, δ, ppm): 8.46-8.42 (m, 1H), 7.63-7.59 (m, 2H), 7.51-7.41 (m, 2H), 7.38-7.33 (m, 2H), 7.31 (br s, 1H), 7.02-6.97 (m, 1H), 6.90-6.85 (m, 1H). MS=211 (MH)+.

Example 2

[8-(2-Methoxy-phenyl)-[1,2,4]triazolo[1,5-a]pyridin-2-yl]-(4-morpholin-4-yl-phenyl)-amine

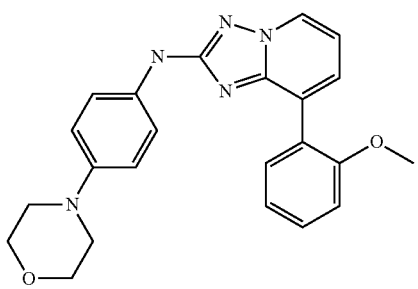 [SMILES: COc1ccccc1-c1cccn2nc(Nc3ccc(N4CCOCC4)cc3)nc12]

2a) To a solution of 3-bromo-pyridin-2-ylamine (9.72 g, 56.2 mmol) in 1,4-dioxane (100 mL) was added dropwise ethoxycarbonyl isothiocyanate (6.70 mL, 56.7 mmol). The mixture was stirred under an atmosphere of nitrogen for 18 hours. The volatiles were evaporated to yield a waxy solid. The recovered material was triturated with hexane (250 mL). N-(3-Bromo-2-pyridinyl)-N'-carboethoxy-thiourea was isolated and was used without further purification. $^1$H NMR (400 MHz, (D$_3$C)$_2$SO, δ, ppm): 11.46 (s, 1H), 11.43 (s, 1H), 8.49 (dd, J=4.6, 1.5 Hz, 1H), 8.18 (dd, J=8.0, 1.5 Hz, 1H), 7.33 (dd, J=8.0, 4.7 Hz, 1H), 4.23 (q, J=7.1 Hz, 2H), 1.27 (t, J=7.2 Hz, 3H). MS=215 (MH)+.

2b) To a stirred suspension of hydroxylamine hydrochloride (17.4 g, 25.0 mmol) and N,N-diisopropylethylamine (26.0 mL, 14.9 mmol) in a mixture of methanol (70 mL) and ethanol (70 mL) was added N-(3-bromo-2-pyridinyl)-N'-carboethoxy-thiourea. The mixture was stirred for 2 hours at room temperature then heated to 60° C. for 18 hours. The suspension was cooled to room temperature, filtered and rinsed with methanol, water then methanol. 8-Bromo-[1,2,4]triazolo[1,5-a]pyridin-2-ylamine was isolated as an off-white solid (8.41 g, 70%). $^1$H NMR (400 MHz, (D$_3$C)$_2$SO, δ, ppm): 8.58 (d, J=6.4 Hz, 1H), 7.73 (d, J=7.6 Hz, 1H), 6.80 (t, J=7.0 Hz, 1H), 6.25 (s, 2H). MS=213, 215 (MH)+.

2c) An oven dried tube was charged with palladium acetate (0.20 g, 0.89 mmol) and triphenylphosphine (0.60 g, 2.3 mmol). The tube was evacuated under high vacuum and backflushed under a stream of nitrogen for 5 minutes. 1,4-Dioxane (10 mL) was added and the mixture was stirred under nitrogen for 10 minutes. 8-Bromo-[1,2,4]triazolo[1,5-a]pyridin-2-ylamine (1.0 g, 4.7 mmol), 2-methoxybenzeneboronic acid (1.1 g, 7.0 mmol), N,N-dimethylformamide (10 mL) and 1.50 M of sodium carbonate in water (10 mL) were added. The mixture was stirred for 2 minutes at room temperature under nitrogen then the tube was sealed and heated at 80° C. for 18 hours. The mixture was transferred to a round bottom flask and the volatiles were evaporated under reduced pressure. Water (100 mL) was added and the mixture was stirred when a precipitate was formed. The solid was collected by filtration, rinsed with water, air dried, triturated with ether/dichloromethane (4:1; 10 mL), filtered and rinsed with ether. 8-(2-Methoxy-phenyl)-[1,2,4]triazolo[1,5-a]pyridin-2-ylamine was isolated (1.0 g, 89%). $^1$H NMR (400 MHz, CDCl$_3$, δ, ppm): 8.50 (d, J=6.5 Hz, 1H), 7.51 (dd, J=7.6, 1.5 Hz, 1H), 7.43-7.36 (m, 2H), 7.13 (d, J=8.1 Hz, 1H), 7.02 (t, J=7.3 Hz, 1H), 6.91 (t, J=7.0 Hz, 1H), 5.96 (br s, 2H), 3.73 (s, 3H). MS=241 (MH)+.

2d) To an oven dried tube was added palladium acetate (10.0 mg, 0.0445 mmol) and 9,9-dimethyl-4,5-bis(diphenylphosphino)xanthene (75.0 mg, 0.130 mmol), 8-(2-methoxy-phenyl)-[1,2,4]triazolo[1,5-a]pyridin-2-ylamine (100.0 mg, 0.4162 mmol), 4-(4-bromo-phenyl)-morpholine (120.0 mg, 0.4956 mmol), cesium carbonate (270 mg, 0.83 mmol) and 1,4-dioxane (5 mL). The tube was evacuated and backflushed with nitrogen three times. The tube was sealed and heated at 80° C. for 72 hours. The mixture was cooled to room temperature, diluted with dichloromethane (10 mL), filtered through a plug of diatomaceous earth, rinsed with dichloromethane and evaporated. The material was purified via chromatography utilizing an ISCO automated purification apparatus (amine modified silica gel column 5%→100% ethyl acetate in hexanes). The title compound, [8-(2-Methoxy-phenyl)-[1,2,4]triazolo[1,5-a]pyridin-2-yl]-(4-morpholin-4-yl-phenyl)-amine, was isolated as a pale yellow foam (0.034 g, 20%). $^1$H NMR (400 MHz, CDCl$_3$, δ, ppm): 8.39 (dd, J=6.7, 1.1 Hz, 1H), 7.61 (dd, J=7.5, 1.7 Hz, 1H), 7.51 (dd, J=7.3, 0.9 Hz, 1H), 7.50-7.45 (m, 2H), 7.43-7.37 (m, 1H), 7.12-7.07 (m, 1H), 7.05 (d, J=8.2 Hz, 1H), 6.96-6.87 (m, 3H), 6.67 (s, 1H), 3.89-3.85 (m, 4H), 3.81 (s, 3H), 3.12-3.08 (m, 4H). MS=402 (MH)+.

Example 3

[8-(2-Methoxy-phenyl)-[1,2,4]triazolo[1,5-a]pyridin-2-yl]-phenyl-amine (0.054 g, 41%), was a byproduct of the reaction and was isolated as a off-white solid. MP=141-145°

C. ¹H NMR (400 MHz, CDCl₃, δ, ppm): 8.42 (dd, J=6.6, 0.9 Hz, 1H), 7.62 (dd, J=7.5, 1.7, 1H), 7.58-7.52 (m, 3H), 7.44-7.38 (m, 1H), 7.36-7.30 (m, 2H), 7.10 (t, J=7.5 Hz, 1H), 7.05 (d, J=8.3 Hz, 1H), 6.97 (t, J=7.4 Hz, 1H), 6.93 (t, J=7.1 Hz, 1H), 6.87 (s, 1H), 3.82 (s, 3H). MS=317 (MH)+.

Example 4

[8-(4-Methanesulfonyl-phenyl)-[1,2,4]triazolo[1,5-a]pyridin-2-yl]-(4-morpholin-4-yl-phenyl)-amine

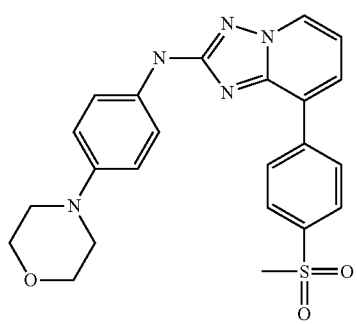 [SMILES: CS(=O)(=O)c1ccc(-c2cccn3nc(Nc4ccc(N5CCOCC5)cc4)nc23)cc1]

4a) 8-(4-Methanesulfonyl-phenyl)-[1,2,4]triazolo[1,5-a]pyridin-2-ylamine was prepared from 8-bromo-[1,2,4]triazolo[1,5-a]pyridin-2-ylamine (0.75 g, 3.5 mmol) and (4-methylsulfonylphenyl)boronic acid (1.0 g, 5.0 mmol) in a manner analogous to Step 2c. The product was isolated as tan solid (0.60 g, 59%). MP=236-239° C. ¹H NMR (400 MHz, (D₃C)₂SO, δ, ppm): 8.63 (d, J=6.3 Hz, 1H), 8.38 (d, J=7.9 Hz, 2H), 8.03 (d, J=7.9 Hz, 2H), 7.84 (d, J=7.3 Hz, 1H), 7.03 (t, J=7.0 Hz, 1H), 6.21 (br s, 2H), 3.28 (s, 3H). MS=289 (MH)+.

4b) [8-(4-Methanesulfonyl-phenyl)-[1,2,4]triazolo[1,5-a]pyridin-2-yl]-(4-morpholin-4-yl-phenyl)-amine and [8-(4-methanesulfonyl-phenyl)-[1,2,4]triazolo[1,5-a]pyridin-2-yl]-phenyl-amine were prepared from 8-(4-methanesulfonyl-phenyl)-[1,2,4]triazolo[1,5-a]pyridin-2-ylamine (100.0 mg, 0.3468 mmol) and 4-(4-bromo-phenyl)-morpholine (100.0 mg, 0.4130 mmol) in a manner analogous to Example 2d. [8-(4-Methanesulfonyl-phenyl)-[1,2,4]triazolo[1,5-a]pyridin-2-yl]-(4-morpholin-4-yl-phenyl)-amine was isolated as a pale yellow solid (0.063 g, 40%). MP=244-246° C. ¹H NMR (400 MHz, CDCl₃, δ, ppm): 8.49-8.45 (m, 1H), 8.25-8.20 (m, 2H), 8.11-8.06 (m, 2H), 7.63 (dd, J=7.4, 0.9 Hz, 1H), 7.53-7.48 (m, 2H), 6.99 (t, J=7.0 Hz, 1H), 6.97-6.93 (m, 2H), 6.73 (s, 1H), 3.90-3.86 (m 4H), 3.14-3.09 (m, 7H). MS=450 (MH)+.

Example 5

8-(4-Methanesulfonyl-phenyl)-[1,2,4]triazolo[1,5-a]pyridin-2-ylamine, was a byproduct of the above reaction and was isolated as a tan solid (0.039 g, 31%). MP=197-201° C. ¹H NMR (400 MHz, CDCl₃, δ, ppm): 8.51 (dd, J=6.6, 0.9 Hz, 1H), 8.26-8.21 (m, 2H), 8.11-8.06 (m, 2H), 7.66 (dd, J=7.3, 0.9 Hz, 1H), 7.61-7.57 (m, 2H), 7.39-7.32 (m, 2H), 7.05-6.99 (m, 2H), 6.94 (s, 1H), 3.10 (s, 3H). MS=365 (MH)+.

Examples 6

(4-Morpholin-4-yl-phenyl)-(8-pyridin-3-yl-[1,2,4]triazolo[1,5-a]pyridin-2-yl)-amine

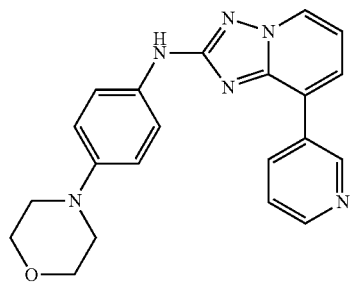 [SMILES: c1cncc(-c2cccn3nc(Nc4ccc(N5CCOCC5)cc4)nc23)c1]

6a) 8-Pyridin-3-yl-[1,2,4]triazolo[1,5-a]pyridin-2-ylamine was prepared from 8-bromo-[1,2,4]triazolo[1,5-a]pyridin-2-ylamine (1.0 g, 4.7 mmol) and 3-pyridylboronic acid (0.81 g, 6.6 mmol) in a manner analogous to Step 2c. The product of the reaction was isolated as a white solid (0.92 g, 93%). MP=185-187° C. ¹H NMR (400 MHz, (D₃C)₂SO, δ, ppm): 9.28 (d, J=2.1 Hz, 1H), 8.62-8.58 (m, 2H), 8.49 (ddd, J=8.1, 1.8, 1.8 Hz, 1H), 7.82 (dd, J=7.4, 0.7 Hz, 1H), 7.53 (dd, J=8.0, 4.7 Hz, 1H), 7.01 (t, J=7.0 Hz, 1H), 6.18 (br s, 2H). MS=212 (MH)+.

6b) (4-Morpholin-4-yl-phenyl)-(8-pyridin-3-yl-[1,2,4]triazolo[1,5-a]pyridin-2-yl)-amine and phenyl-(8-pyridin-3-yl-[1,2,4]triazolo[1,5-a]pyridin-2-yl)-amine were prepared from 8-pyridin-3-yl-[1,2,4]triazolo[1,5-a]pyridin-2-ylamine (70.0 mg, 0.331 mmol) and 4-(4-bromo-phenyl)-morpholine (100.0 mg, 0.4130 mmol) in a manner analogous to Example 2d. (4-Morpholin-4-yl-phenyl)-(8-pyridin-3-yl-[1,2,4]triazolo[1,5-a]pyridin-2-yl)-amine was isolated as a yellow solid (0.025 g, 20%). MP=226-228° C. ¹H NMR (400 MHz, CDCl₃, δ, ppm): 9.16 (d, J=1.9 Hz, 1H), 8.66 (dd, J=4.8, 1.4 Hz, 1H), 8.46-8.41 (m, 2H), 7.61 (dd, J=7.4, 1.1 Hz, 1H), 7.54-7.49 (m, 2H), 7.45 (dd, J=7.9, 4.8 Hz, 1H), 7.00-6.93 (m, 3H), 6.69 (s, 1H), 3.90-3.86 (m, 4H), 3.14-3.09 (m, 4H). MS=373 (MH)+.

Example 7

Phenyl-(8-pyridin-3-yl-[1,2,4]triazolo[1,5-a]pyridin-2-yl)-amine, was a byproduct of the above reaction and was isolated as a yellow solid (0.007 g, 7%). MP=211-212° C. ¹H NMR (400 MHz, CDCl₃, δ, ppm): 9.16 (d, J=2.1 Hz, 1H), 8.67 (dd, J=4.7, 1.4 Hz, 1H), 8.48 (d, J=6.8 Hz, 1H), 8.44 (ddd, J=7.8, 1.8, 1.8 Hz, 1H), 7.65-7.58 (m, 3H), 7.46 (dd, J=8.0, 4.8 Hz, 1H), 7.39-7.34 (m, 2H), 7.04-6.98 (m, 2H), 6.87 (s, 1H). MS=288 (MH)+.

Example 8

[8-(6-Methoxy-pyridin-3-yl)-[1,2,4]triazolo[1,5-a]pyridin-2-yl]-(4-morpholin-4-yl-phenyl)-amine

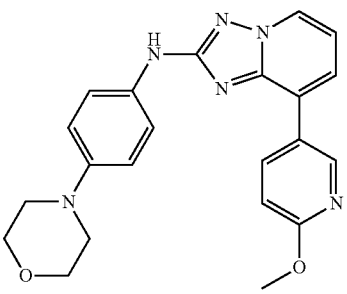 [SMILES: COc1ccc(-c2cccn3nc(Nc4ccc(N5CCOCC5)cc4)nc23)cn1]

8a) 8-(6-Methoxy-pyridin-3-yl)-[1,2,4]triazolo[1,5-a]pyridin-2-ylamine was prepared from 8-bromo-[1,2,4]triazolo[1,5-a]pyridin-2-ylamine (1.0 g, 4.7 mmol) and 2-methoxypyridine-5-boronic acid (1.0 g, 6.6 mmol) in a manner analogous to Step 2c. The product of the reaction was isolated as a tan solid (0.58 g, 51%). MP=157-158° C. $^1$H NMR (400 MHz, (D$_3$C)$_2$SO, δ, ppm): 8.91 (d, J=2.5 Hz, 1H), 8.54 (dd, J=6.6, 0.9 Hz, 1H), 8.44 (dd, J=8.7, 2.5 Hz, 1H), 7.73 (dd, J=7.6, 1.0 Hz, 1H), 6.97 (t, J=6.9 Hz, 1H), 6.96 (d, J=8.7 Hz, 1H), 6.12 (s, 2H), 3.92 (s, 3H). MS=242 (MH)+.

8b) [8-(6-Methoxy-pyridin-3-yl)-[1,2,4]triazolo[1,5-a]pyridin-2-yl]-(4-morpholin-4-yl-phenyl)-amine and phenyl-(8-pyridin-3-yl-[1,2,4]triazolo[1,5-a]pyridin-2-yl)-amine were prepared from 8-(6-methoxy-pyridin-3-yl)-[1,2,4]triazolo[1,5-a]pyridin-2-ylamine (100.0 mg, 0.4145 mmol) and 4-(4-bromo-phenyl)-morpholine (120.0 mg, 0.4956 mmol) in analogous manner to Example 2d. [8-(6-Methoxy-pyridin-3-yl)-[1,2,4]triazolo[1,5-a]pyridin-2-yl]-(4-morpholin-4-yl-phenyl)-amine was isolated as a yellow solid (0.037 g, 22%). MP=200-202° C. $^1$H NMR (400 MHz, CDCl$_3$, δ, ppm): 8.75 (d, J=2.3 Hz, 1H), 8.39 (d, J=6.3 Hz, 1H), 8.29 (dd, J=8.8, 2.6 Hz, 1H), 7.54-7.48 (m, 3H), 7.00-6.87 (m, 4H), 6.67 (s, 1H), 4.01 (s, 3H), 3.90-3.85 (m, 4H), 3.13-3.09 (m, 4H). MS=403 (MH)+.

Example 9

Phenyl-(8-pyridin-3-yl-[1,2,4]triazolo[1,5-a]pyridin-2-yl)-amine, was a byproduct of the above reaction and was isolated as an off-white solid (0.055 g, 40%). MP=185-187° C. $^1$H NMR (400 MHz, CDCl$_3$, δ, ppm): 8.75 (d, J=2.2 Hz, 1H), 8.43 (d, J=6.5 Hz, 1H), 8.30 (dd, J=8.7, 2.4 Hz, 1H), 7.60 (d, J=7.9 Hz, 2H), 7.54 (d, J=7.1 Hz, 1H), 7.36 (t, J=7.7 Hz, 2H), 7.03-6.94 (m, 2H), 6.92-6.85 (m, 2H), 4.01 (s, 3H). MS=318 (MH)+.

Example 10

[8-(4-Methanesulfonyl-phenyl)-[1,2,4]triazolo[1,5-a]pyridin-2-yl]-[4-(2-pyrrolidin-1-yl-ethoxy)-phenyl]-amine

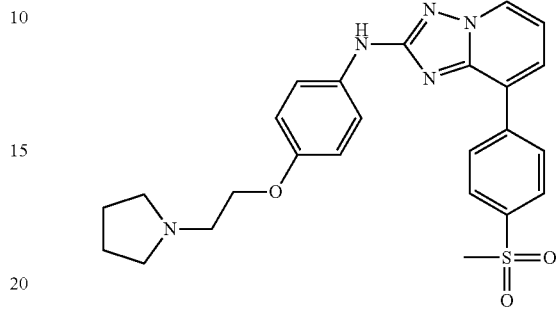

[8-(4-Methanesulfonyl-phenyl)-[1,2,4]triazolo[1,5-a]pyridin-2-yl]-[4-(2-pyrrolidin-1-yl-ethoxy)-phenyl]-amine was prepared from 8-(4-methanesulfonyl-phenyl)-[1,2,4]triazolo[1,5-a]pyridin-2-ylamine (100.0 mg, 0.3468 mmol) and 1-[2-(4-bromo-phenoxy)-ethyl]-pyrrolidine (0.10 mL, 0.48 mmol) in a manner analogous to Step 2d. The title compound was isolated as a yellow solid (0.025 g, 15%). MP=170-173° C. $^1$H NMR (400 MHz, CDCl$_3$, δ, ppm): 8.49-8.45 (m, 1H), 8.25-8.20 (m, 2H), 8.10-8.06 (m, 2H), 7.65-7.61 (m, 1H), 7.51-7.46 (m, 2H), 7.00 (t, J=6.9 Hz, 1H), 6.97-6.93 (m, 2H), 6.70 (s, 1H), 4.11 (t, J=6.1 Hz, 2H), 3.10 (s, 3H), 2.91 (t, J=6.0 Hz, 2H), 2.67-2.60 (m, 4H), 1.86-1.87 (m, 4H). MS=478 (MH)+.

Example 11

(4-Morpholin-4-yl-phenyl)-(8-pyridin-4-yl-[1,2,4]triazolo[1,5-a]pyridin-2-yl)-amine

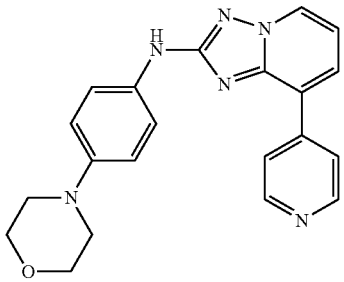 [SMILES: c1cc(-c2ccncc2)c2nc(Nc3ccc(N4CCOCC4)cc3)nn2c1]

11a) 8-Pyridin-4-yl-[1,2,4]triazolo[1,5-a]pyridin-2-ylamine was prepared from 8-bromo-[1,2,4]triazolo[1,5-a]pyridin-2-ylamine (1.0 g, 4.7 mmol) and 4-pyridylboronic acid (0.81 g, 6.6 mmol) in a manner analogous to Step 2c. The product of the reaction was isolated as a pale yellow solid (0.54 g, 54%). MP=209-215° C. $^1$H NMR (400 MHz, (D$_3$C)$_2$SO, δ, ppm): 8.69 (dd, J=4.8, 1.4 Hz, 2H), 8.65 (dd, J=6.5, 0.8 Hz, 1H), 8.18 (dd, J=4.7, 1.6 Hz, 2H), 7.94 (dd, J=7.5, 0.9 Hz, 1H), 7.03 (t, J=6.8 Hz, 1H), 6.24 (s, 2H). MS=212 (MH)+.

11b) (4-Morpholin-4-yl-phenyl)-(8-pyridin-4-yl-[1,2,4]triazolo[1,5-a]pyridin-2-yl)-amine was prepared from 8-Pyridin-4-yl-[1,2,4]triazolo[1,5-a]pyridin-2-ylamine (100.0 mg, 0.4734 mmol) and 4-(4-Bromo-phenyl)-morpholine (160.0 mg, 0.6608 mmol) in an anlogous manner to Step 2d. The title compound was isolated as yellow solid (0.035 g, 20%). MP=266-270° C. $^1$H NMR (400 MHz, CDCl$_3$, δ, ppm): 9.54 (s, 1H), 8.86 (d, J=6.5 Hz, 1H), 8.75-8.70 (m, 2H), 8.23-8.20 (m, 2H), 8.04 (d, J=7.3 Hz, 1H), 7.62-7.57 (m, 2H), 7.14 (t, J=7.0 Hz, 1H), 6.96-6.90 (m, 2H), 3.76-3.72 (m, 4H), 3.05-3.00 (m, 4H). MS=373 (MH)+.

Example 12

[5-(4-Methanesulfonyl-phenyl)-[1,2,4]triazolo[1,5-a]pyridin-2-yl]-(4-morpholin-4-yl-phenyl)-amine

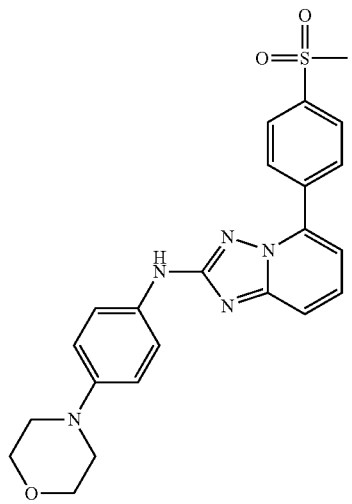 [SMILES: CS(=O)(=O)c1ccc(-c2cccc3nc(Nc4ccc(N5CCOCC5)cc4)nn23)cc1]

12a) N-(6-Bromo-2-pyridinyl)-N'-carboethoxy-thiourea was prepared from 6-bromo-pyridin-2-ylamine (1.0 g, 5.8 mmol) in a manner analogous to Step 2a. The product of the reaction was isolated as a yellow solid. $^1$H NMR (400 MHz, CDCl$_3$, δ, ppm): 12.03 (br s, 1H), 8.81 (d, J=8.0 Hz, 1H), 8.06 (br s, 1H), 7.60 (t, J=8.0 Hz, 1H), 7.32 (d, J=7.7 Hz, 1H), 4.31 (q, J=7.1 Hz, 2H), 1.35 (t, J=7.2 Hz, 3H). MS=306 (MH)+.

12b) 5-Bromo-[1,2,4]triazolo[1,5-a]pyridin-2-ylamine was prepared from N-(6-bromo-2-pyridinyl)-N'-carboethoxy-thiourea (1.8 g, 5.9 mmol) in a manner analogous to Step 2b. The product was isolated as an off-white solid (0.71 g, 56%). MP=203-205° C. $^1$H NMR (400 MHz, (D$_3$C)$_2$SO, δ, ppm): 7.40-7.32 (m, 2H), 7.23-7.20 (m, 1H), 6.26 (br s, 2H). MS=215 (MH)+.

12c) [5-(4-Methanesulfonyl-phenyl)-[1,2,4]triazolo[1,5-a]pyridin-2-yl]-(4-morpholin-4-yl-phenyl)-amine was prepared from 5-(4-methanesulfonyl-phenyl)-[1,2,4]triazolo[1,5-a]pyridin-2-ylamine (100.0 mg, 0.3468 mmol) and 4-(4-bromo-phenyl)-morpholine (101.0 mg, 0.4172 mmol) in a manner analogous to Step 2d. The title compound was isolated as a yellow solid (0.018 g, 12%). MP=247-249° C. $^1$H NMR (400 MHz, CDCl$_3$, δ, ppm): 8.28-8.24 (m, 2H), 8.15-8.11 (m, 2H), 7.55-7.51 (m, 2H), 7.49-7.44 (m, 2H), 7.04-7.01 (m, 1H), 6.96-6.91 (m, 2H), 6.68 (s, 2H), 3.90-3.85 (m, 4H), 3.15 (s, 3H), 3.14-3.10 (m, 4H). MS=450 (MH)+.

Example 13

[8-(3-Methanesulfonyl-phenyl)-[1,2,4]triazolo[1,5-a]pyridin-2-yl]-[4-(2-pyrrolidin-1-yl-ethoxy)-phenyl]-amine

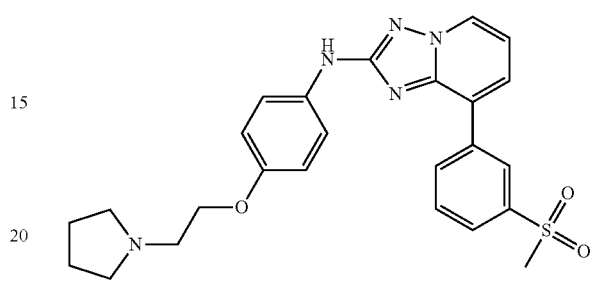

13a) 8-(3-Methanesulfonyl-phenyl)-[1,2,4]triazolo[1,5-a]pyridin-2-ylamine was prepared from 8-bromo-[1,2,4]triazolo[1,5-a]pyridin-2-ylamine (1.0 g, 4.7 mmol) and 3-(methanesulfonyl)phenyl boronic acid (1.0 g, 5.0 mmol) in a manner analogous to Step 2c. The reaction product was isolated as an off-white solid (0.99 g, 73%). MP=173-183° C. $^1$H NMR (400 MHz, (D$_3$C)$_2$SO, δ, ppm): 8.64-8.60 (m, 1H), 8.59 (t, J=1.6 Hz, 1H), 8.50-8.46 (m, 1H), 7.98-7.94 (m, 1H), 7.86-7.83 (m, 1H), 7.78 (dd, J=7.8, 7.8 Hz, 1H), 7.02 (dd, J=7.1, 7.1 Hz, 1H), 6.18 (s, 1H), 3.29 (S, 3H). MS=289 (MH)+.

13b) [8-(3-Methanesulfonyl-phenyl)-[1,2,4]triazolo[1,5-a]pyridin-2-yl]-[4-(2-pyrrolidin-1-yl-ethoxy)-phenyl]-amine and [8-(3-Methanesulfonyl-phenyl)-[1,2,4]triazolo[1,5-a]pyridin-2-yl]-phenyl-amine were prepared from 8-(3-methanesulfonyl-phenyl)-[1,2,4]triazolo[1,5-a]pyridin-2-ylamine (100.0 mg, 0.3468 mmol) and 1-[2-(4-bromo-phenoxy)-ethyl]-pyrrolidine (90.0 L, 0.434 mmol) in a manner analogous to Step 2d. The title compound 8-(3-Methanesulfonyl-phenyl)-[1,2,4]triazolo[1,5-a]pyridin-2-yl]-[4-(2-pyrrolidin-1-yl-ethoxy)-phenyl]-amine was isolated as a yellow foam (0.047 g, 28%). $^1$H NMR (400 MHz, CDCl$_3$, δ, ppm): 8.66 (t, J=1.7 Hz, 1H), 8.47-8.44 (m, 1H), 8.39-8.35 (m, 1H), 8.01-7.97 (m, 1H), 7.26 (dd, J=7.8, 7.8 Hz, 1H), 7.68-7.65 (m, 1H), 7.54-7.48 (m, 2H), 6.99 (dd, J=7.0, 7.0 Hz, 1H), 6.96-6.92 (m, 2H), 6.91 (s, 1H), 4.11 (t, J=6.1 Hz, 2H), 3.13 (s, 3H), 2.91 (t, J=6.1 Hz, 2H), 2.68-2.58 (m, 4H), 1.85-1.78 (m, 4H). MS=478 (MH)+.

Example 14

[8-(3-Methanesulfonyl-phenyl)-[1,2,4]triazolo[1,5-a]pyridin-2-yl]-phenyl-amine, was a byproduct of the above reaction and was isolated as a off-white foam (0.031 g, 24%). $^1$H NMR (400 MHz, CDCl$_3$, δ, ppm): 8.68 (t, J=1.8 Hz, 1H), 8.49 (dd, J=6.7, 1.3 Hz, 1H), 8.38 (ddd, J=7.7, 1.1, 1.1 Hz, 1H), 8.01 (ddd, J=7.8, 1.3, 1.3 Hz, 1H), 7.74 (dd, J=7.8, 7.8 Hz, 1H), 7.70-7.60 (m, 5H), 7.58-7.51 (m, 1H), 7.49-7.43 (m, 2H), 7.40-7.34 (m, 2H), 7.04-6.99 (m, 2H), 6.91 (s, 1H), 3.14 (s, 3H). MS=365 (MH)+.

Example 15

(8-pyridin-4-yl-[1,2,4]triazolo[1,5-a]pyridin-2-yl)-[4-(2-pyrrolidin-1-yl-ethoxy)-phenyl]-amine

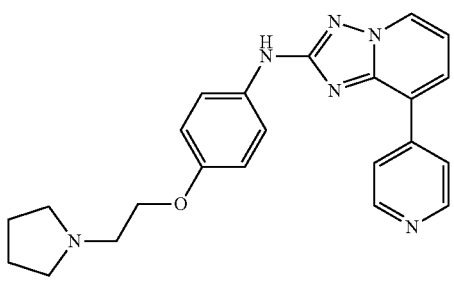 [SMILES: c1cc(-c2ccncc2)c2nc(Nc3ccc(OCCN4CCCC4)cc3)nn2c1]

(8-pyridin-4-yl-[1,2,4]triazolo[1,5-a]pyridin-2-yl)-[4-(2-pyrrolidin-1-yl-ethoxy)-phenyl]-amine and phenyl-(8-pyridin-4-yl-[1,2,4]triazolo[1,5-a]pyridin-2-yl)-[4-(2-pyrrolidin-1-yl-ethoxy)-phenyl]-amine were prepared from 8-pyridin-4-yl-[1,2,4]triazolo[1,5-a]pyridin-2-ylamine (50.0 mg, 0.237 mmol) and 1-[2-(4-bromo-phenoxy)-ethyl]-pyrrolidine (58.8 L, 0.284 mmol) with sodium tert-butoxide (50.0 mg, 0.520 mmol) as the base in a manner analogous to Step 2d. The title compound, (8-pyridin-4-yl-[1,2,4]triazolo[1,5-a]pyridin-2-yl)-[4-(2-pyrrolidin-1-yl-ethoxy)-phenyl]-amine, was isolated as a yellow solid (0.006 g). $^1$H NMR (400 MHz, (D$_3$C)$_2$SO, δ, ppm): 9.59 (s, 1H), 8.87 (d, J=6.6 Hz, 1H), 8.74-8.71 (m, 2H), 8.2-8.20 (m, 2H), 8.05 (d, J=7.3 Hz, 1H), 7.65-7.59 (m, 2H), 7.17-7.12 (m, 2H), 6.94-6.89 (m, 2H), 4.02 (t, J=5.9 Hz, 2H), 2.77 (t, J=5.9 Hz, 2H), 2.55-2.50 (m, 4H), 1.73-1.64 (m, 4H). MS=401 (MH)+.

Example 16

Phenyl-(8-pyridin-4-yl-[1,2,4]triazolo[1,5-a]pyridin-2-yl)-[4-(2-pyrrolidin-1-yl-ethoxy)-phenyl]-amine, was a byproduct of the reaction and was isolated as a yellow foam (0.020 g, 21%). $^1$H NMR (400 MHz, (D$_3$C)$_2$SO, δ, ppm): 8.80 (d, J=6.5 Hz, 1H), 8.67-8.63 (m, 2H), 8.14-8.10 (m, 2H), 8.05 (d, J=7.1 Hz, 1H), 7.39-7.31 (m, 4H), 7.27-7.22 (m, 2H), 7.19-7.11 (m, 2H), 7.02-6.97 (m, 2H), 4.10 (t, J=5.8 Hz, 2H), 2.81 (t, J=5.6 Hz, 2H), 2.57-2.50 (m, 4H), 1.74-1.66 (m, 4H). MS=477 (MH)+.

Example 17

[8-(3-Methanesulfonyl-phenyl)-[1,2,4]triazolo[1,5-a]pyridin-2-yl]-(4-morpholin-4-yl-phenyl)-amine

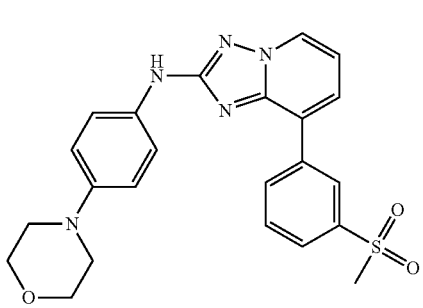 [SMILES: CS(=O)(=O)c1cccc(-c2cccn3nc(Nc4ccc(N5CCOCC5)cc4)nc23)c1]

The title compound was prepared from 8-(3-methanesulfonyl-phenyl)-[1,2,4]triazolo[1,5-a]pyridin-2-ylamine (100.0 mg, 0.3468 mmol) and 4-(4-bromo-phenyl)-morpholine (101.0 mg, 0.4172 mmol) in a manner analogous to Step 2d and was isolated as a pale yellow solid (0.025 g, 16%). MP=202-204° C. $^1$H NMR (400 MHz, CDCl$_3$, δ, ppm): 8.68 (t, J=1.6, 1H), 8.46 (dd, J=6.9, 0.9 Hz, 1H), 8.39-8.35 (m, 1H), 8.01-7.98 (m, 1H), 7.73 (dd, J=7.7, 7.7 Hz, 1H), 7.67 (dd, J=7.5, 0.8 Hz, 1H), 7.56-7.50 (m, 2H), 7.01-6.94 (m, 3H), 6.72 (s, 1H), 3.90-3.86 (m, 4H), 3.14-3.10 (m, 7H). MS=450 (MH)+.

Example 18

[8-(4-Methanesulfonyl-phenyl)-[1,2,4]triazolo[1,5-a]pyridin-2-yl]-(4-piperidin-1-yl-phenyl)-amine

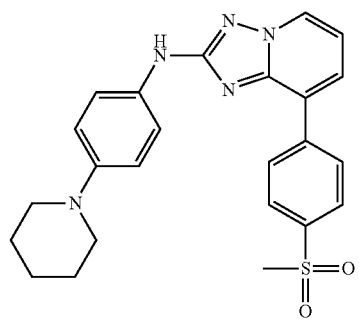 [SMILES: CS(=O)(=O)c1ccc(-c2cccn3nc(Nc4ccc(N5CCCCC5)cc4)nc23)cc1]

[8-(4-Methanesulfonyl-phenyl)-[1,2,4]triazolo[1,5-a]pyridin-2-yl]-(4-piperidin-1-yl-phenyl)-amine was prepared from 8-(4-methanesulfonyl-phenyl)-[1,2,4]triazolo[1,5-a]pyridin-2-ylamine (100.0 mg, 0.3468 mmol) and 1-(4-bromo-phenyl)-piperidine (110.0 mg, 0.4581 mmol) in a manner analogous to Step 2d. The title compound was isolated as a yellow solid (0.039 g, 25%). MP=229-234° C. $^1$H NMR (400 MHz, CDCl$_3$, δ, ppm): 8.48-8.45 (m, 1H), 8.25-8.20 (m, 2H), 8.11-8.06 (m, 2H), 7.64-7.61 (m, 1H), 7.49-7.44 (m, 1H), 7.01-6.95 (m, 3H), 6.68 (s, 1H), 3.12-3.07 (m, 7H), 1.77-1.70 (m, 4H), 1.60-1.53 (m, 2H). MS=448 (MH)+.

Example 19

[8-(4-Methanesulfonyl-phenyl)-[1,2,4]triazolo[1,5-a]pyridin-2-yl]-(4-methoxy-phenyl)-amine

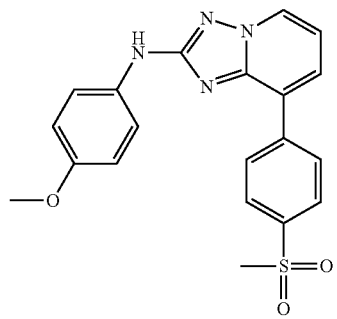 [SMILES: COc1ccc(Nc2nc3c(-c4ccc(S(C)(=O)=O)cc4)cccn3n2)cc1]

19a) To a suspension of sodium hydride, 60% disp. in mineral oil (3:2, sodium hydride: mineral oil, 1.0 g, 25 mmol) in 1,4-dioxane (50 mL, 600 mmol) was added 3-bromo-pyridin-2-ylamine (2.68 g, 15.5 mmol). The mixture was stirred for 5 minutes at room temperature under an atmosphere of nitrogen. 1-Isothiocyanato-4-methoxy-benzene (2.35 mL, 17.0 mmol) was slowly added to the suspension. Slow gas evolution was noted and the suspension slowly thickened to a slurry. The mixture was stirred at room temperature for 18 hours and the volatiles were evaporated to a yield a tan solid. To the solid was added saturated aqueous ammonium chloride solution (100 mL). Gas evolution and exotherm noted. The mixture was stirred for 30 minutes and the waxy solid was filtered. The solid was triturated with ether (50 mL), filtered and rinsed with ether. 1-(3-Bromo-pyridin-2-yl)-3-(4-methoxy-phenyl)-thiourea was isolated as a yellow solid (4.96 g, 95%). $^1$H NMR (400 MHz, (D$_3$C)$_2$SO, δ, ppm): 12.85 (s, 1H), 8.75 (s, 1H), 8.38 (dd, J=4.8, 1.2 HZ, 1H), 8.24 (dd, J=7.9, 1.3 Hz, 1H), 7.56-7.50 (m, 2H), 7.15 (dd, J=7.9, 4.9 Hz, 1H), 7.00-6.95 (m, 2H), 3.77 (s, 3H). MS=338, 340 (MH)+.

19b) To a suspension of 1-(3-Bromo-pyridin-2-yl)-3-(4-methoxy-phenyl)-thiourea (9.37 g, 27.7 mmol) in 1,4-dioxane (180 mL) was added dimethyl sulfate (2.60 mL, 27.5 mmol). The mixture was stirred at room temperature for 18 hours then heated at 60° C. for 18 hours to complete reaction. The mixture was cooled to room temperature and the volatiles were evaporated. To residue was added saturated aqueous sodium carbonate and shaken. The resulting precipitate was filtered, rinsed with water, dissolved in dichloromethane, dried over magnesium sulfate, filtered and evaporated to a red viscous oil (9.44 g) and was taken on to the next step without purification.

19c) To a solution of the red oil in 1,4-dioxane (100 mL) was added potassium carbonate (20.0 g, 145 mmol) followed by hydroxylamine hydrochloride (9.6 g, 140 mmol). The suspension was heated at 90° C. for 4 days. The mixture was cooled to room temperature and filtered through a plug of diatomaceous earth, the volatiles were evaporated and to the residue was added water (200 mL). The mixture was extracted with ethyl acetate (200 mL), washed with water (2×100 mL), dried over magnesium sulfate, filtered and evaporated to an orange waxy solid (8.81 g) and taken on to the next step without further purification.

19d) To a suspension of the orange waxy solid and potassium carbonate (3.0 g) in acetonitrile (100 mL, 2000 mmol) was added by slow addition 20% phosgene in toluene (1:4, phosgene:toluene, 22 mL, 42 mmol). The mixture was stirred for 36 hours. The suspension was filtered through a plug of diatomaceous earth and the filtrate was evaporated to a resin. To the residue was added water (100 mL) and extracted with dichloromethane (2×100 mL). The organic layer was dried over magnesium sulfate, filtered and evaporated. The residue was purified via chromatography utilizing an ISCO automated purification apparatus with an amine modified silica gel column (140 g) with ethyl acetate:hexane solvent gradient. (8-Bromo-[1,2,4]triazolo[1,5-a]pyridin-2-yl)-(4-methoxy-phenyl)-amine was isolated as a tan solid (5.2 g, 58%). $^1$H NMR (400 MHz, (D$_3$C)$_2$SO, δ, ppm): 9.67 (s, 1H), 8.79 (dd, J=6.7, 0.9 Hz, 1H), 7.86 (dd, J=7.7, 0.9 Hz, 1H), 7.60-7.55 (m, 2H), 6.94-6.88 (m, 3H), 3.72 (s, 3H). MS=319, 321 (MH)+.

19e) The title compound, [8-(4-Methanesulfonyl-phenyl)-[1,2,4]triazolo[1,5-a]pyridin-2-yl]-(4-methoxy-phenyl)-amine, was prepared from (8-bromo-[1,2,4]triazolo[1,5-a]pyridin-2-yl)-(4-methoxy-phenyl)-amine (253.0 mg, 0.7927 mmol) and (4-methylsulfonylphenyl)boronic acid (175.0 mg, 0.8749 mmol) with Pd(dppf)Cl$_2$ (0.058 g) as the catalyst in a manner analogous to Step 2c and was isolated as a yellow solid (0.21 g, 67%). MP=208-212° C. $^1$H NMR (400 MHz, CDCl$_3$, δ, ppm): 8.47 (d, J=6.6 Hz, 1H), 8.23 (d, J=8.5 Hz, 2H), 8.09 (d, J=8.5 Hz, 2H), 7.64 (d, J=7.4 Hz, 1H), 7.00 (dd, J=6.8, 6.8 Hz, 1H), 6.95-6.90 (m, 2H), 6.71 (s, 1H), 3.82 (s, 3H), 3.10 (s, 3H). MS=395 (MH)+.

Example 20

(2-Methoxy-phenyl)-[8-(4-trifluoromethyl-phenyl)-[1,2,4]triazolo[1,5-a]pyridin-2-yl]-amine

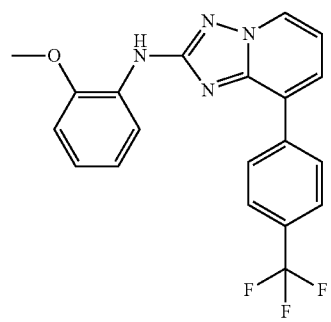 [SMILES: COc1ccccc1Nc1nc2c(-c3ccc(C(F)(F)F)cc3)cccn2n1]

20a) 1-(3-Bromo-pyridin-2-yl)-3-(2-methoxy-phenyl)-thiourea was prepared from 3-bromo-pyridin-2-ylamine (5.0 g, 29.0 mmol) and 1-isothiocyanato-2-methoxy-benzene (4.0 mL, 29.0 mmol) in a manner analogous to Step 19a. The reaction product was isolated as a yellow solid (8.46 g, 86%). $^1$H NMR (400 MHz, (D$_3$C)$_2$SO, δ, ppm): 13.62 (br s, 1H), 8.75-8.65 (m, 2H), 8.21 (dd, J=5.1, 1.5 Hz, 1H), 7.91 (dd, J=8.0, 1.6, Hz, 1H), 7.21 (dt, J=7.9, 1.5 Hz, 1H), 7.06-7.00 (m, 1H), 6.98-6.94 (m, 1H), 6.91 (dd, J=7.9, 5.0 Hz, 1H), 3.93 (s, 3H). MS=340 (MH)+.

20b) (8-Bromo-[1,2,4]triazolo[1,5-a]pyridin-2-yl)-(2-methoxy-phenyl)-amine was prepared from 1-(3-bromo-pyridin-2-yl)-3-(2-methoxy-phenyl)-thiourea (2.0 g) in a manner analogous to Step 19b. The reaction product was isolated as a white solid (0.47 g, 25%). MP=186-187° C. $^1$H NMR (400 MHz, CDCl$_3$, δ, ppm): 8.42 (d, J=6.7 Hz, 1H), 8.31 (dd, J=8.0, 1.1 Hz, 1H), 7.72 (s, 1H), 7.65 (d, J=7.6 Hz, 1H), 7.06-7.01 (m, 1H), 6.95 (ddd, J=8.1, 8.1, 1.1 Hz, 1H), 6.91-6.88 (m, 1H), 6.78-6.73 (m, 1H), 3.90 (s, 3H). MS=319, 321 (MH)+.

20c) (2-Methoxy-phenyl)-[8-(4-trifluoromethyl-phenyl)-[1,2,4]triazolo[1,5-a]pyridin-2-yl]-amine was prepared from (8-bromo-[1,2,4]triazolo[1,5-a]pyridin-2-yl)-(2-methoxy-phenyl)-amine (50.0 mg, 0.157 mmol) and (4-trifluoromethylphenyl)boronic acid (33.0 mg, 0.174 mmol) with Pd(dppf)Cl$_2$ (0.012 g) as the catalyst in a manner analogous to Step 2e. The reaction product was isolated as a white solid (0.032 g, 53%). MP=184-186° C. $^1$H NMR (400 MHz, CDCl$_3$, δ, ppm): 8.49 (dd, J=6.8, 0.9 Hz, 1H), 8.38 (dd, J=8.0, 1.3 Hz, 1H), 8.14 (d, J=8.4 Hz, 2H), 7.78 (d, J=8.3 Hz, 2H), 7.63-7.58 (m, 2H), 7.08-6.88 (m, 4H), 3.92 (s, 3H). MS=385 (MH)+.

Example 21

(2-Methoxy-phenyl)-[8-(3-trifluoromethyl-phenyl)-[1,2,4]triazolo[1,5-a]pyridin-2-yl]-amine

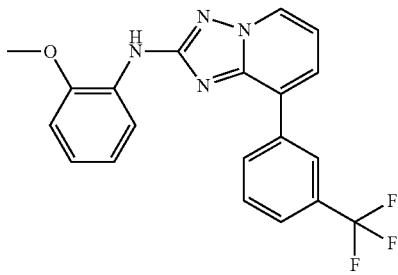 [SMILES: COc1ccccc1Nc1nc2c(-c3cccc(C(F)(F)F)c3)cccn2n1]

(2-Methoxy-phenyl)-[8-(3-trifluoromethyl-phenyl)-[1,2,4]triazolo[1,5-a]pyridin-2-yl]-amine was prepared from (8-bromo-[1,2,4]triazolo[1,5-a]pyridin-2-yl)-(2-methoxy-phenyl)-amine (50.0 mg, 0.157 mmol) and (3-trifluoromethylphenyl)boronic acid (33.0 mg, 0.174 mmol) with Pd(dppf)Cl$_2$ (0.012 g) as the catalyst in a manner analogous to Step 2c. The reaction product was isolated as a white solid (0.042 g, 70%). MP=137-141° C. $^1$H NMR (400 MHz, CDCl$_3$, δ, ppm): 8.47 (dd, J=6.7, 0.9 Hz, 1H), 8.43 (dd, J=8.0, 1.3 Hz, 1H), 8.34 (s, 1H), 8.25 (d, J=7.4 Hz, 1H), 7.71-7.58 (m, 4H), 7.08-6.98 (m, 4H), 3.93 (s, 3H). MS=385 (MH)+.

Example 22

(2-Methoxy-phenyl)-(8-phenyl-[1,2,4]triazolo[1,5-a]pyridin-2-yl)-amine

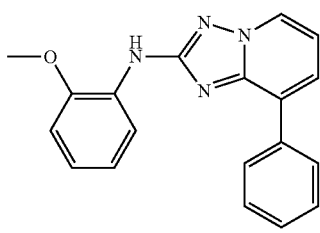 [SMILES: COc1ccccc1Nc1nc2c(-c3ccccc3)cccn2n1]

(2-Methoxy-phenyl)-(8-phenyl-[1,2,4]triazolo[1,5-a]pyridin-2-yl)-amine was prepared from (8-bromo-[1,2,4]triazolo[1,5-a]pyridin-2-yl)-(2-methoxy-phenyl)-amine (50.0 mg, 0.157 mmol) and phenylboronic acid (21.0 mg, 0.172 mmol) with Pd(dppf)Cl$_2$ (0.012 g) as the catalyst in a manner analogous to Step 2c and was isolated as a white solid (0.012 g, 24%). MP=155-157° C. $^1$H NMR (400 MHz, CDCl$_3$, δ, ppm): 8.44 (dd, J=6.6, 0.9 Hz, 1H), 8.40 (dd, J=8.0, 1.4 Hz, 1H), 8.02-7.97 (m, 2H), 7.61 (s, 1H), 7.56 (dd, J=7.4, 0.9 Hz, 1H), 7.55-7.50 (m, 2H), 7.45-7.40 (m, 1H), 7.07-7.02 (m, 1H), 6.98-6.88 (m, 3H), 3.91 (s, 3H). MS=317 (MH)+.

Example 23

3-[2-(2-Methoxy-phenylamino)-[1,2,4]triazolo[1,5-a]pyridin-8-yl]-N-methyl-benzamide

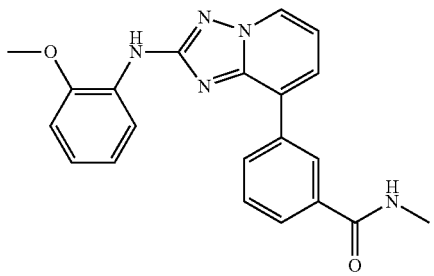

3-[2-(2-Methoxy-phenylamino)-[1,2,4]triazolo[1,5-a]pyridin-8-yl]-N-methyl-benzamide was prepared from (8-bromo-[1,2,4]triazolo[1,5-a]pyridin-2-yl)-(2-methoxy-phenyl)-amine (50.0 mg, 0.157 mmol) and 3-methylaminocarbonylbenzeneboronic acid (31.0 mg, 0.173 mmol) with Pd(dppf)Cl$_2$ (0.012 g) as the catalyst in a manner analogous to Step 2c and was isolated as a yellow solid (0.048 g, 82%). MP=199-202° C. $^1$H NMR (400 MHz, CDCl$_3$, δ, ppm): 8.48-8.44 (m, 2H), 8.40 (dd, J=7.9, 1.3 Hz, 1H), 8.15 (d, J=7.8 Hz, 1H), 7.85 (d, J=7.8 Hz, 1H), 7.65-7.57 (m, 3H), 7.07-6.99 (m, 4H), 6.30 (br s, 1H), 3.92 (s, 3H), 3.07 (d, J=4.9 Hz, 3H). MS=374 (MH)+.

Example 24

4-[2-(2-Methoxy-phenylamino)-[1,2,4]triazolo[1,5-a]pyridin-8-yl]-N-methyl-benzamide

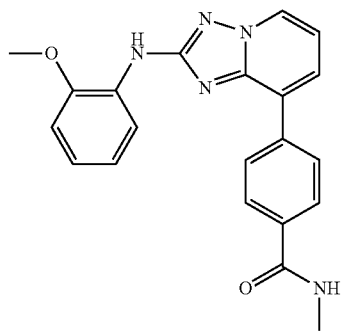

4-[2-(2-Methoxy-phenylamino)-[1,2,4]triazolo[1,5-a]pyridin-8-yl]-N-methyl-benzamide was prepared from (8-bromo-[1,2,4]triazolo[1,5-a]pyridin-2-yl)-(2-methoxy-phenyl)-amine (50.0 mg, 0.157 mmol) and 4-(N-methylaminocarbonyl)phenylboronic acid (31.0 mg, 0.173 mmol) with Pd(dppf)Cl$_2$ (0.012 g) as the catalyst in a manner analogous to Step 2c and was isolated as a pale yellow solid (0.023 g, 39%). MP=275-278° C. $^1$H NMR (400 MHz, CDCl$_3$, δ, ppm): 8.48-8.45 (m, 1H), 8.41-8.37 (m, 1H), 8.11 (d, J=8.2 Hz, 2H), 7.91 (d, J=8.2 Hz, 2H), 7.64-7.59 (m, 2H), 7.08-7.02 (m, 1H), 7.00-6.88 (m, 3H), 6.17 (br s, 1H), 3.92 (s, 3H), 3.07 (d, J=4.7 Hz, 3H). MS=374 (MH)+.

Example 25

[8-(4-Methanesulfonyl-phenyl)-[1,2,4]triazolo[1,5-a]pyridin-2-yl]-(2-methoxy-phenyl)-amine

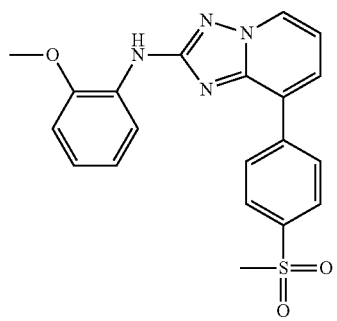 [SMILES: COc1ccccc1Nc1nc2c(-c3ccc(S(C)(=O)=O)cc3)cccn2n1]

[8-(4-Methanesulfonyl-phenyl)-[1,2,4]triazolo[1,5-a]pyridin-2-yl]-(2-methoxy-phenyl)-amine was prepared from (8-bromo-[1,2,4]triazolo[1,5-a]pyridin-2-yl)-(2-methoxy-phenyl)-amine (100.0 mg, 0.3133 mmol) and (4-methylsulfonylphenyl)boronic acid (75.0 mg, 0.375 mmol) in a manner analogous to Step 2c and was isolated as a pale yellow solid (0.097 g, 78%). MP=211-213° C. $^1$H NMR (400 MHz, CDCl$_3$, δ, ppm): 8.53-8.49 (m, 1H), 8.38 (dd, J=8.0, 1.3 Hz, 1H), 8.24 (d, J=8.4 Hz, 2H), 8.10 (d, J=8.5 Hz, 2H), 7.66-7.62 (m, 1H), 7.61 (s, 1H), 7.08-6.89 (m, 4H), 3.92 (s, 3H), 3.11 (s, 3H). MS=395 (MH)+.

Example 26

[8-(4-Methanesulfonyl-phenyl)-[1,2,4]triazolo[1,5-a]pyridin-2-yl]-[4-(2-morpholin-4-yl-ethoxy)-phenyl]-amine

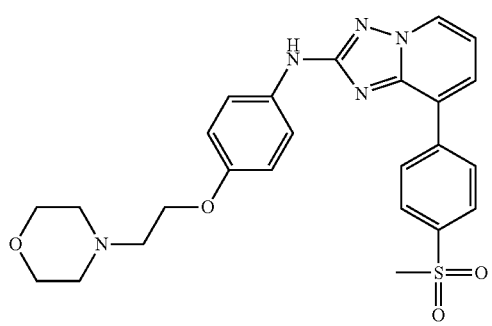 [SMILES: CS(=O)(=O)c1ccc(-c2cccn3nc(Nc4ccc(OCCN5CCOCC5)cc4)nc23)cc1]

26a) To a suspension of [8-(4-methanesulfonyl-phenyl)-[1,2,4]triazolo[1,5-a]pyridin-2-yl]-(4-methoxy-phenyl)-amine (150.0 mg, 0.3803 mmol) in dichloromethane (10 mL, was added dropwise 1.0 M of boron tribromide in dichloromethane (1.2 mL, 1.2 mmol). The mixture was stirred for 1 hour at room temperature then methanol (5 mL) was added slowly. The mixture was evaporated to dryness. Additional methanol (10 mL) was added and the mixture was evaporated to dryness. The brown solid was suspended in saturated sodium bicarbonate (10 mL) and extracted with ethyl acetate (3×20 mL). The combined organic layers were dried over magnesium sulfate, filtered and evaporated to a solid. 4-[8-(4-Methanesulfonyl-phenyl)-[1,2,4]triazolo[1,5-a]pyridin-2-ylamino]-phenol was isolated without further purification as a light brown solid (0.115 g, 80%). $^1$H NMR (400 MHz, CDCl$_3$, δ, ppm): 8.47 (dd, J=6.7, 0.9 Hz, 1H), 8.22 (d, J=8.4 Hz, 2H), 8.08 (d, J=8.5 Hz, 2H), 7.64 (dd, J=7.4, 0.8 Hz, 1H), 7.44 (d, J=8.7 Hz, 2H), 7.00 (dd, J=7.1, 7.1 Hz, 1H), 6.84 (d, J=8.6 Hz, 2H), 6.73 (s, 1H), 4.72 (br s, 1H), 3.09 (s, 3H). MS=381 (MH)+.

26b) A suspension of 4-[8-(4-methanesulfonyl-phenyl)-[1,2,4]triazolo[1,5-a]pyridin-2-ylamino]-phenol (50.0 mg, 0.131 mmol), 4-(2-chloroethyl)-morpholine hydrochloride (27.0 mg, 0.145 mmol) and potassium carbonate (36.0 mg, 0.260 mmol) in acetonitrile (1 mL) was heated at 70° C. for 18 hours. The mixture was cooled to room temperature, diluted with acetonitrile (10 mL), filtered through a plug of diatomaceous earth and evaporated to an orange resin. The residue was purified via chromatography utilizing an ISCO automated purification apparatus with silica gel column (12 g) and 0%→10% methanol:dichloromethane solvent gradient. The title compound, [8-(4-Methanesulfonyl-phenyl)-[1,2,4]triazolo[1,5-a]pyridin-2-yl]-[4-(2-morpholin-4-yl-ethoxy)-phenyl]-amine, was isolated as a yellow foam (0.047 g, 72%). $^1$H NMR (400 MHz, CDCl$_3$, δ, ppm): 8.47 (d, J=6.5 Hz, 1H), 8.23 (d, J=8.4 Hz, 2H), 8.07 (d, J=8.3 Hz, 2H), 7.64 (d, J=7.4 Hz, 1H), 7.51-7.46 (m, 2H), 7.00 (t, J=7.0 Hz, 1H), 6.96-6.90 (m, 2H), 6.73 (s, 1H), 4.12 (t, J=5.8 Hz, 2H), 3.77-3.72 (m, 4H), 3.10 (s, 3H), 2.80 (t, J=5.6 Hz, 2H), 2.62-2.55 (m, 4H). MS=494 (MH)+.

Example 27

[8-(4-Methanesulfonyl-phenyl)-[1,2,4]triazolo[1,5-a]pyridin-2-yl]-(3-morpholin-4-yl-phenyl)-amine

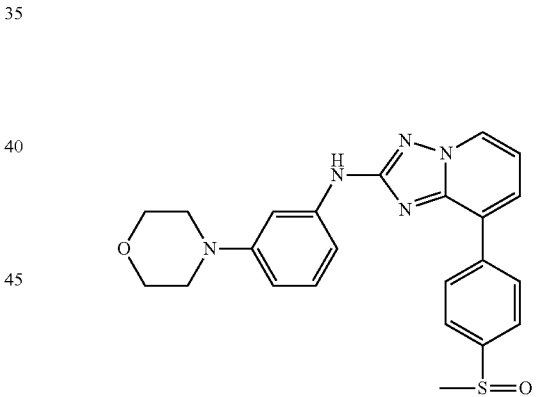

[8-(4-Methanesulfonyl-phenyl)-[1,2,4]triazolo[1,5-a]pyridin-2-yl]-(3-morpholin-4-yl-phenyl)-amine was prepared from 8-(4-methanesulfonyl-phenyl)-[1,2,4]triazolo[1,5-a]pyridin-2-ylamine (100.0 mg, 0.3468 mmol) and 4-(3-bromo-phenyl)-morpholine (126.0 mg, 0.5202 mmol) in a manner analogous to Step 2d and was isolated as a yellow solid (0.022 g, 14%). MP=234-236° C. $^1$H NMR (400 MHz, CDCl$_3$, δ, ppm): 8.50 (dd, J=6.6, 1.1 Hz, 1H), 8.26-8.22 (m, 2H), 8.10-8.05 (m, 2H), 7.66 (dd, J=7.3, 1.1 Hz, 1H), 7.36 (t, J=2.2 Hz, 1H), 7.25 (t, J=8.0 Hz, 1H), 7.05-6.98 (m, 2H), 6.85 (s, 1H), 6.59 (dd, J=8.3, 1.9 Hz, 1H), 3.91-3.87 (m, 4H), 3.24-3.20 (m, 4H), 3.10 (s, 3H). MS=450 (MH)+.

Example 28

[8-(4-Methanesulfonyl-phenyl)-[1,2,4]triazolo[1,5-a]pyridin-2-yl]-(5,5,8,8-tetramethyl-5,6,7,8-tetrahydro-naphthalen-2-yl)-amine

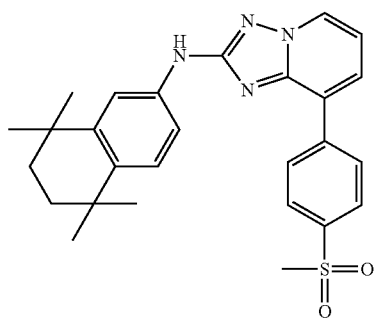 [SMILES: CC1(C)CCC(C)(C)c2cc(Nc3nc4c(-c5ccc(S(C)(=O)=O)cc5)cccn4n3)ccc21]

[8-(4-Methanesulfonyl-phenyl)-[1,2,4]triazolo[1,5-a]pyridin-2-yl]-(5,5,8,8-tetramethyl-5,6,7,8-tetrahydro-naphthalen-2-yl)-amine was prepared from 8-(4-methanesulfonyl-phenyl)-[1,2,4]triazolo[1,5-a]pyridin-2-ylamine (100.0 mg, 0.3468 mmol) and 6-bromo-1,1,4,4-tetramethyl-1,2,3,4-tetrahydro-naphthalene (140.0 mg, 0.5239 mmol) in a manner analogous to Step 2d and was isolated as a yellow foam (0.049 g, 30%). $^1$H NMR (400 MHz, CDCl$_3$, δ, ppm): 8.47 (dd, J=6.7, 1.1 Hz, 1H), 8.29-8.25 (m, 2H), 8.10-8.05 (m, 2H), 7.65 (dd, J=7.5, 1.2 Hz, 1H), 7.57 (d, J=2.3 Hz, 1H), 7.36-7.27 (m, 2H), 7.00 (dd, J=7.2, 7.2 Hz, 1H), 6.76 (s, 1H), 3.10 (s, 3H), 1.74-1.66 (m, 4H), 1.33 (s, 6H), 1.28 (s, 6H). MS=475 (MH)+.

Example 29

[8-(3-Methanesulfonyl-phenyl)-[1,2,4]triazolo[1,5-a]pyridin-2-yl]-(3-morpholin-4-yl-phenyl)-amine

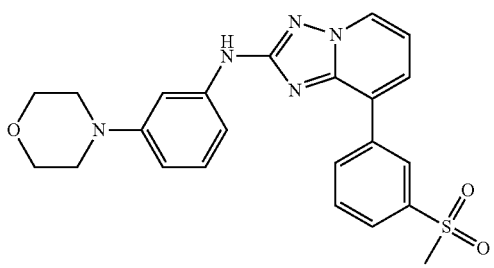 [SMILES: CS(=O)(=O)c1cccc(-c2cccn3nc(Nc4cccc(N5CCOCC5)c4)nc23)c1]

[8-(3-Methanesulfonyl-phenyl)-[1,2,4]triazolo[1,5-a]pyridin-2-yl]-(3-morpholin-4-yl-phenyl)-amine was prepared from 8-(3-methanesulfonyl-phenyl)-[1,2,4]triazolo[1,5-a]pyridin-2-ylamine (100.0 mg, 0.3468 mmol) and 4-(3-bromo-phenyl)-morpholine (126.0 mg, 0.5204 mmol) in a manner analogous to Step 2d and was isolated as a tan foam (0.018 g, 12%). $^1$H NMR (400 MHz, CDCl$_3$, δ, ppm): 8.60-8.58 (m, 1H), 8.48 (dd, J=6.7, 1.1 Hz, 1H), 8.46-8.42 (m, 1H), 8.02-7.98 (m, 1H), 7.72 (t, J=7.8 Hz, 1H), 7.68 (dd, J=7.5, 1.1 Hz, 1H), 7.33-7.30 (m, 1H), 7.25 (t, J=8.0 Hz, 1H), 7.06 (dd, J=7.8, 1.5 Hz, 1H), 7.01 (dd, J=7.2, 7.2 Hz, 1H), 6.85 (s, 1H), 6.58 (dd, J=8.4, 2.1 Hz, 1H), 3.91-3.86 (m, 4H), 3.25-3.20 (m, 4H), 3.13 (s, 3H). MS=450 (MH)+.

Example 30

(4-Methoxy-phenyl)-[8-(4-methyl-piperazin-1-yl)-[1,2,4]triazolo[1,5-a]pyridin-2-yl]-amine

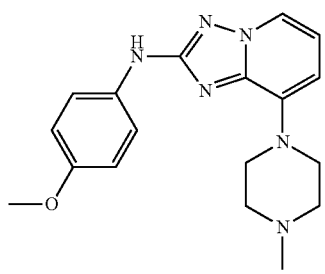 [SMILES: COc1ccc(Nc2nc3c(N4CCN(C)CC4)cccn3n2)cc1]

To an oven dried tube was added (8-bromo-[1,2,4]triazolo[1,5-a]pyridin-2-yl)-(4-methoxy-phenyl)-amine (50.0 mg, 0.157 mmol), 1-methyl-piperazine (21.0 L, 0.189), palladium acetate (7.0 mg, 0.031 mmol), dicyclohexyl-(2',4',6'-triisopropyl-biphenyl-2-yl)-phosphane (15.0 mg, 0.0315 mmol, X-Phos), potassium phosphate (83.0 mg, 0.391 mmol) and 1,4-dioxane (3 mL) and kept under an atmosphere of nitrogen. The tube was evacuated and backflushed with nitrogen three times. The tube was sealed and heated at 100° C. for 18 hours. The mixture was cooled to room temperature and diluted with dichloromethane (10 mL). The suspension was filtered and the filtrate was evaporated. The residue was purified via chromatography using amine modified silica gel column (4.7 g) and 5%→100% ethyl acetate:hexane solvent gradient. The title compound was isolated as a tan foam (0.025 g, 47%). $^1$H NMR (400 MHz, CDCl$_3$, δ, ppm): 8.04 (dd, J=6.5, 1.0 Hz, 1H), 7.51-7.46 (m, 2H), 6.93-6.88 (m, 2H), 6.74 (dd, J=7.8, 1.0 Hz, 1H), 6.58 (s, 1H), 3.80 (s, 3H), 3.55-3.45 (m, 4H), 2.71-2.65 (m, 4H), 2.39 (s, 3H). MS=339 (MH)+.

Example 31

8-(1,1-dioxidothiomorpholin-4-yl)-N-(4-methoxyphenyl)[1,2,4]triazolo[1,5-a]pyridin-2-amine

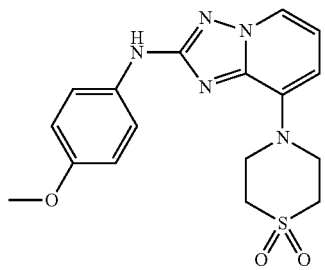 [SMILES: COc1ccc(Nc2nc3c(N4CCS(=O)(=O)CC4)cccn3n2)cc1]

8-(1,1-dioxidothiomorpholin-4-yl)-N-(4-methoxyphenyl)[1,2,4]triazolo[1,5-a]pyridin-2-amine was prepared from (8-bromo-[1,2,4]triazolo[1,5-a]pyridin-2-yl)-(4-methoxyphenyl)-amine (50.0 mg, 0.157 mmol) and thiomorpholine 1,1-dioxide (25.0 mg, 0.185 mmol) in a manner analogous to Example 30. Product isolated as a tan solid (0.052 g, 89%).

MP=231-234° C. ¹H NMR (400 MHz, CDCl₃, δ, ppm): 8.11 (dd, J=6.4, 1.1 Hz, 1H), 7.50-7.45 (m, 2H), 6.94-6.89 (m, 2H), 6.77 (dd, J=7.7, 6.7 Hz, 1H), 6.73 (dd, J=7.6, 0.9 Hz, 1H), 6.57 (s, 1H), 4.12-4.06 (m, 4H), 3.81 (s, 3H), 3.28-3.23 (m, 4H). MS=374 (MH)+.

Example 32

[8-(4-Methanesulfonyl-phenyl)-[1,2,4]triazolo[1,5-a]pyridin-2-yl]-[4-(4-methyl-piperazin-1-yl)-phenyl]-amine

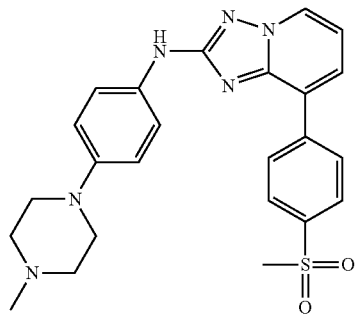 [SMILES: CN1CCN(c2ccc(Nc3nc4c(-c5ccc(S(C)(=O)=O)cc5)cccn4n3)cc2)CC1]

32a) To a solution of 1-(4-bromo-phenyl)-piperazine (1.47 g, 6.10 mmol) and acetic acid (0.42 mL, 7.4 mmol) in methanol (25 mL) was added 37% formaldehyde in water/methanol (56.7:37:6.3, water:formaldehyde:methanol, 5.6 mL, 180 mmol). The mixture was stirred at room temperature for 18 hours. The suspension was cooled to 5° C. in an ice/water bath and Sodium cyanoborohydride (4.98 g, 79.2 mmol) was added in small portions. The mixture was stirred and warmed to room temperature for 18 hours. The mixture was slowly poured into saturated aqueous ammonium chloride (200 mL) and stirred for 1 hour. The mixture was extracted with dichloromethane (3×75 mL). The combined organic layers were dried over magnesium sulfate, filtered and evaporated to an oily solid. The material was placed under high vacuum for 18 hours to yield a white solid (1.54 g). 1-(4-Bromo-phenyl)-4-methyl-piperazine was isolated as a white solid (1.54 g, 99%) and was used without further purification. ¹H NMR (400 MHz, CDCl₃, δ, ppm): 7.36-7.31 (m, 2H), 6.82-6.76 (m, 2H), 3.20-3.15 (m, 4H), 2.60-2.55 (m, 4H), 2.36 (s, 3H). MS=255, 257 (MH)+.

32b) [8-(4-Methanesulfonyl-phenyl)-[1,2,4]triazolo[1,5-a]pyridin-2-yl]-[4-(4-methyl-piperazin-1-yl)-phenyl]-amine was prepared from 8-(4-methanesulfonyl-phenyl)-[1,2,4]triazolo[1,5-a]pyridin-2-ylamine (75.0 mg, 0.260 mmol) and 1-(4-bromo-phenyl)-4-methyl-piperazine (73.0 mg, 0.286 mmol) with 2,2'-bis-dicyclohexylphosphanyl-biphenyl (29.0 mg, 0.0530 mmol) as the ligand in a manner analogous to Step 2d. The reaction product was isolated as pale yellow solid (0.022 g, 18%). MP=242-244° C. ¹H NMR (400 MHz, CDCl₃, δ, ppm): 8.47 (dd, J=6.7, 1.1 Hz, 1H), 8.25-8.20 (m, 2H), 8.10-8.06 (m, 2H), 7.63 (dd, J=7.4, 1.1 Hz, 1H), 7.51-7.46 (m, 2H), 7.01-6.95 (m, 2H), 6.67 (s, 1H), 3.20-3.15 (m, 4H), 3.10 (s, 3H), 2.62-2.58 (m, 4H), 2.36 (s, 3H). MS=463 (MH)+.

Example 33

[8-(4-Methanesulfonyl-piperazin-1-yl)-[1,2,4]triazolo[1,5-a]pyridin-2-yl]-(4-methoxy-phenyl)-amine

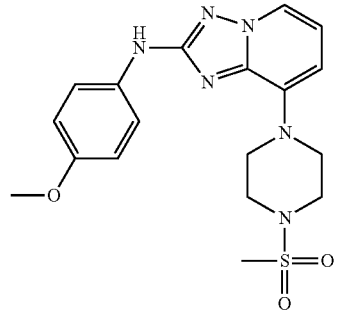 [SMILES: COc1ccc(Nc2nc3c(N4CCN(S(C)(=O)=O)CC4)cccn3n2)cc1]

[8-(4-Methanesulfonyl-piperazin-1-yl)-[1,2,4]triazolo[1,5-a]pyridin-2-yl]-(4-methoxy-phenyl)-amine was prepared from (8-bromo-[1,2,4]triazolo[1,5-a]pyridin-2-yl)-(4-methoxy-phenyl)-amine (50.0 mg, 0.157 mmol) and 1-methanesulfonyl-piperazine (29.0 mg, 0.176 mmol) in a manner analogous to example 30. The title compound was isolated as an off-white solid (0.021 g, 33%). MP=240-241° C. ¹H NMR (400 MHz, CDCl₃, δ, ppm): 8.11 (dd, J=6.5, 1.1 Hz, 1H), 7.51-7.46 (m, 2H), 6.93-6.88 (m, 2H), 6.77 (dd, J=7.7, 6.6 Hz, 1H), 6.73 (s, 1H), 6.71 (dd, J=7.7, 1.0 Hz, 1H), 3.81 (s, 3H), 3.59-3.54 (m, 4H), 3.50-3.45 (m, 4H), 2.83 (s, 3H). MS=403 (MH)+.

Example 34

[8-(1-Methanesulfonyl-1,2,3,6-tetrahydro-pyridin-4-yl)-[1,2,4]triazolo[1,5-a]pyridin-2-yl]-(4-methoxy-phenyl)-amine

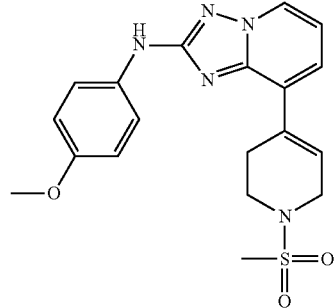 [SMILES: COc1ccc(Nc2nc3c(C4=CCN(S(C)(=O)=O)CC4)cccn3n2)cc1]

34a) 4-[2-(4-Methoxy-phenylamino)-[1,2,4]triazolo[1,5-a]pyridin-8-yl]-3,6-dihydro-2H-pyridine-1-carboxylic acid tert-butyl ester was prepared from (8-bromo-[1,2,4]triazolo[1,5-a]pyridin-2-yl)-(4-methoxy-phenyl)-amine (150.0 mg, 0.4700 mmol) and 4-(4,4,5,5-tetramethyl-[1,3,2]dioxaborolan-2-yl)-3,6-dihydro-2H-pyridine-1-carboxylic acid tert-butyl ester (160.0 mg, 0.5174 mmol) with Pd(dppf)Cl₂ (0.035 g) as the catalyst in a manner analogous to Step 19e. The reaction product was isolated as a clear viscous oil. $^1$H NMR (400 MHz, CDCl$_3$, δ, ppm): 8.30 (dd, J=6.6, 1.0 Hz, 1H), 7.52-7.47 (m, 2H), 7.33-7.29 (m, 1H), 7.25-7.20 (m, 1H), 6.94-6.89 (m, 2H), 6.84 (dd, J=7.3, 7.3 Hz, 1H), 6.63 (s, 1H), 4.23-4.19 (m, 2H), 3.81 (s, 3H), 3.73-3.67 (m, 2H), 2.69-2.62 (m, 2H), 1.50 (s, 9H). MS=422 (MH)+.

34b) To a solution of 4-[2-(4-methoxy-phenylamino)-[1,2,4]triazolo[1,5-a]pyridin-8-yl]-3,6-dihydro-2H-pyridine-1-carboxylic acid tert-butyl ester (100.0 mg, 0.2372 mmol) in dichloromethane (2 mL, 30 mmol) was added trifluoroacetic Acid (1 mL, 10 mmol). The mixture was stirred at room temperature for 4 days then evaporated to a resin. The residue was dissolved in dichloromethane (20 mL) and stirred with saturated aqueous potassium carbonate for 10 minutes. The organic layer was separated, dried over magnesium sulfate, filtered and evaporated. (4-Methoxy-phenyl)-[8-(1,2,3,6-tetrahydro-pyridin-4-yl)-[1,2,4]triazolo[1,5-a]pyridin-2-yl]-amine was isolated yellow-brown resin (0.047 g, 62%) and was used without further purification. $^1$H NMR (400 MHz, CDCl$_3$, δ, ppm): 8.29 (dd, J=6.6, 0.9 Hz, 1H), 7.52-7.47 (m, 2H), 7.32 (dd, J=7.4, 0.8 Hz, 1H), 7.29-7.25 (m, 1H), 6.94-6.89 (m, 2H), 6.83 (dd, J=7.2, 6.7 Hz, 1H), 6.71 (s, 1H), 3.81 (s, 3H), 3.68-3.64 (m, 2H), 3.17 (t, J=5.7 Hz, 2H), 2.61-2.55 (m, 2H). MS=322 (MH)+.

34c) To a solution of (4-methoxy-phenyl)-[8-(1,2,3,6-tetrahydro-pyridin-4-yl)-[1,2,4]triazolo[1,5-a]pyridin-2-yl]-amine (47.0 mg, 0.146 mmol) and triethylamine (31.0 uL, 0.222 mmol) in dichloromethane (2 mL) was added dropwise methanesulfonyl chloride (14.0 L, 0.181 mmol). The mixture was stirred at room temperature for 1 hour then diluted with dichloromethane (20 mL) and water (20 mL). The organic was washed with water and saturated aqueous sodium bicarbonate (10 mL), dried over magnesium sulfate, filtered and evaporated. The residue was purified via chromatography using amine modified silica gel column (4.7 g) using 5%→100% ethyl acetate:hexane solvent gradient. The title compound, [8-(1-Methanesulfonyl-1,2,3,6-tetrahydro-pyridin-4-yl)-[1,2,4]triazolo[1,5-a]pyridin-2-yl]-(4-methoxy-phenyl)-amine, was isolated as a yellow solid (0.037 g, 63%). MP=194-198° C. $^1$H NMR (400 MHz, CDCl$_3$, δ, ppm): 8.33 (dd, J=6.6, 0.9 Hz, 1H), 7.52-7.47 (m, 2H), 7.32 (dd, J=7.5, 0.8 Hz, 1H), 7.29-7.25 (m, 1H), 6.94-6.89 (m, 2H), 6.86 (dd, J=7.5, 6.8 Hz, 1H), 6.73 (s, 1H), 4.10-4.06 (m, 2H), 3.81 (s, 3H), 3.57 (t, J=5.7 Hz, 2H), 2.87 (s, 3H), 2.84-2.78 (m, 2H). MS=400 (MH)+.

Example 35

[8-(4-Methanesulfonyl-phenyl)-[1,2,4]triazolo[1,5-a]pyridin-2-yl]-[3-(4-methyl-piperazin-1-yl)-phenyl]-amine

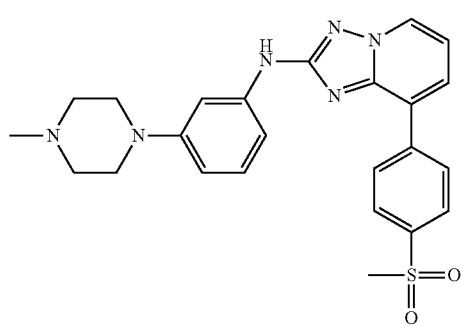 [SMILES: CN1CCN(c2cccc(Nc3nc4c(-c5ccc(S(C)(=O)=O)cc5)cccn4n3)c2)CC1]

35a) 1-(3-Bromo-phenyl)-4-methyl-piperazine was prepared from 1-(3-bromo-phenyl)-piperazine (1.33 g, 5.52 mmol) in a manner analogous to Step 32a. The reaction product was isolated as a pale yellow oil (1.4 g, 100%). $^1$H NMR (400 MHz, CDCl$_3$, δ, ppm): 7.10 (dd, J=8.2, 8.2 Hz, 1H), 7.04 (dd, J=2.1, 2.1 Hz, 1H), 6.95 (ddd, J=7.8, 1.7, 0.7 Hz, 1H), 6.83 (ddd, J=8.3, 2.4, 0.6 Hz, 1H), 3.23-3.18 (m, 4H), 2.58-2.54 (m, 4H), 2.35 (s, 3H). MS=255, 257 (MH)+.

35b) [8-(4-Methanesulfonyl-phenyl)-[1,2,4]triazolo[1,5-a]pyridin-2-yl]-[3-(4-methyl-piperazin-1-yl)-phenyl]-amine was prepared from 8-(4-methanesulfonyl-phenyl)-[1,2,4]triazolo[1,5-a]pyridin-2-ylamine (75.0 mg, 0.260 mmol) and 1-(3-bromo-phenyl)-4-methyl-piperazine (80.0 mg, 0.314 mmol) with 2,2'-bis-dicyclohexylphosphanyl-biphenyl (30.0 mg, 0.0549 mmol) as the ligand in a manner analogous to Step 2d and was isolated as a yellow solid (0.072 g, 60%). MP=232-234° C. $^1$H NMR (400 MHz, CDCl$_3$, δ, ppm): 8.49 (d, J=7.2 Hz, 1H), 8.25 (d, J=7.5 Hz, 2H), 8.08 (d, J=7.9 Hz, 2H), 7.65 (d, J=7.7 Hz, 1H), 7.38 (s, 1H), 7.27-7.20 (m, 1H), 7.04-6.95 (m, 2H), 6.84 (s, 1H), 6.60 (d, J=8.0 Hz, 1H), 3.30-3.25 (m, 4H), 3.10 (s, 3H), 2.63-2.58 (m, 4H), 2.38 (s, 3H). MS=463 (MH)+.

Example 36

6-(4-Methanesulfonyl-phenyl)-[1,2,4]triazolo[1,5-a]pyridin-2-yl]-(4-morpholin-4-yl-phenyl)-amine

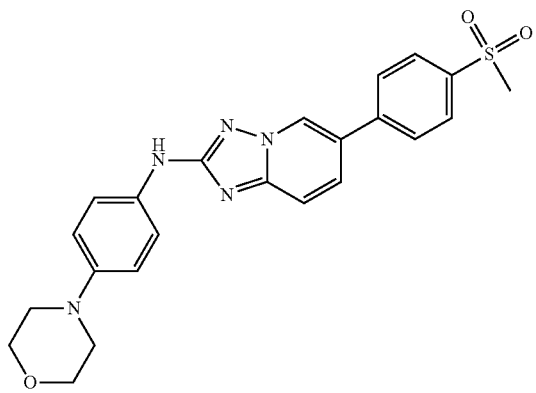 [SMILES: CS(=O)(=O)c1ccc(-c2ccc3nc(Nc4ccc(N5CCOCC5)cc4)nn3c2)cc1]

36a) N-(5-bromo-2-pyridinyl)-N'-carboethoxy-thiourea was prepared from 2-amino-5-bromopyridine (10.0 g, 0.0578 mol) in a manner analogous to Step 2a. The reaction product was isolated as a yellow solid and used without further purification. $^1$H NMR (400 MHz, (D$_3$C)$_2$SO, δ, ppm): 12.14 (br s, 1H), 11.72 (br s, 1H), 8.67-8.55 (m, 1H), 8.53 (d, J=2.4 Hz, 1H), 8.13 (dd, J=9.0, 2.5 Hz, 1H), 4.23 (q, J=7.0 Hz, 2H), 1.26 (t, J=7.0 Hz, 3H). MS=304, 306 (MH)+.

36b) 6-Bromo-[1,2,4]triazolo[1,5-a]pyridin-2-ylamine was prepared from N-(5-bromo-2-pyridinyl)-N'-carboethoxy-thiourea in a manner analogous to Step 2b. The reaction product was isolated as a white solid (7.84 g, 63%). MP=187-189° C. $^1$H NMR (400 MHz, (D$_3$C)$_2$SO, δ, ppm): 8.92 (d, J=1.9 Hz, 1H), 7.55 (dd, J=9.2, 1.9 Hz, 1H), 7.33 (d, J=9.4 Hz, 1H), 6.13 (br s, 2H). MS=213, 215 (MH)+.

36c) 6-(4-Methanesulfonyl-phenyl)-[1,2,4]triazolo[1,5-a]pyridin-2-ylamine was prepared from 6-bromo-[1,2,4]triazolo[1,5-a]pyridin-2-ylamine (200.0 mg, 0.9388 mmol) and (4-methylsulfonylphenyl)boronic acid (210.0 mg, 1.050 mmol) in a manner analogous to Step 2c. The reaction product was isolated as an off-white solid (0.158 g, 58%). MP=301-303° C. $^1$H NMR (400 MHz, (D$_3$C)$_2$SO, δ, ppm): 9.08-9.05 (m, 1H), 8.06-7.97 (m, 4H), 7.86 (dd, J=9.2, 1.7 Hz, 1H), 7.48 (d, J=9.1 Hz, 1H), 6.15 (s, 2H), 3.26 (s, 3H). MS=289 (MH)+.

36d) 6-(4-Methanesulfonyl-phenyl)-[1,2,4]triazolo[1,5-a]pyridin-2-yl]-(4-morpholin-4-yl-phenyl)-amine was prepared from 6-(4-methanesulfonyl-phenyl)-[1,2,4]triazolo[1,5-a]pyridin-2-ylamine (50.0 mg, 0.173 mmol) and 4-(4-bromo-phenyl)-morpholine (51.0 mg, 0.211 mmol) with 2,2'-bis-dicyclohexylphosphanyl-biphenyl (20.0 mg, 0.0366 mmol) as the ligand in a manner analogous to Step 2d. The title compound was isolated as a yellow solid (0.011 g, 14%). MP=>300° C. $^1$H NMR (400 MHz, (D$_3$C)$_2$SO, δ, ppm): 9.41 (s, 1H), 9.28 (s, 1H), 8.09 (d, J=7.7 Hz, 2H), 8.03-7.96 (m, 3H), 7.64 (d, J=8.8 Hz, 1H), 7.59 (d, J=7.9 Hz, 2H), 6.93 (d, J=8.0 Hz, 2H), 3.77-3.71 (m, 4H), 3.28 (s, 3H), 3.05-3.00 (m, 4H). MS=450 (MH)+.

Example 37

[6-(4-Methanesulfonyl-phenyl)-[1,2,4]triazolo[1,5-a]pyridin-2-yl]-[4-(4-methyl-piperazin-1-yl)-phenyl]-amine

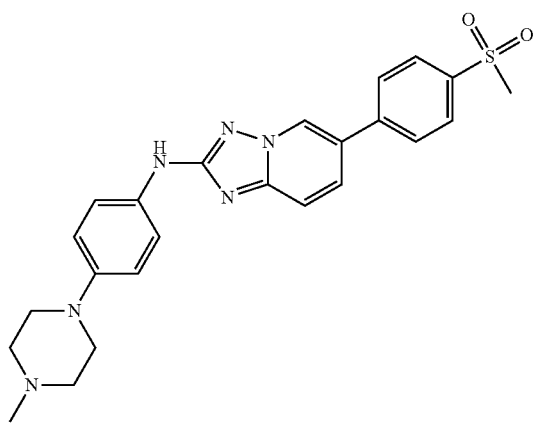 [SMILES: CN1CCN(c2ccc(Nc3nc4ccc(-c5ccc(S(C)(=O)=O)cc5)cn4n3)cc2)CC1]

37a) [6-(4-Methanesulfonyl-phenyl)-[1,2,4]triazolo[1,5-a]pyridin-2-yl]-[4-(4-methyl-piperazin-1-yl)-phenyl]-amine was prepared from 6-(4-methanesulfonyl-phenyl)-[1,2,4]triazolo[1,5-a]pyridin-2-ylamine (50.0 mg, 0.173 mmol) and 1-(4-bromo-phenyl)-4-methyl-piperazine (54.0 mg, 0.212 mmol) with 2,2'-Bis-dicyclohexylphosphanyl-biphenyl (20.0 mg, 0.0366 mmol) as the ligand in a manner analogous to Step 2d and was isolated as a yellow solid (0.009 g, 10%). MP=260-264° C. $^1$H NMR (400 MHz, (D$_3$C)$_2$SO, δ, ppm): 8.68-8.67 (m, 1H), 8.09-8.04 (m, 2H), 7.79-7.74 (m, 2H), 7.68 (dd, J=9.1, 1.8 Hz, 1H), 7.55 (d, J=9.3 Hz, 1H), 7.51-7.46 (m, 2H), 7.00-6.95 (m, 2H), 6.64 (s, 1H), 3.20-3.15 (m, 4H), 3.11 (s, 3H), 2.62-2.58 (m, 4H), 2.36 (s, 3H). MS=463 (MH)+.

Example 38

N(8)-(4-Methanesulfonyl-phenyl)-N(2)-(4-methoxy-phenyl)-[1,2,4]triazolo[1,5-a]pyridine-2,8-diamine

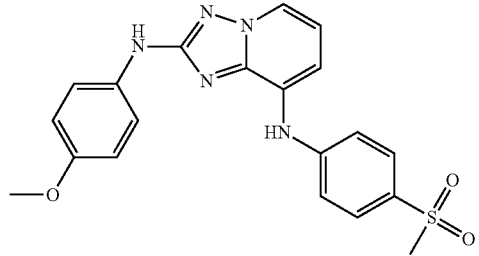 [SMILES: COc1ccc(Nc2nc3c(Nc4ccc(S(C)(=O)=O)cc4)cccn3n2)cc1]

N(8)-(4-Methanesulfonyl-phenyl)-N(2)-(4-methoxy-phenyl)-[1,2,4]triazolo[1,5-a]pyridine-2,8-diamine was prepared from (8-bromo-[1,2,4]triazolo[1,5-a]pyridin-2-yl)-(4-methoxy-phenyl)-amine (50.0 mg, 0.157 mmol) and 4-methanesulfonyl-phenylamine (33.0 mg, 0.193 mmol) in a manner analogous to Example 30. The title compound was isolated as a brown foam (0.013 g, 20%). $^1$H NMR (400 MHz, CDCl$_3$, δ, ppm): 8.08 (d, J=6.1 Hz, 1H), 7.89 (d, J=7.5 Hz, 2H), 7.49 (d, J=7.9 Hz, 2H), 7.35-7.30 (m, 3H), 6.95-6.90 (m, 3H), 6.85-6.80 (m, 1H), 6.58 (s, 1H), 3.82 (s, 3H), 3.07 (s, 3H). MS=410 (MH)+.

Example 39

(4-Methoxy-phenyl)-[8-(1H-pyrazol-4-yl)-[1,2,4]triazolo[1,5-a]pyridin-2-yl]-amine

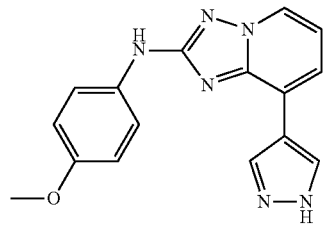 [SMILES: COc1ccc(Nc2nc3c(-c4cn[nH]c4)cccn3n2)cc1]

(4-Methoxy-phenyl)-[8-(1H-pyrazol-4-yl)-[1,2,4]triazolo[1,5-a]pyridin-2-yl]-amine was prepared from (8-bromo-[1,2,4]triazolo[1,5-a]pyridin-2-yl)-(4-methoxy-phenyl)-amine (200.0 mg, 0.6266 mmol) and 1H-pyrazole-4-boronic acid (75.0 mg, 0.670 mmol) with Pd(dppf)Cl$_2$ (50.0 mg) as the catalyst in a manner analogous to Step 2c and was isolated as a brown solid (0.065 g, 34%). MP=224-226° C. $^1$H NMR (400 MHz, (D$_3$C)$_2$SO, δ, ppm): 13.03 (br s, 1H), 9.38 (s, 1H), 8.59 (d, J=6.5 Hz, 1H), 8.49 (s, 2H), 7.85 (d, J=7.2 Hz, 1H), 7.64 (d, J=8.0 Hz, 2H), 7.11 (t, J=7.2 Hz, 1H), 6.91 (d, J=8.4 Hz, 2H), 3.73 (s, 3H). MS=307 (MH)+.

Example 40

[8-(4-Methanesulfonyl-phenyl)-[1,2,4]triazolo[1,5-a]pyridin-2-yl]-(3-methoxy-phenyl)-amine

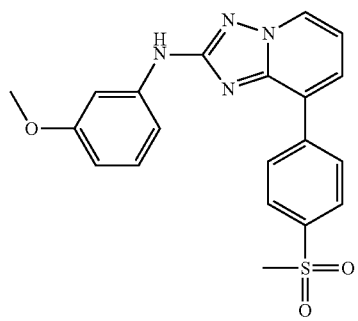 [SMILES: COc1cccc(Nc2nc3c(-c4ccc(S(C)(=O)=O)cc4)cccn3n2)c1]

[8-(4-Methanesulfonyl-phenyl)-[1,2,4]triazolo[1,5-a]pyridin-2-yl]-(3-methoxy-phenyl)-amine was prepared from (8-bromo-[1,2,4]triazolo[1,5-a]pyridin-2-yl)-(3-methoxy-phenyl)-amine (200.0 mg, 0.6266 mmol) and (4-methylsulfonylphenyl)boronic acid (150.0 mg, 0.7499 mmol) with Pd(dppf)Cl$_2$ (50.0 mg) as the catalyst in a manner analogous to Step 2c and was isolated as a yellow solid (0.097 g, 39%). MP=204-206° C. $^1$H NMR (400 MHz, CDCl$_3$, δ, ppm): 8.50 (d, J=6.1 Hz, 1H), 8.24 (d, J=7.8 Hz, 2H), 8.08 (d, J=7.7 Hz, 2H), 7.66 (d, J=7.4 Hz, 1H), 7.37 (s, 1H), 7.28-7.22 (m, 1H), 7.08-7.00 (m, 2H), 6.92 (s, 1H), 6.58 (d, J=7.6 Hz, 1H), 3.86 (s, 3H), 3.10 (s, 3H). MS=395 (MH)+.

Example 41

N(8)-(1-Methanesulfonyl-piperidin-4-yl)-N(2)-(4-methoxy-phenyl)-[1,2,4]triazolo[1,5-a]pyridine-2,8-diamine

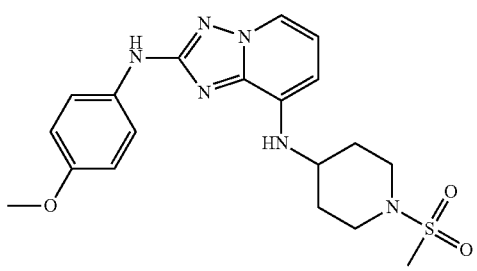 [SMILES: COc1ccc(Nc2nc3c(NC4CCN(S(C)(=O)=O)CC4)cccn3n2)cc1]

N(8)-(1-Methanesulfonyl-piperidin-4-yl)-N(2)-(4-methoxy-phenyl)-[1,2,4]triazolo[1,5-a]pyridine-2,8-diamine was prepared from 8-bromo-[1,2,4]triazolo[1,5-a]pyridin-2-yl)-(4-methoxy-phenyl)-amine (75.0 mg, 0.235 mmol) and 1-methanesulfonyl-piperidin-4-ylamine (50.0 mg, 0.280 mmol) in a manner analogous Example 30 and was isolated as a tan foam (0.025 g, 26%). $^1$H NMR (400 MHz, CDCl$_3$, δ, ppm): 7.84 (d, J=6.5 Hz, 1H), 7.49 (d, J=7.5 Hz, 2H), 6.93 (d, J=7.5 Hz, 2H), 6.72 (t, J=8.0 Hz, 1H), 6.59 (s, 1H), 6.38 (d, J=7.7 Hz, 1H), 4.64 (d, J=7.4 Hz, 1H), 3.83 (s, 3H), 3.81-3.74 (m, 2H), 3.63-3.53 (m, 1H), 3.02 (t, J=11.4 Hz, 2H), 2.85 (s, 3H), 2.28-2.20 (m, 2H), 1.81-1.69 (m, 2H). MS=417 (MH)+.

Example 42

[8-(1-Methanesulfonyl-1H-pyrazol-4-yl)-[1,2,4]triazolo[1,5-a]pyridin-2-yl]-(4-methoxy-phenyl)-amine

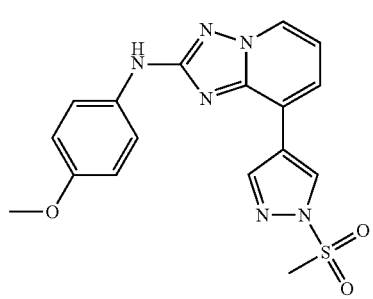 [SMILES: COc1ccc(Nc2nc3c(-c4cnn(S(C)(=O)=O)c4)cccn3n2)cc1]

[8-(1-Methanesulfonyl-1H-pyrazol-4-yl)-[1,2,4]triazolo[1,5-a]pyridin-2-yl]-(4-methoxy-phenyl)-amine was prepared from (4-methoxy-phenyl)-[8-(1H-pyrazol-4-yl)-[1,2,4]triazolo[1,5-a]pyridin-2-yl]-amine (100.0 mg, 0.3264 mmol) in a manner analogous to Step 34c and was isolated as an off-white solid (0.078 g, 62%). MP=196-198° C. $^1$H NMR (400 MHz, (D$_3$C)$_2$SO, δ, ppm): 9.56 (s, 1H), 9.19 (s, 1H), 8.84 (s, 1H), 8.74 (d, J=6.5 Hz, 1H), 8.09 (d, J=7.3 Hz, 1H), 7.64 (d, J=8.5 Hz, 2H), 7.09 (t, J=7.0 Hz, 1H), 6.91 (d, J=8.4 Hz, 2H), 3.73 (s, 3H), 3.65 (s, 3H), MS=385 (MH)+.

Example 43

[8-(4-Methanesulfonyl-phenyl)-[1,2,4]triazolo[1,5-a]pyridin-2-yl]-(4-morpholin-4-ylmethyl-phenyl)-amine

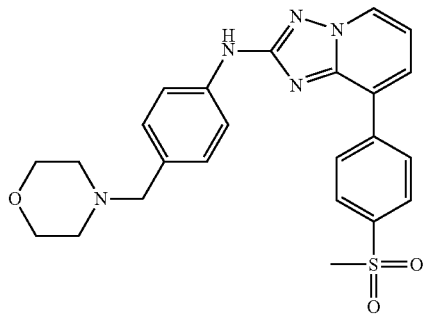 [SMILES: CS(=O)(=O)c1ccc(-c2cccn3nc(Nc4ccc(CN5CCOCC5)cc4)nc23)cc1]

[8-(4-Methanesulfonyl-phenyl)-[1,2,4]triazolo[1,5-a]pyridin-2-yl]-(4-morpholin-4-ylmethyl-phenyl)-amine was prepared from 8-(4-methanesulfonyl-phenyl)-[1,2,4]triazolo[1,5-a]pyridin-2-ylamine (50.0 mg, 0.173 mmol) and 4-(4-bromo-benzyl)-morpholine (55.0 mg, 0.215 mmol) with 2,2'-bis-dicyclohexylphosphanyl-biphenyl (20.0 mg, 0.0366 mmol) as the ligand in a manner analogous to Step 2d and was isolated as a yellow foam (0.006 g, 7%). $^1$H NMR (400 MHz, CDCl$_3$, δ, ppm): 8.50 (d, J=6.6 Hz, 1H), 8.23 (d, J=8.3 Hz, 2H), 8.09 (d, J=8.3 Hz, 2H), 7.66 (d, J=7.4 Hz, 1H), 7.55 (d, J=8.4 Hz, 2H), 7.32 (d, J=8.2 Hz, 2H), 7.03 (t, J=6.7 Hz, 1H), 6.86 (s, 1H), 3.74-3.69 (m, 4H), 3.48 (s, 2H), 3.11 (s, 3H), 2.48-2.43 (m, 4H). MS=464 (MH)+.

Example 44

[8-(4-Methanesulfonyl-phenyl)-[1,2,4]triazolo[1,5-a]pyridin-2-yl]-[4-(4-methyl-piperazin-1-ylmethyl)-phenyl]-amine

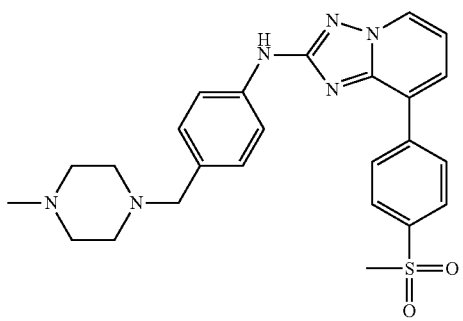 [SMILES: CN1CCN(Cc2ccc(Nc3nc4c(-c5ccc(S(C)(=O)=O)cc5)cccn4n3)cc2)CC1]

[8-(4-Methanesulfonyl-phenyl)-[1,2,4]triazolo[1,5-a]pyridin-2-yl]-[4-(4-methyl-piperazin-1-ylmethyl)-phenyl]-amine was prepared from 8-(4-methanesulfonyl-phenyl)-[1,2,4]triazolo[1,5-a]pyridin-2-ylamine (50.0 mg, 0.173 mmol) and 1-(4-bromo-benzyl)-4-methyl-piperazine (56.0 mg, 0.208 mmol) with 2,2'-bis-dicyclohexylphosphanyl-biphenyl (20.0 mg, 0.0366 mmol) as the ligand in a manner analogous to Step 2d and was isolated as a pale yellow foam (0.010 g, 12%). $^1$H NMR (400 MHz, CDCl$_3$, δ, ppm): 8.50 (d, J=6.4 Hz, 1H), 8.24 (d, J=8.2 Hz, 2H), 8.09 (d, J=8.2 Hz, 2H), 7.66 (d, J=7.1 Hz, 1H), 7.54 (d, J=7.8 Hz, 2H), 7.31 (d, J=7.9 Hz, 2H), 7.02 (t, J=6.7 Hz, 1H), 6.86 (s, 1H), 3.49 (s, 2H), 3.11 (s, 3H), 2.46 (br s, 8H), 2.29 (s, 3H). MS=477 (MH)+.

Example 45

1,1,2,2,3,3,4,4,4-Nonafluoro-butane-1-sulfonic acid 4-[8-(4-methanesulfonyl-phenyl)-[1,2,4]triazolo[1,5-a]pyridin-2-ylamino]-phenyl ester

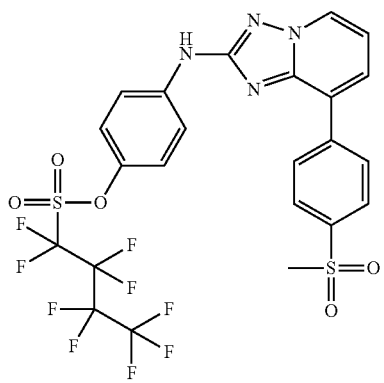 [SMILES: CS(=O)(=O)c1ccc(-c2cccn3nc(Nc4ccc(OS(=O)(=O)C(F)(F)C(F)(F)C(F)(F)C(F)(F)F)cc4)nc23)cc1]

To a suspension of 4-[8-(4-methanesulfonyl-phenyl)-[1,2,4]triazolo[1,5-a]pyridin-2-ylamino]-phenol (100.0 mg, 0.2629 mmol) and triethylamine (55.0 L, 0.395 mmol) in acetonitrile (1 mL) was added 1,1,2,2,3,3,4,4,4-nonafluoro-butane-1-sulfonyl fluoride (60.0 L, 0.341 mmol). The mixture was stirred for 1 hour at room temperature then partitioned between water (25 mL) and ethyl acetate (25 mL). The organic was rinsed with saturated aqueous sodium chloride, dried over magnesium sulfate, filtered and evaporated. The residue was purified via chromatography using silica gel column (12 g) and ethyl acetate:hexane solvent gradient. The title compound was isolated as a pale yellow foam (0.128 g, 73%). $^1$H NMR (400 MHz, CDCl$_3$, δ, ppm): 8.51 (d, J=6.6 Hz, 1H), 8.22 (d, J=7.5 Hz, 2H), 8.09 (d, J=7.8 Hz, 2H), 7.71-7.64 (m, 3H), 7.29-7.25 (m, 2H), 7.11 (s, 1H), 7.08 (t, J=7.0 Hz, 1H), 3.10 (s, 3H). MS=663 (MH)+.

Example 46

[8-(4-Methanesulfonyl-phenyl)-[1,2,4]triazolo[1,5-a]pyridin-2-yl]-(3-morpholin-4-ylmethyl-phenyl)-amine

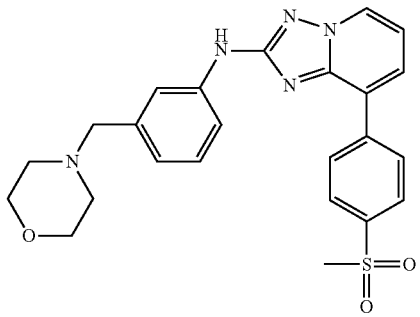 [SMILES: CS(=O)(=O)c1ccc(-c2cccn3nc(Nc4cccc(CN5CCOCC5)c4)nc23)cc1]

[8-(4-Methanesulfonyl-phenyl)-[1,2,4]triazolo[1,5-a]pyridin-2-yl]-(3-morpholin-4-ylmethyl-phenyl)-amine was prepared from 8-(4-methanesulfonyl-phenyl)-[1,2,4]triazolo[1,5-a]pyridin-2-ylamine (50.0 mg, 0.173 mmol) and 4-(3-bromo-benzyl)-morpholine (54.0 mg, 0.211 mmol) with 2,2'-bis-dicyclohexylphosphanyl-biphenyl (20.0 mg, 0.0366 mmol) as the ligand in a manner analogous to Step 2d and was isolated as an orange foam (0.021 g, 26%). $^1$H NMR (400 MHz, CDCl$_3$, δ, ppm): 8.51 (d, J=6.5 Hz, 1H), 8.24 (d, J=7.4 Hz, 2H), 8.09 (d, J=7.3 Hz, 2H), 7.66 (d, J=7.0 Hz, 1H), 7.58 (d, J=8.0 Hz, 1H), 7.49 (s, 1H), 7.35-7.29 (m, 1H), 7.05-6.97 (m, 2H), 6.87 (s, 1H), 3.75-3.70 (m, 4H), 3.54 (s, 2H), 3.11 (s, 3H), 2.52-2.45 (m, 4H). MS=464 (MH)+.

Example 47

N(8)-(2-Methanesulfonyl-phenyl)-N(2)-(4-methoxy-phenyl)-[1,2,4]triazolo[1,5-a]pyridine-2,8-diamine

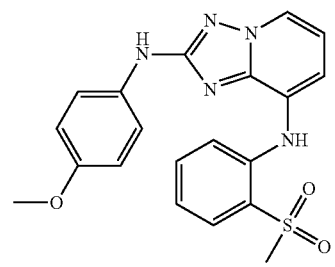 [SMILES: COc1ccc(Nc2nc3c(Nc4ccccc4S(C)(=O)=O)cccn3n2)cc1]

N(8)-(2-Methanesulfonyl-phenyl)-N(2)-(4-methoxy-phenyl)-[1,2,4]triazolo[1,5-a]pyridine-2,8-diamine was prepared from (8-bromo-[1,2,4]triazolo[1,5-a]pyridin-2-yl)-(4-methoxy-phenyl)-amine (50.0 mg, 0.157 mmol) and 2-methanesulfonyl-phenylamine; hydrochloride (39.0 mg, 0.188 mmol) in a manner analogous to Example 30 and was isolated as a tan foam (0.022 g, 34%). $^1$H NMR (400 MHz, CDCl$_3$, δ, ppm): 8.46 (s, 1H), 8.11 (d, J=7.1 Hz, 1H), 7.98 (d, J=7.8 Hz, 1H), 7.58-7.47 (m, 4H), 7.29-7.24 (m, 1H), 7.15-7.09 (m, 1H), 6.91 (d, J=7.7 Hz, 2H), 6.81-6.76 (m, 1H), 6.68 (s, 1H), 3.81 (s, 3H), 3.14 (s, 3H). MS=410 (MH)+.

Example 48

[8-(4-Methanesulfonylmethyl-phenyl)-[1,2,4]triazolo[1,5-a]pyridin-2-yl]-[4-(4-methyl-piperazin-1-yl)-phenyl]-amine

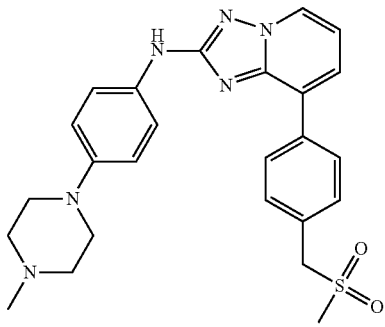 [SMILES: CN1CCN(c2ccc(Nc3nc4c(-c5ccc(CS(C)(=O)=O)cc5)cccn4n3)cc2)CC1]

48a) A suspension of (4-bromomethylphenyl)boronic acid (2.0 g, 9.3 mmol) and sodium methanesulfinate (1.4 g, 14 mmol) in Ethanol (30 mL) was heated at 60° C. for 24 hours. The mixture was evaporated to dryness and the residue was suspended in water. The precipitate was filtered, rinsed with water and air dried. The reaction product was isolated as an off-white solid (1.18 g, 59%). $^1$H NMR (400 MHz, (D$_3$C)$_2$SO, δ, ppm): 8.09 (s, 2H), 7.79 (d, J=7.9 Hz, 2H), 7.37 (d, J=7.9 Hz, 2H), 4.47 (s, 2H), 2.88 (s, 3H). MS=135 (M—SO$_2$CH$_3$)+.

48b) 8-(4-Methanesulfonylmethyl-phenyl)-[1,2,4]triazolo[1,5-a]pyridin-2-ylamine was prepared from 8-bromo-[1,2,4]triazolo[1,5-a]pyridin-2-ylamine (200.0 mg, 0.9388 mmol) and (4-methanesulfonylmethylphenyl)boronic acid (240.0 mg, 1.121 mmol) with Pd(dppf)Cl$_2$ (130.0 mg) as the catalyst in a manner analogous to Step 2c. The reaction product was isolated as a pale yellow solid (0.051 g, 18%). $^1$H NMR (400 MHz, (D$_3$C)$_2$SO, δ, ppm): 8.56 (dd, J=6.6, 1.0 Hz, 1H), 8.12 (d, J=8.3 Hz, 2H), 7.73 (dd, J=7.5, 1.0 Hz, 1H), 7.52 (d, J=8.3 Hz, 2H), 6.99 (dd, J=7.3, 7.3 Hz, 1H), 6.11 (s, 1H), 4.55 (s, 2H), 2.94 (s, 3H). MS=303 (MH)+.

48c) [8-(4-Methanesulfonylmethyl-phenyl)-[1,2,4]triazolo[1,5-a]pyridin-2-yl]-[4-(4-methyl-piperazin-1-yl)-phenyl]-amine was prepared from 8-(4-methanesulfonylmethyl-phenyl)-[1,2,4]triazolo[1,5-a]pyridin-2-ylamine (50.0 mg, 0.165 mmol) and 1-(4-bromo-phenyl)-4-methyl-piperazine (51.0 mg, 0.200 mmol) with 2,2'-bis-dicyclohexylphosphanyl-biphenyl (20.0 mg, 0.0366 mmol) as the ligand in a manner analogous to Step 2d. The title compound was isolated as a yellow foam (0.009 g, 11%). $^1$H NMR (400 MHz, CDCl$_3$, δ, ppm): 8.44-8.40 (m, 1H), 8.08 (d, J=8.1 Hz, 2H), 7.60-7.54 (m, 3H), 7.51-7.46 (m, 2H), 7.00-6.93 (m, 3H), 6.70 (s, 1H), 4.32 (s, 2H), 3.21-3.14 (m, 4H), 2.83 (s, 3H), 2.66-2.56 (m, 4H), 2.37 (s, 3H). MS=477 (MH)+.

Example 49

[8-(4-Methanesulfonyl-phenyl)-[1,2,4]triazolo[1,5-a]pyridin-2-yl]-[4-(4-morpholin-4-yl-piperidin-1-yl)-phenyl]-amine

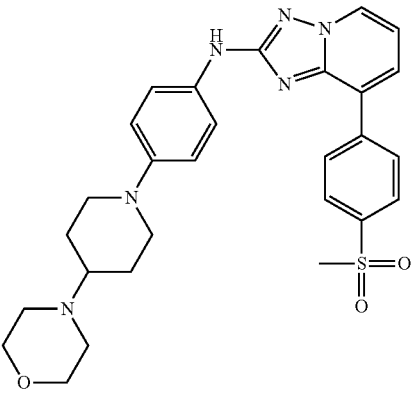 [SMILES: CS(=O)(=O)c1ccc(-c2cccn3nc(Nc4ccc(N5CCC(N6CCOCC6)CC5)cc4)nc23)cc1]

49a) A round bottom flask equipped with a drying tube was charged with 4-piperidin-4-yl-morpholine (0.21 g, 1.2 mmol), cupric acetate (0.34 g, 1.9 mmol), 4-bromobenzeneboronic acid (0.50 g, 2.5 mmol), pyridine (0.20 mL, 2.5 mmol) and dichloromethane (5 mL, 80 mmol). The blue suspension was stirred open to the air for 6 days at room temperature. Water (25 mL) was added to the green-brown suspension and stirred for 10 minutes. The mixture was extracted with ethyl acetate (3×25 mL). The combined organic layer was washed with saturated aqueous sodium chloride (25 mL), dried over magnesium sulfate, filtered and evaporated. The residue was purified via chromatography using silica gel column (40 g) and 0%→8% methanol: dichloromethane solvent gradient. 4-[1-(4-Bromo-phenyl)-piperidin-4-yl]-morpholine was isolated as a tan solid (0.168 g, 41%). MP=146-149° C. $^1$H NMR (400 MHz, CDCl$_3$, δ, ppm): 7.32 (d, J=7.5 Hz, 2H), 6.79 (d, J=7.8 Hz, 2H), 3.76-3.71 (m, 4H), 3.68 (d, J=12.8 Hz, 2H), 2.71 (t, J=12.3 Hz, 2H), 2.60-2.54 (m, 4H), 2.37-2.27 (m, 1H), 1.93 (d, J=11.3 Hz, 2H), 1.69-1.58 (m, 2H). MS=325, 327 (MH)+.

49b) [8-(4-Methanesulfonyl-phenyl)-[1,2,4]triazolo[1,5-a]pyridin-2-yl]-[4-(4-morpholin-4-yl-piperidin-1-yl)-phenyl]-amine was prepared from 8-(4-methanesulfonyl-phenyl)-[1,2,4]triazolo[1,5-a]pyridin-2-ylamine (50.0 mg, 0.173 mmol) and 4-[1-(4-bromo-phenyl)-piperidin-4-yl]-morpholine (65.0 mg, 0.200 mmol) with 2,2'-bis-dicyclohexylphosphanyl-biphenyl (20.0 mg, 0.0366 mmol) as the ligand in a manner analogous to Step 2d. The title compound was isolated as a yellow solid (0.044 g, 48%). MP=253-254° C. $^1$H NMR (400 MHz, CDCl$_3$, δ, ppm): 8.47 (d, J=6.3 Hz, 1H), 8.23 (d, J=7.5 Hz, 2H), 8.08 (d, J=8.2 Hz, 2H), 7.63 (d, J=7.3 Hz, 1H), 7.47 (d, J=7.1 Hz, 2H), 7.01-6.95 (m, 3H), 6.68 (s, 1H), 3.77-3.72 (m, 4H), 3.69-3.62 (m, 2H), 3.10 (s, 3H), 2.74-2.65 (m, 2H), 2.62-2.57 (m, 4H), 2.36-2.28 (m, 1H), 1.98-1.92 (m, 2H), 1.75-1.63 (m, 2H). MS=533 (MH)+.

Example 50

[8-(4-Methanesulfonyl-phenyl)-[1,2,4]triazolo[1,5-a]pyridin-2-yl]-[4-(1-methyl-piperidin-4-yl)-phenyl]-amine

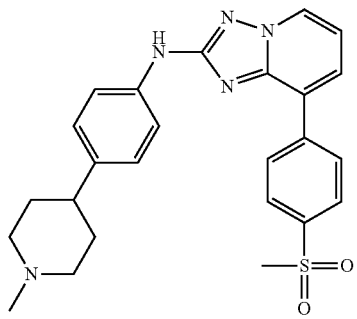 [SMILES: CN1CCC(c2ccc(Nc3nc4c(-c5ccc(S(C)(=O)=O)cc5)cccn4n3)cc2)CC1]

50a) 4-(4-Bromo-phenyl)-1-methyl-piperidine; hydrochloride was prepared from 4-(4-bromo-phenyl)-piperidine; hydrochloride (1.0 g, 3.6 mmol) in a manner analogous to Step 34c. The reaction product was isolated an off-white solid (0.94 g) and was used without further purification. $^1$H NMR (400 MHz, $(D_3C)_2SO$, δ, ppm): 10.58 (br s, 1H), 7.54 (d, J=7.2 Hz, 2H), 7.21 (d, J=7.3 Hz, 2H), 3.46 (d, J=11.4 Hz, 2H), 3.09-2.97 (m, 2H), 2.83-2.70 (m, 4H), 2.00-1.87 (m, 4H). MS=254, 256 (MH)+.

50b) [8-(4-Methanesulfonyl-phenyl)-[1,2,4]triazolo[1,5-a]pyridin-2-yl]-[4-(1-methyl-piperidin-4-yl)-phenyl]-amine was prepared from 8-(4-methanesulfonyl-phenyl)-[1,2,4]triazolo[1,5-a]pyridin-2-ylamine (75.0 mg, 0.260 mmol) and 4-(4-bromo-phenyl)-1-methyl-piperidine; hydrochloride (100.0 mg, 0.3441 mmol) with 2,2'-bis-dicyclohexylphosphanyl-biphenyl (30.0 mg, 0.0549 mmol) as the ligand in a manner analogous to Step 2d. The title compound was isolated as a yellow foam (0.070 g, 58%). $^1$H NMR (400 MHz, CDCl$_3$, δ, ppm): 8.49 (d, J=6.8 Hz, 1H), 8.23 (d, J=8.2 Hz, 2H), 8.08 (d, J=8.1 Hz, 2H), 7.65 (d, J=7.4 Hz, 1H), 7.51 (d, J=8.2 Hz, 2H), 7.23 (d, J=8.2 Hz, 2H), 7.01 (t, J=6.7 Hz, 1H), 6.85 (s, 1H), 3.10 (s, 3H), 3.01-2.94 (m, 2H), 2.51-2.41 (m, 1H), 2.33 (s, 3H), 2.10-2.01 (m, 2H), 1.87-1.77 (m, 4H). MS=462 (MH)+.

Example 51

[8-(4-Methanesulfonyl-phenyl)-[1,2,4]triazolo[1,5-a]pyridin-2-yl]-{4-[4-(4-methyl-piperazin-1-yl)-piperidin-1-yl]-phenyl}-amine

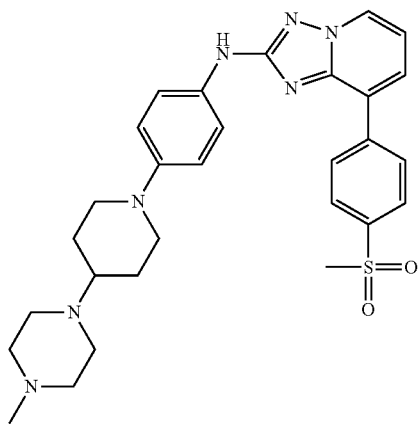 [SMILES: CN1CCN(C2CCN(c3ccc(Nc4nc5c(-c6ccc(S(C)(=O)=O)cc6)cccn5n4)cc3)CC2)CC1]

51a) 1-[1-(4-Bromo-phenyl)-piperidin-4-yl]-4-methyl-piperazine was prepared from 1-methyl-4-piperidin-4-yl-piperazine (0.50 g, 2.7 mmol) and 4-bromobenzeneboronic acid (0.50 g, 2.5 mmol) in a manner analogous to Step 49a. The reaction product isolated as a tan solid (0.077 g, 9%). $^1$H NMR (400 MHz, CDCl$_3$, δ, ppm): 7.32 (d, J=7.9 Hz, 2H), 6.79 (d, J=7.7 Hz, 2H), 3.72-3.65 (m, 2H), 2.85-2.35 (m, 14H), 2.00-1.90 (m, 2H), 1.73-1.60 (m, 2H). MS=338, 340 (MH)+.

51b) [8-(4-Methanesulfonyl-phenyl)-[1,2,4]triazolo[1,5-a]pyridin-2-yl]-{4-[4-(4-methyl-piperazin-1-yl)-piperidin-1-yl]-phenyl}-amine was prepared from 8-(4-methanesulfonyl-phenyl)-[1,2,4]triazolo[1,5-a]pyridin-2-ylamine (55.0 mg, 0.191 mmol) and 1-[1-(4-bromo-phenyl)-piperidin-4-yl]-4-methyl-piperazine (70.0 mg, 0.207 mmol) with 2,2'-bis-dicyclohexylphosphanyl-biphenyl (22.0 mg, 0.0402 mmol) as the ligand in a manner analogous to Step 2d. The title compound was isolated as yellow solid (0.014 g, 13%). MP=237-240° C. $^1$H NMR (400 MHz, CDCl$_3$, δ, ppm): 8.49 (d, J=6.6 Hz, 1H), 8.23 (d, J=7.7 Hz, 2H), 8.08 (d, J=8.0 Hz, 2H), 7.63 (d, J=7.2 Hz, 1H), 7.46 (d, J=8.4 Hz, 2H), 7.01-6.95 (m, 3H), 6.66 (s, 1H), 3.70-3.62 (m, 2H), 3.10 (s, 3H), 2.73-2.32 (m, 11H), 2.30 (s, 3H), 1.98-1.90 (m, 2H), 1.77-165 (m, 2H). MS=546 (MH)+.

Example 52

[4-(4-Methyl-piperazin-1-yl)-phenyl]-{8-[4-(propane-2-sulfonyl)-phenyl]-[1,2,4]triazolo[1,5-a]pyridin-2-yl}-amine

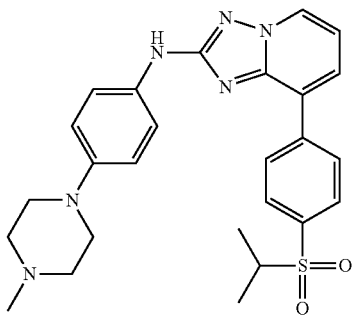 [SMILES: CC(C)S(=O)(=O)c1ccc(-c2cccn3nc(Nc4ccc(N5CCN(C)CC5)cc4)nc23)cc1]

52a) 8-[4-(Propane-2-sulfonyl)-phenyl]-[1,2,4]triazolo[1,5-a]pyridin-2-ylamine was prepared from 8-bromo-[1,2,4]triazolo[1,5-a]pyridin-2-ylamine (500.0 mg, 2.347 mmol) and 4-isopropylsulfonylbenzeneboronic acid (650.0 mg, 2.850 mmol) in a manner analogous to Step 2c. The reaction product was isolated as an off-white solid (0.317 g, 42%). MP=175-177° C. $^1$H NMR (400 MHz, $(D_3C)_2SO$, δ, ppm): 8.64 (d, J=6.6 Hz, 1H), 8.39 (d, J=7.4 Hz, 2H), 7.96 (d, J=7.5 Hz, 2H), 7.85 (d, J=7.4 Hz, 1H), 7.06-7.00 (m, 1H), 6.21 (br s, 2H), 3.54-3.42 (m, 1H), 1.19 (d, J=6.5 Hz, 6H). MS=317 (MH)+.

52b) [4-(4-Methyl-piperazin-1-yl)-phenyl]-{8-[4-(propane-2-sulfonyl)-phenyl]-[1,2,4]triazolo[1,5-a]pyridin-2-yl}-amine was prepared from 8-[4-(propane-2-sulfonyl)-phenyl]-[1,2,4]triazolo[1,5-a]pyridin-2-ylamine (75.0 mg, 0.237 mmol) and 1-(4-bromo-phenyl)-4-methyl-piperazine (75.0 mg, 0.294 mmol) with 2,2'-bis-dicyclohexylphosphanyl-biphenyl (48.0 mg, 0.0877 mmol) as the ligand in a manner analogous to Step 2d. The title compound was isolated as a yellow foam (0.051 g, 44%). $^1$H NMR (400 MHz, CDCl$_3$, δ, ppm): 8.46 (d, J=6.7 Hz, 1H), 8.25 (d, J=7.8 Hz, 2H), 8.02 (d, J=7.8 Hz, 2H), 7.65 (d, J=7.3 Hz, 1H), 7.49 (d, J=7.8 HZ, 2H), 7.01-6.95 (m, 3H), 6.69 (s, 1H), 3.30-3.15 (m, 5H), 2.63-2.58 (m, 4H), 2.36 (s, 3H), 1.36 (d, J=6.7 Hz, 6H). MS=491 (MH)+.

Example 53

[3-(4-Methyl-piperazin-1-yl)-phenyl]-{8-[4-(propane-2-sulfonyl)-phenyl]-[1,2,4]triazolo[1,5-a]pyridin-2-yl}-amine

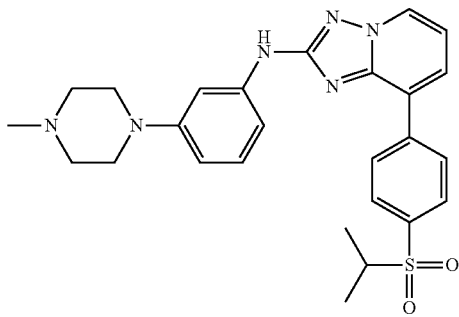 [SMILES: CC(C)S(=O)(=O)c1ccc(-c2cccn3nc(Nc4cccc(N5CCN(C)CC5)c4)nc23)cc1]

[3-(4-Methyl-piperazin-1-yl)-phenyl]-{8-[4-(propane-2-sulfonyl)-phenyl]-[1,2,4]triazolo[1,5-a]pyridin-2-yl}-amine prepared from 8-[4-(propane-2-sulfonyl)-phenyl]-[1,2,4]triazolo[1,5-a]pyridin-2-ylamine (75.0 mg, 0.237 mmol) and 1-(3-bromo-phenyl)-4-methyl-piperazine (75.0 mg, 0.294 mmol) with 2,2'-bis-dicyclohexylphosphanyl-biphenyl (48.0 mg, 0.0878 mmol) as the ligand in a manner analogous to Step 2d and was isolated as a yellow foam (0.070 g, 60%). $^1$H NMR (400 MHz, CDCl$_3$, δ, ppm): 8.49 (d, J=6.7 Hz, 1H), 8.27 (d, J=7.7 Hz, 2H), 8.01 (d, J=7.9 Hz, 2H), 7.67 (d, J=7.3 Hz, 1H), 7.39 (s, 1H), 7.26-7.20 (m, 1H), 7.04-6.95 (m, 2H), 6.85 (s, 1H), 6.60 (d, J=7.7 Hz, 1H), 3.31-3.19 (m, 5H), 2.63-2.58 (m, 4H), 2.38 (s, 3H), 1.35 (d, J=6.7 Hz, 6H). MS=491 (MH)+.

Example 54

N,N-Dimethyl-4-{2-[4-(4-methyl-piperazin-1-yl)-phenylamino]-[1,2,4]triazolo[1,5-a]pyridin-8-yl}-benzenesulfonamide

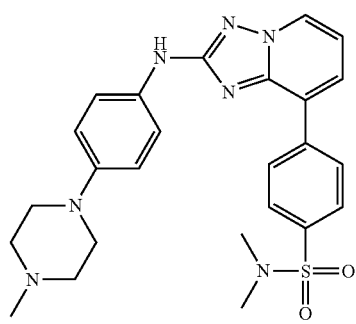

54a) 4-(2-Amino-[1,2,4]triazolo[1,5-a]pyridin-8-yl)-N,N-dimethyl-benzenesulfonamide was prepared from 8-bromo-[1,2,4]triazolo[1,5-a]pyridin-2-ylamine (150.0 mg, 0.7041 mmol) and N,N-dimethyl-4-(4,4,5,5-tetramethyl-[1,3,2]dioxaborolan-2-yl)-benzenesulfonamide (210.0 mg, 0.6748 mmol) in a manner analogous to Step 2c. The reaction product was isolated as a tan solid (0.074 g, 34%). MP=188-190° C. $^1$H NMR (400 MHz, (D$_3$C)$_2$SO, δ, ppm): 8.63 (d, J=6.4 Hz, 1H), 8.38 (d, J=8.2 Hz, 2H), 7.88-7.82 (m, 3H), 7.03 (t, J=6.8 Hz, 1H), 6.21 (br s, 2H), 2.66 (s, 6H). MS=318 (MH)+.

54b) N,N-Dimethyl-4-{2-[4-(4-methyl-piperazin-1-yl)-phenylamino]-[1,2,4]triazolo[1,5-a]pyridin-8-yl}-benzenesulfonamide was prepared from 4-(2-amino-[1,2,4]triazolo[1,5-a]pyridin-8-yl)-N,N-dimethyl-benzenesulfonamide (75.0 mg, 0.236 mmol) and 1-(4-bromo-phenyl)-4-methyl-piperazine (75.0 mg, 0.294 mmol) with 2,2'-bis-dicyclohexylphosphanyl-biphenyl (48.0 mg, 0.0878 mmol) as the ligand in a manner analogous to Step 2d. The title compound was isolated as a yellow foam (0.034 g, 29%). $^1$H NMR (400 MHz, CDCl$_3$, δ, ppm): 8.45 (d, J=6.7 Hz, 1H), 8.22 (d, J=8.1 Hz, 2H), 7.91 (d, J=7.8 Hz, 2H), 7.63 (d, J=6.3 Hz, 1H), 7.49 (d, J=7.8 Hz, 2H), 7.00-6.95 (m, 3H), 6.69 (s, 1H), 3.20-3.15 (m, 4H), 2.78 (s, 6H), 2.63-2.58 (m, 4H), 2.36 (s, 3H). MS=492 (MH)+.

Example 55

[8-(2-Methoxy-phenyl)-[1,2,4]triazolo[1,5-a]pyridin-2-yl]-[4-(4-methyl-piperazin-1-yl)-phenyl]-amine

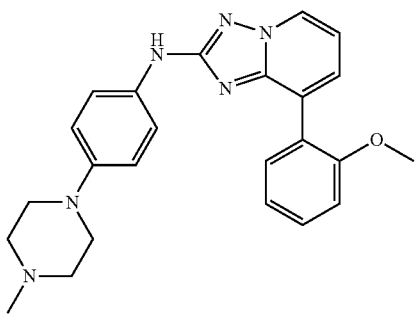 [SMILES: COc1ccccc1-c1cccn2nc(Nc3ccc(N4CCN(C)CC4)cc3)nc12]

55a) 8-(2-Methoxy-phenyl)-[1,2,4]triazolo[1,5-a]pyridin-2-ylamine was prepared from 8-bromo-[1,2,4]triazolo[1,5-a]pyridin-2-ylamine (1.0 g, 0.0047 mol) and 2-methoxybenzeneboronic acid (1.1 g, 0.0070 mol) in a manner analogous to Step 2c. The reactin product was isolated as a brown solid (1.0 g) and was used without further purification. $^1$H NMR (400 MHz, (D$_3$C)$_2$SO, δ, ppm): 8.50 (d, J=6.5 Hz, 1H), 7.51 (dd, J=7.6, 1.5 Hz, 1H), 7.43-7.36 (m, 2H), 7.13 (d, J=8.1 Hz, 1H), 7.02 (t, J=7.3 Hz, 1H), 6.91 (t, J=7.0 Hz, 1H), 5.96 (br s, 2H), 3.73 (s, 3H). MS=241 (MH)+.

55b) [8-(2-Methoxy-phenyl)-[1,2,4]triazolo[1,5-a]pyridin-2-yl]-[4-(4-methyl-piperazin-1-yl)-phenyl]-amine was prepared from 8-(2-Methoxy-phenyl)-[1,2,4]triazolo[1,5-a]pyridin-2-ylamine (75.0 mg, 0.312 mmol) and 1-(4-Bromophenyl)-4-methyl-piperazine (90.0 mg, 0.353 mmol) with 2,2'-Bis-dicyclohexylphosphanyl-biphenyl (34.0 mg, 0.0622 mmol) as the ligand in a manner analogous to Step 2d. The title compound was isolated as a pale yellow foam (0.063 g, 49%). $^1$H NMR (400 MHz, CDCl$_3$, δ, ppm): 8.39 (d, J=6.2 Hz, 1H), 7.62 (d, J=7.6 Hz, 1H), 7.51 (d, J=6.9 Hz, 1H), 7.45 (d, J=7.5 Hz, 2H), 7.40 (t, J=7.8 Hz, 1H), 7.09 (t, J=7.3 Hz, 1H), 7.04 (d, J=8.0 Hz, 1H), 6.95 (d, J=7.6 Hz, 2H), 6.91-6.86 (m, 1H), 6.65 (s, 1H), 3.81 (s, 3H), 3.17-3.12 (m, 4H), 2.61-2.56 (m, 4H), 2.36 (s, 3H). MS=415 (MH)+.

Example 56

[8-(2-Methoxy-phenyl)-[1,2,4]triazolo[1,5-a]pyridin-2-yl]-[3-(4-methyl-piperazin-1-yl)-phenyl]-amine

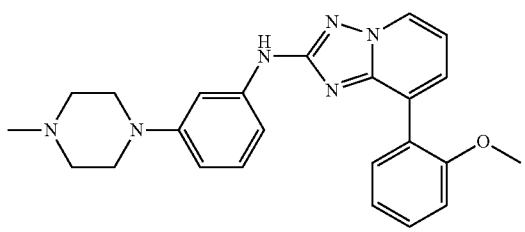

[8-(2-Methoxy-phenyl)-[1,2,4]triazolo[1,5-a]pyridin-2-yl]-[3-(4-methyl-piperazin-1-yl)-phenyl]-amine was prepared from 8-(2-methoxy-phenyl)-[1,2,4]triazolo[1,5-a]pyridin-2-ylamine (75.0 mg, 0.312 mmol) and 1-(3-bromo-phenyl)-4-methyl-piperazine (90.0 mg, 0.353 mmol) with 2,2'-bis-dicyclohexylphosphanyl-biphenyl (34.0 mg, 0.0622 mmol) as the ligand in a manner analogous to Step 2d and was isolated as a pale yellow foam (0.069 g, 53%). $^1$H NMR (400 MHz, CDCl$_3$, δ, ppm): 8.40 (d, J=6.5 Hz, 1H), 7.65 (d, J=7.2 Hz, 1H), 7.54 (d, J=7.3 Hz, 1H), 7.43-7.35 (m, 2H), 7.19 (d, J=7.9 Hz, 1H), 7.11-7.02 (m, 2H), 6.94-6.89 (m, 2H), 6.79 (s, 1H), 6.55 (d, J=7.9 Hz, 1H), 3.81 (s, 3H), 3.27-3.22 (m, 4H), 2.60-2.55 (m, 4H), 2.36 (s, 3H). MS=415 (MH)+.

Example 57

[8-(4-Methanesulfonyl-phenyl)-[1,2,4]triazolo[1,5-a]pyridin-2-yl]-[3-(4-morpholin-4-yl-piperidin-1-yl)-phenyl]-amine

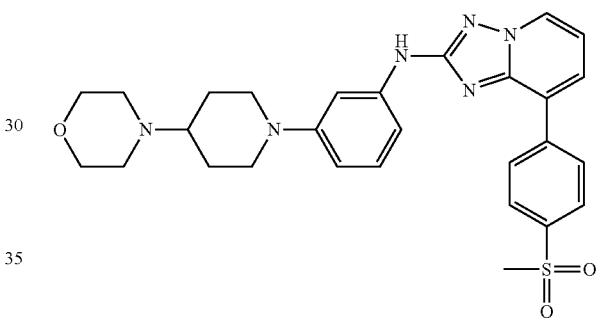

57a) 4-[1-(3-Bromo-phenyl)-piperidin-4-yl]-morpholine was prepared from 4-piperidin-4-yl-morpholine (0.21 g, 1.2 mmol) and 3-bromophenylboronic acid (0.50 g, 2.5 mmol) in a manner analogous to Step 49a. The reaction product was isolated as a tan resin (0.238 g, 59%). $^1$H NMR (400 MHz, CDCl$_3$, δ, ppm): 7.08 (t, J=7.1 Hz, 1H), 7.03 (s, 1H), 6.92 (d, J=7.3 Hz, 1H), 6.83 (d, J=8.6 Hz, 1H), 3.75-3.68 (m, 6H), 2.79-2.70 (m, 2H), 2.60-2.55 (m, 4H), 2.37-2.28 (m, 1H), 1.97-1.89 (m, 2H), 1.68-1.56 (m, 2H). MS=325, 327 (MH)+.

57b) [8-(4-Methanesulfonyl-phenyl)-[1,2,4]triazolo[1,5-a]pyridin-2-yl]-[3-(4-morpholin-4-yl-piperidin-1-yl)-phenyl]-amine was prepared from 8-(4-methanesulfonyl-phenyl)-[1,2,4]triazolo[1,5-a]pyridin-2-ylamine (75.0 mg, 0.260 mmol) and 4-[1-(3-bromo-phenyl)-piperidin-4-yl]-morpholine (100.0 mg, 0.3075 mmol) with 2,2'-bis-dicyclohexylphosphanyl-biphenyl (30.0 mg, 0.0549 mmol) as the ligand in a manner analogous to Step 2d. The title compound was isolated as a yellow solid (0.035 g, 25%). MP=230-236° C. $^1$H NMR (400 MHz, CDCl$_3$, δ, ppm): 8.49 (d, J=6.4 Hz, 1H), 8.26 (d, J=8.0 Hz, 2H), 8.08 (d, J=7.1 Hz, 2H), 7.66 (d, J=8.0 Hz, 2H), 7.35 (s, 1H), 7.24-7.18 (m, 1H), 7.01 (d, J=6.7 Hz, 1H), 6.96 (d, J=7.9 Hz, 1H), 6.84 (s, 1H), 6.60 (d, J=8.4 Hz, 1H), 3.81 (d, J=11.7 Hz, 2H), 3.77-3.72 (m, 4H), 3.10 (s, 3H), 2.78 (t, J=11.8 Hz, 2H), 2.63-2.58 (m, 4H), 2.40-2.30 (m, 1H), 1.97 (d, J=12.7 Hz, 2H), 1.74-1.62 (m, 2H). MS=533 (MH)+.

Example 58

[8-(4-Methanesulfonyl-phenyl)-[1,2,4]triazolo[1,5-a]pyridin-2-yl]-{3-[4-(4-methyl-piperazin-1-yl)-piperidin-1-yl]-phenyl}-amine

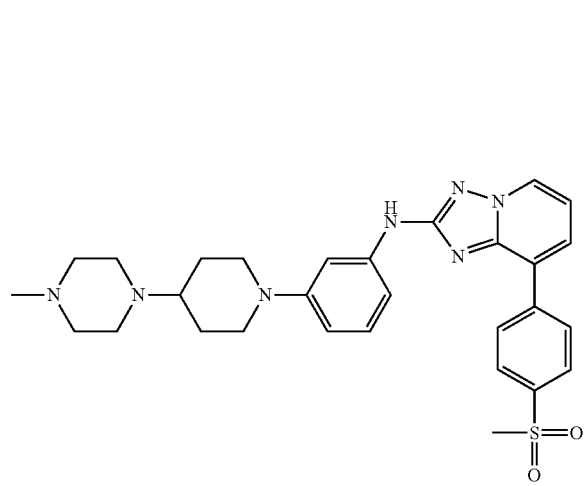 [SMILES: CN1CCN(C2CCN(c3cccc(Nc4nc5c(-c6ccc(S(C)(=O)=O)cc6)cccn5n4)c3)CC2)CC1]

58a) 1-[1-(3-Bromo-phenyl)-piperidin-4-yl]-4-methyl-piperazine was prepared from 3-bromophenylboronic acid (0.50 g, 2.5 mmol) and 1-methyl-4-piperidin-4-yl-piperazine (0.23 g, 1.2 mmol) in a manner analogous to Step 49a. The reaction product was isolated as a brown viscous oil (0.069 mg, 16%). $^1$H NMR (400 MHz, CDCl$_3$, δ, ppm): 7.08 (t, J=8.0 Hz, 1H), 7.03 (s, 1H), 6.91 (d, J=8.0 Hz, 1H), 6.82 (d, J=8.0 Hz, 1H), 3.72 (d, J=11.7 Hz, 2H), 2.78-2.33 (m, 11H), 2.30 (s, 3H), 1.93 (d, J=12.9 Hz, 2H), 1.69-1.57 (m, 2H). MS=338, 340 (MH)+.

58b) [8-(4-Methanesulfonyl-phenyl)-[1,2,4]triazolo[1,5-a]pyridin-2-yl]-{3-[4-(4-methyl-piperazin-1-yl)-piperidin-1-yl]-phenyl}-amine was prepared from 8-(4-methanesulfonyl-phenyl)-[1,2,4]triazolo[1,5-a]pyridin-2-ylamine (55.0 mg, 0.191 mmol) and 1-[1-(3-bromo-phenyl)-piperidin-4-yl]-4-methyl-piperazine (69.0 mg, 0.204 mmol) with 2,2'-bis-dicyclohexylphosphanyl-biphenyl (23.0 mg, 0.0421 mmol) as the ligand in a manner analogous to Step 2d. The title compound was isolated as a yellow solid (0.035 g, 34%). MP=237-239° C. $^1$H NMR (400 MHz, CDCl$_3$, δ, ppm): 8.49 (d, J=6.5 Hz, 1H), 8.25 (d, J=6.9 Hz, 2H), 8.08 (d, J=7.7 Hz, 2H), 7.65 (d, J=7.1 Hz, 1H), 7.31 (s, 1H), 7.24-7.18 (m, 1H), 7.04-6.95 (m, 2H), 6.82 (s, 1H), 6.60 (d, J=7.9 Hz, 1H), 3.81 (d, J=11.4 Hz, 2H), 3.10 (s, 3H), 2.77 (t, J=12.2 Hz, 2H), 2.72-2.33 (m, 9H), 2.30 (s, 3H), 1.96 (d, J=11.2 Hz, 2H), 1.75-1.63 (m, 2H). MS=546 (MH)+.

Example 59

[8-(3-Methanesulfonyl-phenyl)-[1,2,4]triazolo[1,5-a]pyridin-2-yl]-[4-(4-methyl-piperazin-1-yl)-phenyl]-amine

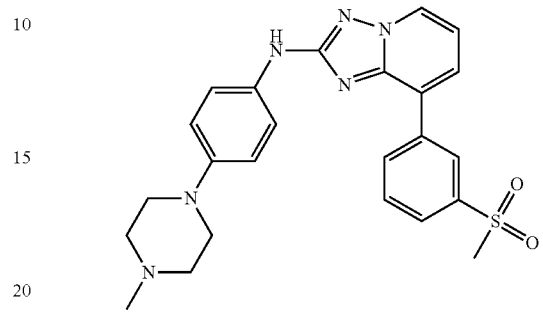

[8-(3-Methanesulfonyl-phenyl)-[1,2,4]triazolo[1,5-a]pyridin-2-yl]-[4-(4-methyl-piperazin-1-yl)-phenyl]-amine was prepared from 8-(3-methanesulfonyl-phenyl)-[1,2,4]triazolo[1,5-a]pyridin-2-ylamine (75.0 mg, 0.260 mmol) and 1-(4-bromo-phenyl)-4-methyl-piperazine (80.0 mg, 0.314 mmol) with 2,2'-bis-dicyclohexylphosphanyl-biphenyl (30.0 mg, 0.0549 mmol) as the ligand in a manner analogous to Step 2d and was isolated as a yellow foam (0.068 g, 56%). $^1$H NMR (400 MHz, CDCl$_3$, δ, ppm): 8.66 (s, 1H), 8.45 (d, J=6.5 Hz, 1H), 8.38 (d, J=7.7 Hz, 1H), 7.99 (d, J=7.7 Hz, 1H), 7.73 (d, J=6.9 Hz, 1H), 7.66 (d, J=7.4 Hz, 1H), 7.50 (d, J=7.7 Hz, 1H), 7.00-6395 (m, 3H), 6.70 (s, 1H), 3.19-0.314 (m, 4H), 3.12 (s, 3H), 2.62-2.57 (m, 4H), 2.36 (s, 3H). MS=463 (MH)+.

Example 60

[8-(3-Methanesulfonyl-phenyl)-[1,2,4]triazolo[1,5-a]pyridin-2-yl]-[3-(4-methyl-piperazin-1-yl)-phenyl]-amine

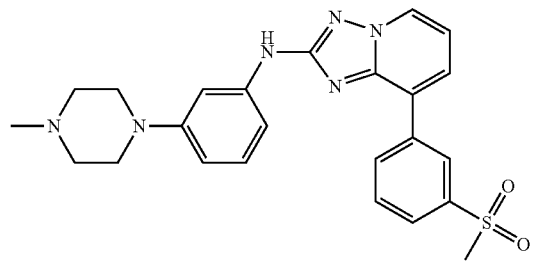 [SMILES: CN1CCN(c2cccc(Nc3nc4c(-c5cccc(S(C)(=O)=O)c5)cccn4n3)c2)CC1]

[8-(3-Methanesulfonyl-phenyl)-[1,2,4]triazolo[1,5-a]pyridin-2-yl]-[3-(4-methyl-piperazin-1-yl)-phenyl]-amine was prepared from 8-(3-methanesulfonyl-phenyl)-[1,2,4]triazolo[1,5-a]pyridin-2-ylamine (75.0 mg, 0.260 mmol) and 1-(3-bromo-phenyl)-4-methyl-piperazine (80.0 mg, 0.314 mmol) with 2,2'-bis-dicyclohexylphosphanyl-biphenyl (30.0 mg, 0.0549 mmol) as the ligand in a manner analogous to Step 2d and was isolated as a yellow foam (0.050 g, 42%). $^1$H NMR (400 MHz, CDCl$_3$, δ, ppm): 8.59 (s, 1H), 8.49-8.43 (m, 2H), 8.00 (d, J=7.5 Hz, 1H), 7.75-7.65 (m, 2H), 7.30-7.20 (m, 2H), 7.06 (d, J=7.7 Hz, 1H), 7.00 (t, J=6.6 Hz, 1H), 6.85 (s, 1H), 6.60 (d, J=8.0 Hz, 1H), 3.30-3.25 (m, 4H), 3.13 (s, 3H), 2.62-2.57 (m, 4H), 2.37 (s, 3H). MS=463 (MH)+.

Example 61

[8-(4-Methanesulfonyl-phenyl)-[1,2,4]triazolo[1,5-a]pyridin-2-yl]-[3-(1-methyl-piperidin-4-yl)-phenyl]-amine

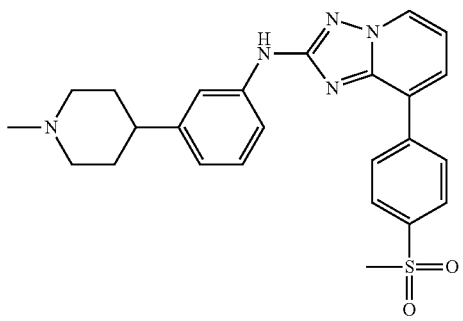 [SMILES: CN1CCC(c2cccc(Nc3nc4c(-c5ccc(S(C)(=O)=O)cc5)cccn4n3)c2)CC1]

61a) 4-(3-Bromo-phenyl)-1-methyl-piperidine hydrochloride was prepared from 4-(3-bromo-phenyl)-piperidine; hydrochloride (1.0 g, 3.6 mmol) in a manner analogous to Step 34c. The reaction product was isolated as a white solid (0.43 g, 41%) and was used without further purification. $^1$H NMR (400 MHz, (D$_3$C)$_2$SO, δ, ppm): 10.52 (s, 1H), 7.47-7.41 (m, 2H), 7.37-7.21 (m, 2H), 3.52-3.41 (m, 2H), 3.10-2.95 (m, 2H), 2.85-2.78 (m, 1H), 2.75 (s, 3H), 2.15-2.78 (m, 4H).

61b) [8-(4-Methanesulfonyl-phenyl)-[1,2,4]triazolo[1,5-a]pyridin-2-yl]-[3-(1-methyl-piperidin-4-yl)-phenyl]-amine was prepared from 8-(4-methanesulfonyl-phenyl)-[1,2,4]triazolo[1,5-a]pyridin-2-ylamine (75.0 mg, 0.260 mmol) and 4-(3-bromo-phenyl)-1-methyl-piperidine; hydrochloride (90.0 mg, 0.310 mmol) with 2,2'-bis-dicyclohexylphosphanyl-biphenyl (30.0 mg, 0.0549 mmol) as the ligand in a manner analogous to Step 2d. The title compound was isolated as a tan solid (0.031 g, 26%). MP=208-210° C. $^1$H NMR (400 MHz, CDCl$_3$, δ, ppm): 8.51 (d, J=6.5 Hz, 1H), 8.08 (d, J=8.3 Hz, 2H), 8.10 (d, J=7.3 Hz, 2H), 7.66 (d, J=6.6 Hz, 1H), 7.55 (s, 1H), 7.38 (d, J=8.7 Hz, 1H), 7.31-7.25 (m, 1H), 7.02 (t, J=7.4 Hz, 1H), 6.91-6.85 (m, 2H), 3.10 (s, 3H), 3.01 (d, J=10.9 Hz, 2H), 2.57-2.45 (m, 1H), 2.35 (S, 3H), 2.11-2.03 (m, 2H), 1.92-1.83 (m, 4H). MS=462 (MH)+.

Example 62

N-Methyl-N-(4-{2-[4-(4-methyl-piperazin-1-yl)-phenylamino]-[1,2,4]triazolo[1,5-a]pyridin-8-yl}-phenyl)-methanesulfonamide

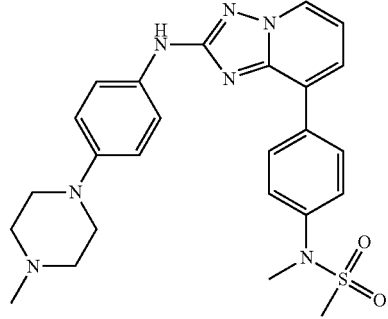 [SMILES: CN1CCN(c2ccc(Nc3nc4c(-c5ccc(N(C)S(C)(=O)=O)cc5)cccn4n3)cc2)CC1]

62a) To a suspension of N-[4-(4,4,5,5-Tetramethyl-1,3,2-dioxaborolan-2-yl)-phenyl]-methanesulfonamide (0.50 g, 1.7 mmol) and potassium carbonate (0.28 g, 2.0 mmol) in acetone (10 mL) was added methyl iodide (0.12 mL, 2.0 mmol). The mixture was stirred at room temperature for 18 hours under an atmosphere of nitrogen then diluted with dichloromethane (20 mL), filtered through a plug of diatomaceous earth, rinsed with dichloromethane and evaporated. The material was subjected to high vacuum for 18 hours. N-Methyl-N-[4-(4,4,5,5-tetramethyl-1,3,2-dioxaborolan-2-yl)-phenyl]-methanesulfonamide was isolated as a yellow solid (0.50 g, 95%) and was used without further purification. $^1$H NMR (400 MHz, CDCl$_3$, δ, ppm): 7.83 (d, J=7.9 Hz, 2H), 7.39 (d, J=7.8 Hz, 2H), 3.34 (s, 3H), 2.82 (s, 3H), 1.34 (s, 12H). MS=312 (MH)+.

62b) N-[4-(2-Amino-[1,2,4]triazolo[1,5-a]pyridin-8-yl)-phenyl]-N-methyl-methanesulfonamide was prepared from 8-bromo-[1,2,4]triazolo[1,5-a]pyridin-2-ylamine (300.0 mg, 1.408 mmol) and N-methyl-N-[4-(4,4,5,5-tetramethyl-1,3,2-dioxaborolan-2-yl)-phenyl]-methanesulfonamide (500.0 mg, 1.607 mmol) in a manner analogous to Step 2c. The reaction product was isolated as an off-white solid (0.33 g, 73%). MP=245-247° C. $^1$H NMR (400 MHz, (D$_3$C)$_2$SO, δ, ppm): 8.55 (d, J=5.8 Hz, 1H), 8.12 (d, J=7.5 Hz, 2H), 7.72 (d, J=7.1, 1H), 7.52 (d, J=7.2 Hz, 2H), 6.98 (t, J=6.2 Hz, 1H), 6.11 (s, 2H), 3.29 (s, 3H), 2.98 (s, 3H). MS=318 (MH)+.

62c) N-Methyl-N-(4-{2-[4-(4-methyl-piperazin-1-yl)-phenylamino]-[1,2,4]triazolo[1,5-a]pyridin-8-yl}-phenyl)-methanesulfonamide was prepared from N-[4-(2-amino-[1,2,4]triazolo[1,5-a]pyridin-8-yl)-phenyl]-N-methyl-methanesulfonamide (75.0 mg, 0.236 mmol) and 1-(4-bromo-phenyl)-4-methyl-piperazine (70.0 mg, 0.274 mmol) with 2,2'-bis-dicyclohexylphosphanyl-biphenyl (26.0 mg, 0.0476 mmol) as the ligand in a manner analogous to Step 2d. The title compound was isolated as a tan solid (0.027 g, 23%). MP=205-206° C. $^1$H NMR (400 MHz, CDCl$_3$, δ, ppm): 8.41 (d, J=6.5 Hz, 1H), 8.04 (d, J=7.7 Hz, 2H), 7.57-7.46 (m, 5H), 6.99-6.91 (m, 3H), 6.66 (s, 1H), 3.38 (s, 3H), 3.19-3.14 (m, 4H), 2.90 (s, 3H), 2.62-2.57 (m, 4H), 2.36 (s, 3H). MS=492 (MH)+.

Example 63

N-Methyl-N-(4-{2-[3-(4-methyl-piperazin-1-yl)-phenylamino]-[1,2,4]triazolo[1,5-a]pyridin-8-yl}-phenyl)-methanesulfonamide

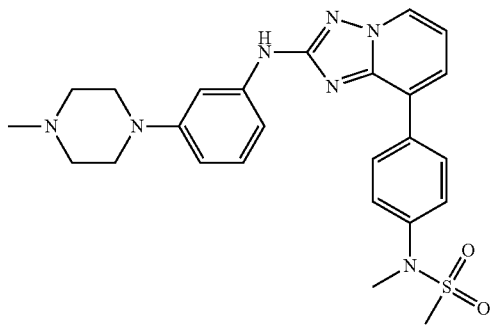 [SMILES: CN1CCN(c2cccc(Nc3nc4c(-c5ccc(N(C)S(C)(=O)=O)cc5)cccn4n3)c2)CC1]

N-Methyl-N-(4-{2-[3-(4-methyl-piperazin-1-yl)-phenylamino]-[1,2,4]triazolo[1,5-a]pyridin-8-yl}-phenyl)-methanesulfonamide was prepared from N-[4-(2-amino-[1,2,4]triazolo[1,5-a]pyridin-8-yl)-phenyl]-N-methyl-methanesulfonamide (75.0 mg, 0.236 mmol) and 1-(3-bromo-phenyl)-4-methyl-piperazine (70.0 mg, 0.274 mmol) with 2,2'-bis-dicyclohexylphosphanyl-biphenyl (26.0 mg, 0.0476 mmol) as the ligand in an analogous manner to Step 2d and was isolated as a tan solid (0.038 g, 33%). MP=202-204° C. $^1$H NMR (400 MHz, CDCl$_3$, δ, ppm): 8.43 (d, J=6.9 Hz, 1H), 8.06 (d, J=7.4 Hz, 2H), 7.58 (d, J=7.1 Hz, 1H), 7.52 (d, J=7.4 Hz, 2H), 7.36 (s, 1H), 7.25-7.19 (m, 1H), 7.00-6.95 (m, 2H), 6.83 (s, 1H), 6.59 (d, J=8.4 Hz, 1H), 3.39 (s, 3H), 3.30-3.25 (m, 4H), 2.90 (s, 3H), 2.63-2.58 (m, 4H), 2.37 (s, 3H). MS=492 (MH)+.

Example 64

[4-(4-Methyl-piperazin-1-yl)-phenyl]-[8-(4-trifluoromethyl-phenyl)-[1,2,4]triazolo[1,5-a]pyridin-2-yl]-amine

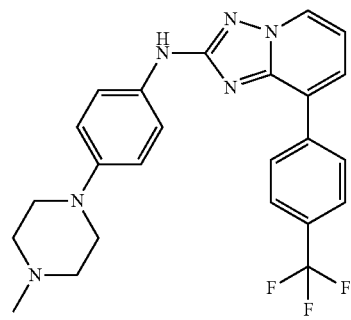 [SMILES: CN1CCN(c2ccc(Nc3nc4c(-c5ccc(C(F)(F)F)cc5)cccn4n3)cc2)CC1]

64a) 8-(4-Trifluoromethyl-phenyl)-[1,2,4]triazolo[1,5-a]pyridin-2-ylamine was prepared from 8-bromo-[1,2,4]triazolo[1,5-a]pyridin-2-ylamine (504.7 mg, 2.369 mmol) and (4-trifluoromethylphenyl)boronic acid (500.0 mg, 2.632 mmol) in a manner analogous to Step 2c. The reaction product was isolated as a yellow solid (0.64 g, 97%). MP=186-187° C. $^1$H NMR (400 MHz, (D$_3$C)$_2$SO, δ, ppm): 8.62 (d, J=6.3 Hz, 1H), 8.34 (d, J=8.0 Hz, 2H), 7.88-7.80 (m, 3H), 7.02 (t, J=6.8 Hz, 1H), 6.18 (s, 2H). MS=279 (MH)+.

64b) [4-(4-Methyl-piperazin-1-yl)-phenyl]-[8-(4-trifluoromethyl-phenyl)-[1,2,4]triazolo[1,5-a]pyridin-2-yl]-amine was prepared from 8-(4-trifluoromethyl-phenyl)-[1,2,4]triazolo[1,5-a]pyridin-2-ylamine (75.0 mg, 0.270 mmol) and 1-(4-bromo-phenyl)-4-methyl-piperazine (80.0 mg, 0.314 mmol) with 2,2'-bis-dicyclohexylphosphanyl-biphenyl (30.0 mg, 0.0549 mmol) as the ligand in a manner analogous to Step 2d. The title compound was isolated as a yellow solid (0.033 g, 27%). MP=214-216° C. $^1$H NMR (400 MHz, CDCl$_3$, δ, ppm): 8.44 (d, J=6.5 Hz, 1H), 8.12 (dm J=8.7 Hz, 2H), 7.77 (d, J=7.4 Hz, 2H), 7.59 (d, J=7.4 Hz, 1H), 7.49 (d, J=7.6 Hz, 2H), 7.00-6.93 (m, 3H), 6.66 (s, 1H), 3.20-3.15 (m, 4H), 2.62-2.57 (m, 4H), 2.36 (s, 3H). MS=453 (MH)+.

Example 65

[3-(4-Methyl-piperazin-1-yl)-phenyl]-[8-(4-trifluoromethyl-phenyl)-[1,2,4]triazolo[1,5-a]pyridin-2-yl]-amine

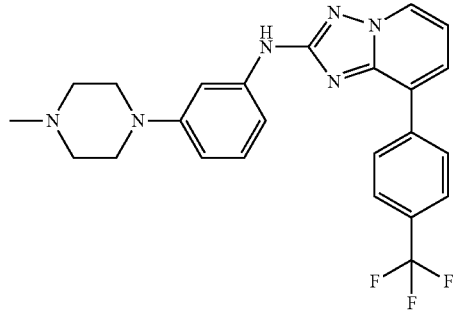 [SMILES: CN1CCN(c2cccc(Nc3nc4c(-c5ccc(C(F)(F)F)cc5)cccn4n3)c2)CC1]

[3-(4-Methyl-piperazin-1-yl)-phenyl]-[8-(4-trifluoromethyl-phenyl)-[1,2,4]triazolo[1,5-a]pyridin-2-yl]-amine was prepared from 8-(4-trifluoromethyl-phenyl)-[1,2,4]triazolo[1,5-a]pyridin-2-ylamine (75.0 mg, 0.270 mmol) and 1-(3-bromo-phenyl)-4-methyl-piperazine (80.0 mg, 0.314 mmol) with 2,2'-bis-dicyclohexylphosphanyl-biphenyl (30.0 mg, 0.0549 mmol) as the ligand in a manner analogous to Step 2d and was isolated as a yellow solid (0.043 g, 35%). MP=234-236° C. $^1$H NMR (400 MHz, CDCl$_3$, δ, ppm): 8.46 (d, J=7.0 Hz, 1H), 8.15 (d, J=7.7 Hz, 2H), 7.76 (d, J=8.2 Hz, 2H), 7.62 (d, J=7.2 Hz, 1H), 7.48 (s, 1H), 7.25-7.19 (m, 1H), 7.02-6.97 (m, 1H), 6.92 (d, J=7.3 Hz, 1H), 6.83 (s, 1H), 6.59 (d, J=7.8 Hz, 1H), 3.30-3.25 (m, 4H), 2.62-2.57 (m, 4H), 2.37 (s, 3H). MS=435 (MH)+.

Example 66

[8-(2-Methanesulfonyl-phenyl)-[1,2,4]triazolo[1,5-a]pyridin-2-yl]-[4-(4-methyl-piperazin-1-yl)-phenyl]-amine

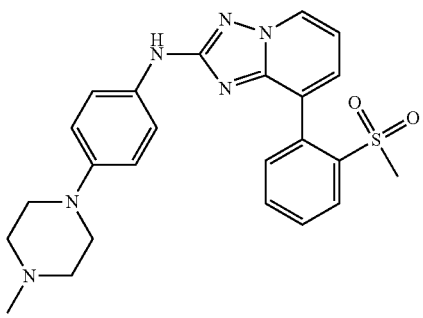 [SMILES: CN1CCN(c2ccc(Nc3nc4c(-c5ccccc5S(C)(=O)=O)cccn4n3)cc2)CC1]

66a) 8-(2-Methanesulfonyl-phenyl)-[1,2,4]triazolo[1,5-a]pyridin-2-ylamine was prepared from 8-bromo-[1,2,4]triazolo[1,5-a]pyridin-2-ylamine (0.50 g, 2.3 mmol) and 2-(methylsulfonyl)phenylboronic acid (0.56 g, 2.8 mmol) in a manner analogous to Step 2c. The reaction product was isolated as a pale yellow solid (0.249 g, 37%). $^1$H NMR (400 MHz, $(D_3C)_2SO$, δ, ppm): 8.56 (d, J=6.6 Hz, 1H), 8.10 (d, J=7.8 Hz, 1H), 7.79 (t, J=7.6 Hz, 1H), 7.73 (d, J=7.7 Hz, 1H), 7.48 (d, J=7.3 Hz, 1H), 7.36 (d, J=7.1 Hz, 1H), 6.93 (d, J=6.9 Hz, 1H), 5.99 (s, 2H), 3.16 (s, 3H). MS=289 (MH)+.

66b) [8-(2-Methanesulfonyl-phenyl)-[1,2,4]triazolo[1,5-a]pyridin-2-yl]-[4-(4-methyl-piperazin-1-yl)-phenyl]-amine was prepared from 8-(2-methanesulfonyl-phenyl)-[1,2,4]triazolo[1,5-a]pyridin-2-ylamine (75.0 mg, 0.260 mmol) and 1-(4-bromo-phenyl)-4-methyl-piperazine (80.0 mg, 0.314 mmol) with 2,2'-bis-dicyclohexylphosphanyl-biphenyl (30.0 mg, 0.0549 mmol) as the ligand in a manner analogous to Step 2d. The title compound was isolated as a yellow foam (0.067 g, 56%). $^1$H NMR (400 MHz, CDCl$_3$, δ, ppm): 8.47 (d, J=6.6 Hz, 1H), 8.24 (d, J=7.7 Hz, 1H), 7.74 (t, J=7.0 Hz, 1H), 7.67 (t, J=7.4 Hz, 1H), 7.47 (t, J=8.0 Hz, 2H), 7.41 (d, J=7.8 Hz, 2H), 6.99-6.91 (m, 3H), 6.57 (s, 1H), 3.17-3.12 (m, 4H), 2.97 (s, 3H), 2.61-2.56 (m, 4H), 2.36 (s, 3H). MS=463 (MH)+.

Example 67

[8-(2-Methanesulfonyl-phenyl)-[1,2,4]triazolo[1,5-a]pyridin-2-yl]-[3-(4-methyl-piperazin-1-yl)-phenyl]-amine

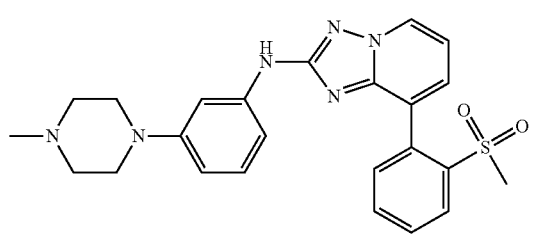 [SMILES: CN1CCN(c2cccc(Nc3nc4c(-c5ccccc5S(C)(=O)=O)cccn4n3)c2)CC1]

[8-(2-Methanesulfonyl-phenyl)-[1,2,4]triazolo[1,5-a]pyridin-2-yl]-[3-(4-methyl-piperazin-1-yl)-phenyl]-amine was prepared from 8-(2-methanesulfonyl-phenyl)-[1,2,4]triazolo[1,5-a]pyridin-2-ylamine (75.0 mg, 0.260 mmol) and 1-(3-bromo-phenyl)-4-methyl-piperazine (80.0 mg, 0.314 mmol) with 2,2'-bis-dicyclohexylphosphanyl-biphenyl (30.0 mg, 0.0549 mmol) as the ligand in a manner analogous to Step 2d and was isolated as a yellow foam (0.074 g, 62%). $^1$H NMR (400 MHz, CDCl$_3$, δ, ppm): 8.49 m (d, J=6.6 Hz, 1H), 8.24 (d, J=7.9 Hz, 1H), 7.74 (t, J=6.8 Hz, 1H), 7.67 (t, J=7.8 Hz, 1H), 7.49 (d, J=7.3 Hz, 2H), 7.29-7.25 (m, 1H), 7.19 (t, J=7.8 Hz, 1H), 6.99 (t, J=6.9 Hz, 1H), 6.90 (d, J=7.9 Hz, 1H), 6.73 (s, 1H), 6.57 (d, J=8.2 Hz, 1H), 3.24-3.19 (m, 4H), 2.96 (s, 3H), 2.59-2.54 (m, 4H), 2.36 (s, 3H). MS=463 (MH)+.

Example 68

N(8)-(2-Methanesulfonyl-phenyl)-N(2)-[3-(4-methyl-piperazin-1-yl)-phenyl]-[1,2,4]triazolo[1,5-a]pyridine-2,8-diamine

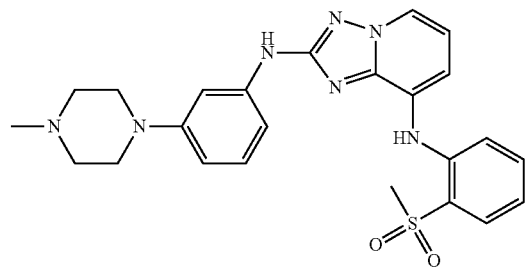 [SMILES: CN1CCN(c2cccc(Nc3nc4c(Nc5ccccc5S(C)(=O)=O)cccn4n3)c2)CC1]

68a) To a cooled, stirred suspension of 8-bromo-[1,2,4]triazolo[1,5-a]pyridin-2-ylamine (0.961 g, 4.51 mmol) and copper(II)chloride dihydrate (0.20 g, 1.2 mmol) in 12 M of hydrochloric acid (10.0 mL) at 5° C. was added dropwise a solution of sodium nitrite (0.37 g, 5.4 mmol) in water (2 mL). Gentle gas evolution was noted. The mixture was stirred for 30 minutes at 5° C. then at room temperature for 18 hours. The yellow mixture was diluted with water (80 mL) and the resulting precipitate was filtered, rinsed with water and dried in-the-air. 8-Bromo-2-chloro-[1,2,4]triazolo[1,5-a]pyridine was isolated as a pale yellow solid (0.947 g, 90%) and was used without further purification. $^1$H NMR (400 MHz, $(D_3C)_2SO$, δ, ppm): 8.98 (d, J=6.9 Hz, 1H), 8.10 (d, J=7.8 Hz, 1H), 7.22 (t, J=7.0 Hz, 1H). MS=232, 234, 236 (MH)+.

68b) (2-Chloro-[1,2,4]triazolo[1,5-a]pyridin-8-yl)-(2-methanesulfonyl-phenyl)-amine was prepared from 8-bromo-2-chloro-[1,2,4]triazolo[1,5-a]pyridine (234.0 mg, 1.007 mmol) and 2-methanesulfonyl-phenylamine; hydrochloride (220.0 mg, 1.059 mmol) with 9,9-dimethyl-4,5-bis(diphenylphosphino)xanthene (105.0 mg, 0.1815 mmol) as the ligand in a manner analogous to Step 2d. The reaction product was isolated as a pale yellow solid (0.115 g, 35%). MP=180-182° C. $^1$H NMR (400 MHz, CDCl$_3$, δ, ppm): 8.52 (s, 1H), 8.18 (d, J=6.7 Hz, 1H), 8.00 (d, J=8.0 Hz, 1H), 7.60-7.54 (m, 1H), 7.51 (d, J=8.2, 1H), 7.34 (d, J=7.7 Hz, 1H), 7.18 (t, J=7.2 Hz, 1H), 6.98 (t, J=7.2 Hz, 1H), 3.12 (s, 3H). MS=323, 325 (MH)+.

68c) N(8)-(2-Methanesulfonyl-phenyl)-N(2)-[3-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(2-methanesulfonyl-phenyl)-amine (95.0 mg, 0.294 mmol) and 3-(4-methylpiperazin-1-yl)aniline (70.0 mg, 0.366 mmol) with 2,2'-bis-dicyclohexylphosphanyl-biphenyl (32.0 mg, 0.0585 mmol) as the ligand in a manner analogous to Step 2d. The title compound was isolated as a light brown foam (0.077 g, 55%). ¹H NMR (400 MHz, CDCl₃, δ, ppm): 8.51 (s, 1H), 8.11 (d, J=6.5, 1H), 7.98 (d, J=7.8 Hz, 1H), 7.58-7.51 (m, 2H), 7.43 (s, 1H), 7.30-7.25 (m, 1H), 7.20 (t, J=8.1 Hz, 1H), 6.92 (d, J=8.0 Hz, 1H), 6.84-6.78 (m, 2H), 6.57 (d, J=8.1 Hz, 1H), 3.33-3.5 (m, 4H), 3.13 (s, 3H), 2.70-2.57 (m, 4H), 2.39 (s, 3H). MS=478 (MH)+.

Example 69

N(2),N(8)-Bis-(2-methanesulfonyl-phenyl)-[1,2,4]triazolo[1,5-a]pyridine-2,8-diamine

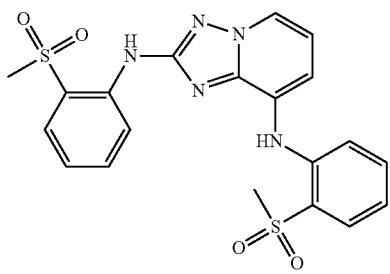 [SMILES: CS(=O)(=O)c1ccccc1Nc1nc2c(Nc3ccccc3S(C)(=O)=O)cccn2n1]

69a) 2,8-Dibromo-[1,2,4]triazolo[1,5-a]pyridine was prepared from 8-bromo-[1,2,4]triazolo[1,5-a]pyridin-2-ylamine (0.50 g, 2.3 mmol) with copper(II) bromide (0.140 g, 0.627 mmol) and 48% aqueous hydrobromic acid (5 mL, 40 mmol) in a manner analogous to Step 68a. the reaction product was isolated as a pale yellow solid (0.55 g, 85%). MP=150-151° C. ¹H NMR (400 MHz, (D₃C)₂SO, δ, ppm): 8.99 (d, J=6.7 Hz, 1H), 8.08 (d, J=7.7 Hz, 1H), 7.20 (t, J=7.4 Hz, 1H). MS=276, 278, 280 (MH)+.

69b) N(2),N(8)-Bis-(2-methanesulfonyl-phenyl)-[1,2,4]triazolo[1,5-a]pyridine-2,8-diamine was prepared from 2,8-dibromo-[1,2,4]triazolo[1,5-a]pyridine (100.0 mg, 0.3611 mmol) and 2-methanesulfonyl-phenylamine; hydrochloride (90.0 mg, 0.433 mmol) with 9,9-dimethyl-4,5-bis(diphenylphosphino)xanthene (42.0 mg, 0.0726 mmol) as the ligand in a manner analogous to Step 2d. The title compound was isolated as an off-white solid (0.022 g, 13%). MP=271-273° C. ¹H NMR (400 MHz, CDCl₃, δ, ppm): 9.17 (s, 1H), 8.71 (d, J=9.3 Hz, 1H), 8.51 (s, 1H), 8.14 (d, J=5.1 Hz, 1H), 8.00 (d, J=8.0 Hz, 1H), 7.92 (d, J=8.4 Hz, 1H), 7.65 (t, J=7.0 Hz, 1H), 7.59-7.50 (m, 2H), 7.31 (d, J=6.9 Hz, 1H), 7.18-7.08 (m, 2H), 6.88 (t, J=7.0 Hz, 1H), 3.15 (s, 3H), 3.11 (s, 3H). MS=458 (MH)+.

Example 70

5-{4-[(1,1-dioxidothiomorpholin-4-yl)methyl]phenyl}-N-[4-(4-methylpiperazin-1-yl)phenyl][1,2,4]triazolo[1,5-a]pyridin-2-amine

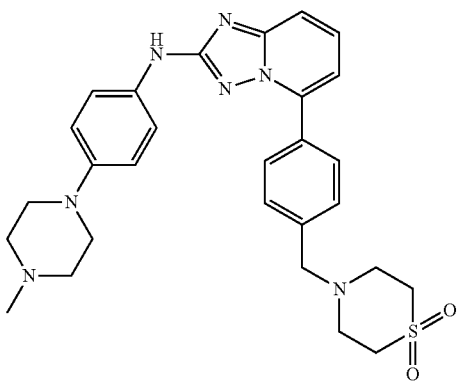 [SMILES: CN1CCN(c2ccc(Nc3nc4cccc(-c5ccc(CN6CCS(=O)(=O)CC6)cc5)n4n3)cc2)CC1]

70a) A suspension of (4-bromomethylphenyl)boronic acid (2.00 g, 9.31 mmol), thiomorpholine 1,1-dioxide (1.50 g, 11.1 mmol) and potassium carbonate (2.60 g, 18.8 mmol) in acetone (25 mL, 340 mmol) was heated at 40° C. for 18 hours then cooled to room temperature. The volatiles were evaporated and the residue was suspended in saturated aqueous ammonium chloride (100 mL). The aqueous was decanted from the waxy solid and the solid was dissolved in methanol (50 mL), filtered to remove insoluble salts and evaporated. 4-[(4-boronophenyl)methyl]-thiomorpholine 1,1-dioxide was isolated as a tan foam. The crude material was used without further purification.

70b) 5-{4-[(1,1-dioxidothiomorpholin-4-yl)methyl]phenyl}[1,2,4]triazolo[1,5-a]pyridin-2-amine was prepared from 5-bromo-[1,2,4]triazolo[1,5-a]pyridin-2-ylamine and 4-[(4-boronophenyl)methyl]-thiomorpholine 1,1-dioxide in a manner analogous to Step 2c. The reaction product was taken on to the next step.

70c) 5-{4-[(1,1-dioxidothiomorpholin-4-yl)methyl]phenyl}-N-[4-(4-methylpiperazin-1-yl)phenyl][1,2,4]triazolo[1,5-a]pyridin-2-amine was prepared from 5-{4-[(1,1-dioxidothiomorpholin-4-yl)methyl]phenyl}[1,2,4]triazolo[1,5-a]pyridin-2-amine (75.0 mg, 0.210 mmol) and 1-(4-bromophenyl)-4-methyl-piperazine (65.0 mg, 0.255 mmol) with 2,2'-bis-dicyclohexylphosphanyl-biphenyl (22.0 mg, 0.0402 mmol) as the ligand in a manner analogous to Step 2d. The title compound was isolated as a yellow foam (0.045 g, 40%). ¹H NMR (400 MHz, CDCl₃, δ, ppm): 8.00 (d, J=7.0 Hz, 2H), 7.52-7.43 (m, 6H), 6.98-6.91 (m, 3H), 6.67 (s, 1H), 3.76 (s, 2H), 3.18-3.03 (m, 12H), 2.62-2.56 (m, 4H), 2.36 (s, 3H). MS=532 (MH)+.

Example 71

5-{4-[(1,1-dioxidothiomorpholin-4-yl)methyl]phenyl}-N-[3-(4-methylpiperazin-1-yl)phenyl][1,2,4]triazolo[1,5-a]pyridin-2-amine

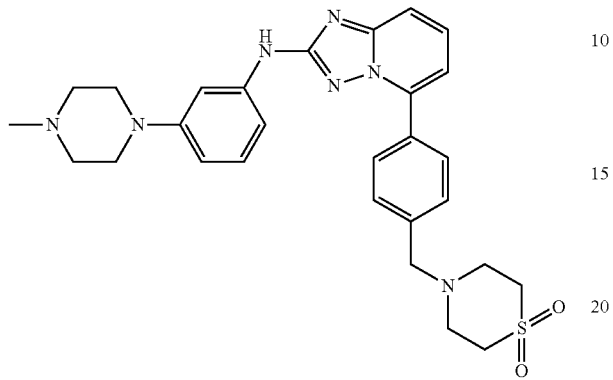

5-{4-[(1,1-dioxidothiomorpholin-4-yl)methyl]phenyl}-N-[3-(4-methylpiperazin-1-yl)phenyl][1,2,4]triazolo[1,5-a]pyridin-2-amine was prepared from 5-{4-[(1,1-dioxidothiomorpholin-4-yl)methyl]phenyl}[1,2,4]triazolo[1,5-a]pyridin-2-amine (75.0 mg, 0.210 mmol) and 1-(3-bromophenyl)-4-methyl-piperazine (65.0 mg, 0.255 mmol) with 2,2'-bis-dicyclohexylphosphanyl-biphenyl (22.0 mg, 0.0402 mmol) as the ligand in a manner analogous to Step 2d and was isolated as an off-white solid (0.052 g, 47%). MP=150-152° C. $^1$H NMR (400 MHz, CDCl$_3$, δ, ppm): 8.02 (d, J=7.7 Hz, 2H), 7.55-7.42 (m, 5H), 7.17 (t, J=7.8 Hz, 1H), 6.97 (d, J=7.0 Hz, 1H), 6.87-6.80 (m, 2H), 6.55 (d, J=8.3 Hz, 1H), 3.76 (s, 2H), 3.24-3.19 (m, 4H), 3.14-3.03 (m, 8H), 2.58-2.53 (m, 4H), 2.36 (s, 3H). MS=532 (MH)+.

Example 72

N(8)-(2-Methanesulfonyl-phenyl)-N(2)-[4-(4-methyl-piperazin-1-yl)-phenyl]-[1,2,4]triazolo[1,5-a]pyridine-2,8-diamine

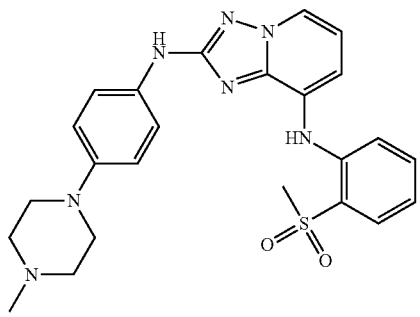 [SMILES: CN1CCN(c2ccc(Nc3nc4c(Nc5ccccc5S(C)(=O)=O)cccn4n3)cc2)CC1]

N(8)-(2-Methanesulfonyl-phenyl)-N(2)-[4-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(2-methanesulfonyl-phenyl)-amine (57.0 mg, 0.176 mmol) and 4-(4-methyl-piperazin-1-yl)-phenylamine (37.0 mg, 0.193 mmol) with 2,2'-bis-dicyclohexylphosphanyl-biphenyl (20.0 mg, 0.0366 mmol) as the ligand in a manner analogous to Step 2d and was isolated as a tan foam (0.037 g, 44%). $^1$H NMR (400 MHz, CDCl$_3$, δ, ppm): 8.46 (s, 1H), 8.11 (d, J=6.1 Hz, 1H), 7.98 (d, J=7.7 Hz, 1H), 7.57-7.45 (m, 4H), 7.11 (t, J=7.3 Hz, 1H), 6.96 (d, J=7.7 Hz, 2H), 6.78 (t, J=7.0 Hz, 1H), 6.67 (s, 1H), 3.18-3.12 (m, 7H), 2.62-2.57 (m, 4H), 2.36 (s, 3H). MS=478 (MH)+.

Example 73

[5-(4-Methanesulfonyl-phenyl)-[1,2,4]triazolo[1,5-a]pyridin-2-yl]-[4-(2-pyrrolidin-1-yl-ethoxy)-phenyl]-amine

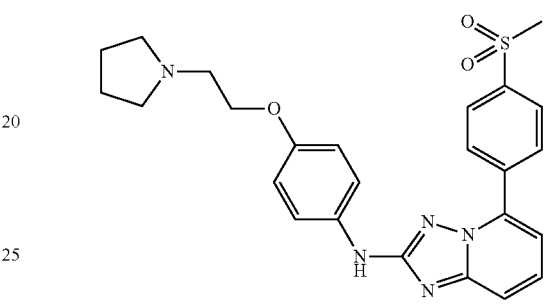

73a) To a solution of 6-bromo-pyridin-2-ylamine (10.00 g, 57.8 mmol) in 1,4-dioxane (100 mL) was added dropwise ethoxycarbonyl isothiocyanate (6.80 mL, 58.0 mmol). The mixture was stirred under an atmosphere of nitrogen for 18 hours. The volatiles were evaporated to yield a waxy solid which was triturated with hexane (250 mL) and filtered. The recovered solid was consistent for the desired N-(5-bromo-2-pyridinyl)-N'-carboethoxy-thiourea and was used without further purification. $^1$H NMR (400 MHz, CDCl$_3$, δ, ppm): 12.10 (s, 1H), 8.80 (d, J=7.9 Hz, 1H), 8.25 (br s, 1H), 7.60 (t, J=15 Hz, 8 Hz, 1H), 7.31 (d, J=8 Hz, 1H) 4.31 (q, J=21.4 Hz, 7.5 Hz, 2H), 1.35 (14.4 Hz, 7.5 Hz, 3H). MS=215 (MH)+.

73b) To a stirred suspension of hydroxylamine hydrochloride (20.0 g, 288 mmol) and N,N-diisopropylethylamine (30.0 mL, 172 mmol) in a mixture of methanol (80 mL) and ethanol (80 mL) was added N-(3-bromo-2-pyridinyl)-N'-carboethoxy-thiourea. The mixture was stirred for 2 hours at room temperature then heated to 60° C. for 18 hours. The suspension was cooled to room temperature, filtered and rinsed with methanol, water then methanol. The recovered off-white solid was consistent for 5-bromo-[1,2,4]triazolo[1,5-a]pyridin-2-ylamine (9.04 g, 74%). $^1$H NMR (400 MHz, (D$_3$C)$_2$SO, δ, ppm): 7.36 (m, 2H), 7.22 (d, J=7.5 Hz, 1H), 6.27 (br s, 2H) MS=213, 215 (MH)+.

73c) A dry tube was charged with tetrakis(triphenylphopshine)palladium(0) (1.29 g, 1.1 mmol), 5-bromo-[1,2,4]triazolo[1,5-a]pyridin-2-ylamine (2.98 g, 14.0 mmol), (4-methylsulfonylphenyl) boronic acid (3.08 g, 15.4 mmol), sodium carbonate (3.26 g, 31.04 mmol), dioxane (30 mL), N,N-dimethylformamide (60 mL) and water (30 mL). The tube was evacuated with a high vacuum and backflushed under a stream of nitrogen three times. The mixture was stirred for 2 minutes at room temperature under nitrogen then the tube was sealed and heated at 80° C. for 18 hours. The mixture was transferred to a round bottom flask and evaporated under reduced pressure. Water (100 mL) was added and solution extracted with dichloromethane (3 portions of 50 mL). The combined organic was dried over magnesium sulfate, filtered and evaporated. The solid was triturated with ether/dichloromethane (4:1; 10 mL), filtered and rinsed with ether. The recovered material was consistent for 5-(4-methanesulfonyl-phenyl)-[1,2,4]triazolo[1,5-a]pyridin-2-ylamine (1.3 g, 33%). $^1$H NMR (400 MHz, CDCl$_3$, δ, ppm): 8.21 (d, J=8.0 Hz, 2H) 8.08 (d, J=8.0 Hz, 2H), 7.55 (m, 1H), 7.44 (d, J=9.1 Hz, 1H), 7.13 (d, J=7.5 Hz, 1H), 6.10 (br s, 2H) 3.31 (s, 3H). MS=289 (MH)+.

73d) To an oven dried tube was added palladium acetate (16.0 mg, 0.0000713 mol), 9,9-dimethyl-4,5-bis(diphenylphosphino)xanthene (41.0 mg, 0.0713 mmol), 1,4-dioxane (5 mL), 1-[2-(4-bromo-phenoxy)-ethyl]-pyrrolidine (87 μL, 0.412 mmol), 5-(4-methanesulfonyl-phenyl)-[1,2,4]triazolo[1,5-a]pyridin-2-ylamine (100.0 mg, 0.346 mmol), and cesium carbonate (240 mg, 0.73 mmol) were added all-at-once. The reaction mixture was evacuated with high vacuum and repressurized with nitrogen three times. The tube was sealed and heated at 80° C. for 24 hours. The mixture was cooled to room temperature, filtered through a plug of diatomaceous earth, rinsed with dichloromethane and evaporated. The material was purified via chromatography utilizing an ISCO automated purification apparatus using a silica gel column (40 g) with 0%→20% methanol in dichloromethane solvent gradient. [5-(4-Methanesulfonyl-phenyl)-[1,2,4]triazolo[1,5-a]pyridin-2-yl]-[4-(2-pyrrolidin-1-yl-ethoxy)-phenyl]-amine was isolated as an orange gummy solid (0.011 g, 7%). $^1$H NMR (400 MHz, (D$_3$C)$_2$SO, δ, ppm): 9.47 (s, 1H), 8.32 (d, J=8.5 Hz, 2H), 8.13 (d, J=8.5 Hz, 2H), 7.67 (m, 2H), 7.59 (d, J=9.6 Hz, 2H), 7.28 (d, J=6.4 Hz, 1H). 6.91 (d, J=8.5 Hz, 2H), 4.10 (br s, 2H), 3.34 (s, 3H), 2.54 (s, 2H), 1.78 (br s, 2H), 1.24 (br s, 2H). MS=478 (MH)+.

Example 74

[5-(4-Methanesulfonyl-phenyl)-[1,2,4]triazolo[1,5-a]pyridin-2-yl]-phenyl-amine (0.022 g, 17%), was a byproduct of the above reaction and was isolated as an off-white solid. MP=221° C. dec. $^1$H NMR (400 MHz, (D$_3$C)$_2$SO, δ, ppm): 9.66 (s, 1H), 8.32 (d, J=8.5 Hz, 2H), 8.14 (d, J=8.5 Hz, 2H), 7.68 (m, 4H), 7.28 (m, 3H), 6.87 (m, 1H), 3.34 (s, 3H). MS=365 (MH)+.

Example 75

4-{4-[5-(4-Methanesulfonyl-phenyl)-[1,2,4]triazolo [1,5-a]pyridin-2-ylamino]-phenyl}-piperazine-1-carboxylic acid tert-butyl ester

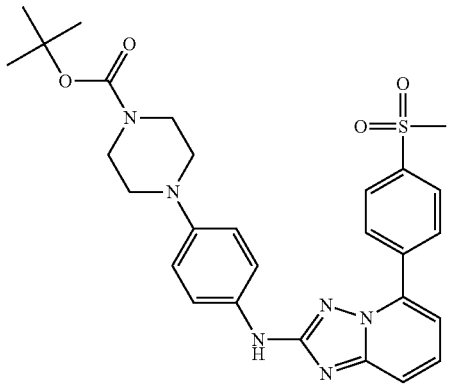 [SMILES: CC(C)(C)OC(=O)N1CCN(c2ccc(Nc3nc4cccc(-c5ccc(S(C)(=O)=O)cc5)n4n3)cc2)CC1]

To an oven dried tube was added palladium acetate (16.0 mg, 0.0713 mmol), 9,9-dimethyl-4,5-bis(diphenylphosphino)xanthene (41.0 mg, 0.0713 mmol), toluene (5 mL), 4-(4-bromophenyl)piperazine-1-carboxylic acid tert-butyl ester (0.142 g, 0.412 mmol), 5-(4-methanesulfonyl-phenyl)-[1,2,4]triazolo[1,5-a]pyridin-2-ylamine (100.0 mg, 0.346 mmol), and sodium tert-butoxide (71 mg, 0.73 mmol) were added in one portion. The reaction mixture was evacuated with high vacuum and repressurized with nitrogen three times. The tube was sealed and heated at 80° C. for 24 hours. The mixture was cooled to room temperature, filtered through a plug of diatomaceous earth, rinsed with dichloromethane and evaporated. The material was purified via preparative HPLC on a Phenomenex Luna column using 0.1% TFA in MeCN and 0.1% TFA in water as eluent. The title compound, 4-{4-[5-(4-Methanesulfonyl-phenyl)-[1,2,4]triazolo[1,5-a]pyridin-2-ylamino]-phenyl}-piperazine-1-carboxylic acid tert-butyl ester, was isolated as the TFA salt as a brown-green powder (0.011 g, 6%). $^1$H NMR (400 MHz, (D$_3$C)$_2$SO, δ, ppm): 9.47 (br s, 1H), 8.32 (d, J=8.4 Hz, 2H), 8.13 (d, J=8.4 Hz, 2H), 7.68 (m, 2H), 7.57 (m, 2H), 7.28 (m, 1H), 6.99 (m, 2H), 3.52-3.45 (m, 4H), 3.34 (s, 3H), 3.04 (s, 4H), 1.42 (s, 9H). MS=549 (MH)+.

Example 76

(5-Phenyl-[1,2,4]triazolo[1,5-a]pyridin-2-yl)-[4-(2-pyrrolidin-1-yl-ethoxy)-phenyl]-amine

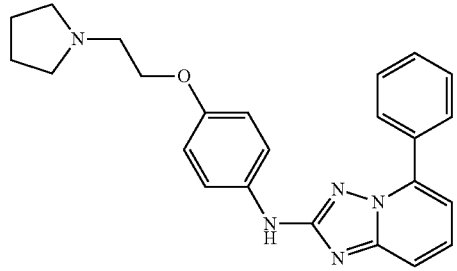 [SMILES: c1ccc(-c2cccc3nc(Nc4ccc(OCCN5CCCC5)cc4)nn23)cc1]

76a) 5-Phenyl-[1,2,4]triazolo[1,5-a]pyridin-2-ylamine was prepared from 5-bromo-[1,2,4]triazolo[1,5-a]pyridin-2-ylamine (3.00 g, 14.0 mmol) and phenyl boronic acid (1.8 g, 15.0 mmol), in a manner analogous to Step 73c. The product was isolated as a white powder (0.567 g, 19%) after chromatography on an Isco silica gel column (80 g) using methanol in dichloromethane as the eluent. $^1$H NMR (400 MHz, (D$_3$C)$_2$SO, δ, ppm): 7.94 (d, J=6.9 Hz, 2H), 7.52 (m, 4H), 7.37 (m, 1H), 7.02 (d, J=6.5 Hz, 1H), 6.02 (s, 2H). MS=210 (MH)+.

76b) (5-Phenyl-[1,2,4]triazolo[1,5-a]pyridin-2-yl)-[4-(2-pyrrolidin-1-yl-ethoxy)-phenyl]-amine was prepared from 5-phenyl-[1,2,4]triazolo[1,5-a]pyridin-2-ylamine (100.0 mg, 0.476 mmol) and 1-[2-(4-bromo-phenoxy)-ethyl]-pyrrolidine (119 μl, 0.571 mmol) in a manner analogous to Example 75. The title compound (5-Phenyl-[1,2,4]triazolo[1,5-a]pyridin-2-yl)-[4-(2-pyrrolidin-1-yl-ethoxy)-phenyl]-amine was isolated as the TFA salt as a off white solid (0.0037 g, 2%). $^1$H NMR (400 MHz, (D$_3$C)$_2$SO, δ, ppm): 10.05 (br s, 1H), 9.48 (s, 1H), 8.04 (d, J=8.5 Hz, 2H), 7.61 (m, 7H), 7.18 (d, J=7.5 Hz, 1H), 6.95 (d, J=8.5 Hz, 2H), 4.25 (m, 2H), 3.80-3.40 (m, 4H), 3.12 (m, 2H), 2.03 (m, 2H), 1.89 (m, 2H). MS=400 (MH)+.

Example 77

4-[4-(5-Phenyl-[1,2,4]triazolo[1,5-a]pyridin-2-ylamino)-phenyl]-piperazine-1-carboxylic acid tert-butyl ester

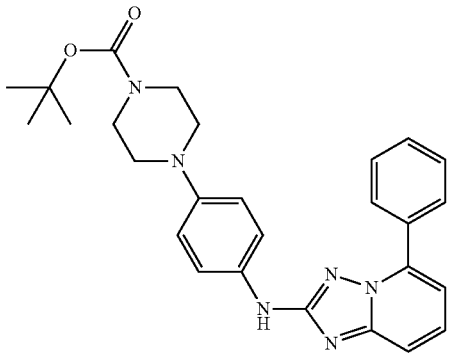 [SMILES: CC(C)(C)OC(=O)N1CCN(c2ccc(Nc3nc4cccc(-c5ccccc5)n4n3)cc2)CC1]

5-Phenyl-[1,2,4]triazolo[1,5-a]pyridin-2-ylamine (100.0 mg, 0.476 mmol), 4-(4-bromo-phenyl)-piperazine-1-carboxylic acid tert-butyl ester (194 mg, 0.571 mmol), 2,2'-bis(dicyclohexylphosphino)-1,1'-biphenyl (52 mg, 0.095 mmol), palladium acetate (10.67 mg, 0.048 mmol), sodium tert-butoxide (137 mg, 1.4 mmol) and dioxane (2 mL) were added all-at-once to an oven dried reaction tube. The reaction mixture was evacuated with high vacuum and repressurized with nitrogen three times. The tube was sealed and heated at 80° C. for 24 hours. The mixture was cooled to room temperature, filtered through a plug of diatomaceous earth, rinsed with dichloromethane and evaporated. The material was purified via preparative HPLC on a Phenomenex Luna column using 0.1% TFA in MeCN and 0.1% TFA in Water as eluent. The title compound was isolated as the TFA salt. MP=71-73° C. $^1$H NMR (400 MHz, (D$_3$C)$_2$SO, δ, ppm): 9.52 (br s, 1H), 8.04 (m, 2H), 7.61 (m, 7H), 7.13 (m, 3H), 3.58-3.48 (m, 4H), 3.11 (m, 4H), 1.43 (s, 9H). MS=471 (MH)+.

Example 78

[5-(3-Methanesulfonyl-phenyl)-[1,2,4]triazolo[1,5-a]pyridin-2-yl]-(4-morpholin-4-yl-phenyl)-amine

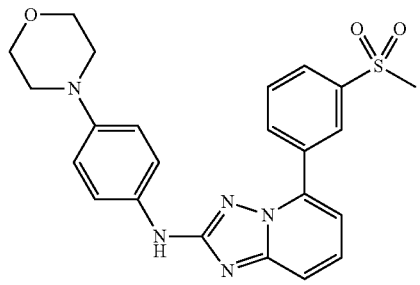 [SMILES: CS(=O)(=O)c1cccc(-c2cccc3nc(Nc4ccc(N5CCOCC5)cc4)nn23)c1]

78a) 5-(3-Methanesulfonyl-phenyl)-[1,2,4]triazolo[1,5-a]pyridin-2-ylamine was prepared from 5-bromo-[1,2,4]triazolo[1,5-a]pyridin-2-ylamine (3.00 g, 14.0 mmol) and 3-methanesulfonyl phenyl boronic acid (3.08 g, 15.0 mmol), in a manner analogous to Step 73c. The residue was purified on a 80 g Isco silica gel column using a gradient of 0-20% methanol in dichloromethane as an eluent. 5-(3-Methanesulfonyl-phenyl)-[1,2,4]triazolo[1,5-a]pyridin-2-ylamine (2.10 g, 52%) was isolated as a beige powder. MP=181-182° C. $^1$H NMR (400 MHz, (D$_3$C)$_2$SO, δ, ppm): 8.45 (s, 1H), 8.32 (d, J=8.0 Hz, 1H), 8.06 (d, J=8.5 Hz, 1H), 7.82 (t, J=16.1 Hz, 8.5 Hz, 1H), 7.55 (t, J=16.1 Hz, 8.5 Hz, 1H), 7.43 (d, J=9.1 Hz, 1H), 7.15 (d, J=7.0 Hz, 1H), 6.09 (s, 2H), 3.30 (s, 3H). MS=289 (MH)+.

78b) [5-(3-Methanesulfonyl-phenyl)-[1,2,4]triazolo[1,5-a]pyridin-2-yl]-(4-morpholin-4-yl-phenyl)-amine was prepared from 5-(3-methanesulfonyl-phenyl)-[1,2,4]triazolo[1,5-a]pyridin-2-ylamine (137 mg, 0.475 mmol) and 4-(4-bromo-phenyl)-morpholine (138 mg, 0.57 mmol) in a manner analogous to Example 77 to yield [5-(3-methanesulfonyl-phenyl)-[1,2,4]triazolo[1,5-a]pyridin-2-yl]-(4-morpholin-4-yl-phenyl)-amine (53.8 mg, 24%) as a yellow powder following purification on a 40 g Isco silica gel column using 0-5% methanol in dichloromethane as an eluent. MP=163° C. $^1$H NMR (400 MHz, (D$_3$C)$_2$SO, δ, ppm): 9.38 (s, 1H), 8.76 (m, 1H), 8.35 (d, J=8.0 Hz, 1H), 8.11 (d, J=8.0 Hz, 1H), 7.88 (t, J=15.5 Hz, 8.5 Hz, 1H), 7.67 (m, 1H), 7.57 (m, 3H), 7.32 (d, J=7.5 Hz, 1H), 6.88 (d, J=8.50 Hz, 2H), 3.73 (m, 4H), 3.33 (s, 3H), 2.99 (m, 4H). MS=450 (MH)+.

Example 79

[5-(3-Methanesulfonyl-phenyl)-[1,2,4]triazolo[1,5-a]pyridin-2-yl]-(3-methoxy-phenyl)-amine

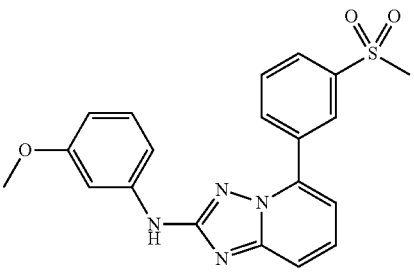

[5-(3-Methanesulfonyl-phenyl)-[1,2,4]triazolo[1,5-a]pyridin-2-yl]-(3-methoxyphenyl)-amine was prepared from 5-(3-methanesulfonyl-phenyl)-[1,2,4]triazolo[1,5-a]pyridin-2-ylamine (100 mg, 0.35 mmol) and 1-bromo-3-methoxy benzene (52 μL, 0.42 mmol) in a manner analogous to Example 77 to yield [5-(3-methanesulfonyl-phenyl)-[1,2,4]triazolo[1,5-a]pyridin-2-yl]-(3-methoxyphenyl)-amine (104 mg, 75%) as a yellow powder following purification on a 12 g Isco silica gel column using 0-5% methanol in dichloromethane as an eluent. MP=180° C. $^1$H NMR (400 MHz, (D$_3$C)$_2$SO, δ, ppm): 9.66 (s, 1H), 8.62 (m, 1H), 8.40 (d, J=8.0 Hz, 1H), 8.11 (d, J=8.0 Hz, 1H), 7.87 (t, J=16.1 Hz, 8.0 Hz, 1H), 7.68 (m, 2H), 7.32 (m, 2H), 7.25 (d, J=8.6 Hz, 1H), 7.15 (t, J=16.5 Hz, 8.0 Hz, 1H), 6.45 (dd, J=8.0 Hz, 2.7 Hz, 1H), 3.69 (s, 3H), 3.33 (s, 3H). MS=395 (MH)+.

Example 80

[5-(3-Methanesulfonyl-phenyl)-[1,2,4]triazolo[1,5-a]pyridin-2-yl]-(2-methoxy-phenyl)-amine

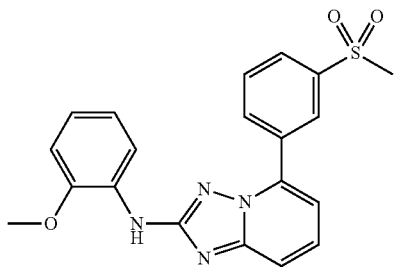

[5-(3-Methanesulfonyl-phenyl)-[1,2,4]triazolo[1,5-a]pyridin-2-yl]-(2-methoxyphenyl)-amine was prepared from 5-(3-methanesulfonyl-phenyl)-[1,2,4]triazolo[1,5-a]pyridin-2-ylamine (100 mg, 0.35 mmol) and 1-bromo-2-methoxy benzene (52 µL, 0.42 mmol) in a manner analogous to Example 77 to yield [5-(3-methanesulfonyl-phenyl)-[1,2,4]triazolo[1,5-a]pyridin-2-yl]-(2-methoxyphenyl)-amine (52 mg, 38%) as a yellow powder following purification on a 12 g Isco silica gel column using 0-5% methanol in dichloromethane as an eluent. MP=88° C. $^1$H NMR (400 MHz, $(D_3C)_2SO$, δ, ppm): 9.78 (br s, 1H), 8.79 (m. 1H), 8.36 (d, J=7.1 Hz, 1H), 8.20 (d, J=7.1 Hz, 1H), 8.12 (d, J=7.1 Hz, 1H), 8.00 (s, 1H), 7.89 (t, J=12.9, 8.2, 1H), 7.72 (m, 1H), 7.65 (d, J=9.4 Hz, 1H), 7.38 (d, J=8.2 Hz, 1H), 7.05 (d, J=5.9 Hz, 1H), 6.92 (m, 2H), 3.87 (s, 3H), 3.32 (s, 3H). MS=395 (MH)+.

Example 81

[5-(4-Methanesulfonyl-phenyl)-[1,2,4]triazolo[1,5-a]pyridin-2-yl]-[4-(4-methyl-piperazin-1-yl)-phenyl]-amine

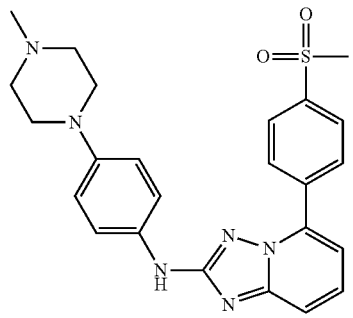 [SMILES: CN1CCN(c2ccc(Nc3nc4cccc(-c5ccc(S(C)(=O)=O)cc5)n4n3)cc2)CC1]

[5-(4-Methanesulfonyl-phenyl)-[1,2,4]triazolo[1,5-a]pyridin-2-yl]-[4-(4-methyl-piperazin-1-yl)-phenyl]-amine was prepared from 5-(4-methanesulfonyl-phenyl)-[1,2,4]triazolo[1,5-a]pyridin-2-ylamine (75 mg, 0.26 mmol) and 1-(4-bromo-phenyl)-4-methyl-piperazine (73 mg, 0.28 mmol) in a manner analogous to Example 77 to yield [5-(4-methanesulfonyl-phenyl)-[1,2,4]triazolo[1,5-a]pyridin-2-yl]-[4-(4-methyl-piperazin-1-yl)-phenyl]-amine TFA salt (19 mg, 16%) as a yellow powder following purification via preparative HPLC on a Phenomenex Luna column using 0.1% TFA in MeCN and 0.1% TFA in Water as eluent. $^1$H NMR (400 MHz, $(D_3C)_2SO$, δ, ppm): 9.46 (s, 1H), 8.31 (d, J=9.6 Hz, 2H), 8.14 (d, J=9.6 Hz, 2H), 7.66 (m, 2H) 7.57 (d, J=12.8 Hz, 2H), 7.28 (d, J=8.0 Hz, 1H), 6.96 (d, J=11.2 Hz, 2H), 3.69 (m, 2H), 3.34 (s, 3H), 3.16 (m, 2H), 2.91 (m, 2H), 2.86 (m, 3H). MS=463 (MH)+.

Example 82

[5-(3-Methanesulfonyl-phenyl)-[1,2,4]triazolo[1,5-a]pyridin-2-yl]-[4-(4-methyl-piperazin-1-yl)-phenyl]-amine

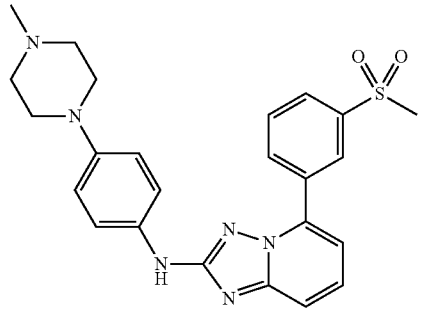 [SMILES: CN1CCN(c2ccc(Nc3nc4cccc(-c5cccc(S(C)(=O)=O)c5)n4n3)cc2)CC1]

[5-(3-Methanesulfonyl-phenyl)-[1,2,4]triazolo[1,5-a]pyridin-2-yl]-[4-(4-methyl-piperazin-1-yl)-phenyl]-amine was prepared from 5-(3-methanesulfonyl-phenyl)-[1,2,4]triazolo[1,5-a]pyridin-2-ylamine (75 mg, 0.26 mmol) and 1-(4-bromo-phenyl)-4-methyl-piperazine (73 mg, 0.28 mmol) in a manner analogous to Example 77 to yield [5-(3-methanesulfonyl-phenyl)-[1,2,4]triazolo[1,5-a]pyridin-2-yl]-[4-(4-methyl-piperazin-1-yl)-phenyl]-amine TFA salt (7 mg, 7%) as a yellow powder following purification via preparative HPLC on a Phenomenex Luna column using 0.1% TFA in MeCN and 0.1% TFA in Water as eluent. $^1$H NMR (400 MHz, $(D_3C)_2SO$, δ, ppm): 9.90 (br s, 1H), 9.46 (s, 1H), 8.77 (s, 1H), 8.35 (d, J=8.0 Hz, 1H), 8.11 (d, J=8.0 Hz, 1H), 7.88 (t, J=16.1 Hz, 8.0 Hz, 1H), 7.69 (m, 1H), 7.60 (m, 3H), 7.33 (d, J=6.5 Hz, 1H), 6.95 (d, J=9.1 Hz, 2H), 3.65 (m, 2H), 3.33 (s, 3H), 3.16 (m, 2H), 2.91 (m, 2H), 2.85 (s, 3H). MS=463 (MH)+.

Example 83

N-(3-{2-[4-(4-Methyl-piperazin-1-yl)-phenylamino]-[1,2,4]triazolo[1,5-a]pyridin-5-yl}-phenyl)-methanesulfonamide

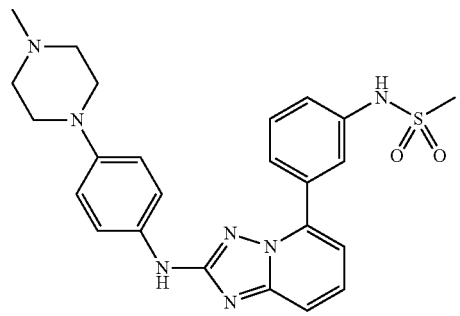 [SMILES: CN1CCN(c2ccc(Nc3nc4cccc(-c5cccc(NS(C)(=O)=O)c5)n4n3)cc2)CC1]

83a) N-[3-(2-Amino-[1,2,4]triazolo[1,5-a]pyridin-5-yl)-phenyl]-methanesulfonamide was prepared from 5-bromo-

[1,2,4]triazolo[1,5-a]pyridine-2-ylamine (1.80 g, 8.45 mmol) and 3-methylsulfonylaminophenyl boronic acid (2.0 g, 9.30 mmol), in a manner analogous to Step 73c. The residue was purified on an 80 g Isco silica gel column using a gradient of 0-7% methanol in dichloromethane as an eluent. N-[3-(2-Amino-[1,2,4]triazolo[1,5-a]pyridin-5-yl)-phenyl]-methanesulfonamide (461 mg, 18%) was isolated as a beige powder. $^1$H NMR (400 MHz, (D$_3$C)$_2$SO, δ, ppm): 9.94 (s, 1H), 7.72 (s, 1H), 7.64 (d, J=7.5 Hz, 1H), 7.51 (m, 2H), 7.38 (d, J=8.6 Hz, 1H), 7.32 (d, J=7.5 Hz, 1H), 6.97 (d, J=7.5 Hz, 1H), 6.03 (br s, 2H), 3.08 (s, 3H). MS=304 (MH)+.

83b) 5 N-[3-(2-Amino-[1,2,4]triazolo[1,5-a]pyridin-5-yl)-phenyl]-methanesulfonamide (162 mg, 0.534 mmol) and 1-(4-bromo-phenyl)-4-methyl-piperazine (150 mg, 0.587 mmol) were combined in a manner analogous to Example 77 to yield N-(3-{2-[4-(4-methyl-piperazin-1-yl)-phenylamino]-[1,2,4]triazolo[1,5-a]pyridin-5-yl}-phenyl)-methanesulfonamide TFA salt (13.75 mg, 5%) as a yellow powder following purification via preparative HPLC on a Phenomenex Luna column using 0.1% TFA in MeCN and 0.1% TFA in Water as eluent. $^1$H NMR (400 MHz, (D$_3$C)$_2$SO, δ, ppm): 9.99 (s, 1H), 9.41 (s, 1H), 7.81 (s, 1H), 7.74 (d, J=8.0 Hz, 1H), 7.64 (t, J=8.3 Hz, 1H), 7.50-7.61 (m, 3H), 7.08-7.42 (m, 3H), 6.93 (d, J=7.2 Hz, 2H), 3.67 (m, 2H), 3.18 (m, 4H), 3.07 (s, 3H), 2.86 (br s, 5H). MS=478 (MH)+.

Example 84

N-(4-{2-[4-(4-Methyl-piperazin-1-yl)-phenylamino]-[1,2,4]triazolo[1,5-a]pyridin-5-yl}-phenyl)-methanesulfonamide

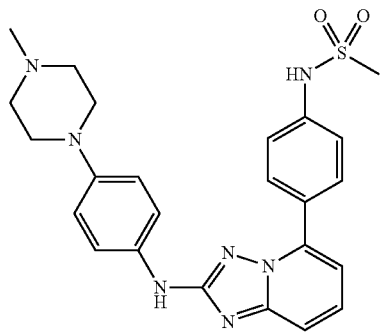 [SMILES: CN1CCN(c2ccc(Nc3nc4cccc(-c5ccc(NS(C)(=O)=O)cc5)n4n3)cc2)CC1]

84a) N-[4-(2-Amino-[1,2,4]triazolo[1,5-a]pyridin-5-yl)-phenyl]-methanesulfonamide was prepared from 5-bromo-[1,2,4]triazolo[1,5-a]pyridine-2-ylamine (1.80 g, 8.45 mmol) and 4-methylsulfonylaminophenyl boronic acid (2.0 g, 9.30 mmol), in a manner analogous to Step 73c. The residue was purified on a 40 g Isco silica gel column using a gradient of 0-15% methanol in dichloromethane as an eluent. N-[4-(2-Amino-[1,2,4]triazolo[1,5-a]pyridin-5-yl)-phenyl]-methanesulfonamide (389 mg, 15%) was isolated as a beige powder. $^1$H NMR (400 MHz, (D$_3$C)$_2$SO, δ, ppm): 10.06 (s, 1H), 7.96 (d, J=10.7 Hz, 2H), 7.49 (t, J=17.1 Hz, 7.5 Hz, 1H), 7.34 (d, J=8.6 Hz, 3H), 7.00 (d, J=7.5 Hz, 1H), 6.01 (s, 2H), 3.09 (s, 3H). MS=304 (MH)+.

84b) N-[4-(2-Amino-[1,2,4]triazolo[1,5-a]pyridin-5-yl)-phenyl]-methanesulfonamide (162 mg, 0.534 mmol) and 1-(4-bromo-phenyl)-4-methyl-piperazine (150 mg, 0.587 mmol) were combined in a manner analogous to Example 77 to yield N-(3-{2-[4-(4-methyl-piperazin-1-yl)-phenylamino]-[1,2,4]triazolo[1,5-a]pyridin-5-yl}-phenyl)-methanesulfonamide TFA salt (14 mg, 6%) as a yellow powder following purification via preparative HPLC on a Phenomenex Luna column using 0.1% TFA in MeCN and 0.1% TFA in Water as eluent. $^1$H NMR (400 MHz, (D$_3$C)$_2$SO, δ, ppm): 10.13 (s, 1H), 9.40 (s, 1H), 8.05 (d, J=7.5 Hz, 1H), 7.58 (m, 3H), 7.39 (d, J=7.5 Hz, 2H), 7.27 (d, J=8.6 Hz, 2H), 6.95 (d, J=9.6 Hz, 2H), 4.16 (m, 2H), 3.68 (m, 2H), 3.20 (m, 3H), 3.12 (s, 3H), 2.86 (m, 5H). MS=478 (MH)+.

Example 85

[5-(4-Methanesulfonyl-phenyl)-[1,2,4]triazolo[1,5-a]pyridin-2-yl]-(4-morpholin-4-ylmethyl-phenyl)-amine

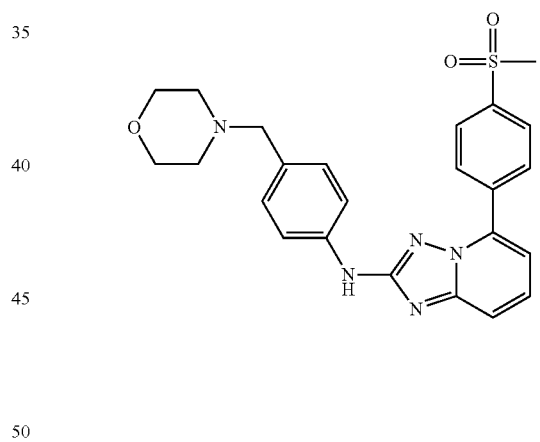

[5-(4-Methanesulfonyl-phenyl)-[1,2,4]triazolo[1,5-a]pyridin-2-yl]-(4-morpholin-4-ylmethyl-phenyl)-amine was prepared from 5-(4-methanesulfonyl-phenyl)-[1,2,4]triazolo[1,5-a]pyridine-2-ylamine (125 mg, 0.43 mmol) and 4-(4-bromobenzyl)morpholine (122 mg, 0.48 mmol) in a manner analogous to Example 77 to yield 5-(4-methanesulfonyl-phenyl)-[1,2,4]triazolo[1,5-a]pyridin-2-yl]-(4-morpholin-4-ylmethyl-phenyl)-amine (73 mg, 37%) as an off-white powder following purification on a 4 g Isco silica gel column using methanol in dichloromethane (0-20%) as eluent. MP=222-223° C. $^1$H NMR (400 MHz, (D$_3$C)$_2$SO, δ, ppm): 9.66 (s, 1H), 8.32 (d, J=7.50 Hz, 2H), 8.15 (d, J=7.50 Hz, 2H), 7.66 (m, 4H), 7.30 (d, J=6.42 Hz, 1H), 7.20 (d, J=8.60 Hz, 2H), 3.55 (br s, 4H), 3.40-3.32 (m, 5H), 2.32 (br s, 4H). MS=465 (MH)+.

Example 86

[5-(4-Methanesulfonyl-phenyl)-[1,2,4]triazolo[1,5-a]pyridin-2-yl]-[4-(4-methyl-piperazin-1-ylmethyl)-phenyl]-amine

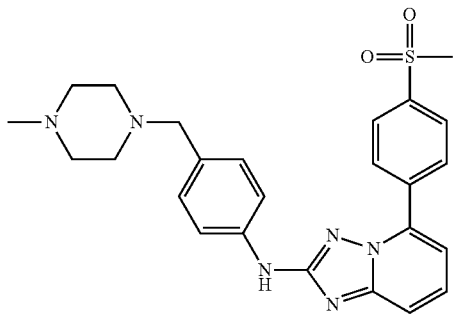

[5-(4-Methanesulfonyl-phenyl)-[1,2,4]triazolo[1,5-a]pyridin-2-yl]-[4-(4-methyl-piperazin-1-ylmethyl)-phenyl]-amine was prepared from 5-(4-methanesulfonyl-phenyl)-[1,2,4]triazolo[1,5-a]pyridin-2-ylamine (125 mg, 0.43 mmol) and 1-(4-bromobenzyl)-4-methylpiperazine (129 mg, 0.48 mmol) in a manner analogous to Example 77 to yield [5-(4-methanesulfonyl-phenyl)-[1,2,4]triazolo[1,5-a]pyridin-2-yl]-[4-(4-methyl-piperazin-1-ylmethyl)-phenyl]-amine (82 mg, 40%) as a yellow powder following purification on a 4 g Isco silica gel column using methanol in dichloromethane (0-20%) as eluent. MP=207-208° C. $^1$H NMR (400 MHz, $(D_3C)_2SO$, δ, ppm): 9.64 (s, 1H), 8.33 (d, J=8.0 Hz, 2H), 8.14 (d, J=8.0 Hz, 2H), 7.68 (m, 2H), 7.61 (d, J=8.6 Hz, 2H), 7.30 (d, J=7.0 Hz, 1H), 7.18 (d, J=7.5 Hz, 2H), 3.40-3.33 (m, 5H), 2.46-2.18 (m, 8H), 2.14 (s, 3H). MS=477 (MH)+.

Example 87

[5-(4-Methanesulfonyl-phenyl)-[1,2,4]triazolo[1,5-a]pyridin-2-yl]-(4-morpholin-4-ylmethyl-phenyl)-amine

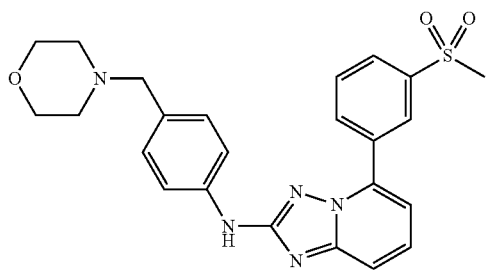 [SMILES: CS(=O)(=O)c1cccc(-c2cccc3nc(Nc4ccc(CN5CCOCC5)cc4)nn23)c1]

[5-(3-Methanesulfonyl-phenyl)-[1,2,4]triazolo[1,5-a]pyridin-2-yl]-(4-morpholin-4-ylmethyl-phenyl)-amine was prepared from 5-(3-methanesulfonyl-phenyl)-[1,2,4]triazolo[1,5-a]pyridin-2-ylamine (125 mg, 0.43 mmol) and 4-(4-bromobenzyl)morpholine (122 mg, 0.48 mmol) in a manner analogous to Example 77 to yield 5-(3-methanesulfonyl-phenyl)-[1,2,4]triazolo[1,5-a]pyridin-2-yl]-(4-morpholin-4-ylmethyl-phenyl)-amine (118 mg, 59%) as an off-white powder following purification on a 4 g Isco silica gel column using methanol in dichloromethane (0-20%) as eluent. MP=210-211° C. $^1$H NMR (400 MHz, $(D_3C)_2SO$, δ, ppm): 9.64 (s, 1H), 8.78 (s, 1H), 8.36 (d, J=7.50 Hz, 1H), 8.11 (d, J=7.50, 1H), 7.89 (t, J=15.0 Hz, 7.50 Hz, 1H), 7.70 (m, 1H), 7.63 (m, 3H), 7.35 (d, J=7.50 Hz, 1H), 7.18 (d, J=9.6 Hz, 2H) 3.55 (m, 4H), 3.40-3.28 (m, 5H), 2.32 (m, 4H). MS=464 (MH)+.

Example 88

[5-(3-Methanesulfonyl-phenyl)-[1,2,4]triazolo[1,5-a]pyridin-2-yl]-[4-(4-methyl-piperazin-1-ylmethyl)-phenyl]-amine

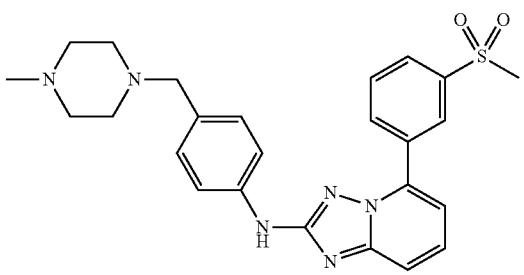

[5-(3-Methanesulfonyl-phenyl)-[1,2,4]triazolo[1,5-a]pyridin-2-yl]-[4-(4-methyl-piperazin-1-ylmethyl)-phenyl]-amine was prepared from 5-(3-methanesulfonyl-phenyl)-[1,2,4]triazolo[1,5-a]pyridin-2-ylamine (125 mg, 0.43 mmol) and 1-(4-bromobenzyl)-4-methylpiperzine (129 mg, 0.48 mmol) in a manner analogous to Example 77 to yield [5-(3-methanesulfonyl-phenyl)-[1,2,4]triazolo[1,5-a]pyridin-2-yl]-[4-(4-methyl-piperazin-1-ylmethyl)-phenyl]-amine (91 mg, 44%) as an off-white powder following purification on a 4 g Isco silica gel column using methanol in dichloromethane (0-20%) as eluent. MP=232-234° C. $^1$H NMR (400 MHz, $(D_3C)_2SO$, δ, ppm): 9.62 (br s, 1H), 8.78 (s, 1H), 8.36 (d, J=7.50 Hz, 1H), 8.11 (d, J=7.50 Hz, 1H), 7.87 (t, J=17.1 Hz, 8.5 Hz, 1H), 7.70 (m, 1H), 7.62 (m, 3H), 7.35 (d, J=7.5 Hz, 1H), 7.16 (d, 9.63 Hz, 2H), 3.37-3.30 (m, 5H), 2.31 (br s, 8H), 2.15 (s, 3H). MS=477 (MH)+.

Example 89

[1-[5-(3-Methanesulfonyl-phenyl)-[1,2,4]triazolo[1,5-a]pyridin-2-yl]-3-[4-(4-methyl-piperazin-1-yl)-phenyl]-urea

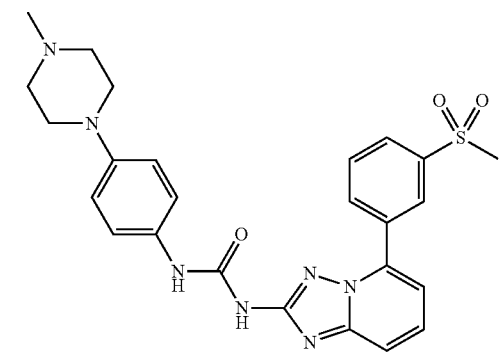 [SMILES: CN1CCN(c2ccc(NC(=O)Nc3nc4cccc(-c5cccc(S(C)(=O)=O)c5)n4n3)cc2)CC1]

[1-[5-(3-Methanesulfonyl-phenyl)-[1,2,4]triazolo[1,5-a]pyridin-2-yl]-3-[4-(4-methyl-piperazin-1-yl)-phenyl]-urea was prepared from 5-(3-methanesulfonyl-phenyl)-[1,2,4]triazolo[1,5-a]pyridin-2-ylamine (50 mg, 0.20 mmol) and 1-(4-isocyanato-phenyl)-4-methyl-piperazine (133 mg, 0.52 mmol) in refluxing THF for 24 hours. The reaction was evaporated and purified via preparative HPLC on a Phenomenex Luna column using 0.1% TFA in MeCN and 0.1% TFA in Water as eluent. 1-[5-(3-Methanesulfonyl-phenyl)-[1,2,4]triazolo[1,5-a]pyridin-2-yl]-3-[4-(4-methyl-piperazin-1-yl)-phenyl]-urea TFA salt (2.3 mg, 3.3%) was isolated as an off-white film. $^1$H NMR (400 MHz, D$_3$COD, δ, ppm): 8.62 (s, 1H), 8.34 (d, J=8.5 Hz, 1H), 8.15 (d, J=8.5 Hz, 1H), 7.71-7.89 (m, 3H), 7.40 (m, 3H), 7.02 (d, J=7.50 Hz, 2H), 3.50-3.25 (m, 8H), 3.19 (s, 3H), 2.96 (s, 3H). MS=506 (MH)+.

Example 90

1-[5-(4-Methanesulfonyl-phenyl)-[1,2,4]triazolo[1,5-a]pyridin-2-yl]-3-[4-(4-methyl-piperazin-1-yl)-phenyl]-urea

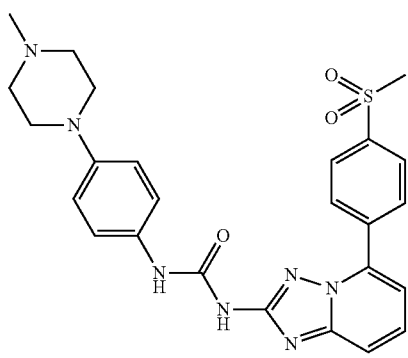 [SMILES: CN1CCN(c2ccc(NC(=O)Nc3nc4cccc(-c5ccc(S(C)(=O)=O)cc5)n4n3)cc2)CC1]

[1-[5-(4-Methanesulfonyl-phenyl)-[1,2,4]triazolo[1,5-a]pyridin-2-yl]-3-[4-(4-methyl-piperazin-1-yl)-phenyl]-urea was prepared from 5-(4-methanesulfonyl-phenyl)-[1,2,4]triazolo[1,5-a]pyridin-2-ylamine (50 mg, 0.20 mmol) and 1-(4-isocyanato-phenyl)-4-methyl-piperazine (133 mg, 0.52 mmol) in refluxing THF for 24 hours. The reaction was evaporated and purified via preparative HPLC on a Phenomenex Luna column using 0.1% TFA in MeCN and 0.1% TFA in water as eluent. 1-[5-(4-Methanesulfonyl-phenyl)-[1,2,4]triazolo[1,5-a]pyridin-2-yl]-3-[4-(4-methyl-piperazin-1-yl)-phenyl]-urea TFA salt (1.4 mg, 1.5%) was isolated as an off-white film. $^1$H NMR (400 MHz, D$_3$COD, δ, ppm): 8.28 (d, J=8.6 Hz, 2H), 8.17 (d, J=8.6 Hz, 2H), 7.71-7.84 (m, 2H), 7.38 (m, 3H), 7.02 (d, J=8.6 Hz, 2H), 3.50-3.20 (m, 11H), 2.83 (s, 3H). MS=506 (MH)+.

Example 91

[5-(4-Methanesulfonyl-phenyl)-[1,2,4]triazolo[1,5-a]pyridin-2-yl]-(4-methoxy-phenyl)-amine

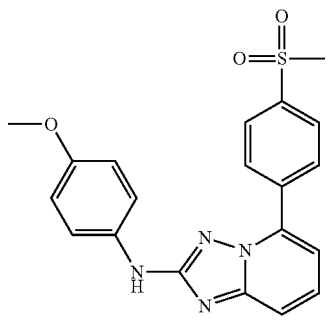

[5-(4-Methanesulfonyl-phenyl)-[1,2,4]triazolo[1,5-a]pyridin-2-yl]-(4-methoxy-phenyl)-amine was prepared from 5-(4-methanesulfonyl-phenyl)-[1,2,4]triazolo[1,5-a]pyridin-2-ylamine (115 mg, 0.40 mmol) and p-bromoanisole (82 mg, 0.44 mmol) in a manner analogous to Example 77 to yield [5-(4-methanesulfonyl-phenyl)-[1,2,4]triazolo[1,5-a]pyridin-2-yl]-(4-methoxy-phenyl)-amine (17 mg, 11%) as a yellow powder following purification on a 12 g Isco silica gel column using methanol in dichloromethane (0-10%) as eluent. MP=229° C. (dec.). $^1$H NMR (400 MHz, (D$_3$C)$_2$SO, δ, ppm): 9.43 (s, 1H), 8.32 (d, J=7.50 Hz, 2H), 8.14 (d, J=7.50 Hz, 2H), 7.54-7.71 (m, 4H), 7.27 (d, J=6.4 Hz, 1H), 6.87 (d, J=7.5 Hz, 2H), 3.71 (s, 3H), 3.34 (s, 3H). MS=395 (MH)+.

Example 92

[5-(4-Methanesulfonyl-phenyl)-[1,2,4]triazolo[1,5-a]pyridin-2-yl]-[3-(4-methyl-piperazin-1-yl)-phenyl]-amine

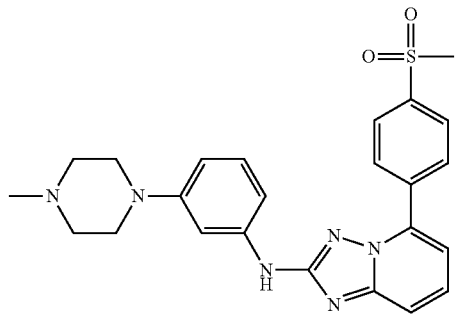

[5-(4-Methanesulfonyl-phenyl)-[1,2,4]triazolo[1,5-a]pyridin-2-yl]-[3-(4-methyl-piperazin-1-yl)-phenyl]-amine was prepared from 5-(4-methanesulfonyl-phenyl)-[1,2,4]triazolo[1,5-a]pyridin-2-ylamine (75 mg, 0.26 mmol) and 1-(3-bromo-phenyl)-4-methyl-piperazine (73 mg, 0.29 mmol) in a manner analogous to Example 77 to yield [5-(4-Methanesulfonyl-phenyl)-[1,2,4]triazolo[1,5-a]pyridin-2-yl]-[3-(4-methyl-piperazin-1-yl)-phenyl]-amine (52 mg, 43%) as a yellow powder following purification on a 12 g Isco silica gel column using methanol in dichloromethane (0-10%) as eluent. MP=251° C. $^1$H NMR (400 MHz, (D$_3$C)$_2$SO, δ, ppm):

9.52 (s, 1H), 8.33 (d, J=8.6 Hz, 2H), 8.12 (d, J=8.6 Hz, 2H), 7.61-7.72 (m, 2H), 7.53 (s, 1H), 7.26 (d, J=7.5 Hz, 1H), 7.07 (t, J=15.0 Hz, 8.6 Hz, 1H), 6.86 (d, J=7.5 Hz, 1H), 6.45 (d, J=7.5 Hz, 1H), 3.33 (s, 3H), 3.04 (s, 4H), 2.44 (s, 4H), 2.22 (s, 3H). MS=463 (MH)+.

Example 93

(4-Methanesulfonyl-phenyl)-[5-(4-methanesulfonyl-phenyl)-[1,2,4]triazolo[1,5-a]pyridin-2-yl]-amine

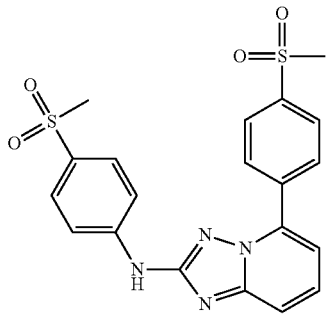 [SMILES: CS(=O)(=O)c1ccc(Nc2nc3cccc(-c4ccc(S(C)(=O)=O)cc4)n3n2)cc1]

(4-Methanesulfonyl-phenyl)-[5-(4-methanesulfonyl-phenyl)-[1,2,4]triazolo[1,5-a]pyridin-2-yl]-amine was prepared from 5-(4-methanesulfonyl-phenyl)-[1,2,4]triazolo[1,5-a]pyridin-2-ylamine (75 mg, 0.26 mmol) and 1-bromo-4-methanesulfonyl benzene (73 mg, 0.29 mmol) in a manner analogous to Example 77 to yield (4-methanesulfonyl-phenyl)-[5-(4-methanesulfonyl-phenyl)-[1,2,4]triazolo[1,5-a]pyridin-2-yl]-amine TFA salt (11 mg, 43%) as a white powder following purification via preparative HPLC on a Phenomenex Luna column using 0.1% TFA in MeCN and 0.1% TFA in Water as eluent. $^1$H NMR (400 MHz, (D$_3$C)$_2$SO, δ, ppm): 10.36 (s, 1H), 8.32 (d, J=8.6 Hz, 2H), 8.17 (d, J=8.6 Hz, 2H) 7.74 (m, 6H), 7.37 (s, 1H), 3.34 (s, 3H), 3.13 (s, 3H). MS=484 (MH)+.

Example 94

(3-Methanesulfonyl-phenyl)-[5-(4-methanesulfonyl-phenyl)-[1,2,4]triazolo[1,5-a]pyridin-2yl]-amine

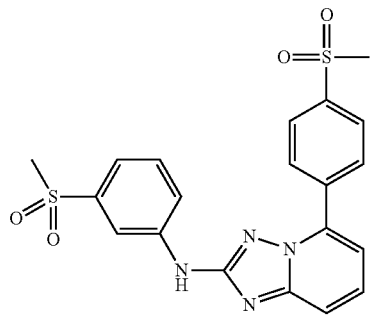 [SMILES: CS(=O)(=O)c1ccc(-c2cccc3nc(Nc4cccc(S(C)(=O)=O)c4)nn23)cc1]

(3-Methanesulfonyl-phenyl)-[5-(4-methanesulfonyl-phenyl)-[1,2,4]triazolo[1,5-a]pyridin-2-yl]-amine was prepared from 5-(4-methanesulfonyl-phenyl)-[1,2,4]triazolo[1,5-a]pyridin-2-ylamine (75 mg, 0.26 mmol) and 1-bromo-3-methanesulfonyl benzene (73 mg, 0.29 mmol) in a manner analogous to Example 77 to yield (3-methanesulfonyl-phenyl)-[5-(4-methanesulfonyl-phenyl)-[1,2,4]triazolo[1,5-a]pyridin-2-yl]-amine (47 mg, 39%) as a white powder following trituration with methanol. MP=279° C. $^1$H NMR (400 MHz, (D$_3$C)$_2$SO, δ, ppm): 10.18 (s, 1H), 8.49 (s, 1H), 8.37 (d, J=8.0 Hz, 2H), 8.15 (d, J=8.0 Hz, 2H), 7.70-7.81 (m, 3H), 7.55 (t, J=17.4 Hz, 8.0 Hz, 1H), 7.36-7.45 (m, 2H), 3.30 (s, 3H), 3.17 (s, 3H). MS=443 (MH)+.

Example 95

5-{4-[(1,1-dioxidothiomorpholin-4-yl)methyl]phenyl}-N-(4-methoxyphenyl)[1,2,4]triazolo[1,5-a]pyridin-2-amine

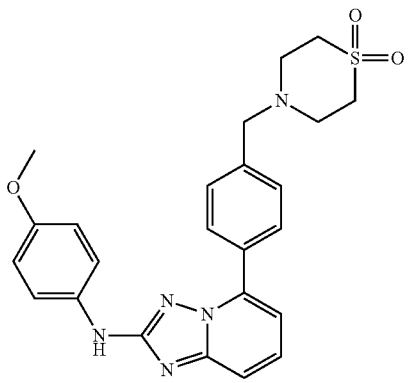 [SMILES: COc1ccc(Nc2nc3cccc(-c4ccc(CN5CCS(=O)(=O)CC5)cc4)n3n2)cc1]

95a) 5-{4-[(1,1-dioxidothiomorpholin-4-yl)methyl]phenyl}[1,2,4]triazolo[1,5-a]pyridin-2-amine was prepared from 5-bromo-[1,2,4]triazolo[1,5-a]pyridin-2-ylamine (368 mg, 1.73 mmol) and 4-[(4-boronophenyl)methyl]-thiomorpholine 1,1-dioxide (0.512 mg, 1.90 mmol), in a manner analogous to Step 73c. The residue was purified on a 12 g Isco silica gel column using a gradient of 0-15% methanol in dichloromethane as an eluent. 5-{4-[(1,1-dioxidothiomorpholin-4-yl)methyl]phenyl}[1,2,4]triazolo[1,5-a]pyridin-2-amine (490 mg, 79%) was isolated as a beige foam. $^1$H NMR (400 MHz, (D$_3$C)$_2$SO, δ, ppm): 7.93 (d, J=8.5 Hz, 2H), 7.50 (m, 3H), 7.37 (d, J=7.8 Hz, 1H), 7.07 (d, J=7.8 Hz, 1H), 6.02 (s, 2H), 3.78 (s, 2H), 3.15 (s, 4H), 2.91 (s, 4H). MS=358 (MH)+.

95b) 5-{4-[(1,1-dioxidothiomorpholin-4-yl)methyl]phenyl}[1,2,4]triazolo[1,5-a]pyridin-2-amine (50 mg, 0.140 mmol) and 1-bromo-4-methoxy benzene (29 mg, 0.154 mmol) were combined in a manner analogous to Example 77 to yield 5-{4-[(1,1-dioxidothiomorpholin-4-yl)methyl]phenyl}-N-(4-methoxyphenyl)[1,2,4]triazolo[1,5-a]pyridin-2-amine (28 mg, 42%) as a beige solid. The material was purified via trituration with methanol. MP=241° C. $^1$H NMR (400 MHz, (D$_3$C)$_2$SO, δ, ppm): 9.37 (s, 1H), 8.03 (d, J=8.1 Hz, 2H), 7.51-7.67 (m, 6H), 7.17 (d, J=6.4 Hz, 1H), 6.85 (d, J=8.6 Hz, 2H), 3.80 (s, 2H), 3.69 (s, 3H), 3.15 (br s, 4H), 2.92 (br s, 4H). MS=464 (MH)+.

Example 96

[2-(4-Methyl-piperazin-1-yl)-[1,2,4]triazolo[1,5-a]pyridin-8-yl]-(3-nitro-benzyl)-amine

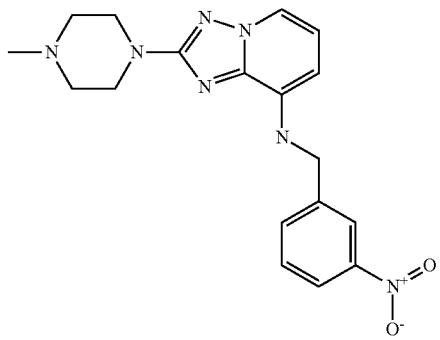 [SMILES: CN1CCN(c2nc3c(NCc4cccc([N+](=O)[O-])c4)cccn3n2)CC1]

96a) To an oven dried tube was added palladium acetate and 9,9-dimethyl-4,5-bis(diphenylphosphino) xanthene. The mixture was evacuated under vacuum and purged with nitrogen three times. The mixture was kept under a stream of Nitrogen. Nitrogen purged 1,4-Dioxane was added and stirred at room temperature for 30 minutes. 8-Bromo-2-chloro-[1,2,4]triazolo[1,5-a]pyridine (from Example 68a), 3-nitro-benzyl-ammonium chloride and cesium carbonate were added all-at-once. The mixture was stirred at room temperature for 10 minutes. The tube was sealed and heated at 80° C. for 18 hours before being cooled to room temperature. The mixture was filtered through a plug of celite, rinsed with dichloromethane and evaporated to provide a brown solid. ISCO silica gel chromatography (0-100% EtOAc in hexanes) afforded (2-chloro-[1,2,4]triazolo[1,5-a]pyridin-8-yl)-(3-nitro-benzyl)-amine $^1$H NMR (400 MHz, (D$_3$C)$_2$SO, δ, ppm): 8.28 (s, 1H), 8.10 (d, J=6.8 Hz, 2H), 7.85 (d, J=7.6 Hz, 1H), 7.62 (dd, J=8.2 Hz, 7.7 Hz, 1H), 7.47 (m, 1H), 6.95 (dd, J=7.4 Hz, 7.7 Hz, 1H), 6.47 (d, J=7.6 Hz, 1H), 4.61 (d, J=6.2 Hz, 2H). MS=304.0 (MH)+.

96b) (2-Chloro-[1,2,4]triazolo[1,5-a]pyridin-8-yl)-(3-nitro-benzyl)-amine was dissolved in piperazine, 1-methyl- and the reaction was heated to 200° C. in the microwave for 60 minutes. The reaction was diluted with water and extracted with dichloromethane. The organic layer was dried over MgSO$_4$, filtered, and concentrated. The resulting residue was purified via Gilson HPLC to provide the title compound [2-(4-Methyl-piperazin-1-yl)-[1,2,4]triazolo[1,5-a]pyridin-8-yl]-(3-nitro-benzyl)-amine was obtained as a yellow lyophilate (43%). $^1$H NMR (400 MHz, (D$_3$C)$_2$SO, δ, ppm): 9.80 (bs, 1H), 8.25 (s, 1H), 8.10 (d, J=8.0 Hz, 1H), 7.91 (d, J=6.8 Hz, 1H), 7.85 (d, J=7.5 Hz, 1H), 7.63 (dd, J=7.7 Hz, 7.7 Hz, 1H), 6.87 (bs, 1H), 6.71 (dd, J=6.7 Hz, 7.3 Hz, 1H), 6.32 (d, J=7.4 Hz, 1H), 4.61 (s, 2H), 4.23 (d, J=14 Hz, 2H), 3.51 (d, J=11.8 Hz, 2H), 3.28 (m, 2H), 3.17 (m, 2H), 2.50 (s, 3H). MS=368.1 (MH)+.

Example 97

(3-Amino-benzyl)-[2-(4-methyl-piperazin-1-yl)-[1,2,4]triazolo[1,5-a]pyridin-8-yl]-amine was recovered as a byproduct of the reaction and was obtained as a brown lyophilate (29%). $^1$H NMR (400 MHz, (D$_3$C)$_2$SO, δ, ppm): 9.98 (bs, 1H), 7.90 (d, J=6.3 Hz, 1H), 7.25 (bs, 1H), 7.03 (m, 2H), 6.90 (m, 1H), 6.71 (m, 1H), 6.78 (bs, 2H), (6.25 (d, J=7.6 Hz, 1H), 4.43 (bs, 2H), 4.21 (m, 2H), 3.50 (m, 2H), 3.38 (m, 2H), 2.85 (m, 2H), 2.50 (s, 3H). MS=338.1 (MH)+.

Example 98

(2-Morpholin-4-yl-[1,2,4]triazolo[1,5-a]pyridin-8-yl)-(3-nitro-benzyl)-amine

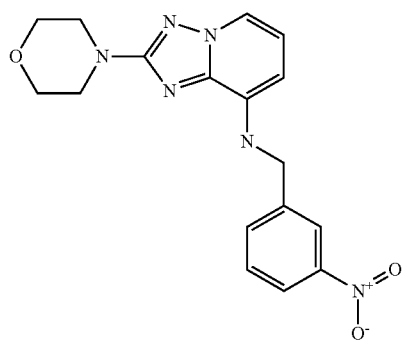 [SMILES: O=[N+]([O-])c1cccc(CNc2cccn3nc(N4CCOCC4)nc23)c1]

(2-Morpholin-4-yl-[1,2,4]triazolo[1,5-a]pyridin-8-yl)-(3-nitro-benzyl)-amine was prepared in a manner analogous to Step 96b using morpholine. The title compound was obtained as a pale yellow lyophilate (8%). $^1$H NMR (400 MHz, (D$_3$C)$_2$SO, δ, ppm): 8.25 (s, 1H), 8.09 (d, J=8.0 Hz, 1H), 7.85-7.83 (m, 2H), 6.82 (bs, 1H), 6.65 (dd, J=7.4 Hz, 7.2 Hz, 1H) 6.27 (d, J=7.6 Hz, 1H), 4.60 (s, 2H), 3.72 (bm, 4H), 3.46 (bm, 4H). MS=355.0 (MH)+.

Example 99

[2-(4-Amino-piperidin-1-yl)-[1,2,4]triazolo[1,5-a]pyridin-8-yl]-pyridin-3-ylmethyl-amine

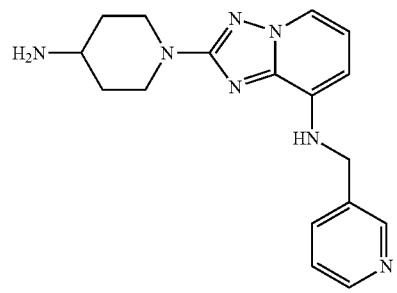 [SMILES: NC1CCN(c2nc3c(NCc4cccnc4)cccn3n2)CC1]

[2-(4-Amino-piperidin-1-yl)-[1,2,4]triazolo[1,5-a]pyridin-8-yl]-pyridin-3-ylmethyl-amine was prepared in a manner analogous to Step 96b using 4-amino-1-methylpiperidine. The title product was isolated as a yellow film (20%). $^1$H NMR (400 MHz, CD$_3$OD, δ, ppm): 8.75 (s, 1H), 8.64 (d, J=5.5 Hz, 1H), 8.42 (d, J=7.6 Hz, 1H), 7.86 (dd, J=6.9 Hz, 6.8 Hz, 1H), 7.77 (d, J=6.5 Hz, 1H), 6.68 (m, 1H), 6.35 (d, J=7.6 Hz, 1H), 4.69 (m, 2H), 4.29 (bd, J=13.6 Hz, 2H), 3.02 (dd, J=13.0 Hz, 2H), 2.86 (bs, 1H), 2.02 (bd, J=12.4 Hz, 2H), 1.63 (bd, J=8.8 Hz, 2H). MS=355.0 (MH)+.

Example 101

N(2)-(2-Morpholin-4-yl-ethyl)-N(8)-pyridin-3-ylmethyl-[1,2,4]triazolo[1,5-a]pyridine-2,8-diamine

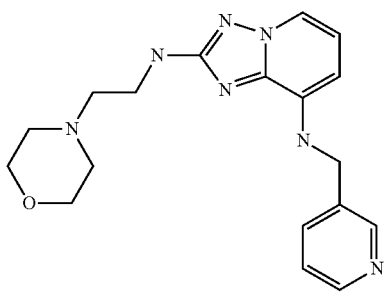 [SMILES: c1cncc(CNc2cccn3nc(NCCN4CCOCC4)nc23)c1]

N(2)-(2-Morpholin-4-yl-ethyl)-N(8)-pyridin-3-ylmethyl-[1,2,4]triazolo[1,5-a]pyridine-2,8-diamine was prepared in a manner analogous to Step 96b using N-(2-aminoethyl)morpholine. The title compound was isolated as a dark green film (70%). $^1$H NMR (400 MHz, CD$_3$OD, δ, ppm): 8.87 (s, 1H), 8.77 (d, J=5.4 Hz, 1H), 8.62 (8.0 Hz, 1H), 8.04 (m, 1H), 7.89 (d, J=6.5 Hz, 1H), 6.82 (dd, J=7.2 Hz, 6.9 Hz, 1H), 6.52 (d, J=7.8 Hz, 1H), 4.80 (s, 2H), 3.95 (bm, 4H), 3.81 (m, 2H), 3.62 (bm, 2H), 3.51 (m, 2H), 3.31 (bm, 2H). MS=354.2 (MH)+.

Example 102

8-(4-Methanesulfonyl-phenyl)-6-trifluoromethyl-[1,2,4]triazolo[1,5-a]pyridin-2-yl]-[3-(4-methyl-piperazin-1-yl)-phenyl]-amine

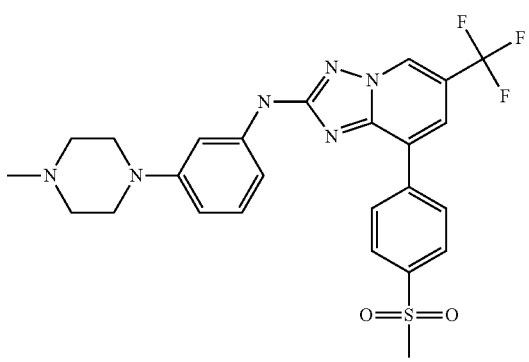 [SMILES: CN1CCN(c2cccc(Nc3nc4c(-c5ccc(S(C)(=O)=O)cc5)cc(C(F)(F)F)cn4n3)c2)CC1]

102a) 8-Bromo-6-trifluoromethyl-[1,2,4]triazolo[1,5-a]pyridin-2-ylamine was prepared from 3-bromo-5-trifluoromethyl-pyridin-2-ylamine, ethoxycarbonylisothiocyanate, and hydroxylamine hydrochloride in a manner analogous to Steps 2a-b. $^1$H NMR (400 MHz, (D$_3$C)$_2$SO, δ, ppm): 9.24 (s, 1H), 8.08 (s, 1H), 6.62 (bs, 2H). MS=282.9 (MH)+.

102b) 8-(4-Methanesulfonyl-phenyl)-6-trifluoromethyl-[1,2,4]triazolo[1,5-a]pyridin-2-ylamine was prepared from 8-bromo-6-trifluoromethyl-[1,2,4]triazolo[1,5-a]pyridin-2-ylamine and (4-methylsulfonylphenyl)boronic acid in a manner analogous to Step 2c to afford a white solid (67%) MP=236-237° C. $^1$H NMR (400 MHz, (D$_3$C)$_2$SO, δ, ppm): 9.28 (s, 1H), 8.42 (d, J=7.8 Hz, 2H), 8.07 (s, 1H), 8.06 (d, J=7.8 Hz, 2H), 6.58 (bs, 2H), 3.29 (s, 3H). MS=356.33 (MH)+.

102c) [8-(4-Methanesulfonyl-phenyl)-6-trifluoromethyl-[1,2,4]triazolo[1,5-a]pyridin-2-yl]-[3-(4-methyl-piperazin-1-yl)-phenyl]-amine was prepared from 8-(4-methanesulfonyl-phenyl)-6-trifluoromethyl-[1,2,4]triazolo[1,5-a]pyridin-2-ylamine and 1-(3-bromo-phenyl)-4-methyl-piperazine in a manner analogous to Step 2d and was isolated as a yellow solid (2% yield). $^1$H NMR (400 MHz, (D$_3$C)$_2$SO, δ, ppm): 8.84 (s, 1H), 8.28 (d, J=8.3 Hz, 2H), 8.14 (d, J=7.2 Hz, 2H), 7.81 (s, 1H), 6.95 (m, 2H), 6.64 (d, 1H), 3.32 (bm, 4H), 3.14 (s, 3H), 2.67 (bm, 4H), 2.44 (s, 3H). MS=531.1 (MH)+.

Example 103

[8-(4-Methanesulfonyl-phenyl)-6-trifluoromethyl-[1,2,4]triazolo[1,5-a]pyridin-2-yl]-[4-(4-methyl-piperazin-1-yl)-phenyl]-amine

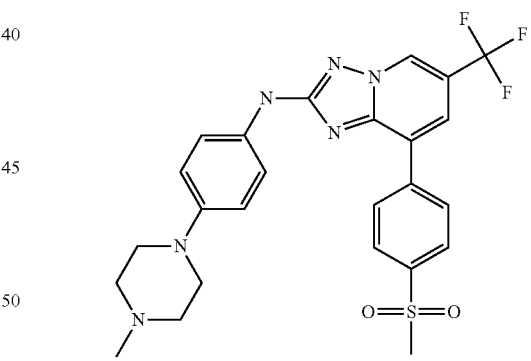

[8-(4-Methanesulfonyl-phenyl)-6-trifluoromethyl-[1,2,4]triazolo[1,5-a]pyridin-2-yl]-[4-(4-methyl-piperazin-1-yl)-phenyl]-amine was prepared from 8-(4-methanesulfonyl-phenyl)-6-trifluoromethyl-[1,2,4]triazolo[1,5-a]pyridin-2-ylamine and 1-(4-bromo-phenyl)-4-methyl-piperazine in a manner analogous to Step 2d and was isolated as a yellow solid (21% yield). MP 126-134° C. $^1$H NMR (400 MHz, (CDCl$_3$, δ, ppm): 8.82 (s, 1H), 8.25 (d, J=7.8 Hz, 2H), 8.13 (d, J=7.3 Hz, 2H), 7.79 (s, 1H), 7.49 (d, J=8.2 Hz, 2H), 6.99 (d, J=8.2 Hz, 2H), 6.88 (s, 1H), 3.21 (bm, 4H), 3.13 (s, 3H), 2.66 (bm, 4H), 2.40 (s, 3H). MS=531.0 (MH)+.

Example 104

[8-(4-Methanesulfonyl-phenyl)-6-trifluoromethyl-[1,2,4]triazolo[1,5-a]pyridin-2-yl]-[6-(4-methyl-piperazin-1-yl)-pyridin-3-yl]-amine

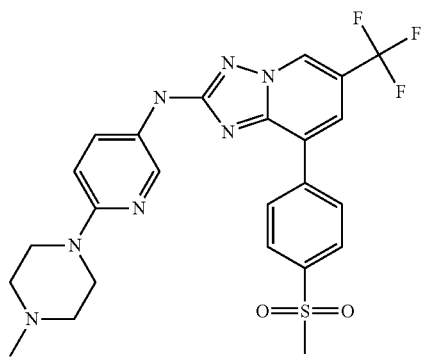 [SMILES: CN1CCN(c2ccc(Nc3nc4c(-c5ccc(S(C)(=O)=O)cc5)cc(C(F)(F)F)cn4n3)cn2)CC1]

[8-(4-Methanesulfonyl-phenyl)-6-trifluoromethyl-[1,2,4]triazolo[1,5-a]pyridin-2-yl]-[6-(4-methyl-piperazin-1-yl)-pyridin-3-yl]-amine was prepared from 8-(4-methanesulfonyl-phenyl)-6-trifluoromethyl-[1,2,4]triazolo[1,5-a]pyridin-2-ylamine and 1-(5-bromo-pyridin-2-yl)-4-methyl-piperazine in a manner analogous to Step 2d and was isolated as a yellow solid (16% yield). MP 210-215° C. $^1$H NMR (400 MHz, (CDCl$_3$, δ, ppm): 8.79 (s, 1H), 8.38 (s, 1H), 8.25 (d, J=8.5 Hz, 2H), 8.14 (d, J=7.3 Hz, 2H), 7.90 (d, 1H), 7.80 (s, 1H), 7.49 (d, J=8.2 Hz, 2H), 6.99 (d, J=8.2 Hz, 2H), 6.96 (d, 1H), 6.88 (s, 1H), 3.21 (bm, 4H), 3.13 (s, 3H), 2.66 (bm, 4H), 1.57 (s, 3H). MS=532.1 (MH)+.

Example 105

[6-Fluoro-8-(4-methanesulfonyl-phenyl)-[1,2,4]triazolo[1,5-a]pyridin-2-yl]-bis-[3-(4-methyl-piperazin-1-yl)-phenyl]-amine

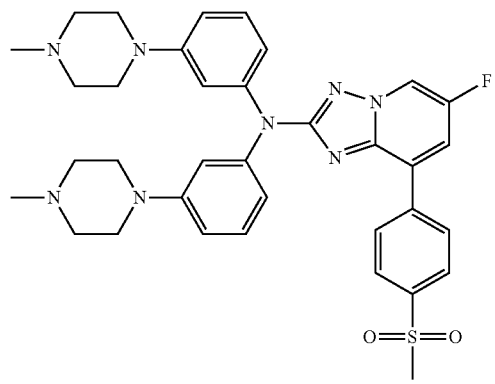 [SMILES: CN1CCN(c2cccc(N(c3cccc(N4CCN(C)CC4)c3)c3nc4c(-c5ccc(S(C)(=O)=O)cc5)cc(F)cn4n3)c2)CC1]

105a) To a solution of 5-Fluoro-pyridin-2-ylamine (3.00 g, 26.8 mmol) in acetic acid (30.0 mL, 528 mmol) at 80° C. was added bromine (5.50 mL, 107 mmol) in acetic acid (5.50 mL, 96.7 mmol). The temperature was maintained for one hour. The reaction was poured over ice, neutralized, and extracted with EtOAc. The organic layer was purified with ISCO silica gel chromatography to afford 3-bromo-5-fluoro-pyridine-2-ylamine. 6-Fluoro-8-bromo-[1,2,4]triazolo[1,5-a]pyridin-2-ylamine was prepared from 3-bromo-5-fluoro-pyridine-2-ylamine in a manner analogous to Steps 2a-b to afford a white solid (80%). MP=243-246° C. $^1$H NMR (400 MHz, (D$_3$C)$_2$SO, δ, ppm): 8.97 (s, 1H), 7.99 (d, J=8.5 Hz, 1H), 6.28 (bs, 2H). MS=231.0 (MH)+.

105b) 6-Fluoro-8-(4-methanesulfonyl-phenyl)-[1,2,4]triazolo[1,5-a]pyridin-2-ylamine prepared from 8-Bromo-6-fluoro-[1,2,4]triazolo[1,5-a]pyridin-2-ylamine and (4-Methylsulfonylphenyl)boronic acid in a manner analogous to Step 2c to afford a tan solid (45%). MP=226-234° C. $^1$H NMR (400 MHz, (D$_3$C)$_2$SO, δ, ppm): 9.00 (s, 1H), 8.43 (d, J=7.8 Hz, 2H), 8.06-8.00 (m, 3H), 6.27 (bs, 2H), 3.28 (s, 3H). MS=307.0 (MH)+.

105c) [6-Fluoro-8-(4-methanesulfonyl-phenyl)-[1,2,4]triazolo[1,5-a]pyridin-2-yl]-bis-[3-(4-methyl-piperazin-1-yl)-phenyl]-amine was formed from 6-fluoro-8-(4-methanesulfonyl-phenyl)-[1,2,4]triazolo[1,5-a]pyridin-2-ylamine and 1-(3-bromo-phenyl)-4-methyl-piperazine in a manner analogous to Step 2d and was isolated as a yellow solid (14% yield). $^1$H NMR (400 MHz, CDCl$_3$, δ, ppm): 8.32 (m, 2H), 8.10 (d, J=7.8 Hz, 2H), 7.70 (d, J=9.4 Hz, 1H), 7.55 (s, 1H), 7.49-7.46 (m, 1H), 7.40-7.35 (m, 2H), 7.17-7.13 (m, 2H), 7.01 (s, 1H), 6.71 (d, J=8.0 Hz, 1H), 6.54 (d, J=8.0 Hz, 1H), 3.31 (bm, 4H), 3.18 (bm, 4H), 3.12 (s, 3H), 2.62 (bm, 4H), 2.58 (bm, 4H), 2.40 (s, 3H), 2.38 (s, 3H).

Example 106

[6-Fluoro-8-(4-methanesulfonyl-phenyl)-[1,2,4]triazolo[1,5-a]pyridin-2-yl]-[4-(4-methyl-piperazin-1-yl)-phenyl]-amine

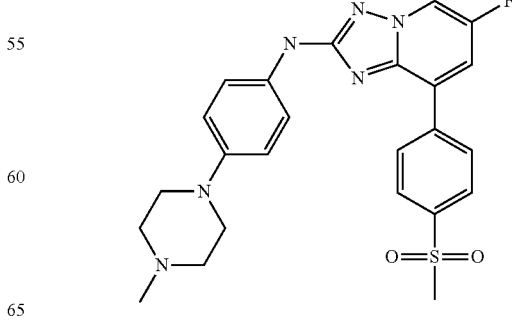

[6-Fluoro-8-(4-methanesulfonyl-phenyl)-[1,2,4]triazolo[1,5-a]pyridin-2-yl]-[4-(4-methyl-piperazin-1-yl)-phenyl]-amine was prepared from 6-fluoro-8-(4-methanesulfonyl-phenyl)-[1,2,4]triazolo[1,5-a]pyridin-2-ylamine and 1-(4-bromo-phenyl)-4-methyl-piperazine in a manner analogous to Step 2d and was isolated as an orange solid (23% yield). $^1$H NMR (400 MHz, CDCl$_3$, δ, ppm): 8.45 (s, 1H), 8.26 (d, J=8.0 Hz, 2H), 8.11 (d, J=7.7 Hz, 2H), 7.58 (d, J=9.0 Hz, 1H), 7.48 (dd, J=11.5 Hz, 7.8 Hz, 2H), 6.98 (d, J=7.9 Hz, 2H), 6.76 (s, 1H), 3.27 (bm, 4H), 3.12 (s, 3H), 2.62 (bm, 4H), 2.38 (s, 3H).

Example 107

[5-(4-Methanesulfonyl-phenyl)-[1,2,4]triazolo[1,5-a]pyrazin-2-yl]-[3-(4-methyl-piperazin-1-yl)-phenyl]-amine

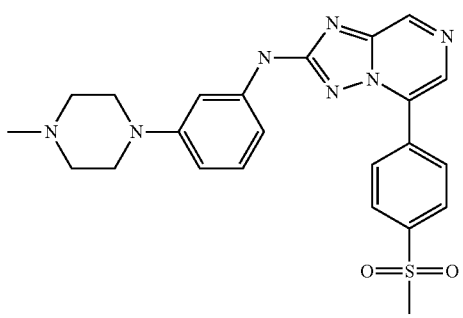 [SMILES: CN1CCN(c2cccc(Nc3nc4cncc(-c5ccc(S(C)(=O)=O)cc5)n4n3)c2)CC1]

107a) 6-(4-Methanesulfonyl-phenyl)-pyrazin-2-ylamine was prepared from 6-chloro-pyrazin-2-ylamine and (4-methylsulfonylphenyl)boronic acid in a manner analogous to Step 2c to afford an off-white solid (99%). $^1$H NMR (400 MHz, (D$_3$C)$_2$SO, δ, ppm): 8.39 (s, 1H), 8.25 (d, 7.6 Hz, 2H) 8.02 (d, 7.6 Hz, 2H), 7.95 (s, 1H), 6.70 (bs, 2H), 3.26 (s, 3H).

107b) 5-(4-Methanesulfonyl-phenyl)-[1,2,4]triazolo[1,5-a]pyrazin-2-ylamine was prepared from 6-(4-methanesulfonyl-phenyl)-pyrazin-2-ylamine in a manner analogous to Steps 2a-b. (37%), MS=291.1 (MH)+.

107c) [5-(4-Methanesulfonyl-phenyl)-[1,2,4]triazolo[1,5-a]pyrazin-2-yl]-[3-(4-methyl-piperazin-1-yl)-phenyl]-amine was prepared from 5-(4-methanesulfonyl-phenyl)-[1,2,4]triazolo[1,5-a]pyrazin-2-ylamine and 1-(3-bromo-phenyl)-4-methyl-piperazine in a manner analogous to Step 2d and was isolated as a pale orange lyophilate (3% yield). $^1$H NMR (400 MHz, CDCl$_3$, δ, ppm): 10.0 (s, 1H), 9.62 (bs, 1H), 9.14 (s, 1H), 8.42-8.40 (m, 3H), 8.20 (d, J=8.2 Hz, 2H), 7.58 (s, 1H), 7.18 (m, 1H), 7.05 (d, J=8.4 Hz, 1H), 6.60 (d, J=8.4 Hz, 1H), 3.72 (bd, 2H), 3.52 (bd, 2H), 3.39 (s, 3H), 3.17 (m, 2H), 2.93 (m, 2H), 2.87 (s, 3H). MS=464.1 (MH)+.

Example 108

[5-(4-Methanesulfonyl-phenyl)-[1,2,4]triazolo[1,5-a]pyrazin-2-yl]-[5-(4-methyl-piperazin-1-yl)-pyridin-3-yl]-amine

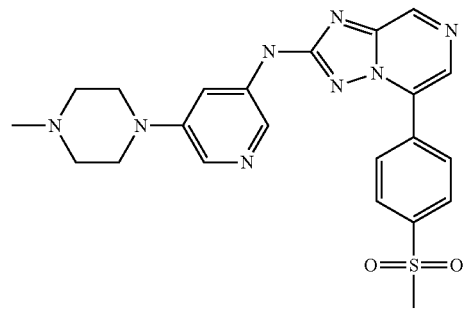

108a) 1-(5-Bromo-pyridin-3-yl)-4-methyl-piperazine was prepared from 3,5-dibromo-pyridine (1.00 g, 4.22 mmol) and piperazine, 1-methyl-(0.936 mL, 8.44 mmol) which were combined and heated in a microwave vial to 180° C. for 2 hours. The reaction mixture was taken up in dichloromethane and purified by silica gel chromatography 0-10% methanol in dichloromethane to afford a clear oil (37%). $^1$H NMR (400 MHz, (D$_3$C)$_2$SO, δ, ppm): 8.20 (s, 1H), 8.11 (s, 1H), 7.29 (m, 1H), 3.25 (bm, 4H), 2.58 (bm, 4H), 2.35 (s, 3H).

108b) [5-(4-Methanesulfonyl-phenyl)-[1,2,4]triazolo[1,5-a]pyrazin-2-yl]-[5-(4-methyl-piperazin-1-yl)-pyridin-3-yl]-amine was prepared from 5-(4-methanesulfonyl-phenyl)-[1,2,4]triazolo[1,5-a]pyrazin-2-ylamine and 1-(5-bromo-pyridin-3-yl)-4-methyl-piperazine in a manner analogous to Step 2d and was isolated as an off-white lyophilate (4% yield). $^1$H NMR (400 MHz, CDCl$_3$, δ, ppm): 10.5 (bs, 1H), 9.86 (bs, 1H), 9.22 (s, 1H), 8.49 (s, 1H), 8.40 (d, J=7.9 Hz, 2H), 8.35 (s, 1H), 8.19 (d, J=7.6 Hz, 2H), 8.05 (d, J=16.5 Hz, 2H), 3.84 (bm, 2H), 3.55 (bm, 2H), 3.38 (s, 3H), 3.20 (bm, 2H), 3.09 (bm, 2H), 2.88 (s, 3H). MS=465.1 (MH)+.

Example 109

N(8)-(3-Methanesulfonyl-phenyl)-N(2)-[4-(4-methyl-piperazin-1-yl)-phenyl]-[1,2,4]triazolo[1,5-a]pyridine-2,8-diamine

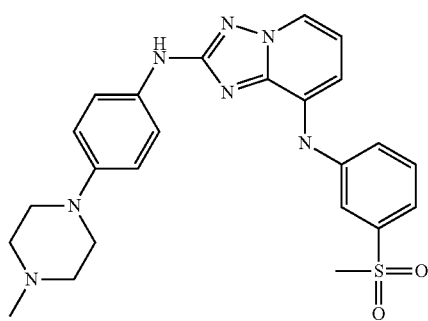 [SMILES: CN1CCN(c2ccc(Nc3nc4c(Nc5cccc(S(C)(=O)=O)c5)cccn4n3)cc2)CC1]

109a) (2-Chloro-[1,2,4]triazolo[1,5-a]pyridin-8-yl)-(3-methanesulfonyl-phenyl)-amine was prepared from 8-bromo-2-chloro-[1,2,4]triazolo[1,5-a]pyridine (250.0 mg, 1.075 mmol) and 3-methanesulfonyl-phenylamine; hydrochloride (245.0 mg, 1.180 mmol) in a manner analogous to Example 2d. Product was isolated as a pale yellow solid (0.268 g, 77%). $^1$H NMR (400 MHz, CDCl$_3$, δ, ppm): 8.10 (d, J=6.7 Hz, 1H), 7.87 (s, 1H), 7.64 (d, J=7.6 Hz, 1H), 7.58 (t, J=8.0 Hz, 1H), 7.46 (d, J=7.7 Hz, 1H), 7.30-7.25 (m, 1H), 7.03 (s, 1H), 6.99 (t, J=6.9 Hz, 1H), 3.09 (s, 3H). MS=323, 325 (MH)+.

109b) N(8)-(3-Methanesulfonyl-phenyl)-N(2)-[4-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(3-methanesulfonyl-phenyl)-amine (75.0 mg, 0.232 mmol) and 4-(4-methyl-piperazin-1-yl)-phenylamine (50.0 mg, 0.261 mmol) with 2,2'-bis-dicyclohexylphosphanyl-biphenyl (25.0 mg, 0.0457 mmol) as the ligand in a manner analogous to Example 2d. Product isolated as a tan foam (0.009 g, 8%). $^1$H NMR (400 MHz, CDCl$_3$, δ, ppm): 8.02 (d, J=6.2 Hz, 1H), 7.81 (s, 1H), 7.59-7.43 (m, 5H), 7.20 (d, J=8.0 Hz, 1H), 6.97 (d, J=7.5 Hz, 2H), 6.85 (s, 1H), 6.79 (t, J=7.4 Hz, 1H), 6.59 (s, 1H), 3.19-3.14 (m, 4H), 3.07 (s, 3H), 2.62-2.57 (m, 4H), 2.36 (s, 3H). MS=478 (MH)+.

Example 110

N(8)-(3-Methanesulfonyl-phenyl)-N(2)-[3-(4-methyl-piperazin-1-yl)-phenyl]-[1,2,4]triazolo[1,5-a]pyridine-2,8-diamine

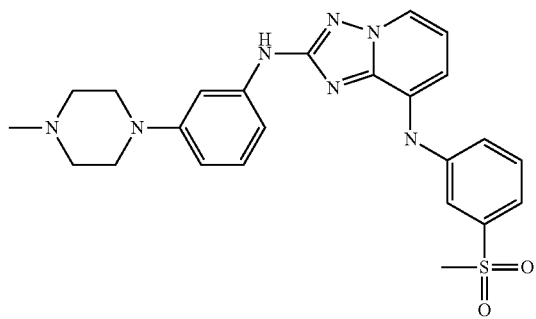 [SMILES: CN1CCN(c2cccc(Nc3nc4c(Nc5cccc(S(C)(=O)=O)c5)cccn4n3)c2)CC1]

N(8)-(3-Methanesulfonyl-phenyl)-N(2)-[3-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(3-methanesulfonyl-phenyl)-amine (75.0 mg, 0.232 mmol) and 3-(4-methylpiperazin-1-yl)aniline (50.0 mg, 0.261 mmol) with 2,2'-bis-dicyclohexylphosphanyl-biphenyl (25.0 mg, 0.0457 mmol) as the ligand in a manner analogous to Example 2d. Product isolated as a tan foam (0.013 g, 12%). $^1$H NMR (400 MHz, CDCl$_3$, δ, ppm): 8.05 (d, J=6.1 Hz, 1H), 7.81 (s, 1H), 7.60-7.50 (m, 2H), 7.45 (d, J=7.3 Hz, 1H), 7.27-7.18 (m, 3H), 7.09 (d, J=7.3 Hz, 1H), 6.85 (s, 1H), 6.81 (t, J=7.1 Hz, 1H), 6.75 (s, 1H), 6.60 (d, J=8.3 Hz, 1H), 3.30-3.25 (m, 4H), 3.08 (s, 3H), 2.62-2.57 (m, 4H), 2.37 (s, 3H). MS=478 (MH)+.

Example 111

N-Methyl-N-(3-{2-[3-(4-methyl-piperazin-1-yl)-phenylamino]-[1,2,4]triazolo[1,5-a]pyridin-8-ylamino}-pyridin-2-yl)-methanesulfonamide

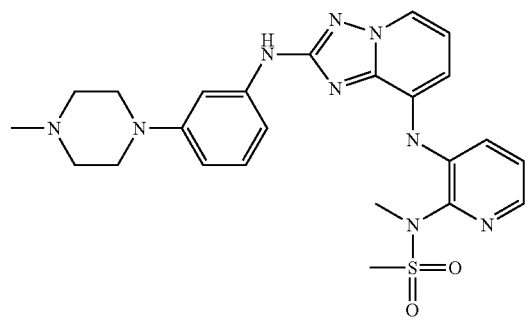 [SMILES: CN1CCN(c2cccc(Nc3nc4c(Nc5cccnc5N(C)S(C)(=O)=O)cccn4n3)c2)CC1]

111a) N-(3-Amino-pyridin-2-yl)-N-methyl-methanesulfonamide was prepared from N-methyl-N-(3-nitro-pyridin-2-yl)-methanesulfonamide (6.20 g, 26.8 mmol)(prepared as described in J. Med. Chem., 2007, 50, 3431) via hydrogenation using a Paar apparatus with 10% Palladium on Carbon (50% Wet)(5:45:50, Palladium:carbon black:Water, 5.71 g, 2.68 mmol) and Hydrogen (50 psi) in 2:1 ethyl acetate:methanol (150 mL). The mixture was shaken on a Paar apparatus until adsorption of hydrogen ceased. The mixture was degassed, backflushed with nitrogen, filtered through a plug of diatomaceous earth and rinsed with dichloromethane. The filtrate was evaporated under reduced pressure. Product isolated as brown solid (5.15 g, 95%). $^1$H NMR (400 MHz, CDCl$_3$, δ, ppm): 7.85 (dd, J=3.7, 2.5 Hz, 1H), 7.10-7.08 (m, 2H), 4.24 (br s, 2H), 3.23 (s, 3H), 3.08 (s, 3H). MS=202 (MH)+.

111b) N-[3-(2-Chloro-[1,2,4]triazolo[1,5-a]pyridin-8-ylamino)-pyridin-2-yl]-N-methyl-methanesulfonamide was prepared from N-(3-amino-pyridin-2-yl)-N-methyl-methanesulfonamide (238.0 mg, 1.183 mmol) and 8-bromo-2-chloro-[1,2,4]triazolo[1,5-a]pyridine (250.0 mg, 1.075 mmol) in a manner analogous to Example 2d. Product isolated as a pale yellow foam (0.185 g, 48%). $^1$H NMR (400 MHz, CDCl$_3$, δ, ppm): 8.18-8.15 (m, 1H), 8.11 (d, J=6.8 Hz, 1H), 7.81 (d, J=8.0 Hz, 1H), 7.50 (s, 1H), 7.32-7.25 (m, 1H), 7.17 (d, J=7.5 Hz, 1H), 6.93 (t, J=7.3 Hz, 1H), 3.31 (s, 3H), 3.07 (s, 3H). MS=353, 355 (MH)+.

111c) N-Methyl-N-(3-{2-[3-(4-methyl-piperazin-1-yl)-phenylamino]-[1,2,4]triazolo[1,5-a]pyridin-8-ylamino}-pyridin-2-yl)-methanesulfonamide was prepared from N-[3-(2-chloro-[1,2,4]triazolo[1,5-a]pyridin-8-ylamino)-pyridin-2-yl]-N-methyl-methanesulfonamide (75.0 mg, 0.212 mmol) and 3-(4-methylpiperazin-1-yl)aniline (45.0 mg, 0.235 mmol) with 2,2'-bis-dicyclohexylphosphanyl-biphenyl (23.0 mg, 0.0421 mmol) as the ligand in a manner analogous to Example 2d. Product isolated as a brown foam (0.017 g, 16%). $^1$H NMR (400 MHz, CDCl$_3$, δ, ppm): 8.11-8.06 (m, 2H), 7.78 (d, J=7.5 Hz, 1H), 7.52 (s, 1H), 7.28-7.19 (m, 3H), 7.12 (d, J=7.5 Hz, 1H), 7.06 (d, J=7.9 Hz, 1H), 6.84 (s, 1H), 6.78-6.73 (m, 1H), 6.57 (d, J=8.0 Hz, 1H), 3.32 (s, 3H), 3.29-3.24 (m, 4H), 3.09 (s, 3H), 2.62-2.57 (m, 4H), 2.36 (s, 3H). MS=518 (MH)+.

Example 112

(4-Methanesulfonyl-phenyl)-[8-(4-methanesulfonyl-phenyl)-[1,2,4]triazolo[1,5-a]pyridin-2-yl]-amine

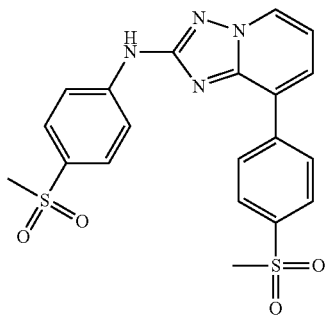 [SMILES: CS(=O)(=O)c1ccc(Nc2nc3c(-c4ccc(S(C)(=O)=O)cc4)cccn3n2)cc1]

(4-Methanesulfonyl-phenyl)-[8-(4-methanesulfonyl-phenyl)-[1,2,4]triazolo[1,5-a]pyridin-2-yl]-amine was prepared from 8-(4-methanesulfonyl-phenyl)-[1,2,4]triazolo[1,5-a]pyridin-2-ylamine (75.0 mg, 0.260 mmol) and 1-bromo-4-methanesulfonyl-benzene (75.0 mg, 0.319 mmol) with 2,2'-bis-dicyclohexylphosphanyl-biphenyl (30.0 mg, 0.0549 mmol) as the ligand in a manner analogous to Example 2d. Product isolated as tan solid (0.063 g, 55%). MP=280-282° C. $^1$H NMR (400 MHz, CDCl$_3$, δ, ppm): 8.56 (d, J=5.7 Hz, 1H), 8.22 (d, J=8.0 Hz, 2H), 8.10 (d, J=7.6 Hz, 2H), 7.92 (d, J=7.8 Hz, 2H), 7.77 (d, J=7.3 Hz, 2H), 7.72 (d, J=7.3 Hz, 1H), 7.32 (s, 1H), 7.14-7.09 (m, 1H), 3.11 (s, 3H), 3.06 (s, 3H). MS=443 (MH)+.

Example 113

(3-Methanesulfonyl-phenyl)-[8-(4-methanesulfonyl-phenyl)-[1,2,4]triazolo[1,5-a]pyridin-2-yl]-amine

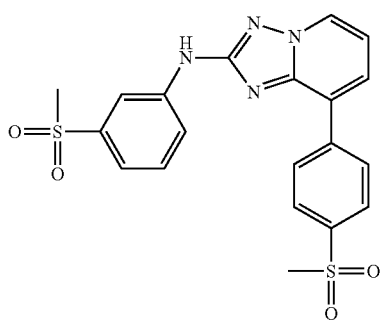 [SMILES: CS(=O)(=O)c1ccc(-c2cccn3nc(Nc4cccc(S(C)(=O)=O)c4)nc23)cc1]

(3-Methanesulfonyl-phenyl)-[8-(4-methanesulfonyl-phenyl)-[1,2,4]triazolo[1,5-a]pyridin-2-yl]-amine was prepared from 8-(4-methanesulfonyl-phenyl)-[1,2,4]triazolo[1,5-a]pyridin-2-ylamine (75.0 mg, 0.260 mmol) and 1-bromo-3-methanesulfonyl-benzene (75.0 mg, 0.319 mmol) with 2,2'-bis-dicyclohexylphosphanyl-biphenyl (30.0 mg, 0.0549 mmol) as the ligand in a manner analogous to Example 2d. Product isolated as a yellow solid (0.089 g, 77%). MP=230-234° C. $^1$H NMR (400 MHz, CDCl$_3$, δ, ppm): 8.55 (d, J=6.9 Hz, 1H), 8.47 (s, 1H), 8.26 (d, J=7.9 Hz, 2H), 8.12 (d, J=7.5 Hz, 2H), 7.74-7.69 (m, 2H), 7.58-7.50 (m, 2H), 7.17 (s, 1H), 7.12-7.07 (m, 1H), 3.11 (s, 6H). MS=443 (MH)+.

Example 114

N-{4-[(1,1-dioxidothiomorpholin-4-yl)methyl]phenyl}-8-[4-(methylsulfonyl)phenyl][1,2,4]triazolo[1,5-a]pyridin-2-amine

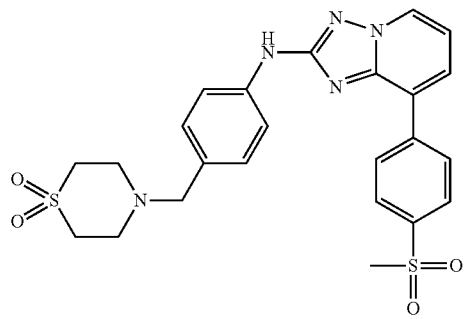 [SMILES: CS(=O)(=O)c1ccc(-c2cccn3nc(Nc4ccc(CN5CCS(=O)(=O)CC5)cc4)nc23)cc1]

114a) To a well stirred suspension of thiomorpholine 1,1-dioxide (0.36 g, 2.7 mmol) and potassium carbonate (0.37 g, 2.7 mmol) in acetone (5 mL) was added 1-bromo-4-chloromethyl-benzene (0.50 g, 2.4 mmol). The mixture was stirred for 48 hours at room temperature. The mixture was filtered and the volatiles were evaporated. The residue was suspended in ether (100 mL), filtered and evaporated to a solid. The material was purified via chromatography utilizing an ISCO automated purification apparatus (24 g silica gel column 10%→100% ethyl acetate in hexane). 4-(4-Bromo-benzyl)-thiomorpholine 1,1-dioxide was isolated as a white solid (0.72 g, 97%). $^1$H NMR (400 MHz, CDCl$_3$, δ, ppm): 7.47 (d, J=7.6 Hz, 2H), 7.19 (d, J=7.7 Hz, 2H), 3.60 (s, 2H), 3.08-2.94 (m, 8H). MS=304, 306 (MH)+.

114b) N-{4-[(1,1-dioxidothiomorpholin-4-yl)methyl]phenyl}-8-[4-(methylsulfonyl)phenyl][1,2,4]triazolo[1,5-a]pyridin-2-amine was prepared from 8-(4-methanesulfonyl-phenyl)-[1,2,4]triazolo[1,5-a]pyridin-2-ylamine (75.0 mg, 0.260 mmol) and 4-(4-bromo-benzyl)-thiomorpholine 1,1-dioxide (90.0 mg, 0.296 mmol) with 2,2'-bis-dicyclohexylphosphanyl-biphenyl (25.0 mg, 0.0457 mmol) as the ligand in a manner analogous to Example 2d. Product isolated as a pale yellow foam (0.039 g, 29%). $^1$H NMR (400 MHz, CDCl$_3$, δ, ppm): 8.50 (d, J=6.7 Hz, 1H), 8.23 (d, J=7.4 Hz, 2H), 8.09 (d, J=8.0 Hz, 2H), 7.67 (d, J=6.9 Hz, 1H), 7.56 (d, J=7.2 Hz, 2H), 7.29 (d, J=7.8 Hz, 2H), 7.04 (t, J=7.2 Hz, 1H), 6.94 (s, 1H), 3.62 (s, 2H), 3.10 (s, 3H), 3.08-3.03 (m, 4H), 3.02-2.97 (m, 4H). MS=512 (MH)+.

Example 115

N-{4-[(1,1-dioxidothiomorpholin-4-yl)methyl]phenyl}-5-[4-(methylsulfonyl)phenyl][1,2,4]triazolo[1,5-a]pyridin-2-amine

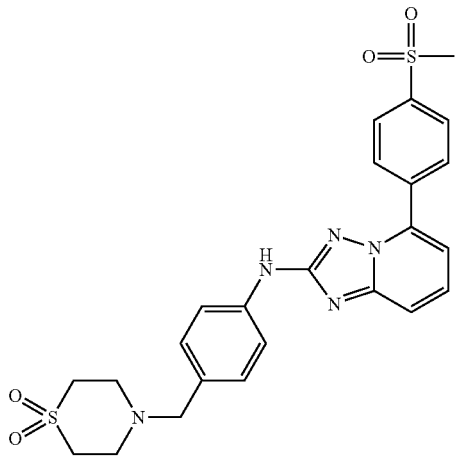 [SMILES: CS(=O)(=O)c1ccc(-c2cccc3nc(Nc4ccc(CN5CCS(=O)(=O)CC5)cc4)nn23)cc1]

N-{4-[(1,1-dioxidothiomorpholin-4-yl)methyl]phenyl}-5-[4-(methylsulfonyl)phenyl][1,2,4]triazolo[1,5-a]pyridin-2-amine was prepared from 5-(4-methanesulfonyl-phenyl)-[1,2,4]triazolo[1,5-a]pyridin-2-ylamine (75.0 mg, 0.260 mmol) and 4-(4-bromo-benzyl)-thiomorpholine 1,1-dioxide (90.0 mg, 0.296 mmol) with 2,2'-bis-dicyclohexylphosphanyl-biphenyl (25.0 mg, 0.0457 mmol) as the ligand in a manner analogous to Example 2d. Product isolated as a pale orange foam (0.040 g, 30%). $^1$H NMR (400 MHz, CDCl$_3$, δ, ppm): 8.25 (d, J=7.9 Hz, 2H), 8.14 (d, J=7.4 Hz, 2H), 7.59-7.56 (m, 2H), 7.52 (d, J=7.8 Hz, 2H), 7.29-7.25 (m, 2H), 7.08-7.03 (m, 1H), 6.94 (s, 1H), 3.61 (s, 2H), 3.16 (s, 3H), 3.08-3.03 (m, 4H), 3.01-2.96 (m, 4H). MS=512 (MH)+.

Example 116

[8-(4-Methanesulfonyl-phenyl)-[1,2,4]triazolo[1,5-a]pyridin-2-yl]-[3-(4-methyl-piperazin-1-ylmethyl)-phenyl]-amine

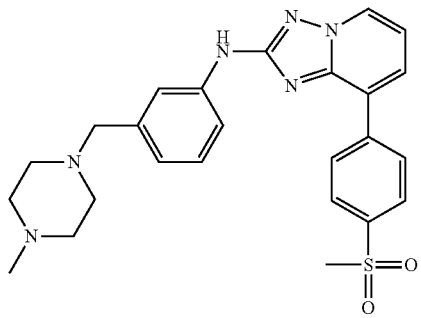 [SMILES: CN1CCN(Cc2cccc(Nc3nc4c(-c5ccc(S(C)(=O)=O)cc5)cccn4n3)c2)CC1]

[8-(4-Methanesulfonyl-phenyl)-[1,2,4]triazolo[1,5-a]pyridin-2-yl]-[3-(4-methyl-piperazin-1-ylmethyl)-phenyl]-amine was prepared from 8-(4-methanesulfonyl-phenyl)-[1,2,4]triazolo[1,5-a]pyridin-2-ylamine (75.0 mg, 0.260 mmol) and 1-(3-bromo-benzyl)-4-methyl-piperazine (77.0 mg, 0.286 mmol) with 2,2'-bis-dicyclohexylphosphanyl-biphenyl (29.0 mg, 0.0530 mmol) as the ligand in a manner analogous to Example 2d. Product isolated as a yellow foam (0.036 g, 29%). $^1$H NMR (400 MHz, CDCl$_3$, δ, ppm): 8.51 (d, J=6.6 Hz, 1H), 8.24 (d, J=8.5 Hz, 2H), 8.09 (d, J=8.5 Hz, 2H), 7.66 (dd, J=7.4, 0.9 Hz, 1H), 7.58 (dd, J=7.8, 1.9 Hz, 1H), 7.46 (s, 1H), 7.31 (t, J=7.8 Hz, 1H), 7.02 (t, J=7.2 Hz, 1H), 6.98 (d, J=7.5 Hz, 1H), 6.90 (s, 1H), 3.54 (s, 2H), 3.10 (s, 3H), 2.70-2.32 (m, 8H), 2.29 (s, 3H). MS=477 (MH)+.

Example 117

[5-(4-Methanesulfonyl-phenyl)-[1,2,4]triazolo[1,5-a]pyridin-2-yl]-(3-morpholin-4-ylmethyl-phenyl)-amine

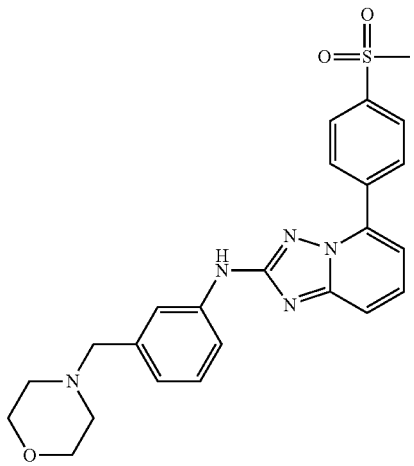 [SMILES: CS(=O)(=O)c1ccc(-c2cccc3nc(Nc4cccc(CN5CCOCC5)c4)nn23)cc1]

[5-(4-Methanesulfonyl-phenyl)-[1,2,4]triazolo[1,5-a]pyridin-2-yl]-(3-morpholin-4-ylmethyl-phenyl)-amine was prepared from 5-(4-methanesulfonyl-phenyl)-[1,2,4]triazolo[1,5-a]pyridin-2-ylamine (75.0 mg, 0.260 mmol) and 4-(3-bromo-benzyl)-morpholine (75.0 mg, 0.293 mmol) with 2,2'-bis-dicyclohexylphosphanyl-biphenyl (29.0 mg, 0.0530 mmol) as the ligand in a manner analogous to Example 2d. Product isolated as yellow foam (0.042 g, 35%). $^1$H NMR (400 MHz, CDCl$_3$, δ, ppm): 8.27 (d, J=8.5 Hz, 2H), 8.14 (d, J=8.5 Hz, 2H), 7.59-7.47 (m, 4H), 7.29 (t, J=7.8 Hz, 1H), 7.06 (dd, J=4.5, 3.9 Hz, 1H), 6.97 (d, J=7.4 Hz, 1H), 6.94 (s, 1H), 3.73-3.67 (m, 4H), 3.50 (s, 2H), 3.15 (s, 3H), 2.50-2.42 (m, 4H). MS=464 (MH)+.

Example 118

[5-(4-Methanesulfonyl-phenyl)-[1,2,4]triazolo[1,5-a]pyridin-2-yl]-[3-(4-methyl-piperazin-1-ylmethyl)-phenyl]-amine

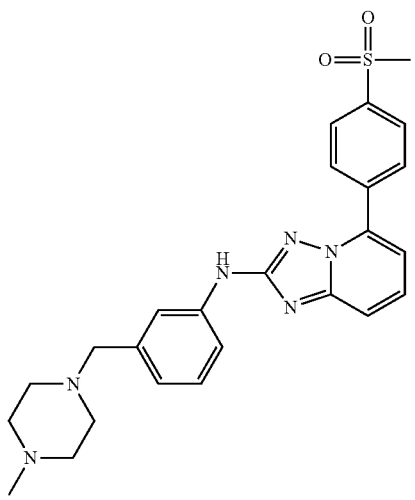 [SMILES: CN1CCN(Cc2cccc(Nc3nc4cccc(-c5ccc(S(C)(=O)=O)cc5)n4n3)c2)CC1]

[5-(4-Methanesulfonyl-phenyl)-[1,2,4]triazolo[1,5-a]pyridin-2-yl]-[3-(4-methyl-piperazin-1-ylmethyl)-phenyl]-amine was prepared from 5-(4-methanesulfonyl-phenyl)-[1,2,4]triazolo[1,5-a]pyridin-2-ylamine (75.0 mg, 0.260 mmol) and 1-(3-bromo-benzyl)-4-methyl-piperazine (77.0 mg, 0.286 mmol) with 2,2'-bis-dicyclohexylphosphanyl-biphenyl (25.0 mg, 0.0457 mmol) as the ligand in a manner analogous to Example 2d. Product isolated as a yellow foam (0.043, 35%). $^1$H NMR (400 MHz, CDCl$_3$, δ, ppm): 8.27 (d, J=8.6 Hz, 2H), 8.13 (d, J=8.6 Hz, 2H), 7.59-7.51 (m, 3H), 7.45-7.43 (m, 1H), 7.28 (t, J=7.8 Hz, 1H), 7.06 (dd, J=5.1, 3.3 Hz, 1H), 6.98-6.94 (m, 2H), 3.50 (s, 2H), 3.15 (s, 3H), 2.70-2.32 (m, 8H), 2.28 (s, 3H). MS=477 (MH)+.

Example 119

N-{4-[2-({4-[(1,1-dioxidothiomorpholin-4-yl)methyl]phenyl}amino)[1,2,4]triazolo[1,5-a]pyridin-8-yl]phenyl}-N-methylmethanesulfonamide

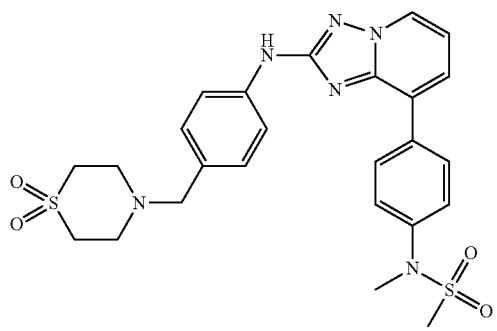 [SMILES: CN(c1ccc(-c2cccn3nc(Nc4ccc(CN5CCS(=O)(=O)CC5)cc4)nc23)cc1)S(C)(=O)=O]

N-{4-[2-({4-[(1,1-dioxidothiomorpholin-4-yl)methyl]phenyl}amino)[1,2,4]triazolo[1,5-a]pyridin-8-yl]phenyl}-N-methylmethanesulfonamide was prepared from N-[4-(2-amino-[1,2,4]triazolo[1,5-a]pyridin-8-yl)-phenyl]-N-methyl-methanesulfonamide (75.0 mg, 0.236 mmol) and 4-(4-bromo-benzyl)-thiomorpholine 1,1-dioxide (80.0 mg, 0.263 mmol) with 2,2'-bis-dicyclohexylphosphanyl-biphenyl (25.0 mg, 0.0457 mmol) as the ligand in a manner analogous to Example 2d. Product isolated as an orange solid (0.083 g, 65%). MP=177-180° C. $^1$H NMR (400 MHz, CDCl$_3$, δ, ppm): 8.45 (dd, J=6.7, 1.1 Hz, 1H), 8.04 (d, J=8.6 Hz, 2H), 7.60-7.52 (m, 5H), 7.28 (d, J=8.5 Hz, 2H), 7.00 (t, J=6.9 Hz, 1H), 6.89 (s, 1H), 3.62 (s, 2H), 3.39 (s, 3H), 3.08-2.96 (m, 8H), 2.90 (s, 3H). MS=541 (MH)+.

Example 120

N-{3-[(1,1-dioxidothiomorpholin-4-yl)methyl]phenyl}-8-[4-(methylsulfonyl)phenyl][1,2,4]triazolo[1,5-a]pyridin-2-amine

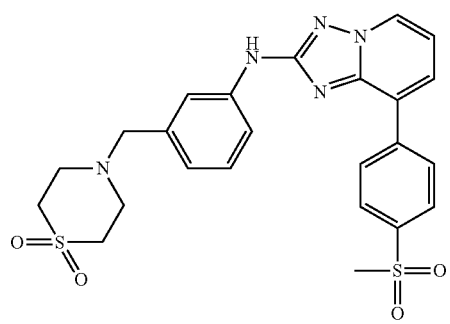 [SMILES: CS(=O)(=O)c1ccc(-c2cccn3nc(Nc4cccc(CN5CCS(=O)(=O)CC5)c4)nc23)cc1]

120a) To a suspension of thiomorpholine 1,1-dioxide (0.72 g, 5.4 mmol) and potassium carbonate (0.74 g, 5.4 mmol) in acetone (10 mL) was added bromo-3-chloromethyl-benzene (0.62 mL, 4.9 mmol). The mixture was stirred at room temperature for 18 hours. The mixture was diluted with dichloromethane (50 mL), filtered through a plug of diatomaceous earth and evaporated to a waxy solid. The material was purified via chromatography utilizing an ISCO automated purification apparatus (24 g silica gel column 10%→100% ethyl acetate in hexane). 4-(3-Bromo-benzyl)-thiomorpholine 1,1-dioxide was isolated as a clear viscous oil that solidified to a white solid (1.0 g, 67%). $^1$H NMR (400 MHz, CDCl$_3$, δ, ppm): 7.49 (s, 1H), 7.41 (ddd, J=6.9, 1.9, 1.9 Hz, 1H), 7.25-7.19 (m, 2H), 3.62 (s, 2H), 3.10-2.96 (m, 8H). MS=304, 306 (MH)+.

120b) N-{3-[(1,1-dioxidothiomorpholin-4-yl)methyl]phenyl}-8-[4-(methylsulfonyl)phenyl][1,2,4]triazolo[1,5-a]pyridin-2-amine was prepared from 8-(4-methanesulfonyl-phenyl)-[1,2,4]triazolo[1,5-a]pyridin-2-ylamine (75.0 mg, 0.260 mmol) and 4-(3-bromo-benzyl)-thiomorpholine 1,1-dioxide (90.0 mg, 0.296 mmol) with 2,2'-bis-dicyclohexylphosphanyl-biphenyl (29.0 mg, 0.0530 mmol) as the ligand in a manner analogous to Example 2d. Product isolated as a pale yellow foam (0.046 g, 34%). $^1$H NMR (400 MHz, CDCl$_3$, δ, ppm): 8.52 (dd, J=6.7, 1.0 Hz, 1H), 8.23 (d, J=8.H Hz, 2H), 8.09 (d, J=8.4 Hz, 2H), 7.68 (dd, J=7.4, 0.9 Hz, 1H), 7.62-7.60 (m, 1H), 7.48 (dd, J=8.1, 1.8 Hz, 1H), 7.32 (t, J=7.7 Hz, 1H), 7.05 (t, J=7.1 Hz, 1H), 6.97-6.93 (m, 2H), 3.70 (s, 2H), 3.13-3.01 (m, 11H). MS=512 (MH)+.

Example 121

N-{3-[(1,1-dioxidothiomorpholin-4-yl)methyl]phenyl}-5-[4-(methylsulfonyl)phenyl][1,2,4]triazolo[1,5-a]pyridin-2-amine

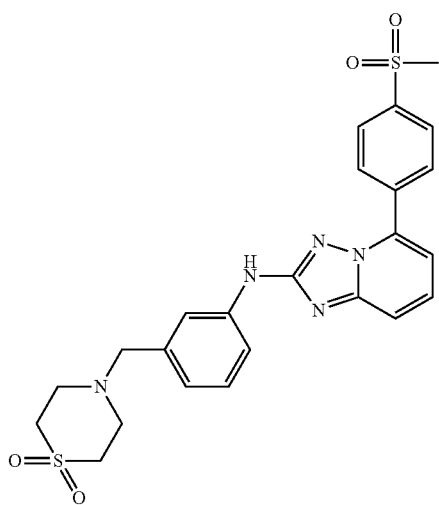 [SMILES: CS(=O)(=O)c1ccc(-c2cccc3nc(Nc4cccc(CN5CCS(=O)(=O)CC5)c4)nn23)cc1]

N-{3-[(1,1-dioxidothiomorpholin-4-yl)methyl]phenyl}-5-[4-(methylsulfonyl)phenyl][1,2,4]triazolo[1,5-a]pyridin-2-amine was prepared from 5-(4-methanesulfonyl-phenyl)-[1,2,4]triazolo[1,5-a]pyridin-2-ylamine (75.0 mg, 0.260 mmol) and 4-(3-bromo-benzyl)-thiomorpholine 1,1-dioxide (90.0 mg, 0.296 mmol) with 2,2'-bis-dicyclohexylphosphanyl-biphenyl (25.0 mg, 0.0457 mmol) as the ligand in a manner analogous to Example 2d. Product isolated as a yellow foam (0.042 g, 32%). $^1$H NMR (400 MHz, CDCl$_3$, δ, ppm): 8.26 (d, J=8.5 Hz, 2H), 8.14 (d, J=8.5 Hz, 2H), 7.45 (dd, J=8.2, 1.8 Hz, 1H), 7.30 (t, J=7.7 Hz, 1H), 7.07 (t, J=4.3 Hz, 1H), 6.96-6.91 (m, 2H), 3.65 (s, 2H), 3.16 (s, 3H), 3.07-2.97 (m, 8H). MS=512 (MH)+.

Example 122

N-Methyl-N-[3-({2-[4-(4-methyl-piperazin-1-yl)-phenylamino]-[1,2,4]triazolo[1,5-a]pyridin-8-ylamino}-methyl)-pyridin-2-yl]-methanesulfonamide

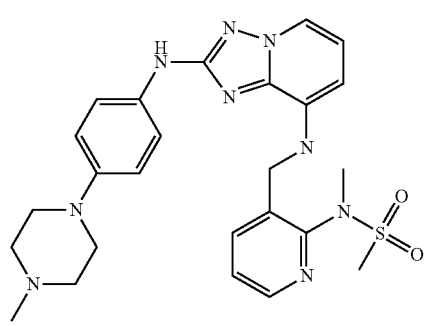 [SMILES: CN1CCN(c2ccc(Nc3nc4c(NCc5cccnc5N(C)S(C)(=O)=O)cccn4n3)cc2)CC1]

122a) N-(3-Aminomethyl-pyridin-2-yl)-N-methyl-methanesulfonamide was prepared from N-(3-cyano-pyridin-2-yl)-N-methyl-methanesulfonamide (3.35 g, 15.8 mmol)(prepared as described in *J. Heterocyclic Chemistry*, 1979, 16, 1361-1363) via hydrogenation using a Paar apparatus with 10% palladium on carbon (50% Wet)(5:45:50, Palladium:carbon black:Water, 5.71 g, 2.68 mmol) and hydrogen (50 psi) in 7M ammonia in methanol (100 mL). The mixture was shaken on a Paar apparatus until adsorption of hydrogen ceased. The mixture was degassed, backflushed with nitrogen, filtered through a plug of diatomaceous earth and rinsed with dichloromethane. The filtrate was evaporated under reduced pressure. Product isolated as pale yellow oil (3.20, 93%). $^1$H NMR (400 MHz, CDCl$_3$, δ, ppm): 8.37 (dd, J=4.6, 1.7 Hz, 1H), 7.92 (dd, J=7.7, 1.7 Hz, 1H), 7.32 (dd, J=7.7, 4.8 Hz, 1H), 4.04 (s, 2H), 3.26 (s, 3H), 3.08 (s, 3H). MS=216 (MH)+.

122b) N-{3-[(2-Chloro-[1,2,4]triazolo[1,5-a]pyridin-8-ylamino)-methyl]-pyridin-2-yl}-N-methyl-methanesulfonamide was prepared from 8-bromo-2-chloro-[1,2,4]triazolo[1,5-a]pyridine (100.0 mg, 0.4302 mmol) and N-(3-aminomethyl-pyridin-2-yl)-N-methyl-methanesulfonamide (102.0 mg, 0.4738 mmol) in a manner analogous to Example 2d. Product isolated as a tan solid (0.056 g, 35%). $^1$H NMR (400 MHz, CDCl$_3$, δ, ppm): 8.43 (d, J=4.6 Hz, 1H), 8.11 (d, J=6.5 Hz, 1H), 7.76 (d, J=7.6 Hz, 1H), 7.40-7.32 (m, 2H), 6.93 (t, J=7.5 Hz, 1H), 6.26 (d, J=7.9 Hz, 1H), 4.62 (d, J=6.3, 2H), 3.24 (s, 3H), 3.16 (s, 3H). MS=367, 369 (MH)+.

122c) N-Methyl-N-[3-({2-[4-(4-methyl-piperazin-1-yl)-phenylamino]-[1,2,4]triazolo[1,5-a]pyridin-8-ylamino}-methyl)-pyridin-2-yl]-methanesulfonamide was prepared from N-{3-[(2-chloro-[1,2,4]triazolo[1,5-a]pyridin-8-ylamino)-methyl]-pyridin-2-yl}-N-methyl-methanesulfonamide (75.0 mg, 0.204 mmol) and 4-(4-methyl-piperazin-1-yl)-phenylamine (47.0 mg, 0.246 mmol) with 2,2'-bis-dicyclohexylphosphanyl-biphenyl (25.0 mg, 0.0457 mmol) as the ligand in a manner analogous to Example 2d. Product isolated as a brown foam (0.030 g, 28%). $^1$H NMR (400 MHz, CDCl$_3$, δ, ppm): 8.40 (dd, J=4.7, 1.6 Hz, 1H), 7.84 (d, J=7.7 Hz, 1H), 7.80 (d, J=6.7 Hz, 1H), 7.48 (d, J=8.9 Hz, 2H), 7.29-7.24 (m, 1H), 6.96 (d, J=8.9 Hz, 2H), 6.63 (t, J=7.4 Hz, 1H), 6.56 (s, 1H), 6.28 (d, J=7.6 Hz, 1H), 5.28 (t, J=6.2 Hz, 1H), 4.76 (d, J=6.3 Hz, 2H), 3.32 (s, 3H), 3.18-3.13 (m, 4H), 3.09 (s, 3H), 2.62-2.57 (m, 4H), 2.36 (s, 3H). MS=522 (MH)+.

Example 123

N-Methyl-N-[3-({2-[4-(1-methyl-piperidin-4-yl)-phenylamino]-[1,2,4]triazolo[1,5-a]pyridin-8-ylamino}-methyl)-pyridin-2-yl]-methanesulfonamide

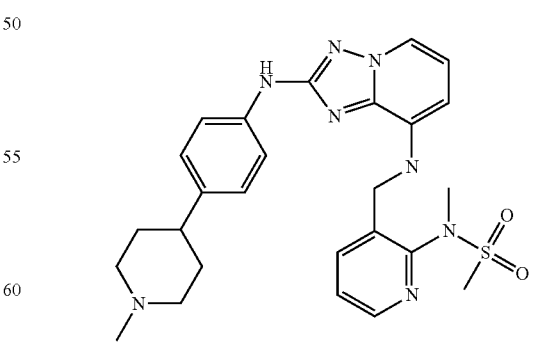

N-Methyl-N-[3-({2-[4-(1-methyl-piperidin-4-yl)-phenylamino]-[1,2,4]triazolo[1,5-a]pyridin-8-ylamino}-methyl)-pyridin-2-yl]-methanesulfonamide was prepared from N-{3-[(2-chloro-[1,2,4]triazolo[1,5-a]pyridin-8-ylamino)- methyl]-pyridin-2-yl}-N-methyl-methanesulfonamide (75.0 mg, 0.204 mmol) and 4-(1-methyl-piperidin-4-yl)-phenylamine (47.0 mg, 0.247 mmol) with 2,2'-bis-dicyclohexylphosphanyl-biphenyl (25.0 mg, 0.0457 mmol) as the ligand in a manner analogous to Example 2d. Product isolated as a yellow foam (0.061 g, 57%). $^1$H NMR (400 MHz, CDCl$_3$, δ, ppm): 8.41 (dd, J=4.7, 1.5 Hz, 1H), 7.87-7.80 (m, 2H), 7.50 (d, J=8.5 Hz, 2H), 7.29-7.25 (m, 1H), 7.20 (d, J=8.5 Hz, 2H), 6.69-6.62 (m, 2H), 6.30 (d, J=7.6 Hz, 1H), 5.29 (t, 5.8 Hz, 1H), 4.77 (d, J=6.2 Hz, 2H), 3.32 (s, 3H), 3.09 (s, 3H), 3.01-2.94 (m, 2H), 2.50-2.40 (m, 1H), 2.33 (s, 3H), 3.10-2.00 (m, 2H), 1.87-1.73 (m, 4H). MS=521 (MH)+.

Example 124

N-Methyl-N-[3-({2-[4-(2-pyrrolidin-1-yl-ethoxy)-phenylamino]-[1,2,4]triazolo[1,5-a]pyridin-8-ylamino}-methyl)-pyridin-2-yl]-methanesulfonamide

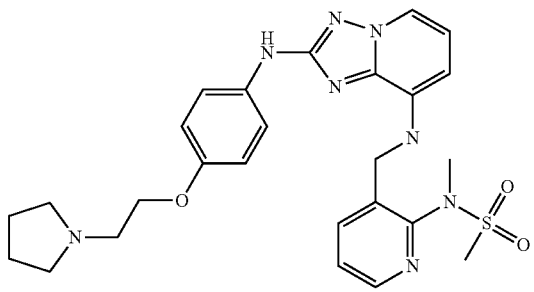 [SMILES: CN(c1ncccc1CNc1cccn2nc(Nc3ccc(OCCN4CCCC4)cc3)nc12)S(C)(=O)=O]

N-Methyl-N-[3-({2-[4-(2-pyrrolidin-1-yl-ethoxy)-phenylamino]-[1,2,4]triazolo[1,5-a]pyridin-8-ylamino}-methyl)-pyridin-2-yl]-methanesulfonamide was prepared from N-{3-[(2-chloro-[1,2,4]triazolo[1,5-a]pyridin-8-ylamino)-methyl]-pyridin-2-yl}-N-methyl-methanesulfonamide and 4-(2-pyrrolidin-1-yl-ethoxy)-phenylamine (51.0 mg, 0.247 mmol)(prepared as described in J. Med. Chem., 2006, 49, 4451-4454) with 2,2'-bis-dicyclohexylphosphanyl-biphenyl (25.0 mg, 0.0457 mmol) as the ligand in a manner analogous to Example 2d. Product isolated as a tan foam (0.021 g, 19%). $^1$H NMR (400 MHz, CDCl$_3$, δ, ppm): 8.42-8.39 (m, 1H), 7.85 (d, J=7.6 z, 1H), 7.80 (d, J=6.6 Hz, 1H), 7.48 (d, J=8.9 Hz, 2H), 7.30-7.25 (m, 1H), 6.92 (d, J=9.0 Hz, 2H), 6.64 (t, J=7.4 Hz, 1H), 6.52 (s, 1H), 6.29 (d, J=7.8 Hz, 1H), 5.27 (t, J=6.2, 1H), 4.77 (d, J=6.4 Hz, 2H), 4.10 (t, J=6.0 Hz, 2H), 3.32 (s, 3H), 3.09 (s, 3H), 2.90 (t, J=6.0 Hz, 2H), 2.68-2.58 (m, 4H), 1.86-1.76 (m, 4H). MS=537 (MH)+.

Example 125

N(8)-(2-Methanesulfonyl-phenyl)-N(2)-[4-(1-methyl-piperidin-4-yl)-phenyl]-[1,2,4]triazolo[1,5-a]pyridine-2,8-diamine

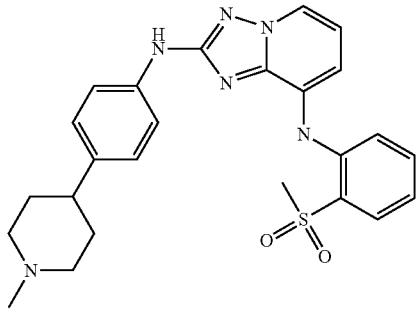 [SMILES: CN1CCC(c2ccc(Nc3nc4c(Nc5ccccc5S(C)(=O)=O)cccn4n3)cc2)CC1]

N(8)-(2-Methanesulfonyl-phenyl)-N(2)-[4-(1-methyl-piperidin-4-yl)-phenyl]-[1,2,4]triazolo[1,5-a]pyridine-2,8-diamine was prepared from (2-chloro-[1,2,4]triazolo[1,5-a]pyridin-8-yl)-(2-methanesulfonyl-phenyl)-amine (75.0 mg, 0.232 mmol) and 4-(1-methyl-piperidin-4-yl)-phenylamine (53.0 mg, 0.279 mmol) with 2,2'-bis-dicyclohexylphosphanyl-biphenyl (25.0 mg, 0.0457 mmol) as the ligand in a manner analogous to Example 2d. Product isolated as a tan foam (0.063 g, 57%). $^1$H NMR (400 MHz, CDCl$_3$, δ, ppm): 8.47 (s, 1H), 8.13 (d, J=6.8 Hz, 1H), 7.98 (dd, J=7.8, 1.2 Hz, 1H), 7.58-7.48 (m, 4H), 7.29-7.25 (m, 1H), 7.21 (d, J=8.4 Hz, 1H), 7.14-7.09 (m, 1H), 6.83-6.77 (m, 2H), 3.14 (s, 3H), 3.01-2.94 (m, 2H), 2.50-2.40 (m, 1H), 2.33 (s, 3H), 2.10-2.00 (m, 2H), 1.87-1.73 (m, 4H). MS=477 (MH)+.

Example 126

N(8)-(2-Methanesulfonyl-phenyl)-N(2)-[4-(2-pyrrolidin-1-yl-ethoxy)-phenyl]-[1,2,4]triazolo[1,5-a]pyridine-2,8-diamine

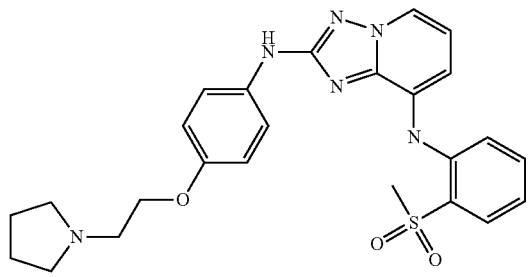 [SMILES: CS(=O)(=O)c1ccccc1Nc1cccn2nc(Nc3ccc(OCCN4CCCC4)cc3)nc12]

N(8)-(2-Methanesulfonyl-phenyl)-N(2)-[4-(2-pyrrolidin-1-yl-ethoxy)-phenyl]-[1,2,4]triazolo[1,5-a]pyridine-2,8-diamine was prepared from (2-chloro-[1,2,4]triazolo[1,5-a]pyridin-8-yl)-(2-methanesulfonyl-phenyl)-amine (75.0 mg, 0.232 mmol) and 4-(2-pyrrolidin-1-yl-ethoxy)-phenylamine (58.0 mg, 0.281 mmol)(prepared as described in J. Med. Chem., 2006, 49, 4451-4454) with 2,2'-bis-dicyclohexylphosphanyl-biphenyl (25.0 mg, 0.0457 mmol) as the ligand in a manner analogous to Example 2d. Product isolated as a yellow foam (0.064 g, 56%). ¹H NMR (400 MHz, CDCl₃, δ, ppm): 8.46 (s, 1H), 8.11 (d, J=6.7 Hz, 1H), 7.98 (dd, J=7.9, 1.1 Hz, 1H), 7.57-7.50 (m, 2H), 7.48 (d, J=9.0 Hz, 2H), 7.28-7.24 (m, 1H), 7.14-7.09 (m, 1H), 6.93 (d, J=9.0 Hz, 2H), 6.79 (t, J=6.4 Hz, 1H), 6.68 (s, 1H), 4.10 (t, J=6.1 Hz, 2H), 3.14 (s, 3H), 2.90 (t, J=5.9 Hz, 2H), 2.68-2.58 (m, 4H), 1.86-1.76 (m, 4H). MS=493 (MH)+.

Example 127

N-Methyl-N-(3-{2-[4-(4-methyl-piperazin-1-yl)-phenylamino]-[1,2,4]triazolo[1,5-a]pyridin-8-yl}-phenyl)-methanesulfonamide

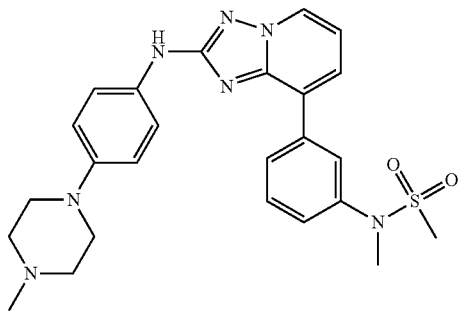 [SMILES: CN1CCN(c2ccc(Nc3nc4c(-c5cccc(N(C)S(C)(=O)=O)c5)cccn4n3)cc2)CC1]

127a) A round bottom flask was charged with potassium carbonate (0.56 g, 4.0 mmol) and acetone (20 mL). To the suspension was added N-[3-(4,4,5,5-tetramethyl-1,3,2-dioxaborolan-2-yl)-phenyl]-methanesulfonamide (1.0 g, 3.4 mmol) followed by iodomethane (0.25 mL, 4.0 mmol). The mixture was stirred at room temperature for 18 hours. The mixture was diluted with dichloromethane (20 mL), filtered through a plug of diatomaceous earth, rinsed with dichloromethane and evaporated to a viscous oil. The material was subjected to high vacuum for 18 hours. N-Methyl-N-[3-(4,4,5,5-tetramethyl-1,3,2-dioxaborolan-2-yl)-phenyl]-methanesulfonamide was isolated as pale yellow solid (1.03 g, 98%). ¹H NMR (400 MHz, CDCl₃, δ, ppm): 7.76-7.70 (m, 2H), 7.53 (d, J=7.9 Hz, 1H), 7.39 (t, J=7.5 Hz, 1H), 3.34 (s, 3H), 2.86 (s, 3H), 1.35 (s, 12H). MS=312 (MH)+.

127b) N-[3-(2-Amino-[1,2,4]triazolo[1,5-a]pyridin-8-yl)-phenyl]-N-methyl-methanesulfonamide was prepared from 8-bromo-[1,2,4]triazolo[1,5-a]pyridin-2-ylamine (500.0 mg, 2.347 mmol) and N-methyl-N-[3-(4,4,5,5-tetramethyl-1,3,2-dioxaborolan-2-yl)-phenyl]-methanesulfonamide (800.0 mg, 2.571 mmol) in a manner analogous to Example 2c. Product isolated as a white foam (0.529 g, 71%). ¹H NMR (400 MHz, (D₃C)₂SO, δ, ppm): 8.57 (d, J=6.5 Hz, 1H), 8.13-8.10 (m, 1H), 8.07 (d, J=7.9 Hz, 1H), 7.75 (d, J=7.5 Hz, 1H), 7.53 (t, J=8.0 Hz, 1H), 7.45 (d, J=8.0 Hz, 1H), 6.99 (t, J=6.9 Hz, 1H), 6.12 (s, 2H), 3.31 (s, 3H), 3.01 (s, 3H). MS=318 (MH)+.

127c) N-Methyl-N-(3-{2-[4-(4-methyl-piperazin-1-yl)-phenylamino]-[1,2,4]triazolo[1,5-a]pyridin-8-yl}-phenyl)-methanesulfonamide was prepared from N-[3-(2-amino-[1,2,4]triazolo[1,5-a]pyridin-8-yl)-phenyl]-N-methyl-methanesulfonamide (75.0 mg, 0.236 mmol) and 1-(4-bromo-phenyl)-4-methyl-piperazine (67.0 mg, 0.262 mmol) with 2,2'-bis-dicyclohexylphosphanyl-biphenyl (25.0 mg, 0.0457 mmol) as the ligand in a manner analogous to Example 2d. Product isolated as a yellow foam (0.033 g, 28%). ¹H NMR (400 MHz, CDCl₃, δ, ppm): 8.41 (d, J=6.6, 1H), 8.13 (s, 3H), 7.93 (d, J=7.9 Hz, 1H), 7.59 (d, J=7.4 Hz, 1H), 7.56-7.45 (m, 3H), 7.44 (dd, J=8.2, 1.2 Hz, 1H), 6.98-6.92 (m, 3H), 6.64 (s, 1H), 3.42 (s, 3H), 3.19-3.14 (m, 4H), 2.89 (s, 3H), 2.63-2.57 (m, 4H), 2.36 (s, 3H). MS=492 (MH)+.

Example 128

N-Methyl-N-(3-{2-[4-(2-pyrrolidin-1-yl-ethoxy)-phenylamino]-[1,2,4]triazolo[1,5-a]pyridin-8-yl}-phenyl)-methanesulfonamide

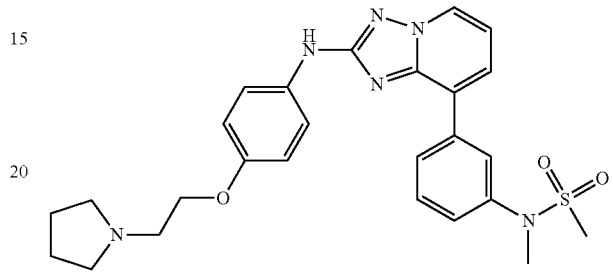

N-Methyl-N-(3-{2-[4-(2-pyrrolidin-1-yl-ethoxy)-phenylamino]-[1,2,4]triazolo[1,5-a]pyridin-8-yl}-phenyl)-methanesulfonamide was prepared from N-[3-(2-amino-[1,2,4]triazolo[1,5-a]pyridin-8-yl)-phenyl]-N-methyl-methanesulfonamide (75.0 mg, 0.236 mmol) and 1-[2-(4-bromo-phenoxy)-ethyl]-pyrrolidine (71.0 mg, 0.263 mmol) with 2,2'-bis-dicyclohexylphosphanyl-biphenyl (25.0 mg, 0.0457 mmol) as the ligand in a manner analogous to Example 2d. Product isolated as a tan foam (0.018 g, 15%). ¹H NMR (400 MHz, CDCl₃, δ, ppm): 8.31 (d, J=6.4 Hz, 1H), 8.13 (s, 3H), 7.93 (d, J=7.8 Hz, 1H), 7.60 (d, J=7.4 Hz, 1H), 7.56-7.46 (m, 3H), 7.46 (d, J=8.9 Hz, 1H), 6.98-6.90 (m, 3H), 6.68 (s, 1H), 4.11 (t, J=6.0 Hz, 2H), 3.41 (s, 3H), 2.96-2.88 (m, 5H), 2.64 (br s, 4H), 1.87-1.77 (m, 4H). MS=507 (MH)+.

Example 129

N-Methyl-N-(3-{2-[3-(1-methyl-piperidin-4-yl)-phenylamino]-[1,2,4]triazolo[1,5-a]pyridin-8-yl}-phenyl)-methanesulfonamide

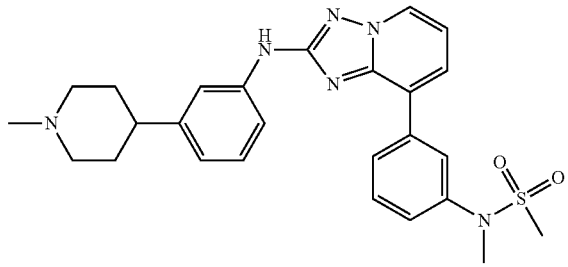 [SMILES: CN1CCC(c2cccc(Nc3nc4c(-c5cccc(N(C)S(C)(=O)=O)c5)cccn4n3)c2)CC1]

129a) A mixture of 4-(3-bromo-phenyl)-piperidine; hydrochloride (1.0 g, 3.6 mmol), 37% formaldehyde in water (3.7 mL, 120 mmol), Acetic acid (0.25 mL, 4.4 mmol) and methanol (20 mL) was stirred for 15 minutes at room temperature. The mixture was cooled to 10° C. in an ice/water bath. Sodium cyanoborohydride (3.0 g, 48 mmol) was added portionwise. A mild exotherm was noted. The mixture was stirred and warmed to room temperature over 18 hours. The mixture was poured into saturated aqueous ammonium chloride (200 mL) and stirred for 1 hour at room temperature. The mixture was extracted with dichloromethane (3×75 ml). The combined organic layers were dried over magnesium sulfate, filtered and evaporated to an oil. The residue was triturated in ether (200 mL) and filtered. The filtrate was evaporated to an oil (0.585 g). The oil was dissolved in ether and stirred. Hydrogen chloride (2.0M in ether, 2.0 mL) was added dropwise and stirred for 30 minutes. The precipitate was filtered and rinsed with ether. 4-(3-Bromo-phenyl)-1-methyl-piperidine hydrochloride was isolated as a crude white solid (0.432 g, 41%). $^1$H NMR (400 MHz, (D$_3$C)$_2$SO, δ, ppm): 10.52 (s, 1H), 7.47-7.41 (m, 2H), 7.37-7.21 (m, 2H), 3.52-3.41 (m, 2H), 3.10-2.95 (m, 2H), 2.85-2.78 (m, 1H), 2.75 (s, 3H), 2.15-2.78 (m, 4H). MS=254, 256 (MH)+.

129b) N-Methyl-N-(3-{2-[3-(1-methyl-piperidin-4-yl)-phenylamino]-[1,2,4]triazolo[1,5-a]pyridin-8-yl}-phenyl)-methanesulfonamide was prepared from N-[3-(2-amino-[1,2,4]triazolo[1,5-a]pyridin-8-yl)-phenyl]-N-methyl-methanesulfonamide (75.0 mg, 0.236 mmol) and 4-(3-bromo-phenyl)-1-methyl-piperidine; hydrochloride (76.0 mg, 0.262 mmol) with 2,2'-bis-dicyclohexylphosphanyl-biphenyl (25.0 mg, 0.0457 mmol) as the ligand in a manner analogous to Example 2d. Product isolated as a pale yellow foam (0.093 g, 80%). $^1$H NMR (400 MHz, CDCl$_3$, δ, ppm): 8.46 (d, J=6.6 Hz, 1H), 8.10-8.07 (m, 1H), 7.98 (d, J=7.8 Hz, 1H), 7.61 (d, J=7.2 Hz, 1H), 7.54 (t, J=8.0 Hz, 1H), 7.49 (d, J=8.0 Hz, 1H), 7.46-7.40 (m, 2H), 7.27 (t, J=7.9 Hz, 1H), 6.98 (t, J=7.1 Hz, 1H), 6.88 (d, J=7.7 Hz, 1H), 6.83 (s, 1H), 3.42 (s, 3H), 3.03-2.96 (m, 2H), 2.90 (s, 3H), 2.55-2.45 (m, 1H), 2.34 (s, 3H), 2.12-2.00 (m, 2H), 1.90-1.80 (m, 4H). MS=491 (MH)+.

Example 130

N-Methyl-N-(2-{2-[3-(1-methyl-piperidin-4-yl)-phenylamino]-[1,2,4]triazolo[1,5-a]pyridin-8-yl}-phenyl)-methanesulfonamide

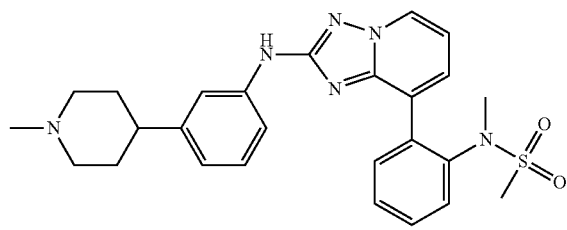 [SMILES: CN1CCC(c2cccc(Nc3nc4c(-c5ccccc5N(C)S(C)(=O)=O)cccn4n3)c2)CC1]

130a) A round bottom flask was charged with potassium carbonate (0.56 g, 4.0 mmol) and acetone (20 mL). To the suspension was added N-[2-(4,4,5,5-Tetramethyl-1,3,2-dioxaborolan-2-yl)-phenyl]-methanesulfonamide (1.0 g, 3.4 mmol) followed by iodomethane (0.25 mL, 4.0 mmol). The mixture was stirred at room temperature for 18 hours. The mixture was diluted with dichloromethane (20 mL), filtered through a plug of diatomaceous earth, rinsed with dichloromethane and evaporated to a viscous oil. The material was subjected to high vacuum for 18 hours. N-Methyl-N-[2-(4,4,5,5-tetramethyl-1,3,2-dioxaborolan-2-yl)-phenyl]-methanesulfonamide was isolated as a white solid (1.01 g, 95%). $^1$H NMR (400 MHz, CDCl$_3$, δ, ppm): 7.81 (dd, J=7.5, 1.4 Hz, 1H), 7.47 (ddd, J=7.9, 7.9, 1.5 Hz, 1H), 7.38 (dd, J=7.9 Hz, 1H), 7.35-7.30 (m, 1H), 3.32 (s, 3H), 2.93 (s, 3H). MS=334 (M+Na)+.

130b) N-[2-(2-Amino-[1,2,4]triazolo[1,5-a]pyridin-8-yl)-phenyl]-N-methyl-methanesulfonamide was prepared from 8-bromo-[1,2,4]triazolo[1,5-a]pyridin-2-ylamine (625.0 mg, 2.934 mmol) and N-methyl-N-[2-(4,4,5,5-tetramethyl-1,3,2-dioxaborolan-2-yl)-phenyl]-methanesulfonamide (1000.0 mg, 3.2133 mmol) in a manner analogous to Example 2c. Product was isolated as white solid (0.479 g, 51%). $^1$H NMR (400 MHz, (D$_3$C)$_2$SO, δ, ppm): 8.52 (d, J=6.5 Hz, 1H), 7.62 (d, J=7.4 Hz, 1H), 7.55-7.42 (m, 3H), 7.35 (d, J=7.2 Hz, 1H), 6.94 (t, J=7.1 Hz, 1H), 5.94 (s, 2H), 3.10 (s, 3H), 2.85 (s, 3H). MP=209-211° C. MS=318 (MH)+.

130c) N-Methyl-N-(2-{2-[3-(1-methyl-piperidin-4-yl)-phenylamino]-[1,2,4]triazolo[1,5-a]pyridin-8-yl}-phenyl)-methanesulfonamide was prepared from N-[2-(2-amino-[1,2,4]triazolo[1,5-a]pyridin-8-yl)-phenyl]-N-methyl-methanesulfonamide (75.0 mg, 0.236 mmol) and 4-(3-bromo-phenyl)-1-methyl-piperidine; hydrochloride (76.0 mg, 0.262 mmol) with 2,2'-bis-dicyclohexylphosphanyl-biphenyl (25.0 mg, 0.0457 mmol) as the ligand in a manner analogous to Example 2d. Product isolated as a pale yellow foam (0.099 g, 85%). $^1$H NMR (400 MHz, CDCl$_3$, δ, ppm): 8.48 (dd, J=6.8, 0.9 Hz, 1H), 7.59-7.36 (m, 7H), 7.28-7.23 (m, 1H), 6.98 (t, J=7.1 Hz, 1H), 6.86 (d, J=7.6 Hz, 1H), 6.76 (s, 1H), 3.17 (s, 3H), 3.02-2.95 (m, 2H), 2.74 (s, 3H), 2.53-2.43 (m, 1H), 2.34 (s, 3H), 2.10-2.00 (m, 2H), 1.89-1.78 (m, 4H). MS=491 (MH)+.

Example 131

N-Methyl-N-(3-{2-[4-(4-methyl-piperazin-1-yl)-phenylamino]-[1,2,4]triazolo[1,5-a]pyridin-8-ylamino}-pyridin-2-yl)-methanesulfonamide

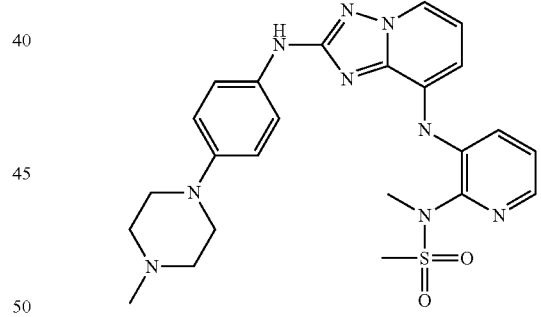

N-Methyl-N-(3-{2-[4-(4-methyl-piperazin-1-yl)-phenylamino]-[1,2,4]triazolo[1,5-a]pyridin-8-ylamino}-pyridin-2-yl)-methanesulfonamide was prepared from N-[3-(2-chloro-[1,2,4]triazolo[1,5-a]pyridin-8-ylamino)-pyridin-2-yl]-N-methyl-methanesulfonamide (75.0 mg, 0.212 mmol) and 4-(4-methyl-piperazin-1-yl)-phenylamine (50.0 mg, 0.261 mmol) with 2,2'-bis-dicyclohexylphosphanyl-biphenyl (25.0 mg, 0.0457 mmol) as the ligand in a manner analogous to Example 2d. Product isolated as a tan foam (0.035 g, 32%). $^1$H NMR (400 MHz, CDCl$_3$, δ, ppm): 8.09 (dd, J=4.5, 1.3 Hz, 1H), 8.06 (d, J=6.6 Hz, 1H), 7.78 (dd, J=8.3, 1.3 Hz, 1H), 7.53 (s, 1H), 7.50 (d, J=8.9 Hz, 2H), 7.28-7.23 (m, 1H), 7.12 (d, J=7.7 Hz, 1H), 6.97 (d, J=9.0 Hz, 2H), 6.74 (t, J=7.3 Hz, 1H), 6.68 (s, 1H), 3.33 (s, 3H), 3.19-3.14 (m, 4H), 3.10 (s, 3H), 2.62-2.57 (m, 4H), 2.36 (s, 3H). MS=508 (MH)+.

Example 132

N-Methyl-N-(3-{2-[4-(2-pyrrolidin-1-yl-ethoxy)-phenylamino]-[1,2,4]triazolo[1,5-a]pyridin-8-ylamino}-pyridin-2-yl)-methanesulfonamide

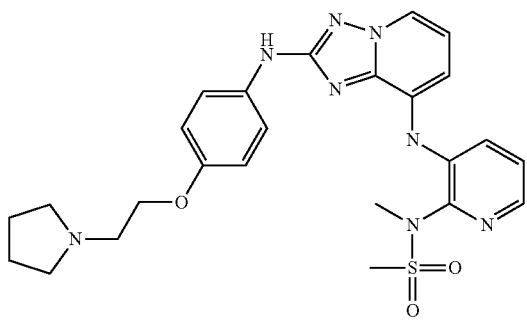

N-Methyl-N-(3-{2-[4-(2-pyrrolidin-1-yl-ethoxy)-phenylamino]-[1,2,4]triazolo[1,5-a]pyridin-8-ylamino}-pyridin-2-yl)-methanesulfonamide was prepared from N-[3-(2-chloro-[1,2,4]triazolo[1,5-a]pyridin-8-ylamino)-pyridin-2-yl]-N-methyl-methanesulfonamide (75.0 mg, 0.212 mmol) and 4-(2-pyrrolidin-1-yl-ethoxy)-phenylamine (53.0 mg, 0.257 mmol)(prepared as described in *J. Med. Chem.*, 2006, 49, 4451-4454) with 2,2'-bis-dicyclohexylphosphanyl-biphenyl (25.0 mg, 0.0457 mmol) as the ligand in a manner analogous to Example 2d. Product isolated as a brown foam (0.023 g, 21%). $^1$H NMR (400 MHz, CDCl$_3$, δ, ppm): 8.09 (dd, J=4.6, 1.5 Hz, 1H), 8.05 (d, J=6.5 Hz, 1H), 7.78 (dd, J=8.1, 1.4 Hz, 1H), 7.55 (s, 1H), 7.50 (d, J=9.0 Hz, 2H), 7.28-7.23 (m, 1H), 7.13 (d, J=7.7 Hz, 1H), 6.93 (d, J=9.0 Hz, 2H), 6.74 (t, J=7.2 Hz, 1H), 6.69 (s, 1H), 4.11 (t, J=6.1 Hz, 2H), 3.33 (s, 3H), 3.10 (s, 3H), 2.09 (t, J=6.0 Hz, 2H), 2.67-2.57 (m, 4H), 1.87-1.77 (m, 4H). MS=523 (MH)+.

Example 133

N-Methyl-N-(3-{2-[4-(1-methyl-piperidin-4-yl)-phenylamino]-[1,2,4]triazolo[1,5-a]pyridin-8-ylamino}-pyridin-2-yl)-methanesulfonamide

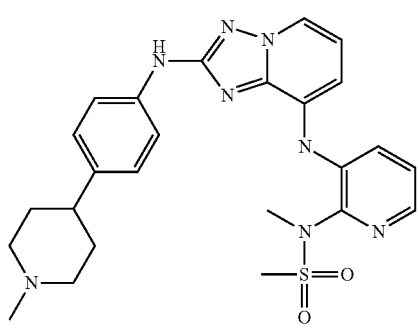 [SMILES: CN1CCN(c2ccc(Nc3nc4c(Nc5cccnc5N(C)S(C)(=O)=O)cccn4n3)cc2)CC1]

N-Methyl-N-(3-{2-[4-(1-methyl-piperidin-4-yl)-phenylamino]-[1,2,4]triazolo[1,5-a]pyridin-8-ylamino}-pyridin-2-yl)-methanesulfonamide was prepared from N-[3-(2-chloro-[1,2,4]triazolo[1,5-a]pyridin-8-ylamino)-pyridin-2-yl]-N-methyl-methanesulfonamide (75.0 mg, 0.212 mmol) and 4-(1-methyl-piperidin-4-yl)-phenylamine (49.0 mg, 0.258 mmol) with 2,2'-bis-dicyclohexylphosphanyl-biphenyl (25.0 mg, 0.0457 mmol) as the ligand in a manner analogous to Example 2d. Product isolated as a tan foam (0.029 g, 27%). $^1$H NMR (400 MHz, CDCl$_3$, δ, ppm): 8.09 (dd, J=4.6, 1.4 Hz, 1H), 8.07 (d, J=6.9 Hz, 1H), 7.79 (dd, J=8.2, 1.3 Hz, 1H), 7.57 (s, 1H), 7.53 (d, J=8.5 Hz, 2H), 7.28-7.24 (m, 1H), 7.21 (d, J=8.4 Hz, 2H), 7.13 (d, J=7.6 Hz, 1H), 6.82 (s, 1H), 6.76 (t, J=7.0 Hz, 1H), 3.33 (s, 3H), 3.01-2.94 (m, 2H), 2.50-2.40 (m, 1H), 2.33 (s, 3H), 2.10-2.00 (m, 2H), 1.87-1.74 (m, 4H). MS=507 (MH)+.

Example 134

N-(3-{[2-(4-Methanesulfonyl-phenylamino)-[1,2,4]triazolo[1,5-a]pyridin-8-ylamino]-methyl}-pyridin-2-yl)-N-methyl-methanesulfonamide

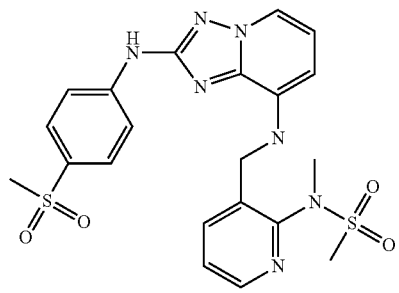 [SMILES: CN(c1ncccc1CNc1cccn2nc(Nc3ccc(S(C)(=O)=O)cc3)nc12)S(C)(=O)=O]

N-(3-{[2-(4-Methanesulfonyl-phenylamino)-[1,2,4]triazolo[1,5-a]pyridin-8-ylamino]-methyl}-pyridin-2-yl)-N-methyl-methanesulfonamide was prepared from N-{3-[(2-chloro-[1,2,4]triazolo[1,5-a]pyridin-8-ylamino)-methyl]-pyridin-2-yl}-N-methyl-methanesulfonamide (75.0 mg, 0.204 mmol) and 4-methanesulfonyl-phenylamine (39.0 mg, 0.228 mmol) with 2,2'-bis-dicyclohexylphosphanyl-biphenyl (25.0 mg, 0.0457 mmol) as the ligand in a manner analogous to Example 2d. Product isolated as a tan foam (0.009 g, 9%). $^1$H NMR (400 MHz, CDCl$_3$, δ, ppm): 8.43 (dd, J=4.6, 1.4 Hz, 1H), 7.92-7.83 (m, 4H), 7.76 (d, J=8.8 Hz, 2H), 7.29 (dd, J=7.7, 4.7 Hz, 1H), 7.12 (s, 1H), 6.74 (t, J=7.5 Hz, 1H), 6.38 (d, J=7.7 Hz, 1H), 5.37 (t, J=6.4 Hz, 1H), 4.78 (d, J=6.3 Hz, 2H), 3.33 (s, 3H), 3.10 (s, 3H), 3.05 (s, 3H). MS=502 (MH)+.

Example 135

N-(3-{[2-(3-Methanesulfonyl-phenylamino)-[1,2,4]triazolo[1,5-a]pyridin-8-ylamino]-methyl}-pyridin-2-yl)-N-methyl-methanesulfonamide

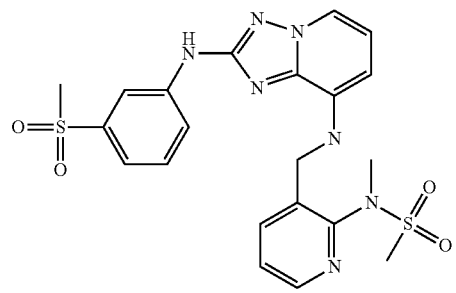 [SMILES: CN(c1ncccc1CNc1cccn2nc(Nc3cccc(S(C)(=O)=O)c3)nc12)S(C)(=O)=O]

N-(3-{[2-(3-Methanesulfonyl-phenylamino)-[1,2,4]triazolo[1,5-a]pyridin-8-ylamino]-methyl}-pyridin-2-yl)-N-methyl-methanesulfonamide was prepared from N-{3-[(2-chloro-[1,2,4]triazolo[1,5-a]pyridin-8-ylamino)-methyl]-pyridin-2-yl}-N-methyl-methanesulfonamide (75.0 mg, 0.204 mmol) and 3-methanesulfonyl-phenylamine; hydrochloride (39.0 mg, 0.188 mmol) with 2,2'-bis-dicyclohexylphosphanyl-biphenyl (25.0 mg, 0.0457 mmol) as the ligand in a manner analogous to Example 2d. Product isolated as a tan foam (0.010 g, 11%). $^1$H NMR (400 MHz, CDCl$_3$, δ, ppm): 8.42 (dd, J=4.8, 1.5 Hz, 1H), 8.24 (s, 1H), 7.88-7.83 (m, 3H), 7.53 (d, J=4.9 Hz0, 1H), 7.29 (dd, J=7.7, 4.7 Hz, 1H), 6.96 (s, 1H), 6.72 (t, J=7.5 Hz, 1H), 6.36 (d, J=7.7 HZ, 1H), 5.36 (t, J=6.3 Hz, 1H), 4.78 (d, J=6.1 Hz, 1H), 3.33 (s, 3H), 3.10 (s, 6H). MS=502 (MH)+.

Example 136

N-Methyl-N-[3-({2-[3-(4-methyl-piperazin-1-yl)-phenylamino]-[1,2,4]triazolo[1,5-a]pyridin-8-ylamino}-methyl)-pyridin-2-yl]-methanesulfonamide

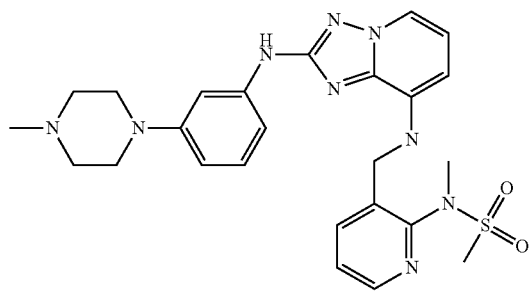 [SMILES: CN1CCN(c2cccc(Nc3nc4c(NCc5cccnc5N(C)S(C)(=O)=O)cccn4n3)c2)CC1]

N-Methyl-N-[3-({2-[3-(4-methyl-piperazin-1-yl)-phenylamino]-[1,2,4]triazolo[1,5-a]pyridin-8-ylamino}-methyl)-pyridin-2-yl]-methanesulfonamide was prepared from N-{3-[(2-chloro-[1,2,4]triazolo[1,5-a]pyridin-8-ylamino)-methyl]-pyridin-2-yl}-N-methyl-methanesulfonamide (75.0 mg, 0.204 mmol) and 3-(4-methylpiperazin-1-yl)aniline (44.0 mg, 0.230 mmol) with 2,2'-bis-dicyclohexylphosphanyl-biphenyl (25.0 mg, 0.0457 mmol) as the ligand in a manner analogous to Example 2d. Product isolated as a pale yellow foam (0.037 g, 35%). $^1$H NMR (400 MHz, CDCl$_3$, δ, ppm): 8.41 (d, J=4.6, 1.6 Hz, 1H), 7.86-7.81 (m, 2H), 7.29-7.25 (m, 1H), 7.24-7.19 (m, 2H), 7.06 (dd, J=8.1, 1.6 Hz, 1H), 6.71 (s, 1H), 6.65 (t, J=7.5 Hz, 1H), 6.57 (dd, J=8.0, 1.7 Hz, 1H), 6.30 (d, J=7.7 Hz, 1H), 5.29 (t, J=6.3 Hz, 1H), 4.76 (d, J=6.2 Hz, 2H), 3.32 (s, 3H), 3.29-3.24 (m, 4H), 3.09 (s, 3H), 2.62-2.57 (m, 4H), 2.36 (s, 3H). MS=522 (MH)+.

Example 137

N-[3-({2-[2-Methoxy-4-(4-methyl-piperazin-1-yl)-phenylamino]-[1,2,4]triazolo[1,5-a]pyridin-8-ylamino}-methyl)-pyridin-2-yl]-N-methyl-methanesulfonamide

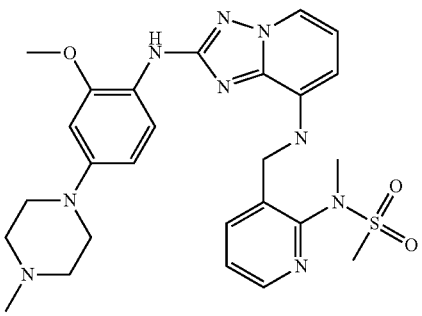 [SMILES: COc1cc(N2CCN(C)CC2)ccc1Nc1nc2c(NCc3cccnc3N(C)S(C)(=O)=O)cccn2n1]

N-[3-({2-[2-Methoxy-4-(4-methyl-piperazin-1-yl)-phenylamino]-[1,2,4]triazolo[1,5-a]pyridin-8-ylamino}-methyl)-pyridin-2-yl]-N-methyl-methanesulfonamide was prepared from N-{3-[(2-chloro-[1,2,4]triazolo[1,5-a]pyridin-8-ylamino)-methyl]-pyridin-2-yl}-N-methyl-methanesulfonamide (75.0 mg, 0.204 mmol) and 2-methoxy-4-(4-methyl-piperazin-1-yl)-phenylamine (50.0 mg, 0.226 mmol) with 2,2'-bis-dicyclohexylphosphanyl-biphenyl (25.0 mg, 0.0457 mmol) as the ligand in a manner analogous to Example 2d. Product isolated as a brown foam (0.049 g, 43%). $^1$H NMR (400 MHz, CDCl$_3$, δ, ppm): 8.40 (dd, J=4.7, 1.6 Hz, 1H), 8.19 (d, J=8.6 Hz, 1H), 7.85 (dd, J=7.7, 1.6 Hz, 1H), 7.82 (d, J=6.7 HZ, 1H), 7.29-7.25 (m, 1H), 7.17 (s, 1H), 6.65-6.57 (m, 3H), 6.28 (d, J=7.7 Hz, 1H), 5.29 (t, J=6.1 Hz, 1H), 4.76 (d, J=6.3 Hz, 2H), 3.89 (s, 3H), 3.32 (s, 3H), 3.18-3.13 (m, 4H), 3.09 (s, 3H), 2.63-2.58 (m, 4H), 2.37 (s, 3H). MS=552 (MH)+.

Example 138

N(8)-(2-Methanesulfonyl-benzyl)-N(2)-[4-(4-methyl-piperazin-1-yl)-phenyl]-[1,2,4]triazolo[1,5-a]pyridine-2,8-diamine

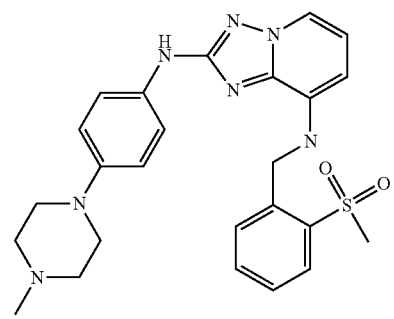 [SMILES: CN1CCN(c2ccc(Nc3nc4c(NCc5ccccc5S(C)(=O)=O)cccn4n3)cc2)CC1]

138a) (2-Chloro-[1,2,4]triazolo[1,5-a]pyridin-8-yl)-(2-methanesulfonyl-benzyl)-amine was prepared from 8-bromo-2-chloro-[1,2,4]triazolo[1,5-a]pyridine (470.0 mg, 2.022 mmol) and 2-methanesulfonyl-benzylamine; hydrochloride (500.0 mg, 2.255 mmol) in a manner analogous to Example 2d. Product isolated as a yellow solid (0.45 g, 66%). MP=161-163° C. $^1$H NMR (400 MHz, CDCl$_3$, δ, ppm): 8.11 (d, J=7.6 Hz, 1H), 7.92 (d, J=6.6 Hz, 1H), 7.64-7.60 (m, 2H), 7.56-7.51 (m, 1H), 6.88 (t, J=7.5 Hz, 1H), 6.53 (d, J=7.8 Hz, 1H), 5.43 (t, J=5.9 Hz, 1H), 4.98 (d, J=6.1 Hz, 2H), 3.15 (s, 3H). MS=337, 339 (MH)+.

138b) N(8)-(2-Methanesulfonyl-benzyl)-N(2)-[4-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(2-methanesulfonyl-benzyl)-amine (75.0 mg, 0.223 mmol) and 4-(4-methyl-piperazin-1-yl)-phenylamine (47.0 mg, 0.246 mmol) with 2,2'-bis-dicyclohexylphosphanyl-biphenyl (25.0 mg, 0.0457 mmol) as the ligand in a manner analogous to Example 2d. Product isolated as a tan foam (0.035 g, 32%). $^1$H NMR (400 MHz, CDCl$_3$, δ, ppm): 8.11 (d, J=7.9 Hz, 1H), 7.84 (d, J=6.5 Hz, 1H), 7.67-7.59 (m, 2H), 7.55-7.50 (m, 1H), 7.47 (d, J=8.8 Hz, 2H), 6.96 (d, J=8.9 Hz, 2H), 6.68 (t, J=7.3 Hz, 1H), 6.55 (s, 1H), 6.41 (d, J=7.7 Hz, 1H), 5.19 9t, J=6.1 Hz, 1H), 4.96 (d, J=6.1 Hz, 2H), 3.20-3.14 (m, 7H), 2.69-2.58 (m, 4H), 2.39 (s, 3H). MS=492 (MH)+.

Example 139

N(8)-(2-Methanesulfonyl-benzyl)-N(2)-[3-(4-methyl-piperazin-1-yl)-phenyl]-[1,2,4]triazolo[1,5-a]pyridine-2,8-diamine

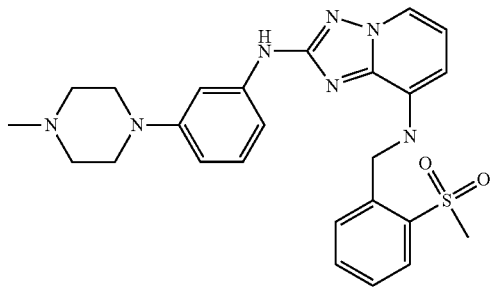 [SMILES: CN1CCN(c2cccc(Nc3nc4c(NCc5ccccc5S(C)(=O)=O)cccn4n3)c2)CC1]

N(8)-(2-Methanesulfonyl-benzyl)-N(2)-[3-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(2-methanesulfonyl-benzyl)-amine (75.0 mg, 0.223 mmol) and 3-(4-methylpiperazin-1-yl)aniline (47.0 mg, 0.246 mmol) with 2,2'-bis-dicyclohexylphosphanyl-biphenyl (25.0 mg, 0.0457 mmol) as the ligand in a manner analogous to Example 2d. Product isolated as a tan foam (0.023 g, 21%). $^1$H NMR (400 MHz, CDCl$_3$, δ, ppm): 8.11 (d, J=8.0 Hz, 1H), 7.85 (d, J=6.5 Hz, 1H), 7.66-7.59 (m, 2H), 7.54-7.49 (m, 1H), 7.27-7.23 (m, 1H), 7.21 (t, J=8.2 Hz, 1H), 7.02 (d, J=9.2 Hz, 1H), 6.72-6.67 (m, 2H), 6.57 (dd, J=8.2, 1.6 Hz, 1H), 6.43 (d, J=7.6 hZ, 1H), 5.33 (t, J=6.1 Hz, 1H), 4.96 (d, J=6.2 Hz, 2H), 3.29-3.24 (m, 4H), 3.16 (s, 3H), 2.61-2.56 (m, 4H), 2.36 (s, 3H). MS=492 (MH)+.

Example 140

N(8)-(2-Methanesulfonyl-benzyl)-N(2)-[4-(1-methyl-piperidin-4-yl)-phenyl]-[1,2,4]triazolo[1,5-a]pyridine-2,8-diamine

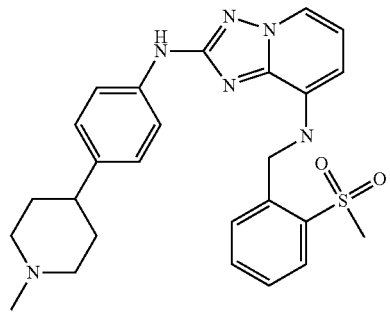 [SMILES: CN1CCC(c2ccc(Nc3nc4c(NCc5ccccc5S(C)(=O)=O)cccn4n3)cc2)CC1]

N(8)-(2-Methanesulfonyl-benzyl)-N(2)-[4-(1-methyl-piperidin-4-yl)-phenyl]-[1,2,4]triazolo[1,5-a]pyridine-2,8-diamine was prepared from (2-chloro-[1,2,4]triazolo[1,5-a]pyridin-8-yl)-(2-methanesulfonyl-benzyl)-amine (75.0 mg, 0.223 mmol) and 4-(1-methyl-piperidin-4-yl)-phenylamine (47.0 mg, 0.247 mmol) with 2,2'-bis-dicyclohexylphosphanyl-biphenyl (25.0 mg, 0.0457 mmol) as the ligand in a manner analogous to Example 2d. Product isolated as a tan foam (0.042 g, 38%). $^1$H NMR (400 MHz, CDCl$_3$, δ, ppm): 8.11 (d, J=8.2 Hz. 1H), 7.85 (d, J=6.7 Hz, 1H), 7.67-7.59 (m, 2H), 7.55-7.46 (m, 3H), 7.20 (d, J=8.5 Hz, 2H), 6.69 (t, J=7.4 Hz, 1H), 6.37 (s, 1H), 6.42 (d, J=7.6 Hz, 1H), 5.29 (t, J=6.1 Hz, 1H), 4.96 (d, J=6.1 Hz, 2H), 3.16 (s, 3H), 3.01-2.94 (m, 2H), 2.50-2.39 (m, 1H), 2.33 (s, 3H), 2.10-2.00 (m, 2H), 1.86-1.73 (m, 4H). MS=491 (MH)+.

Example 141

N(8)-(2-Methanesulfonyl-benzyl)-N(2)-[4-(2-pyrrolidin-1-yl-ethoxy)-phenyl]-[1,2,4]triazolo[1,5-a]pyridine-2,8-diamine

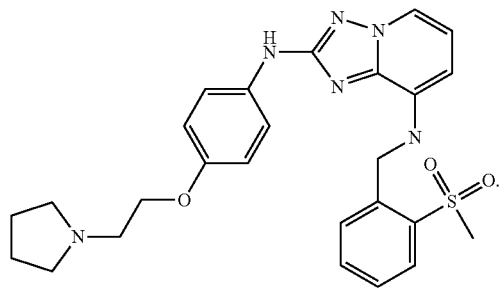 [SMILES: CS(=O)(=O)c1ccccc1CNc1cccn2nc(Nc3ccc(OCCN4CCCC4)cc3)nc12]

N(8)-(2-Methanesulfonyl-benzyl)-N(2)-[4-(2-pyrrolidin-1-yl-ethoxy)-phenyl]-[1,2,4]triazolo[1,5-a]pyridine-2,8-diamine was prepared from (2-chloro-[1,2,4]triazolo[1,5-a]pyridin-8-yl)-(2-methanesulfonyl-benzyl)-amine (75.0 mg, 0.223 mmol) and 4-(2-pyrrolidin-1-yl-ethoxy)-phenylamine (51.0 mg, 0.247 mmol) with 2,2'-bis-dicyclohexylphosphanyl-biphenyl (25.0 mg, 0.0457 mmol) as the ligand in a manner analogous to Example 2d. Product isolated as a tan foam (0.037 g, 33%). $^1$H NMR (400 MHz, CDCl$_3$, δ, ppm): 8.11 (d, J=7.8 Hz, 1H), 7.84 (d, J=6.6 Hz, 1H), 7.67-7.58 (m, 2H), 7.52 (t, J=6.9 Hz, 1H), 7.46 (d, J=8.8 Hz, 2H), 6.92 (d, J=8.8 Hz, 2H), 6.68 (t, J=7.5 Hz, 1H), 6.52 (s, 1H), 6.42 (d, J=7.6 Hz, 1H), 5.28 (t, J=6.0 Hz, 1H), 4.96 (d, J=6.2 Hz, 2H), 4.12 (t, J=5.6 Hz, 2H), 3.16 (s, 3H), 2.96-2.88 (m, 2H), 2.67 (br s, 4H), 1.89-1.76 (m, 4H). MS=507 (MH)+.

Example 142

(S)-1-(4-{3-[8-(4-Methanesulfonyl-phenyl)-[1,2,4]triazolo[1,5-a]pyridin-2-ylamino]-phenyl}-piperazin-1-yl)-propan-2-ol

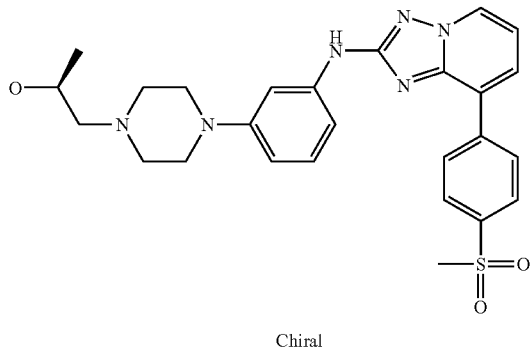 [SMILES: C[C@H](O)CN1CCN(c2cccc(Nc3nc4c(-c5ccc(S(C)(=O)=O)cc5)cccn4n3)c2)CC1]

Chiral 142a) 2-Chloro-8-(4-methanesulfonyl-phenyl)-[1,2,4]triazolo[1,5-a]pyridine was prepared from 8-(4-methanesulfonyl-phenyl)-[1,2,4]triazolo[1,5-a]pyridin-2-ylamine (1.0 g, 3.46 mmol) in a manner analogous to Example 68a and was isolated as a pale yellow solid (1.01 g, 95%). $^1$H NMR (400 MHz, (D$_3$C)$_2$SO, δ, ppm): 9.03 (d, J=6.8 Hz, 1H), 8.32 (d, J=8.3 Hz, 2H), 8.14 (d, J=7.5 Hz, 1H), 8.10 (d, J=8.3 Hz, 2H), 7.45 (t, J=7.0 Hz. 1H), 3.29 (s, 3H). MS=308 (MH)+.

142b) (S)-1-(4-{3-[8-(4-Methanesulfonyl-phenyl)-[1,2,4]triazolo[1,5-a]pyridin-2-ylamino]-phenyl}-piperazin-1-yl)-propan-2-ol was prepared from 2-chloro-8-(4-methanesulfonyl-phenyl)-[1,2,4]triazolo[1,5-a]pyridine (100.0 mg, 0.3249 mmol) and (S)-1-[4-(3-Amino-phenyl)-piperazin-1-yl]-propan-2-ol (84.0 mg, 0.357 mmol) with 2,2'-bis-dicyclohexylphosphanyl-biphenyl (36.0 mg, 0.0658 mmol) as the ligand in a manner analogous to Example 2d. Product isolated as a yellow foam (0.085 g, 51%). $^1$H NMR (400 MHz, CDCl$_3$, δ, ppm): 8.49 (d, J=6.6 Hz, 1H), 8.25 (d, J=8.4 Hz, 2H), 8.08 (d, J=8.4 Hz, 2H), 7.66 (d, J=7.3 Hz, 1H), 7.40 (s, 1H), 7.23 (t, J=8.2 Hz, 1H), 7.02 (t, J=7.1 Hz, 1H), 6.98-6.95 (m, 1H), 6.87 (s, 1H), 6.61-6.57 (m, 1H), 3.97-3.87 (m, 1H), 3.33-3.21 (m, 5H), 3.10 (s, 3H), 2.90-2.82 (m, 2H), 2.62-2.55 (m 2H), 2.43-2.30 (m, 2H), 1.17 (d, J=6.1 Hz, 3H). MS=507 (MH)+.

Example 143

(R)-1-(4-{3-[8-(4-Methanesulfonyl-phenyl)-[1,2,4]triazolo[1,5-a]pyridin-2-ylamino]-phenyl}-piperazin-1-yl)-propan-2-ol

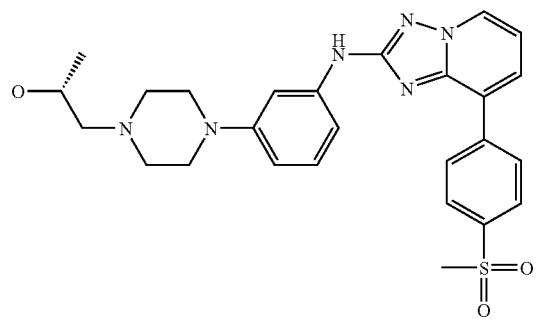

Chiral (R)-1-(4-{3-[8-(4-Methanesulfonyl-phenyl)-[1,2,4]triazolo[1,5-a]pyridin-2-ylamino]-phenyl}-piperazin-1-yl)-propan-2-ol was prepared from 2-chloro-8-(4-methanesulfonyl-phenyl)-[1,2,4]triazolo[1,5-a]pyridine (100.0 mg, 0.3249 mmol) and (R)-1-[4-(3-amino-phenyl)-piperazin-1-yl]-propan-2-ol (84.0 mg, 0.357 mmol) with 2,2'-bis-dicyclohexylphosphanyl-biphenyl (36.0 mg, 0.0658 mmol) as the ligand in a manner analogous to Example 2d. Product isolated as a yellow foam (0.105 g, 63%). $^1$H NMR (400 MHz, CDCl$_3$, δ, ppm): 8.49 (d, J=6.4 Hz, 1H), 8.25 (d, J=8.4 Hz, 2H), 8.07 (d, J=8.4 Hz, 2H), 7.66 (d, J=7.3 Hz, 1H), 7.40 (s, 1H), 7.23 (t, J=8.2 Hz, 1H), 7.02 (t, J=7.1 Hz, 1H), 6.98-6.94 (m, 1H), 6.88 (s, 1H), 6.59 (dd, J=8.2, 1.7 Hz, 1H), 3.97-3.87 (m, 1H), 3.33-3.21 (m, 5H), 3.10 (S, 3H), 2.90-2.82 (m, 2H), 2.62-2.55 (m, 2H), 2.43-2.30 (m, 2H), 1.17 (d, J=6.1 Hz, 3H). MS=507 (MH)+.

Example 144

1-(4-{3-[8-(4-Methanesulfonyl-phenyl)-[1,2,4]triazolo[1,5-a]pyridin-2-ylamino]-phenyl}-piperazin-1-yl)-2-methyl-propan-2-ol

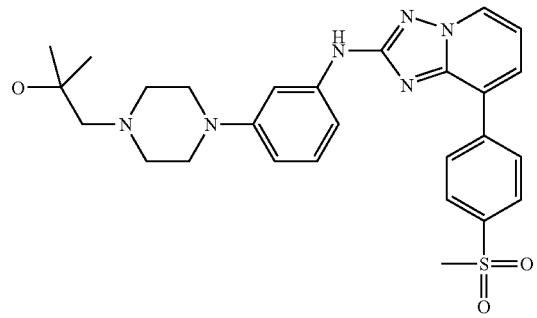 [SMILES: CC(C)(O)CN1CCN(c2cccc(Nc3nc4c(-c5ccc(S(C)(=O)=O)cc5)cccn4n3)c2)CC1]

1-(4-{3-[8-(4-Methanesulfonyl-phenyl)-[1,2,4]triazolo[1,5-a]pyridin-2-ylamino]-phenyl}-piperazin-1-yl)-2-methyl-propan-2-ol was prepared from 2-chloro-8-(4-methanesulfonyl-phenyl)-[1,2,4]triazolo[1,5-a]pyridine (100.0 mg, 0.3249 mmol) and 1-[4-(3-amino-phenyl)-piperazin-1-yl]-2-methyl-propan-2-ol (89.0 mg, 0.357 mmol) with 2,2'-bis-dicyclohexylphosphanyl-biphenyl (36.0 mg, 0.0658 mmol) as the ligand in a manner analogous to Example 2d. Product isolated as a yellow foam (0.117 g, 68%). $^1$H NMR (400 MHz, CDCl$_3$, δ, ppm): 8.49 (d, J=6.1 Hz, 1H), 8.25 (d, J=8.4 Hz, 2H), 8.07 (d, J=8.4 Hz, 2H), 7.66 (d, J=7.4 Hz, 1H), 7.37 (s, 1H), 7.22 (t, J=8.2 Hz, 1H), 7.02 (t, J=7.0 Hz, 1H), 6.96 (dd, J=8.1, 1.3 Hz, 1H), 6.88 (s, 1H), 6.59 (dd, J=8.1, 1.7 Hz, 1H), 3.29-3.23 (m, 4H), 3.10 (s, 3H), 2.87-2.81 (m, 4H), 2.42 (s, 2H), 1.22 (s, 6H). MS=521 (MH)+.

Example 145

[8-(4-Methanesulfonyl-phenyl)-[1,2,4]triazolo[1,5-a]pyridin-2-yl]-(7-morpholin-4-yl-6,7,8,9-tetrahydro-5H-benzocyclohepten-2-yl)-amine

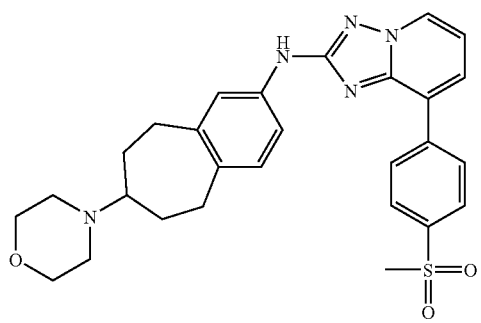 [SMILES: CS(=O)(=O)c1ccc(-c2cccn3nc(Nc4ccc5c(c4)CCC(N4CCOCC4)CC5)nc23)cc1]

[8-(4-Methanesulfonyl-phenyl)-[1,2,4]triazolo[1,5-a]pyridin-2-yl]-(7-morpholin-4-yl-6,7,8,9-tetrahydro-5H-benzocyclohepten-2-yl)-amine was prepared from 2-chloro-8-(4-methanesulfonyl-phenyl)-[1,2,4]triazolo[1,5-a]pyridine (100.0 mg, 0.3249 mmol) and 7-morpholin-4-yl-6,7,8,9-tetrahydro-5H-benzocyclohepten-2-ylamine (88.0 mg, 0.357 mmol) with 2,2'-bis-dicyclohexylphosphanyl-biphenyl (36.0 mg, 0.0658 mmol) as the ligand in a manner analogous to Example 2d. Product isolated as a yellow foam (0.107 g, 63%). $^1$H NMR (400 MHz, CDCl$_3$, δ, ppm): 8.50 (d, J=6.6 Hz, 1H), 8.23 (d, J=8.5 Hz, 2H), 8.08 (d, J=8.4 Hz, 2H), 7.65 (d, J=7.4 Hz, 1H), 7.36 (dd, J=8.1, 2.2 Hz, 1H), 7.31 (d, J=2.0 Hz, 1H), 7.10 (d, J=8.1 Hz, 1H), 7.01 (t, J=7.1 Hz, 1H), 6.81 (s, 1H), 3.73-3.67 (m, 4H), 3.10 (s, 3H), 2.85 (ddd, J=13.7, 13.7, 7.5 Hz, 2H), 2.76-2.51 (m, 7H), 2.10 (ddd, J=11.2, 11.2, 11.2 Hz, 2H), 1.44 (dddd, J=23.3, 11.5, 11.5, 11.5 Hz, 2H). MS=518 (MH)+.

Example 146

N-Methyl-N-(3-{[2-(1-methyl-2-oxo-2,3-dihydro-1H-indol-5-ylamino)-[1,2,4]triazolo[1,5-a]pyridin-8-ylamino]-methyl}-pyridin-2-yl)-methanesulfonamide

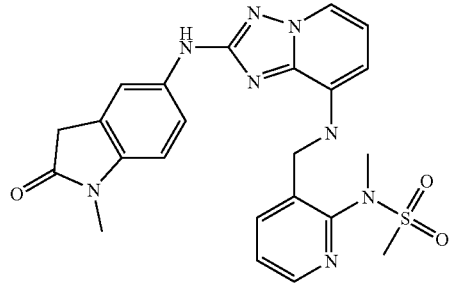 [SMILES: CN1C(=O)Cc2cc(Nc3nc4c(NCc5cccnc5N(C)S(C)(=O)=O)cccn4n3)ccc21]

N-Methyl-N-(3-{[2-(1-methyl-2-oxo-2,3-dihydro-1H-indol-5-ylamino)-[1,2,4]triazolo[1,5-a]pyridin-8-ylamino]-methyl}-pyridin-2-yl)-methanesulfonamide was prepared from N-{3-[(2-chloro-[1,2,4]triazolo[1,5-a]pyridin-8-ylamino)-methyl]-pyridin-2-yl}-N-methyl-methanesulfonamide (75.0 mg, 0.204 mmol) and 5-amino-1-methyl-1,3-dihydro-indol-2-one (37.0 mg, 0.228 mmol) with 2,2'-bis-dicyclohexylphosphanyl-biphenyl (23.0 mg, 0.0421 mmol) as the ligand in a manner analogous to Example 2d. Product isolated as a green-brown foam (0.017 g, 17%). $^1$H NMR (400 MHz, CDCl$_3$, δ, ppm): 8.41 (d, J=4.8 Hz, 1H), 7.85 (d, J=7.7 Hz, 1H), 7.81 (d, J=6.6 Hz, 1H), 7.65 (s, 1H), 7.38 (d, J=8.5 Hz, 1H), 7.30-7.25 (m, 1H), 6.78 (d, J=8.4 Hz, 1H), 6.66 (t, J=7.3 Hz, 1H), 6.62 (s, 1H), 6.31 (d, J=7.8 Hz, 1H), 5.31 (t, J=6.2 Hz, 1H), 4.76 (d, J=6.2 Hz, 2H), 3.57 (s, 2H), 3.32 (s, 3H), 3.21 (s, 3H), 3.09 (s, 3H). MS=493 (MH)+.

Example 147

N-Methyl-N-[2-({2-[4-(4-methyl-piperazin-1-yl)-phenylamino]-[1,2,4]triazolo[1,5-a]pyridin-8-ylamino}-methyl)-phenyl]-methanesulfonamide

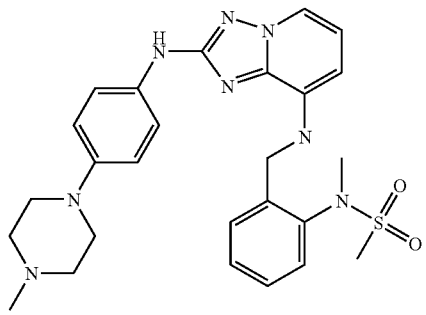

147a) To a round bottom flask was added 2-fluoro-benzonitrile (1.0 g, 8.2 mmol), N-Methyl-methanesulfonamide (1.0 g, 9.2 mmol), potassium carbonate (1.7 g, 12 mmol) and N,N-dimethylformamide (5 mL). The mixture was heated at 80° C. for 18 hours. The mixture was cooled to room temperature and water (50 mL) was added. The mixture was extracted with ethyl acetate (75 mL). The organic layer was washed with water (2×25 mL) and saturated aqueous sodium chloride (25 mL), dried over magnesium sulfate, filtered and evaporated to a waxy solid. The recovered solid was triturated with hexane, filtered and dried. N-(2-Cyano-phenyl)-N-methyl-methanesulfonamide was isolated as a pale yellow solid (0.74 g, 42%). $^1$H NMR (400 MHz, CDCl$_3$, δ, ppm): 7.72 (d, J=7.7 Hz, 1H), 7.70-7.64 (m, 1H), 7.56 (d, J=8.0 Hz, 1H), 7.47 (t, J=7.6 Hz, 1H), 3.40 (s, 3H), 3.13 (s, 3H). MS=211 (MH)+.

147b) N-(2-Aminomethyl-phenyl)-N-methyl-methanesulfonamide was prepared from N-(2-cyano-phenyl)-N-methyl-methanesulfonamide (0.75 g, 3.5 mmol) via hydrogenation using a Paar apparatus with 10% Palladium on Carbon (50% Wet)(5:45:50, palladium:carbon black:water, 0.75 g, 0.35 mmol) and hydrogen (50 psi) in 7M ammonia in methanol (50 mL). The mixture was shaken on a Paar apparatus until adsorption of hydrogen ceased. The mixture was degassed, backflushed with nitrogen, filtered through a plug of diatomaceous earth and rinsed with dichloromethane. The filtrate was evaporated under reduced pressure. Product isolated as a tan viscous oil (0.76 g, 100%). $^1$H NMR (400 MHz, CDCl$_3$, δ, ppm): 7.54 (d, J=7.7 Hz, 1H), 7.38 (ddd, J=7.6, 0.9, 0.9 Hz, 1H), 7.30 (ddd, J=7.9, 1.3, 1.3 Hz, 1H), 7.24 (dd, J=7.9, 0.8 HZ, 1H), 4.00 (br s, 2H), 3.26 (s, 3H), 2.99 (s, 3H). MS=215 (MH)+.

147c) N-{2-[(2-Chloro-[1,2,4]triazolo[1,5-a]pyridin-8-ylamino)-methyl]-phenyl}-N-methyl-methanesulfonamide was prepared from 8-bromo-2-chloro-[1,2,4]triazolo[1,5-a]pyridine (0.74 g, 3.2 mmol) and N-(2-aminomethyl-phenyl)-N-methyl-methanesulfonamide (0.76 g, 3.5 mmol) in a manner analogous to Example 2d. Product isolated as a white foam (0.847 g, 72%). $^1$H NMR (400 MHz, CDCl$_3$, δ, ppm): 7.87 (d, J=6.5 Hz, 1H), 7.51-7.47 (m, 1H), 7.40-7.28 (m, 3H), 6.84 (t, J=7.5 Hz, 1H), 6.47 (d, J=7.8 Hz, 1H), 5.38 (t, J=5.4 Hz, 1H), 4.73 (d, J=6.1 Hz, 2H), 3.30 (s, 3H), 3.00 (s, 3H). MS=366 (MH)+.

147d) N-Methyl-N-[2-({2-[4-(4-methyl-piperazin-1-yl)-phenylamino]-[1,2,4]triazolo[1,5-a]pyridin-8-ylamino}-methyl)-phenyl]-methanesulfonamide was prepared from N-{2-[(2-chloro-[1,2,4]triazolo[1,5-a]pyridin-8-ylamino)-methyl]-phenyl}-N-methyl-methanesulfonamide (75.0 mg, 0.205 mmol) and 4-(4-methyl-piperazin-1-yl)-phenylamine (44.0 mg, 0.230 mmol) with 2,2'-bis-dicyclohexylphosphanyl-biphenyl (23.0 mg, 0.0421 mmol) as the ligand in a manner analogous to Example 2d. Product isolated as a tan foam (0.053 g, 50%). $^1$H NMR (400 MHz, CDCl$_3$, δ, ppm): 7.79 (d, J=6.6 Hz, 1H), 7.55-7.50 (m, 1H), 7.47 (d, J=8.8 Hz, 2H), 7.38-7.28 (m, 3H), 6.95 (d, J=8.8 Hz, 2H), 6.65 (t, J=7.5 Hz, 1H), 6.53 (s, 1H), 6.35 (d, J=7.7 Hz, 1H), 5.21 (t, J=6.0 Hz, 1H), 4.71 (d, J=6.1 Hz, 2H), 3.30 (s, 3H), 3.18-3.12 (m, 4H), 3.00 (s, 3H), 2.62-2.57 (m, 4H), 2.36 (s, 3H). MS=521 (MH)+.

Example 148

N-Methyl-N-[2-({2-[3-(4-methyl-piperazin-1-yl)-phenylamino]-[1,2,4]triazolo[1,5-a]pyridin-8-ylamino}-methyl)-phenyl]-methanesulfonamide

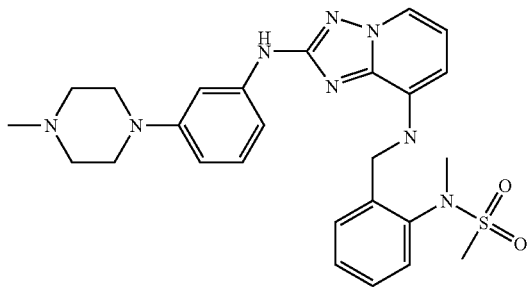 [SMILES: CN1CCN(c2cccc(Nc3nc4c(NCc5ccccc5N(C)S(C)(=O)=O)cccn4n3)c2)CC1]

N-Methyl-N-[2-({2-[3-(4-methyl-piperazin-1-yl)-phenylamino]-[1,2,4]triazolo[1,5-a]pyridin-8-ylamino}-methyl)-phenyl]-methanesulfonamide was prepared from N-{2-[(2-chloro-[1,2,4]triazolo[1,5-a]pyridin-8-ylamino)-methyl]-phenyl}-N-methyl-methanesulfonamide (75.0 mg, 0.205 mmol) and 3-(4-methylpiperazin-1-yl)aniline (44.0 mg, 0.230 mmol) with 2,2'-bis-dicyclohexylphosphanyl-biphenyl (23.0 mg, 0.0421 mmol) as the ligand in a manner analogous to Example 2d. Product isolated as a tan foam (0.054 g, 50%). $^1$H NMR (400 MHz, CDCl$_3$, δ, ppm): 7.81 (d, J=6.6 Hz, 1H), 7.55-7.51 (m, 1H), 7.38-7.28 (m, 3H), 7.24-7.18 (m, 2H), 7.04 (d, J=8.1 Hz, 1H), 6.71-6.64 (m, 2H), 6.56 (d, J=8.2 Hz, 1H), 6.37 (d, J=7.7 Hz, 1H), 5.22 (t, J=6.1 Hz, 1H), 4.72 (d, J=6.0 Hz, 2H), 3.31 (s, 3H), 3.28-3.23 (m, 4H), 3.00 (s, 3H), 2.61-2.56 (m, 4H), 2.36 (s, 3H). MS=521 (MH)+.

Example 149

N-Methyl-N-[2-({2-[4-(1-methyl-piperidin-4-yl)-phenylamino]-[1,2,4]triazolo[1,5-a]pyridin-8-ylamino}-methyl)-phenyl]-methanesulfonamide

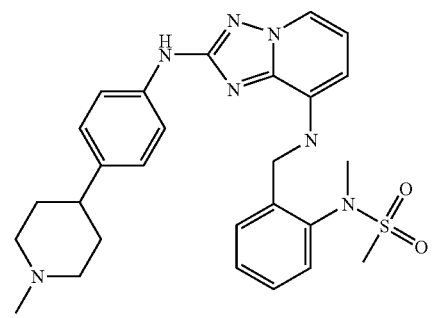

N-Methyl-N-[2-({2-[4-(1-methyl-piperidin-4-yl)-phenylamino]-[1,2,4]triazolo[1,5-a]pyridin-8-ylamino}-methyl)-phenyl]-methanesulfonamide was prepared from N-{2-[(2-chloro-[1,2,4]triazolo[1,5-a]pyridin-8-ylamino)-methyl]-phenyl}-N-methyl-methanesulfonamide (75.0 mg, 0.205 mmol) and 4-(1-methyl-piperidin-4-yl)-phenylamine (44.0 mg, 0.231 mmol) with 2,2'-bis-dicyclohexylphosphanyl-biphenyl (23.0 mg, 0.0421 mmol) as the ligand in a manner analogous to Example 2d. Product isolated as a tan foam (0.019 g, 18%). $^1$H NMR (400 MHz, CDCl$_3$, δ, ppm): 7.81 (d, J=6.6 Hz, 1H), 7.55-7.47 (m, 3H), 7.38-7.28 (m, 3H), 7.20 (d, J=8.4 Hz, 2H), 6.69-6.64 (m, 2H), 6.37 (d, J=7.7 Hz, 1H), 5.23 (t, J=5.9 Hz, 1H), 4.72 d, J=6.1 Hz, 2H), 3.31 (s, 3H), 3.02-2.95 (m, 5H), 2.50-2.40 (m, 1H), 2.33 (s, 3H), 2.10-2.00 (m, 2H), 1.88-1.74 (m, 4H). MS=520 (MH)+.

Example 150

N-Methyl-N-[2-({2-[4-(2-pyrrolidin-1-yl-ethoxy)-phenylamino]-[1,2,4]triazolo[1,5-a]pyridin-8-ylamino}-methyl)-phenyl]-methanesulfonamide

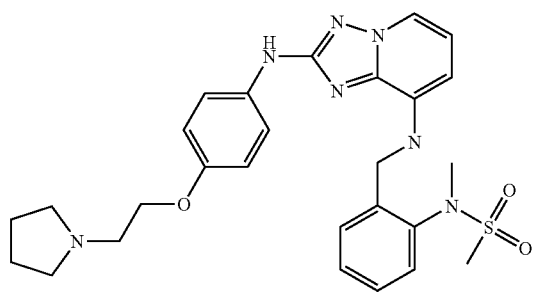 [SMILES: CN(c1ccccc1CNc1cccn2nc(Nc3ccc(OCCN4CCCC4)cc3)nc12)S(C)(=O)=O]

N-Methyl-N-[2-({2-[4-(2-pyrrolidin-1-yl-ethoxy)-phenylamino]-[1,2,4]triazolo[1,5-a]pyridin-8-ylamino}-methyl)-phenyl]-methanesulfonamide was prepared from N-{2-[(2-chloro-[1,2,4]triazolo[1,5-a]pyridin-8-ylamino)-methyl]-phenyl}-N-methyl-methanesulfonamide (75.0 mg, 0.205 mmol) and 4-(2-pyrrolidin-1-yl-ethoxy)-phenylamine (48.0 mg, 0.233 mmol) with 2,2'-bis-dicyclohexylphosphanyl-biphenyl (23.0 mg, 0.0421 mmol) as the ligand in a manner analogous to Example 2d. Product isolated as a tan foam (0.026 g, 24%). $^1$H NMR (400 MHz, CDCl$_3$, δ, ppm): 7.79 (d, J=6.7 Hz, 1H), 7.55-7.45 (m, 3H), 7.38-7.28 (m, 3H), 6.92 (d, J=8.9 Hz, 2H), 6.65 (t, J=7.5 Hz, 1H), 6.51 (s, 1H), 6.36 (d, J=7.7 Hz, 1H), 5.21 (t, J=5.7 Hz, 1H), 4.72 (d, J=6.1 Hz, 2H), 4.10 (t, J=6.0 Hz, 2H), 3.31 (s, 3H), 3.00 (s, 3H), 2.90 (t, J=5.9 Hz, 2H), 2.66-2.59 (m, 4H), 1.85-1.77 (m, 4H). MS=536 (MH)+.

Example 151

N(2)-[4-(4-Methyl-piperazin-1-yl)-phenyl]-N(8)-pyridin-3-ylmethyl-[1,2,4]triazolo[1,5-a]pyridine-2,8-diamine

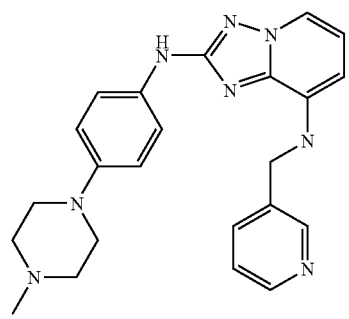 [SMILES: CN1CCN(c2ccc(Nc3nc4c(NCc5cccnc5)cccn4n3)cc2)CC1]

N(2)-[4-(4-Methyl-piperazin-1-yl)-phenyl]-N(8)-pyridin-3-ylmethyl-[1,2,4]triazolo[1,5-a]pyridine-2,8-diamine was prepared from (2-chloro-[1,2,4]triazolo[1,5-a]pyridin-8-yl)-pyridin-3-ylmethyl-amine (75.0 mg, 0.289 mmol) and 4-(4-methyl-piperazin-1-yl)-phenylamine (61.0 mg, 0.319 mmol) with 2,2'-bis-dicyclohexylphosphanyl-biphenyl (25.0 mg, 0.0457 mmol) as the ligand in a manner analogous to Example 2d. Product isolated as a tan foam (0.075 g, 63%). $^1$H NMR (400 MHz, CDCl$_3$, δ, ppm): 8.66 (s, 1H), 8.55 (d, J=4.1 Hz, 1H), 7.83 (d, J=6.5 Hz, 1H), 7.72 (d, J=7.8 Hz, 1H), 7.47 (d, J=8.9 Hz, 2H), 7.31-7.25 (m, 1H), 6.95 (d, J=8.9 Hz, 2H), 6.66 (t, J=7.3 Hz, 1H), 6.57 (s, 1H), 6.30 (d, J=7.7 Hz, 1H), 5.08 (t, J=5.6 Hz, 1H), 4.50 (d, J=5.8 Hz, 2H), 3.17-3.13 (m, 4H), 2.62-2.57 (m, 4H), 2.36 (s, 3H). MS=415 (MH)+.

Example 152

2-(4-{3-[8-(4-Methanesulfonyl-phenyl)-[1,2,4]triazolo[1,5-a]pyridin-2-ylamino]-phenyl}-piperazin-1-yl)-ethanol

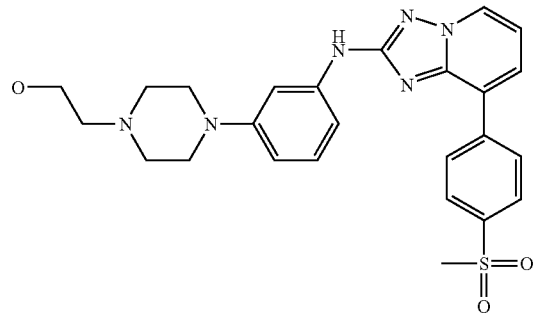 [SMILES: CS(=O)(=O)c1ccc(-c2cccn3nc(Nc4cccc(N5CCN(CCO)CC5)c4)nc23)cc1]

2-(4-{3-[8-(4-Methanesulfonyl-phenyl)-[1,2,4]triazolo[1,5-a]pyridin-2-ylamino]-phenyl}-piperazin-1-yl)-ethanol was prepared from 2-chloro-8-(4-methanesulfonyl-phenyl)-[1,2,4]triazolo[1,5-a]pyridine (75.0 mg, 0.244 mmol) and 2-[4-(3-amino-phenyl)-piperazin-1-yl]-ethanol (60.0 mg, 0.271 mmol) with 2,2'-bis-dicyclohexylphosphanyl-biphenyl (33.0 mg, 0.0604 mmol) as the ligand in a manner analogous to Example 2d. Product isolated as a yellow foam (0.052 g, 43%). $^1$H NMR (400 MHz, CDCl$_3$, δ, ppm): 8.49 (d, J=6.5 Hz, 1H), 8.26 (d, J=8.4 Hz, 2H), 8.08 (d, J=8.4 Hz, 2H), 7.66 (d, J=7.5 Hz, 1H), 7.45 (s, 1H), 7.23 (t, J=8.0 Hz, 1H), 7.02 (t, J=7.1 Hz, 1H), 6.96-6.92 (m, 1H), 6.87 (s, 1H), 6.62-6.58 (m, 1H), 3.70 (t, J=5.3 Hz, 2H), 3.30-3.26 (m, 4H), 3.11 (s, 3H), 3.74-2.70 (m, 4H), 2.64 (t, J=5.3 Hz, 2H). MS=493 (MH)+.

Example 153

N(2)-[3-(4-Methyl-piperazin-1-yl)-phenyl]-N(8)-pyridin-3-ylmethyl-[1,2,4]triazolo[1,5-a]pyridine-2,8-diamine

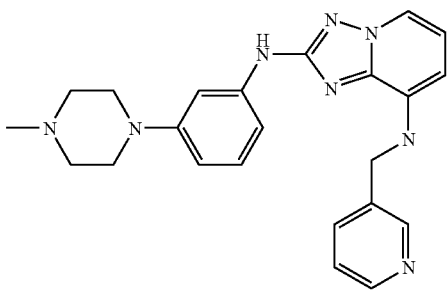 [SMILES: CN1CCN(c2cccc(Nc3nc4c(NCc5cccnc5)cccn4n3)c2)CC1]

N(2)-[3-(4-Methyl-piperazin-1-yl)-phenyl]-N(8)-pyridin-3-ylmethyl-[1,2,4]triazolo[1,5-a]pyridine-2,8-diamine was prepared from (2-chloro-[1,2,4]triazolo[1,5-a]pyridin-8-yl)-pyridin-3-ylmethyl-amine (75.0 mg, 0.289 mmol) and 3-(4-methylpiperazin-1-yl)aniline (61.0 mg, 0.319 mmol) with 2,2'-bis-dicyclohexylphosphanyl-biphenyl (33.0 mg, 0.0604 mmol) as the ligand in a manner analogous to Example 2d. Product isolated as a pale yellow foam (0.017 g, 14%). $^1$H NMR (400 MHz, CDCl$_3$, δ, ppm): 8.66 (s, 1H), 8.56 (d, J=4.6 Hz, 1H), 7.85 (d, J=6.6 Hz, 1H), 7.72 (d, J=7.9 Hz, 1H), 7.31-7.25 (m, 1H), 7.24-7.18 (m, 2H), 7.06 (d, J=7.9 Hz, 1H), 6.75 (s, 1H), 6.68 (t, J=7.3 Hz, 1H), 6.57 (d, J=8.3 Hz, 1H), 6.32 (d, J=7.8 Hz, 1H), 5.18 (t, J=5.5 Hz, 1H), 4.51 (d, J=5.7, 2H), 3.28-3.23 (m, 4H), 2.61-2.56 (m, 4H), 2.36 (s, 3H). MS=415 (MH)+.

Example 154

N(8)-Pyridin-3-ylmethyl-N(2)-[4-(2-pyrrolidin-1-yl-ethoxy)-phenyl]-[1,2,4]triazolo[1,5-a]pyridine-2,8-diamine

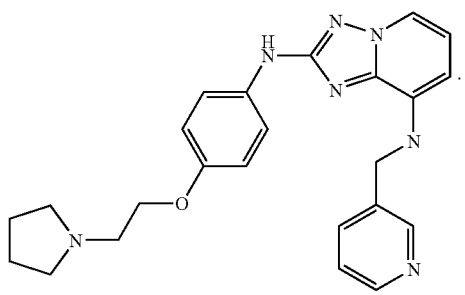 [SMILES: c1cncc(CNc2cccn3nc(Nc4ccc(OCCN5CCCC5)cc4)nc23)c1]

N(8)-Pyridin-3-ylmethyl-N(2)-[4-(2-pyrrolidin-1-yl-ethoxy)-phenyl]-[1,2,4]triazolo[1,5-a]pyridine-2,8-diamine was prepared from (2-chloro-[1,2,4]triazolo[1,5-a]pyridin-8-yl)-pyridin-3-ylmethyl-amine (75.0 mg, 0.289 mmol) and 4-(2-pyrrolidin-1-yl-ethoxy)-phenylamine (67.0 mg, 0.325 mmol) with 2,2'-bis-dicyclohexylphosphanyl-biphenyl (33.0 mg, 0.0604 mmol) as the ligand in a manner analogous to Example 2d. Product isolated as a yellow foam (0.031 g, 25%). $^1$H NMR (400 MHz, CDCl$_3$, δ, ppm): 8.67 (s, 1H), 8.56 (d, J=4.2 Hz, 1H), 7.83 (d, J=6.6 Hz, 1H), 7.73 (d, J=8.0 Hz, 1H), 7.47 (d, J=8.8 Hz, 2H), 7.31-7.25 (m, 1H), 6.92 (d, J=8.8 Hz, 2H), 6.66 (t, J=7.1 Hz, 1H), 6.56 (s, 1H), 6.31 (d, J=7.6 Hz, 1H), 5.18 (t, J=5.4 Hz, 1H), 4.51 (d, J=5.6 Hz, 2H), 4.10 (t, J=6.0 Hz, 2H), 2.89 (t, J=5.9 Hz, 2H), 2.66-2.59 (m, 4H), 1.85-1.77 (m, 4H). MS=430 (MH)+.

Example 155

N-{3-[(2-{4-[4-(2-Hydroxy-ethyl)-piperazin-1-yl]-phenylamino}-[1,2,4]triazolo[1,5-a]pyridin-8-ylamino)-methyl]-pyridin-2-yl}-N-methyl-methane-sulfonamide

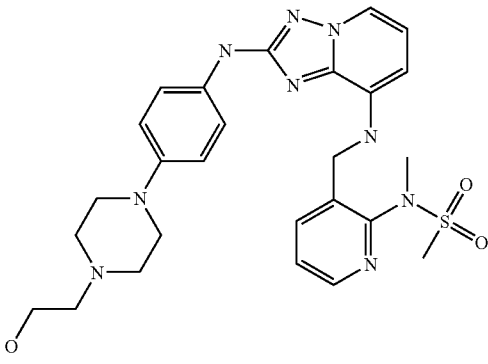 [SMILES: CN(c1ncccc1CNc1cccn2nc(Nc3ccc(N4CCN(CCO)CC4)cc3)nc12)S(C)(=O)=O]

N-{3-[(2-{4-[4-(2-Hydroxy-ethyl)-piperazin-1-yl]-phenylamino}-[1,2,4]triazolo[1,5-a]pyridin-8-ylamino)-methyl]-pyridin-2-yl}-N-methyl-methanesulfonamide was prepared from N-{3-[(2-chloro-[1,2,4]triazolo[1,5-a]pyridin-8-ylamino)-methyl]-pyridin-2-yl}-N-methyl-methanesulfonamide (75.0 mg, 0.204 mmol) and 2-[4-(4-amino-phenyl)-piperazin-1-yl]-ethanol (50.0 mg, 0.226 mmol) with 2,2'-Bis-dicyclohexylphosphanyl-biphenyl (26.0 mg, 0.0476 mmol) as the ligand in a manner analogous to Example 2d. Product isolated as a tan foam (0.052 g, 46%). $^1$H NMR (400 MHz, CDCl$_3$, δ, ppm): 8.41 (d, J=4.5 Hz, 1H), 7.85 (d, J=7.2 Hz, 1H), 7.81 (d, J=6.7 Hz, 1H), 7.48 (d, J=8.8 Hz, 2H), 7.30-7.25 (m, 1H), 6.96 (d, J=8.8 Hz, 2H), 6.64 (t, J=7.3 Hz, 1H), 6.56 (s, 1H), 6.29 (d, J=7.7 Hz, 1H), 5.33-5.28 (m, 1H), 4.17 (d, J=6.1 Hz, 2H), 3.67 (t, J=5.3 Hz, 2H), 3.32 (s, 3H), 3.18-3.13 (m, 4H), 3.09 (s, 3H), 2.72-2.67 (m, 4H), 2.62 (t, J=5.4 Hz, 2H). MS=552 (MH)+.

Example 156

N-Methyl-N-[2-({2-[4-(4-methyl-piperazin-1-yl)-phenylamino]-[1,2,4]triazolo[1,5-a]pyridin-8-ylamino}-methyl)-benzyl]-methanesulfonamide

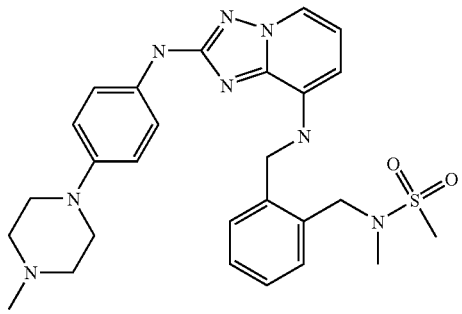 [SMILES: CN1CCN(c2ccc(Nc3nc4c(NCc5ccccc5CN(C)S(C)(=O)=O)cccn4n3)cc2)CC1]

156a) To a suspension of N-methyl-methanesulfonamide (0.61 g, 5.6 mmol) and potassium carbonate (1.0 g, 7.6 mmol) in Acetone (10 mL) was added 2-bromomethyl-benzonitrile (1.0 g, 5.1 mmol). The mixture was stirred at room temperature for 18 hours. The mixture was diluted with dichloromethane (30 mL), filtered through a plug of diatomaceous earth and evaporated to a yellow waxy solid (1.2 g). N-(2-Cyano-benzyl)-N-methyl-methanesulfonamide was isolated as yellow waxy solid (1.2 g, 100%). $^1$H NMR (400 MHz, CDCl$_3$, δ, ppm): 7.73-7.63 (m, 3H), 7.44 (t, J=7.5 Hz, 1H), 4.56 (s, 2H), 2.95 (s, 3H), 2.84 (s, 3H). MS=225 (MH)+.

156 b) To a Paar bottle (250 mL) was added 10% palladium on carbon (50% wet)(1.1 g, 0.52 mmol) followed by a solution of N-(2-cyano-benzyl)-N-methyl-methanesulfonamide (1.28 g, 5.71 mmol) in 7 M of ammonia in methanol (50 mL). The mixture was degassed and charged with Hydrogen (50 psi). The mixture was shaken on a Paar apparatus until adsorption of hydrogen ceased. The mixture was degassed and kept under an atmosphere of nitrogen. The mixture was filtered through a plug of diatomaceous earth, rinsed with dichloromethane and evaporated. N-(2-Aminomethyl-benzyl)-N-methyl-methanesulfonamide was isolated as tan viscous oil (1.28 g, 98%). $^1$H NMR (400 MHz, CDCl$_3$, δ, ppm): 7.41 (d, J=7.4 Hz, 1H), 7.36-7.24 (m, 3H), 4.40 (s, 2H), 3.99 (s, 2H), 2.89 (s, 3H), 2.72 (s, 3H). MS=229 (MH)+.

156 c) N-{2-[(2-Chloro-[1,2,4]triazolo[1,5-a]pyridin-8-ylamino)-methyl]-benzyl}-N-methyl-methanesulfonamide was prepared 8-bromo-2-chloro-[1,2,4]triazolo[1,5-a]pyridine (500.0 mg, 2.151 mmol) and N-(2-aminomethyl-benzyl)-N-methyl-methanesulfonamide (540.0 mg, 2.365 mmol) in a manner analogous to Example 2d. $^1$H NMR (400 MHz, CDCl$_3$, δ, ppm): 7.88 (d, J=6.7 Hz, 1H), 7.46-7.42 (m, 1H), 7.38-7.30 (m, 3H), 6.88 (t, J=7.6 Hz, 1H), 6.50 (d, J=7.9 Hz, 1H), 5.25-5.19 (m, 1H), 4.60 (d, J=5.5 Hz, 2H), 4.40 (s, 2H), 2.87 (s, 3H), 2.73 (s, 3H). MS=380 (MH)+.

156 d) N-Methyl-N-[2-({2-[4-(4-methyl-piperazin-1-yl)-phenylamino]-[1,2,4]triazolo[1,5-a]pyridin-8-ylamino}-methyl)-benzyl]-methanesulfonamide was prepared from N-{2-[(2-chloro-[1,2,4]triazolo[1,5-a]pyridin-8-ylamino)-methyl]-benzyl}-N-methyl-methanesulfonamide (75.0 mg, 0.197 mmol) and 4-(4-methyl-piperazin-1-yl)-phenylamine (42.0 mg, 0.220 mmol) with 2,2'-Bis-dicyclohexylphosphanyl-biphenyl (22.0 mg, 0.0402 mmol) as the ligand in a manner analogous to Example 2d. Product isolated as a brown lyophilate as the trifluoroacetic acid salt (0.006 g, 6%). $^1$H NMR (400 MHz, (D$_3$C)$_2$SO, δ, ppm): 9.50 (br s, 1H), 9.20 (s, 1H), 7.94 (d, J=6.7 Hz, 1H), 7.63 (d, J=9.1 Hz, 2H), 7.39-7.34 (m, 2H), 7.30-7.26 (m, 2H), 6.96 (d, J=8.8 Hz, 2H), 6.70 (t, J=7.4 Hz, 1H), 6.34 (br s, 1H), 6.24 (d, J=7.4 Hz, 1H), 4.62-4.59 (m, 2H), 4.40 (s, 2H), 3.71-3.65 (m, 2H), 3.23-3.13 (m, 2H), 3.03 (s, 3H), 2.92-2.82 (m, 4H), 2.65 (s, 3H). MS=535 (MH)+.

Example 157

N-Methyl-N-[2-({2-[3-(4-methyl-piperazin-1-yl)-phenylamino]-[1,2,4]triazolo[1,5-a]pyridin-8-ylamino}-methyl)-benzyl]-methanesulfonamide

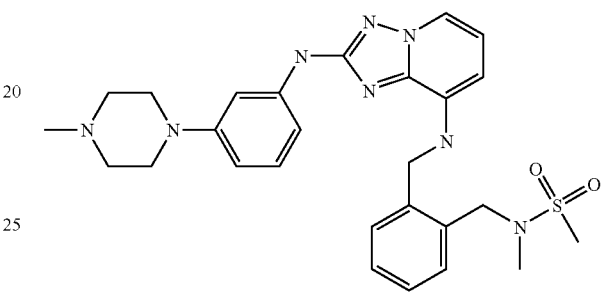

N-Methyl-N-[2-({2-[3-(4-methyl-piperazin-1-yl)-phenylamino]-[1,2,4]triazolo[1,5-a]pyridin-8-ylamino}-methyl)-benzyl]-methanesulfonamide was prepared from N-{2-[(2-chloro-[1,2,4]triazolo[1,5-a]pyridin-8-ylamino)-methyl]-benzyl}-N-methyl-methanesulfonamide (75.0 mg, 0.197 mmol) and 3-(4-Methylpiperazin-1-yl)aniline (42.0 mg, 0.220 mmol) with 2,2'-bis-dicyclohexylphosphanyl-biphenyl (26.0 mg, 0.0476 mmol) as the ligand in analogous manner to Example 2d. Product isolated as a tan lyophilate as the trifluoroacetic acid salt (0.006 g, 6%). $^1$H NMR (400 MHz, (D$_3$C)$_2$SO, δ, ppm): 9.56 (br s, 1H), 9.32 (s, 1H), 7.96 (d, J=6.5 Hz, 1H), 7.39-7.26 (m, 6H), 7.16 (t, J=7.9 Hz, 1H), 6.73 (t, J=7.1 Hz, 1H), 6.54 (d, J=8.9 Hz, 1H), 6.44-6.39 (m, 1H), 6.24 (d, J=7.3 Hz, 1H), 4.64-4.59 (m, 2H), 4.40 (s, 2H), 3.83-3.77 (m, 2H), 3.24-3.14 (m, 3H), 3.03 (s, 3H), 3.00-2.92 (m, 3H), 2.89-2.85 (m, 3H), 2.65 (s, 3H). MS=535 (MH)+.

Example 158

N-Methyl-N-[2-({2-[4-(2-pyrrolidin-1-yl-ethoxy)-phenylamino]-[1,2,4]triazolo[1,5-a]pyridin-8-ylamino}-methyl)-benzyl]-methanesulfonamide

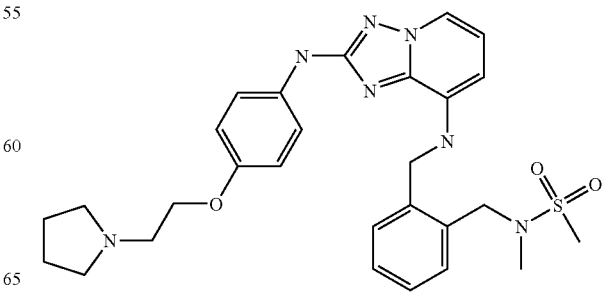

N-Methyl-N-[2-({2-[4-(2-pyrrolidin-1-yl-ethoxy)-phenylamino]-[1,2,4]triazolo[1,5-a]pyridin-8-ylamino}-methyl)-benzyl]-methanesulfonamide was prepared from N-{2-[(2-chloro-[1,2,4]triazolo[1,5-a]pyridin-8-ylamino)-methyl]-benzyl}-N-methyl-methanesulfonamide (75.0 mg, 0.197 mmol) and 4-(2-pyrrolidin-1-yl-ethoxy)-phenylamine (45.0 mg, 0.218 mmol) with 2,2'-bis-dicyclohexylphosphanyl-biphenyl (26.0 mg, 0.0476 mmol) as the ligand in a manner analogous to Example 2d. Product isolated as a brown lyophilate as the trifluoractic acid salt (0.004 g, 4%). $^1$H NMR (400 MHz, (D$_3$C)$_2$SO, δ, ppm): 9.65 (br s, 1H), 9.26 (s, 1H), 7.94 (d, J=6.6 Hz, 1H), 7.68 (d, J=9.0 Hz, 2H), 7.39-7.34 (m, 2H), 7.31-7.26 (m, 2H), 6.97 (d, J=8.9 Hz, 2H), 6.71 (t, J=6.9 Hz, 1H), 6.36 (br s, 1H), 6.25 (d, J=7.2 Hz, 1H), 4.63-4.59 (m, 2H), 4.40 (s, 2H), 4.24 (t, J=4.9 Hz, 2H), 3.64-3.54 (m, 4H), 3.18-3.09 (m, 2H), 3.03 (s, 3H), 2.65 (s, 3H), 2.09-1.99 (m, 2H), 1.95-1.85 (m, 2H). MS=550 (MH)+.

Example 159

N-Methyl-N-[2-({2-[4-(1-methyl-piperidin-4-yl)-phenylamino]-[1,2,4]triazolo[1,5-a]pyridin-8-ylamino}-methyl)-benzyl]-methanesulfonamide

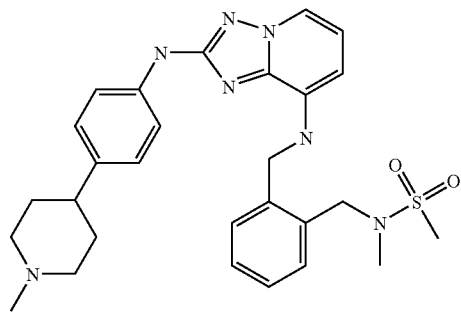

N-Methyl-N-[2-({2-[4-(1-methyl-piperidin-4-yl)-phenylamino]-[1,2,4]triazolo[1,5-a]pyridin-8-ylamino}-methyl)-benzyl]-methanesulfonamide was prepared from N-{2-[(2-chloro-[1,2,4]triazolo[1,5-a]pyridin-8-ylamino)-methyl]-benzyl}-N-methyl-methanesulfonamide (75.0 mg, 0.197 mmol) and 4-(1-methyl-piperidin-4-yl)-phenylamine (42.0 mg, 0.221 mmol) with 2,2'-bis-dicyclohexylphosphanyl-biphenyl (26.0 mg, 0.0476 mmol) as the ligand in analogous manner to Example 2d. Product isolated as tan lyophilate as the trifluoroacetic acid salt (0.007 g, 7%). $^1$H NMR (400 MHz, (D$_3$C)$_2$SO, δ, ppm): 9.39 (s, 1H), 9.21 (br s, 1H), 7.95 (d, J=6.8 Hz, 1H), 7.68 (d, J=8.5 Hz, 2H), 7.39-7.34 (m, 2H), 7.30-7.26 (m, 2H), 7.14 (d, J=8.5 Hz, 2H), 6.72 (t, J=7.2 Hz, 1H), 6.39 (br s, 1H), 6.25 (d, J=8.1 Hz, 1H), 4.63-4.59 (m, 2H), 4.40 (s, 2H), 3.55-3.45 (m, 2H), 3.10-3.00 (m, 6H), 2.83-2.80 (m, 3H), 2.65 (s, 3H), 2.04-1.96 (m, 2H), 1.84-1.72 (m, 2H). MS=534 (MH)+.

Example 160

N(8)-(3-Methanesulfonyl-benzyl)-N(2)-[4-(4-methyl-piperazin-1-yl)-phenyl]-[1,2,4]triazolo[1,5-a]pyridine-2,8-diamine

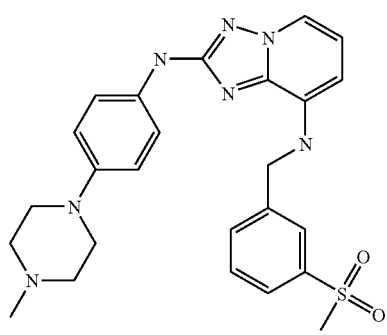 [SMILES: CN1CCN(c2ccc(Nc3nc4c(NCc5cccc(S(C)(=O)=O)c5)cccn4n3)cc2)CC1]

160a) 3-Methanesulfonyl-benzylamine was prepared from 3-methanesulfonyl-benzonitrile (0.984 g, 5.43 mmol) in a manner analogous to Example 156b. Product isolated as a pale yellow oil (0.946 g, 94%). $^1$H NMR (400 MHz, CDCl$_3$, δ, ppm): 7.93 (s, 1H), 7.83 (d, J=7.7 Hz, 1H), 7.64 (d, J=7.6 Hz, 1H), 7.54 (t, J=7.7 Hz, 1H), 4.00 (s, 2H), 3.06 (s, 3H). MS=186 (MH)+.

160 b) (2-Chloro-[1,2,4]triazolo[1,5-a]pyridin-8-yl)-(3-methanesulfonyl-benzyl)-amine was prepared from 8-bromo-2-chloro-[1,2,4]triazolo[1,5-a]pyridine (500.0 mg, 2.151 mmol) and 3-methanesulfonyl-benzylamine (450.0 mg, 2.429 mmol) in a manner analogous to Example 2d. Product isolated as a pale yellow solid (0.429 g, 59%). $^1$H NMR (400 MHz, CDCl$_3$, δ, ppm): 7.97 (s, 1H), 7.93-7.87 (m, 2H), 7.68 (d, J=7.7 Hz, 1H), 7.58 (t, J=7.7 Hz, 1H), 6.85 (t, J=7.4 Hz, 1H), 6.35 (d, J=7.8 Hz, 1H), 5.51-5.44 (m, 1H), 4.59 (d, J=5.8 Hz, 2H), 3.07 (s, 3H). MS=337, 339 (MH)+.

160 c) N(8)-(3-Methanesulfonyl-benzyl)-N(2)-[4-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(3-methanesulfonyl-benzyl)-amine (75.0 mg, 0.223 mmol) and 4-(4-methyl-piperazin-1-yl)-phenylamine (47.0 mg, 0.246 mmol) with 2,2'-bis-dicyclohexylphosphanyl-biphenyl (23.0 mg, 0.0421 mmol) as the ligand in a manner analogous to Example 2d. Product isolated as a brown lyophilate as the trifluoroacetic acid salt (0.004 g, 4%). $^1$H NMR (400 MHz, (D$_3$C)$_2$SO, δ, ppm): 9.50 (br s, 1H), 9.17 (s, 1H), 7.98-7.93 (m, 2H), 7.81 (d, J=8.0 Hz, 1H), 7.74 (d, J=7.8 Hz, 1H), 7.65-7.59 (m, 3H), 6.96 (d, J=8.9 Hz, 2H), 6.70 (t, J=7.5 Hz, 1H), 6.64 (br s, 1H), 6.32 (d, J=7.6 Hz, 1H), 4.65-4.60 (m, 2H), 3.72-3.65 (m, 2H), 3.23-3.13 (m, 6H), 2.92-2.82 (m, 6H). MS=492 (MH)+.

Example 161

N(8)-(3-Methanesulfonyl-benzyl)-N(2)-[3-(4-methyl-piperazin-1-yl)-phenyl]-[1,2,4]triazolo[1,5-a]pyridine-2,8-diamine

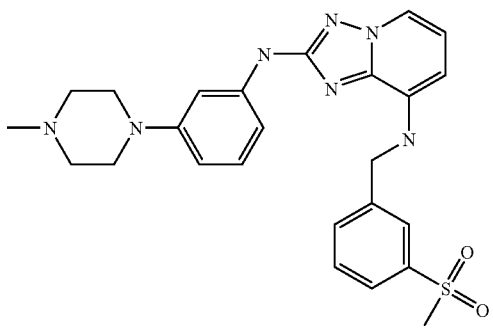 [SMILES: CN1CCN(c2cccc(Nc3nc4c(NCc5cccc(S(C)(=O)=O)c5)cccn4n3)c2)CC1]

N(8)-(3-Methanesulfonyl-benzyl)-N(2)-[3-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(3-methanesulfonyl-benzyl)-amine (75.0 mg, 0.223 mmol) and 3-(4-methylpiperazin-1-yl)aniline (47.0 mg, 0.246 mmol) with 2,2'-bis-dicyclohexylphosphanyl-biphenyl (23.0 mg, 0.0421 mmol) as the ligand in a manner analogous to Example 2d. Product isolated as tan lyophilate as the trifluoroacetic acid salt (0.003 g, 3%). $^1$H NMR (400 MHz, $(D_3C)_2SO$, δ, ppm): 9.57 (br s, 1H), 9.30 (s, 1H), 7.98-7.95 (m, 2H), 7.81 (d, J=7.3 Hz, 1H), 7.74 (d, J=7.5 Hz, 1H), 7.62 (t, J=7.7 Hz, 1H), 7.35-7.30 (m, 2H), 7.16 (t, J=8.0 Hz, 1H), 6.74 (t, J=7.3 Hz, 1H), 6.69 (br s, 1H), 6.55 (d, J=8.4 Hz, 1H), 6.34 (d, J=7.9 Hz, 1H), 4.65-4.62 (m, 2H), 3.83-3.76 (m, 2H), 3.24-3.13 (m, 7H), 3.01-2.92 (m, 2H), 2.89-2.86 (m, 3H). MS=492 (MH)+.

Example 162

N(8)-(3-Methanesulfonyl-benzyl)-N(2)-[4-(1-methyl-piperidin-4-yl)-phenyl]-[1,2,4]triazolo[1,5-a]pyridine-2,8-diamine

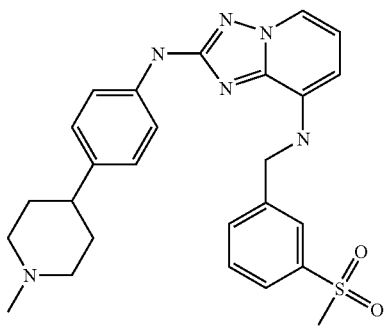

N(8)-(3-Methanesulfonyl-benzyl)-N(2)-[4-(1-methyl-piperidin-4-yl)-phenyl]-[1,2,4]triazolo[1,5-a]pyridine-2,8-diamine was prepared from (2-chloro-[1,2,4]triazolo[1,5-a]pyridin-8-yl)-(3-methanesulfonyl-benzyl)-amine (75.0 mg, 0.223 mmol) and 4-(1-methyl-piperidin-4-yl)-phenylamine (47.0 mg, 0.247 mmol) with 2,2'-bis-dicyclohexylphosphanyl-biphenyl (23.0 mg, 0.0421 mmol) as the ligand in a manner analogous to Example 2d. Product isolated as tan lyophilate as the trifluoroacetic acid salt (0.005 g, 5%). $^1$H NMR (400 MHz, $(D_3C)_2SO$, δ, ppm): 9.37 (s, 1H), 9.23 (br s, 1H), 7.98-7.94 (m, 2H), 7.81 (d, J=7.3 Hz, 1H), 7.74 (d, J=7.4 Hz, 1H), 7.68 (d, J=8.3 Hz, 2H), 7.62 (t, J=7.8 Hz, 1H), 7.14 (d, J=8.4 Hz, 2H), 6.73 (t, J=7.1 Hz, 1H), 6.68 (br s, 1H), 6.33 (d, J=7.9 Hz, 1H), 4.65-4.61 (m, 2H), 3.55-3.45 (m, 2H), 3.19 (s, 3H), 3.12-3.00 (m, 2H), 2.85-2.79 (m, 3H), 2.76-2.68 (m, 1H), 2.04-1.96 (m, 2H), 1.85-1.71 (m, 2H). MS=491 (MH)+.

Example 163

3-({2-[4-(4-Methyl-piperazin-1-yl)-phenylamino]-[1,2,4]triazolo[1,5-a]pyridin-8-ylamino}-methyl)-pyrrolidine-1-carboxylic acid tert-butyl ester

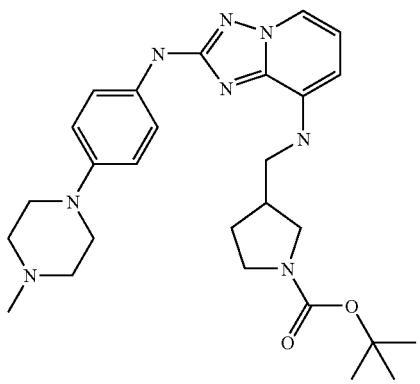 [SMILES: CN1CCN(c2ccc(Nc3nc4c(NCC5CCN(C(=O)OC(C)(C)C)C5)cccn4n3)cc2)CC1]

163a) 3-[(2-Chloro-[1,2,4]triazolo[1,5-a]pyridin-8-ylamino)-methyl]-pyrrolidine-1-carboxylic acid tert-butyl ester was prepared from 8-bromo-2-chloro-[1,2,4]triazolo[1,5-a]pyridine (500.0 mg, 2.151 mmol) and 3-aminomethyl-pyrrolidine-1-carboxylic acid tert-butyl ester (475.0 mg, 2.372 mmol) in a manner analogous to Example 2d. Product isolated as pale yellow viscous oil (0.544 g, 72%). $^1$H NMR (400 MHz, CDCl$_3$, δ, ppm): 7.88 (d, J=6.6 Hz, 1H), 6.89 (t, J=7.3 Hz, 1H), 6.72 (d, J=7.9 Hz, 1H), 4.98 (br s, 1H), 3.65-3.08 (m, 6H), 2.64-2.51 (m, 1H), 2.15-2.05 (m, 1H), 1.80-1.65 (m, 1H), 1.47 (s, 9H).

163 b) 3-({2-[4-(4-Methyl-piperazin-1-yl)-phenylamino]-[1,2,4]triazolo[1,5-a]pyridin-8-ylamino}-methyl)-pyrrolidine-1-carboxylic acid tert-butyl ester was prepared from 3-[(2-chloro-[1,2,4]triazolo[1,5-a]pyridin-8-ylamino)-methyl]-pyrrolidine-1-carboxylic acid tert-butyl ester (500.0 mg, 1.421 mmol) and 4-(4-methyl-piperazin-1-yl)-phenylamine (300.0 mg, 1.568 mmol) with 2,2'-bis-dicyclohexylphosphanyl-biphenyl (78.0 mg, 0.143 mmol) as the ligand in a manner analogous to Example 2d. Product isolated as a tan foam (0.284 g, 39%). $^1$H NMR (400 MHz, CDCl$_3$, δ, ppm): 7.81 (d, J=6.5 Hz, 1H), 7.46 (d, J=8.9 Hz, 2H), 6.96 (d, J=8.9 Hz, 2H), 6.71 (t, J=7.3 Hz, 1H), 6.59 (s, 1H), 6.35 (d, J=7.7 Hz, 1H), 4.75 (br s, 1H), 3.66-3.05 (m, 10H), 2.63-2.52 (m, 5H), 2.36 (s, 3H), 2.15-2.04 (m, 1H), 1.80-1.65 (m, 1H), 1.46 (s, 9H). MS=507 (MH)+.

Example 164

N(8)-(2-Methanesulfonylmethyl-phenyl)-N(2)-[4-(4-methyl-piperazin-1-yl)-phenyl]-[1,2,4]triazolo[1,5-a]pyridine-2,8-diamine

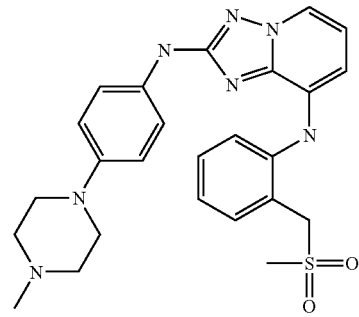 [SMILES: CN1CCC(c2ccc(Nc3nc4c(Nc5ccccc5CS(C)(=O)=O)cccn4n3)cc2)CC1]

164 a) A suspension of o-Nitrobenzylbromide (5.71 g, 26.4 mmol) and sodium methanesulfinate (4.0 g, 40.0 mmol) in ethanol (70 mL) was stirred at room temperature for 18 hours. The volatiles were evaporated under reduced pressure. To the residue was added water (50 mL) and stirred for 30 minutes. The suspension was filtered, rinsed with water and air dried. 1-Methanesulfonylmethyl-2-nitro-benzene was isolated as a yellow solid (5.36 g, 94%). MP=115-117° C. $^1$H NMR (400 MHz, CDCl$_3$, δ, ppm): 8.10 (d, J=8.1 Hz, 1H), 7.74-7.65 (m, 2H), 7.62-7.58 (m, 1H), 4.80 (s, 2H), 2.91 (s, 3H).

164 b) 2-Methanesulfonylmethyl-phenylamine was prepared from 1-methanesulfonylmethyl-2-nitro-benzene (1.0 g, 4.6 mmol) in a manner analogous to Example 111a. Product isolated as an off-white solid (0.84 g, 98%). $^1$H NMR (400 MHz, CDCl$_3$, δ, ppm): 7.20 (t, J=7.5 Hz, 1H), 7.09 (d, J=7.5 Hz, 1H), 6.86-6.76 (m, 2H), 4.30 (s, 2H), 4.28 (br s, 2H), 2.87 (s, 3H). MS=186 (MH)+.

164 c) (2-Chloro-[1,2,4]triazolo[1,5-a]pyridin-8-yl)-(2-methanesulfonylmethyl-phenyl)-amine was prepared from 8-bromo-2-chloro-[1,2,4]triazolo[1,5-a]pyridine (500.0 mg, 2.151 mmol) and 2-methanesulfonylmethyl-phenylamine (440.0 mg, 2.375 mmol) in a manner analogous to Example 2d. Product isolated as a tan solid (0.62 g, 51%). $^1$H NMR (400 MHz, CDCl$_3$, δ, ppm): 8.02 (d, J=5.9 Hz, 1H), 7.71 (s, 1H), 7.53 (d, J=8.3 Hz, 1H), 7.47-7.41 (m, 3H), 6.89-6.81 (m, 2H), 4.41 (s, 2H), 2.93 (s, 3H). MS=337, 339 (MH)+.

164 d) N(8)-(2-Methanesulfonylmethyl-phenyl)-N(2)-[4-(4-methyl-piperazin-1-yl)-phenyl]-[1,2,4]triazolo[1,5-a]pyridine-2,8-diamine was prepare from (2-chloro-[1,2,4]triazolo[1,5-a]pyridin-8-yl)-(2-methanesulfonylmethyl-phenyl)-amine (75.0 mg, 0.223 mmol) and 4-(4-Methyl-piperazin-1-yl)-phenylamine (47.0 mg, 0.246 mmol) with 2,2'-bis-dicyclohexylphosphanyl-biphenyl (25.0 mg, 0.0457 mmol) as the ligand in a manner analogous to Example 2d. Product isolated as a brown foam (0.013 g, 12%). $^1$H NMR (400 MHz, CDCl$_3$, δ, ppm): 7.96 (d, J=6.8 Hz, 1H), 7.70 (s, 1H), 7.56 (d, J=8.2 Hz, 1H), 7.51 (d, J=8.8 Hz, 2H), 7.43-7.37 (m, 2H), 7.18 (t, J=7.4 Hz, 1H), 6.96 (d, J=8.8 Hz, 2H), 6.83 (d, J=7.8 Hz, 1H), 6.70 (s, 1H), 6.67 (t, J=7.1 Hz, 1H), 4.45 (s, 2H), 3.18-3.13 (m, 4H), 2.94 (s, 3H), 2.62-2.57 (m, 4H), 2.36 (s, 3H). MS=492 (MH)+.

Example 165

N(8)-(2-Methanesulfonylmethyl-phenyl)-N(2)-[4-(1-methyl-piperidin-4-yl)-phenyl]-[1,2,4]triazolo[1,5-a]pyridine-2,8-diamine

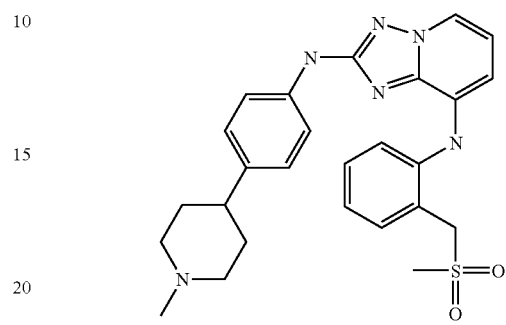

N(8)-(2-Methanesulfonylmethyl-phenyl)-N(2)-[4-(1-methyl-piperidin-4-yl)-phenyl]-[1,2,4]triazolo[1,5-a]pyridine-2,8-diamine was prepared from (2-chloro-[1,2,4]triazolo[1,5-a]pyridin-8-yl)-(2-methanesulfonylmethyl-phenyl)-amine (75.0 mg, 0.223 mmol) and 4-(1-methyl-piperidin-4-yl)-phenylamine (47.0 mg, 0.247 mmol) with 2,2'-bis-dicyclohexylphosphanyl-biphenyl (25.0 mg, 0.0457 mmol) as the ligand in a manner analogous to Example 2d. Product isolated as a tan foam (0.016 g, 15%). $^1$H NMR (400 MHz, CDCl$_3$, δ, ppm): 7.97 (d, J=6.6 Hz, 1H), 7.74 (s, 1H), 7.59-7.52 (m, 3H), 7.44-7.37 (m, 2H), 7.23-7.15 (m, 3H), 6.87-6.84 (m, 2H), 6.69 (t, J=7.3 Hz, 1H), 4.45 (s, 2H), 3.01-2.93 (m, 5H), 2.50-2.40 (m, 1H), 2.32 (s, 3H), 2.09-2.01 (m, 2H), 1.87-1.74 (m, 4H). MS=491 (MH)+.

Example 166

N-Methyl-N-(3-{[2-(2-methyl-2,3-dihydro-1H-isoindol-5-ylamino)-[1,2,4]triazolo[1,5-a]pyridin-8-ylamino]-methyl}-pyridin-2-yl)-methanesulfonamide

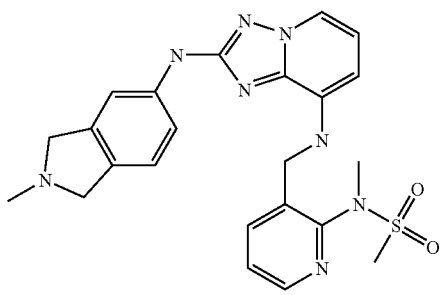 [SMILES: CN1Cc2ccc(Nc3nc4c(NCc5cccnc5N(C)S(C)(=O)=O)cccn4n3)cc2C1]

166a) To a cooled solution of 2,3-dihydro-1H-isoindole (8.80 g, 73.8 mmol) in acetonitrile (80 mL) at −10° C. was added trifluoroacetic anhydride (36.1 mL, 255 mmol) dropwise. Potassium nitrate (7.50 g, 74.2 mmol) was added in one portion to the stirred mixture. The mixture was stirred at −10°

C. for 1 hour. To the mixture was added saturated aqueous sodium bicarbonate (100 mL) slowly. Vigorous gas evolution was noted. The mixture was stirred for 1 hour and allowed to warm to room temperature. The mixture was basified with saturated aqueous sodium carbonate (100 mL). The thick suspension was filtered. The solid was washed with water (200 mL), dissolved in dichloromethane (300 mL) and separated. The organic layer was dried over magnesium sulfate, filtered and evaporated to a tan solid (17.97 g). The material was purified via flash chromatography using an ISCO automated purification apparatus (silica gel column and 10%→100% Ethyl Acetate:Hexane). 2,2,2-Trifluoro-1-(5-nitro-1,3-dihydro-isoindol-2-yl)-ethanone was isolated as a crude orange solid (16.8 g, 85%). $^1$H NMR (400 MHz, CDCl$_3$, δ, ppm): 8.28-8.23 (m, 1H), 8.20 (d, J=17.6 Hz, 1H), 7.50 (dd, J=21.7, 8.40 Hz, 1H), 5.14 (s, 2H), 5.02 (s, 2H). MS=261 (MH)+.

166 b) To a solution of 2,2,2-Trifluoro-1-(5-nitro-1,3-dihydro-isoindol-2-yl)-ethanone (16.8 g, 64.6 mmol) in acetonitrile (300 mL, 6000 mmol) at 0° C. was added 33% aqueous sodium hydroxide (100 mL) slowly with vigorous stirring. The mixture was stirred at 0° C. for 1 hour then allowed to warm to room temperature for 4 hours. The reaction mixture was transferred to a separation funnel and the layers separated. The organic layer was dried over sodium sulfate, filtered and evaporated to a dark oily material. The residue was dissolved in dichloromethane (500 mL) and separated. The organic layer was dried over magnesium sulfate, filtered and evaporated to yield a dark viscous oil (12 g) and was placed under high vacuum for 4 hours. Crude 5-Nitro-2,3-dihydro-1H-isoindole was isolated as a dark brown waxy solid (10 g, 94%). $^1$H NMR (400 MHz, CDCl$_3$, δ, ppm): 8.16-8.09 (m, 2H), 7.39 (d, J=8.1 Hz, 1H), 4.36 (s, 4H). MS=165 (MH)+.

166 c) To a stirred solution of crude 5-nitro-2,3-dihydro-1H-isoindole (9.0 g, 55 mmol) and 4-dimethylaminopyridine (0.33 g, 2.7 mmol) in N,N-dimethylformamide (50 mL) was added di-tert-Butyldicarbonate (14 mL, 6.0.0 mmol) and the mixture was stirred for 18 hours at room temperature. To the mixture was added water (150 mL) and the mixture was stirred vigorously for 30 minutes. The resulting precipitate was filtered, rinsed with water and dried by suction. Crude 5-nitro-1,3-dihydro-isoindole-2-carboxylic acid tert-butyl ester was isolated as brown solid (7.88 g, 54%). $^1$H NMR (400 MHz, CDCl$_3$, δ, ppm): 8.20-8.09 (m, 2H), 7.41 (dd, J=21.1, 8.6 Hz, 1H), 4.77 (s, 2H), 4.74 (s, 2H), 1.53 (s, 9H). MS=287 (M+Na)+.

166 d) 5-Amino-1,3-dihydro-isoindole-2-carboxylic acid tert-butyl ester was prepared from crude 5-nitro-1,3-dihydro-isoindole-2-carboxylic acid tert-butyl ester (3.0 g, 11 mmol) in a manner analogous to Example 111a. Product isolated as a brown viscous oil (2.21 g, 83%). $^1$H NMR (400 MHz, CDCl$_3$, δ, ppm): 7.01 (dd, J=19.7, 8.1 Hz, 1H), 6.62-6.52 (m, 2H), 4.61-4.51 (m, 4H), 3.66 (br s, 2H), 1.51 (s, 9H). MS=235 (MH)+.

166 e) To a cooled solution of 2.0 M of lithium tetrahydroborate in tetrahydrofuran (13 mL, 26 mmol) at 5° C. was added dropwise a solution of 5-amino-1,3-dihydro-isoindole-2-carboxylic acid tert-butyl ester (1.0 g, 4.3 mmol) in tetrahydrofuran (50 mL). Gas evolution was noted. The mixture was stirred for 1 hour at 5° C. then warmed to room temperature and stirred for 24 hours. The mixture was cooled to 5° C. in a ice/water bath and the reaction was quenched by addition of sodium sulfate decahydrate (3 g). Gas evolution noted. The mixture was stirred for 2 hours at room temperature. The suspension was filtered through a plug of diatomaceous earth and rinsed with tetrahydrofuran. The filtrate was dried over magnesium sulfate, filtered and evaporated. The residue was purified via flash chromatography (silica gel column and 0%→20% methanol: dichloromethane). 2-Methyl-2,3-dihydro-1H-isoindol-5-ylamine was isolated as an orange solid (0.271 g, 43%). $^1$H NMR (400 MHz, (D$_3$C)$_2$SO, δ, ppm): 6.82 (d, J=7.9 Hz, 1H), 6.41 (s, 1H), 6.37 (d, J=8.1 Hz, 1H), 4.86 (br s, 2H), 3.64 (s, 2H), 3.62 (s, 2H), 2.42 (s, 3H). MS=149 (MH)+.

166 f) N-Methyl-N-(3-{[2-(2-methyl-2,3-dihydro-1H-isoindol-5-ylamino)-[1,2,4]triazolo[1,5-a]pyridin-8-ylamino]-methyl}-pyridin-2-yl)-methanesulfonamide was prepared from N-{3-[(2-chloro-[1,2,4]triazolo[1,5-a]pyridin-8-ylamino)-methyl]-pyridin-2-yl}-N-methyl-methanesulfonamide (75.0 mg, 0.204 mmol) and 2-methyl-2,3-dihydro-1H-isoindol-5-ylamine (34.0 mg, 0.229 mmol) with 2,2'-bis-dicyclohexylphosphanyl-biphenyl (25.0 mg, 0.0457 mmol) as the ligand in a manner analogous to Example 2d. Product isolated as tan foam (0.048 g, 49%). $^1$H NMR (400 MHz, CDCl$_3$, δ, ppm): 8.41 (d, J=3.6 Hz, 1H), 7.87-7.81 (m, 2H), 7.53 (s, 1H), 7.33-7.25 (m, 2H), 7.14 (d, J=8.1 Hz, 1H), 6.72 (s, 1H), 6.66 (t, J=7.4 Hz, 1H), 6.30 (d, J=7.6 Hz, 1H), 5.33-5.29 (m, 1H), 4.77 (d, J=6.2 Hz, 2H), 3.94 (s, 2H), 3.88 (s, 2H), 3.32 (s, 3H), 3.09 (s, 3H), 2.60 (s, 3H). MS=479 (MH)+.

Example 167

N-Methyl-N-(2-{[2-(2-methyl-2,3-dihydro-1H-isoindol-5-ylamino)-[1,2,4]triazolo[1,5-a]pyridin-8-ylamino]-methyl}-phenyl)-methanesulfonamide

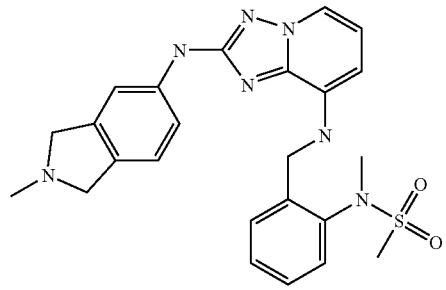 [SMILES: CN1Cc2ccc(Nc3nc4c(NCc5ccccc5N(C)S(C)(=O)=O)cccn4n3)cc2C1]

N-Methyl-N-(2-{[2-(2-methyl-2,3-dihydro-1H-isoindol-5-ylamino)-[1,2,4]triazolo[1,5-a]pyridin-8-ylamino]-methyl}-phenyl)-methanesulfonamide was prepared from N-{2-[(2-chloro-[1,2,4]triazolo[1,5-a]pyridin-8-ylamino)-methyl]-phenyl}-N-methyl-methanesulfonamide (75.0 mg, 0.205 mmol) and 2-methyl-2,3-dihydro-1H-isoindol-5-ylamine (34.0 mg, 0.229 mmol) with 2,2'-bis-dicyclohexylphosphanyl-biphenyl (25.0 mg, 0.0457 mmol) as the ligand in a manner analogous to Example 2d. Product isolated as a tan foam (0.052 g, 53%). $^1$H NMR (400 MHz, CDCl$_3$, δ, ppm): 7.82 (d, J=6.6 Hz, 1H), 7.55-7.50 (m, 2H), 7.37-7.28 (m, 4H), 7.13 (d, J=7.9 Hz, 1H), 6.70-6.65 (m, 2H), 6.37 (d, J=7.7 Hz, 1H), 5.23 (t, J=5.7 Hz, 1H), 4.73 (d, J=6.3 Hz, 2H), 3.94 (s, 2H), 3.88 (s, 2H), 3.31 (s, 3H), 3.01 (s, 3H), 2.60 (s, 3H). MS=478 (MH)+.

Example 168

[8-(4-Methanesulfonyl-phenyl)-[1,2,4]triazolo[1,5-a]pyridin-2-yl]-(2-methyl-2,3-dihdro-1H-isoindol-5-yl)-amine

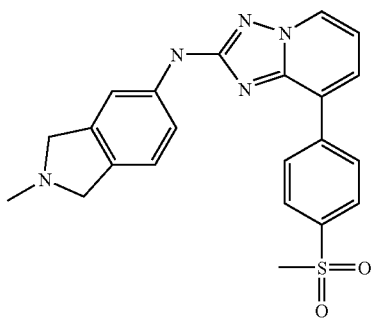 [SMILES: CN1Cc2ccc(Nc3nc4c(-c5ccc(S(C)(=O)=O)cc5)cccn4n3)cc2C1]

[8-(4-Methanesulfonyl-phenyl)-[1,2,4]triazolo[1,5-a]pyridin-2-yl]-(2-methyl-2,3-dihydro-1H-isoindol-5-yl)-amine was prepared from 2-chloro-8-(4-methanesulfonyl-phenyl)-[1,2,4]triazolo[1,5-a]pyridine (75.0 mg, 0.244 mmol) and 2-methyl-2,3-dihydro-1H-isoindol-5-ylamine (40.0 mg, 0.270 mmol) with 2,2'-bis-dicyclohexylphosphanyl-biphenyl (25.0 mg, 0.0457 mmol) as the ligand in a manner analogous to Example 2d. Product isolated as a yellow foam (0.049 g, 48%). $^1$H NMR (400 MHz, CDCl$_3$, δ, ppm): 8.50 (d, J=6.7 Hz, 1H), 8.23 (d, J=8.4 Hz, 2H), 8.08 (d, J=8.3 Hz, 2H), 7.65 (d, J=7.3 Hz, 1H), 7.51 (s, 1H), 7.32 (d, J=8.3 Hz, 1H), 7.15 (d, J=8.1 Hz, 1H), 7.02 (t, J=7.0 Hz, 1H), 6.98 (s, 1H), 3.94 (s, 2H), 3.88 (s, 2H), 3.09 (s, 3H), 2.61 (s, 3H). MS=420 (MH)+.

Example 169

N-Methyl-N-[3-({2-[4-(4-methyl-piperazin-1-yl)-phenylamino]-[1,2,4]triazolo[1,5-a]pyridin-8-ylamino}-methyl)-phenyl]-methanesulfonamide

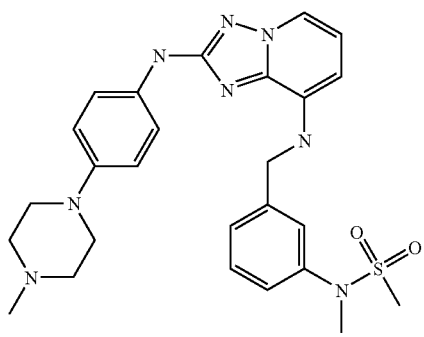 [SMILES: CN1CCN(c2ccc(Nc3nc4c(NCc5cccc(N(C)S(C)(=O)=O)c5)cccn4n3)cc2)CC1]

169 a) To a suspension of N-(3-bromo-phenyl)-methanesulfonamide (1.0 g, 4.0 mmol) and potassium carbonate (0.61 g, 4.4 mmol) in acetone (10 mL) was added iodomethane (0.30 mL, 4.8 mmol). The mixture was stirred at room temperature for 18 hours, diluted with dichloromethane (30 mL), filtered through a plug of diatomaceous earth and evaporated under reduced pressure. N-(3-Bromo-phenyl)-N-methyl-methanesulfonamide was isolated a tan viscous oil (1.08 g, 100%). $^1$H NMR (400 MHz, CDCl$_3$, δ, ppm): 7.53 (s, 1H), 7.43 (d, J=7.9 Hz, 1H), 7.35 (d, J=8.2 Hz, 1H), 7.29-7.23 (m, 1H), 3.32 (s, 3H), 2.86 (s, 3H). MS=286, 288 (MH)+.

169 b) A suspension of N-(3-bromo-phenyl)-N-methyl-methanesulfonamide (1.0 g, 3.8 mmol) and copper cyanide (0.78 g, 8.7 mmol) in N,N-dimethylformamide (5 mL) was heated at 150° C. for 18 hours. The mixture was cooled to room temperature. A solution of potassium cyanide (5 g) and water (50 mL) was added to the vigorously stirred dark mixture and was stirred for 1 hour. The mixture was extracted with ethyl acetate (3×20 mL). The combined organic layers were washed with water (2×30 mL) then saturated aqueous sodium chloride (30 mL), dried over magnesium sulfate and filtered. The filtrate was evaporated to a yellow oil (1.0 g). The residue was purified via flash chromatography (silica gel column and 5%→50% ethyl acetate:hexane). N-(3-Cyano-phenyl)-N-methyl-methanesulfonamide was isolated as a tan solid (0.184 g, 23%). $^1$H NMR (400 MHz, CDCl$_3$, δ, ppm): 7.69-7.64 (m, 2H), 7.58 (d, J=7.7 Hz, 1H), 7.54-7.49 (m, 1H), 3.36 (s, 3H), 2.88 (s, 3H). MS=211 (MH)+.

169 c) -(3-Aminomethyl-phenyl)-N-methyl-methanesulfonamide was prepared from N-(3-Cyano-phenyl)-N-methyl-methanesulfonamide (0.184 g, 0.875 mmol) in a manner analogous to Example 156b. Product isolated as a tan viscous oil (0.184 g, 98%). $^1$H NMR (400 MHz, CDCl$_3$, δ, ppm): 7.39-7.33 (m, 2H), 7.28-7.23 (m, 2H), 3.90 (s, 2H), 3.33 (s, 3H), 2.86 (s, 3H). MS=215 (MH)+.

169 d) N-{3-[(2-Chloro-[1,2,4]triazolo[1,5-a]pyridin-8-ylamino)-methyl]-phenyl}-N-methyl-methanesulfonamide was prepared from 8-bromo-2-chloro-[1,2,4]triazolo[1,5-a]pyridine (184.0 mg, 0.7915 mmol) and N-(3-aminomethyl-phenyl)-N-methyl-methanesulfonamide (188.0 mg, 0.8773 mmol) in a manner analogous to Example 2d. Product isolated as a yellow resin (0.082 g, 28%). $^1$H NMR (400 MHz, CDCl$_3$, δ, ppm): 7.89 (d, J=6.7 Hz, 1H), 7.42-7.36 (m, 2H), 7.33-7.29 (m, 2H), 6.85 (t, J=7.4 Hz, 1H), 6.39 (d, J=7.8 Hz, 1H), 5.43-5.38 (m, 1H), 4.49 (d, J=5.7 Hz, 2H), 3.32 (s, 3H), 2.83 (s, 3H). MS=366, 368 (MH)+.

169 e) N-Methyl-N-[3-({2-[4-(4-methyl-piperazin-1-yl)-phenylamino]-[1,2,4]triazolo[1,5-a]pyridin-8-ylamino}-methyl)-phenyl]-methanesulfonamide was prepared from N-{3-[(2-chloro-[1,2,4]triazolo[1,5-a]pyridin-8-ylamino)-methyl]-phenyl}-N-methyl-methanesulfonamide (82.0 mg, 0.224 mmol) and 4-(4-methyl-piperazin-1-yl)-phenylamine (48.0 mg, 0.251 mmol) with 2,2'-bis-dicyclohexylphosphanyl-biphenyl (25.0 mg, 0.0457 mmol) as the ligand in a manner analogous to Example 2d. Product isolated as a tan foam (0.024 g, 21%). $^1$H NMR (400 MHz, CDCl$_3$, δ, ppm): 7.82 (d, J=6.6 Hz, 1H), 7.47 (d, J=8.8 Hz, 2H), 7.42-7.28 (m, 4H), 6.96 (d, J=8.8 Hz, 2H), 6.65 (t, J=7.2 Hz, 1H), 6.54 (s, 1H), 6.29 (d, J=7.6 Hz, 1H), 5.19 (t, J=5.6 Hz, 1H), 4.49 (d, J=5.6 Hz, 2H), 3.30 (s, 3H), 3.17-3.13 (m, 4H), 2.81 (s, 3H), 2.62-2.57 (m, 4H), 2.36 (s, 3H). MS=521 (MH)+.

Example 170

N(8)-(1-Methanesulfonyl-pyrrolidin-2-ylmethyl)-N(2)-[4-(4-methyl-piperazin-1-yl)-phenyl]-[1,2,4]triazolo[1,5-a]pyridine-2,8-diamine

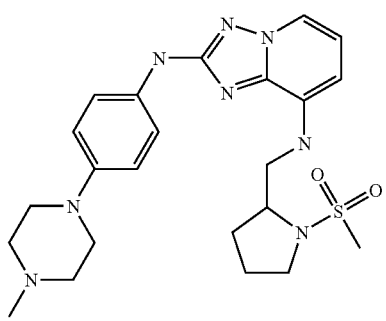 [SMILES: CN1CCN(c2ccc(Nc3nc4c(NCC5CCCN5S(C)(=O)=O)cccn4n3)cc2)CC1]

170 a) 2-[(2-Chloro-[1,2,4]triazolo[1,5-a]pyridin-8-ylamino)-methyl]-pyrrolidine-1-carboxylic acid tert-butyl ester was prepared from 8-bromo-2-chloro-[1,2,4]triazolo[1,5-a]pyridine (500.0 mg, 2.151 mmol) and 2-aminomethyl-pyrrolidine-1-carboxylic acid tert-butyl ester (475.0 mg, 2.372 mmol) in a manner analogous to Example 2d. Product isolated as a yellow viscous oil (0.411 g, 54%). MS=374, 376 (MH)+.

170 b) 2-({2-[4-(4-Methyl-piperazin-1-yl)-phenylamino]-[1,2,4]triazolo[1,5-a]pyridin-8-ylamino}-methyl)-pyrrolidine-1-carboxylic acid tert-butyl ester was prepared from 2-[(2-chloro-[1,2,4]triazolo[1,5-a]pyridin-8-ylamino)-methyl]-pyrrolidine-1-carboxylic acid tert-butyl ester (400.0 mg, 1.137 mmol) and 4-(4-methyl-piperazin-1-yl)-phenylamine (240.0 mg, 1.255 mmol) with 2,2'-bis-dicyclohexylphosphanyl-biphenyl (63.0 mg, 0.115 mmol) as the ligand in a manner analogous to Example 2d. Product isolated as a tan resin (0.090 g, 16%). $^1$H NMR (400 MHz, CDCl$_3$, δ, ppm): 7.81-7.74 (m, 1H), 7.47 (d, J=7.6 Hz, 2H), 6.95 (dm J=8.8 Hz, 2H), 6.74-6.45 (m, 3H), 5.40-4.90 (m, 1H), 4.23-4.06 (m, 1H), 3.56-3.05 (m, 8H), 2.63-2.57 (m, 4H), 2.36 (s, 3H), 2.05-1.80 (m, 4H), 1.56-1.44 (m, 9H). MS=507 (MH)+.

170 c) To a solution of 2-({2-[4-(4-Methyl-piperazin-1-yl)-phenylamino]-[1,2,4]triazolo[1,5-a]pyridin-8-ylamino}-methyl)-pyrrolidine-1-carboxylic acid tert-butyl ester (90.0 mg, 0.178 mmol) in dichloromethane (1 mL) was added trifluoroacetic acid (0.0547 mL, 0.710 mmol). The mixture was stirred at room temperature for 18 hours then the volatiles were evaporated under reduced pressure. Crude N(2)-[4-(4-Methyl-piperazin-1-yl)-phenyl]-N(8)-pyrrolidin-2-ylmethyl-[1,2,4]triazolo[1,5-a]pyridine-2,8-diamine as the bis-trifluoroacetic acid salt was isolated as a red-brown resin. The residue was suspended in dichloromethane (2 mL) and triethylamine (0.148 mL, 1.06 mmol) was added. The mixture was cooled to 5° C. and methanesulfonyl chloride (0.0165 mL, 0.213 mmol) was added. The mixture was stirred for 1 hour at 5° C. then warmed to room temperature and stirred for 1 hour. The reaction mixture was poured into saturated aqueous sodium carbonate (10 mL) and extracted with dichloromethane (3×10 mL). The combined organic layers were washed with water (10 mL) then saturated aqueous sodium chloride (10 mL), dried over magnesium sulfate, filtered and evaporated to a dark resin. The residue was purified via reverse phase chromatography using a Gilson apparatus (0%→50% acetonitrile:water (w/0.1% TFA modifier)). Collected desired fractions, basified with saturated aqueous sodium carbonate and extracted with dichloromethane (3×10 mL). The combined organic layers were dried over magnesium sulfate, filtered and evaporated. N(8)-(1-Methanesulfonyl-pyrrolidin-2-ylmethyl)-N(2)-[4-(4-methyl-piperazin-1-yl)-phenyl]-[1,2,4]triazolo[1,5-a]pyridine-2,8-diamine was isolated as a pale yellow foam (0.033 g, 38%). $^1$H NMR (400 MHz, CDCl$_3$, δ, ppm): 7.80 (d, J=6.5 Hz, 1H), 7.47 (d, J=8.8 Hz, 2H), 6.96 (d, J=8.9 Hz, 2H), 6.71 (t, J=7.4 Hz, 1H), 6.55 (d, J=7.9 Hz, 1H), 6.52 (s, 1H), 5.09 (t, J=6.4 Hz, 1H), 4.03-3.94 (m, 1H), 3.63-3.55 (m, 1H), 3.53-3.46 (m, 1H), 3.39-3.25 (m, 2H), 3.18-3.13 (m, 4H), 2.88 (s, 3H), 2.62-2.57 (m, 4H), 2.36 (s, 3H), 2.11-1.91 (m, 4H). MS=485 (MH)+.

Example 171

N-Methyl-N-(2-{2-[4-(4-methyl-piperazin-1-yl)-phenylamino]-[1,2,4]triazolo[1,5-a]pyridin-8-ylamino}-benzyl)-methanesulfonamide

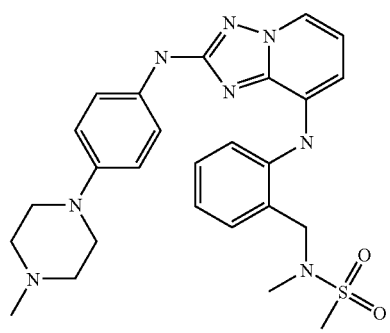 [SMILES: CN1CCN(c2ccc(Nc3nc4c(Nc5ccccc5CN(C)S(C)(=O)=O)cccn4n3)cc2)CC1]

171 a) To a suspension of potassium carbonate (1.2 g, 8.7 mmol) in was added N-methyl-methanesulfonamide (0.70 g, 6.4 mmol) followed by o-nitrobenzylchloride (1.0 g, 5.8 mmol). The mixture was heated at 50° C. for 18 hours. The mixture was cooled to room temperature and diluted with water (50 mL) and stirred for 30 minutes. The resulting precipitate was filtered and rinsed with water. The solid was dissolved in dichloromethane (25 mL), dried over magnesium sulfate, filtered, evaporated under reduced pressure then placed under high vacuum for 2 hours. N-Methyl-N-(2-nitro-benzyl)-methanesulfonamide was isolated as an orange-brown solid (1.12 g, 78%). $^1$H NMR (400 MHz, CDCl$_3$, δ, ppm): 8.07 (d, J=8.0 Hz, 1H), 7.82 (d, J=7.9 Hz, 1H), 7.70 (t, J=7.4 Hz, 1H), 7.49 (t, J=7.7 Hz, 1H), 4.73 (s, 2H), 2.96 (s, 3H), 2.88 (s, 3H). MS=245 (MH)+.

171 b) N-(2-Amino-benzyl)-N-methyl-methanesulfonamide was prepared from N-methyl-N-(2-nitro-benzyl)-methanesulfonamide (1.12 g, 4.58 mmol) in a manner analogous to Example 111a Product isolated as a dark purple solid (0.90 g, 92%). $^1$H NMR (400 MHz, CDCl$_3$, δ, ppm): 7.16 (t, J=7.4 Hz, 1H), 7.00 (d, J=7.5 Hz, 1H), 6.71-6.66 (m, 2H), 4.28 (br s, 2H), 4.19 (s, 2H), 2.89 (s, 3H), 2.73 (s, 3H). MS=237 (M+Na)+.

171 c) N-[2-(2-Chloro-[1,2,4]triazolo[1,5-a]pyridin-8-ylamino)-benzyl]-N-methyl-methanesulfonamide was prepared from 8-bromo-2-chloro-[1,2,4]triazolo[1,5-a]pyridine (500.0 mg, 2.151 mmol) and N-(2-amino-benzyl)-N-methyl-methanesulfonamide (507.0 mg, 2.366 mmol) in a manner analogous to Example 2d. Product isolated as a tan foam (0.53 g, 67%). $^1$H NMR (400 MHz, CDCl$_3$, δ, ppm): 8.01 (d, J=6.4

Hz, 1H), 7.48-7.41 (m, 2H), 7.38 (t, J=7.4 Hz, 1H), 7.21 (t, J=7.4 Hz, 1H), 7.10 (s, 1H), 6.90-6.81 (m, 2H), 4.36 (s, 2H), 3.02 (s, 3H), 2.76 (s, 3H). MS=366 (MH)+.

171 d) N-Methyl-N-(2-{2-[4-(4-methyl-piperazin-1-yl)-phenylamino]-[1,2,4]triazolo[1,5-a]pyridin-8-ylamino}-benzyl)-methanesulfonamide was prepared from N-[2-(2-chloro-[1,2,4]triazolo[1,5-a]pyridin-8-ylamino)-benzyl]-N-methyl-methanesulfonamide (75.0 mg, 0.205 mmol) and 4-(4-methyl-piperazin-1-yl)-phenylamine (44.0 mg, 0.230 mmol) with 2,2'-bis-dicyclohexylphosphanyl-biphenyl (25.0 mg, 0.0457 mmol) as the ligand in a manner analogous to Example 2d. Product isolated as a brown foam (0.019 g, 18%). $^1$H NMR (400 MHz, CDCl$_3$, δ, ppm): 7.94 (d, J=6.5 Hz, 1H), 7.51 (d, J=8.7 Hz, 2H), 7.45-7.39 (m, 2H), 7.35 (t, J=7.2 Hz, 1H), 7.13 (t, J=7.4 Hz, 1H), 7.00-6.94 (m, 3H), 6.81 (d, J=7.7 Hz, 1H), 6.68 (t, J=7.2 Hz, 1H), 6.60 (s, 1H), 4.36 (s, 2H), 3.18-3.13 (m, 4H), 2.91 (s, 3H), 2.78 (s, 3H), 2.62-2.57 (m, 4H), 2.36 (s, 3H). MS=521 (MH)+.

Example 172

N-Methyl-N-(2-{2-[3-(4-methyl-piperazin-1-yl)-phenylamino]-[1,2,4]triazolo[1,5-a]pyridin-8-ylamino}-benzyl)-methanesulfonamide

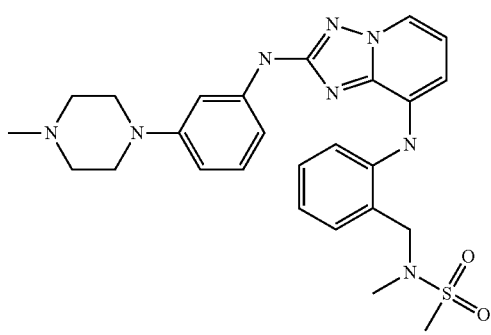 [SMILES: CN1CCN(c2cccc(Nc3nc4c(Nc5ccccc5CN(C)S(C)(=O)=O)cccn4n3)c2)CC1]

N-Methyl-N-(2-{2-[3-(4-methyl-piperazin-1-yl)-phenylamino]-[1,2,4]triazolo[1,5-a]pyridin-8-ylamino}-benzyl)-methanesulfonamide was prepared from N-[2-(2-chloro-[1,2,4]triazolo[1,5-a]pyridin-8-ylamino)-benzyl]-N-methyl-methanesulfonamide (75.0 mg, 0.205 mmol) and 3-(4-methylpiperazin-1-yl)aniline (44.0 mg, 0.230 mmol) with 2,2'-bis-dicyclohexylphosphanyl-biphenyl (25.0 mg, 0.0457 mmol) as the ligand in a manner analogous to Example 2d. Product isolated as a tan foam (0.033 g, 31%). $^1$H NMR (400 MHz, CDCl$_3$, δ, ppm): 7.98 (d, J=6.5 Hz, 1H), 7.45-7.39 (m, 2H), 7.35 (t, J=7.6 Hz, 1H), 7.23 (d, J=8.0 Hz, 1H), 7.18-7.11 (m, 3H), 6.96 (s, 1H), 6.81 (d, J=7.9 Hz, 1H), 6.77 (s, 1H), 6.70 (t, J=7.0 Hz, 1H), 6.58 (d, J=8.0 Hz, 1H), 4.36 (s, 2H), 3.28-3.23 (m, 4H), 2.91 (s, 3H), 2.78 (s, 3H), 2.61-2.56 (m, 4H), 2.36 (s, 3H). MS=521 (MH)+.

Example 173

N-Methyl-N-(2-{2-[4-(2-pyrrolidin-1-yl-ethoxy)-phenylamino]-[1,2,4]triazolo[1,5-a]pyridin-8-ylamino}-benzyl)-methanesulfonamide

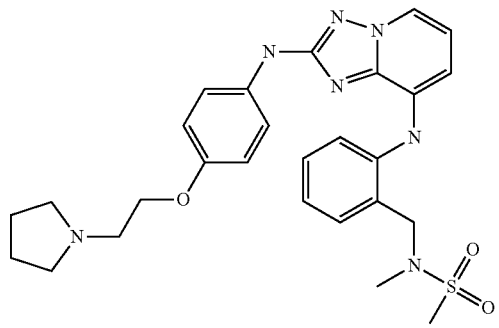 [SMILES: CN(Cc1ccccc1Nc1cccn2nc(Nc3ccc(OCCN4CCCC4)cc3)nc12)S(C)(=O)=O]

N-Methyl-N-(2-{2-[4-(2-pyrrolidin-1-yl-ethoxy)-phenylamino]-[1,2,4]triazolo[1,5-a]pyridin-8-ylamino}-benzyl)-methanesulfonamide was prepared from N-[2-(2-chloro-[1,2,4]triazolo[1,5-a]pyridin-8-ylamino)-benzyl]-N-methyl-methanesulfonamide (75.0 mg, 0.205 mmol) and 4-(2-pyrrolidin-1-yl-ethoxy)-phenylamine (47.0 mg, 0.228 mmol) with 2,2'-bis-dicyclohexylphosphanyl-biphenyl (25.0 mg, 0.0457 mmol) as the ligand in a manner analogous to Example 2d. Product isolated as a tan foam (0.017 g, 15%). $^1$H NMR (400 MHz, CDCl$_3$, δ, ppm): 7.95 (d, J=6.7 Hz, 1H), 7.51 (d, J=8.9 Hz, 2H), 7.46-7.31 (m, 3H), 7.13 (t, J=7.4 Hz, 1H), 6.99 (s, 1H), 6.94 (d, J=8.9 Hz, 2H), 6.83 (d, J=7.7 Hz, 1H), 6.69 (t, J=7.1 Hz, 1H), 6.62 (s, 1H), 4.36 (s, 2H), 4.11 (t, J=6.0 Hz, 2H), 2.93-2.87 (m, 5H), 2.78 (s, 3H), 2.68-2.58 (m, 4H), 1.85-1.78 (m, 4H). MS=536 (MH)+.

Example 174

N-Methyl-N-(2-{2-[4-(1-methyl-piperidin-4-yl)-phenylamino]-[1,2,4]triazolo[1,5-a]pyridin-8-ylamino}-benzyl)-methanesulfonamide

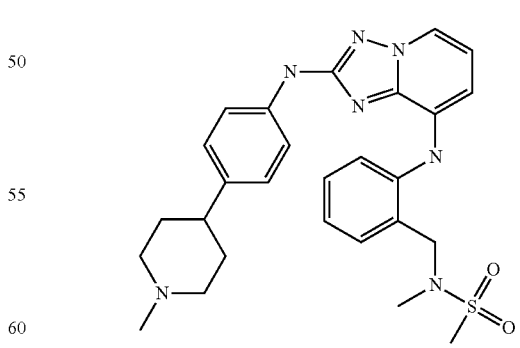

N-Methyl-N-(2-{2-[4-(1-methyl-piperidin-4-yl)-phenylamino]-[1,2,4]triazolo[1,5-a]pyridin-8-ylamino}-benzyl)-methanesulfonamide was prepared from N-[2-(2-chloro-[1,2,4]triazolo[1,5-a]pyridin-8-ylamino)-benzyl]-N-methyl-methanesulfonamide (75.0 mg, 0.205 mmol) and 4-(1- methyl-piperidin-4-yl)-phenylamine (44.0 mg, 0.231 mmol) with 2,2'-bis-dicyclohexylphosphanyl-biphenyl (25.0 mg, 0.0457 mmol) as the ligand in a manner analogous to Example 2d. Product isolated as a tan foam (0.068 g, 64%). $^1$H NMR (400 MHz, CDCl$_3$, δ, ppm): 7.96 (d, J=6.5 Hz, 1H), 7.54 (d, J=8.3 Hz, 2H), 7.46-7.38 (m, 2H), 7.35 (t, J=7.5 Hz, 1H), 7.21 (d, J=8.4 Hz, 2H), 7.13 (t, J=7.5 Hz, 1H), 7.00 (s, 1H), 6.83 (d, J=7.8 Hz, 1H), 6.76 (s, 1H), 6.70 (t, J=7.0 Hz, 1H), 4.36 (s, 2H), 2.95 (d, J=11.2 Hz, 2H), 2.91 (s, 3H), 2.78 (s, 3H), 2.50-2.40 (m, 1H), 2.33 (s, 3H), 2.10-2.00 (m, 2H), 1.87-1.73 (m, 4H). MS=520 (MH)+.

Example 175

N-Methyl-N-(3-{2-[4-(4-methyl-piperazin-1-yl)-phenylamino]-[1,2,4]triazolo[1,5-a]pyridin-8-yl}-benzyl)-methanesulfonamide

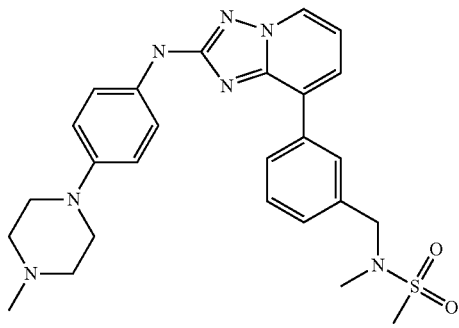 [SMILES: CN1CCN(c2ccc(Nc3nc4c(-c5cccc(CN(C)S(C)(=O)=O)c5)cccn4n3)cc2)CC1]

175 a) A suspension of [3-(bromomethyl)phenyl]boronic acid (1.0 g, 4.6 mmol), N-methyl-methanesulfonamide (0.56 g, 5.1 mmol) and potassium carbonate (1.9 g, 14 mmol) in acetone (10 mL) was stirred for 6 hours at room temperature. The mixture was diluted with dichloromethane (50 mL), filtered through a plug of diatomaceous earth and evaporated under reduced pressure. Crude (3-{[methyl(methylsulfonyl)amino]methyl}phenyl)boronic acid was isolated as a yellow viscous oil (1.08 g, 88%). MS=266 (M+Na)+.

175 b) N-[3-(2-Chloro-[1,2,4]triazolo[1,5-a]pyridin-8-yl)-benzyl]-N-methyl-methanesulfonamide was prepared from 8-bromo-2-chloro-[1,2,4]triazolo[1,5-a]pyridine (500.0 mg, 2.151 mmol) and (3-{[methyl(methylsulfonyl)amino]methyl}phenyl)boronic acid (650.0 mg, 2.674 mmol) in a manner analogous to Example 2c. Product isolated as a pale yellow foam (0.331 g, 44%). $^1$H NMR (400 MHz, CDCl$_3$, δ, ppm): 8.51 (d, J=6.8 Hz, 1H), 7.99-7.95 (m, 2H), 7.74 (d, J=7.4 Hz, 1H), 7.54 (t, J=7.6 Hz, 1H), 7.45 (d, J=7.6 Hz, 1H), 7.18 (t, J=7.1 Hz, 1H), 4.42 (s, 2H), 2.92 (s, 3H), 2.84 (s, 3H). MS=351 (MH)+.

175 c) N-Methyl-N-(3-{2-[4-(4-methyl-piperazin-1-yl)-phenylamino]-[1,2,4]triazolo[1,5-a]pyridin-8-yl}-benzyl)-methanesulfonamide was prepared from N-[3-(2-chloro-[1,2,4]triazolo[1,5-a]pyridin-8-yl)-benzyl]-N-methyl-methanesulfonamide (75.0 mg, 0.214 mmol) and 4-(4-methyl-piperazin-1-yl)-phenylamine (45.0 mg, 0.235 mmol) with 2,2'-bis-dicyclohexylphosphanyl-biphenyl (24.0 mg, 0.0439 mmol) as the ligand in a manner analogous to Example 2d. Product isolated as a yellow foam (0.007 g, 6%). $^1$H NMR (400 MHz, CDCl$_3$, δ, ppm): 8.41 (d, J=6.7 Hz, 1H), 7.99 (d, J=7.7 Hz, 1H), 7.95 (s, 1H), 7.57 (d, J=7.4 Hz, 1H), 7.55-7.46 (m, 3H), 7.42 (d, J=7.4 Hz, 1H), 7.00-6.91 (m, 3H), 6.65 (s, 3H), 4.42 (s, 2H), 3.19-3.14 (m, 4H), 2.87 (s, 3H), 2.83 (s, 3H), 2.63-2.57 (m, 4H), 2.37 (s, 3H). MS=506 (MH)+.

Example 176

N-Methyl-N-(3-{2-[3-(4-methyl-piperazin-1-yl)-phenylamino]-[1,2,4]triazolo[1,5-a]pyridin-8-yl}-benzyl)-methanesulfonamide

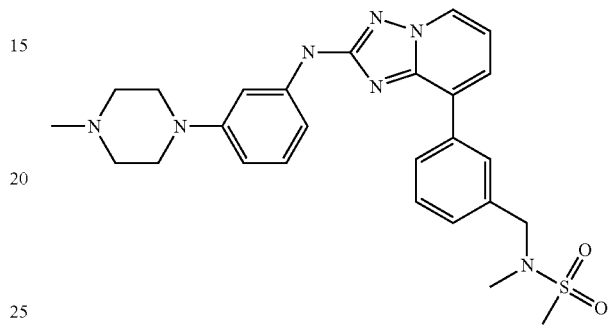

N-Methyl-N-(3-{2-[3-(4-methyl-piperazin-1-yl)-phenylamino]-[1,2,4]triazolo[1,5-a]pyridin-8-yl}-benzyl)-methanesulfonamide was prepared from N-[3-(2-chloro-[1,2,4]triazolo[1,5-a]pyridin-8-yl)-benzyl]-N-methyl-methanesulfonamide (75.0 mg, 0.214 mmol) and 3-(4-methylpiperazin-1-yl)aniline (45.0 mg, 0.235 mmol) with 2,2'-bis-dicyclohexylphosphanyl-biphenyl (24.0 mg, 0.0439 mmol) as the ligand in a manner analogous to Example 2d. Product isolated as a yellow foam (0.053 g, 49%). $^1$H NMR (400 MHz, CDCl$_3$, δ, ppm): 8.43 (d, J=6.7 Hz, 1H), 8.05 (d, J=7.7 Hz, 1H), 7.93 (s, 1H), 7.60 (d, J=7.4 Hz, 1H), 7.52 (t, J=7.7 Hz, 1H), 7.42 (d, J=7.9 Hz, 1H), 7.32 (s, 1H), 7.22 (t, J=8.0 Hz, 1H), 7.01 (d, J=8.0 Hz, 1H), 6.97 (t, J=7.2 Hz, 1H), 6.84 (s, 1H), 6.58 (dd, J=8.2, 1.5 Hz, 1H), 4.42 (s, 2H), 3.29-3.25 (m, 4H), 2.88 (s, 3H), 2.83 (s, 3H), 2.62-2.57 (m, 4H), 2.37 (s, 3H). MS=506 (MH)+.

Example 177

N-Methyl-N-(3-{2-[4-(2-pyrrolidin-1-yl-ethoxy)-phenylamino]-[1,2,4]triazolo[1,5-a]pyridin-8-yl}-benzyl)-methanesulfonamide

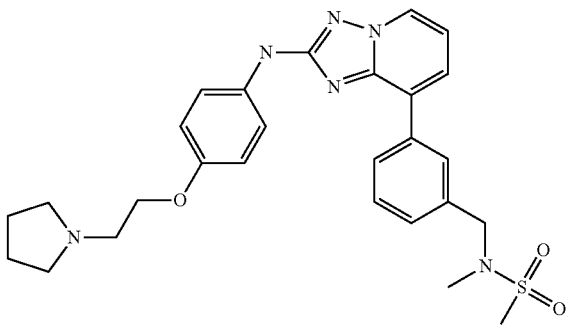 [SMILES: CN(Cc1cccc(-c2cccn3nc(Nc4ccc(OCCN5CCCC5)cc4)nc23)c1)S(C)(=O)=O]

N-Methyl-N-(3-{2-[4-(2-pyrrolidin-1-yl-ethoxy)-phenylamino]-[1,2,4]triazolo[1,5-a]pyridin-8-yl}-benzyl)-methanesulfonamide was prepared from N-[3-(2-chloro-[1,2,4]triazolo[1,5-a]pyridin-8-yl)-benzyl]-N-methyl-methanesulfonamide (75.0 mg, 0.214 mmol) and 4-(2-pyrrolidin-1-yl-ethoxy)-phenylamine (49.0 mg, 0.238 mmol) with 2,2'-bis-dicyclohexylphosphanyl-biphenyl (24.0 mg, 0.0439 mmol) as the ligand in a manner analogous to Example 2d. Product isolated as a tan foam (0.050 g, 45%). $^1$H NMR (400 MHz, CDCl$_3$, δ, ppm): 8.41 (d, J=6.5 Hz, 1H), 8.01-7.95 (m, 2H), 7.58 (d, J=7.4 Hz, 1H), 7.52 (t, J=7.8 Hz, 1H), 7.48 (d, J=8.8 Hz, 2H), 7.42 (d, J=7.5 Hz, 1H), 6.97-6.91 (m, 3H), 6.68 (s, 1H), 4.42 (s, 2H), 4.11 (t, J=6.0 Hz, 2H), 2.90 (t, J=5.9 Hz, 2H), 2.87 (s, 3H), 2.83 (s, 3H), 2.67-2.57 (m, 4H), 1.87-1.77 (m, 4H). MS=521 (MH)+.

Example 178

N-Methyl-N-(3-{2-[4-(1-methyl-piperidin-4-yl)-phenylamino]-[1,2,4]triazolo[1,5-a]pyridin-8-yl}-benzyl)-methanesulfonamide

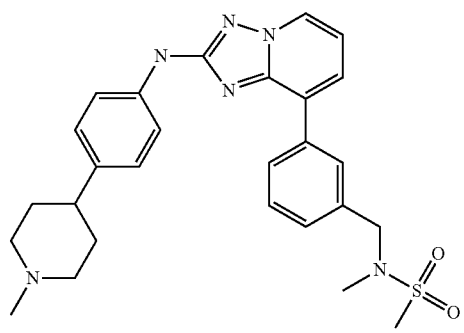 [SMILES: CN1CCC(c2ccc(Nc3nc4c(-c5cccc(CN(C)S(C)(=O)=O)c5)cccn4n3)cc2)CC1]

N-Methyl-N-(3-{2-[4-(1-methyl-piperidin-4-yl)-phenylamino]-[1,2,4]triazolo[1,5-a]pyridin-8-yl}-benzyl)-methanesulfonamide was prepared from N-[3-(2-chloro-[1,2,4]triazolo[1,5-a]pyridin-8-yl)-benzyl]-N-methyl-methanesulfonamide (75.0 mg, 0.214 mmol) and 4-(1-methyl-piperidin-4-yl)-phenylamine (45.0 mg, 0.236 mmol) with 2,2'-bis-dicyclohexylphosphanyl-biphenyl (24.0 mg, 0.0439 mmol) as the ligand in a manner analogous to Example 2d. Product isolated as a yellow foam (0.039 g, 36%). $^1$H NMR (400 MHz, CDCl$_3$, δ, ppm): 8.43 (d, J=6.5 Hz, 1H), 7.99 (d, J=7.8 Hz, 1H), 7.96 (s, 1H), 7.59 (d, J=7.1 Hz, 1H), 7.55-7.50 (m, 3H), 7.42 (d, J=7.5 Hz, 1H), 7.21 (d, J=8.3 Hz, 2H), 6.96 (t, J=7.0 Hz, 1H), 6.81 (s, 1H), 4.42 (s, 2H), 3.01-2.94 (m, 2H), 2.87 (s, 3H), 2.83 (s, 3H), 2.50-2.40 (m, 1H), 2.33 (s, 3H), 2.09-2.00 (m, 2H), 1.87-1.73 (m, 4H). MS=505 (MH)+.

Example 179

4-{3-[8-(4-Methanesulfonyl-phenyl)-[1,2,4]triazolo[1,5-a]pyridin-2-ylamino]-phenyl}-piperazine-1-carboxylic acid tert-butyl ester

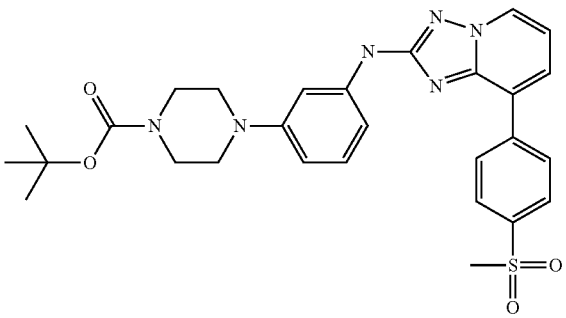 [SMILES: CC(C)(C)OC(=O)N1CCC(c2cccc(Nc3nc4c(-c5ccc(S(C)(=O)=O)cc5)cccn4n3)c2)CC1]

179 a) A suspension of 1-(3-nitro-phenyl)-piperazine hydrochloride (1.0 g, 4.1 mmol) and potassium carbonate (0.62 g, 4.5 mmol) in acetonitrile (10 mL) at room temperature was added di-tert-butyldicarbonate (1.0 g, 4.6 mmol) and was stirred at room temperature for 3 days. The mixture was poured into water (50 mL) and extracted with dichloromethane (3×50 mL). The combined organic layers were washed with water (50 mL) and saturated aqueous sodium chloride (50 mL). The organic layer was dried over magnesium sulfate, filtered and evaporated under reduced pressure. 4-(3-Nitro-phenyl)-piperazine-1-carboxylic acid tert-butyl ester was isolated as a yellow solid (1.169 g, 93%). $^1$H NMR (400 MHz, CDCl$_3$, δ, ppm): 7.72 (s, 1H), 7.69 (d, J=8.0 Hz, 1H), 7.39 (t, J=8.2 Hz, 1H), 7.19 (dd, J=8.2, 1.7 Hz, 1H), 3.63-3.58 (m, 4H), 3.27-3.21 (m, 4H), 1.49 (s, 9H). MS=330 (M+Na)+.

179 b) (3-Amino-phenyl)-piperazine-1-carboxylic acid tert-butyl ester was prepared from 4-(3-nitro-phenyl)-piperazine-1-carboxylic acid tert-butyl ester (1.17 g, 3.81 mmol) in a manner analogous to Example 111a. Product isolated as a yellow solid (0.993 g, 94%). $^1$H NMR (400 MHz, CDCl$_3$, δ, ppm): 7.05 (t, J=7.7 Hz, 1H), 6.35 (d, J=8.8 Hz, 1H), 6.26-6.22 (m, 2H), 3.61 (br s, 2H), 3.57-3.53 (m, 4H), 3.12-3.07 (m, 4H), 1.48 (s, 9H). MS=278 (MH)+.

179 c) 4-{3-[8-(4-Methanesulfonyl-phenyl)-[1,2,4]triazolo[1,5-a]pyridin-2-ylamino]-phenyl}-piperazine-1-carboxylic acid tert-butyl ester was prepared from 2-chloro-8-(4-methanesulfonyl-phenyl)-[1,2,4]triazolo[1,5-a]pyridine (500.0 mg, 1.625 mmol) and 4-(3-Amino-phenyl)-piperazine-1-carboxylic acid tert-butyl ester (500.0 mg, 1.803 mmol) with 2,2'-bis-dicyclohexylphosphanyl-biphenyl (90.0 mg, 0.165 mmol) as the ligand in a manner analogous to Example 2d. Product isolated as a yellow foam (0.70 g, 79%). $^1$H NMR (400 MHz, CDCl$_3$, δ, ppm): 8.51 (d, J=6.6 Hz, 1H), 8.24 (d, J=8.3 Hz, 2H), 8.08 (d, J=8.4 Hz, 2H), 7.66 (d, J=7.4 Hz, 1H), 7.32 (s, 1H), 7.24 (t, J=8.1 Hz, 1H), 7.05-6.99 (m, 2H), 6.89 (s, 1H), 6.59 (d, J=8.2 Hz, 1H), 3.63-3.58 (m, 4H), 3.22-3.17 (m, 4H), 3.10 (s, 3H), 1.50 (s, 9H). MS=549 (MH)+.

Example 180

4-{3-[8-(4-Methanesulfonyl-phenyl)-[1,2,4]triazolo[1,5-a]pyridin-2-ylamino]-phenyl}-piperidine-1-carboxylic acid tert-butyl ester

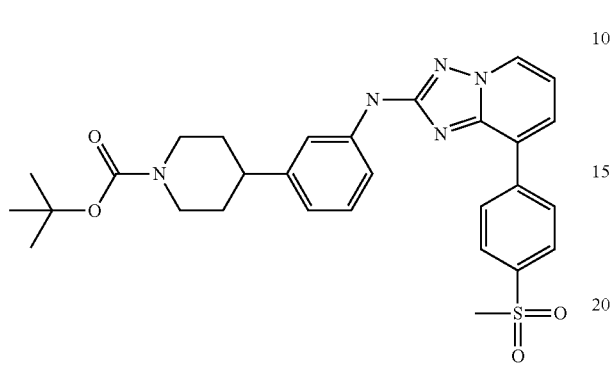

180 a) 4-(3-Nitro-phenyl)-3,6-dihydro-2H-pyridine-1-carboxylic acid tert-butyl ester was prepared from 1-bromo-3-nitro-benzene (3.0 g, 15 mmol) and 4-(4,4,5,5-tetramethyl-[1,3,2]dioxaborolan-2-yl)-3,6-dihydro-2H-pyridine-1-carboxylic acid tert-butyl ester (5.0 g, 16 mmol) in a manner analogous to Example 2c. Product isolated as a yellow oil (3.95 g, 88%). $^1$H NMR (400 MHz, CDCl$_3$, δ, ppm): 8.23 (s, 1H), 8.11 (d, J=8.1 Hz, 1H), 7.69 (d, J=7.7 Hz, 1H), 7.51 (t, J=7.8 Hz, 1H), 6.20 (br s, 1H), 4.12 (s, 2H), 3.70-3.65 (m, 2H), 2.56 (s, 2H), 1.50 (s, 9H).

180 b) 4-(3-Amino-phenyl)-piperidine-1-carboxylic acid tert-butyl ester was prepared from 4-(3-nitro-phenyl)-3,6-dihydro-2H-pyridine-1-carboxylic acid tert-butyl ester (1.0 g, 3.3 mmol) in a manner analogous to Example 111a. Product isolated as a light purple solid (0.84 g, 92%). $^1$H NMR (400 MHz, CDCl$_3$, δ, ppm): 7.09 (t, J=7.6 Hz, 1H), 6.61 (d, J=7.5 Hz, 1H), 6.56-6.52 (m, 2H), 4.22 (br s, 2H), 3.62 (br s, 2H), 2.82-2.72 (m, 2H), 2.59-2.49 (m, 1H), 1.80 (d, J=13.0 Hz, 2H), 1.68-1.53 (m, 2H), 1.48 (s, 9H).

180 c) 4-{3-[8-(4-Methanesulfonyl-phenyl)-[1,2,4]triazolo[1,5-a]pyridin-2-ylamino]-phenyl}-piperidine-1-carboxylic acid tert-butyl ester was prepared from 2-chloro-8-(4-methanesulfonyl-phenyl)-[1,2,4]triazolo[1,5-a]pyridine (500.0 mg, 1.625 mmol) and 4-(3-amino-phenyl)-piperidine-1-carboxylic acid tert-butyl ester (500.0 mg, 1.809 mmol) with 2,2'-bis-dicyclohexylphosphanyl-biphenyl (90.0 mg, 0.165 mmol) as the ligand in a manner analogous to Example 2d. Product isolated as a yellow foam (0.59 g, 66%). $^1$H NMR (400 MHz, CDCl$_3$, δ, ppm): 8.52 (d, J=6.6 Hz, 1H), 8.23 (d, J=8.4 Hz, 2H), 8.09 (d, J=8.4 Hz, 2H), 7.66 (d, J=7.4 Hz, 1H), 7.47-7.41 (m, 2H), 7.30 (t, J=7.6 Hz, 1H), 7.03 (t, J=7.0 Hz, 1H), 6.92-6.85 (m, 2H), 4.27 (br m, 2H), 3.10 (s, 3H), 2.83 (t, J=11.9 Hz, 2H), 2.73-2.63 (m, 1H), 1.84 (d, J=13.1 Hz, 2H), 1.73-1.60 (m, 2H), 1.49 (s, 9H). MS=538 (MH)+.

Example 181

[8-(4-Methanesulfonyl-phenyl)-[1,2,4]triazolo[1,5-a]pyridin-2-yl]-(3-piperazin-1-yl-phenyl)-amine

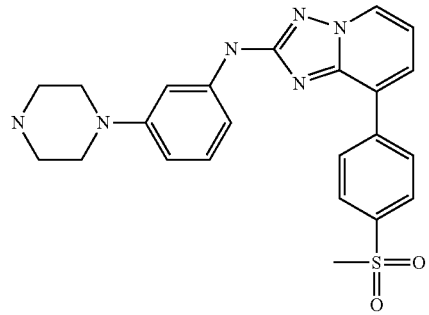 [SMILES: CS(=O)(=O)c1ccc(-c2cccn3nc(Nc4cccc(N5CCNCC5)c4)nc23)cc1]

To a solution of 4-{3-[8-(4-Methanesulfonyl-phenyl)-[1,2,4]triazolo[1,5-a]pyridin-2-ylamino]-phenyl}-piperazine-1-carboxylic acid tert-butyl ester (250.0 mg, 0.4556 mmol) in dichloromethane (1 mL) was added dropwise trifluoroacetic acid (0.40 mL, 5.2 mmol) and the mixture was stirred at room temperature for 6 hours. The mixture was diluted with dichloromethane (20 mL) and saturated aqueous sodium carbonate (10 mL) was added dropwise. The mixture was stirred for 30 minutes. The layers were separated and the aqueous was washed with dichloromethane (3×10 mL). The combined organic layers were dried over magnesium sulfate, filtered and evaporated under reduced pressure. [8-(4-Methanesulfonyl-phenyl)-[1,2,4]triazolo[1,5-a]pyridin-2-yl]-(3-piperazin-1-yl-phenyl)-amine was isolated as a yellow foam (0.168 g, 82%). $^1$H NMR (400 MHz, CDCl$_3$, δ, ppm): 8.49 (d, J=6.7 Hz, 1H), 8.25 (d, J=8.4 Hz, 2H), 8.08 (d, J=8.4 Hz, 2H), 7.65 (d, J=7.2 Hz, 1H), 7.36 (s, 1H), 7.23 (t, J=8.3 Hz, 1H), 7.04-6.96 (m, 2H), 6.86 (s, 1H), 6.60 (d, J=8.3 Hz, 1H), 3.24-3.19 (m, 4H), 3.10 (s, 3H), 3.09-3.04 (m, 4H). MS=449 (MH)+.

Example 182

[8-(4-Methanesulfonyl-phenyl)-[1,2,4]triazolo[1,5-a]pyridin-2-yl]-(3-piperidin-4-yl-phenyl)-amine

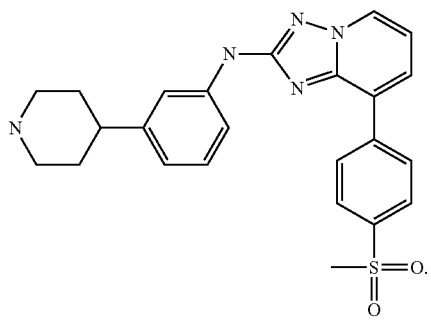 [SMILES: CS(=O)(=O)c1ccc(-c2cccn3nc(Nc4cccc(C5CCNCC5)c4)nc23)cc1]

[8-(4-Methanesulfonyl-phenyl)-[1,2,4]triazolo[1,5-a]pyridin-2-yl]-(3-piperidin-4-yl-phenyl)-amine was prepared from 4-{3-[8-(4-methanesulfonyl-phenyl)-[1,2,4]5-a]pyridin-2-ylamino]-phenyl}-piperidine-1-carboxylic acid tert-butyl ester (250.0 mg, 0.4565 mmol) in an manner analogous to Example 181. Product isolated as a yellow foam (0.153 g, 75%). $^1$H NMR (400 MHz, CDCl$_3$, δ, ppm): 8.51 (d, J=6.6 Hz, 1H), 8.26 (d, J=8.3 Hz, 2H), 8.10 (d, J=8.3 Hz, 2H), 7.66 (d, J=7.4 Hz, 1H), 7.54 (s, 1H), 7.39 (d, J=8.1 Hz, 1H), 7.29 (t, J=7.8 Hz, 1H), 7.02 (t, J=7.1 Hz, 1H), 6.91-6.86 (m, 2H), 3.26-3.20 (m, 2H), 3.10 (s, 3H), 2.83-2.75 (m, 2H), 2.71-2.61 (m, 1H), 1.92-1.85 (m, 2H), 1.78-1.66 (m, 2H). MS=448 (MH)+.

Example 183

2-(4-{3-[8-(4-Methanesulfonyl-phenyl)-[1,2,4]triazolo[1,5-a]pyridin-2-ylamino]-phenyl}-piperazin-1-yl)-acetamide

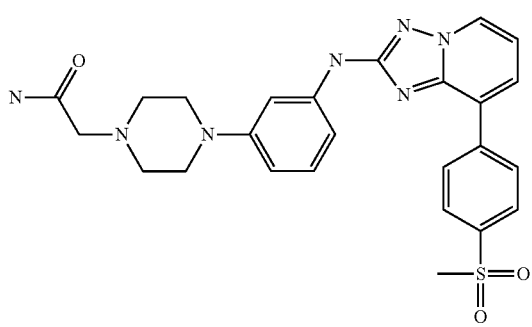

A suspension of [8-(4-methanesulfonyl-phenyl)-[1,2,4]triazolo[1,5-a]pyridin-2-yl]-(3-piperazin-1-yl-phenyl)-amine (100.0 mg, 0.2229 mmol), 2-chloroacetamide (23.0 mg, 0.246 mmol) and sodium iodide (3.0 mg, 0.020 mmol) in acetonitrile (2 mL) was stirred and heated at 70° C. for 6 hours. The suspension was cooled to room temperature, diluted with water (30 mL). The precipitate was filtered and rinsed with water. The recovered yellow solid was triturated with methanol (5 mL), filtered and placed under high vacuum overnight. 2-(4-{3-[8-(4-Methanesulfonyl-phenyl)-[1,2,4]triazolo[1,5-a]pyridin-2-ylamino]-phenyl}-piperazin-1-yl)-acetamide and was isolated as a yellow solid (0.075 g, 67%). MP=271-275° C. $^1$H NMR (400 MHz, (D$_3$C)$_2$SO, δ, ppm): 9.62 (s, 1H), 8.86 (d, J=6.5 Hz, 1H), 8.43 (d, J=7.5 Hz, 2H), 8.06 (d, J=7.6 Hz, 2H), 7.96 (d, J=7.5 Hz, 1H), 7.53 (s, 1H), 7.26-7.06 (m, 5H), 6.50 (d, J=6.5 Hz, 1H), 3.29 (s, 3H), 3.20-3.15 (m, 4H), 2.93 (s, 2H), 2.64-2.58 (m, 4H). MS=506 (MH)+.

Example 184

2-(4-{3-[8-(4-Methanesulfonyl-phenyl)-[1,2,4]triazolo[1,5-a]pyridin-2-ylamino]-phenyl}-piperidin-1-yl)-acetamide

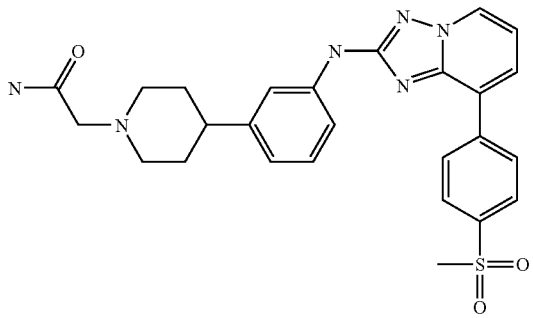 [SMILES: CS(=O)(=O)c1ccc(-c2cccn3nc(Nc4cccc(N5CCN(CC(N)=O)CC5)c4)nc23)cc1]

2-(4-{3-[8-(4-Methanesulfonyl-phenyl)-[1,2,4]triazolo[1,5-a]pyridin-2-ylamino]-phenyl}-piperidin-1-yl)-acetamide was prepared from [8-(4-methanesulfonyl-phenyl)-[1,2,4]triazolo[1,5-a]pyridin-2-yl]-(3-piperidin-4-yl-phenyl)-amine (100.0 mg, 0.2234 mmol) in an analogous manner to Example 183. Product was isolated as an off-white solid (0.073 g, 61%). MP=257-261° C. $^1$H NMR (400 MHz, (D$_3$C)$_2$SO, δ, ppm): 9.72 (s, 1H), 8.88 (d, J=6.5 Hz, 1H), 8.45 (d, J=7.8 Hz, 2H), 8.08 (d, J=8.2 Hz, 2H), 7.98 (d, J=7.6 Hz, 1H), 7.74 (s, 1H), 7.50 (d, J=8.0 Hz, 1H), 7.25-7.15 (m, 3H), 7.10 (s, 1H), 6.80 (d, J=7.8 Hz, 1H), 3.29 (s, 3H), 2.95 (d, J=10.8 Hz, 2H), 2.90 (s, 2H), 2.50-2.40 (m, 1H), 2.23-2.13 (m, 2H), 1.84-1.72 (m, 4H). MS=505 (MH)+.

Example 185

N-Methyl-N-{2-[(methyl-{2-[4-(4-methyl-piperazin-1-yl)-phenylamino]-[1,2,4]triazolo[1,5-a]pyridin-8-yl}-amino)-methyl]-phenyl}-methanesulfonamide

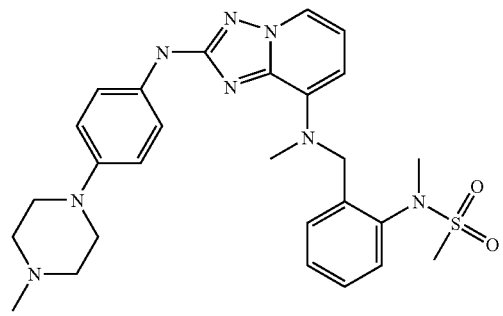 [SMILES: CN1CCN(c2ccc(Nc3nc4c(N(C)Cc5ccccc5N(C)S(C)(=O)=O)cccn4n3)cc2)CC1]

185 a) To a solution of N-{2-[(2-chloro-[1,2,4]triazolo[1,5-a]pyridin-8-ylamino)-methyl]-phenyl}-N-methyl-methanesulfonamide (250.0 mg, 0.6834 mmol) in acetonitrile (1 mL, 20 mmol) at room temperature was added sodium hydride, 60% disp. in mineral oil (33.0 mg, 0.825 mmol) followed by iodomethane (46.80 uL, 0.7517 mmol). The mixture was stirred at room temperature for 2 hours then additional iodomethane (10 uL) was added and the mixture was stirred at room temperature overnight. The mixture was quenched with water (20 mL) and extracted with dichloromethane (3×20 mL). The combined organic layers were dried over magnesium sulfate, filtered and evaporated to a tan resin. The recovered material was purified via chromatography using an ISCO automated purification apparatus (silica gel column 24 g 20%→80% ethyl acetate:hexane solvent gradient). N-(2-{[(2-Chloro-[1,2,4]triazolo[1,5-a]pyridin-8-yl)-methyl-amino}-methyl]-phenyl)-N-methyl-methanesulfonamide was isolated as tan foam (0.207 g, 80%). $^1$H NMR (400 MHz, CDCl$_3$, δ, ppm): 7.96 (d, J=6.6 Hz, 1H), 7.35-7.27 (m, 4H), 6.89-6.84 (m, 1H), 6.54 (d, J=8.0 Hz, 1H), 5.54-5.40 (br m, 1H), 5.06-4.90 (br m, 1H), 3.32 (s, 3H), 3.24 (s, 3H), 3.01 (s, 3H). MS=380, 382 (MH)+.

185 b) N-Methyl-N-{2-[(methyl-{2-[4-(4-methyl-piperazin-1-yl)-phenylamino]-[1,2,4]triazolo[1,5-a]pyridin-8-yl}-amino)-methyl]-phenyl}-methanesulfonamide was prepared from N-(2-{[(2-chloro-[1,2,4]triazolo[1,5-a]pyridin-8-yl)-methyl-amino]-methyl}-phenyl)-N-methyl-methanesulfonamide (75.0 mg, 0.197 mmol) and 4-(4-methyl-piperazin-1-yl)-phenylamine (42.0 mg, 0.220 mmol) with 2,2'-bis-dicyclohexylphosphanyl-biphenyl (18.0 mg, 0.0329 mmol) as the ligand in a manner analogous to Example 2d. Product isolated as a tan foam (0.023 g, 21%). 7.94 (d, J=6.6 Hz, 1H), 7.56-7.51 (m, 1H), 7.40 (d, J=8.1 Hz, 2H), 7.35-7.28 (m, 3H), 6.88 (d, J=8.1 Hz, 2H), 6.70 (t, J=7.3 Hz, 1H), 6.57-6.50 (m, 2H), 5.35-5.23 (m, 1H), 5.12-5.00 (m, 1H), 3.23 (s, 3H), 3.15-3.10 (m, 4H), 3.07 (s, 3H), 2.99 (s, 3H), 2.63-2.58 (m, 4H), 2.36 (s, 3H). MS=535 (MH)+.

Example 186

(±)-(cis)-3-Hydroxy-4-{3-[8-(4-methanesulfonyl-phenyl)-[1,2,4]triazolo[1,5-a]pyridin-2-ylamino]-phenyl}-piperidine-1-carboxylic acid tert-butyl ester

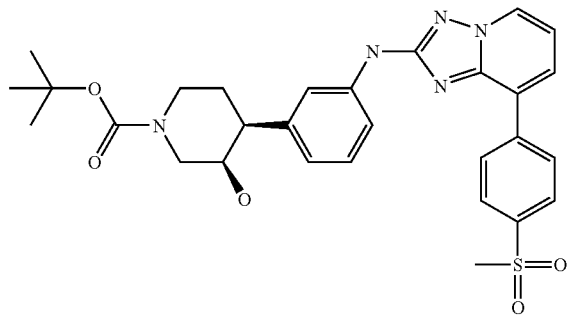 [SMILES: CC(C)(C)OC(=O)N1CC[C@@H](c2cccc(Nc3nc4c(-c5ccc(S(C)(=O)=O)cc5)cccn4n3)c2)[C@@H](O)C1]

186 a) To a round bottom flask was added palladium acetate (0.49 g, 2.2 mmol), triphenylphosphine (2.38 g, 9.06 mmol) and 1,4-dioxane (40 mL). The mixture was stirred for 15 minutes under an atmosphere of nitrogen until a bright yellow suspension resulted. 1-Bromo-3-nitro-benzene (3.0 g, 15 mmol), 4-(4,4,5,5-Tetramethyl-[1,3,2]dioxaborolan-2-yl)-3,6-dihydro-2H-pyridine-1-carboxylic acid tert-butyl ester (5.0 g, 16 mmol) and 1.50 M of sodium carbonate in water (24.5 mL, 36.8 mmol) were added. The mixture was stirred and heated at 80° C. for 24 hours. The mixture was cooled to room temperature and the volatiles were evaporated under reduced pressure. To the residue was added water (100 mL) then extracted with dichloromethane (3×50 mL). The combined organic layers were washed with water (2×50 mL) and saturated aqueous sodium chloride (50 mL), dried over magnesium sulfate, filtered and evaporated. The residue was purified via chromatography using an ISCO automated purification apparatus (silica gel column 80 g 5%→25% ethyl acetate:hexane solvent gradient). 4-(3-Nitro-phenyl)-3,6-dihydro-2H-pyridine-1-carboxylic acid tert-butyl ester was isolated as a yellow oil (3.95 g, 88%). $^1$H NMR (400 MHz, CDCl$_3$, δ, ppm): 8.23 (s, 1H), 8.11 (d, J=8.1 Hz, 1H), 7.69 (d, J=7.7 Hz, 1H), 7.51 (t, J=7.8 Hz, 1H), 6.20 (br s, 1H), 4.12 (s, 2H), 3.70-3.65 (m, 2H), 2.56 (s, 2H), 1.50 (s, 9H).

186 b) To a solution of 4-(3-nitro-phenyl)-3,6-dihydro-2H-pyridine-1-carboxylic acid tert-butyl ester (0.50 g, 1.6 mmol) in dichloromethane (5 mL) was added m-CPBA 70-75% (0.57 g, 2.3 mmol). The mixture was stirred at room temperature for 18 hours. The reaction was quenched by the addition of saturated aqueous sodium thiosulfate solution followed by saturated aqueous sodium bicarbonate. The mixture was stirred for 1 hour. The mixture was extracted with dichloromethane (3×20 mL). The combined organic layers were dried over magnesium sulfate, filtered and evaporated. The residue was purified via chromatography (silica gel column 40 g and 10%→80% ethyl acetate:hexane solvent gradient). 6-(3-Nitro-phenyl)-7-oxa-3-aza-bicyclo[4.1.0]heptane-3-carboxylic acid tert-butyl ester was isolated as a yellow oil (0.335 g, 64%). $^1$H NMR (400 MHz, CDCl$_3$, δ, ppm): 8.24 (s, 1H), 8.17 (d, J=7.9 Hz, 1H), 7.70 (d, J=7.8 Hz, 1H), 7.55 (t, J=7.9 Hz, 1H), 4.22-3.98 (m, 1H), 3.90-3.62 (m, 2H), 3.31-3.14 (m, 2H), 2.56-2.46 (m, 1H), 2.25-2.12 (m, 1H), 1.49 (s, 9H). MS=343 (M+Na)+.

186 c) (±)-(cis)-4-(3-Amino-phenyl)-3-hydroxy-piperidine-1-carboxylic acid tert-butyl ester was prepared from 6-(3-nitro-phenyl)-7-oxa-3-aza-bicyclo[4.1.0]heptane-3-carboxylic acid tert-butyl ester (0.335 g, 1.04 mmol) in a manner analogous to Example 111a. Product isolated as tan foam (0.0286 g, 94%). $^1$H NMR (400 MHz, CDCl$_3$, δ, ppm): 7.13 (t, J=7.6 Hz, 1H), 6.72-6.50 (m, 3H), 4.31 (br s, 2H), 3.93 (br s, 1H), 3.03-2.93 (m, 1H), 2.87-2.69 (m, 2H), 2.28-2.15 (m, 1H), 1.64-1.52 (m, 4H), 1.48 (s, 9H). MS=315 (M+Na)+.

186 d) (±)-(cis)-3-Hydroxy-4-{3-[8-(4-methanesulfonyl-phenyl)-[1,2,4]triazolo[1,5-a]pyridin-2-ylamino]-phenyl}-piperidine-1-carboxylic acid tert-butyl ester was prepared from 2-chloro-8-(4-methanesulfonyl-phenyl)-[1,2,4]triazolo[1,5-a]pyridine (270.0 mg, 0.8773 mmol) and (±)-(cis)-4-(3-amino-phenyl)-3-hydroxy-piperidine-1-carboxylic acid tert-butyl ester (286.0 mg, 0.9782 mmol) with 2,2'-bis-dicyclohexylphosphanyl-biphenyl (77.0 mg, 0.141 mmol) as the ligand in a manner analogous to Example 2d. Product isolated as a yellow solid (0.313 g, 63%). MP=166-170° C. $^1$H NMR (400 MHz, CDCl$_3$, δ, ppm): 8.51 (d, J=6.6 Hz, 1H), 8.23 (d, J=7.8 Hz, 2H), 8.09 (d, J=7.8 Hz, 2H), 7.66 (d, J=7.5 Hz, 1H), 7.53 (s, 1H), 7.48 (d, J=7.6 Hz, 1H), 7.33 (t, J=7.5 Hz, 1H), 7.03 (t, J=6.8 Hz, 1H), 6.96-6.90 (m, 2H), 4.35 (br s, 2H), 4.02 (br s, 1H), 3.11 (s, 3H), 3.08-3.00 (m, 1H), 2.90-2.80 (m, 2H), 2.36-2.24 (m, 1H), 1.72-1.60 (m, 2H), 1.50 (s, 9H). MS=586 (M+Na)+.

Example 187

{3-[4-(3-Fluoro-propyl)-piperazin-1-yl]-phenyl}-[8-(4-methanesulfonyl-phenyl)-[1,2,4]triazolo[1,5-a]pyridin-2-yl]-amine

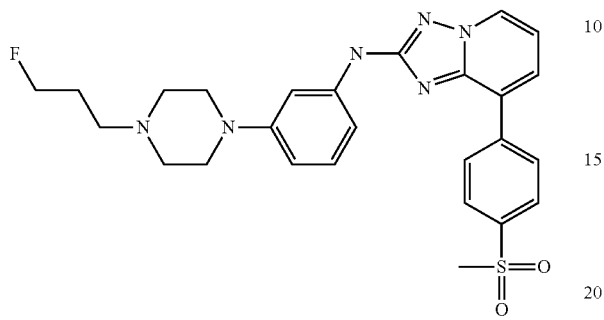

187 a) To a suspension of 1-(3-nitro-phenyl)-piperazine; hydrochloride (1.0 g, 4.1 mmol) and potassium carbonate (0.62 g, 4.5 mmol) in acetonitrile (10 mL) was added 1-fluoro-3-iodo-propane (0.85 g, 4.5 mmol) and was stirred at room temperature for 3 days. The mixture was poured into water (50 mL) and extracted with dichloromethane (3×20 mL). The combined organic layers were washed with saturated aqueous sodium chloride (10 mL), dried over magnesium sulfate, filtered and evaporated. 1-(3-Fluoro-propyl)-4-(3-nitro-phenyl)-piperazine was isolated as a viscous orange oil (0.886 g, 80%). $^1$H NMR (400 MHz, CDCl$_3$, δ, ppm): 7.71 (s, 1H), 7.65 (d, J=8.2 Hz, 1H), 7.37 (t, J=8.2 Hz, 1H), 7.18 (dd, J=8.3, 1.9 Hz, 1H), 4.54 (ddd, J=47.2, 5.9, 5.9 Hz, 2H), 3.32-3.27 (m, 4H), 2.65-2.60 (m, 4H), 2.55 (t, J=7.2 Hz, 2H), 2.00-1.85 (m, 2H). MS=268 (MH)+.

187 b) 3-[4-(3-Fluoro-propyl)-piperazin-1-yl]-phenylamine was prepared from 1-(3-fluoro-propyl)-4-(3-nitro-phenyl)-piperazine (0.20 g, 0.75 mmol) in a manner analogous to Example 111a. Product isolated as a tan waxy solid (0.18 g, 100%). $^1$H NMR (400 MHz, CDCl$_3$, δ, ppm): 7.04 (t, J=8.1 Hz, 1H), 6.36 (d, J=8.3 Hz, 1H), 6.26 (s, 1H), 6.21 (d, J=7.9 Hz, 1H), 4.62-4.44 (m, 2H), 3.60 (br s, 2H), 3.20-3.15 (m, 4H), 2.62-2.57 (m, 4H), 2.53 (t, J=7.2 Hz, 2H), 2.00-1.85 (m, 2H). MS=238 (MH)+.

187 c) {3-[4-(3-Fluoro-propyl)-piperazin-1-yl]-phenyl}-[8-(4-methanesulfonyl-phenyl)-[1,2,4]triazolo[1,5-a]pyridin-2-yl]-amine was prepared from 2-chloro-8-(4-methanesulfonyl-phenyl)-[1,2,4]triazolo[1,5-a]pyridine (220.0 mg, 0.7148) and 3-[4-(3-fluoro-propyl)-piperazin-1-yl]-phenylamine (180.0 mg, 0.7585 mmol) with 2,2'-bis-dicyclohexylphosphanyl-biphenyl (60.0 mg, 0.110 mmol) as the ligand in a manner analogous to Example 2d. Product isolated as a tan solid (0.264 g, 73%). MP=157-169° C. $^1$H NMR (400 MHz, CDCl$_3$, δ, ppm): 8.49 (d, J=6.7 Hz, 1H), 8.26 (d, J=8.0 Hz, 2H), 8.09 (d, J=8.0 Hz, 2H), 7.66 (d, J=7.4 Hz, 1H), 7.46 (br s, 1H), 7.22 (t, J=8.0 Hz, 1H), 7.02 (t, J=7.0 Hz, 1H), 6.93 (d, J=7.6 Hz, 1H), 6.89 (s, 1H), 6.59 (d, J=8.0 Hz, 1H), 4.64-4.48 (m, 2H), 3.30 (br s, 4H), 3.11 (s, 3H), 2.93-2.40 (m, 6H), 2.08-1.90 (m, 2H). MS=509 (MH)+.

Example 188

(±)-(cis)-4-{3-[8-(4-Methanesulfonyl-phenyl)-[1,2,4]triazolo[1,5-a]pyridin-2-ylamino]-phenyl}-piperidin-3-ol

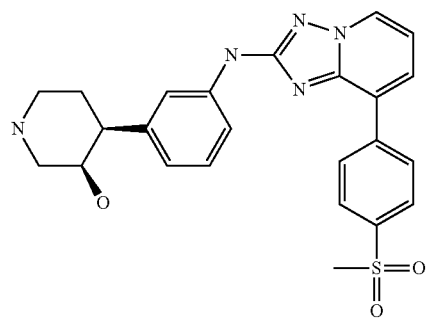 [SMILES: CS(=O)(=O)c1ccc(-c2cccn3nc(Nc4cccc([C@@H]5CCNC[C@@H]5O)c4)nc23)cc1]

(±)-(cis)-4-{3-[8-(4-Methanesulfonyl-phenyl)-[1,2,4]triazolo[1,5-a]pyridin-2-ylamino]-phenyl}-piperidin-3-ol was prepared from (±)-(cis)-3-hydroxy-4-{3-[8-(4-methanesulfonyl-phenyl)-[1,2,4]triazolo[1,5-a]pyridin-2-ylamino]-phenyl}-piperidine-1-carboxylic acid tert-butyl ester (204.0 mg, 0.3619 mmol) in a manner analogous to Example 181. Product isolated as a yellow foam (0.111 g, 66%). $^1$H NMR (400 MHz, CDCl$_3$, δ, ppm): 8.50 (d, J=6.6 Hz, 1H), 8.26 (d, J=8.0 Hz, 2H), 8.09 (d, J=8.0 Hz, 2H), 7.66 (d, J=7.0 Hz, 1H), 7.61 (s, 1H), 7.44 (d, J=7.7 Hz, 1H), 7.32 (t, J=7.6 Hz, 1H), 7.02 (t, J=6.7 Hz, 1H), 6.97-6.92 (m, 2H), 3.91 (br s, 1H), 3.23 (d, J=12.8 Hz, 1H), 3.10 (s, 1H), 2.92 (d, J=12.5 Hz, 1H), 2.85 (d, J=12.3 Hz, 1H), 2.76 (t, J=12.6 Hz, 1H), 2.26-2.13 (m, 1H), 1.72-1.65 (m, 2H). MS=464 (MH)+.

Example 189

N-Methyl-N-(2-{2-[4-(4-methyl-piperazin-1-yl)-phenylamino]-[1,2,4]triazolo[1,5-a]pyridin-8-ylethynyl}-phenyl)-methanesulfonamide

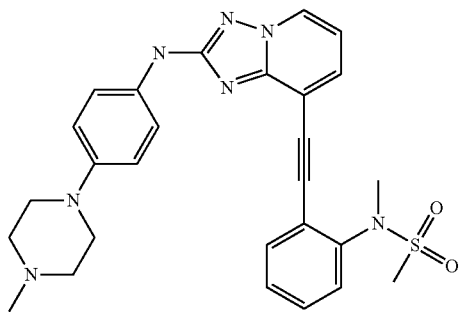 [SMILES: CN1CCN(c2ccc(Nc3nc4c(C#Cc5ccccc5N(C)S(C)(=O)=O)cccn4n3)cc2)CC1]

189 a) To a mixture of 2-ethynyl-phenylamine (126.0 mg, 1.075 mmol) and N,N-diisopropylethylamine (2 mL, 10 mmol) in N,N-dimethylformamide (1 mL) at room temperature under an atmosphere of nitrogen was added 8-bromo-2-chloro-[1,2,4]triazolo[1,5-a]pyridine (250.0 mg, 1.075 mmol), bBis(triphenylphosphine)palladium(II) chloride (10.0 mg, 0.0142 mmol) and copper(I) iodide (7.0 mg, 0.037 mmol). The mixture was stirred at room temperature for 18 hours then was poured into 0.1N hydrochloric acid (100 mL) and extracted with ethyl acetate (3×30 mL). The combined organic layers were washed with water (2×20 mL) and saturated aqueous sodium chloride (20 mL), dried over magnesium sulfate, filtered and evaporated. The residue was purified using preparatory silica gel plates (20 cm×20 cm 100% dichloromethane). 2-(2-Chloro-[1,2,4]triazolo[1,5-a]pyridin-8-ylethynyl)-phenylamine was isolated as a yellow solid (0.158 g, 55%). $^1$H NMR (400 MHz, CDCl$_3$, δ, ppm): 8.43 (d, J=6.7 Hz, 1H), 7.66 (d, J=7.4 Hz, 1H), 7.39 (d, J=7.7 Hz, 1H), 7.19 (t, J=7.8 Hz, 1H), 7.07 (t, J=7.0 Hz, 1H), 6.77-6.67 (m, 2H), 4.81 (br s, 2H). MS=269, 271 (MH)+.

189 b) To a cooled solution of 2-(2-chloro-[1,2,4]triazolo[1,5-a]pyridin-8-ylethynyl)-phenylamine (840.0 mg, 3.126 mmol) and N,N-diisopropylethylamine (2.8 mL, 16 mmol) in 1,2-dichloroethane (10 mL) in a ice/water bath at 5° C. was added dropwise methanesulfonyl chloride (0.64 mL, 8.2 mmol). The mixture was stirred 1 hour at 5° C. then at room temperature overnight. 0.1N hydrochloric acid (50 mL) was added to reaction mixture, stirred for 20 minutes then extracted with ethyl acetate (3×50 mL). The combined organic layers were washed with water (50 mL) and saturated aqueous sodium chloride (50 mL), dried over magnesium sulfate, filtered and evaporated to a tan solid (1.34 g). To a suspension of the tan solid (1.34 g) from in tetrahydrofuran (10 mL,) was added 1.0 M of tetra-n-butylammonium fluoride in tetrahydrofuran (12.50 mL, 12.50 mmol). The mixture was stirred at room temperature for 18 hours. The volatiles were evaporated to yield a viscous oil. Hydrochloric acid (2N, 30 mL) was added to viscous oil and stirred then was extracted with ethyl acetate (3×50 mL). The combined organic layers were dried over magnesium sulfate, filtered and evaporated. The residue was purified via chromatography (silica gel column 40 g 20%→100% ethyl acetate:hexane). N-[2-(2-Chloro-[1,2,4]triazolo[1,5-a]pyridin-8-ylethynyl)-phenyl]-methanesulfonamide was isolated as a tan solid (0.90 g, 83%). $^1$H NMR (400 MHz, CDCl$_3$, δ, ppm): 8.50 (d, J=6.7 Hz, 1H), 7.93 (br s, 1H), 7.75 (d, J=8.4 Hz, 1H), 7.71 (d, J=7.3 Hz, 1H), 7.57 (d, J=7.8 Hz, 1H), 7.44 (t, J=7.9 Hz, 1H), 7.19 (t, J=7.8 Hz, 1H), 7.11 (t, J=7.1 Hz, 1H), 3.17 (s, 3H). MS=347, 349 (MH)+.

189 c) To a suspension of N-[2-(2-chloro-[1,2,4]triazolo[1,5-a]pyridin-8-ylethynyl)-phenyl]-methanesulfonamide (900.0 mg, 2.595 mmol) and cesium carbonate (950.0 mg, 2.916 mmol) in acetonitrile (5 mL) was added iodomethane (0.25 mL, 4.0 mmol). The reaction flask was capped and the mixture was stirred at room temperature over weekend. The volatiles were evaporated. The recovered solid was triturated with water (30 mL), filtered and rinsed with water then was dissolved in dichloromethane (50 mL) and was separated. The organic layer was dried over magnesium sulfate, filtered and evaporated. N-[2-(2-Chloro-[1,2,4]triazolo[1,5-a]pyridin-8-ylethynyl)-phenyl]-N-methyl-methanesulfonamide was isolated as a tan solid (0.871 g, 93%). $^1$H NMR (400 MHz, CDCl$_3$, δ, ppm): 8.51 (d, J=6.7 Hz, 1H), 7.78 (d, J=7.4 Hz, 1H), 7.68 (d, J=7.6 Hz, 1H), 7.52 (d, J=7.8 Hz, 1H), 7.46 (t, J=7.4 Hz, 1H), 7.38 (t, J=7.5 Hz, 1H), 7.10 (t, J=7.1 Hz, 1H), 3.54 (s, 3H), 3.21 (s, 3H). MS=361, 363 (MH)+.

189 d) N-Methyl-N-(2-{2-[4-(4-methyl-piperazin-1-yl)-phenylamino]-[1,2,4]triazolo[1,5-a]pyridin-8-ylethynyl}-phenyl)-methanesulfonamide was prepared from N-[2-(2-chloro-[1,2,4]triazolo[1,5-a]pyridin-8-ylethynyl)-phenyl]-N-methyl-methanesulfonamide (125.0 mg, 0.3464 mmol) and 4-(4-methyl-piperazin-1-yl)-phenylamine (73.0 mg, 0.382 mmol) with 2,2'-bis-dicyclohexylphosphanyl-biphenyl (37.0 mg, 0.0677 mmol) as the ligand in a manner analogous to Example 2d. Product isolated as a yellow foam (0.138 g, 77%). $^1$H NMR (400 MHz, CDCl$_3$, δ, ppm): 8.40 (d, J=6.6 Hz, 1H), 7.65 (d, J=7.6 Hz, 1H), 7.61 (d, J=7.4 Hz, 1H), 7.55-7.48 (m, 3H), 7.43 (t, J=7.5 Hz, 1H), 7.37 (t, J=7.5 Hz, 1H), 7.00 (d, J=7.7 Hz, 2H), 6.86 (t, J=7.0 Hz, 1H), 6.73 (s, 1H), 3.61 (s, 3H), 3.23-3.16 (m, 7H), 2.63-2.58 (m, 4H), 2.37 (s, 3H). MS=516 (MH)+.

Example 190

{3-[1-(2-Methanesulfonyl-ethyl)-piperidin-4-yl]-phenyl}-[8-(4-methanesulfonyl-phenyl)-[1,2,4]triazolo[1,5-a]pyridin-2-yl]-amine

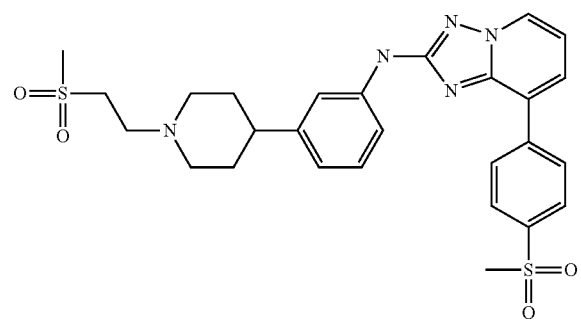 [SMILES: CS(=O)(=O)CCN1CCC(c2cccc(Nc3nc4c(-c5ccc(S(C)(=O)=O)cc5)cccn4n3)c2)CC1]

{3-[1-(2-Methanesulfonyl-ethyl)-piperidin-4-yl]-phenyl}-[8-(4-methanesulfonyl-phenyl)-[1,2,4]triazolo[1,5-a]pyridin-2-yl]-amine was prepared from [8-(4-methanesulfonyl-phenyl)-[1,2,4]triazolo[1,5-a]pyridin-2-yl]-(3-piperidin-4-yl-phenyl)-amine and 1-chloro-2-methanesulfonyl-ethane (75.0 mg, 0.526 mmol) in a manner analogous to Example 183. Product isolated as a pale yellow solid (0.164 g, 65%). MP=217-219° C. $^1$H NMR (400 MHz, CDCl$_3$, δ, ppm): 8.50 (d, J=6.5 Hz, 1H), 8.27 (d, J=7.7 Hz, 2H), 8.09 (d, J=7.5 Hz, 2H), 7.68 (d, J=7.0 Hz, 1H), 7.63 (s, 1H), 7.36-7.27 (m, 2H), 7.04 (t, J=6.5 Hz, 1H), 6.90-6.85 (m, 2H), 3.24 (t, J=6.5 Hz, 2H), 3.12-3.05 (m, 8H), 2.94 (t, J=6.7 Hz, 2H), 2.62-2.52 (m, 1H), 2.25-2.16 (m, 2H), 1.98-1.90 (m, 2H), 1.85-1.72 (m, 2H). MS=554 (MH)+.

Example 191

(±)-2-((cis)-3-Hydroxy-4-{3-[8-(4-methanesulfonyl-phenyl)-[1,2,4]triazolo[1,5-a]pyridin-2-ylamino]-phenyl}-piperidin-1-yl)-acetamide

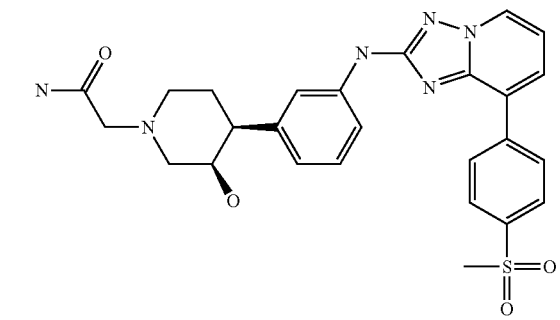 [SMILES: CS(=O)(=O)c1ccc(-c2cccn3nc(Nc4cccc([C@@H]5CCN(CC(N)=O)C[C@@H]5O)c4)nc23)cc1]

(±)-2-((cis)-3-Hydroxy-4-{3-[8-(4-methanesulfonyl-phenyl)-[1,2,4]triazolo[1,5-a]pyridin-2-ylamino]-phenyl}-piperidin-1-yl)-acetamide was prepared from (±)-(cis)-4-{3-[8-(4-methanesulfonyl-phenyl)-[1,2,4]triazolo[1,5-a]pyridin-2-ylamino]-phenyl}-piperidin-3-ol (70.0 mg, 0.151 mmol) in analogous manner to Example 183. Product isolated as a yellow solid (0.034 g, 43%). MP=173-175° C. $^1$H NMR (400 MHz, (D$_3$C)$_2$SO, δ, ppm): 9.67 (s, 1H), 8.86 (d, J=6.3 Hz, 1H), 8.45 (d, J=7.9 Hz, 2H), 8.07 (d, J=7.7 Hz, 2H), 7.98 (d, J=7.5 Hz, 1H), 7.70 (s, 1H), 7.65 (s, 1H), 7.53 (d, J=7.8 Hz, 1H), 7.23-7.12 (m, 3H), 6.85 (d, J=7.9 Hz, 1H), 4.44 (d, J=9.3 Hz, 1H), 3.81-3.75 (m, 1H), 3.29 (s, 3H), 2.95-2.82 (m, 4H), 2.62-2.55 (m, 1H), 2.42-2.37 (m, 1H), 2.32-2.15 (m, 2H), 1.62-1.55 (m, 1H). MS=521 (MH)+.

Example 192

N-Methyl-N-(2-{2-[3-(4-methyl-piperazin-1-yl)-phenylamino]-[1,2,4]triazolo[1,5-a]pyridin-8-ylethynyl}-phenyl)-methanesulfonamide

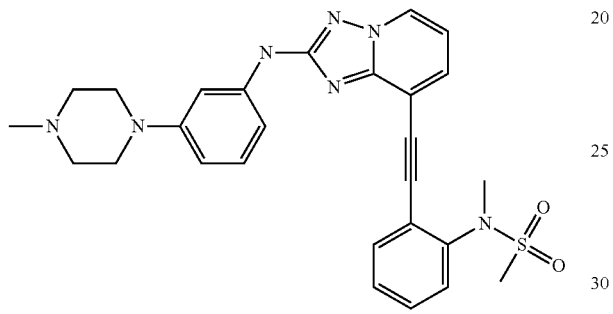

N-Methyl-N-(2-{2-[3-(4-methyl-piperazin-1-yl)-phenylamino]-[1,2,4]triazolo[1,5-a]pyridin-8-ylethynyl}-phenyl)-methanesulfonamide was prepared from N-[2-(2-chloro-[1,2,4]triazolo[1,5-a]pyridin-8-ylethynyl)-phenyl]-N-methyl-methanesulfonamide (75.0 mg, 0.208 mmol) and 3-(4-methylpiperazin-1-yl)aniline (45.0 mg, 0.235 mmol) with 2,2'-Bis-dicyclohexylphosphanyl-biphenyl (25.0 mg, 0.0457 mmol) as the ligand in an analogous manner to Example 2d. Product isolated as a tan foam (0.055 g, 51%). $^1$H NMR (400 MHz, CDCl$_3$, δ, ppm): 8.43 (d, J=6.9 Hz, 1H), 7.68-7.61 (m, 2H), 7.54 (d, J=7.7 Hz, 1H), 7.44 (t, J=7.7 Hz, 1H), 7.37 (t, J=7.2 Hz, 1H), 7.30-7.25 (m, 1H), 7.19 (d, J=8.2 Hz, 1H), 7.15 (s, 1H), 6.91-6.85 (m, 2H), 6.62 (d, J=8.0 Hz, 1H), 3.61 (s, 3H), 3.31-3.26 (m, 4H), 3.22 (s, 3H), 2.62-2.57 (m, 4H), 2.37 (s, 3H). MS=516 (MH)+.

Example 193

N-Methyl-N-{2-[2-(2-methyl-2,3-dihydro-1H-isoindol-5-ylamino)-[1,2,4]triazolo[1,5-a]pyridin-8-ylethynyl]-phenyl}-methanesulfonamide

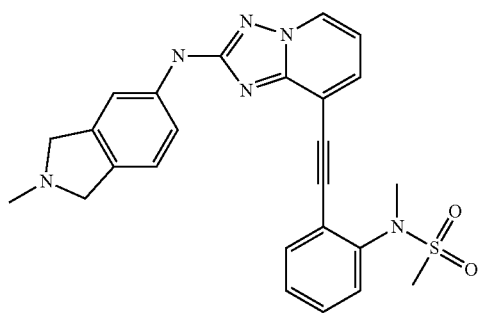 [SMILES: CN1Cc2ccc(Nc3nc4c(C#Cc5ccccc5N(C)S(C)(=O)=O)cccn4n3)cc2C1]

N-Methyl-N-{2-[2-(2-methyl-2,3-dihydro-1H-isoindol-5-ylamino)-[1,2,4]triazolo[1,5-a]pyridin-8-ylethynyl]-phenyl}-methanesulfonamide was prepared from N-[2-(2-chloro-[1,2,4]triazolo[1,5-a]pyridin-8-ylethynyl)-phenyl]-N-methyl-methanesulfonamide (75.0 mg, 0.208 mmol) and 2-methyl-2,3-dihydro-1H-isoindol-5-ylamine (35.0 mg, 0.236 mmol) with 2,2'-bis-dicyclohexylphosphanyl-biphenyl (25.0 mg, 0.0457 mmol) as the ligand in a manner analogous to Example 2d. Product isolated as a tan foam (0.004 g, 4%). $^1$H NMR (400 MHz, CDCl$_3$, δ, ppm): 8.43 (d, J=6.9 Hz, 1H), 7.68-7.61 (m, 2H), 7.56-7.49 (m, 2H), 7.47-7.35 (m, 3H), 7.20 (d, J=7.9 Hz, 1H), 6.94 (s, 1H), 6.89 (t, J=7.0 Hz, 1H), 3.96 (s, 2H), 3.90 (s, 2H), 3.61 (s, 3H), 3.21 (s, 3H), 2.61 (s, 3H). MS=473 (MH)+.

Example 194

N-Methyl-N-[2-(2-{2-[4-(4-methyl-piperazin-1-yl)-phenylamino]-[1,2,4]triazolo[1,5-a]pyridin-8-yl}-ethyl)-phenyl]-methanesulfonamide

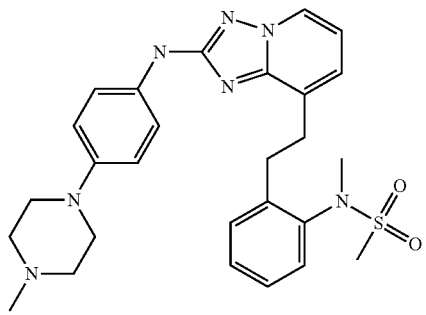

To a Paar bottle was added N-methyl-N-(2-{2-[4-(4-methyl-piperazin-1-yl)-phenylamino]-[1,2,4]triazolo[1,5-a]pyridin-8-ylethynyl}-phenyl)-methanesulfonamide (50.0 mg, 0.0970 mmol), 10% palladium on carbon (50% wet)(25.0 mg, 0.0117 mmol) and 2:1 ethyl acetate:methanol (10 mL). The mixture was degassed and charged with hydrogen (38 psi). The mixture was shaken on a Paar apparatus for 1 hour. The mixture was degassed and kept under an atmosphere of Nitrogen. The mixture was filtered through a plug of diatomaceous earth and rinsed with dichloromethane. The filtrate was evaporated. N-Methyl-N-[2-(2-{2-[4-(4-methyl-piperazin-1-yl)-phenylamino]-[1,2,4]triazolo[1,5-a]pyridin-8-yl}-ethyl)-phenyl]-methanesulfonamide was isolated as a pale yellow foam (0.037 g, 73%). $^1$H NMR (400 MHz, (D$_3$C)$_2$SO, δ, ppm): 9.31 (s, 1H), 8.58 (d, J=6.6 Hz, 1H), 7.55 (d, J=7.8 Hz, 2H), 7.48-7.44 (m, 1H), 7.35-7.26 (m, 3H), 7.23 (d, J=7.0 Hz, 1H), 6.92-6.84 (m, 3H), 3.23-3.00 (m, 14H), 2.48-2.43 (m, 4H), 2.22 (s, 3H). MS=520 (MH)+.

Example 195

N-Methyl-N-(2-{2-[4-(4-methyl-piperazin-1-yl)-phenylamino]-[1,2,4]triazolo[1,5-a]pyridin-8-yloxymethyl}-phenyl)-methanesulfonamide

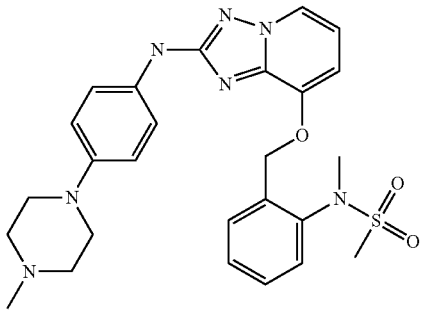 [SMILES: CN1CCN(c2ccc(Nc3nc4c(OCc5ccccc5N(C)S(C)(=O)=O)cccn4n3)cc2)CC1]

195 a) To a cooled, stirred solution of 2-amino-benzoic acid ethyl ester (10.0 g, 60.5 mmol) in ether (50 mL) at 5° C. was added triethylamine (8.44 mL, 60.5 mmol). methanesulfonyl chloride (4.68 mL, 60.5 mmol) in ethyl acetate (50 mL) was added dropwise to the mixture, was stirred for 1 hour at 5° C. then at room temperature for 18 hours. Water (100 mL) was added to the stirring mixture and was extracted with ethyl acetate (3×50 mL). The combined organic was washed with water (2×50 mL) and saturated aqueous sodium chloride. The organic layer was dried over magnesium sulfate, filtered and evaporated. The residue was stirred with warm methanol (30 mL) for 30 minutes and cooled to room temperature. The crystalline material was filtered and rinsed with a minimum of methanol. 2-Methanesulfonylamino-benzoic acid ethyl ester was isolated as a white solid (7.0 g, 48%). $^1$H NMR (400 MHz, CDCl$_3$, δ, ppm): 10.52 (br s, 1H), 8.07 (d, J=8.0 Hz, 1H), 7.74 (d, J=8.5 Hz, 1H), 7.56 (t, J=7.8 Hz, 1H), 7.13 (t, J=7.7 Hz, 1H), 4.40 (q, J=7.0 Hz, 2H), 3.06 (s, 3H), 1.42 (t, J=7.0 Hz, 3H). MS=266 (M+Na)+.

195 b) To a stirred suspension of 2-methanesulfonylamino-benzoic acid ethyl ester (1.0 g, 4.1 mmol) and cesium carbonate (1.5 g, 4.5 mmol) in acetonitrile (10 mL) was added iodomethane (0.28 mL, 4.5 mmol). The mixture was stirred at room temperature for 18 hours then diluted with dichloromethane (30 mL), filtered through a plug of diatomaceous earth and evaporated. 2-(Methanesulfonyl-methyl-amino)-benzoic acid ethyl ester was isolated as a clear viscous oil (1.08 g, 100%). $^1$H NMR (400 MHz, CDCl$_3$, δ, ppm): 7.90 (d, J=7.7 Hz, 1H), 7.55 (t, J=7.7 Hz, 1H), 7.47-7.38 (m, 2H), 4.38 (q, J=7.0 Hz, 2H), 3.32 (s, 3H), 2.96 (s, 3H), 1.41 (t, J=7.1 Hz, 3H). MS=280 (M+Na)+.

195 c) To a cooled, stirred suspension of 2.0 M of lithium tetrahydroborate in tetrahydrofuran (0.630 mL, 1.26 mmol) at 5° C. was added dropwise a solution of 2-(methanesulfonyl-methyl-amino)-benzoic acid ethyl ester (1.08 g, 4.20 mmol) in tetrahydrofuran (10 mL). Gas evolution was noted. The mixture was stirred for 10 minutes at 5° C. then at room temperature for 3 hours. The mixture was cooled to 5° C. and saturated aqueous ammonium chloride (5 mL) was added dropwise. Vigorous gas evolution was noted. The mixture was stirred for 15 minutes then warmed to room temperature for 30 minutes. Sodium sulfate was added to granulate aluminium salts. The mixture was diluted with dichloromethane (50 mL), filtered through a plug of diatomaceous earth and evaporated. N-(2-Hydroxymethyl-phenyl)-N-methyl-methanesulfonamide was isolated as a yellow oil (0.931 g, 100%). $^1$H NMR (400 MHz, CDCl$_3$, δ, ppm): 7.61 (d, J=7.3 Hz, 1H), 7.44-7.35 (m, 2H), 7.28-7.24 (m, 1H), 4.74 (br s, 2H), 3.29 (s, 3H), 2.98 (s, 3H), 2.90-2.81 (m, 1H). MS=238 (M+Na)+.

196 d) To a stirred mixture of N-(2-hydroxymethyl-phenyl)-N-methyl-methanesulfonamide (0.90 g, 4.2 mmol) and carbon tetrabromide (2.40 g, 7.24 mmol) in dry tetrahydrofuran (50 mL) was added triphenylphosphine (1.90 g, 7.23 mmol). The mixture was stirred at room temperature for 18 hours. The volatiles were evaporated under reduced pressure. The residue was triturated with ethyl acetate (30 mL) then filtered and evaporated under reduced pressure. The residue was purified via chromatography (silica gel column 40 g 5%→100% ethyl acetate:hexane). N-(2-Bromomethyl-phenyl)-N-methyl-methanesulfonamide was isolated as pale yellow solid (0.86 g, 74%), $^1$H NMR (400 MHz, CDCl$_3$, δ, ppm): 7.57-7.52 (m, 1H), 7.41-7.34 (m, 2H), 7.30-7.25 (m, 1H), 5.29-4.30 (br m, 2H), 3.34 (s, 3H), 2.98 (s, 3H).

195 e) To a suspension of 2-amino-[1,2,4]triazolo[1,5-a]pyridin-8-ol (0.20 g, 1.3 mmol) and cesium carbonate (0.47 g, 1.4 mmol) in dry acetone (5 mL, 70 mmol) was added N-(2-bromomethyl-phenyl)-N-methyl-methanesulfonamide (0.40 g, 1.4 mmol). The mixture was stirred for 2 hours at room temperature then heated at 40° C. for 18 hours. The mixture was cooled to room temperature and the volatiles were evaporated. The residue was triturated with water (30 mL). The water was decanted and the waxy solid was dissolved in dichloromethane (30 mL) and washed with water. The organic layer was dried over magnesium sulfate, filtered and evaporated. The recovered material was purified via chromatography (silica gel column 40 g and 0%→10% methanol:dichloromethane). N-[2-(2-Amino-[1,2,4]triazolo[1,5-a]pyridin-8-yloxymethyl)-phenyl]-N-methyl-methanesulfonamide was isolated as an orange viscous oil (0.129 g, 28%). $^1$H NMR (400 MHz, CDCl$_3$, δ, ppm): 7.96 (d, J=6.7 Hz, 1H), 7.73-7.68 (m, 1H), 7.40-7.28 (m, 3H), 6.88 (d, J=7.8 Hz, 1H), 6.71 (t, J=7.1 Hz, 1H), 5.48 (br s, 2H), 4.44 (s, 2H), 3.31 (s, 3H), 2.99 (s, 3H).

196 f) N-[2-(2-Chloro-[1,2,4]triazolo[1,5-a]pyridin-8-yloxymethyl)-phenyl]-N-methyl-methanesulfonamide was prepared from N-[2-(2-amino-[1,2,4]triazolo[1,5-a]pyridin-8-yloxymethyl)-phenyl]-N-methyl-methanesulfonamide (0.129 g, 0.371 mmol) in a manner analogous to Example 68a. Product isolated as a yellow solid (0.102 g, 75%). $^1$H NMR (400 MHz, CDCl$_3$, δ, ppm): 8.15 (d, J=6.5 Hz, 1H), 7.73-7.69 (m, 1H), 7.45-7.38 (m, 2H), 7.35-7.30 (m, 1H), 7.03 (d, J=7.9 Hz, 1H), 6.96 (t, J=6.8 Hz, 1H), 5.70-5.30 (m, 2H), 3.32 (s, 3H), 2.99 (s, 3H). MS=367, 369 (MH)+.

195 g) N-Methyl-N-(2-{2-[4-(4-methyl-piperazin-1-yl)-phenylamino]-[1,2,4]triazolo[1,5-a]pyridin-8-yloxymethyl}-phenyl)-methanesulfonamide was prepared from N-[2-(2-chloro-[1,2,4]triazolo[1,5-a]pyridin-8-yloxymethyl)-phenyl]-N-methyl-methanesulfonamide (102.0 mg, 0.2781 mmol) and 4-(4-methyl-piperazin-1-yl)-phenylamine (60.0 mg, 0.314 mmol) with 2,2'-bis-dicyclohexylphosphanyl-biphenyl (30.0 mg, 0.0549 mmol) as the ligand in a manner analogous to Example 2d. Product isolated as a brown foam (0.016 g, 11%). $^1$H NMR (400 MHz, CDCl$_3$, δ, ppm): 8.07 (d, J=6.7 Hz, 1H), 7.74-7.69 (m, 1H), 7.46 (d, J=8.1 Hz, 2H), 7.43-7.38 (m, 2H), 7.34-7.30 (m, 1H), 6.96 (d, J=8.1 Hz, 2H), 6.90 (d, J=7.8 Hz, 1H), 6.73 (t, J=7.3 Hz, 1H), 6.62 (s, 1H), 5.49 (br s, 2H), 3.32 (s, 3H), 3.18-3.13 (m, 4H), 2.99 (s, 3H), 2.62-2.57 (m, 4H), 2.36 (s, 3H). MS=522 (MH)+.

Example 196

N-Methyl-N-[2-((E)-2-{2-[4-(4-methyl-piperazin-1-yl)-phenylamino]-[1,2,4]triazolo[1,5-a]pyridin-8-yl}-vinyl)-phenyl]-methanesulfonamide

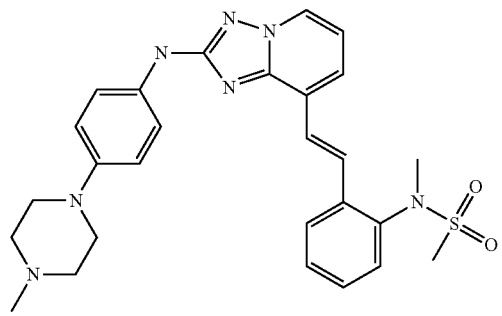 [SMILES: CN1CCN(c2ccc(Nc3nc4c(/C=C/c5ccccc5N(C)S(C)(=O)=O)cccn4n3)cc2)CC1]

196 a) To a suspension of 8-bromo-2-chloro-[1,2,4]triazolo[1,5-a]pyridine (0.50 g, 2.2 mmol), potassium vinyltrifluoroborate (0.34 g, 2.6 mmol) and [1,1'-bis(diphenylphosphino)ferrocene]dichloropalladium(II), complex with dichloromethane (1:1) (35 mg, 0.043 mmol) in 1-propanol (10 mL) was added triethylamine (0.30 mL, 2.2 mmol). The mixture was heated at 90° C. for 6 hours under an atmosphere of nitrogen. The mixture was cooled to room temperature and the volatiles were evaporated under reduced pressure. The residue was diluted with dichloromethane (50 mL) and filtered through a plug of diatomaceous earth. The filtrate was washed with 2N Hydrochloric acid (2×10 mL) and saturated aqueous sodium chloride, dried over magnesium sulfate, filtered and evaporated. The residue was purified via chromatography (silica gel column 24 g and 0%→2% methanol:dichloromethane). 2-Chloro-8-vinyl-[1,2,4]triazolo[1,5-a]pyridine was isolated as a white solid (0.336 g, 87%). $^1$H NMR (400 MHz, CDCl$_3$, δ, ppm): 8.40 (d, J=6.8 Hz, 1H), 7.53 (d, J=7.3 Hz, 1H), 7.08-6.94 (m, 2H), 6.59 (d, J=17.6 Hz, 1H), 5.70 (d, J=11.2 Hz, 1H). MS=180, 182 (MH)+.

196 b) To a suspension of N-(2-bromo-phenyl)-methanesulfonamide (5.01 g, 20.0 mmol) and cesium carbonate (7.2 g, 22 mmol) in acetonitrile (20 mL) was added iodomethane (1.4 mL, 22 mmol). The mixture was stirred at room temperature for 24 hours then diluted with dichloromethane (30 mL), filtered through a plug of diatomaceous earth and evaporated. N-(2-Bromo-phenyl)-N-methyl-methanesulfonamide was isolated as a pale orange solid (5.22 g, 98%). $^1$H NMR (400 MHz, CDCl$_3$, δ, ppm): 7.65 (d, J=8.0 Hz, 1H), 7.50 (d, J=7.9 Hz, 1H), 7.37 (t, J=7.4 Hz, 1H), 7.23 (t, J=8.2 Hz, 1H), 3.29 (s, 3H), 3.06 (s, 3H). MS=286, 288 (MH)+.

196 c) A tube was charged with 2-chloro-8-vinyl-[1,2,4]triazolo[1,5-a]pyridine (100.0 mg, 0.5568 mmol), N-(2-bromo-phenyl)-N-methyl-methanesulfonamide (140.0 mg, 0.5300 mmol), palladium acetate (4.0 mg, 0.018 mmol) and tri-o-tolylphosphine (26.0 mg, 0.0854 mmol), triethylamine (0.35 mL, 2.5 mmol) and acetonitrile (1 mL) under an atmosphere of nitrogen. The tube was sealed and the mixture was heated at 100° C. for 18 hours then cooled to room temperature, diluted with dichloromethane (30 mL) and washed with 2N Hydrochloric acid (10 mL). The organic layer was separated, dried over magnesium sulfate, filtered and evaporated. The residued was purified via chromatography (silica gel column 24 g and 10%→90% ethyl acetate:hexane). N-{2-[(E)-2-(2-Chloro-[1,2,4]triazolo[1,5-a]pyridin-8-yl)-vinyl]-phenyl}-N-methyl-methanesulfonamide was isolated as a tan foam (0.133 g, 69%). $^1$H NMR (400 MHz, CDCl$_3$, δ, ppm): 8.52 (d, J=16.1 Hz, 1H), 8.40 (d, J=6.8 Hz, 1H), 7.86 (d, J=7.1 Hz, 1H), 7.65 (d, J=7.4 Hz, 1H), 7.46-7.30 (m, 3H), 7.20-7.05 (m, 2H), 3.36 (s, 3H), 3.19 (s, 3H). MS=363, 365 (MH)+.

196 d) N-Methyl-N-[2-((E)-2-{2-[4-(4-methyl-piperazin-1-yl)-phenylamino]-[1,2,4]triazolo[1,5-a]pyridin-8-yl}-vinyl)-phenyl]-methanesulfonamide was prepared from N-{2[(E)-2-(2-chloro-[1,2,4]triazolo[1,5-a]pyridin-8-yl)-vinyl]-phenyl}-N-methyl-methanesulfonamide (133.0 mg, 0.3666 mmol) and 4-(4-methyl-piperazin-1-yl)-phenylamine (70.0 mg, 0.366 mmol) with 2,2'-bis-dicyclohexylphosphanyl-biphenyl (30.0 mg, 0.0549 mmol) as the ligand in a manner analogous to Example 2d. Product isolated as a yellow solid (0.055 g, 29%). $^1$H NMR (400 MHz, CDCl$_3$, δ, ppm): 8.49 (d, J=16.4 Hz, 1H), 8.31 (d, J=6.3 Hz, 1H), 7.85 (d, J=7.6 Hz, 1H), 7.53-7.48 (m, 3H), 7.43-7.28 (m, 4H), 6.98 (d, J=7.8 Hz, 2H), 6.87 (t, J=6.9 Hz, 1H), 6.68 (s, 1H), 3.35 (s, 3H), 3.20-3.15 (m, 4H), 3.03 (s, 3H), 2.63-2.58 (m, 4H), 2.36 (s, 3H). MS=4518 (MH)+.

Example 197

N-Methyl-N-[2-(1-{2-[4-(4-methyl-piperazin-1-yl)-phenylamino]-[1,2,4]triazolo[1,5-a]pyridin-8-ylamino}-ethyl)-phenyl]-methanesulfonamide

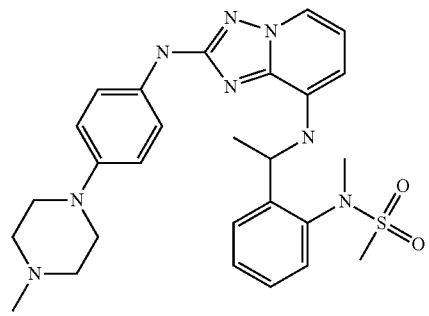 [SMILES: CC(Nc1cccn2nc(Nc3ccc(N4CCN(C)CC4)cc3)nc12)c1ccccc1N(C)S(C)(=O)=O]

197 a) A round bottom flask was charged with (2-nitro-phenyl)-acetic acid methyl ester (4.22 g, 21.6 mmol) (prepared as described in *Organic Letters*, 2009, 11, 1345-1348), iodomethane (2.8 mL, 45 mmol) and dry dimethyl sulfoxide (20 mL). Cesium carbonate (18 g, 56 mmol) was added and the mixture was stirred at room temperature under an atmosphere of nitrogen for 18 hours. Water (50 mL) was added and the mixture was extracted with ethyl acetate (3×30 mL). The combined organic layers were washed with water (2×30 mL), saturated aqueous sodium chloride (30 mL), dried over magnesium sulfate, filtered and evaporated. 2-(2-Nitro-phenyl)-propionic acid methyl ester was isolated as a red oil (3.24 g, 71%). $^1$H NMR (400 MHz, CDCl$_3$, δ, ppm): 7.93 (d, J=8.1 Hz, 1H), 7.60 (t, J=7.6 Hz, 1H), 7.49 (d, J=7.8 Hz, 1H), 7.43 (t, J=7.7 Hz, 1H), 4.32 (q, J=7.0 Hz, 1H), 3.67 (s, 3H), 1.61 (d, J=7.0 Hz, 3H). MS=232 (MH)+.

197 b) 2-(2-Amino-phenyl)-propionic acid methyl ester was prepared from 2-(2-nitro-phenyl)-propionic acid methyl ester (1.22 g, 5.83 mmol) in a manner analogous to Example 111a. Product isolated as a crude tan oil (1.0 g, 96%). $^1$H NMR (400 MHz, CDCl$_3$, δ, ppm): 7.16 (d, J=7.6 Hz, 1H), 7.08 (t, J=7.6 Hz, 1H), 6.79 (t, J=7.5 Hz, 1H), 6.70 (d, J=7.9 Hz, 1H), 3.99 (br s, 2H), 3.82 (q, J=7.2 Hz, 1H), 3.67 (s, 3H), 1.54 (d, J=7.2 Hz, 3H). MS=148 [(M-OCH3)]+.

197 c) 2-(2-Methanesulfonylamino-phenyl)-propionic acid methyl ester was prepared from 2-(2-Amino-phenyl)-propionic acid methyl ester (1.0 g, 5.6 mmol) in a manner analogous to Example 189b. Product isolated as a yellow viscous oil (0.843 g, 59%). $^1$H NMR (400 MHz, CDCl$_3$, δ, ppm): 7.52 (d, J=7.7 Hz, 1H), 7.46 (s, 1H), 7.37-7.21 (m, 3H), 4.05 (q, J=7.1 Hz, 1H), 3.69 (s, 3H), 3.07 (s, 3H), 1.58 (d, J=7.1 Hz, 1H). MS=280 (M+Na)+.

197 d) 2-[2-(Methanesulfonyl-methyl-amino)-phenyl]-propionic acid methyl ester was prepared from 2-(2-methanesulfonylamino-phenyl)-propionic acid methyl ester (0.843 g, 3.28 mmol) in a manner analogous to Example 189c. Product isolated as a pale yellow solid (0.880 g, 99%). $^1$H NMR (400 MHz, CDCl$_3$, δ, ppm): 7.46 (d, J=7.6 Hz, 1H), 7.40-7.26 (m, 3H), 4.47-4.30 (m, 1H), 3.70-3.63 (m, 3H), 3.28-3.22 (m, 3H), 2.99 (s, 3H), 1.56-1.44 (m, 3H). MS=294 (M+Na)+.

197 e) To a solution of 2-[2-(Methanesulfonyl-methyl-amino)-phenyl]-propionic acid methyl ester (0.880 g, 3.24 mmol) in methanol (15 mL) and water (10 mL) was added lithium hydroxide monohydrate (0.687 g, 16.4 mmol). The mixture was stirred at room temperature for 24 hours then extracted with dichloromethane (3×30 mL). The combined organic layers were dried over magnesium sulfate, filtered and evaporated. 2-[2-(Methanesulfonyl-methyl-amino)-phenyl]-propionic acid was isolated as a yellow viscous oil (0.755 g, 91%). $^1$H NMR (400 MHz, CDCl$_3$, δ, ppm): 9.73 (br s, 1H), 7.51-7.28 (m, 4H), 4.53-4.34 (m, 1H), 3.32-3.25 (m, 3H), 3.05-2.98 (m, 3H), 1.56-1.40 (m, 3H). MS=280 (M+Na)+.

197 f) To a solution of 2-[2-(methanesulfonyl-methyl-amino)-phenyl]-propionic acid (0.755 g, 2.93 mmol) and diphenylphosphonic azide (0.95 mL, 4.4 mmol) in dichloromethane (25 mL) was added triethylamine (0.65 mL, 4.7 mmol). The mixture was stirred at room temperature for 24 hours then cooled to 5° C. and 2N Hydrochloric acid (30 mL) was added and the mixture stirred for 10 minutes. The layers were separated and the aqueous was washed with dichloromethane (2×10 mL). The combined organic layers were dried over magnesium sulfate, filtered and evaporated. The residue dissolved in tert-butyl alcohol (10 mL, 100 mmol) and heated at 80° C. for 18 hours. The volatiles were evaporated and the residue was dissolved in ethyl acetate (50 mL). The organic layer was washed with saturated aqueous sodium carbonate (30 mL), dried over magnesium sulfate, filtered and evaporated. The residue was dissolved in dichloromethane (5 mL) and trifluoroacetic acid (2 mL, 20 mmol) was added. The mixture was stirred at room temperature overnight. The volatiles were evaporated. The residue was dissolved in ethyl acetate (50 mL) and was extracted with 2N Hydrochloric acid (3×20 mL). The combined acidic aqueous layers were basified with 2M sodium hydroxide to pH 10. The basic aqueous layer was extracted with dichloromethane (3×20 mL). The combined organic layers were dried over magnesium sulfate, filtered and evaporated. N-[2-(1-Amino-ethyl)-phenyl]-N-methyl-methanesulfonamide was isolated as a crude tan viscous oil (0.380 g, 56%).

197 g) N-{2-[1-(2-Chloro-[1,2,4]triazolo[1,5-a]pyridin-8-ylamino)-ethyl]-phenyl}-N-methyl-methanesulfonamide was prepared from 8-bromo-2-chloro-[1,2,4]triazolo[1,5-a]pyridine (350.0 mg, 1.506 mmol) and N-[2-(1-amino-ethyl)-phenyl]-N-methyl-methanesulfonamide (380.0 mg, 1.664 mmol) in a manner analogous to Example 2d. Product isolated as a yellow foam (0.315 g, 55%). $^1$H NMR (400 MHz, CDCl$_3$, δ, ppm): 7.83-7.79 (m, 1H), 7.62-7.25 (m, 4H), 6.85-6.71 (m, 1H), 6.61-6.43 (m, 1H), 5.42-6.13 (m, 2H), 3.35-3.26 (m, 3H), 3.08-3.00 (m, 3H), 1.70-1.53 (m, 3H). MS=402 (M+Na)+.

197 h) N-Methyl-N-[2-(1-{2-[4-(4-methyl-piperazin-1-yl)-phenylamino]-[1,2,4]triazolo[1,5-a]pyridin-8-ylamino}-ethyl)-phenyl]-methanesulfonamide was prepared from N-{2-[1-(2-chloro-[1,2,4]triazolo[1,5-a]pyridin-8-ylamino)-ethyl]-phenyl}-N-methyl-methanesulfonamide (75.0 mg, 0.197 mmol) and 4-(4-methyl-piperazin-1-yl)-phenylamine (42.0 mg, 0.220 mmol) with 2,2'-bis-dicyclohexylphosphanyl-biphenyl (18.0 mg, 0.0329 mmol) as the ligand in a manner analogous to Example 2d. Product isolated as a pale yellow solid (0.008 g, 8%). $^1$H NMR (400 MHz, CDCl$_3$, δ, ppm): 7.77-7.25 (m, 8H), 7.00-6.93 (m, 2H), 6.65-6.30 (m, 3H), 5.40-5.24 (m, 1H), 5.00-4.91 (m, 1H), 3.35-3.29 (m, 3H), 3.19-3.13 (m, 4H), 3.07-3.01 (m, 3H), 2.63-2.58 (m, 4H), 2.36 (s, 3H), 1.72-1.55 (m, 3H). MS=535 (MH)+.

Example 198

{8-[4-(Dimethyl-phosphinoyl)-phenyl]-[1,2,4]triazolo[1,5-a]pyridin-2-yl}-[3-(4-methyl-piperazin-1-yl)-phenyl]-amine

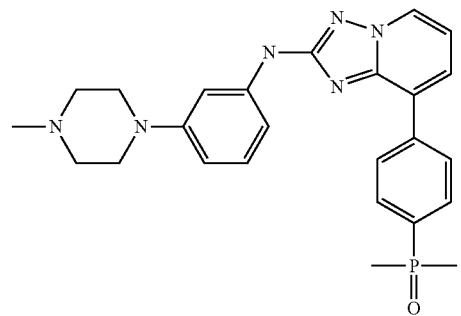

198 a) 8-(4-Bromo-phenyl)-2-chloro-[1,2,4]triazolo[1,5-a]pyridine was prepared from 8-bromo-2-chloro-[1,2,4]triazolo[1,5-a]pyridine (1.0 g, 4.5 mmol) and 4-bromobenzeneboronic acid (1.0 g, 5.0 mmol) in a manner analogous to Example 2c. Product isolated as an off-white solid (1.0 g, 72%). $^1$H NMR (400 MHz, CDCl$_3$, δ, ppm): 8.51 (d, J=6.5 Hz, 1H), 7.88 (d, J=7.1 Hz, 2H), 7.70 (d, J=7.0 Hz, 1H), 7.65 (d, J=7.1 Hz, 2H), 7.16 (t, J=7.5 Hz, 1H). MS=310, 312 (MH)+.

198 b) To an oven dried tube was added 8-(4-bromo-phenyl)-2-chloro-[1,2,4]triazolo[1,5-a]pyridine (0.90 g, 2.9 mmol), methylphosphinoylmethane (0.24 g, 3.1 mmol)(prepared as described in WO2005/009348), palladium acetate (13.5 mg, 0.0601 mmol), 9,9-dimethyl-4,5-bis(diphenylphosphino)xanthene (36.0 mg, 0.0622 mmol), cesium carbonate (1422.0 mg, 4.3644 mmol) and 1,4-dioxane (9 mL). The tube was evacuated, carefully, and backflushed with nitrogen. The tube was sealed and heated at 90° C. for 24 hours then cooled to room temperature, diluted with dichloromethane (30 mL), filtered through a plug of diatomaceous earth and evaporated. The residue was purified via chromatography using an ISCO automated purification apparatus (silica gel column 40 g and 0%→7% dichloromethane:methanol). 2-Chloro-8-[4-(dimethyl-phosphinoyl)-phenyl]-[1,2,4]triazolo[1,5-a]pyridine was isolated as a white solid (0.303 g, 34%). MP=220-223° C. $^1$H NMR (400 MHz, CDCl$_3$, δ, ppm): 8.55 (d, J=6.9 Hz, 1H), 8.11 (d, J=7.7 Hz, 2H), 7.94-7.86 (m, 2H), 7.77 (t, J=7.4 Hz, 1H), 7.21 (t, J=6.9 Hz, 1H), 1.80 (s, 3H), 1.77 (s, 3H). MS=306, 308 (MH)+.

198 c) {8-[4-(Dimethyl-phosphinoyl)-phenyl]-[1,2,4]triazolo[1,5-a]pyridin-2-yl}-[3-(4-methyl-piperazin-1-yl)-phenyl]-amine was prepared from 2-chloro-8-[4-(dimethylphosphinoyl)-phenyl]-[1,2,4]triazolo[1,5-a]pyridine (100.0 mg, 0.3271 mmol) and 3-(4-methylpiperazin-1-yl)aniline (70.0 mg, 0.366 mmol) with 2,2'-bis-dicyclohexylphosphanyl-biphenyl (28.0 mg, 0.0512 mmol) as the ligand in a manner analogous to Example 2d. Product isolated as a tan solid (0.097 g, 64%). MP=243-246° C. $^1$H NMR (400 MHz, CDCl$_3$, δ, ppm): 8.46 (d, J=6.2 Hz, 1H), 8.15 (d, J=8.0 Hz, 2H), 7.92-7.84 (m, 2H), 7.63-7.50 (m, 1H), 7.34 (s, 1H), 7.23 (t, J=8.2 Hz, 1H), 7.02-6.96 (m, 2H), 6.84 (s, 1H), 6.59 (d, J=7.8 Hz, 1H), 3.30-3.25 (m, 4H), 2.63-2.58 (m, 4H), 2.37 (s, 3H), 1.80 (s, 3H), 1.77 (s, 3H). MS=461 (MH)+.

Example 199

{8-[4-(Dimethyl-phosphinoyl)-phenyl]-[1,2,4]triazolo[1,5-a]pyridin-2-yl}-(2-methanesulfonyl-ethyl)-{3-[1-(2-methanesulfonyl-ethyl)-piperidin-4-yl]-phenyl}-amine

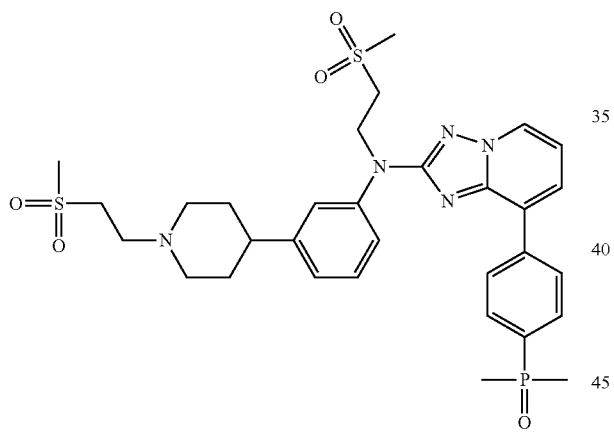

{8-[4-(Dimethyl-phosphinoyl)-phenyl]-[1,2,4]triazolo[1,5-a]pyridin-2-yl}-{3-[1-(2-methanesulfonyl-ethyl)-piperidin-4-yl]-phenyl}-amine was prepared from {8-[4-(dimethyl-phosphinoyl)-phenyl]-[1,2,4]triazolo[1,5-a]pyridin-2-yl}-(3-piperidin-4-yl-phenyl)-amine in a manner analogous to Example 183. Byproduct isolated as an off-white foam (0.070 g, 33%). $^1$H NMR (400 MHz, CDCl$_3$, δ, ppm): 8.39 (d, J=6.5 Hz, 1H), 8.19 (d, J=8.1 Hz, 2H), 7.87-7.80 (m, 2H), 7.67 (d, J=7.4 Hz, 1H), 7.41-7.30 (m, 3H), 7.08 (d, J=6.6 Hz, 1H), 6.99 (t, J=7.1 Hz, 1H), 4.52 (t, J=7.0 Hz, 2H), 3.58 (t, J=7.1 Hz, 2H), 3.20 (t, J=6.3 Hz, 2H), 3.10-3.03 (m, 5H), 2.98 (s, 3H), 2.91 (t, J=6.2 Hz, 2H), 2.56 (t, J=12.2 Hz, 1H), 2.19 (t, J=11.6 Hz, 2H), 1.93 (d, J=12.1 Hz, 2H), 1.81-1.69 (m, 8H). MS=658 (MH)+.

Example 200

N-Methyl-N-(2-{[2-(7-morpholin-4-yl-6,7,8,9-tetrahydro-5H-benzocyclohepten-2-ylamino)-[1,2,4]triazolo[1,5-a]pyridin-8-ylamino]-methyl}-phenyl)-methanesulfonamide

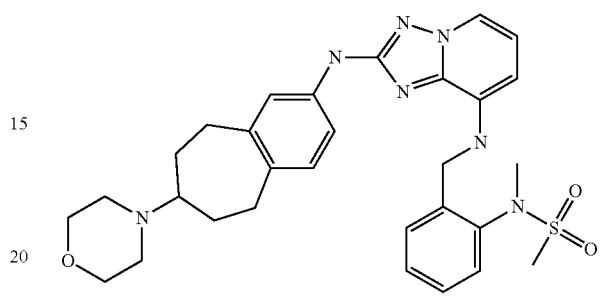

N-Methyl-N-(2-{[2-(7-morpholin-4-yl-6,7,8,9-tetrahydro-5H-benzocyclohepten-2-ylamino)-[1,2,4]triazolo[1,5-a]pyridin-8-ylamino]-methyl}-phenyl)-methanesulfonamide was prepared from N-{2-[(2-chloro-[1,2,4]triazolo[1,5-a]pyridin-8-ylamino)-methyl]-phenyl}-N-methyl-methanesulfonamide (100.0 mg, 0.2733 mmol) and 7-morpholin-4-yl-6,7,8,9-tetrahydro-5H-benzocyclohepten-2-ylamine (75.0 mg, 0.304 mmol) with 2,2'-bis-dicyclohexylphosphanyl-biphenyl (25.0 mg, 0.0457 mmol) as the ligand in a manner analogous to Example 2d. Product isolated as a tan foam (0.019 g, 12%). MP=118-135° C. $^1$H NMR (400 MHz, CDCl$_3$, δ, ppm): 7.81 (d, J=6.8 Hz, 1H), 7.55-7.50 (m, 1H), 7.37-7.28 (m, 5H), 7.07 (d, J=7.8 Hz, 1H), 6.67 (t, J=7.0 Hz, 1H), 6.62 (s, 1H), 6.36 (d, J=7.4 Hz, 1H), 5.26-5.20 (m, 1H), 4.72 (d, J=5.1 Hz, 2H), 3.70 (br s, 4H), 3.31 (s, 3H), 3.01 (s, 3H), 2.91-2.50 (m, 9H), 2.15-2.00 (m, 2H), 1.53-1.35 (m, 2H). MS=576 (MH)+.

Example 201

N-(2-{[2-(Isoquinolin-6-ylamino)-[1,2,4]triazolo[1,5-a]pyridin-8-ylamino]-methyl}-phenyl)-N-methyl-methanesulfonamide

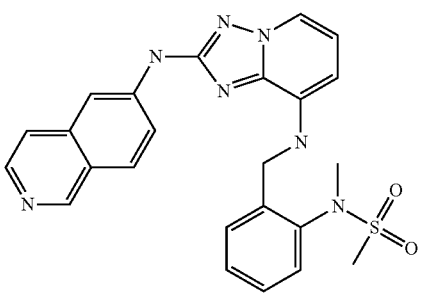 [SMILES: CN(c1ccccc1CNc1cccn2nc(Nc3ccc4cnccc4c3)nc12)S(C)(=O)=O]

N-(2-{[2-(Isoquinolin-6-ylamino)-[1,2,4]triazolo[1,5-a]pyridin-8-ylamino]-methyl}-phenyl)-N-methyl-methanesulfonamide was prepared from N-{2-[(2-chloro-[1,2,4]triazolo[1,5-a]pyridin-8-ylamino)-methyl]-phenyl}-N-methyl-methanesulfonamide (100.0 mg, 0.2733 mmol) and isoquinolin-6-ylamine (45.0 mg, 0.312 mmol) with 2,2'-bis-dicyclohexylphosphanyl-biphenyl (25.0 mg, 0.0457 mmol) as the ligand in a manner analogous to Example 2d. Product isolated as a yellow foam (0.079 g, 61%). $^1$H NMR (400 MHz, CDCl$_3$, δ, ppm): 9.09 (s, 1H), 8.43 (d, J=5.1 Hz, 1H), 8.28 (s, 1H), 7.92-7.87 (m, 2H), 7.62 (d, J=5.3 Hz, 1H), 7.54 (d, J=6.8 Hz, 2H), 7.40-7.28 (m, 3H), 7.18 (s, 1H), 6.76 (t, J=7.0 Hz, 1H), 6.44 (d, J=7.3 Hz, 1H), 5.39-5.32 (m, 1H), 4.75 (d, J=5.4 Hz, 2H), 3.32 (s, 3H), 3.02 (s, 3H). MS=474 (MH)+.

Example 202

N-Methyl-N-{2-[(2-phenylamino-[1,2,4]triazolo[1,5-a]pyridin-8-ylamino)-methyl]-phenyl}-methanesulfonamide

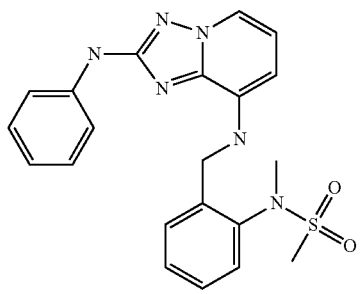 [SMILES: CN(c1ccccc1CNc1cccn2nc(Nc3ccccc3)nc12)S(C)(=O)=O]

N-Methyl-N-{2-[(2-phenylamino-[1,2,4]triazolo[1,5-a]pyridin-8-ylamino)-methyl]-phenyl}-methanesulfonamide was prepared from -{2-[(2-chloro-[1,2,4]triazolo[1,5-a]pyridin-8-ylamino)-methyl]-phenyl}-N-methyl-methanesulfonamide (100.0 mg, 0.2733 mmol) and aniline (28.0 uL, 0.307 mmol) with 2,2'-bis-dicyclohexylphosphanyl-biphenyl (25.0 mg, 0.0457 mmol) as the ligand in a manner analogous to Example 2d. Product isolated as a tan foam (0.049 g, 42%). $^1$H NMR (400 MHz, CDCl$_3$, δ, ppm): 7.82 (d, J=6.7 Hz, 1H), 7.58 (d, J=7.8 Hz, 2H), 7.55-7.49 (m, 1H), 7.37-7.28 (m, 5H), 6.97 (t, J=7.3 Hz, 1H), 6.77 (s, 1H), 6.68 (t, J=7.0 Hz, 1H), 6.38 (d, J=7.7 Hz, 1H), 5.28-5.22 (m, 1H), 4.73 (d, J=5.9 Hz, 2H), 3.31 (s, 3H), 3.00 (s, 3H). MS=423 (MH)+.

Example 203

{8-[4-(Dimethyl-phosphinoyl)-phenyl]-[1,2,4]triazolo[1,5-a]pyridin-2-yl}-{3-[1-(2-methanesulfonyl-ethyl)-piperidin-4-yl]-phenyl}-amine 203 a) To a solution of 4-(3-nitro-phenyl)-3,6-dihydro-2H-pyridine-1-carboxylic acid tert-butyl ester (0.50 g, 1.6 mmol) in dichloromethane (3 mL) was added trifluoroacetic acid (1.2 mL, 16 mmol). The mixture was stirred at room temperature for 2 hours then the volatiles were evaporated. The residue was dissolved in N,N-dimethylformamide (5 mL). Cesium carbonate (0.60 g, 1.8 mmol), sodium iodide (25.0 mg, 0.167 mmol) and 1-chloro-2-methanesulfonyl-ethane (0.26 g, 1.8 mmol) were added. The mixture was heated at 50° C. for 18 hours then cooled to room temperature and water (30 mL) was added. The mixture was extracted with ethyl acetate (3×20 mL). The combined organic layers were washed with water (2×20 mL) and saturated aqueous sodium chloride (20 mL), dried over magnesium sulfate, filtered and evaporated. 1-(2-Methanesulfonyl-ethyl)-4-(3-nitro-phenyl)-1,2,3,6-tetrahydro-pyridine was isolated as an orange viscous oil (0.381 g, 75%). $^1$H NMR (400 MHz, CDCl$_3$, δ, ppm): 8.23 (s, 1H), 8.11 (d, J=8.0 Hz, 1H), 7.70 (d, J=8.0 Hz, 1H), 7.50 (t, J=8.0 Hz, 1H), 6.23 (s, 1H), 3.27 (s, 2H), 3.23 (t, J=6.5 Hz, 2H), 3.07-3.01 (m, 5H), 2.82 (t, J=5.5 Hz, 2H), 2.61 (br s, 2H). MS=311 (MH)+.

203 b) 3-[1-(2-Methanesulfonyl-ethyl)-piperidin-4-yl]-phenylamine was prepared from 1-(2-methanesulfonyl-ethyl)-4-(3-nitro-phenyl)-1,2,3,6-tetrahydro-pyridine (0.38 g, 1.2 mmol) in a manner analogous to Example 111a. Product isolated as a yellow waxy solid (0.34 g, 98%). $^1$H NMR (400 MHz, CDCl$_3$, δ, ppm): 7.09 (t, J=7.4 Hz, 1H), 6.61 (d, J=7.6 Hz, 1H), 6.56-6.52 (m, 2H), 3.62 (br s, 2H), 3.17 (t, J=6.4 Hz, 2H), 3.06 (s, 3H), 3.02 (d, J=10.6 Hz, 2H), 2.90 (t, J=6.3 Hz, 2H), 2.42 (t, J=12.2 Hz, 1H), 2.15 (t, J=11.4 Hz, 2H), 1.85 (d, J=12.8 Hz, 2H), 1.75-1.63 (m, 2H). MS=283 (MH)+.

203 c) {8-[4-(Dimethyl-phosphinoyl)-phenyl]-[1,2,4]triazolo[1,5-a]pyridin-2-yl}-{3-[1-(2-methanesulfonyl-ethyl)-piperidin-4-yl]-phenyl}-amine was prepared from 2-chloro-8-[4-(dimethyl-phosphinoyl)-phenyl]-[1,2,4]triazolo[1,5-a]pyridine (75.0 mg, 0.245 mmol) and 3-[1-(2-methanesulfonyl-ethyl)-piperidin-4-yl]-phenylamine (78.0 mg, 0.276 mmol) with 2,2'-bis-dicyclohexylphosphanyl-biphenyl (21.0 mg, 0.0384 mmol) as the ligand in a manner analogous to Example 2d. Product isolated as an off-white solid (0.078 g, 58%). MP=243-245° C. $^1$H NMR (400 MHz, CDCl$_3$, δ, ppm): 8.47 (d, J=6.9 Hz, 1H), 8.16 (d, J=8.1 Hz, 2H), 7.92-7.85 (m, 2H), 7.64 (d, J=7.3 Hz, 1H), 7.51 (s, 1H), 7.40 (d, J=8.1 Hz, 1H), 7.29 (t, J=7.3 Hz, 1H), 7.01 (t, J=7.1 Hz, 1H), 6.89-6.84 (m, 2H), 3.23 (t, J=6.0 Hz, 2H), 3.11-3.05 (m, 5H), 2.93 (t, J=6.0 Hz, 2H), 2.56 (t, J=12.7 Hz, 1H), 2.21 (t, J=11.6 Hz, 2H), 1.94 (d, J=12.7 Hz, 2H), 1.84-1.71 (m, 8H). MS=552 (MH)+.

Example 204

1-{3-[8-(4-Methanesulfonyl-phenyl)-[1,2,4]triazolo[1,5-a]pyridin-2-ylamino]-phenyl}-4-methyl-piperazin-2-one

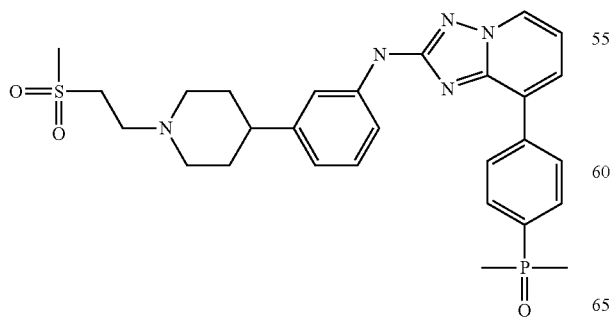

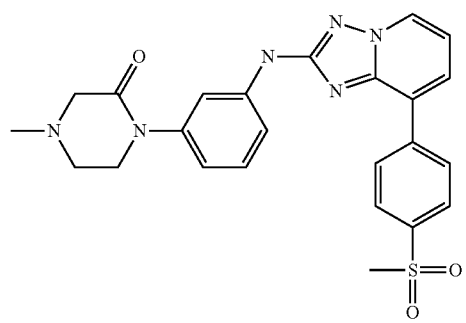

204 a) An oven dried tube was charged with 1-iodo-3-nitrobenzene (2.60 g, 10.4 mmol), 4-methyl-piperazin-2-one (1.00 g, 8.76 mmol), copper(I) iodide (85.0 mg, 0.446 mmol), (1R,2R)—N,N'-dimethyl-cyclohexane-1,2-diamine (0.14 mL, 0.89 mmol), potassium phosphate (3.75 g, 17.7 mmol) and 1,4-dioxane (10 mL). The tube was carefully evacuated and backflushed with nitrogen three times then sealed. The mixture was heated at 90° C. for 24 hours then cooled to room temperature and diluted with dichloromethane (20 mL). The mixture was filtered through a plug of diatomaceous earth and the filtrate was evaporated. The residue was purified via chromatography using an ISCO automated purification apparatus (silica gel column 40 g and 0%→4% methanol:dichloromethane). 4-Methyl-1-(3-nitro-phenyl)-piperazin-2-one was isolated as a red-brown waxy solid (1.13 g, 55%). $^1$H NMR (400 MHz, CDCl$_3$, δ, ppm): 8.20 (s, 1H), 8.13 (d, J=7.5 Hz, 1H), 7.73 (d, J=8.0 Hz, 1H), 7.57 (t, J=8.2 Hz, 1H), 3.79 (t, J=5.1 Hz, 2H), 3.31 (s, 2H), 2.83 (t, J=5.2 Hz, 2H), 2.42 (s, 3H). MS=236 (MH)+.

204 b) 1-(3-Amino-phenyl)-4-methyl-piperazin-2-one was prepared from 4-methyl-1-(3-nitro-phenyl)-piperazin-2-one (1.13 g, 4.80 mmol) in a manner analogous to Example 111a. Product isolated as an orange waxy solid (0.95 g, 96%). $^1$H NMR (400 MHz, CDCl$_3$, δ, ppm): 7.17 (t, J=7.9 Hz, 1H), 6.66-6.57 (m, 3H), 3.71 (br s, 2H), 3.67 (t, J=4.7 Hz, 2H), 3.26 (s, 2H), 2.76 (t, J=4.7 Hz, 2H), 2.40 (s, 3H). MS=206 (MH)+.

204 c) 1-{3-[8-(4-Methanesulfonyl-phenyl)-[1,2,4]triazolo[1,5-a]pyridin-2-ylamino]-phenyl}-4-methyl-piperazin-2-one was prepared from 2-chloro-8-(4-methanesulfonyl-phenyl)-[1,2,4]triazolo[1,5-a]pyridine (100.0 mg, 0.3249 mmol) and 1-(3-amino-phenyl)-4-methyl-piperazin-2-one (75.0 mg, 0.365 mmol) with 2,2'-bis-dicyclohexylphosphanyl-biphenyl (27.0 mg, 0.0494 mmol) as the ligand in a manner analogous to Example 2d. $^1$H NMR (400 MHz, (D$_3$C)$_2$SO, δ, ppm): 9.91 (s, 1H), 8.89 (d, J=6.6 Hz, 1H), 8.44 (d, J=8.2 Hz, 2H), 8.08 (d, J=8.0 Hz, 2H), 7.99 (d, J=7.3 Hz, 1H), 7.86 (s, 1H), 7.51 (d, J=7.9 Hz, 1H), 7.31 (t, J=7.9 Hz, 1H), 7.19 (t, J=7.0 Hz, 1H), 6.85 (d, J=7.7 Hz, 1H), 3.68-3.63 (m, 2H), 3.29 (s, 3H), 3.13 (s, 2H), 2.77-2.72 (m, 2H), 2.31 (s, 3H). MP=234-236° C. MS=477 (MH)+.

Example 205

4-Ethyl-1-{3-[8-(4-methanesulfonyl-phenyl)-[1,2,4]triazolo[1,5-a]pyridin-2-ylamino]-phenyl}-piperazin-2-one

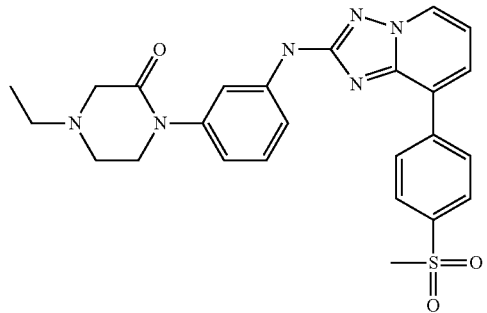 [SMILES: CCN1CCN(c2cccc(Nc3nc4c(-c5ccc(S(C)(=O)=O)cc5)cccn4n3)c2)C(=O)C1]

205 a) 1-(3-nitro-phenyl)-piperazin-2-one was prepared from piperazin-2-one (1.00 g, 9.99 mmol) and 1-iodo-3-nitro-benzene (3.00 g, 12.0 mmol) in a manner analogous to Example 204a. $^1$H NMR (400 MHz, CDCl$_3$, δ, ppm): 8.21 (s, 1H), 8.13 (d, J=8.2 Hz, 1H), 7.74 (d, J=7.8 Hz, 1H), 7.58 (t, J=8.0 Hz, 1H), 3.77 (t, J=4.9 Hz, 2H), 3.74 (s, 2H), 3.28 (t, J=4.8 Hz, 2H). MS=222 (MH)+.

205 b) To a solution of 1-(3-nitro-phenyl)-piperazin-2-one (0.629 g, 2.84 mmol), acetaldehyde (0.20 mL, 3.6 mmol) and acetic acid (0.50 mL, 8.8 mmol) in methanol (10 mL) at room temperature was added solid Sodium cyanoborohydride (0.27 g, 4.3 mmol) in small portions. The mixture was stirred for 18 hours at room temperature. The mixture was evaporated and cold water was slowly added to the residue. The mixture was stirred for 15 minutes and then extracted with dichloromethane (3×20 mL). The combined organic layers were dried over magnesium sulfate, filtered and evaporated. The residue was purified via chromatography using an ISCO automated purification apparatus (silica gel column 40 g and 0%→5% methanol:dichloromethane). 4-Ethyl-1-(3-nitro-phenyl)-piperazin-2-one was isolated as a yellow-orange viscous oil (0.497 g, 70%). $^1$H NMR (400 MHz, CDCl$_3$, δ, ppm): 8.21 (s, 1H), 8.13 (d, J=8.1 Hz, 1H), 7.74 (d, J=7.9 Hz, 1H), 7.57 (t, J=7.8 Hz, 1H), 3.81-3.76 (m, 2H), 3.37-3.33 (m, 2H), 2.89-2.84 (m, 2H), 2.60-2.53 (m, 2H), 1.20-1.14 (m, 3H).

205 c) 1-(3-Amino-phenyl)-4-ethyl-piperazin-2-one was prepared from 4-ethyl-1-(3-nitro-phenyl)-piperazin-2-one (0.497 g, 1.99 mmol) in a manner analogous to Example 111a. $^1$H NMR (400 MHz, CDCl$_3$, δ, ppm): 7.17 (t, J=7.7 Hz, 1H), 6.67-6.57 (m, 3H), 3.71 (br s, 2H), 3.69-3.63 (m, 2H), 3.30 (s, 2H), 2.82-2.77 (m, 2H), 2.53 (q, J=6.8 Hz, 2H), 1.19-1.12 (m, 3H). MS=220 (MH)+.

205 d) 4-Ethyl-1-{3-[8-(4-methanesulfonyl-phenyl)-[1,2,4]triazolo[1,5-a]pyridin-2-ylamino]-phenyl}-piperazin-2-one was prepared from 2-chloro-8-(4-methanesulfonyl-phenyl)-[1,2,4]triazolo[1,5-a]pyridine (100.0 mg, 0.3249 mmol) and 1-(3-amino-phenyl)-4-ethyl-piperazin-2-one (79.0 mg, 0.360 mmol) with 2,2'-bis-dicyclohexylphosphanyl-biphenyl (27.0 mg, 0.0494 mmol) as the ligand in a manner analogous to Example 2d. Product isolated as a yellow solid (0.059 g, 37%). MP=210-212° C. $^1$H NMR (400 MHz, CDCl$_3$, δ, ppm): 8.51 (d, J=6.8 Hz, 1H), 8.24 (d, J=8.0 Hz, 2H), 8.09 (d, J=7.8 Hz, 2H), 7.76 (s, 1H), 7.65 (d, J=6.9 Hz, 1H), 7.42-7.34 (m, 2H), 7.04 (t, J=6.5 Hz. 1H), 6.96-6.92 (m, 2H), 3.80-3.75 (m, 2H), 3.36 (s, 2H), 3.10 (s, 3H), 2.88-2.83 (m, 2H), 2.58 (q, J=7.0 Hz, 2H), 1.18 (t, J=6.4 Hz, 3H). MS=491 (MH)+.

Example 206

[3-(4-Methyl-piperazin-1-yl)-phenyl]-(8-{4-[4-(4-methyl-piperazin-1-yl)-piperidin-1-yl]-phenyl}-[1,2,4]triazolo[1,5-a]pyridin-2-yl)-amine

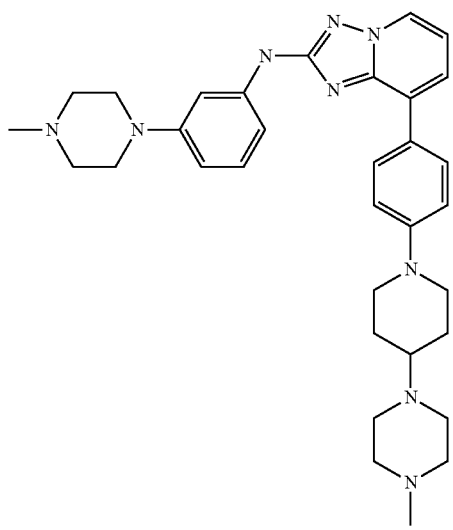 [SMILES: CN1CCN(c2cccc(Nc3nc4c(-c5ccc(N6CCC(N7CCN(C)CC7)CC6)cc5)cccn4n3)c2)CC1]

206 a) 2-Chloro-8-{4-[4-(4-methyl-piperazin-1-yl)-piperidin-1-yl]-phenyl}-[1,2,4]triazolo[1,5-a]pyridine was prepared from 8-(4-bromo-phenyl)-2-chloro-[1,2,4]triazolo[1,5-a]pyridine (100.0 mg, 0.3241 mmol) and 1-methyl-4-piperidin-4-yl-piperazine (66.0 mg, 0.360 mmol) in a manner analogous to Example 2d. Product isolated as a pale yellow solid (0.023 g, 17%). $^1$H NMR (400 MHz, CDCl$_3$, δ, ppm): 8.40 (d, J=6.7 Hz, 1H), 7.93 (d, J=8.0 Hz, 2H), 7.64 (d, J=7.4 Hz, 1H), 7.10 (t, J=6.8 Hz, 1H), 7.03 (d, J=8.3 Hz, 2H), 3.87 (d, J=12.5 Hz, 2H), 2.82 (t, J=12.6 Hz, 2H), 2.70-2.35 (m, 9H), 2.30 (s, 3H), 1.95 (d, J=11.9 Hz, 2H), 1.75-1.60 (m, 2H). MS=411 (MH)+.

206 b) [3-(4-Methyl-piperazin-1-yl)-phenyl]-(8-{4-[4-(4-methyl-piperazin-1-yl)-piperidin-1-yl]-phenyl}-[1,2,4]triazolo[1,5-a]pyridin-2-yl)-amine was prepared from 2-chloro-8-{4-[4-(4-methyl-piperazin-1-yl)-piperidin-1-yl]-phenyl}-[1,2,4]triazolo[1,5-a]pyridine (23.0 mg, 0.0560 mmol) and 3-(4-methylpiperazin-1-yl)aniline (12.0 mg, 0.0627 mmol) with 2,2'-bis-dicyclohexylphosphanyl-biphenyl (5.0 mg, 0.0091 mmol) as the ligand in a manner analogous to Example 2d. Product isolated as a yellow solid (0.014 g, 44%). MP=222-225° C. $^1$H NMR (400 MHz, CDCl$_3$, δ, ppm): 8.33 (d, J=6.6 Hz, 1H), 7.96 (d, J=8.3 Hz, 2H), 7.52 (d, J=7.7 Hz, 1H), 7.48 (s, 1H), 7.21 (t, J=7.6 Hz, 1H), 7.03 (d, J=7.9 Hz, 2H), 6.95-6.89 (m, 2H), 6.82 (s, 1H), 6.57 (d, J=8.4 Hz, 1H), 3.86 (d, J=13.2 Hz, 2H), 3.31-3.26 (m, 4H), 2.81 (t, J=12.2 Hz, 2H), 2.70-2.38 (m, 13H), 2.37 (s, 3H), 2.30 (s, 3H), 1.94 (d, J=11.6 Hz, 2H), 1.75-1.63 (m, 2H). MS=566 (MH)+.

Example 207

1-(3-{8-[4-(Dimethyl-phosphinoyl)-phenyl]-[1,2,4]triazolo[1,5-a]pyridin-2-ylamino}-phenyl)-4-methyl-piperazin-2-one

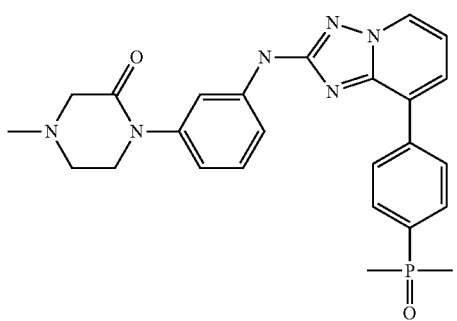

1-(3-{8-[4-(Dimethyl-phosphinoyl)-phenyl]-[1,2,4]triazolo[1,5-a]pyridin-2-ylamino}-phenyl)-4-methyl-piperazin-2-one was prepared from 2-chloro-8-[4-(dimethyl-phosphinoyl)-phenyl]-[1,2,4]triazolo[1,5-a]pyridine (100.0 mg, 0.3271 mmol) and 1-(3-amino-phenyl)-4-methyl-piperazin-2-one (75.0 mg, 0.365 mmol) with 2,2'-bis-dicyclohexylphosphanyl-biphenyl (28.0 mg, 0.0512 mmol) as the ligand in a manner analogous to Example 2d. Product isolated as a pale yellow solid (0.076 g, 49%). MP=208-211° C. $^1$H NMR (400 MHz, CDCl$_3$, δ, ppm): 8.48 (d, J=6.8 Hz, 1H), 8.14 (d, J=7.8 Hz, 2H), 7.92-7.85 (m, 2H), 7.69 (s, 1H), 7.64 (d, J=7.3 Hz, 1H), 7.43 (d, J=8.1 Hz, 1H), 7.37 (t, J=7.9 Hz, 1H), 7.01 (t, J=7.1 Hz, 1H), 6.97-6.90 (m, 2H), 3.80-3.75 (m, 2H), 3.32 (s, 2H), 2.85-2.80 (m, 2H), 2.43 (s, 3H), 1.80 (s, 3H), 1.77 (s, 3H). MS=475 (MH)+.

Example 208

1-(3-{8-[4-(Dimethyl-phosphinoyl)-phenyl]-[1,2,4]triazolo[1,5-a]pyridin-2-ylamino}-phenyl)-4-ethyl-piperazin-2-one

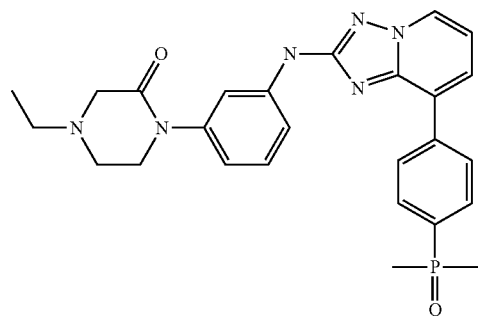 [SMILES: CCN1CCN(c2cccc(Nc3nc4c(-c5ccc(P(C)(C)=O)cc5)cccn4n3)c2)C(=O)C1]

1-(3-{8-[4-(Dimethyl-phosphinoyl)-phenyl]-[1,2,4]triazolo[1,5-a]pyridin-2-ylamino}-phenyl)-4-ethyl-piperazin-2-one was prepared from 2-chloro-8-[4-(dimethyl-phosphinoyl)-phenyl]-[1,2,4]triazolo[1,5-a]pyridine (100.0 mg, 0.3271 mmol) and 1-(3-amino-phenyl)-4-ethyl-piperazin-2-one (79.0 mg, 0.360 mmol) with 2,2'-bis-dicyclohexylphosphanyl-biphenyl (28.0 mg, 0.0512 mmol) as the ligand in a manner analogous to Example 2d. MP=205-207° C. $^1$H NMR (400 MHz, CDCl$_3$, δ, ppm): 8.48 (d, J=6.6 Hz, 1H), 8.13 (d, J=7.9 Hz, 2H), 7.92-7.85 (m, 2H), 7.68 (s, 1H), 7.63 (d, J=7.2 Hz, 1H), 7.44 (d, J=8.0 Hz, 1H), 7.37 (t, J=8.2 Hz, 1H), 7.04-6.97 (m, 2H), 6.93 (d, J=7.5 Hz, 1H), 3.80-3.75 (m, 2H), 3.35 (s, 2H), 2.88-2.83 (m, 2H), 2.57 (q, J=7.0 Hz, 2H), 1.80 (s, 3H), 1.77 (s, 3H), 1.18 (t, J=7.0 Hz, 3H). MS=489 (MH)+.

Example 209

(1-Ethyl-1H-pyrazol-4-yl)-[8-(4-methanesulfonyl-phenyl)-[1,2,4]triazolo[1,5-a]pyridin-2-yl]-amine

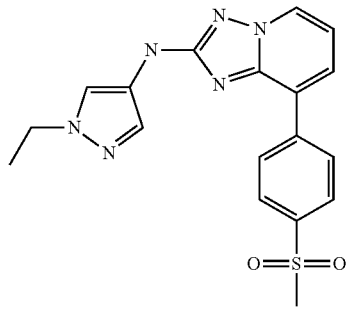 [SMILES: CCn1cc(Nc2nc3c(-c4ccc(S(C)(=O)=O)cc4)cccn3n2)cn1]

(1-Ethyl-1H-pyrazol-4-yl)-[8-(4-methanesulfonyl-phenyl)-[1,2,4]triazolo[1,5-a]pyridin-2-yl]-amine was prepared from 2-chloro-8-(4-methanesulfonyl-phenyl)-[1,2,4]triazolo[1,5-a]pyridine (0.125 g, 0.406 mmol) and 1-ethyl-1H-pyrazol-4-ylamine (0.058 g, 0.52 mmol) with 2,2-bis-dicyclohexylphosphanyl-biphenyl (0.048 g, 0.088 mmol) as the ligand in a manner analogous to Example 2d. Product was isolated as a tan solid (0.09 g, 58%). MP=201-203° C. ¹H NMR (400 MHz, (D₃C)₂SO, δ, ppm): 9.37 (s, 1H), 8.78 (d, J=6.48 Hz, 1H), 8.42 (d, J=8.05 Hz, 2H), 8.06 (d, J=8.09 Hz, 2H), 7.94 (d, J=7.21 Hz, 1H), 7.82 (s, 1H), 7.48 (s, 1H), 7.12 (t, J=7.08 Hz, 2H), 4.10 (q, J=7.08 Hz, 2H), 3.29 (s, 3H), 1.37 (t, J=7.16 Hz, 3H). MS=383 (MH)+.

Example 210

[8-(4-Methanesulfonyl-phenyl)-[1,2,4]triazolo[1,5-a]pyridin-2-yl]-(1,3,5-trimethyl-1H-pyrazol-4-yl)-amine

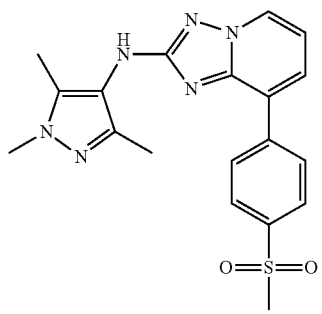 [SMILES: Cc1nn(C)c(C)c1Nc1nc2c(-c3ccc(S(C)(=O)=O)cc3)cccn2n1]

[8-(4-Methanesulfonyl-phenyl)-[1,2,4]triazolo[1,5-a]pyridin-2-yl]-(1,3,5-trimethyl-1H-pyrazol-4-yl)-amine was prepared from 2-chloro-8-(4-methanesulfonyl-phenyl)-[1,2,4]triazolo[1,5-a]pyridine (0.200 g, 0.65 mmol) and 1,3,5-trimethyl-1H-pyrazol-4-ylamine (0.106 g, 0.845 mmol) with 2,2-bis-dicyclohexylphosphanyl-biphenyl (0.048 g, 0.088 mmol) as the ligand in a manner analogous to Example 2d. Product was isolated as an orange solid (0.157 g, 61%). MP=194-196° C. ¹H NMR (400 MHz, (D₃C)₂SO, δ, ppm): 8.65 (d, J=6.56 Hz, 1H), 8.37 (d, J=7.50 Hz, 2H), 8.13 (s, 1H), 8.04 (d, J=7.52 Hz, 2H), 7.86 (d, J=7.47 Hz, 1H), 7.04 (t, J=7.26 Hz, 1H), 3.65 (s, 3H), 3.27 (s, 3H), 2.09 (s, 3H, 1.99 (s, 3H). MS=397 (MH)+.

Example 211

(1-Ethyl-1H-pyrazol-4-yl)-[8-(4-methanesulfonyl-phenoxy)-[1,2,4]triazolo[1,5-a]pyridin-2-yl]-amine

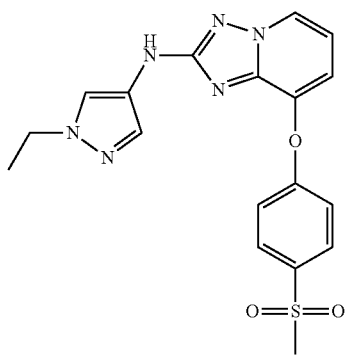 [SMILES: CCn1cc(Nc2nc3c(Oc4ccc(S(C)(=O)=O)cc4)cccn3n2)cn1]

211a) A well stirred mixture of 2-amino-[1,2,4]triazolo[1,5-a]pyridine-8-ol (0.300 g, 2.00 mmol), 1-fluoro-4-methanesulfonyl-benzene (0.418 g, 2.40 mmol), N,N-dimethylacetamide (2 mL) and potassium tert-butoxide (0.448 g, 4.00 mmol) was heated at 130° C. for 18 h under an argon atmosphere. The reaction mixture was evaporated in vacuo and partitioned between dichloromethane and saturated aqueous sodium bicarbonate solution. The aqueous phase was extracted twice with dichloromethane and the combined organic layers were washed with brine, dried over sodium sulfate, filtered, and evaporated in vacuo to furnish a crude product. The crude product was purified by preparative Gilson HPLC method to yield a pure product, which was triturated from a mixture of dichloromethane, methanol, ether and hexane. 8-(4-Methanesulfonyl-phenoxy)-[1,2,4-triazolo[1,5-a]pyridin-2-ylamine was isolated as a white solid (125 mg, 20%). MP=245-247° C. ¹H NMR (400 MHz, (D₃C)₂SO, δ, ppm): 8.53 (d, J=6.56 Hz, 1H), 7.87 (d, J=8.77 Hz, 2H), 7.36 (d, J=7.73 Hz, 1H), 7.15 (d, J=8.76 Hz, 2H), 6.92 (t, J=7.28 Hz, 1H), 6.13 (s, 1H), 3.19 (s, 3H). MS=305 (MH)+.

211b) 2-Chloro-8-(4-methanesulfonyl-phenoxy)-[1,2,4]triazolo[1,5-a]pyridine was prepared in a manner analogous to Example 68a. Product was isolated as a yellow solid (0.455 g, 80%). MP=202-204° C. ¹H NMR (400 MHz, (D₃C)₂SO, δ, ppm): 8.44 (d, J=6.77 Hz, 1H), 7.98 (d, J=8.08 Hz, 2H), 7.21 (t, J=7.76 Hz, 3H), 7.08 (t, J=7.52 Hz, 1H), 3.09 (s, 3H). MS=324 (MH)+.

211c) (1-Ethyl-1H-pyrazol-4-yl)-[8-(4-methanesulfonyl-phenoxy)-[1,2,4]triazolo[1,5-a]pyridin-2-yl]-amine was prepared from 2-chloro-8-(4-methanesulfonyl-phenoxy)-[1,2,4]triazolo[1,5-a]pyridine (0.065 g, 0.20 mmol) and 1-ethyl-1H-pyrazol-4-ylamine (0.029 g, 0.26 mmol) in a manner analogous to Example 2d. Product was isolated as a tan solid (45 mg, 56%). MP=183-185° C. ¹H NMR (400 MHz, (D₃C)₂SO, δ, ppm): 9.27 (s, 1H), 8.67 (d, J=6.51 Hz, 1H), 7.89 (d, J=7.72 Hz, 2H), 7.68 (s, 1H), 7.45 (d, J=7.74 Hz, 1H), 7.35 (s, 1H), 7.22 (d, J=7.29 Hz, 2H), 7.00 (t, J=7.29 Hz, 1H), 4.055 (q, J=7.18 Hz, 2H), 3.20 (s, 3H), 1.32 (t, J=7.06 Hz, 3H). MS=399 (MH)+.

Example 212

4-{4-[8-(4-Methanesulfonyl-phenyl)-[1,2,4]triazolo[1,5-a]pyridin-2-ylamino]-pyrazol-1-yl}-piperidin-1-carboxylic acid tert-butyl ester

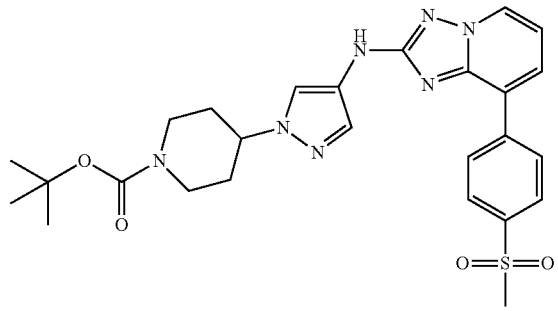 [SMILES: CC(C)(C)OC(=O)N1CCC(n2cc(Nc3nc4c(-c5ccc(S(C)(=O)=O)cc5)cccn4n3)cn2)CC1]

4-{4-[8-(4-Methanesulfonyl-phenyl)-[1,2,4]triazolo[1,5-a]pyridine-2-ylamino]-pyrazol-1-yl}-piperidin-1-carboxylic acid tert-butyl ester was prepared from 2-chloro-8-(4-methanesulfonyl-phenyl)-[1,2,4]triazolo[1,5-a]pyridine (0.150 g, 0.48 mmol) and 4-(4-amino-pyrazol-1-yl)-piperidine-1-carboxylic acid tert-butyl ester (0.168 g, 0.63 mmol) with 2,2-bis-dicyclohexylphosphanyl-biphenyl (0.048 g, 0.088 mmol) as the ligand in a manner analogous to Example 2d. Product was isolated as a tan solid (0.134 g, 51%). MP=Softened at 161-166° C. then melted at 207-209° C. $^1$H NMR (400 MHz, (D$_3$C)$_2$SO, δ, ppm): 9.37 (s, 1H), 8.78 (d, J=6.52 Hz, 1H), 8.42 (d, J=8.00 Hz, 2H), 8.06 (d, J=7.89 Hz, 2H), 7.94 (d, J=7.45 Hz, 1H), 7.85 (s, 1H), 7.52 (s, 1H), 7.12 (t, J=6.89 Hz, 1H), 4.32 (s, 1H), 4.04 (d, J=11.40 Hz, 2H), 3.28 (s, 3H), 2.91 (s, 2H), 2.005 (d, J=11.77 Hz, 2H), 1.76 (q, J=12.21 Hz, 2H), 1.42 (s, 9H). MS=538 (MH)+.

Example 213

[8-(4-Methanesulfonyl-phenyl)-[1,2,4]triazolo[1,5-a]pyridin-2-yl]-(1-piperidin-4-yl-1H-pyrazol-4-yl)-amine

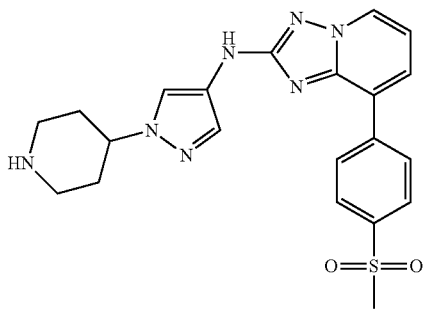 [SMILES: CS(=O)(=O)c1ccc(-c2cccn3nc(Nc4cnn(C5CCNCC5)c4)nc23)cc1]

To a well stirred solution of 4-{4-[8-(4-Methanesulfonyl-phenyl)-[1,2,4]triazolo[1,5-a]pyridin-2-ylamino]-pyrazol-1-yl}-piperidin-1-carboxylic acid tert-butyl ester (100 mg, 0.186 mmol) in dichloromethane (5 mL) was added trifluoroacetic acid (0.65 mL, 8.77 mmol) dropwise at room temperature. After 1 h, the reaction mixture was evaporated in vacuo and partitioned between dichloromethane and saturated aqueous sodium bicarbonate solution. The organic layer was separated and the aqueous layer was extracted twice with dichloromethane. The combined organic layers were washed with brine, dried over sodium sulfate, filtered, and evaporated. The crude product was crystallized from a mixture of dichloromethane, methanol, ether and hexane. [8-(4-Methanesulfonyl-phenyl)-[1,2,4]triazolo[1,5-a]pyridin-2-yl]-(1-piperidin-4-yl-1H-pyrazol-4-yl)-amine was isolated as a greenish-yellow solid (58 mg, 71%). MP=Softened at 154-159° C. then melted at 211-213° C. $^1$H NMR (400 MHz, (D$_3$C)$_2$SO, δ, ppm): 9.37 (s, 1H), 8.79 (d, J=6.48 Hz, 1H), 8.42 (d, J=7.96 Hz, 2H), 8.06 (d, J=7.97 Hz, 2H), 7.94 (d, J=7.45 Hz, 1H), 7.83 (s, 1H), 7.49 (s, 1H), 7.12 (t, J=7.04 Hz, 1H), 4.14 (t, J=11.29 Hz, 1H), 3.29 (s, 3H), 3.035 (d, J=12.28 Hz, 2H), 2.58 (t, J=12.16 Hz, 2H), 1.935 (d, J=11.41 Hz), 1.68-182 (m, 2H). MS=438 (MH)+.

Example 214

[8-(4-Methanesulfonyl-phenoxy)-[1,2,4]triazolo[1,5-a]pyridin-2-yl]-[3-(4-methyl-piperazin-1-yl)-phenyl]-amine

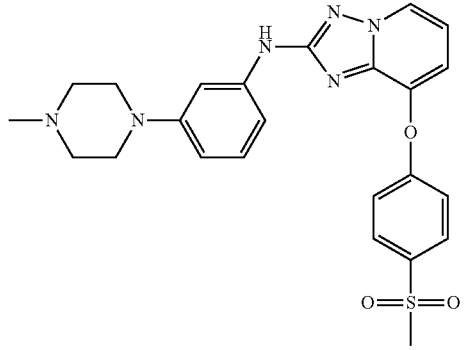 [SMILES: CN1CCN(c2cccc(Nc3nc4c(Oc5ccc(S(C)(=O)=O)cc5)cccn4n3)c2)CC1]

[8-(4-Methanesulfonyl-phenoxy)-[1,2,4]triazolo[1,5-a]pyridin-2-yl]-[3-(4-methyl-piperazin-1-yl)-phenyl]-amine was prepared from 2-chloro-8-(4-methanesulfonyl-phenoxy)-[1,2,4]triazolo[1,5-a]pyridine (0.070 g, 0.21 mmol) and 3-(4-methylpiperazin-1-yl)aniline (0.056 g, 0.29 mmol) in a manner analogous to Example 2d. Product was isolated as a tan solid (56 mg, 54%). MP=Softened at 114-119° C. then melted at 199-201° C. $^1$H NMR (400 MHz, (D$_3$C)$_2$SO, δ, ppm): 9.55 (s, 1H), 8.76 (d, J=6.56 Hz, 1H), 7.89 (d, J=8.00 Hz, 2H), 7.50 (d, J=7.69 Hz, 1H), 7.26 (s, 1H), 7.21 (d, J=8.04 Hz, 2H), 7.10-7.11 (m, 3H), 6.46 (d, J=6.60 Hz, 1H), 3.20 (s, 3H), 3.04 (s, 4H), 2.42 (s, 4H), 2.22 (s, 3H). MS=479 (MH)+.

Example 215

(1-Ethyl-1H-pyrazol-4-yl)-[8-(4-trifluoromethyl-phenyl)-[1,2,4]triazolo[1,5-a]pyridin-2-yl]-amine

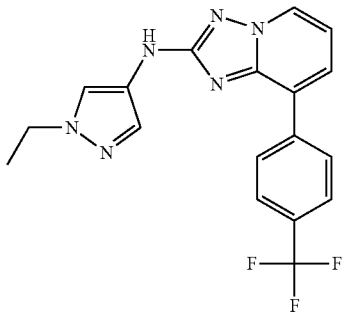 [SMILES: CCn1cc(Nc2nc3c(-c4ccc(C(F)(F)F)cc4)cccn3n2)cn1]

215a) 2-Chloro-8-(4-trifluoromethyl-phenyl)-[1,2,4]triazolo[1,5-a]pyridine was prepared from 8-bromo-2-chloro-[1,2,4-triazolo[1,5-a]pyridine (1.23 g, 5.29 mmol) and (4-trifluoromethyl-phenyl)boronic acid (1.23 g, 6.50 mmol) in a manner analogous to Example 2c. Product was isolated as a white solid (0.95 g, 62%). MP=163-165° C. $^1$H NMR (400 MHz, CDCl$_3$, δ, ppm): 8.65 (d, J=6.77 Hz, 1H), 8.12 (d, J=8.09 Hz, 2H), 7.80 (d, J=8.17 Hz, 2H), 7.77 (d, J=8.40 Hz, 1H), 7.22 (t, J=7.12 Hz, 1H). MS=298 (MH)+.

215b) (1-Ethyl-1H-pyrazol-4-yl)-[8-(4-trifluoromethyl-phenyl)-[1,2,4]triazolo[1,5-a]pyridin-2-yl]-amine was prepared from 2-chloro-8-(4-trifluoromethyl-phenyl)-[1,2,4]triazolo[1,5-a]pyridine (0.100 g, 0.31 mmol) and 1-ethyl-1H-pyrazol-4-ylamine (0.046 g, 0.41 mmol) in a manner analogous to Example 2d. Product was isolated as a tan solid (52 mg, 44%). MP=162-164° C. $^1$H NMR (400 MHz, (D$_3$C)$_2$SO, δ, ppm): 9.37 (s, 1H), 8.77 (d, J=6.36 Hz, 1H), 8.38 (d, J=7.76 Hz, 2H), 7.85-7.97 (m, 3H), 7.81 (s, 1H), 7.47 (s, 1H), 7.11 (t, J=6.80 Hz, 1H), 4.10 (q, J=7.12 Hz, 2H), 1.36 (t, J=6.92 Hz, 3H). MS=373 (MH)+.

Example 216

[1-(2-Pyrrolidin-1-yl-ethyl)-1H-pyrazol-4-yl]-[8-(4-trifluoromethyl-phenyl)-[1,2,4]triazolo[1,5-a]pyridin-2-yl]-amine

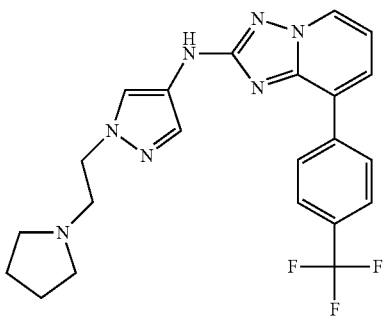 [SMILES: FC(F)(F)c1ccc(-c2cccn3nc(Nc4cnn(CCN5CCCC5)c4)nc23)cc1]

[1-(2-Pyrrolidin-1-yl-ethyl)-1H-pyrazol-4-yl]-[8-(4-trifluoromethyl-phenyl)-[1,2,4]triazolo[1,5-a]pyridin-2-yl]-amine was prepared from 2-chloro-8-(4-trifluoromethyl-phenyl)-[1,2,4]triazolo[1,5-a]pyridine (0.100 g, 0.33 mmol) and 1-(2-pyrrolidin-1-yl-ethyl)-1H-pyrazol-4-ylamine (0.078 g, 0.43 mmol) in a manner analogous to Example 2d. Product was isolated as a tan solid (78 mg, 52%). MP=205-207° C. $^1$H NMR (400 MHz, (D$_3$C)$_2$SO, δ, ppm): 9.35 (s, 1H), 8.76 (d, J=6.44 Hz, 1H), 8.38 (d, J=8.00 Hz, 2H), 7.08-7.93 (m, 3H), 7.84 (s, 1H), 7.47 (s, 1H), 7.11 (t, J=7.08 Hz, 1H), 4.17 (t, J=6.37 Hz, 2H), 2.80 (t, J=6.24 Hz, 2H), 2.45 (s, 4H), 1.64 (s, 4H). MS=442 (MH)+.

Example 217

[8-(4-Methanesulfonyl-phenoxy)-[1,2,4]triazolo[1,5-a]pyridin-2-yl]-(1-(2-pyrrolidin-1-yl-ethyl)-1H-pyrazol-4-yl]-amine

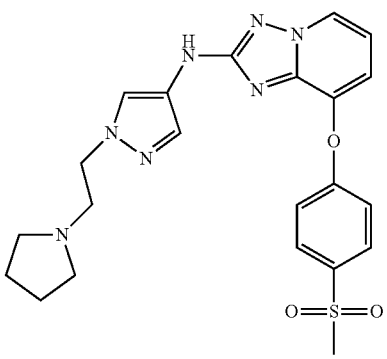 [SMILES: CS(=O)(=O)c1ccc(Oc2cccn3nc(Nc4cnn(CCN5CCCC5)c4)nc23)cc1]

[8-(4-Methanesulfonyl-phenoxy)-[1,2,4]triazolo[1,5-a]pyridin-2-yl]-(1-(2-pyrrolidin-1-yl-ethyl)-1H-pyrazol-4-yl]-amine was synthesized from 2-chloro-8-(4-methanesulfonyl-phenoxy)-[1,2,4]triazolo[1,5-a]pyridine (0.100 g, 0.309 mmol) and 1-(2-pyrrolidin-1-yl-ethyl)-1H-pyrazol-4-ylamine (0.072 g, 0.402 mmol) in a manner analogous to Example 2d. The isolated pure product was treated with 2N hydrogen chloride in dioxane. [8-(4-Methanesulfonyl-phenyl)-[1,2,4]triazolo[1,5-a]pyridin-2-yl]-(1-(2-pyrrolidin-1-yl-ethyl)-1H-pyrazol-4-yl]-amine hydrochloric acid salt was isolated as a tan solid (81 mg, 56%). MP=Softened at 146-149° C. then melted at 215-217° C. $^1$H NMR (400 MHz, (D$_3$C)$_2$SO, δ, ppm): 10.55 (brs, 1H), 9.45 (s, 1H), 8.66 (d, J=6.26 Hz, 1H), 7.89 (d, J=8.13 Hz, 2H), 7.82 (s, 1H), 7.48 (s, 2H), 7.46 (s, 1H), 7.22 (d, J=8.23 Hz, 2H), 7.02 (t, J=6.93 Hz, 1H), 4.48 (brs, 2H), 4.18 (brs, 3H), 3.585 (d, J=4.90 Hz, 2H), 3.43 (brs, 2H), 2.92 (brs, 2H), 1.95 (brs, 2H), 1.82 (brs, 2H). MS=468 (MH)+.

Example 219

[8-(4-Methanesulfonyl-phenyl)-[1,2,4]triazolo[1,5-a]pyridin-2-yl]-(1-(2-pyrrolidin-1-yl-ethyl)-1H-pyrazol-4-yl]-amine

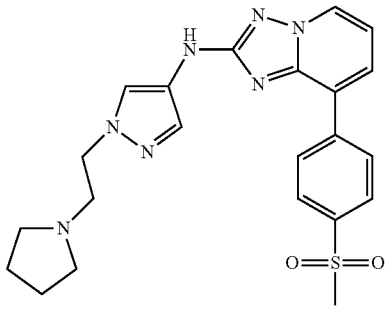 [SMILES: CS(=O)(=O)c1ccc(-c2cccn3nc(Nc4cnn(CCN5CCCC5)c4)nc23)cc1]

219a) A mixture of 4-nitro-1H-pyrazole (5.00 g, 44.22 mmol), 1-(2-chloro-ethyl)-pyrrolidine hydrochloride (8.86 g, 52.42 mmol), acetonitrile (50 mL) and potassium carbonate (19.00 g, 137.50 mmol) was heated at 80° C. under an argon atmosphere for 16 hours. The reaction mixture was evaporated in vacuo and partitioned between water and dichloromethane. The aqueous phase was extracted twice with dichloromethane and the combined organic layers were washed with brine, dried over sodium sulfate, filtered and concentrated. 4-Nitro-1-(2-pyrrolidin-1-yl-ethyl)-1H-pyrazole was isolated as an orange solid (8.50 g, 91%). MP=39-41° C. $^1$H NMR (400 MHz, CDCl$_3$, δ, ppm): 8.29 (s, 1H), 8.06 (s, 1H), 4.27 (t, J=6.22 Hz, 2H), 2.95 (t, J=6.17 Hz, 2H), 2.55 (s, 4H), 1.80 (s, 4H). MS=211 (MH)+.

219b) A mixture of 4-nitro-1-(2-pyrrolidin-1-yl-ethyl)-1H-pyrazole (4.40 g, 20.9 mmol), ethanol (100 mL) and 10% palladium on carbon (0.41 g, 30.7 mmol) was hydrogenated in a Paar shaker at 30 psi under hydrogen for 2 h. The reaction mixture was filtered over diatomaceous earth and the filtrate was evaporated in vacuo. 1-(2-Pyrrolidin-1-yl-ethyl)-1H-pyrazol-4-ylamine was isolated as an orange oil, which became a dark gummy material upon standing at room temperature (3.10 g, 82%). $^1$H NMR (400 MHz, CDCl$_3$, δ, ppm): 7.15 (s, 1H), 7.08 (s, 1H), 4.14 (t, J=7.00 Hz, 2H), 2.88 (t, J=6.97 Hz, 4H), 2.52 (s, 4H), 1.765 (s, 4H). MS=181 (MH)+.

219 c) [8-(4-Methanesulfonyl-phenyl)-[1,2,4]triazolo[1,5-a]pyridin-2-yl]-(1-(2-pyrrolidin-1-yl-ethyl)-1H-pyrazol-4-yl]-amine was synthesized from 2-chloro-8-(4-methanesulfonyl-phenyl)-[1,2,4]triazolo[1,5-a]pyridine (0.150 g, 0.487 mmol) and 1-(2-pyrrolidin-1-yl-ethyl)-1H-pyrazol-4-ylamine (0.105 g, 0.585 mmol) with 2,2-bis-dicyclohexylphosphanyl-biphenyl (0.048 g, 0.088 mmol) as the ligand in a manner analogous to Example 2d. The isolated pure product was treated with 2N hydrogen chloride in dioxane. [8-(4-Methanesulfonyl-phenyl)-[1,2,4]triazolo[1,5-a]pyridin-2-yl]-(1-(2-pyrrolidin-1-yl-ethyl)-1H-pyrazol-4-yl]-amine hydrochloride was isolated as a light green solid (70 mg, 30%). MP=Softened at 155-161° C. then melted at 234-236° C. $^1$H NMR (400 MHz, (D$_3$C)$_2$SO, δ, ppm): 10.47 (s, 1H), 9.57 (s, 1H), 8.80 (d, J=6.44 Hz, 1H), 8.45 (d, J=8.20 Hz, 2H), 8.105 (d, J=8.20 Hz, 2H), 7.99 (d, J=7.09 Hz, 1H), 7.98 (s, 1H), 7.63 (s, 1H), 7.17 (t, J=6.88 Hz, 1H), 4.55 (t, J=5.88 Hz, 2H), 3.655 (d, J=5.44 Hz, 2H), 3.48 (brs, 2H), 3.32 (s, 3H), 2.99 (brs, 2H), 2.00 (brs, 2H), 1.86 (brs, 2H). MS=452 (MH)+.

Example 223

Synthesis of 2-(-Trifluoromethyl-phenylamino)-[1,2,4]triazolo[1,5-a]pyridine-8-ol

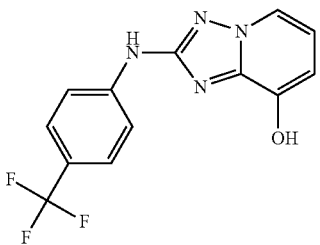 [SMILES: Oc1cccn2nc(Nc3ccc(C(F)(F)F)cc3)nc12]

2-(-Trifluoromethyl-phenylamino)-[1,2,4]triazolo[1,5-a]pyridine-8-ol was isolated as a byproduct from the Example 224a. Product was isolated as an off-white solid (50 mg, 5%). MP=274-276° C. $^1$H NMR (400 MHz, (D$_3$C)$_2$SO, δ, ppm): 10.65 (br s, 1H), 10.03 (s, 1H), 8.29 (br s, 1H), 7.86 (d, J=8.49 Hz, 2H), 7.625 (d, J=8.57 Hz, 2H), 6.82-6.92 (m, 2H). MS=295 (MH)+.

Example 226

7-[5-(2-Methoxymethyl-phenyl)-[1,2,4]triazolo[1,5-a]pyridin-2-ylamino]-1,2,4,5-tetrahydro-benzo[d]azepine-3-carboxylic acid tert-butyl ester

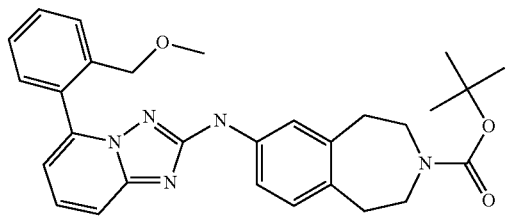 [SMILES: COCc1ccccc1-c1cccc2nc(Nc3ccc4c(c3)CCN(C(=O)OC(C)(C)C)CC4)nn12]

226 a) 2-Chloro-5-(2-methoxymethyl-phenyl)-[1,2,4]triazolo[1,5-a]pyridine was prepared from 8-bromo-2-chloro-[1,2,4]triazolo[1,5-a]pyridine (546.0 mg, 2.35 mmol) and 2-(methoxymethyl)phenylboronic acid (545.0 mg, 3.29 mmol) in a manner analogous to Example 2c. Product was isolated as a white solid (0.384 g, 60%). $^1$H NMR (400 MHz, CDCl$_3$, δ, ppm): 7.72-7.41 (m, 6H), 7.09-7.05 (m, 1H), 4.30 (br s, 2H), 3.16 (s, 3H). MS=274 (MH)+.

226 b) N7-[5-(2-Methoxymethyl-phenyl)-[1,2,4]triazolo[1,5-a]pyridin-2-ylamino]-1,2,4,5-tetrahydro-3-benzazepine-3-carboxylic acid tert-butyl ester was prepared from 2-chloro-5-(2-methoxymethyl-phenyl)-[1,2,4]triazolo[1,5-a]pyridine (365.0 mg, 1.33 mmol) and 7-amino-1,2,4,5-tetrahydro-3-benzazepine-3-carboxylic acid tert-butyl ester (350.0 mg, 1.33 mmol) with 2,2'-bis-dicyclohexylphosphanyl-biphenyl (226.0 mg, 0.41 mmol) as the ligand in a manner analogous to Example 2d. Product isolated as a white foam (0.115 g, 17%). $^1$H NMR (400 MHz, CDCl$_3$, δ, ppm): 7.64 (d, J=7.7 Hz, 1H), 7.59-7.42 (m, 5H), 7.39-7.13 (m, 3H), 7.00 (d, J=7.5 Hz, 1H), 6.92-6.88 (m, 1H), 4.35 (br s, 2H), 3.57-3.47 (m, 4H), 3.20 (s, 3H), 2.85-2.78 (m, 4H), 1.49 (s, 9H). MS=500, 501 (MH)+.

Example 227

1,1'-[1,2,4]triazolo[1,5-a]pyridine-2,5-diyldi-1,2,3,4-tetrahydroquinoline

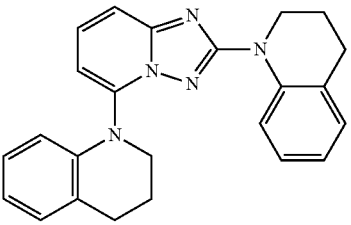 [SMILES: c1ccc2c(c1)CCCN2c1nc2cccc(N3CCCc4ccccc43)n2n1]

1,1'-[1,2,4]triazolo[1,5-a]pyridine-2,5-diyldi-1,2,3,4-tetrahydroquinoline was prepared from 8-bromo-2-chloro-[1,2,4]triazolo[1,5-a]pyridine (500.0 mg, 2.15 mmol) and 1,2,3,4-tetrahydro-quinoline (274.0 mg, 2.04 mmol) in a manner analogous to Example 2d. Byproduct was isolated as a brown solid (0.033 g, 4%). $^1$H NMR (400 MHz, CDCl$_3$, δ, ppm): 8.14 (d, J=8.2 Hz, 1H), 7.40-7.35 (m, 1H), 7.32-7.28 (m, 1H), 7.15-7.05 (m, 3H), 6.98 (t, J=7.5 Hz, 1H), 6.91-6.84 (m, 2H), 6.69-6.62 (m, 2H), 4.09-4.05 (m, 2H), 3.88-3.83 (m, 2H), 2.93 (t, J=6.4 Hz, 2H), 2.82 (t, J=6.4 Hz, 2H), 2.10-1.80 (m, 4H). MS=382 (MH)+.

Example 228

[5-(2-Methoxymethyl-phenyl)-[1,2,4]triazolo[1,5-a]pyridin-2-yl]-(2,3,4,5-tetrahydro-1H-benzo[d]azepin-7-yl)-amine

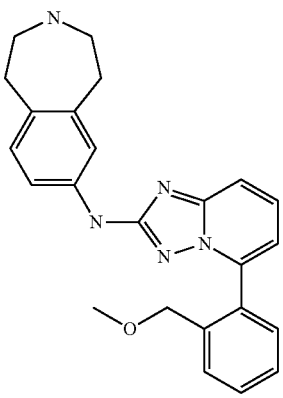 [SMILES: COCc1ccccc1-c1cccc2nc(Nc3ccc4c(c3)CCNCC4)nn12]

7-[5-(2-Methoxymethyl-phenyl)-[1,2,4]triazolo[1,5-a]pyridin-2-ylamino]-1,2,4,5-tetrahydro-benzo[d]azepine-3-carboxylic acid tert-butyl ester (105.0 mg, 0.210 mmol) was stirred in 3M trifluoroacetic acid in dichloromethane (10 mL) for 30 minutes. The volatiles were evaporated and the residue was dissolved in ethyl acetate and washed with sodium carbonate solution (2×) and brine. The organic layer was dried over sodium sulfate, filtered and concentrated. Product isolated as a foam (0.079 g, 89%). $^1$H NMR (400 MHz, CDCl$_3$, δ, ppm): 7.64 (d, J=7.7 Hz, 1H), 7.58-7.41 (m, 5H), 7.25-7.21 (m, 1H), 7.16-7.04 (m, 1H), 6.99 (d, J=8.0 Hz, 1H), 6.91-6.87 (m, 1H), 4.35 (br s, 2H), 3.20 (s, 3H), 2.98-2.81 (m, 8H), 2.02 (br s, 1H). MS=400 (MH)+.

Example 229

2-{7-[5-(2-Methoxymethyl-phenyl)-[1,2,4]triazolo[1,5-a]pyridin-2-ylamino]-1,2,4,5-tetrahydro-benzo[d]azepin-3-yl}-N,N-dimethyl-acetamide

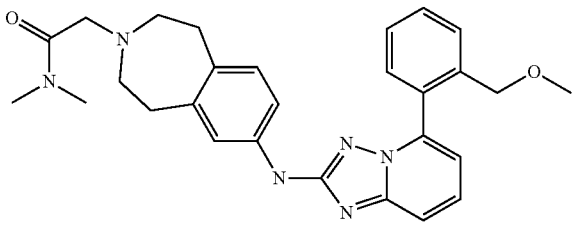 [SMILES: COCc1ccccc1-c1cccc2nc(Nc3ccc4c(c3)CCN(CC(=O)N(C)C)CC4)nn12]

To a solution of [5-(2-Methoxymethyl-phenyl)-[1,2,4]triazolo[1,5-a]pyridin-2-yl]-(2,3,4,5-tetrahydro-1H-benzo[d]azepin-7-yl)-amine (70.0 mg, 0.18 mmol) in acetonitrile (5 mL) was added potassium carbonate (0.0484 g, 0.350 mmol), 2-chloro-N,N-dimethyl-acetamide (0.0270 mL, 0.263 mmol), followed by sodium iodide (0.0263 g, 0.175 mmol) and the reaction was heated at 70° C. for 2.5 hours and cooled to room temperature. The reaction was diluted with chloroform, washed with water then brine. The organic layer was dried over sodium sulfate, filtered and concentrated. The residue was purified via flash chromatography utilizing an ISCO automated purification apparatus (basic alumina column and 0%→10% methanol in dichloromethane). Product was isolated as a yellow foam (0.028 g, 32%). $^1$H NMR (400 MHz, CDCl$_3$, δ, ppm): 7.64 (d, J=7.7 Hz, 1H), 7.59-7.42 (m, 5H), 7.27 (m, 1H), 7.23-7.19 (m, 1H), 6.98 (d, J=7.9 Hz, 1H), 6.93 (s, 1H), 6.91-6.87 (m, 1H), 4.35 (br s, 2H), 3.26 (s, 2H), 3.20 (s, 3H), 3.14 (s, 3H), 2.97 (s, 3H), 2.88-2.83 (m, 4H), 2.69-2.63 (m, 4H). MS=485 (MH)+.

Example 230

[3-(2-Methanesulfonyl-ethyl)-2,3,4,5-tetrahydro-1H-benzo[d]azepin-7-yl]-[5-(2-methoxymethyl-phenyl)-[1,2,4]triazolo[1,5-a]pyridin-2-yl]-amine

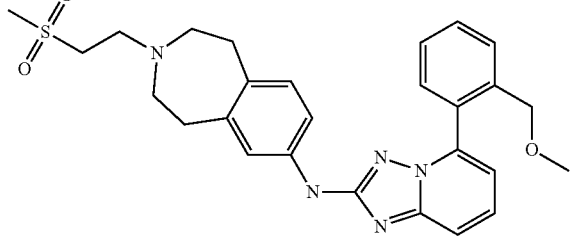

To a solution of [5-(2-Methoxymethyl-phenyl)-[1,2,4]triazolo[1,5-a]pyridin-2-yl]-(2,3,4,5-tetrahydro-1H-3-benzazepin-7-yl)-amine (0.100 g, 0.250 mmol) in N,N-dimethylformamide (3 mL) was added potassium carbonate (0.103 g, 0.751 mmol), 1-chloro-2-methanesulfonyl-ethane (0.053545 g, 0.37548 mmol), followed by sodium iodide (0.037 g, 0.250 mmol) and the reaction was heated at 60° C. overnight then cooled to room temperature. The reaction was diluted with ethyl acetate, washed with water several times, washed with brine, dried over sodium sulfate, and concentrated. Product was isolated as a pale yellow foam (0.062 g, 49%). $^1$H NMR (400 MHz, CDCl$_3$, δ, ppm): 7.64 (d, J=7.7 Hz, 1H), 7.59-7.42 (m, 5H), 7.31-7.29 (m, 1H), 7.24-7.20 (m, 1H), 7.08 (s, 1H), 6.98 (d, J=8.1 Hz, 1H), 6.92-6.88 (m, 1H), 4.35 (br s, 2H), 3.20-3.14 (m, 5H), 3.06 (s, 3H), 3.01 (t, J=6.1 Hz, 2H), 2.87-2.82 (m, 4H), 2.71-2.64 (m, 4H). MS=506 (MH)+.

Example 234

[5-(2-Methoxy-5-trifluoromethyl-phenyl)-[1,2,4]triazolo[1,5-a]pyridine-2-yl]-(2,3,4,5-tetrahydro-1H-benzo[d]azepin-7-yl)-amine

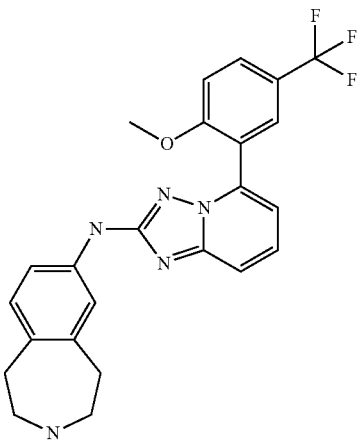 [SMILES: COc1ccc(C(F)(F)F)cc1-c1cccc2nc(Nc3ccc4c(c3)CCNCC4)nn12]

234a) 2-Chloro-5-(2-methoxy-5-trifluoromethyl-phenyl)-[1,2,4]triazolo[1,5-a]pyridine was prepared from 8-bromo-2-chloro[1,2,4]triazolo[1,5-a]pyridine (0.5 g, 2.15 mmol) and 2-methoxy-5-trifluoromethylbenzeneboronic acid (0.71 g, 3.23 mmol) in a manner analogous to Example 2c. Product was isolated as a foam (0.7 g, 82%). ¹H NMR (400 MHz, CDCl₃, δ, ppm): 7.80 (d, J=8.8 Hz, 1H), 7.75-7.70 (m, 2H), 7.68-7.62 (m, 1H), 7.16 (d, J=8.8 Hz, 1H), 7.09 (d, J=6.8 Hz, 1H), 3.87 (s, 3H). MS=328 (MH)+.

234b) 7-[5-(2-Methoxy-5-trifluoromethyl-phenyl)-[1,2,4]triazolo[1,5-a]pyridin-2-yl-amino]-1,2,4,5-tetrahydro-3-benzazepine-3-carboxylic acid tert-butyl ester was prepared from 2-chloro-5-(2-Methoxy-5-trifluoromethyl-phenyl)-[1,2,4]triazolo[1,5-a]pyridine (0.46 g, 1.4 mmol) and 7-amino-1,2,4,5-tetrahydro-3-benzazepine-3-carboxylic acid tert-butyl ester (0.557 g, 2.12 mmol) in a manner analogous to Example 2d. Product was isolated as a foam (0.33 g, 42%). ¹H NMR (400 MHz, CDCl₃, δ, ppm): 7.94 (brs, 1H), 7.80-7.77 (m, 1H), 7.55-7.49 (m, 2H), 7.20-7.15 (m, 1H), 7.05-7.00 (m, 1H), 7.00-6.96 (m, 1H), 6.90 (brs, 1H), 3.88 (s, 3H), 3.60-3.48 (m, 4H), 2.89-2.78 (m, 4H), 1.52 (s, 9H). MS=554 (MH)+.

234c) 7-[5-(2-Methoxy-5-trifluoromethyl-phenyl)-[1,2,4]triazolo[1,5-a]pyridin-2-yl-amino]-1,2,4,5-tetrahydro-3-benzazepine-3-carboxylic acid tert-butyl ester (0.33 g, 6.00 mmol), was dissolved in dichloromethane (10 mL, 156 mmol) and trifluoroacetic acid was added (2 mL, 20.0 mmol). Reaction was stirred at room temperature for 2 hours. Solvent was removed and residue was partitioned between dichloromethane and 1N sodium carbonate. Washed with water and brine, dried over sodium sulfate and concentrated. [5-(2-Methoxy-5-trifluoromethyl-phenyl)-[1,2,4]triazolo[1,5-a]pyridin-2-yl-amino]-1,2,4,5-tetrahydro-3-benzazepin-7-yl)-amine was isolated as a foam (0.27 g, 96%). ¹H NMR (400 MHz, CDCl₃, δ, ppm): 7.94 (brs, 1H), 7.81-7.76 (m, 1H), 7.54-7.50 (m, 2H), 7.25 (brs, 1H), 7.17 (d, J=7.9 Hz, 1H), 7.02 (d, J=7.9 Hz, 1H), 6.99-6.95 (m, 1H), 6.83 (brs, 1H), 3.86 (s, 3H), 3.01-2.92 (m, 4H), 2.90-2.83 (m, 4H). MS=454 (MH)+.

Example 235

[5-(2-Methoxy-5-trifluoromethyl-phenyl)-[1,2,4]triazolo[1,5-a]pyridin-2-yl]-(3-(2-methylsulfanyl-ethyl)-2,3,4,5-tetrahydro-1H-3-benzazepin-7-yl]-amine

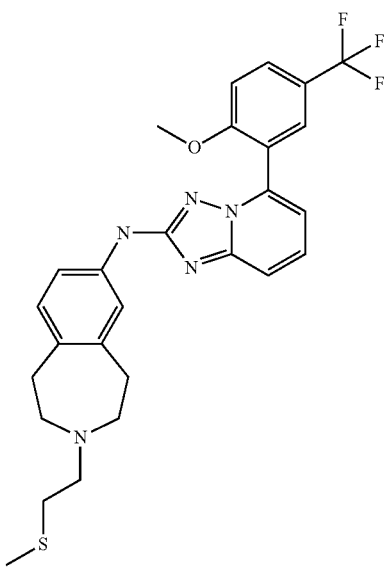 [SMILES: COc1ccc(C(F)(F)F)cc1-c1cccc2nc(Nc3ccc4c(c3)CCN(CCSC)CC4)nn12]

[5-(2-Methoxy-5-trifluoromethyl-phenyl)-[1,2,4]triazolo[1,5-a]pyridin-2-yl-amino]-1,2,4,5-tetrahydro-3-benzazepin-7-yl)-amine (0.1 g, 0.2 mmol) in N,N-dimethylformamide (5 mL, 60 mmol) under an atmosphere of nitrogen was added potassium carbonate (0.09 g, 0.6 mmol), 2-chloroethyl methyl sulfide (0.04 mL, 0.4 mmol), followed by sodium iodide (0.033 g, 0.22 mmol) and reaction was heated to 80° C. overnight. Reaction was diluted with ethyl acetate and washed several times with water, then brine and dried over sodium sulfate. The material was purified via chromatography utilizing an ISCO automated purification apparatus (silica gel 24 g 10% methanol in dichloromethane). [5-(2-Methoxy-5-trifluoromethyl-phenyl)-[1,2,4]triazolo[1,5-a]pyridin-2-yl]-[3-(2-methylsulfamyl-ethy)-2,3,4,5-tetrahydro-1H-3-benzazepin-7-yl)-amine was isolated as a solid (0.055 g, 50%). MP=176-177° C.

¹H NMR (400 MHz, CDCl₃, δ, ppm): 7.95 (brs, 1H), 7.79 (d, J=8.9 Hz, 1H), 7.55-7.50 (m, 2H), 7.30-7.25 (m, 2H), 7.17 (d, J=8.9 Hz, 1H), 7.03-6.96 (m, 2H), 6.90 (brs, 1H), 3.89 (s, 3H), 2.94-2.84 (m, 4H), 2.84-2.63 (m, 8H), 2.16 (s, 3H). MS=528 (MH)+.

Example 236

[5-(2-Methoxy-4-trifluoromethyl-phenyl)-[1,2,4]triazolo[1,5-a]pyridin-2-yl]-(3-(2-methylsulfanyl-ethyl)-2,3,4,5-tetrahydro-1H-3-benzazepin-7-yl]-amine

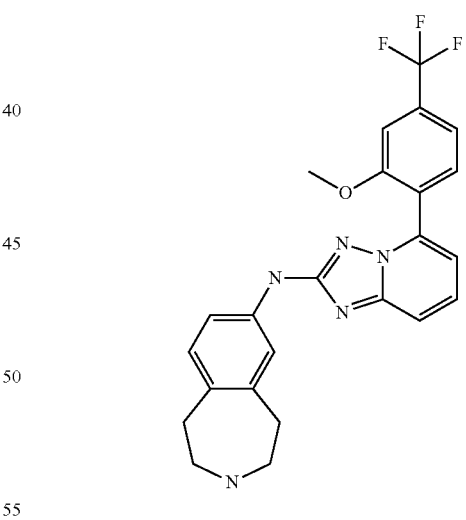

236a) 2-Chloro-5-(2-methoxy-4-trifluoromethyl-phenyl)-[1,2,4]triazolo[1,5-a]pyridine was prepared from 8-bromo-2-chloro[1,2,4]triazolo[1,5-a]pyridine (0.5 g, 2.15 m mol) and 2-methoxy-4-trifluoromethylbenzeneboronic acid (0.71 g, 3.23 mmol), in a manner analogous to Example 2c. Product was isolated as a foam (0.5 g, 70%). ¹H NMR (400 MHz, CDCl₃, δ, ppm): 7.73 (m, 1H), 7.67 (d, J=7.3 Hz, 1H), 7.61 (d, J=8.1 HZ, 1H), 7.40 (d, J=8.1 Hz, 1H), 7.303 (s, 1H), 7.10 (d, J=7.3 Hz, 1H), 3.87 (s, 3H). MS=328 (MH)+.

236b) 7-[5-(2-Methoxy-4-trifluoromethyl-phenyl)-[1,2,4]triazolo[1,5-a]pyridin-2-yl-amino]-1,2,4,5-tetrahydro-3-benzazepine-3-carboxylic acid tert-butyl ester was prepared from 2-chloro-5-(2-Methoxy-4-trifluoromethyl-phenyl)-[1,2,4]triazolo[1,5-a]pyridine (0.5 g, 1.5 mmol), and 7-amino-1,2,4,5-tetrahydro-3-benzazepine-3-carboxylic acid tert-butyl ester (0.6 g, 2.0 mmol). Product was isolated as a foam (0.27 g, 32%). $^1$H NMR (400 MHz, CDCl$_3$, δ, ppm): 7.69 (d, J=7.99 Hz, 1H), 7.56-7.51 (m, 2H), 7.41 (d, J=7.99 Hz, 1H), 7.32-7.28 (m, 2H), 7.06-7.02 (m, 1H), 6.97-6.93 (m, 1H), 6.75 (brs, 1H), 3.86 (s, 3H), 3.62-3.48 (m, 4H), 2.91-2.77 (m, 4H) 1.52 (s, 9H). MS=554 (MH)+.

236c) [5-(2-Methoxy-4-trifluoromethyl-phenyl)-[1,2,4]triazolo[1,5-a]pyridin-2-yl-amino]-1,2,4,5-tetrahydro-3-benzazepin-7-yl)-amine was prepared from 7-[5-(2-methoxy-4-trifluoromethyl-phenyl)-[1,2,4]triazolo[1,5-a]pyridin-2-yl-amino]-1,2,4,5-tetrahydro-3-bezazepine-3-carboxylic acid tert-butyl ester (0.27 g, 0.490 mol) in a manner analogous to Example 234c. Product was isolated as a foam (0.20 g, 90%). $^1$H NMR (400 MHz, CDCl$_3$, δ, ppm): 7.70 (d, J=7.9 Hz, 1H), 7.56-7.50 (m, 2H), 7.40 (d, J=7.9 Hz, 1H), 7.32-7.23 (m, 2H), 7.03 (d, J=7.9 Hz 1H), 6.96-6.92 (m, 2H), 6.80 (brs, 1H), 3.86 (s, 3H), 3.03-2.92 (m, 4H), 2.91-2.84 (m, 4H). MS=454 (MH)+.

Example 237

2-(7-[5-(2-Methoxy-5-trifluoromethyl-phenyl)-[1,2,4]triazolo[1,5-a]pyridine-2-yl]-(2,3,4,5-tetrahydro-1H-benzo[d]azepin-7-yl)-N,N-dimethyl-acetamide

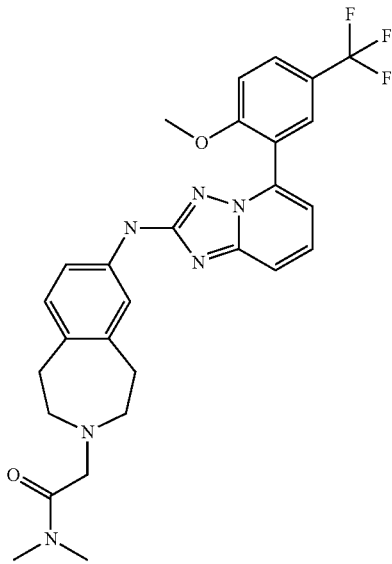 [SMILES: COc1ccc(C(F)(F)F)cc1-c1cccc2nc(Nc3ccc4c(c3)CCN(CC(=O)N(C)C)CC4)nn12]

2-(7-[5-(2-Methoxy-5-trifluoromethyl-phenyl)-[1,2,4]triazolo[1,5-a]pyridin-2-yl]-[3-(2-methylsulfamyl-ethy)-2,3,4,5-tetrahydro-1H-3-benzazepin-7-yl)-N,N-dimethyl-acetamide was prepared from [5-(2-methoxy-5-trifluoromethyl-phenyl)-[1,2,4]triazolo[1,5-a]pyridin-2-yl-amino]-1,2,4,5-tetrahydro-3-benzazepin-7-yl)-amine (0.118 g, 0.26 mmol) and 2-chloro-N,N-dimethyl-acetamide (0.047 g, 0.387 mmol) in a manner analogous to Example 235. Product was isolated as a foam (0.041 g, 29%). $^1$H NMR (400 MHz, CDCl$_3$, δ, ppm): 7.91 (s, 1H), 7.82 (d, J=8.8 Hz, 1H), 7.57-7.52 (m, 2H), 7.39 (s, 1H), 7.33-7.29 (m, 1H), 7. 21 (d, J=8.8 Hz, 1H), 7.06-6.98 (m, 2H), 6.91 (s, 1H), 4.67-4.56 (m, 4H), 3.89 (s, 3H), 3.21 (s, 2H), 3.17-3.09 (m, 4H), 2.99 (s, 6H). MS=539 (MH)+.

Example 238

[3-(2-Methanesulfonyl-ethyl)-2,3,4,5-tetrahydro-1H-3-benzazepin-7-yl]-[5-(2-methoxy-4-trifluoromethyl-phenyl-[1,2,4]triazolo[1,5-a]pyridin-2-yl]-amine

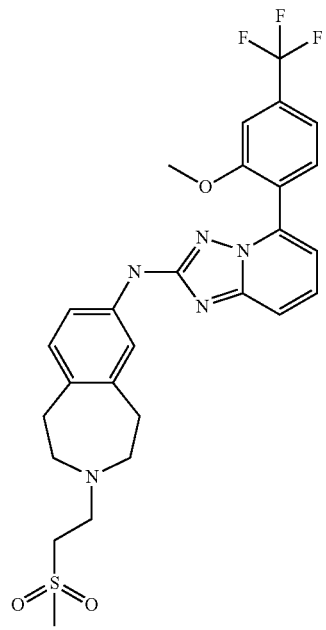 [SMILES: COc1cc(C(F)(F)F)ccc1-c1cccc2nc(Nc3ccc4c(c3)CCN(CCS(C)(=O)=O)CC4)nn12]

[3-(2-Methanesulfonyl-ethyl)-2,3,4,5-tetrahydro-1H-3-benzazepin-7-yl]-[5-(2-methoxy-4-trifluoromethyl-phenyl)-[1,2,4]triazolo[1,5-a]pyridin-2-yl]-amine was prepared from [5-(2-methoxy-4-trifluoromethyl-phenyl)-[1,2,4]triazolo[1,5-a]pyridin-2-yl-amino]-1,2,4,5-tetrahydro-3-benzazepin-7-yl)-amine (0.167 g, 0.368 mmol) and 1-chloro-2-methanesulfonyl-ethane (0.11 g, 0.77 mmol) in a manner analogous to Example 235. Product was isolated as a foam (0.13 g, 63%). $^1$H NMR (400 MHz, CDCl$_3$, δ, ppm): 7.70 (d, J=7.8 Hz, 1H), 7.57-7.50 (m, 2H), 7.40 (d, J=7.8 Hz, 1H), 7.32-7.23 (m, 2H), 7.20 (d, J=8.0 Hz, 1H), 6.97-6.93 (m, 1H), 6.78 (s, 1H), 3.86 (s, 3H), 3.17 (t, J=6.4 Hz, 2H), 3.08 (s, 3H), 3.03 (t, J=6.4 Hz, 2H), 2.90-2.81 (m, 4H), 2.73-2.62 (m, 4H). MS=560 (MH)+.

Example 239

5-(2-Methoxy-5-trifluoromethyl-phenyl)-[1,2,4]triazolo[1,5-a]pyridin-2-yl]-acetamide

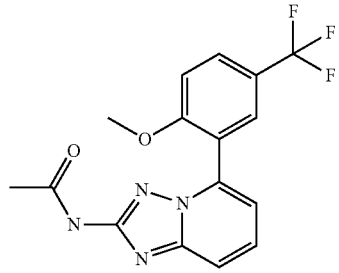 [SMILES: COc1ccc(C(F)(F)F)cc1-c1cccc2nc(NC(C)=O)nn12]

239a) 5-(2-Methoxy-5-trifluoromethyl-phenyl)-[1,2,4]triazolo[1,5-a]pyridine-2-yl-amine was prepared from 5-bromo-[1,2,4]triazolo[1,5-a]pyridine-2-yl-amine (0.5 g, 2.3 mmol), and 2-methoxy-5-trifluoromethylbenzeneboronic acid (0.76 g, 3.4 mmol) in a manner analogous to Example 2c. Product was isolated as a foam (0.63 g, 87%). $^1$H NMR (400 MHz, CDCl$_3$, δ, ppm): 7.79-7.73 (m, 2H), 7.49-7.44 (m, 2H), 7.15 (d, J=8.9 Hz, 1H), 6.85 (t, J=4.2 Hz, 1H), 4.45 (brs, 2H), 3.85 (s, 3H). MS=309 (MH)+.

239b) To a stirred solution of 5-(2-Methoxy-5-trifluoromethyl-phenyl)-[1,2,4]triazolo[1,5-a]pyridine-2-yl-amine (0.076 g, 0.25 mmol) in acetonitrile (5 mL, 100 mmol), was added acetic anhydride (0.015 g, 0.15 mmol), at 0° C. along with pyridine (0.02 mL, 0.2 mmol). The reaction was stirred at RT for one hour. White solid was formed that was taken up in dichloromethane and washed with 1N Hydrochloric acid and brine. Organic layer was dried over sodium sulfate and was purified via chromatography utilizing an ISCO automated purification apparatus (silica gel 40 g 5%→100% ethyl acetate in hexane). Product was isolated as a solid (0.043 g, 84%). MP=260-262° C. $^1$H NMR (400 MHz, CDCl$_3$, δ, ppm): 7.83-7.77 (m, 2H), 7.72 (d, J=8.6 Hz, 1H), 7.60 (t, J=7.6 Hz, 1H), 7.16 (d, J=8.8 Hz, 1H), 7.06 (d, J=8.8 Hz, 1H), 3.87 (s, 3H), 1.6 (s, 3H). MS=351 (MH)+.

Example 241

7-[8-(2-Methoxymethyl-phenyl)-[1,2,4]triazolo[1,5-a]pyridin-2-yl-amino]-1,2,4,5-tetrahydro-3-benzazepine-3-carboxylic acid tert-butyl ester

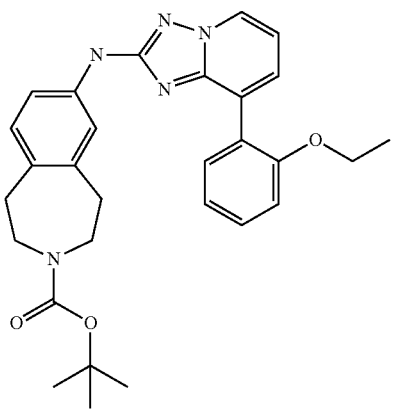 [SMILES: CCOc1ccccc1-c1cccn2nc(Nc3ccc4c(c3)CCN(C(=O)OC(C)(C)C)CC4)nc12]

241a) 2-Chloro-8-(2-methoxymethyl-phenyl)-[1,2,4]triazolo[1,5-a]pyridine was prepared from 8-bromo-2-chloro[1,2,4]triazolo[1,5-a]pyridine (0.71 g, 3.0 mmol) and 2-methoxymethyl)phenylboronic acid (0.71 g, 4.3 mmol) in a manner analogous to Example 2c. Product was isolated as a foam (0.82 g, 98%). $^1$H NMR (400 MHz, CDCl$_3$, δ, ppm): 8.55 (d, J=6.3 Hz, 1H), 7.64-7.57 (m, 2H), 7.50-7.43 (m, 1H), 7.25-7.21 (m, 2H), 7.17 (t, J=7.3 Hz, 1H), 4.37 (s, 2H), 3.27 (s, 3H), MS=328 (MH)+.

241b) 7-[8-(2-Methoxymethyl-phenyl)-[1,2,4]triazolo[1,5-a]pyridin-2-yl-amino]-1,2,4,5-tetrahydro-3-benzazepine-3-carboxylic acid tert-butyl ester was prepared from 2-chloro-8-(2-Methoxymethyl-phenyl)-[1,2,4]triazolo[1,5-a]pyridine (0.40 g, 1.46 mmol) and 7-amino-1,2,4,5-tetrahydro-3-benzazepine-3-carboxylic acid tert-butyl ester (0.46 g, 1.75 mmol) in a manner analogous to Example 2d. Product was isolated as a foam (0.5 g, 70%). $^1$H NMR (400 MHz, CDCl$_3$, δ, ppm): 8.48 (d, J=6 Hz, 1H), 7.61 (d, J=6 Hz, 1H), 7.51-7.42 (m, 4H), 7.00-6.89 (m, 3H), 6.79 (s, 1H), 3.62-3.45 (m, 4H), 3.29 (s, 3H), 2.84-2.74 (m, 4H), 1.52 (s, 9H). MS=500 (MH)+.

Example 242

[8-(2-Methoxymethyl-phenyl)-[1,2,4]triazolo[1,5-a]pyridin-2-yl]-(2,3,4,5-tetrahydro-1H-3-benzazepin-7-yl)amine

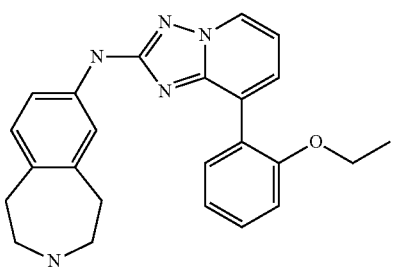 [SMILES: CCOc1ccccc1-c1cccn2nc(Nc3ccc4c(c3)CCNCC4)nc12]

[8-(2-Methoxymethylphenyl)-[1,2,4]triazolo[1,5-a]pyridin-2-yl]-(,2,3,4,5-tetrahydro-1H-3-benzazepin-7-yl)-amine was prepared from [8-(2-methoxymethyl-phenyl)-[1,2,4]triazolo[1,5-a]pyridin-2-yl-amino]-2,3,4,5-tetrahydro-1H-3-benzazepine-3-carboxylic acid tert-butyl ester (0.67 g, 1.3 mmol) in a manner analogous to Example 234c. Product was isolated as a foam (0.50 g, 93%). $^1$H NMR (400 MHz, CDCl$_3$, δ, ppm): 7.94 (brs, 1H), 7.81-7.76 (m, 1H), 7.54-7.50 (m, 2H), 7.25 (brs, 1H), 7.17 (d, J=7.9 Hz 1H), 7.02 (d, J=7.9 Hz, 1H), 6.99-6.95 (m, 1H), 6.83 (brs, 1H), 3.86 (s, 3H), 3.01-2.92 (m, 4H), 2.90-2.83 (m, 4H). MS=400 (MH)+.

Example 243

7[8-(2,2-Difluoro-1,3-benzodioxol-4-yl)-[1,2,4]triazolo[1,5-a]pyridin-2-yl]-amino]-1,2,4,5-tetrahydro-3-benzazepine-3-carboxylic acid tert-butyl ester

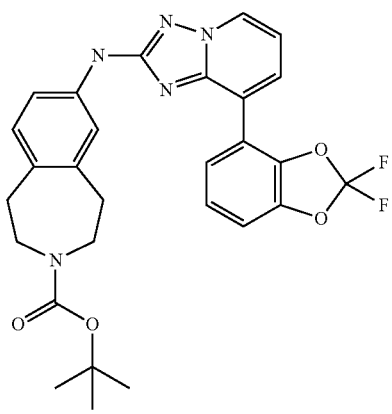 [SMILES: CC(C)(C)OC(=O)N1CCc2ccc(Nc3nc4c(-c5cccc6c5OC(F)(F)O6)cccn4n3)cc2CC1]

243a) 2-Chloro-8-(2,2-difluoro-1,3-benzodioxol-4-yl-[1,2,4]triazolo[1,5-a]pyridine was prepared from 8-bromo-2-chloro[1,2,4]triazolo[1,5-a]pyridine (0.71 g, 3.0 mmol) and 2,2-difluorobenzo[1,3]dioxole-4-boronic acid (0.64 g, 3.2 mmol) in a manner analogous to Example 2c. Product was isolated as a foam (0.63 g, 67%). $^1$H NMR (400 MHz, CDCl$_3$, δ, ppm): 7.84 (d, J=7.5 Hz, 1H), 7.78-7.67 (m, 2H), 7.33-7.23 (m, 2H), 7.36 (d, J=6 Hz, 1H), MS=310 (MH)+.

243b) 7-[8-(2,2-difluoro-1,3-benzodioxol-4-yl)-[1,2,4]triazolo[1,5-a]pyridin-2-yl-amino]-1,2,4,5-tetrahydro-3-benzazepine-3-carboxylic acid tert-butyl ester was prepared from 2-chloro-8-(2,2-difluoro-1,3-benzodioxol-4-yl)-[1,2,4]triazolo[1,5-a]pyridine (0.78 g, 2.5 mmol), and 7-amino-1,2,4,5-tetrahydro-3-benzazepine-3-carboxylic acid tert-butyl ester (0.99 g, 3.778 mmol), in a manner analogous to Example 2d. Product was isolated as a foam (0.78 g, 58%). $^1$H NMR (400 MHz, CDCl$_3$, δ, ppm): 8.48 (d, J=6 Hz, 1, 7.61 (d, J=6 Hz, 1H), 7.51-7.42 (m, 4H), 7.00-6.89 (m, 3H), 6.79 (s, 1H), 3.62-3.45 (m, 4H), 2.84-2.74 (m, 4H), 1.52 (s, 9H). MS=536 (MH)+.

Example 244

[8-(2,2-difluoro-1,3-benzodioxol-4-yl)-[1,2,4]triazolo[1,5-a]pyridin-2-yl]-(2,3,4,5-tetrahydro-1H-3-benzazepin-7-yl)amine

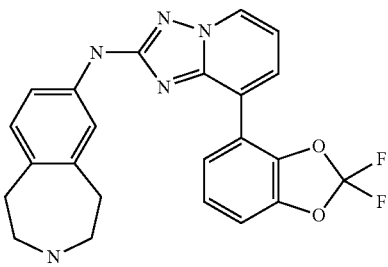 [SMILES: FC1(F)Oc2cccc(-c3cccn4nc(Nc5ccc6c(c5)CCNCC6)nc34)c2O1]

[8-(2,2-difluoro-1,3-benzodioxol-4-yl)-[1,2,4]triazolo[1,5-a]pyridin-2-yl-]-(2,3,4,5-tetrahydro-1H-3-benzazepin-7-yl)-amine was prepared from 7-[8-(2,2-difluoro-1,3-benzodioxol-4-yl)-[1,2,4]triazolo[1,5-a]pyridin-2-yl-amino]-1,2,4,5-tetrahydro-3-benzazepine-3-carboxylic acid tert-butyl ester (1.17 g, 2.18 mmol) in a manner analogous to Example 234c. Product was isolated as a foam (0.90 g, 95%). $^1$H NMR (400 MHz, CDCl$_3$, δ, ppm): 10.39 (s, 1H), 9.1 (brs, 2H), 8.62 (d, J=6.5 Hz, 1H), 7.86 (d, J=8.7 Hz, 1H), 7.59-7.54 (m, 1H), 7.49 (s, 1H), 7.37-7.31 (m, 2H), 7.20 (d, J=8.7 Hz, 1H), 3.44-3.32 (m, 4H), 3.29-3.16 (m, 4H), MS=436 (MH)+.

Example 245

[3-(2-Methanesulfonyl-ethyl-2,3,4,5-tetrahydro-1H-3-benzazepin-7-yl)-[8-(2-Methoxymethyl-phenyl)-[1,2,4]triazolo[1,5-a]pyridin-2-yl]amine

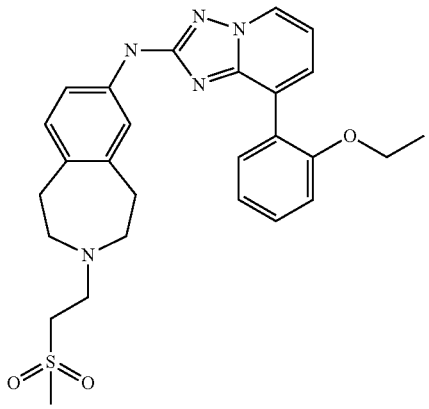 [SMILES: CCOc1ccccc1-c1cccn2nc(Nc3ccc4c(c3)CCN(CCS(C)(=O)=O)CC4)nc12]

[3-(2-Methanesulfonyl-ethyl)-2,3,4,5-tetrahydro-1H-3-benzazepin-7-yl]-[8-(2-methoxymethyl-phenyl)-[1,2,4]triazolo[1,5-a]pyridin-2-yl]-amine was prepared from [8-(2-methoxymethyl-phenyl)-[1,2,4]triazolo[1,5-a]pyridin-2-yl-amino]-1,2,4,5-tetrahydro-3-benzazepin-7-yl)-amine (0.139 g, 0.348 mmol) and 1-chloro-2-methanesulfonyl-ethane (0.10 g, 0.70 mmol), in a manner analogous to Example 235. Product was isolated as a foam (0.05 g, 30%). $^1$H NMR (400 MHz, CDCl$_3$, δ, ppm): 8.48 (d, J=7.4 Hz, 1H), 7.61 (d, J=7.4 Hz, 1H), 7.50-7.42 (m, 4H), 7.36-7.30 (m, 1H), 7.08 (d, J=7.4 Hz, 1H), 6.99-6.95 (m, 1H), 6.89 (d, J=7.4 Hz, 1H), 6.80 (s, 1H), 4.39 (s, 2H), 3.28 (s, 3H), 3.18-3.14 (m, 2H), 3.09 (s, 3H), 3.05-3.00 (m, 2H), 2.84-2.79 (m, 4H), 2.76-2.64 (m, 4H). MS=506 (MH)+.

Example 246

2-(7-[8-(2-Methoxymethyl-phenyl)-[1,2,4]triazolo[1,5-a]pyridin-2-yl]amino]-1,2,4,5-tetrahydro-3-benzazepin-3-yl)-N,N-dimethyl-acetamide

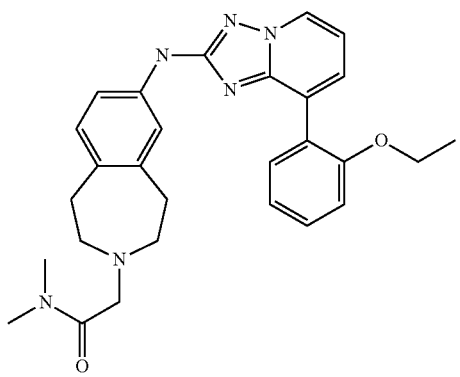 [SMILES: CCOc1ccccc1-c1cccn2nc(Nc3ccc4c(c3)CCN(CC(=O)N(C)C)CC4)nc12]

2-(7-[8-(2-Methoxymethyl-phenyl)-[1,2,4]triazolo[1,5-a]pyridin-2-yl-amino]-1,2,4,5-tetrahydro-3-benzazepin-3-yl)-N,N-dimethyl-acetamide was prepared from [8-(2-methoxymethyl-phenyl)-[1,2,4]triazolo[1,5-a]pyridin-2-yl-amino]-1,2,4,5-tetrahydro-3-benzazepin-7-yl)-amine and 2-chloro-N,N-dimethyl-acetamide (0.07 mL, 0.7 mmol) in a manner analogous to Example 235. Product was isolated as a foam (0.09 g, 40%). $^1$H NMR (400 MHz, CDCl$_3$, δ, ppm): 8.48 (d, J=7.4 Hz, 1H), 7.61 (d, J=7.4 Hz, 1H), 7.50-7.42 (m, 4H), 7.34 (d, J=7.4 Hz, 1H), 7.07 (d, J=7.4 Hz, 1H), 6.98-6.93 (m, 1H), 6.78 (s, 1H), 4.38 (s, 2H), 3.30 (s, 2H), 3.17 (s, 3H), 3.00 (s, 3H), 2.98-2.87 (m, 4H), 2.75-2.64 (m, 4H), MS=485 (MH)+.

Example 247

[8-(2,2-difluoro-1,3-benzodioxol-4-yl)-[1,2,4]triazolo[1,5-a]pyridin-2-yl]-[3-(2-methanesulfonyl-ethyl)-2,3,4,5-tetrahydro-1H-3-benzazepin-7-yl)amine

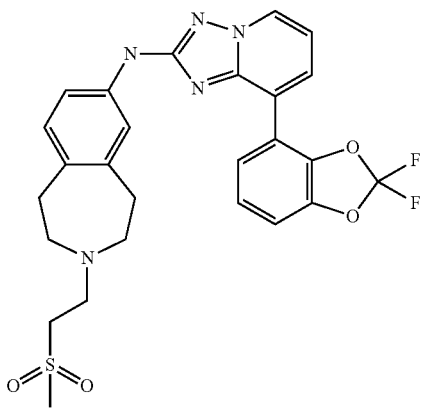 [SMILES: CS(=O)(=O)CCN1CCc2ccc(Nc3nc4c(-c5cccc6c5OC(F)(F)O6)cccn4n3)cc2CC1]

[8-(2-2-difluoro-1,3-benzodioxol-4-yl)-[1,2,4]triazolo[1,5-a]pyridin-2-yl]-[3-(2-methanesulfonyl-ethyl)-2,3,4,5-tetrahydro-3-benzazepin-7-yl)-amine was prepared from [8-(2-2-difluoro-1,3-benzodioxol-4-yl)-[1,2,4]triazolo[1,5-a]pyridin-2-yl]-2,3,4,5-tetrahydro-3-benzazepin-7-yl)-amine and 1-chloro-2-methanesulfonyl-ethane (0.092 g, 0.64 mmol) in a manner analogous to Example 235. Product was isolated as a foam (0.03 g, 17%). $^1$H NMR (400 MHz, CDCl$_3$, δ, ppm): 8.48 (d, J=8.0 Hz, 1H), 8.12 (d, J=8.0 Hz, 1H), 7.85 (d, J=8.0 Hz, 1H), 7.41-7.34 (m, 2H), 7.13 (d, J=8.0 Hz, 1H), 7.09 (d, J=8.0 Hz, 1H), 7.05-7.00 (m, 1H), 6.89 (d, J=8.0 Hz, 1H), 6.85 (s, 1H), 3.21-3.14 (m, 2H), 3.09 (s, 3H), 3.05-2.99 (m, 2H), 2.98-2.88 (m, 4H), 2.85-2.77 (m, 4H), MS=542 (MH)+.

Example 248

2-(7-[8-(2,2-difluoro-1,3-benzodioxol-4-yl)-[1,2,4]triazolo[1,5-a]pyridin-2-yl-amino]-1,2,4,5-tetrahydro-3-benzazepin-3-yl)-N—N-dimethyl-acetamide

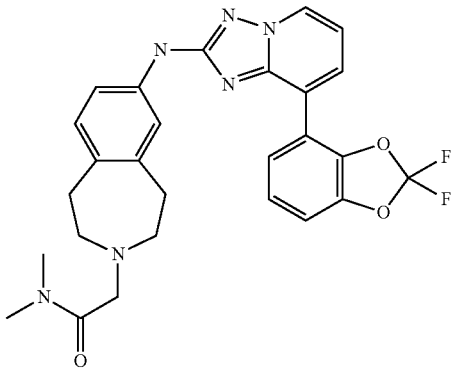 [SMILES: CN(C)C(=O)CN1CCc2ccc(Nc3nc4c(-c5cccc6c5OC(F)(F)O6)cccn4n3)cc2CC1]

2-(7-[8-(2-2-difluoro-1,3-benzodioxol-1,2,4]triazolo[1,5-a]pyridin-2-yl-amino]-1,2,4,5-tetrahydro-3-benzazepin-3-yl)-N,N-dimethyl-ethyl acetamide was prepared from [8-(2-2-difluoro-1,3-benzodioxol-4-yl)-[1,2,4]triazolo[1,5-a]pyridin-2-yl]-2,3,4,5-tetrahydro-3-benzazepin-7-yl)-amine (0.175 g, 0.402 mmol) and 2-chloro-N,N-dimethyl-acetamide (0.06 mL, 0.6 mmol) in a manner analogous to Example 235. Product was isolated as a foam (0.04 g, 19%). $^1$H NMR (400 MHz, CDCl$_3$, δ, ppm): 8.48 (d, J=7.4 Hz, 1H), 8.14 (d, J=8.7 Hz, 1H), 7.85 (d, J=7.4 Hz, 1H), 7.39-7.32 (m, 2H), 7.27-7.22 (m, 1H), 7.13 (d, J=7.4 Hz, 1H), 7.08 (d, J=7.4 Hz, 1H), 7.01 (t, J=6.2 Hz, 1H), 6.85 (s, 1H), 3.30 (s, 2H), 3.16 (s, 3H), 2.99 (s, 3H), 2.98-2.89 (m, 4H), 2.78-2.67 (m, 4H), MS=521 (MH)+.

Example 249

Cyclopropanecarboxylic acid [8-(2-Methoxy-5-trifluoromethyl-phenyl)-[1,2,4]triazolo[1,5-a]pyridin-2-yl]-amide

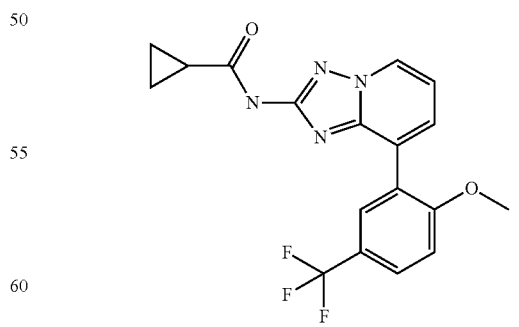

Cyclopropanecarboxylic acid [8-(2-Methoxy-5-trifluoromethyl-phenyl)-[1,2,4]triazolo[1,5-a]pyridine-2-yl]-amide was prepared from 8-(2-methoxy-5-trifluoromethyl-phenyl)-[1,2,4]triazolo[1,5-a]pyridine-2yl-amine (0.07 g, 0.2 mmol) and cyclopropanecarbonyl chloride (0.021 mL, 0.23 mmol) in a manner analogous to Example 240b. Product was isolated as a foam (0.063 g, 70%). $^1$H NMR (400 MHz, CDCl$_3$, δ, ppm): 8.61 (d, J=6.7 Hz, 1H), 7.76-7.66 (m, 2H), 7.60-7.50 (m, 1H), 7.51-7.45 (m, 1H), 7.13-7.06 (m, 1H), 3.86 (s, 3H), 1.56 (m, 1H), 1.19-1.14 (m, 2H), 1.01-0.95 (m, 2H), MS=377 (MH)+.

Example 254

[8-(2-Methoxy-5-trifluoromethyl-phenyl)-[1,2,4]triazolo[1,5-a]pyridin-2-yl]-[4-(4-methyl-piperazine-1-yl)-phenyl]-amine

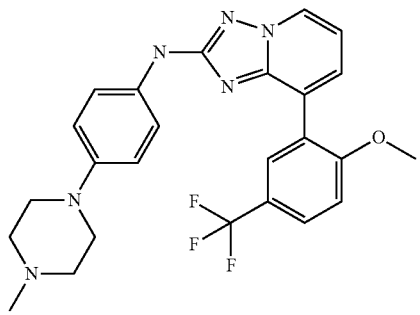 [SMILES: COc1ccc(C(F)(F)F)cc1-c1cccn2nc(Nc3ccc(N4CCN(C)CC4)cc3)nc12]

[8-(2-methoxy-5-trifloromethylphenyl)-[1,2,4]triazolo[1,5-a]pyridin-2-yl]-[4-(4-methyl-piperazin-1-yl)-phenyl]-amine was prepared from 2-chloro-8-(2-methoxy-5-trifluoromethyl-phenyl)-[1,2,4]triazolo[1,5-a]pyridine (0.150 g, 0.5 mmol), and 4-(4-methylpiperazin-1-yl)phenylamine (0.096 g, 0.5 mmol) in a manner analogous to Example 2d. Product was isolated as a foam (0.1 g, 40%). $^1$H NMR (400 MHz, CDCl$_3$, δ, ppm): 8.43 (d, J=7.6 Hz, 1H), 7.94 (s, 1H), 7.68 (d, J=8.2 Hz, 1H), 7.53 (d, J=7.1 Hz, 1H), 7.48 (d, J=7.1 Hz, 2H), 7.12 (d. J=8.2 Hz, 1H), 6.99-6.90 (m, 3H), 6.67 (s, 1H), 3.88 (s, 3H), 3.21-3.11 (m, 4H), 3.06 (s, 3H), 2.65-2.55 (m, 4H). MS=483 (MH)+.

Example 255

[8-(2-Methoxy-5-trifluoromethyl-phenyl)-[1,2,4]triazolo[1,5-a]pyridin-2-yl]-[3-(4-methyl-piperazine-1-yl)-phenyl]-amine

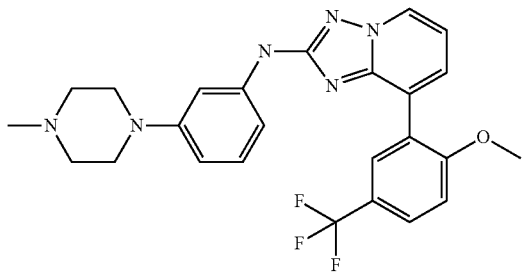

[8-(2-methoxy-5-trifloromethylphenyl)-[1,2,4]triazolo[1,5-a]pyridin-2-yl]-[3-(4-methyl-piperazin-1-yl)-phenyl]-amine was prepared from 2-chloro-8-(2-methoxy-5-trifluoromethyl-phenyl)-[1,2,4]triazolo[1,5-a]pyridine (0.150 g, 0.5 mmol), and 3-(4-methylpiperazin-1-yl)phenylamine (0.096 g, 0.5 mmol) in a manner analogous to Example 2d. Product was isolated as a foam (0.19 g, 86%). $^1$H NMR (400 MHz, CDCl$_3$, δ, ppm): 8.45 (d, J=6.4 Hz, 1H), 7.91 (s, 1H), 7.68 (d, J=7.7 Hz, 1H), 7.53 (d, J=6.4 Hz, 1H), 7.26-7.19 (m, 2H), 7.12 (d, J=7.7 Hz, 1H), 7.04 (d. J=7.7 Hz, 1H), 6.95 (t, J=7.7 Hz, 1H), 6.83 (s, 1H), 6.58 (d, J=7.7 Hz, 1H), 3.88 (s, 3H), 3.28-3.22 (m, 4H), 2.64-2.55 (m, 4H), 2.37 (s, 3H). MS=483 (MH)+.

Example 256

[4-(3-[8-(2-Methoxy-5-trifluoromethyl-phenyl)-[1,2,4]triazolo[1,5-a]pyridin-2-ylamino]-phenyl]-piperazine-1-carboxylic acid tert-butyl ester 4-(3-[8-(2-methoxy-5-trifloromethylphenyl)-[1,2,4]triazolo[1,5-a]pyridin-2-ylamino]-phenyl)-piperazine-1-carboxylic acid tert-butyl ester was prepared from 2-chloro-8-(2-methoxy-5-trifluoromethyl-phenyl)-[1,2,4]triazolo[1,5-a]pyridine (0.150 g, 0.5 mmol), and 4-(3-amino-phenyl)piperazine-1-carboxylic acid tert-butyl ester (0.152 g, 0.548 mmol) in a manner analogous to Example 2d. Product was isolated as a foam (0.19 g, 73%). $^1$H NMR (400 MHz, CDCl$_3$, δ, ppm): 8.47 (d, J=6.1 Hz, 1H), 7.93 (s, 1H), 7.69 (d, J=8.1 Hz, 1H), 7.56 (d, J=6.1 Hz, 1H), 7.46-7.40 (m, 2H), 7.31-7.28 (m, 1H), 7.13 (d, J=8.1 Hz, 1H), 7.00-6.94 (m, 1H), 6.87 (s, 1H), 6.84 (d, J=8.1 Hz, 1H), 3.88 (s, 3H), 2.89-2.75 (m, 2H), 2.73-2.63 (m, 1H), 1.92-1.79 (m, 2H), 1.73-1.63 (m, 4H), 1.52 (s, 9H). MS=568 (MH)+.

Example 247

[8-(2-Methoxy-5-trifluoromethyl-phenyl)-[1,2,4]triazolo[1,5-a]pyridin-2-yl]-(3-piperidin-4-yl-phenyl)-amine

[8-(2-Methoxy-5-trifluoromethyl-phenyl)-[1,2,4]triazolo[1,5-a]pyridin-2-yl]-(3-piperidin-4-yl-phenyl)-amine was prepared from 4-(3-[8-(2-methoxy-5-trifluoromethyl-phenyl)-[1,2,4]triazolo[1,5-a]pyridin-2-ylamino]-phenyl)piperidine-1-carboxylic acid tert-butyl ester (0.19 g, 0.33 mmol) in a manner analogous to Example 234c. Product was isolated as a foam (0.14 g, 89%). ¹H NMR (400 MHz, CDCl₃, δ, ppm): 8.49 (d, J=6.0 Hz, 1H), 7.94 (s, 1H), 7.69 (d, J=8.3 Hz, 1H), 7.55 (d, J=6.0 Hz, 1H), 7.47-7.40 (m, 2H), 7.32-7.29 (m, 1H), 7.13 (d, J=8.3 Hz, 1H), 6.96 (t, J=7.2 Hz, 1H), 6.90-6.84 (m, 2H), 3.89 (s, 3H), 3.31-3.21 (m, 2H), 2.86-2.75 (m, 2H), 2.73-2.61 (m, 1H), 1.84-1.71 (m, 4H). MS=468 (MH)+.

Example 258

[8-(2-Methoxy-5-trifluoromethyl-phenyl)-[1,2,4]triazolo[1,5-a]pyridin-2-yl]-[4-(2-morpholin-4-yl-ethoxy)-phenyl]-amine

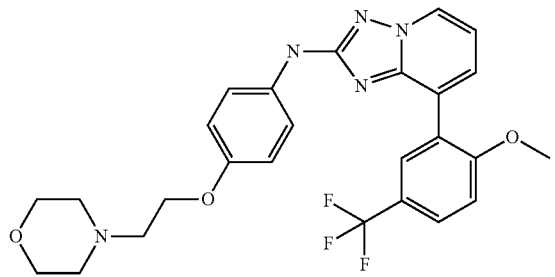 [SMILES: COc1ccc(C(F)(F)F)cc1-c1cccn2nc(Nc3ccc(OCCN4CCOCC4)cc3)nc12]

[8-(2-methoxy-5-trifloromethyl-phenyl)-[1,2,4]triazolo[1,5-a]pyridin-2-yl]-[4-(2-morpholin-4-yl-ethoxy)-phenyl]-amine was prepared from 2-chloro-8-(2-methoxy-5-trifluoromethyl-phenyl)-[1,2,4]triazolo[1,5-a]pyridine (0.150 g, 0.5 mmol), and 4-(morpholin-4-yl-ethoxy)-phenylamine (0.130 g, 0.58 mmol) in a manner analogous to Example 2d. Product was isolated as a foam (0.19 g, 81%). ¹H NMR (400 MHz, CDCl₃, δ, ppm): 8.43 (d, J=6.8 Hz, 1H), 7.96 (s, 1H), 7.68 (d, J=8.9 Hz, 1H), 7.55 (d, J=5.7 Hz, 1H), 7.51-7.46 (m, 2H), 7.12 (d, J=7.9 Hz, 1H), 6.94-6.89 (m, 1H), 6.77 (d, J=6.8 Hz, 1H) 6.71 (s, 1H) 6.65 (d, J=7.9 Hz, 1H), 4.15-4.03 (m, 2H), 3.89 (s, 3H), 3.78-3.71 (m, 4H), 2.86-2.76 (m, 2H), 2.64-2.56 (m, 4H). MS=514 (MH)+.

Example 259

[8-(2-Methoxy-5-trifluoromethyl-phenyl)-[1,2,4]triazolo[1,5-a]pyridin-2-yl]-[4-(2-pyrrolidin-1-yl-ethoxy)-phenyl]-amine

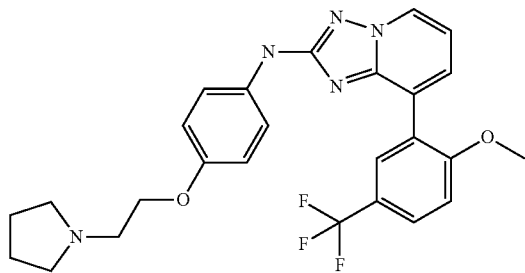 [SMILES: COc1ccc(C(F)(F)F)cc1-c1cccn2nc(Nc3ccc(OCCN4CCCC4)cc3)nc12]

[8-(2-methoxy-5-trifloromethyl-phenyl)-[1,2,4]triazolo[1,5-a]pyridin-2-yl]-[4-(2-pyrrolidin-1-yl-ethoxy)-phenyl]-amine was prepared from 2-chloro-8-(2-methoxy-5-trifluoromethyl-phenyl)-[1,2,4]triazolo[1,5-a]pyridine (0.130 g, 0.4 mmol), and 4-(2-pyrrolidin-1-yl-4-ethoxy)-phenylamine (0.099 g, 0.48 mmol) in a manner analogous to Example 2d. Product was isolated as a foam (0.087 g, 44%). ¹H NMR (400 MHz, CDCl₃, δ, ppm): 8.43 (d, J=6.7 Hz, 1H), 7.94 (s, 1H), 7.68 (d, J=8.9 Hz, 1H), 7.54 (d, J=6.7 Hz, 1H), 7.48 (d, J=6.7 Hz, 2H), 7.39-7.30 (m, 1H), 7.12 (d, J=7.8 Hz, 1H), 6.96-6.90 (m, 2H), 6.73 (s, 1H), 4.17-4.07 (m, 2H), 3.89 (s, 3H), 2.95-2.86 (m, 2H), 2.69-2.60 (m, 4H), 1.87-1.79 (m, 4H). MS=498 (MH)+.

Example 260

[8-(3-Chloro-benzyloxy)-[1,2,4]triazolo[1,5-a]pyridin-2-yl]-[4-(4-methyl-piperazin-1-yl)-phenyl]-amine

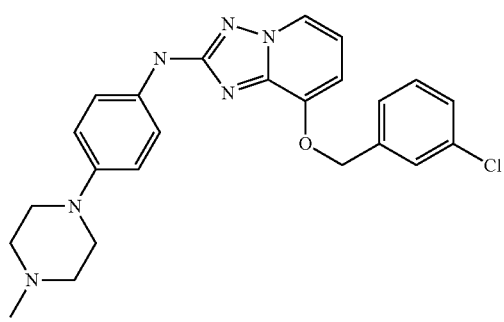 [SMILES: CN1CCN(c2ccc(Nc3nc4c(OCc5cccc(Cl)c5)cccn4n3)cc2)CC1]

260 a) N-(3-Hydroxy-2-pyridinyl)-N'-carboethoxy-thiourea was prepared from 2-amino-pyridin-3-ol (4.00 g, 0.0363 mol) in a manner analogous to Example 2a. The product of the reaction was isolated as a yellow solid.

260 b) 2-Amino-[1,2,4]triazolo[1,5-a]pyridin-8-ol was prepared from N-(3-hydroxy-2-pyridinyl)-N'-carboethoxy-thiourea (1.8 g, 5.9 mmol) in a manner analogous to Example 2b. Product was isolated as a beige solid (3.17 g, 58%). ¹H NMR (400 MHz, (D₃C)₂SO, δ, ppm): 10.18 (bs, 1H), 8.02 (dd, J=6.41 Hz, 1.2 Hz, 1H), 6.71-6.64 (m, 2H), 5.79 (bs, 2H). MS=151.0 (MH)+.

260 c) 2-Amino-[1,2,4]triazolo[1,5-a]pyridin-8-ol (0.200 g, 1.33 mmol) was suspended in acetone (1.9 mL). 1-(bromomethyl)-3-chloro-benzene (0.184 mL, 1.40 mmol) and potassium carbonate (193 mg, 1.40 mmol) were added and the reaction mixture was heated to 80° C. for 1 hour. Reaction mixture was cooled to room temperature, diluted with water, extracted with dichloromethane, dried over magnesium sulfate, filtered, and concentrated. Resulting oil was taken up in dichloromethane and purified via chromatography (silica gel 0-100% ethyl acetate in hexanes). 8-(3-Chloro-benzyloxy)-[1,2,4]triazolo[1,5-a]pyridin-2-ylamine was isolated as an oil which solidified on standing. ¹H NMR (400 MHz, (D₃C)₂SO, δ, ppm): 8.17 (d, J=6.6 Hz, 1H), 7.56 (s, 1H), 7.44-7.42 (m, 3H), 6.99 (d, J=7.9 Hz, 1H), 6.79-6.75 (m, 1H), 5.94 (bs, 2H), 5.30 (s, 2H). MS=275 (MH)+.

260 d) [8-(3-Chloro-benzyloxy)-[1,2,4]triazolo[1,5-a]pyridin-2-yl]-[4-(4-methyl-piperazin-1-yl)-phenyl]-amine was prepared from 8-(3-chloro-benzyloxy)-[1,2,4]triazolo[1,5-a]pyridin-2-ylamine (95.0 mg, 0.346 mmol) and 1-(4-bromophenyl)-4-methyl-piperazine (102 mg, 0.399 mmol in a manner analogous to Example 2d. Product was isolated as a pale orange solid (0.073 g, 47%). MP=135-138° C. ¹H NMR (400 MHz, (D₃C)₂SO, δ, ppm): 9.33 (s, 1H), 8.37 (d, J=6.7 Hz, 1H), 7.58 (s, 1H), 7.51-7.44 (m, 5H), 7.09 (d, J=7.9 Hz, 1H), 6.91-6.86 (m, 3H), 5.35 (s, 2H), 3.04-3.01 (m, 4H), 2.46-2.44 (m, 4H), 2.22 (s, 3H). MS=449 (MH)+.

Example 261

[8-(3-Chloro-benzyloxy)-[1,2,4]triazolo[1,5-a]pyridin-2-yl]-[3-(4-methyl-piperazin-1-yl)-phenyl]-amine

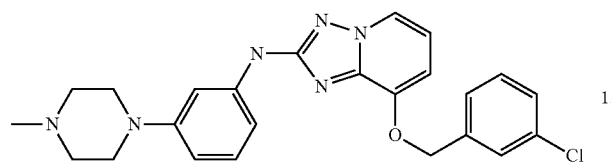

[8-(3-Chloro-benzyloxy)-[1,2,4]triazolo[1,5-a]pyridin-2-yl]-[4-(3-methyl-piperazin-1-yl)-phenyl]-amine was prepared from 8-(3-chloro-benzyloxy)-[1,2,4]triazolo[1,5-a]pyridin-2-ylamine (95.0 mg, 0.346 mmol) and 1-(3-bromophenyl)-4-methyl-piperazine (102 mg, 0.399 mmol in a manner analogous to Example 2d. Product was isolated as a pale orange solid (0.049 g, 32%). MP=78-90° C. (foam). $^1$H NMR (400 MHz, $(D_3C)_2SO$, δ, ppm): 9.46 (s, 1H), 8.40 (d, J=6.6 Hz, 1H), 7.59 (s, 1H), 7.47-7.43 (m, 3H), 7.32 (s, 1H), 7.13-7.09 (m, 3H), 6.93-6.90 (m, 1H), 6.49-6.45 (m, 1H), 5.36 (s, 2H), 3.12-3.10 (m, 4H), 2.45-2.43 (m, 4H), 2.20 (s, 3H). MS=449 (MH)+.

Example 262

2-{2-[4-(4-Methyl-piperazin-1-yl)-phenylamino]-[1,2,4]triazolo[1,5-a]pyridin-8-yloxymethyl}-benzonitrile

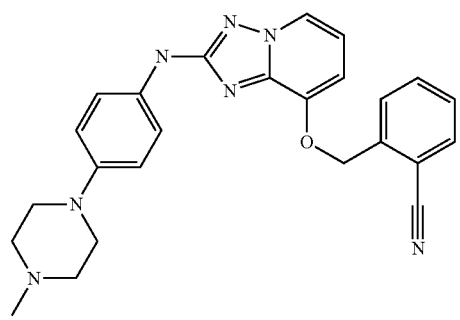 [SMILES: CN1CCN(c2ccc(Nc3nc4c(OCc5ccccc5C#N)cccn4n3)cc2)CC1]

262 a) 2-(2-Amino-[1,2,4]triazolo[1,5-a]pyridin-8-yloxymethyl)-benzonitrile was prepared from 2-amino-[1,2,4]triazolo[1,5-a]pyridin-8-ol (0.200 g, 1.33 mmol) 2-bromomethyl-benzonitrile (0.274 mL, 1.40 mmol) in a manner analogous to Example 260c. Product was isolated as a white solid. $^1$H NMR (400 MHz, $(D_3C)_2SO$, δ, ppm): 8.21 (d, J=6.6 Hz, 1H), 7.94 (d, J=7.8 Hz, 1H), 7.78-7.76 (m, 2H), 7.62-7.58 (m, 1H), 7.07 (d, J=8.0 Hz, 1H), 6.81-6.78 (m, 1H), 5.94 (s, 2H), 5.44 (s, 2H). MS=266 (MH)+.
262 b) 2-{2-[4-(4-Methyl-piperazin-1-yl)-phenylamino]-[1,2,4]triazolo[1,5-a]pyridin-8-yloxymethyl}benzonitrile was prepared from 2-(2-amino-[1,2,4]triazolo[1,5-a]pyridin-8-yloxymethyl)-benzonitrile (115.0 mg, 0.434 mmol) and 1-(4-bromo-phenyl)-4-methyl-piperazine (128 mg, 0.500 mmol) in a manner analogous to Example 2d. Product was isolated as a pale orange solid (0.101 g, 53%). MP=156-157° C. $^1$H NMR (400 MHz, $(D_3C)_2SO$, δ, ppm): 9.32 (s, 1H), 8.40 (d, J=6.5 Hz, 1H), 7.93 (d, J=7.8 Hz, 1H), 7.80 (d, J=4.5 Hz, 2H), 7.62-7.60 (m, 1H), 7.50 (d, J=8.9 Hz, 1H), 7.17 (d, J=8.5 Hz, 1H), 6.98-6.88 (m, 3H), 5.49 (s, 2H), 3.04-3.02 (m, 4H), 2.47-2.44 (m, 4H), 2.22 (s, 3H). MS=440 (MH)+.

Example 263

2-{2-[3-(4-Methyl-piperazin-1-yl)-phenylamino]-[1,2,4]triazolo[1,5-a]pyridin-8-yloxymethyl}-benzonitrile

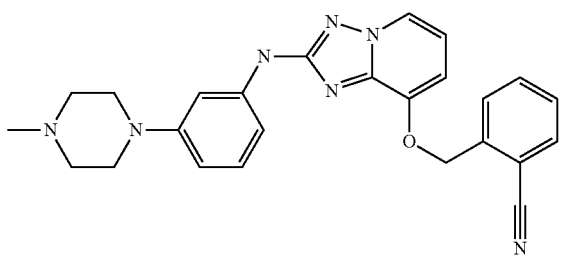 [SMILES: CN1CCN(c2cccc(Nc3nc4c(OCc5ccccc5C#N)cccn4n3)c2)CC1]

2-{2-[3-(4-Methyl-piperazin-1-yl)-phenylamino]-[1,2,4]triazolo[1,5-a]pyridin-8-yloxymethyl}benzonitrile was prepared from 2-(2-amino-[1,2,4]triazolo[1,5-a]pyridin-8-yloxymethyl)-benzonitrile (115.0 mg, 0.434 mmol) and 1-(3-bromo-phenyl)-4-methyl-piperazine (128 mg, 0.500 mmol in a manner analogous to Example 2d. Product was isolated as a pale orange solid (0.111 g, 58%). MP=68-70° C. (foam). $^1$H NMR (400 MHz, $(D_3C)_2SO$, δ, ppm): 9.46 (s, 1H), 8.43 (d, J=6.4 Hz, 1H), 7.95 (d, J=7.9 Hz, 1H), 7.81-7.79 (m, 2H), 7.64-7.62 (m, 1H), 7.33 (s, 1H), 7.20 (d, J=7.2 Hz, 1H), 7.09 (d, J=4.8 Hz, 2H), 6.96-6.92 (m, 1H), 6.47-6.44 (m, 1H), 5.50 (s, 2H), 3.12-3.09 (m, 4H), 2.44-2.42 (m, 4H), 2.22 (s, 3H). MS=440 (MH)+.

Example 264

2-[4-(4-Methyl-piperazin-1-yl)-phenylamino]-[1,2,4]triazolo[1,5-a]pyridin-8-ol

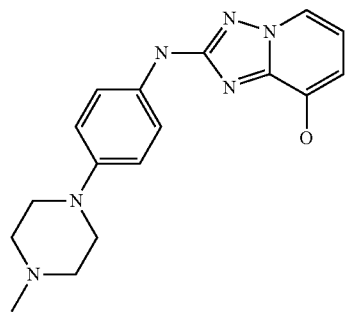 [SMILES: CN1CCN(c2ccc(Nc3nc4c(O)cccn4n3)cc2)CC1]

264) 2-[4-(4-Methyl-piperazin-1-yl)-phenylamino]-[1,2,4]triazolo[1,5-a]pyridin-8-ol was prepared from combining 2-{2-[4-(4-methyl-piperazin-1-yl)-phenylamino]-[1,2,4]triazolo[1,5-a]pyridin-8-yloxymethyl}-benzonitrile (30.0 mg, 0.68 mmol) and 10% palladium on carbon (50% Wet)(5:45:50, palladium:carbon black:water, 30 mg, 0.14 mmol) in methanol (10.0 mL) and shaking under an atmosphere of Hydrogen (45 psi) for 3 hours. Product was isolated as a mustard colored solid (14.0 mg, 63%). $^1$H NMR (400 MHz, $(D_3C)_2SO$, δ, ppm): 10.45 (bs, 1H), 9.12 (s, 1H), 8.21 (dd, J=6.4 Hz, 1.0 Hz, 1H), 7.53 (d, J=8.8 Hz, 2H), 6.88 (d, J=8.8 Hz, 2H), 6.80-6.76 (m, 2H), 3.04-3.02 (m, 4H), 2.47-2.44 (m, 4H), 2.22 (s, 3H). MS=325.2 (MH)+.

Example 265

(4-Methanesulfonyl-phenyl)-(8-methyl-[1,2,4]triazolo[1,5-a]pyridin-2-yl)-amine

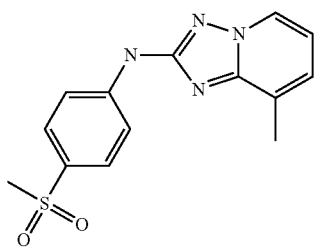 [SMILES: Cc1cccn2nc(Nc3ccc(S(C)(=O)=O)cc3)nc12]

265a) N-(3-methyl-2-pyridinyl)-N'-carboethoxy-thiourea was prepared from 3-methyl-pyridin-2-ylamine (3.93 g, 0.0363 mol) in a manner analogous to Example 2a. Product was isolated as a yellow solid.

265b) 8-Methyl-[1,2,4]triazolo[1,5-a]pyridin-2-ylamine was prepared from N-(3-methyl-2-pyridinyl)-N'-carboethoxy-thiourea (8.6 g, 36 mmol) in a manner analogous to Example 2b. Product was isolated as an off-white solid (3.96 g, 74%). $^1$H NMR (400 MHz, $(D_3C)_2SO$, δ, ppm): 8.36 (d, J=6.6 Hz, 1H), 7.21 (d, J=6.8 Hz, 1H), 6.78 (dd, J=6.8 Hz, 6.8 Hz, 1H), 5.96 (bs, 2H), 2.39 (s, 3H). MS=149.0 (MH)+.

265c) (4-Methanesulfonyl-phenyl)-(8-methyl-[1,2,4]triazolo[1,5-a]pyridin-2-yl)-amine was prepared from 8-methyl-[1,2,4]triazolo[1,5-a]pyridin-2-ylamine (500 mg, 3.37 mmol) and 1-bromo-4-methanesulfonyl-benzene (973 mg, 1.23 mmol) in a manner analogous to Example 2d. Product was isolated as an off-white solid (0.369 g, 36%). MP=227-230° C. $^1$H NMR (400 MHz, $(D_3C)_2SO$, δ, ppm): 10.35 (s, 1H), 8.67 (d, J=6.9 Hz, 1H), 7.88 (d, J=8.9 Hz, 2H), 7.82 (d, J=8.9 Hz, 2H), 7.42 (d, J=7.1 Hz, 1H0, 6.99 (dd, J=7.1 Hz, 7.1 Hz, 1H), 3.14 (s, 3H). MS=303 (MH)+.

Example 266

2-{2-[3-(4-Methyl-piperazin-1-yl)-phenylamino]-[1,2,4]triazolo[1,5-a]pyridin-8-yloxymethyl}-benzamide

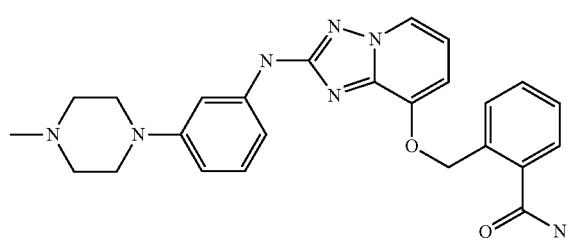 [SMILES: CN1CCN(c2cccc(Nc3nc4c(OCc5ccccc5C(N)=O)cccn4n3)c2)CC1]

266) 2-{2-[3-(4-Methyl-piperazin-1-yl)-phenylamino]-[1,2,4]triazolo[1,5-a]pyridin-8-yloxymethyl}-benzonitrile (0.0300 g, 0.0682 mmol) was dissolved in dimethyl sulfoxide (0.682 mL, 9.62 mmol) and cooled to 0° C. Hydrogen peroxide in water (9 M, 0.341 mL, 3.01 mmol) and potassium carbonate (45.5 mg, 0.329 mmol) were added to the frozen mixture, which was then allowed to warm to room temperature and stirred for an additional 30 min. The solution was cooled to 0° C. and water (11.4 mL, 631 mmol) was added. The precipitated product was filtered off and washed with water. The reaction mixture was purified by reverse phase chromatography. Product was isolated as a white lyophilate as the trifluoroacetic acid salt (6 mg, 20%). $^1$H NMR (400 MHz, $(D_3C)_2SO$, δ, ppm): 9.61 (bs, 1H), 9.55 (s, 1 h), 8.37 (d, J=6.6 Hz, 1H), 7.92 (s, 1H), 7.67 (d, J=7.6 Hz, 1H), 7.60 (d, J=7.7 Hz, 1H), 7.54-7.42 (m, 3H), 7.33-7.32 (m, 1H), 7.23 (d, J=8.3 Hz, 1H), 7.19-7.14 (m, 1H), 7.06 (d, J=7.4 Hz, 1H), 6.93-6.89 (m, 1H), 6.55 (dd, J=8.3 Hz, 1.6 Hz, 1H), 5.55 (s, 2H), 3.77 (d, J=13.9 Hz, 2H), 3.51 (d, J=12.8 Hz, 2H), 3.21-3.16 (m, 2H), 3.00-2.88 (m, 2H), 2.87 (d, J=4.4 Hz, 3H). MS=303 (MH)+.

Example 267

N-{3-[8-(4-Methanesulfonyl-phenyl)-[1,2,4]triazolo[1,5-a]pyridin-2-ylamino]-phenyl}-acetamide

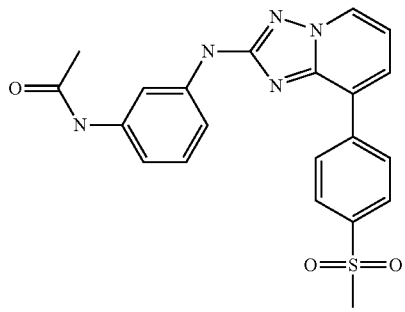 [SMILES: CC(=O)Nc1cccc(Nc2nc3c(-c4ccc(S(C)(=O)=O)cc4)cccn3n2)c1]

267) N-{3-[8-(4-Methanesulfonyl-phenyl)-[1,2,4]triazolo[1,5-a]pyridin-2-ylamino]-phenyl}-acetamide was prepared from 8-(4-methanesulfonyl-phenyl)-[1,2,4]triazolo[1,5-a]pyridin-2-ylamine (70.6 mg, 0.245 mmol) and N-(3-bromo-phenyl)-acetamide (52.4 mg, 0.245 mmol) in a manner analogous to Example 2d. Product isolated as a white lyophilate (19 mg, 18%). $^1$H NMR (400 MHz, $(D_3C)_2SO$, δ, ppm): 9.89 (s, 1H), 9.77 (s, 1H), 8.83 (d, J=6.5 Hz, 1H), 8.46 (d, J=8.4 Hz, 2H), 8.07 (d, J=8.6 Hz, 2H), 7.99-7.95 (m, 2H), 7.40 (d, J=8.0 Hz, 1H), 7.21-7.12 (m, 3H), 3.29 (s, 3H), 2.06 (s, 3H). MS=422 (MH)+.

Example 268

[8-(2-Chloro-5-trifluoromethyl-phenyl)-[1,2,4]triazolo[1,5-a]pyridin-2-yl]-[3-(2-methanesulfonylethyl)-2,3,4,5-tetrahydro-1H-benzo[d]azopin-7-yl]-amine

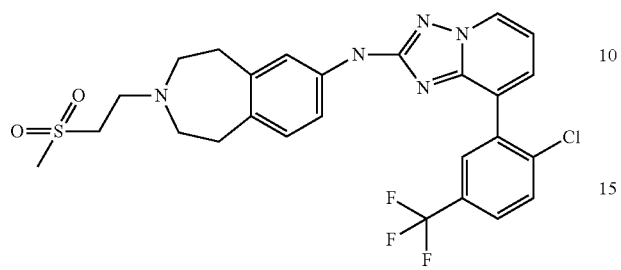

268a) 2-Chloro-8-(2-chloro-5-trifluoromethyl-phenyl)-[1,2,4]triazolo[1,5-a]pyridine was prepared from 8-bromo-2-chloro-[1,2,4]triazolo[1,5-a]pyridine (0.50 g, 2.15 mmol) and 2-chloro-5-trifluoromethylphenylboronic acid (0.72 g, 3.23 mmol) in a manner analogous to Example 2c (0.115 g, 16%). MP=156-158° C. MS=332 (MH)+.

268b) 7-[8-(2-Chloro-5-trifluoromethyl-phenyl)-[1,2,4]triazolo[1,5-a]pyridine-2-ylamino]-1,2,4,5-tetrahydro-3-benzazepine-3-carboxylic acid tert-butyl ester was prepared from 2-chloro-8-(2-chloro-5-trifluoromethyl-phenyl)-[1,2,4]triazolo[1,5-a]pyridine (0.62 g, 1.87 mmol) and 7-amino-1,2,4,5-tetrahydro-3-benzazepin-3-carboxylic acid tert-butyl ester (0.59 g, 2.25 mmol), with 2,2'-bis-dicyclohexylphosphanyl-biphenyl (0.26 g, 0.47 mmol) as the ligand in a manner analogous to Example 2d (0.089 g, 8.5%). MP=88-89° C. $^1$H NMR (400 MHz, (D$_3$C)$_2$SO, δ, ppm): 9.65 (s, 1H), 8.87 (d, 1H), 8.1 (m, 1H), 7.88 (d, 1H), 7.75 (m, 2H), 7.45 (d, 1H), 7.40 (s, 1H), 7.20 (t, 1H), 7.10 (d, 1H), 3.50 (m, 4H), 2.75 (m, 4H), 1.40 (s, 9H). MS=558 (MH)+.

268c) 7-[8-(2-Chloro-5-trifluoromethyl-phenyl)-[1,2,4]triazolo[1,5-a]pyridine-2-ylamino]-1,2,4,5-tetrahydro-3-benzazepine-3-carboxylic acid tert-butyl ester (0.089 mg, 0.16 mmol) in dichloromethane (2.0 mL) was added trifluoroacetic acid (0.10 mL, 1.6 mmoL) dropwise at room temperature, and the reaction was stirred at room temperature for 30 min. The solvent was evaporated, and the residue was diluted with dichloromethane, washed with 5% sodium carbonate solution, brine, dried over sodium sulfate, and concentrated to give the product [8-(2-chloro-5-trifluoromethyl-phenyl)-[1,2,4]triazolo[1,5-a]pyridine-2-yl]-(2,3,4,5-tetrahydro-1H-3-benzazepin-7-yl)-amine (0.052 g, 83%). MS=558 (MH)+.

268d) To a solution of [8-(2-chloro-5-trifluoromethyl-phenyl)-[1,2,4]triazolo[1,5-a]pyridine-2-yl]-(2,3,4,5-tetrahydro-1H-3-benzazepin-7-yl)-amine (0.022 g, 0.044 mmol) in N,N-dimethylformamide (2.0 mL) was added 1-chloro-2-methanesulfonylethane (0.013 g, 0.08 mmoL), potassium carbonate (18.3 mg, 0.132 mmol), and catalytic amount of sodium iodide under nitrogen. The mixture was heated to 80° C. overnight. The reaction was cooled to room temperature, diluted with ethyl acetate, and the solution was washed with 5% of sodium bicarbonate solution, brine, dried over sodium sulfate and concentrated. Preparatory TLC (silica gel 5% methanol in dichloromethane) gave [8-(2-Chloro-5-trifluoromethyl-phenyl)-[1,2,4]triazolo[1,5-a]pyridin-2-yl]-[3-(2-methanesulfonyl-ethyl)-2,3,4,5-tetrahydro-1H-benzo[d]azopin-7-yl]-amine (0.018 g, 72%). MP=110-112° C. $^1$H NMR (400 MHz, (D$_3$C)$_2$SO, δ, ppm): 9.65 (s, 1H), 8.87 (d, 1H), 8.1 (s, 1H), 7.88 (s, 1H), 7.75 (d, 2H), 7.45 (d, 1H), 7.40 (s, 1H), 7.10 (t, 1H), 7.05 (d, 1H), 3.02 (s, 3H), 2.85 (m, 2H), 2.75 (m, 4H), 2.52 (m, 6H). MS=564 (MH)+.

Example 269

[8-(2-Fluoro-5-trifluoromethyl-phenyl)-[1,2,4]triazolo[1,5-a]pyridin-2-ylamino]-[2,3,4,5-tetrahydro-1H-benzo[d]azopin-7-yl]-3-carboxylic acid tert-butyl ester

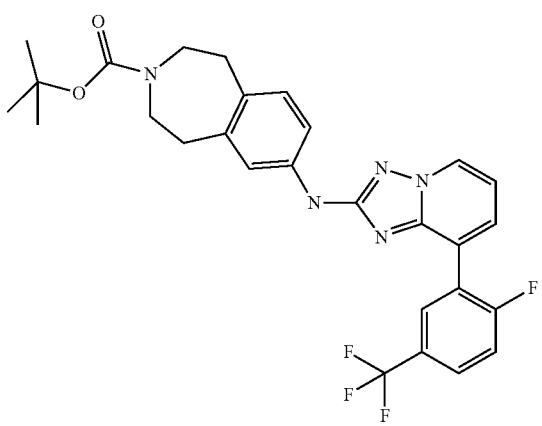 [SMILES: CC(C)(C)OC(=O)N1CCc2ccc(Nc3nc4c(-c5cc(C(F)(F)F)ccc5F)cccn4n3)cc2CC1]

269a) 2-Chloro-8-(2-fluoro-5-trifluoromethyl-phenyl)-[1,2,4]triazolo[1,5-a]pyridine was prepared from 8-bromo-2-chloro-[1,2,4]triazolo[1,5-a]pyridine and 2-fluoro-5-trifluoromethylphenylboronic acid in a manner analogous to Example 2c (0.150 g, 22%). MP=88-89° C. MS=317 (MH)+.

269b) [8-(2-Fluoro-5-trifluoromethyl-phenyl)-[1,2,4]triazolo[1,5-a]pyridin-2-ylamino]-[2,3,4,5-tetrahydro-1H-benzo[d]azopin-7-yl]-3-carboxylic acid tert-butyl ester was prepared from 2-chloro-8-(2-fluoro-5-trifluoromethyl-phenyl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.058 g, 21%). MP=144-146° C. $^1$H NMR (400 MHz, (D$_3$C)$_2$SO, δ, ppm): 9.75 (s, 1H), 8.90 (d, 1H), 8.1 (m, 1H), 7.88 (d, 1H), 7.75 (m, 2H), 7.45 (d, 1H), 7.40 (s, 1H), 7.20 (t, 1H), 7.10 (d, 1H), 3.45 (m, 4H), 2.75 (m, 4H), 1.40 (s, 9H). MS=542 (MH)+.

Example 270

[8-(2-Fluoro-5-trifluoromethyl-phenyl)-[1,2,4]triazolo[1,5-a]pyridin-2-yl]-[2,3,4,5-tetrahydro-1H-benzo[d]azopin-7-yl]-amine

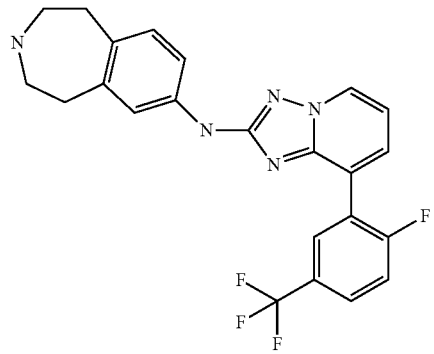 [SMILES: Fc1ccc(C(F)(F)F)cc1-c1cccn2nc(Nc3ccc4c(c3)CCNCC4)nc12]

[8-(2-Fluoro-5-trifluoromethyl-phenyl)-[1,2,4]triazolo[1,5-a]pyridin-2-yl]-[2,3,4,5-tetrahydro-1H-benzo[d]azopin-7-yl]-amine was prepared from [8-(2-Fluoro-5-trifluoromethyl-phenyl)-[1,2,4]triazolo[1,5-a]pyridin-2-ylamino]-[2,3,4,5-tetrahydro-1H-benzo[d]azopin-7-yl]-3-carboxylic acid tert-butyl ester in manner analogous to Example 268c (0.12 g, 86%). MP=137-139° C. $^1$H NMR (400 MHz, (D$_3$C)$_2$SO, δ, ppm): 9.65 (s, 1H), 8.90 (d, 1H), 8.1 (m, 1H), 7.88 (d, 1H), 7.75 (m, 2H), 7.45 (d, 1H), 7.40 (s, 1H), 7.20 (t, 1H), 7.10 (d, 1H), 2.85 (m, 9H). MS=442 (MH)+.

Example 271

[4-{4-[8-(2-Methoxy-pyridin-3-yl)-[1,2,4]triazolo[1,5-a]pyridin-2-ylamino]-phenyl}-piperidine-1-carboxylic acid tert-butyl ester

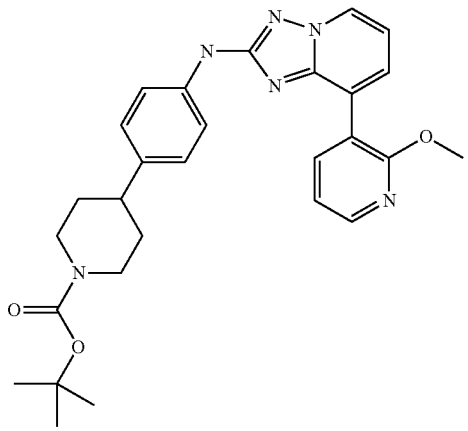 [SMILES: COc1ncccc1-c1cccn2nc(Nc3ccc(C4CCN(C(=O)OC(C)(C)C)CC4)cc3)nc12]

271a) 2-Chloro-8-(2-methoxy-pyridin-3-yl)-[1,2,4]triazolo[1,5-a]pyridine was prepared from 8-bromo-2-chloro-[1,2,4]triazolo[1,5-a]pyridine and 2-fluoro-5-trifluoromethylphenylboronic acid in a manner analogous to Example 2c (0.47 g, 84%). MP=218-219° C. MS=261 (MH)+.
271b) [4-{4-[8-(2-Methoxy-pyridin-3-yl)-[1,2,4]triazolo[1,5-a]pyridin-2-ylamino]-phenyl}-piperidine-1-carboxylic acid tert-butyl ester was prepared from 2-Chloro-8-(2-methoxy-pyridin-3-yl)-[1,2,4]triazolo[1,5-a]pyridine and 4-(4-amino-phenyl)-piperidine-1-carboxylic acid tert-butyl ester with 2,2'-bis-dicyclohexylphosphanyl-biphenyl as the ligand in a manner analogous to Example 2d (0.25 g, 50%). MP=101-103° C. $^1$H NMR (400 MHz, (D$_3$C)$_2$SO, δ, ppm): 9.75 (s, 1H), 8.80 (d, J=6.58 Hz, 1H), 8.25 (m, 1H), 8.05 (d, 1H), 7.75 (m, 1H), 7.55 (m, 2H), 7.02 (m, 4H), 4.05 (m, 2H), 3.90 (s, 3H), 2.6-2.8 (m, 3H), 1.65 (m, 2H), 1.40 (m, 11H). MS=501 (MH)+.

Example 272

8-(2-Methoxy-pyridin-3-yl)-[1,2,4]triazolo[1,5-a]pyridin-2-yl]-(4-piperidin-4-yl-phenyl)-amine

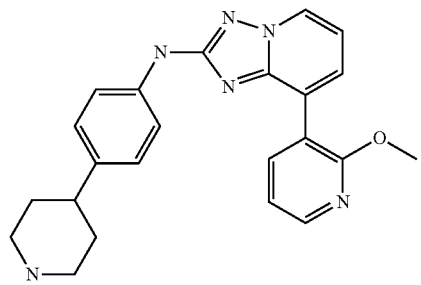 [SMILES: COc1ncccc1-c1cccn2nc(Nc3ccc(C4CCNCC4)cc3)nc12]

8-(2-Methoxy-pyridin-3-yl)-[1,2,4]triazolo[1,5-a]pyridin-2-yl]-(4-piperidin-4-yl-phenyl)-amine was prepared from [4-{4-[8-(2-Methoxy-pyridin-3-yl)-[1,2,4]triazolo[1,5-a]pyridin-2-ylamino]-phenyl}-piperidine-1-carboxylic acid tert-butyl ester in a manner analogous to Example 268c (0.18 g, 94%). MP=184-186° C. $^1$H NMR (400 MHz, (D$_3$C)$_2$SO, δ, ppm): 9.65 (s, 1H), 8.80 (d, 1H), 8.25 (d, 1H), 8.05 (d, 1H), 7.75 (m, 1H), 7.55 (m, 2H), 7.02 (m, 4H), 3.90 (s, 3H), 3.01 (m, 2H), 2.5-2.6 (m, 4H), 1.65 (m, 2H), 1.50 (m, 2H). MS=401 (MH)+.

Example 273

2-(4-{4-[8-(2-Methoxy-pyridin-3-yl)-[1,2,4]triazolo[1,5-a]pyridine-2-ylamino]-phenyl}-piperidin-1-yl)-N,N-dimethyl-acetamide

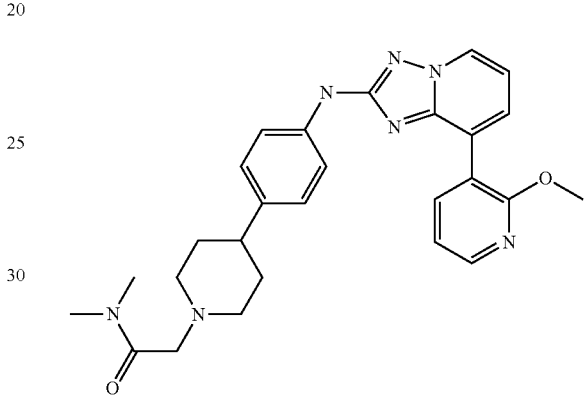

2-(4-{4-[8-(2-Methoxy-pyridin-3-yl)-[1,2,4]triazolo[1,5-a]pyridine-2-ylamino]-phenyl}-piperidin-1-yl)-N,N-dimethyl-acetamide was prepared from 8-(2-Methoxy-pyridin-3-yl)-[1,2,4]triazolo[1,5-a]pyridin-2-yl]-(4-piperidin-4-yl-phenyl)-amine and 2-chloro-N,N-dimethyl-acetamide in a manner analogous to Example 268d (0.085 g, 70%). MP=173-175° C. $^1$H NMR (400 MHz, (D$_3$C)$_2$SO, δ, ppm): 9.75 (s, 1H), 8.80 (d, 1H), 8.25 (m, 1H), 8.05 (d, 1H), 7.75 (m, 1H), 7.55 (m, 2H), 7.02 (m, 4H), 4.05 (m, 2H), 3.90 (s, 3H), 3.20 (s, 2H), 3.05 (s, 3H), 2.95 (m, 2H), 2.75 (s, 3H), 2.40 (m, 1H), 2.10 (m, 2H), 1.60 (m, 4H). MS=486 (MH)+.

Example 274

[8-(2-Methoxy-pyridin-3-yl)-[1,2,4]triazolo[1,5-a]pyridine-2-yl]-quinolin-6-yl-amine

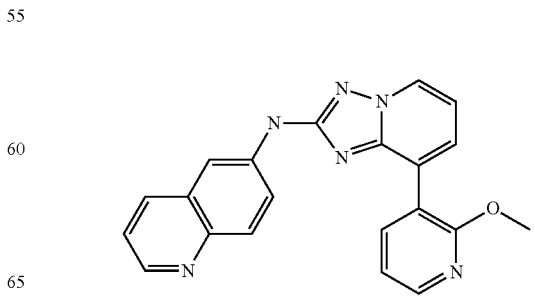

[8-(2-Methoxy-pyridin-3-yl)-[1,2,4]triazolo[1,5-a]pyridine-2-yl]-quinolin-6-yl-amine was prepared from 2-chloro-8-(2-methoxy-pyridin-3-yl)-[1,2,4]triazolo[1,5-a]pyridine and quinolin-6-ylamine in a manner analogous to Example 2d (0.12 g, 65%). MP=247-249° C. $^1$H NMR (400 MHz, (D$_3$C)$_2$SO, δ, ppm): 10.18 (s, 1H), 8.88 (d, J=6.58 Hz, 1H), 8.75 (d, 1H), 8.45 (d, 1H), 8.25 (d, 1H), 8.15 (t, 1H), 7.85-7.90 (m, 2H), 7.55 (m, 1H), 7.42 (m, 1H), 7.10 (m, 1H), 3.90 (s, 3H). MS=369 (MH)+.

Example 275

N,N-Dimethyl-2(4-{4-[8-(2-oxo-1,2-dihydro-pyridin-3-yl)-[1,2,4]triazolo[1,5-a]pyridine-2-ylamino]-phenyl}-piperidin-1-yl)-acetamide

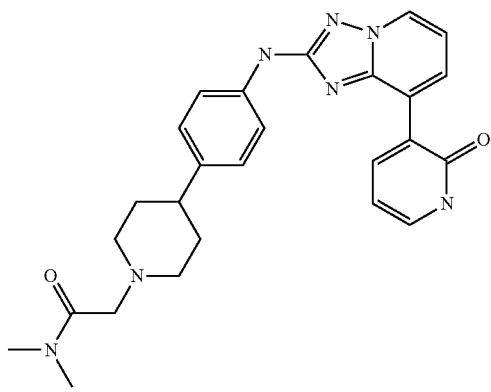 [SMILES: CN(C)C(=O)CN1CCC(c2ccc(Nc3nc4c(-c5ccc[nH]c5=O)cccn4n3)cc2)CC1]

A solution of 2-(4-{4-[8-(2-Methoxy-pyridin-3-yl)-[1,2,4]triazolo[1,5-a]pyridine-2-ylamino]-phenyl}-piperidin-1-yl)-N,N-dimethyl-acetamide (25 mg, 0.052 mmol) in acetic acid (1.3 mL) was added sodium iodide (15.4 mg, 0.103 mmol), and the reaction was stirred at 100° C. for 3 hours. The solvent was evaporated and the residue was diluted with dichloromethane. The dichloromethane solution was washed with 10% sodium thiosulfate solution, brine then dried over sodium sulfate, and concentrated. The product was purified by preparatory TLC (silica gel 10% methanol in dichloromethane) to give the product (13 mg, 54%). MP: >250° C. $^1$H NMR (400 MHz, (D$_3$C)$_2$SO, δ, ppm): 12.0 (bs, 1H), 9.60 (s, 1H), 8.88 (d, J=6.58 Hz, 1H), 8.75 (d, 1H), 8.45 (d, 1H), 7.70 (d, 2H), 7.50 (m, 1H), 7.20 (m, 2H), 7.05 (t, 1H), 6.45 (t, 1H), 3.25 (s, 2H), 3.05 (s, 3H), 2.90 (m, 2H), 2.78 (s, 3H), 2.45 (m, 1H), 2.10 (m, 2H), 1.85-1.90 (m, 4H). MS=472 (MH)+.

Example 276

3-[2-(Quinolin-6-ylamino)-[1,2,4]triazolo[1,5-a]pyridin-8-yl]-1H-pyridin-2-one

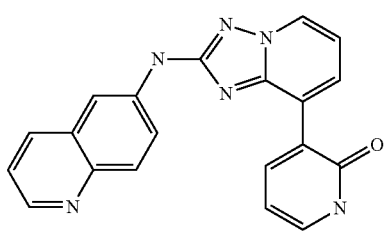 [SMILES: O=c1[nH]cccc1-c1cccn2nc(Nc3ccc4ncccc4c3)nc12]

3-[2-(Quinolin-6-ylamino)-[1,2,4]triazolo[1,5-a]pyridin-8-yl]-1H-pyridin-2-one was prepared from [8-(2-methoxy-pyridin-3-yl)-[1,2,4]triazolo[1,5-a]pyridine-2-yl]-quinolin-6-yl-amine in a manner analogous to Example 275 (0.010 g, 71%). MP: >250° C. $^1$H NMR (400 MHz, (D$_3$C)$_2$SO, δ, ppm): 12.01 (bs, 1H), 10.18 (s, 1H), 8.88 (d, 1H), 8.75 (d, 1H), 8.45 (d, 1H), 8.25 (d, 1H), 7.95 (t, 1H), 7.65-7.75 (m, 2H), 7.05 (t, 1H), 6.49 (t, 1H). MS=355 (H)+.

Example 277

4-{4-[8-(2-Methoxy-5-trifluoromethyl-pyridin-3-yl)-[1,2,4]triazolo[1,5-a]pyridine-2-ylamino]-phenyl}-piperidine-1-carboxylic acid tert-butyl ester

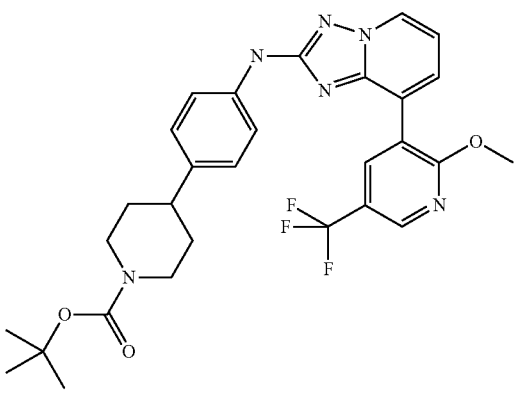 [SMILES: COc1ncc(C(F)(F)F)cc1-c1cccn2nc(Nc3ccc(C4CCN(C(=O)OC(C)(C)C)CC4)cc3)nc12]

277a) 2-Chloro-8-(2-methoxy-5-trifluoromethyl-pyridin-3-yl)-[1,2,4]triazolo[1,5-a]pyridine was prepared from 8-bromo-2-chloro-[1,2,4]triazolo[1,5-a]pyridine and 2-methoxy-5-trifluoromethylpyridineboronic acid in a manner analogous to Example 2c (0.46 g, 65%). MP=183-185° C. MS=329 (MH)+.

277b) [4-{4-[8-(2-Methoxy-5-trifluoromethyl-pyridin-3-yl)-[1,2,4]triazolo[1,5-a]pyridine-2-ylamino]-phenyl}-piperidine-1-carboxylic acid tert-butyl ester was prepared from 2-chloro-8-(2-methoxy-5-trifluoromethyl-pyridin-3-yl)-[1,2,4]triazolo[1,5-a]pyridine and 4-(4-amino-phenyl)-piperidine-1-carboxylic acid tert-butyl ester, with 2,2'-bis-dicyclohexylphosphanyl-biphenyl as the ligand in a manner analogous to Example 2d (0.233 g, 41%). MP=142-144° C. $^1$H NMR (400 MHz, (D$_3$C)$_2$SO, δ, ppm): 9.75 (s, 1H), 8.80 (d, 1H), 8.65 (s, 1H), 8.55 (s, 1H), 7.85 (d, 1H), 7.55 (d, 2H), 7.02 (m, 3H), 4.05 (m, 2H), 3.90 (s, 3H), 2.6-2.8 (m, 3H), 1.65 (m, 2H), 1.40 (m, 11H). MS=569 (MH)+.

Example 278

[8-(2-Methoxy-5-trifluoromethyl-pyridin-3-yl)-[1,2,4]triazolo[1,5-a]pyridine-2-yl]-(4-piperidine-4-yl-phenyl)-amine

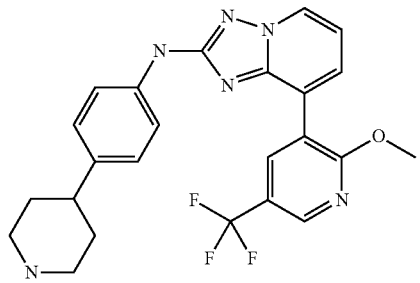 [SMILES: COc1ncc(C(F)(F)F)cc1-c1cccn2nc(Nc3ccc(C4CCNCC4)cc3)nc12]

[8-(2-Methoxy-5-trifluoromethyl-pyridin-3-yl)-[1,2,4]triazolo[1,5-a]pyridine-2-yl]-(4-piperidine-4-yl-phenyl)-amine was prepared from 4-{4-[8-(2-methoxy-5-trifluoromethyl-pyridin-3-yl)-[1,2,4]triazolo[1,5-a]pyridine-2-ylamino]-phenyl}-piperidine-1-carboxylic acid tert-butyl ester in a manner analogous to Example 268c (0.21 g, 93%). MP=106-108° C. $^1$H NMR (400 MHz, $(D_3C)_2SO$, δ, ppm): 9.65 (s, 1H), 8.80 (d, 1H), 8.75 (s, 1H), 8.55 (s, 1H), 7.85 (d, 1H), 7.55 (d, 2H), 7.10 (m, 3H), 3.90 (s, 3H), 3.01 (m, 2H), 2.50 (m, 4H), 1.65 (m, 2H), 1.50 (m, 2H). MS=469 (MH)+.

Example 279

2-(4-{4-[8-(2-Methoxy-5-trifluoromethyl-pyridin-3-yl)-[1,2,4]triazolo[1,5-a]pyridin-2-ylamino]-phenyl}-piperidin-1-yl)-N,N-dimethyl-acetamide

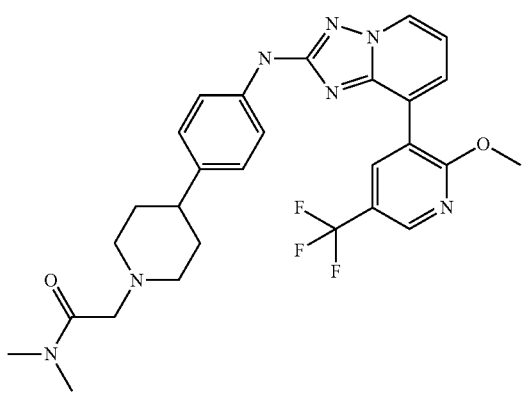

2-(4-{4-[8-(2-Methoxy-5-trifluoromethyl-pyridin-3-yl)-[1,2,4]triazolo[1,5-a]pyridin-2-ylamino]-phenyl}-piperidin-1-yl)-N,N-dimethyl-acetamide prepared from [8-(2-Methoxy-5-trifluoromethyl-pyridin-3-yl)-[1,2,4]triazolo[1,5-a]pyridine-2-yl]-(4-piperidine-4-yl-phenyl)-amine in a manner analogous to Example 273 (0.069 g, 50%). MP=122-124° C. $^1$H NMR (400 MHz, $(D_3C)_2SO$, δ, ppm): 9.61 (s, 1H), 8.83 (d, 1H), 8.70 (s, 1H), 8.56 (s, 1H), 7.80 (m, 1H), 7.59 (m, 2H), 7.14 (m, 3H), 3.99 (s, 3H), 3.14 (bs, 2H), 3.05 (s, 3H), 2.93 (m, 2H), 2.84 (s, 3H), 2.39 (m, 1H), 2.13 (m, 2H), 1.58-1.73 (m, 4H). MS=554 (MH)+.

Example 280

4-{4-[8-(1-(4-Fluoro-phenyl)-1H-pyrazol-4-yl)-[1,2,4]triazolo[1,5-a]pyridine-2-ylamino]-phenyl}-piperidine-1-carboxylic acid tert-butyl ester

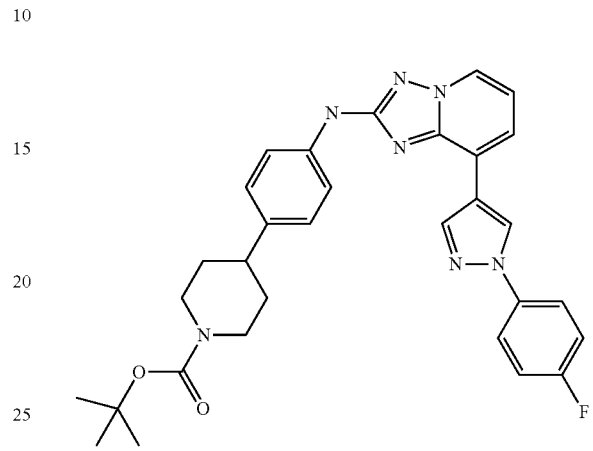

280a) 2-Chloro-8-([1-(4-fluoro-phenyl)1H-pyrazol-4-yl]-[1,2,4]triazolo[1,5-a]pyridine was prepared from 8-bromo-2-chloro-[1,2,4]triazolo[1,5-a]pyridine and 1-(4-fluorophenyl)pyrazole-4-boronic acid in a manner analogous to Example 2c (0.45 g, 67%).

280b) 4-{4-[8-(1-(4-Fluoro-phenyl)-1H-pyrazol-4-yl)-[1,2,4]triazolo[1,5-a]pyridine-2-ylamino]-phenyl}-piperidine-1-carboxylic acid tert-butyl ester was prepared from 2-chloro-8-([1-(4-fluoro-phenyl)1H-pyrazol-4-yl]-[1,2,4]triazolo[1,5-a]pyridine and 4-(4-amino-phenyl)-piperidine-1-carboxylic acid tert-butyl ester with 2,2'-bis-dicyclohexylphosphanyl-biphenyl as the ligand in a manner analogous to Example 2d (0.077 g, 23%). MP=176-178° C. $^1$H NMR (400 MHz, $(D_3C)_2SO$, δ, ppm): 9.62 (s, 1H), 9.26 (s, 1H), 8.76 (m, 2H), 7.95 (m, 3H), 7.65 (m, 2H), 7.45 (m, 2H), 7.15 (m, 2H), 7.09 (m, 1H), 4.08 (m, 2H), 2.80 (m, 2H), 2.63 (m, 1H), 1.73 (m, 2H), 1.48 (m, 2H), 1.42 (s, 9H). MS=554 (MH)+.

Example 281

4-{4-[8-(4-Acetylamino-phenylsulfanyl)-[1,2,4]triazolo[1,5-a]pyridine-2-ylamino]-phenyl}-piperidine-1-carboxylic acid tert-butyl ester

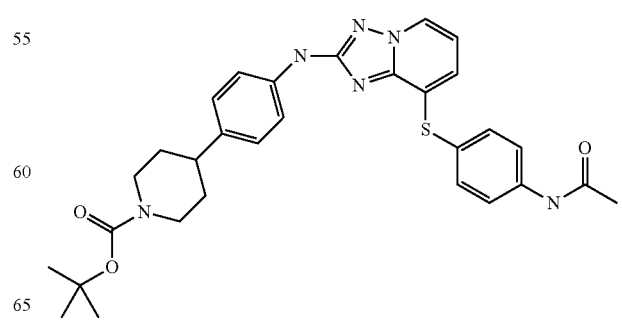

281a) A solution of 8-bromo-2-chloro-[1,2,4]triazolo[1,5-a]pyridine (0.47 g, 2.00 mmol) in dioxane (6.0 mL) was added tris(dibenzylideneacetone)dipalladium(0) (0.256 g, 0.28 mmol), 9,9-dimethyl-4,5-bis(diphenylphosphino)xanthene (0.324 g, 0.56 mmol), N,N-disopropylethylamine (0.52 g, 4.00 mmol), and acetamidothiophenol (0.37 g, 2.20 mmol) under nitrogen. The mixture was degassed with nitrogen for 3 minutes, and then heated to 100° C. for 14 hours. The reaction was cooled to room temperature, filtered through diatomaceous earth, washed with dichloromethane, and concentrated. The residue was diluted with dichloromethane, washed with brine, dried over sodium sulfate, and concentrated. The crude was purified by flash chromatography (silica gel hexane to 5% methanol in dichloromethane) to give N-[4-(2-chloro-[1,2,4]triazolo[1,5-a]pyridine-8-ylsulfanyl)-phenyl]acetamide (0.51 g, 80%). MP=148-150° C. MS=319 (MH)+.

281b) 4-{4-[8-(4-Acetylamino-phenylsulfanyl)-[1,2,4]triazolo[1,5-a]pyridine-2-ylamino]-phenyl}-piperidine-1-carboxylic acid tert-butyl ester was prepared from N-[4-(2-chloro-[1,2,4]triazolo[1,5-a]pyridine-8-ylsulfanyl)-phenyl]acetamide and 4-(4-amino-phenyl)-piperidine-1-carboxylic acid tert-butyl ester with 2,2'-bis-dicyclohexylphosphanyl-biphenyl as the ligand in a manner analogous to Example 2d (0.023 g, 10%). MP=226-228° C. $^1$H NMR (400 MHz, (D$_3$C)$_2$SO, δ, ppm): 10.2 (s, 1H), 9.69 (s, 1H), 8.62 (d, 1H), 7.72 (m, 2H), 7.55 (m, 2H), 7.49 (m, 2H), 7.12 (m, 2H), 6.91 (m, 1H), 4.18 (bs, 2H), 2.78 (bs, 2H), 2.58 (m, 1H), 2.04 (s, 3H), 1.66 (m, 2H), 1.51 (m, 2H), 1.42 (s, 9H). MS=559 (MH)+.

Example 282

4-{4-[8-(1-(4-Fluoro-phenyl)-1H-pyrazol-4-yl)-[1,2,4]triazolo[1,5-a]pyridine-2-yl}-(4-piperidine-4-yl-phenyl)-amine

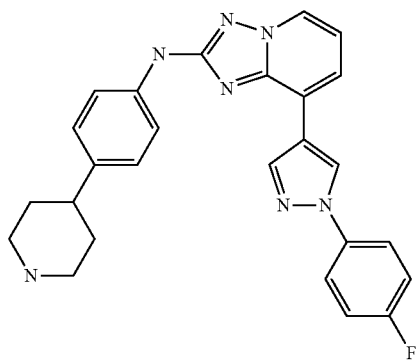 [SMILES: Fc1ccc(-n2cc(-c3cccn4nc(Nc5ccc(C6CCNCC6)cc5)nc34)cn2)cc1]

4-{4-[8-(1-(4-Fluoro-phenyl)-1H-pyrazol-4-yl)-[1,2,4]triazolo[1,5-a]pyridine-2-yl}-(4-piperidine-4-yl-phenyl)-amine was prepared from 4-{4-[8-(1-(4-fluoro-phenyl)-1H-pyrazol-4-yl)-[1,2,4]triazolo[1,5-a]pyridine-2-ylamino]-phenyl}-piperidine-1-carboxylic acid tert-butyl ester in a manner analogous to Example 268c (0.057 g, 99%). MP=245-247° C. $^1$H NMR (400 MHz, (D$_3$C)$_2$SO, δ, ppm): 9.59 (s, 1H), 9.23 (s, 1H), 8.69 (m, 2H), 7.94 (m, 3H), 7.66 (m, 2H), 7.43 (m, 2H), 7.18 (m, 2H), 7.08 (m, 1H), 3.00 (m, 2H), 2.56 (m, 4H), 1.65 (m, 2H), 1.47 (m, 2H). MS=454 (MH)+.

Example 283

2-[4-(4-{8-{1-(4-Fluoro-phenyl)1H-pyrazol-4-yl}-[1,2,4]triazolo[1,5-a]pyridine-2-ylamino}-phenyl)-piperidin-1-yl]-N,N-dimethyl-acetamide

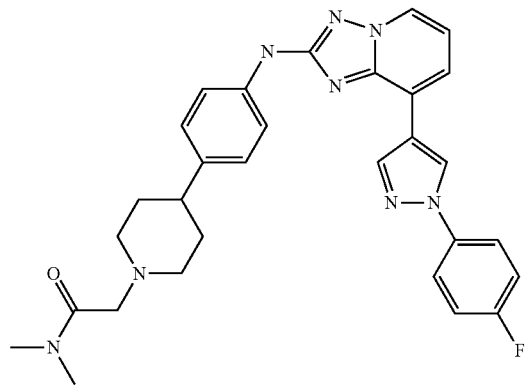 [SMILES: CN(C)C(=O)CN1CCC(c2ccc(Nc3nc4c(-c5cnn(-c6ccc(F)cc6)c5)cccn4n3)cc2)CC1]

2-[4-(4-{8-{1-(4-Fluoro-phenyl)1H-pyrazol-4-yl}-[1,2,4]triazolo[1,5-a]pyridine-2-ylamino}-phenyl)-piperidin-1-yl]-N,N-dimethyl-acetamide was prepared from 4-{4-[8-(1-(4-fluoro-phenyl)-1H-pyrazol-4-yl)-[1,2,4]triazolo[1,5-a]pyridine-2-yl}-(4-piperidine-4-yl-phenyl)-amine in a manner analogous to Example 273 (0.026 g, 44%). MP=131-133° C. $^1$H NMR (400 MHz, (D$_3$C)$_2$SO, δ, ppm): 9.60 (s, 1H), 9.29 (s, 1H), 8.68 (d, 2H), 7.95 (m, 3H), 7.66 (m, 2H), 7.47 (m, 2H), 7.20 (m, 2H), 7.10 (m, 1H), 3.13 (s, 2H), 3.05 (s, 3H), 2.95 (m, 2H), 2.84 (s, 3H), 2.41 (m, 1H), 2.14 (m, 2H), 1.67 (m, 4H). MS=539 (MH)+.

Example 284

4-{4-[8-(5-Methoxy-pyrazin-2-yl)-[1,2,4]triazolo[1,5-a]pyridine-2-ylamino]-phenyl}-piperidine-1-carboxylic acid tert-butyl ester

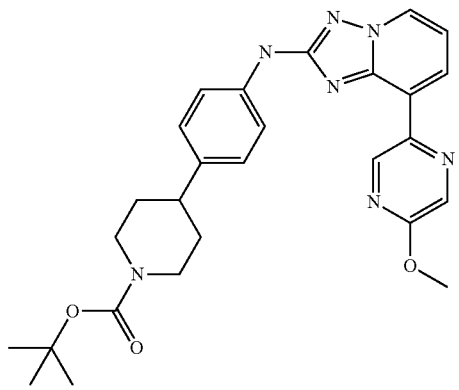 [SMILES: COc1cnc(-c2cccn3nc(Nc4ccc(C5CCN(C(=O)OC(C)(C)C)CC5)cc4)nc23)cn1]

284a) A solution of 8-bromo-2-chloro-[1,2,4]triazolo[1,5-a]pyridine (0.29 g, 1.25 mmol) in anhydrous tetrahydrofuran (6.0 mL) was cooled to −78° C. under nitrogen as n-butyllithium (2N in tetrahydrofuran, 1.87 mmol) was added dropwise. The mixture was stirred at −78° C. for 30 minutes then trimethylboronate (0.213 mL, 1.87 mmol) was added, and the reaction was slowly warmed and stirred at room temperature for 2 hours. Hydrochloric acid solution (2N, 2 mL) was added and the reaction was stirred for 1 hour then extracted with dichloromethane, combined, and concentrated. The crude was triturated with ether to give 2-chloro-[1,2,4]triazolo[1,5-a]pyridine-8-boronic acid (0.174 g, 69%). MP=227-229° C. MS=198 (MH)+.

284b) 2-Chloro-8-(5-methoxy-pyrazin-2-yl)-[1,2,4]triazolo[1,5-a]pyridine was prepared from 8-bromo-2-chloro-[1,2,4]triazolo[1,5-a]pyridine and 2-chloro-[1,2,4]triazolo[1,5-a]pyridine-8-boronic acid in a manner analogous to Example 2c (0.115 g, 51%). %). MP=210° C. (dec.). MS=262 (MH)+.

284c) 4-{4-[8-(5-Methoxy-pyrazin-2-yl)-[1,2,4]triazolo[1,5-a]pyridine-2-ylamino]-phenyl}-piperidine-1-carboxylic acid tert-butyl ester was prepared from 2-chloro-8-(5-methoxy-pyrazin-2-yl)-[1,2,4]triazolo[1,5-a]pyridine and 4-(4-amino-phenyl)-piperidine-1-carboxylic acid tert-butyl ester with 2,2'-bis-dicyclohexylphosphanyl-biphenyl as the ligand in a manner analogous to Example 2d (0.039 g, 19%). MP=193-195° C. $^1$H NMR (400 MHz, (D$_3$C)$_2$SO, δ, ppm): 9.75 (s, 1H), 9.69 (s, 1H), 8.87 d, 1H), 8.49 (m, 1H), 8.35 (m, 1H), 7.65 (m, 2H), 7.20 (m, 3H), 4.08 (m, 2H), 4.02 (s, 3H), 2.80 (m, 2H), 2.62 (m, 1H), 1.72 (m, 2H), 1.51 (m, 2H), 1.40 (s, 9H). MS=502 (MH)+.

Example 285

4-{4-[8-(5-Methoxy-pyrazin-2-yl)-[1,2,4]triazolo[1,5-a]pyridine-2-yl]-(4-piperidin-4-yl-phenyl)-amine

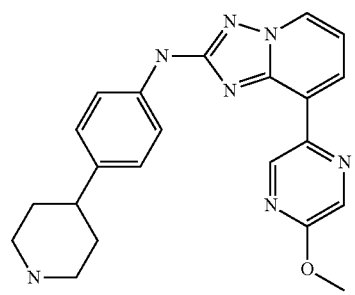 [SMILES: COc1cnc(-c2cccn3nc(Nc4ccc(C5CCNCC5)cc4)nc23)cn1]

4-{4-[8-(5-Methoxy-pyrazin-2-yl)-[1,2,4]triazolo[1,5-a]pyridine-2-yl]-(4-piperidin-4-yl-phenyl)-amine was prepared from 4-{4-[8-(5-methoxy-pyrazin-2-yl)-[1,2,4]triazolo[1,5-a]pyridine-2-ylamino]-phenyl}-piperidine-1-carboxylic acid tert-butyl ester in a manner analogous to Example 268c (0.02 g, 99%). MP=219-221° C. $^1$H NMR (400 MHz, (D$_3$C)$_2$SO, δ, ppm): 9.74 (s, 1H), 9.67 (s, 1H), 8.84 (d, 1H), 8.50 (s, 1H), 8.34 (m, 1H), 7.64 (m, 2H), 7.18 (m, 3H), 4.00 (s, 3H), 3.00 (m, 2H), 2.57 (m, 4H), 1.70 (m, 2H), 1.48 (m, 2H). MS=402 (MH)+.

Example 286

2-(4-{4-[8-(5-Methoxy-pyrazin-2-yl)-[1,2,4]triazolo[1,5-a]pyridine-2-ylamino]-phenyl}-piperidin-1-yl)-N,N-dimethyl-acetamide

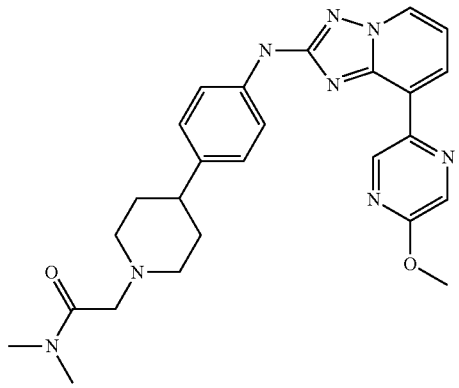

2-(4-{4-[8-(5-Methoxy-pyrazin-2-yl)-[1,2,4]triazolo[1,5-a]pyridine-2-ylamino]-phenyl}-piperidin-1-yl)-N,N-dimethyl-acetamide was prepared from 4-{4-[8-(5-methoxy-pyrazin-2-yl)-[1,2,4]triazolo[1,5-a]pyridine-2-yl]-(4-piperidin-4-yl-phenyl)-amine in a manner analogous to Example 273 (0.009 g, 20%). MP=185-187° C. $^1$H NMR (400 MHz, (D$_3$C)$_2$SO, δ, ppm): 9.73 (s, 1H), 9.68 (s, 1H), 8.84 (d, 1H), 8.51 (s, 1H), 8.35 (m, 1H), 7.66 (m, 2H), 7.21 (m, 3H), 4.00 (s, 3H), 3.14 (s, 2H), 3.05 (s, 3H), 2.93 (m, 2H), 2.82 (s, 3H), 2.43 (m, 1H), 2.13 (m, 2H), 1.60-1.75 (m, 4H). MS=487 (MH)+.

Example 287

4-{4-[8-(1-p-Tolyl-1H-pyrazol-4-yl)-[1,2,4]triazolo[1,5-a]pyridine-2-ylamino]-phenyl}-piperidine-1-carboxylic acid tert-butyl ester

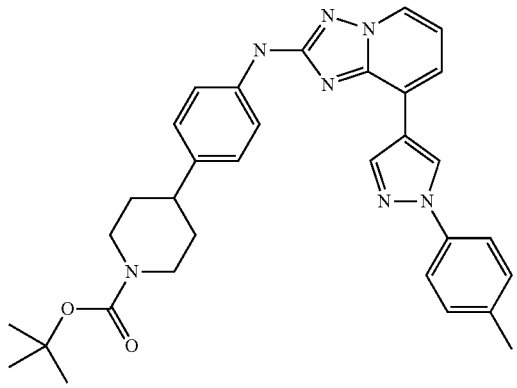 [SMILES: Cc1ccc(-n2cc(-c3cccn4nc(Nc5ccc(C6CCN(C(=O)OC(C)(C)C)CC6)cc5)nc34)cn2)cc1]

287a) 2-Chloro-8-(1-p-tolyl-1H-pyrazol-4-yl)-[1,2,4]triazolo[1,5-a]pyridine was prepared from 8-bromo-2-chloro-[1,2,4]triazolo[1,5-a]pyridine and 1-p-tolyl-pyrazole-4-boronic acid in a manner analogous to Example 2c (0.40 g, 68%).

287b) 4-{4-[8-(1-p-Tolyl-1H-pyrazol-4-yl)-[1,2,4]triazolo[1,5-a]pyridine-2-ylamino]-phenyl}-piperidine-1-carboxylic acid tert-butyl ester was prepared from 2-chloro-8-(1-p-tolyl-1H-pyrazol-4-yl)-[1,2,4]triazolo[1,5-a]pyridine and 4-(4-amino-phenyl)-piperidine-1-carboxylic acid tert-butyl ester with 2,2'-bis-dicyclohexylphosphanyl-biphenyl as the ligand in a manner analogous to Example 2d (0.265 g, 40%). MP=124-125° C. $^1$H NMR (400 MHz, (D$_3$C)$_2$SO, δ, ppm): 9.60 (s, 1H), 9.24 (s, 1H), 8.68 (d, 1H), 8.64 (s, 1H), 7.98 (m, 1H), 7.77 (m, 2H), 7.66 (m, 2H), 7.40 (m, 2H), 7.21 (m, 2H), 4.08 (m, 2H), 2.80 (m, 2H), 2.62 (m, 1H), 2.38 (s, 3H), 1.73 (m, 2H), 1.48 (m, 2H), 1.41 (s, 3H). MS=550 (MH)+.

Example 288

{8-[1-(4-Fluoro-phenyl)-1H-pyrazol-4-yl]-[1,2,4]triazolo[1,5-a]pyridine-2-yl}-[3-(4-methyl-piperazin-1-yl)-phenyl]-amine

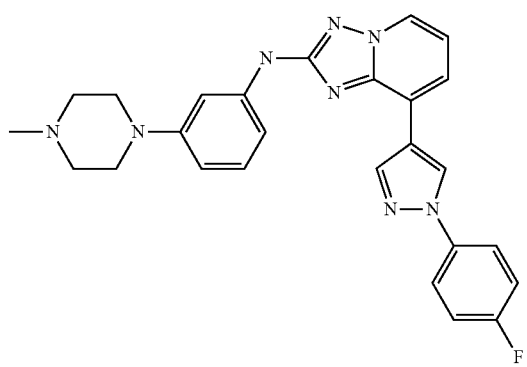 [SMILES: CN1CCN(c2cccc(Nc3nc4c(-c5cnn(-c6ccc(F)cc6)c5)cccn4n3)c2)CC1]

{8-[1-(4-Fluoro-phenyl)-1H-pyrazol-4-yl]-[1,2,4]triazolo[1,5-a]pyridine-2-yl}-[3-(4-methyl-piperazin-1-yl)-phenyl]-amine was prepared from 2-chloro-8-[1-(4-fluorophenyl)-1H-pyrazol-4-yl]-[1,2,4]triazolo[1,5-a]pyridine (Example 280a) and 3-(4-methylpiperazine-1-yl)aniline with 2,2'-bis-dicyclohexylphosphanyl-biphenyl as the ligand in a manner analogous to Example 2d (0.055 g, 20%). MP=216-218° C. $^1$H NMR (400 MHz, (D$_3$C)$_2$SO, δ, ppm): 9.53 (s, 1H), 9.25 (s, 1H), 8.67 (d, 2H), 7.92 (m, 3H), 7.43 (m, 3H), 7.12 (m, 3H), 6.50 (m, 1H), 3.12 (m, 4H), 2.43 (m, 4H), 2.21 (s, 3H). MS=469 (MH)+.

Example 289

(4-Piperidin-4-yl-phenyl)-[8-(1-p-tolyl-1H-pyrazol-4-yl)-[1,2,4]triazolo[1,5-a]pyridine-2-yl]-amine

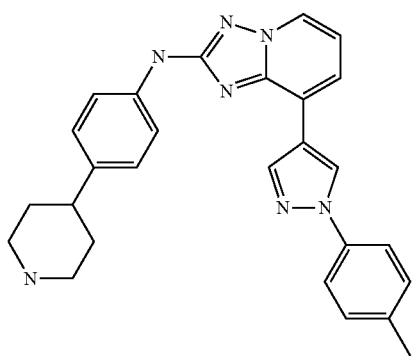 [SMILES: Cc1ccc(-n2cc(-c3cccn4nc(Nc5ccc(C6CCNCC6)cc5)nc34)cn2)cc1]

(4-Piperidin-4-yl-phenyl)-[8-(1-p-tolyl-1H-pyrazol-4-yl)-[1,2,4]triazolo[1,5-a]pyridine-2-yl]-amine was prepared from 4-{4-[8-(1-p-Tolyl-1H-pyrazol-4-yl)-[1,2,4]triazolo[1,5-a]pyridine-2-ylamino]-phenyl}-piperidine-1-carboxylic acid tert-butyl ester in a manner analogous to Example 268c (0.025 g, 30%). MP=216-218° C. $^1$H NMR (400 MHz, (D$_3$C)$_2$SO, δ, ppm): 9.57 (s, 1H), 9.22 (s, 1H), 8.68 (d, 1H), 8.65 (s, 1H), 7.98 (m, 1H), 7.8 (m, 2H), 7.65 (m, 2H), 7.36 (m, 2H), 7.20 (m, 2H), 7.09 (m, 1H), 3.02 (m, 2H), 2.57 (m, 4H), 2.38 (s, 3H), 1.66 (m, 2H), 1.48 (m, 2H). MS=450 (MH)+.

Example 290

N(8)-(2-Methoxy-5-trifluoromethyl-phenyl)-N(2)-[3-(4-methyl-piperazin-1-yl)-phenyl]-[1,2,4]triazolo[1,5-a]pyridine-2,8-diamine

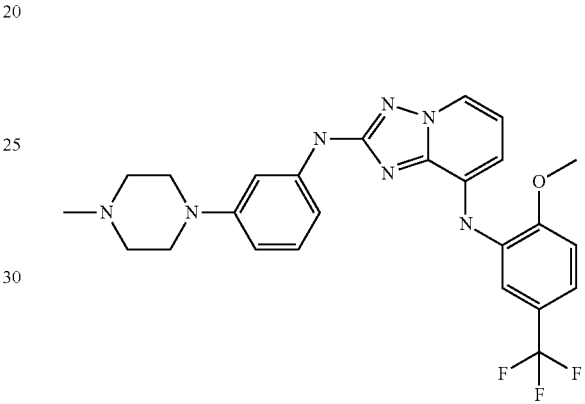

290a) A mixture of 8-bromo-2-chloro-[1,2,4]triazolo[1,5-a]pyridine (0.23 g, 0.99 mmol), 2-methoxy-5-trifluoromethyl-phenylamine (0.226 g, 1.19 mmol), tris(dibenzylideneacetone)dipalladium(0) (0.185 g, 0.2 mmol), dicyclohexyl-(2'-4'-6'-triisopropyl-biphenyl-2-yl)-phosphane (0.19 g, 0.4 mmol), and sodium tert-butoxide (0.29 g, 3.0 mmol) in toluene (10 mL) was degassed with nitrogen for 3 minutes, then heated at 100° C. for 2 hours under argon. The reaction was cooled to room temperature, diluted with dichloromethane, filtered through diatomaceous earth, and concentrated. The residue was diluted with dichloromethane, washed with 10% sodium bicarbonate solution, brine, dried over sodium sulfate and concentrated. The crude product was triturated with ether and dichloromethane to give (2-chloro-[1,2,4]triazolo[1,5-a]pyridine-8-yl)-(2-methoxy-5-trifluoromethyl-phenyl)-amine (0.23 g, 68%). MP=144-146° C. MS=343 (MH)+.

290b) N(8)-(2-Methoxy-5-trifluoromethyl-phenyl)-N(2)-[3-(4-methyl-piperazin-1-yl)-phenyl]-[1,2,4]triazolo[1,5-a]pyridine-2,8-diamine was prepared from (2-chloro-[1,2,4]triazolo[1,5-a]pyridine-8-yl)-(2-methoxy-5-trifluoromethyl-phenyl)-amine, 3-(4-methylpiperazin-1-yl)aniline with 2,2'-bis-dicyclohexylphosphanyl-biphenyl as the ligand in a manner analogous to Example 2d (0.005 g, 20%). MP=198-200° C. $^1$H NMR (400 MHz, (D$_3$C)$_2$SO, δ, ppm): 9.44 (s, 1H), 8.37 (d, 1H), 7.61 (s, 1H), 7.43 (s, 1H), 7.30 (m, 2H), 7.24 (s, 1H), 7.16 (m, 2H), 7.09 (m, 1H), 6.93 (m, 1H), 6.48 (m, 1H), 3.97 (s, 3H), 3.10 (m, 4H), 2.45 (m, 4H), 2.21 (s, 3H). MS=498 (MH)+.

Example 291

7-[8-(2-Isobutoxy-phenyl]-[1,2,4]triazolo[1,5a]pyridine-2-ylamino]-1,2,4,5-tetrahydro-benzo[d]azepine-3-carboxylic acid tert-butyl ester

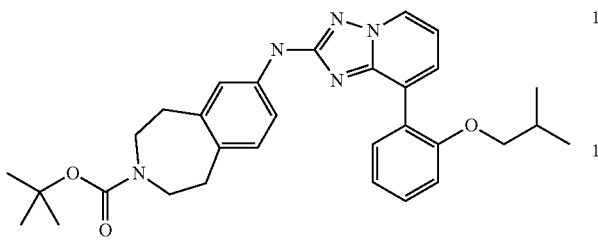

291a) 2-Chloro-8-(2-isobutoxy-phenyl)-[1,2,4]triazolo[1,5-a]pyridine was prepared from 8-bromo-2-chloro-[1,2,4]triazolo[1,5-a]pyridine and 2-isobutoxyphenylboronic acid in a manner analogous to Example 2c (0.46 g, 70%). MS=302 (MH)+.

291b) 7-[8-(2-Isobutoxy-phenyl]-[1,2,4]triazolo[1,5a]pyridine-2-ylamino]-1,2,4,5-tetrahydro-benzo[d]azepine-3-carboxylic acid tert-butyl ester was prepared from 2-chloro-8-(2-isobutoxy-phenyl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.300 g, 61%). MP=124-126° C. $^1$H NMR (400 MHz, (D$_3$C)$_2$SO, δ, ppm): 9.55 (s, 1H), 8.74 (d, 1H), 7.57 (m, 2H), 7.47 (m, 1H), 7.39 (m, 2H), 7.12 (m, 1H), 7.03 (m, 3H), 3.78 (m, 2H), 3.38 (m, 4H), 2.77 (m, 4H), 1.86 (m, 1H), 1.41 (s, 9H), 0.78 (m, 6H). MS=528 (MH)+.

Example 292

[8-(2-Isobutoxy-phenyl]-[1,2,4]triazolo[1,5-a]-pyridin-2-yl)-(2,3,4,5-tetrahydro-1H-benzo[d]azepin-7-yl)-amine

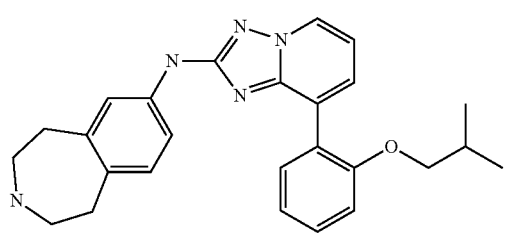 [SMILES: CC(C)COc1ccccc1-c1cccn2nc(Nc3ccc4c(c3)CCNCC4)nc12]

[8-(2-Isobutoxy-phenyl]-[1,2,4]triazolo[1,5-a]-pyridin-2-yl)-(2,3,4,5-tetrahydro-1H-benzo[d]azepin-7-yl)-amine was prepared from 7-[8-(2-isobutoxy-phenyl]-[1,2,4]triazolo[1,5a]pyridine-2-ylamino]-1,2,4,5-tetrahydro-benzo[d]azepine-3-carboxylic acid tert-butyl ester in a manner analogous to Example 268c (0.025 g, 30%). MP=236-238° C. $^1$H NMR (400 MHz, (D$_3$C)$_2$SO, δ, ppm): 9.47 (s, 1H), 8.73 (d, 1H), 7.59 (m, 2H), 7.37 (m, 3H), 7.14 (m, 1H), 7.04 (m, 1H), 7.04 (m, 2H), 6.98 (m, 1H), 3.78 (m, 2H), 2.76 (m, 9H), 1.85 (m, 1H), 0.78 (m, 6H). MS=554 (MH)+.

Example 293

7-[8-(3-Isobutoxy-phenyl]-[1,2,4]triazolo[1,5a]pyridine-2-ylamino]-1,2,4,5-tetrahydro-benzo[d]azepine-3-carboxylic acid tert-butyl ester

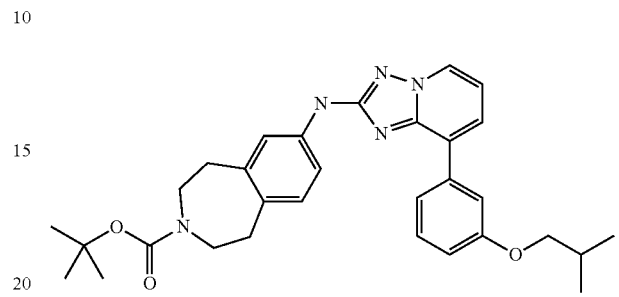

293a) 2-Chloro-8-(3-isobutoxy-phenyl)-[1,2,4]triazolo[1,5-a]pyridine was prepared from 8-bromo-2-chloro-[1,2,4]triazolo[1,5-a]pyridine and 3-isobutoxyphenylboronic acid in a manner analogous to Example 2c (0.39 g, 60%). MS=302 (MH)+.

293b) 7-[8-(3-Isobutoxy-phenyl]-[1,2,4]triazolo[1,5a]pyridine-2-ylamino]-1,2,4,5-tetrahydro-benzo[d]azepine-3-carboxylic acid tert-butyl ester was prepared from 2-chloro-8-(3-isobutoxy-phenyl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.35 g, 80%). MP=116-118° C. $^1$H NMR (400 MHz, (D$_3$C)$_2$SO, δ, ppm): 9.60 (s, 1H), 8.76 (d, 1H), 7.75 (s, 1H), 7.66 (m, 1H), 7.49 (m, 2H), 7.42 (m, 1H), 7.00-7.08 (m, 3H), 3.84 (m, 2H), 3.45 (m, 4H), 2.80 (m, 4H), 2.04 (m, 1H), 1.41 (s, 9H), 1.00 (m, 6H). MS=528 (MH)+.

Example 294

[8-(3-Isobutoxy-phenyl]-[1,2,4]triazolo[1,5a]pyridine-2-yl]-(2,3,4,5-tetrahydro-benzo[d]azepin-7-yl)-amine

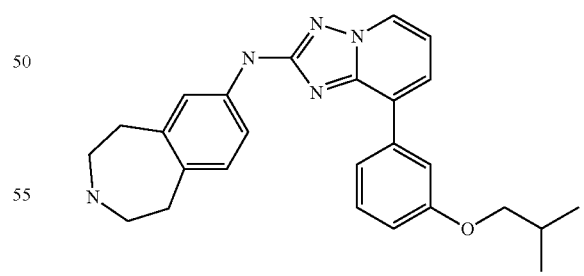

[8-(3-Isobutoxy-phenyl]-[1,2,4]triazolo[1,5a]pyridine-2-yl]-(2,3,4,5-tetrahydro-benzo[d]azepin-7-yl)-amine was prepared from 7-[8-(3-isobutoxy-phenyl]-[1,2,4]triazolo[1,5a]pyridine-2-ylamino]-1,2,4,5-tetrahydro-benzo[d]azepine-3-carboxylic acid tert-butyl ester in a manner analogous to Example 268c (0.20 g, 88%). MP=119-121° C. $^1$H NMR (400 MHz, (D$_3$C)$_2$SO, δ, ppm): 9.55 (s, 1H), 8.76 (d, 1H), 7.84 (m, 1H), 7.76 (s, 1H), 7.69 (m, 1H), 7.47 (m, 1H), 7.42 (m, 2H), 7.10 (m, 1H), 7.00 (m, 2H), 3.83 (m, 2H), 2.79 (m, 8H), 2.06 (m, 1H), 1.01 (m, 6H). MS=428 (MH)+.

Example 295

7-[8-(2-Isobutoxy-4-methyl-phenyl]-[1,2,4]triazolo[1,5a]pyridine-2-ylamino]1,2,4,5-tetrahydro-benzo[d]azepine-3-carboxylic acid tert-butyl ester

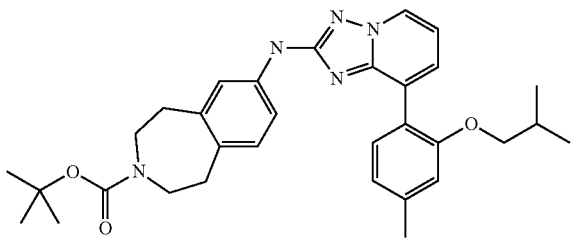 [SMILES: Cc1ccc(-c2cccn3nc(Nc4ccc5c(c4)CCN(C(=O)OC(C)(C)C)CC5)nc23)c(OCC(C)C)c1]

295a) 2-Chloro-8-(2-isobutoxy-4-methylphenyl)-[1,2,4]triazolo[1,5-a]pyridine was prepared from 8-bromo-2-chloro-[1,2,4]triazolo[1,5-a]pyridine and 2-isobutoxy-4-methylphenylboronic acid in a manner analogous to Example 2c (0.48 g, 71%). MS=316 (MH)+.
295b) 7-[8-(2-Isobutoxy-4-methylphenyl]-[1,2,4]triazolo[1,5a]pyridine-2-ylamino]-1,2,4,5-tetrahydro-benzo[d]azepine-3-carboxylic acid tert-butyl ester was prepared 2-chloro-8-(2-isobutoxy-4-methylphenyl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.34 g, 67%). MP=118-120° C. $^1$H NMR (400 MHz, (D$_3$C)$_2$SO, δ, ppm): 9.54 (s, 1H), 8.74 (d, 1H), 7.41 (m, 3H), 7.20 (m, 1H), 7.02 (m, 3H), 3.73 (m, 2H), 3.45 (m, 4H), 2.76 (m, 4H), 2.31 (s, 3H), 1.82 (m, 1H), 1.41 (s, 9H), 0.82 (m, 6H). MS=542 (MH)+.

Example 296

[8-(2-Isobutoxy-4-methyl-phenyl]-[1,2,4]triazolo[1,5a]pyridine-2-yl]-(2,3,4,5-tetrahydro-benzo[d]azepin-7-yl)-amine

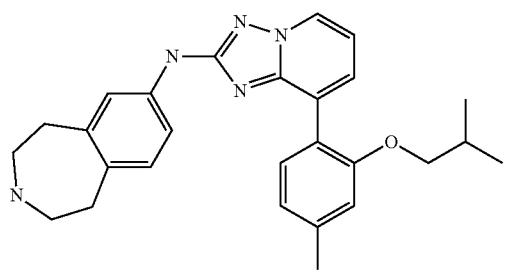 [SMILES: Cc1ccc(-c2cccn3nc(Nc4ccc5c(c4)CCNCC5)nc23)c(OCC(C)C)c1]

[8-(2-Isobutoxy-4-methyl-phenyl]-[1,2,4]triazolo[1,5a]pyridine-2-yl]-(2,3,4,5-tetrahydro-benzo[d]azepin-7-yl)-amine was prepared from 7-[8-(3-Isobutoxy-4-methyl-phenyl]-[1,2,4]triazolo[1,5a]pyridine-2-ylamino]-1,2,4,5-tetrahydro-benzo[d]azepine-3-carboxylic acid tert-butyl ester in a manner analogous to Example 268c (0.24 g, 92%). MP=120-122° C. $^1$H NMR (400 MHz, (D$_3$C)$_2$SO, δ, ppm): 9.44 (s, 1H), 8.73 (d, 1H), 7.53 (m, 1H), 7.37 (m, 3H), 7.17 (m, 1H), 6.97-7.00 (m, 3H), 3.72 (m, 2H), 2.76 (m, 9H), 2.28 (s, 3H), 1.82 (m, 1H), 0.80 (m, 6H). MS=442 (MH)+.

Example 297

7-[8-(1-Methyl-1H-indazol-4-yl)-[1,2,4]triazolo[1,5a]pyridine-2-ylamino]1,2,4,5-tetrahydro-benzo[d]azepine-3-carboxylic acid tert-butyl ester

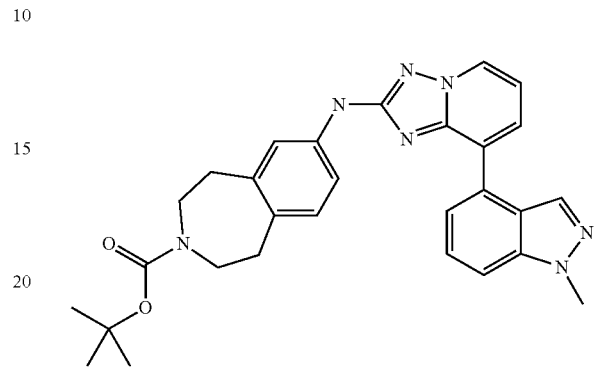

297a) 2-Chloro-8-(1-methyl-1H-indazol-4-yl)-[1,2,4]triazolo[1,5-a]pyridine was prepared from 8-bromo-2-chloro-[1,2,4]triazolo[1,5-a]pyridine and 1-methyl-2H-indazole-4-boronic acid pinacol ester in a manner analogous to Example 2c (0.36 g, 59%). MS=284 (MH)+.
297b) 7-[8-(1-Methyl-1H-indazol-4-yl)-[1,2,4]triazolo[1,5a]pyridine-2-ylamino]1,2,4,5-tetrahydro-benzo[d]azepine-3-carboxylic acid tert-butyl ester was prepared from 2-chloro-8-(1-methyl-1H-indazol-4-yl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.25 g, 59%). MP=146-148° C. $^1$H NMR (400 MHz, (D$_3$C)$_2$SO, δ, ppm): 9.60 (s, 1H), 8.84 (d, J=6.58 Hz, 1H), 8.13 (s, 1H), 7.85 (m, 1H), 7.75 (m, 2H), 7.55 (m, 1H), 7.46 (m, 2H), 7.18 (m, 1H), 7.04 (m, 1H), 4.12 (s, 3H), 3.42 (m, 4H), 2.76 (m, 4H), 1.41 (s, 9H). MS+510 (MH)+.

Example 298

[8-(1-Methyl-1H-indazol-4-yl)-[1,2,4]triazolo[1,5a]pyridine-2-yl]-(2,3,4,5-tetrahydro-benzo[d]azepin-7-yl)-amine

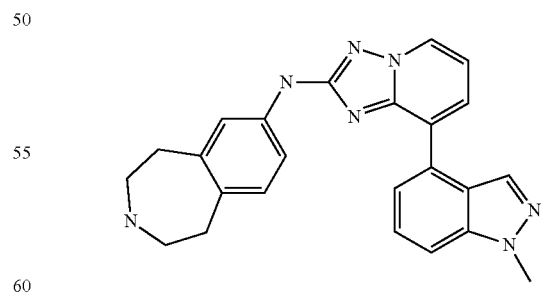

[8-(1-Methyl-1H-indazol-4-yl)-[1,2,4]triazolo[1,5a]pyridine-2-yl]-(2,3,4,5-tetrahydro-benzo[d]azepin-7-yl)-amine was prepared from 7-[8-(1-Methyl-1H-indazol-4-yl)-[1,2,4]triazolo[1,5a]pyridine-2-ylamino]1,2,4,5-tetrahydro-benzo[d]azepine-3-carboxylic acid tert-butyl ester in a manner analogous to Example 268c (0.24 g, 92%). MP=127-129° C.

$^1$H NMR (400 MHz, (D$_3$C)$_2$SO, δ, ppm): 9.51 (s, 1H), 8.84 (d, J=6.58 Hz, 1H), 7.88 (m, 1H), 7.75 (m, 2H), 7.54 (m, 1H), 7.39 (m, 2H), 7.15 (m, 1H), 6.97 (m, 1H), 4.12 (s, 3H), 2.74 (m, 9H). MS=410 (MH)+.

Example 299

[8-(2-Isopropoxy-phenyl]-[1,2,4]triazolo[1,5a]pyridine-2-yl]-(2,3,4,5-tetrahydro-benzo[d]azepin-7-yl)-amine

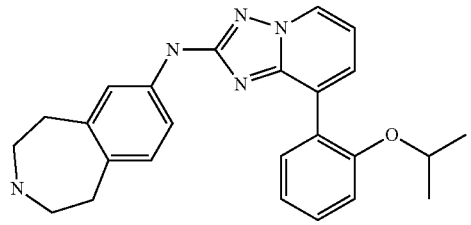 [SMILES: CC(C)Oc1ccccc1-c1cccn2nc(Nc3ccc4c(c3)CCNCC4)nc12]

[8-(2-Isopropoxy-phenyl]-[1,2,4]triazolo[1,5a]pyridine-2-yl]-(2,3,4,5-tetrahydro-benzo[d]azepin-7-yl)-amine was prepared from 7-[8-(2-isopropoxy-phenyl)-[1,2,4]triazolo[1,5a]pyridine-2-ylamino]1,2,4,5-tetrahydro-benzo[d]azepine-3-carboxylic acid tert-butyl ester in a manner analogous to Example 268c (0.065 g, 80%). MP=98-100° C. $^1$H NMR (400 MHz, (D$_3$C)$_2$SO, δ, ppm): 9.47 (s, 1H), 8.73 (d, 1H), 7.59 (m, 2H), 7.40 (m, 2H), 7.35 (s, 1H), 7.04 (m, 2H), 6.97 (m, 1H), 4.57 (m, 1H), 2.75 (m, 9H), 1.17 (m, 6H). MS=414 (MH)+.

Example 300

[8-(2-Ethoxy-4-methyl-phenyl]-[1,2,4]triazolo[1,5a]pyridine-2-yl]-(2,3,4,5-tetrahydro-benzo[d]azepin-7-yl)-amine

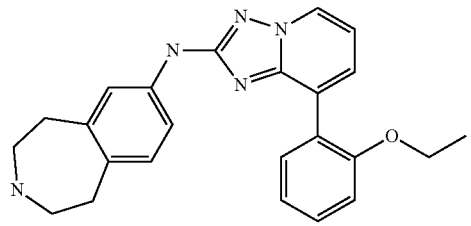 [SMILES: CCOc1ccccc1-c1cccn2nc(Nc3ccc4c(c3)CCNCC4)nc12]

[8-(2-Ethoxy-4-methyl-phenyl]-[1,2,4]triazolo[1,5a]pyridine-2-yl]-(2,3,4,5-tetrahydro-benzo[d]azepin-7-yl)-amine was prepared from 7-[8-(2-ethoxy-phenyl)-[1,2,4]triazolo[1,5a]pyridine-2-ylamino]1,2,4,5-tetrahydro-benzo[d]azepine-3-carboxylic acid tert-butyl ester in a manner analogous to Example 268c (0.060 g, 76%). MP=100-102° C. $^1$H NMR (400 MHz, (D$_3$C)$_2$SO, δ, ppm): 9.48 (s, 1H), 8.73 (d, 1H), 7.59 (m, 2H), 7.41 (m, 2H), 7.36 (s, 1H), 7.15 (m, 1H), 7.06 (m, 2H), 6.99 (m, 1H), 4.06 (m, 2H), 2.76 (m, 9H), 1.18 (m, 3H). MS=400 (MH)+.

Example 301

[8-(2-Cyclopropylmethoxy-phenyl]-[1,2,4]triazolo[1,5a]pyridine-2-yl]-(2,3,4,5-tetrahydro-benzo[d]azepin-7-yl)-amine

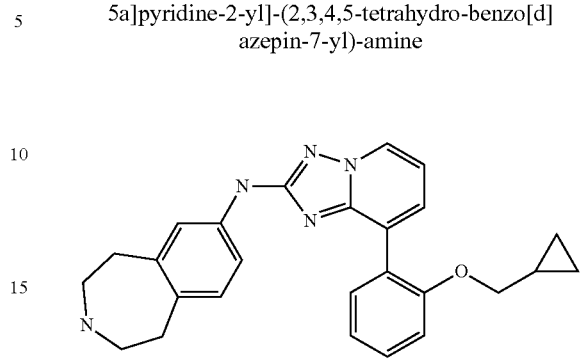

[8-(2-Cyclopropylmethoxy-phenyl]-[1,2,4]triazolo[1,5a]pyridine-2-yl]-(2,3,4,5-tetrahydro-benzo[d]azepin-7-yl)-amine was prepared from 7-[8-(2-cyclopropylmethoxy-phenyl)-[1,2,4]triazolo[1,5a]pyridine-2-ylamino]1,2,4,5-tetrahydro-benzo[d]azepine-3-carboxylic acid tert-butyl ester in a manner analogous to Example 268c (0.076 g, 91%). MP=114-116° C. $^1$H NMR (400 MHz, (D$_3$C)$_2$SO, δ, ppm): 9.48 (s, 1H), 8.75 (d, 1H), 7.61 (m, 2H), 7.39 (m, 2H), 7.34 (s, 1H), 7.14 (m, 1H), 7.04 (m, 2H), 6.99 (m, 1H), 3.88 (m, 2H), 2.74 (m, 9H), 1.05 (m, 1H), 0.39 (m, 2H), 0.19 (m, 2H). MS=426 (MH)+.

Example 302

7-[8-(2-Isopropoxy-phenyl]-[1,2,4]triazolo[1,5a]pyridine-2-ylamino]1,2,4,5-tetrahydro-benzo[d]azepine-3-carboxylic acid tert-butyl ester

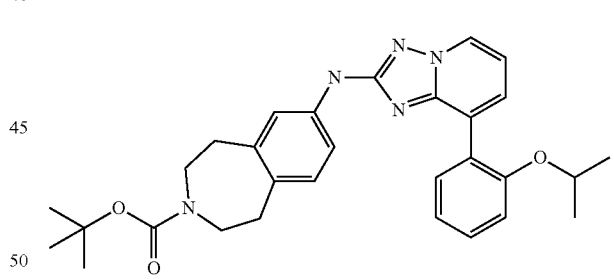

302a) 2-Chloro-8-(2-isopropoxy-phenyl)-[1,2,4]triazolo[1,5-a]pyridine was prepared from 8-bromo-2-chloro-[1,2,4]triazolo[1,5-a]pyridine and 2-isopropoxyphenylboronic acid in a manner analogous to Example 2c (0.24 g, 40%). MS=288 (MH)+.

302b) 7-[8-(2-Isopropoxy-phenyl)-[1,2,4]triazolo[1,5a]pyridine-2-ylamino]-1,2,4,5-tetrahydro-benzo[d]azepine-3-carboxylic acid tert-butyl ester was prepared from 2-chloro-8-(2-isopropxy-phenyl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.35 g, 82%). MP=112-114° C. $^1$H NMR (400 MHz, (D$_3$C)$_2$SO, δ, ppm): 9.54 (s, 1H), 8.73 (d, 1H), 7.60 (m, 2H), 7.48 (s, 1H), 7.38 (m, 2H), 7.17 (m, 1H), 7.05 (m, 3H), 4.57 (m, 1H), 3.44 (m, 4H), 2.80 (m, 4H), 1.41 (s, 9H), 1.15 (m, 6H). MS=514 (MH)+.

Example 303

7-[8-(2-Ethoxy-phenyl]-[1,2,4]triazolo[1,5a]pyridine-2-ylamino]1,2,4,5-tetrahydro-benzo[d]azepine-3-carboxylic acid tert-butyl ester

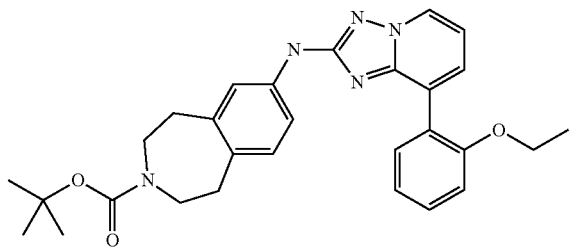 [SMILES: CCOc1ccccc1-c1cccn2nc(Nc3ccc4c(c3)CCN(C(=O)OC(C)(C)C)CC4)nc12]

303a) 2-Chloro-8-(2-ethoxy-phenyl)-[1,2,4]triazolo[1,5-a]pyridine was prepared from 8-bromo-2-chloro-[1,2,4]triazolo[1,5-a]pyridine and 2-ethoxyphenylboronic acid in a manner analogous to Example 2c (0.42 g, 71%). MS=274 (MH)+.
303b) 7-[8-(2-Ethoxy-phenyl]-[1,2,4]triazolo[1,5a]pyridine-2-ylamino]-1,2,4,5-tetrahydro-benzo[d]azepine-3-carboxylic acid tert-butyl ester was prepared from 2-chloro-8-(2-ethoxy-phenyl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.35 g, 84%). MP=127-129° C. $^1$H NMR (400 MHz, (D$_3$C)$_2$SO, δ, ppm): 9.54 (s, 1H), 8.75 (d, 1H), 7.58 (m, 2H), 7.49 (m, 1H), 7.40 (m, 2H), 7.15 (m, 1H), 7.05 (m, 3H), 4.06 (m, 2H), 3.42 (m, 4H), 2.76 (m, 4H), 1.41 (s, 9H), 1.18 (m, 3H). MS=500 (MH)+.

Example 304

7-[8-(2-Cyclopropylmethoxy-phenyl]-[1,2,4]triazolo[1,5a]pyridine-2-ylamino]1,2,4,5-tetrahydro-benzo[d]azepine-3-carboxylic acid tert-butyl ester

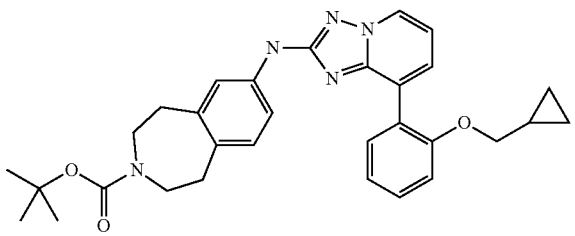 [SMILES: CC(C)(C)OC(=O)N1CCc2ccc(Nc3nc4c(-c5ccccc5OCC5CC5)cccn4n3)cc2CC1]

304a) 2-Chloro-8-(2-cyclopropylmethoxy-phenyl)-[1,2,4]triazolo[1,5-a]pyridine was prepared from 8-bromo-2-chloro-[1,2,4]triazolo[1,5-a]pyridine and 2-cyclopropylmethoxyphenylboronic acid in a manner analogous to Example 2c (0.47 g, 73%). MS=300 (MH)+.
304b) 7-[8-(2-Cyclopropylmethoxy-phenyl]-[1,2,4]triazolo[1,5a]pyridine-2-ylamino]-1,2,4,5-tetrahydro-benzo[d]azepine-3-carboxylic acid tert-butyl ester was prepared from 2-chloro-8-(2-cyclopropylmethoxy-phenyl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.28 g, 65%). MP=130-132° C. $^1$H NMR (400 MHz, (D$_3$C)$_2$SO, δ, ppm): 9.55 (s, 1H), 8.73 (d, 1H), 7.60 (m, 2H), 7.47 (m, 1H), 7.40 (m, 2H), 7.15 (m, 1H), 7.04 (m, 3H), 3.87 (m, 2H), 3.44 (m, 4H), 2.75 (m, 4H), 1.43 (s, 9H), 1.06 (m, 1H), 0.39 (m, 2H), 0.18 (m, 2H). MS=526 (MH)+.

Example 305

[8-(2-Isobutoxy-5-methyl-phenyl]-[1,2,4]triazolo[1,5a]pyridine-2-yl]-(2,3,4,5-tetrahydro-benzo[d]azepin-7-yl)-amine

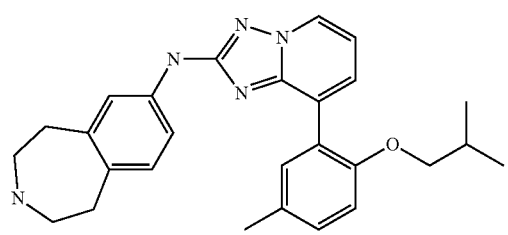 [SMILES: Cc1ccc(OCC(C)C)c(-c2cccn3nc(Nc4ccc5c(c4)CCNCC5)nc23)c1]

[8-(2-Isobutoxy-5-methyl-phenyl]-[1,2,4]triazolo[1,5a]pyridine-2-yl]-(2,3,4,5-tetrahydro-benzo[d]azepin-7-yl)-amine was prepared from 7-[8-(3-isobutoxy-5-methyl-phenyl]-[1,2,4]triazolo[1,5a]pyridine-2-ylamino]-1,2,4,5-tetrahydro-benzo[d]azepine-3-carboxylic acid tert-butyl ester in a manner analogous to Example 268c (0.074 g, 91%). MP=120-122° C. $^1$H NMR (400 MHz, (D$_3$C)$_2$SO, δ, ppm): 9.45 (s, 1H), 8.71 (d, 1H), 7.54 (m, 1H), 7.36 (m, 3H), 7.18 (m, 1H), 7.02 (m, 2H), 6.97 (m, 1H), 3.72 (m, 2H), 2.75 (m, 9H), 2.29 (s, 3H), 1.80 (m, 1H), 0.75 (m, 6H). MS=442 (MH)+.

Example 306

7-[8-(5-Chloro-2-propoxy-phenyl]-[1,2,4]triazolo[1,5a]pyridine-2-ylamino]1,2,4,5-tetrahydro-benzo[d]azepine-3-carboxylic acid tert-butyl ester

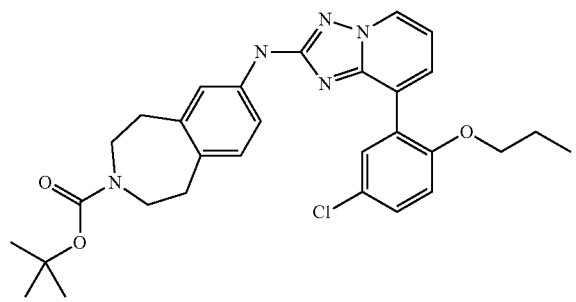 [SMILES: CCCOc1ccc(Cl)cc1-c1cccn2nc(Nc3ccc4c(c3)CCN(C(=O)OC(C)(C)C)CC4)nc12]

306a) 2-Chloro-8-(5-chloro-2-propoxy-phenyl)-[1,2,4]triazolo[1,5-a]pyridine was prepared from 8-bromo-2-chloro-[1,2,4]triazolo[1,5-a]pyridine and 5-chloro-2-propoxyphenylboronic acid in a manner analogous to Example 2c (0.46 g, 66%). MS=323 (MH)+.

306b) 7-[8-(5-Chloro-2-propoxy-phenyl)-[1,2,4]triazolo[1,5a]pyridine-2-ylamino]1,2,4,5-tetrahydro-benzo[d]azepine-3-carboxylic acid tert-butyl ester was prepared from 2-chloro-8-(5-chloro-2-propoxy-phenyl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.14 g, 46%). MP=127-129° C. $^1$H NMR (400 MHz, (D$_3$C)$_2$SO, δ, ppm): 9.60 (s, 1H), 8.76 (d, 1H), 7.72 (s, 1H), 7.65 (m, 1H), 7.42 (m, 3H), 7.20 (m, 1H), 7.05 (m, 2H), 3.97 (m, 2H), 3.43 (m, 4H), 2.77 (m, 4H), 1.59 (m, 2H), 1.41 (s, 9H), 0.78 (m, 3H). MS=549 (MH)+.

Example 307

[8-(5-Chloro-2-propoxy-phenyl)-[1,2,4]triazolo[1,5a]pyridine-2-yl]-(2,3,4,5-tetrahydro-benzo[d]azepin-7-yl)-amine

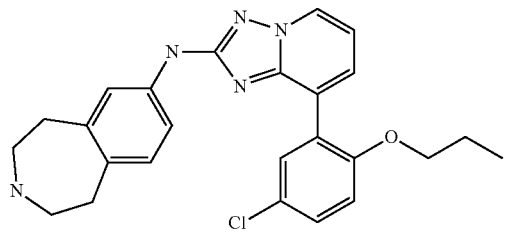 [SMILES: CCCOc1ccc(Cl)cc1-c1cccn2nc(Nc3ccc4c(c3)CCNCC4)nc12]

[8-(5-Chloro-2-propoxy-phenyl)-[1,2,4]triazolo[1,5a]pyridine-2-yl]-(2,3,4,5-tetrahydro-benzo[d]azepin-7-yl)-amine was prepared from 7-[8-(5-Chloro-2-propoxy-phenyl)-[1,2,4]triazolo[1,5a]pyridine-2-ylamino]1,2,4,5-tetrahydro-benzo[d]azepine-3-carboxylic acid tert-butyl ester in a manner analogous to Example 268c (0.075 g, 92%). MP=174-176° C. $^1$H NMR (400 MHz, (D$_3$C)$_2$SO, δ, ppm): 9.54 (s, 1H), 8.77 (d, J=6.58 Hz, 1H), 7.71 (s, 1H), 7.65 (m, 1H), 7.45 (m, 1H), 7.39 (m, 2H), 7.17 (m, 1H), 7.06 (m, 1H), 6.99 (m, 1H), 3.96 (m, 2H), 2.78 (m, 9H), 1.59 (m, 2H), 0.80 (m, 3H). MS=448 (MH)+.

Example 308

2-{7-[8-(5-Chloro-2-propoxy-phenyl)-[1,2,4]triazolo[1,5a]pyridine-2-ylamino]1,2,4,5-tetrahydro-benzo[d]azepin-3-yl)-N,N-dimethyl-acetamide

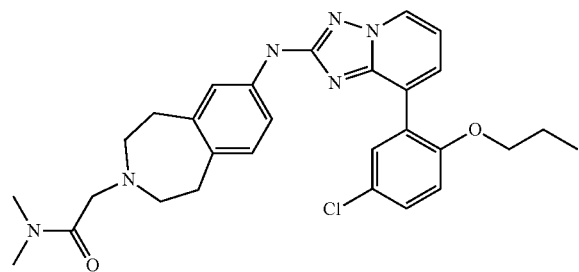 [SMILES: CCCOc1ccc(Cl)cc1-c1cccn2nc(Nc3ccc4c(c3)CCN(CC(=O)N(C)C)CC4)nc12]

2-{7-[8-(5-Chloro-2-propoxy-phenyl)-[1,2,4]triazolo[1,5a]pyridine-2-ylamino]1,2,4,5-tetrahydro-benzo[d]azepin-3-yl)-N,N-dimethyl-acetamide was prepared from [8-(5-chloro-2-propoxy-phenyl)-[1,2,4]triazolo[1,5a]pyridine-2-yl]-(2,3,4,5-tetrahydro-benzo[d]azepin-7-yl)-amine in a manner analogous to Example 273 (0.022 g, 56%). MP=116-118° C. $^1$H NMR (400 MHz, (D$_3$C)$_2$SO, δ, ppm): 9.54 (s, 1H), 8.75 (d, 1H), 7.71 (s, 1H), 7.66 (m, 1H), 7.42 (m, 3H), 7.20 (m, 1H), 7.08 (m, 1H), 6.99 (m, 1H), 3.96 (m, 2H), 3.26 (s, 2H), 3.06 (s, 3H), 2.82 (s, 3H), 2.76 (m, 4H), 2.62 (m, 4H), 1.60 (m, 2H), 0.80 (m, 3H). MS=533 (MH)+.

Example 309

7-[8-(5-Chloro-2-ethoxy-phenyl)-[1,2,4]triazolo[1,5a]pyridine-2-ylamino]1,2,4,5-tetrahydro-benzo[d]azepine-3-carboxylic acid tert-butyl ester

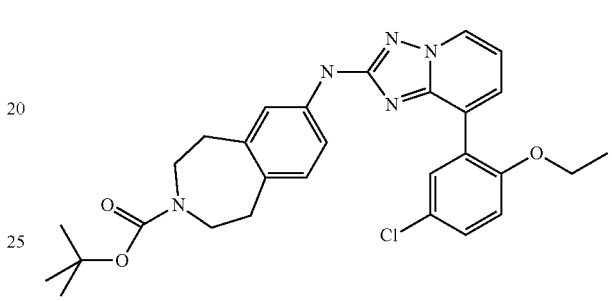

309a) 2-Chloro-8-(2-ethoxy-5-chloro-phenyl)-[1,2,4]triazolo[1,5-a]pyridine was prepared from 8-bromo-2-chloro-[1,2,4]triazolo[1,5-a]pyridine and 2-ethoxy-5-chloro-phenyl-boronic acid in a manner analogous to Example 2c (0.46 g, 66%). MS=322 (MH)+.
309b) 7-[8-(5-Chloro-2-ethoxy-phenyl)-[1,2,4]triazolo[1,5a]pyridine-2-ylamino]1,2,4,5-tetrahydro-benzo[d]azepine-3-carboxylic acid tert-butyl ester was prepared 2-chloro-8-(2-ethoxy-5-chloro-phenyl)-[1,2,4]triazolo[1,5-a]pyridine and 7-amino-1,2,4,5-tetrahydro-3-benzazepin-3-carboxylic acid tert-butyl ester with 2,2'-bis-dicyclohexylphosphanyl-biphenyl as the ligand in a manner analogous to Example 2d (0.15 g, 53%). MP=118-120° C. $^1$H NMR (400 MHz, (D$_3$C)$_2$SO, δ, ppm): 9.57 (s, 1H), 8.77 (d, 1H), 7.72 (s, 1H), 7.67 (m, 1H), 7.47 (m, 3H), 7.20 (m, 1H), 7.05 (m, 2H), 4.06 (m, 2H), 3.43 (m, 4H), 2.77 (m, 4H), 1.41 (s, 9H), 1.22 (m, 3H). MS=535 (MH)+.

Example 310

[8-(5-Chloro-2-ethoxy-phenyl)-[1,2,4]triazolo[1,5a]pyridine-2-yl]-(2,3,4,5-tetrahydro-benzo[d]azepin-7-yl)-amine

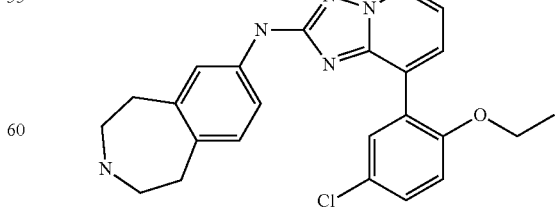

[8-(5-Chloro-2-ethoxy-phenyl)-[1,2,4]triazolo[1,5a]pyridine-2-yl]-(2,3,4,5-tetrahydro-benzo[d]azepin-7-yl)-amine was prepared from 7-[8-(5-chloro-2-ethoxy-phenyl)-[1,2,4]

triazolo[1,5a]pyridine-2-ylamino]1,2,4,5-tetrahydro-benzo[d]azepine-3-carboxylic acid tert-butyl ester in a manner analogous to Example 268c (0.011 g, 10%). MP=260-263° C. ¹H NMR (400 MHz, (D₃C)₂SO, δ, ppm): 9.59 (s, 1H), 8.76 (d, 1H), 7.73 (s, 1H), 7.64 (m, 1H), 7.46 (m, 3H), 7.18 (m, 1H), 7.03 (m, 2H), 4.05 (m, 2H), 2.86-2.95 (m, 9H), 1.21 (m, 3H). MS=434 (MH)+.

Example 311

7-[8-(2-Methoxy-phenyl)-[1,2,4]triazolo[1,5-a]pyridin-2-ylamino]-1,2,4,5-tetrahydro-3-benzazepine-3-carboxylic acid tert-butyl ester

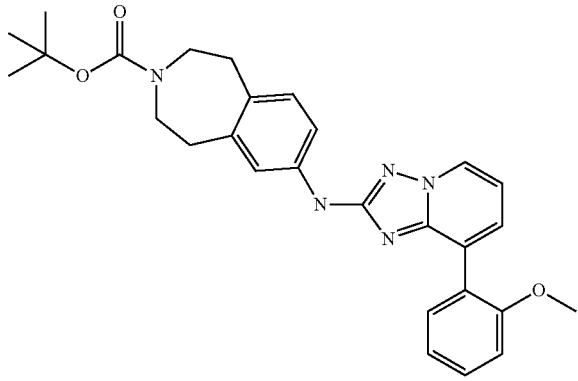 [SMILES: COc1ccccc1-c1cccn2nc(Nc3ccc4c(c3)CCN(C(=O)OC(C)(C)C)CC4)nc12]

311a) A Schlenck flask was charged with palladium acetate (0.0966 g, 0.430 mmol), triphenylphosphine (0.4513 g, 1.721 mmol), and 1,4-dioxane (6 mL) and the mixture was stirred for 5 min until it turned bright yellow. 8-Bromo-2-chloro-[1,2,4]triazolo[1,5-a]pyridine (0.500 g, 2.15 mmol), 2-methoxybenzeneboronic acid (0.490 g, 3.23 mmol), N,N-dimethylformamide (10.00 mL), and 1.00 N sodium carbonate in water (4.3 mL, 4.3 mmol) were added successively and the reaction was heated at 80° C. overnight, cooled to room temperature, diluted with dichloromethane, filtered through diatomaceous earth and concentrated. The reaction was purified via chromatography (silica gel 10%→20% ethyl acetate in hexanes) and concentrated to give 2-chloro-8-(2-methoxyphenyl)-[1,2,4]triazolo[1,5-a]pyridine (0.464 g, 83%). MS=260 (MH)+.

311b) To an oven-dried Schlenck flask under an atmosphere of argon was added 2-chloro-8-(2-methoxy-phenyl)-[1,2,4]triazolo[1,5-a]pyridine (0.460 g, 1.77 mmol), 7-amino-1,2,4,5-tetrahydro-3-benzazepine-3-carboxylic acid tert-butyl ester (0.558 g, 2.12 mmol), palladium acetate (0.0875 g, 0.390 mmol), 2,2-bis-dicyclohexylphosphanyl-biphenyl (0.242 g, 0.443 mmol), cesium carbonate (1.44 g, 4.43 mmol), followed by 1,4-dioxane (12.00 mL) and was degassed under an atmosphere of argon for 5 min and heated at 100° C. overnight, cooled at room temperature, diluted with dichloromethane, filtered through diatomaceous earth and concentrated. The reaction was purified via chromatography (silica gel 20%-30% ethyl acetate/hexanes) and concentrated to give 7-[8-(2-methoxy-phenyl)[1,2,4]triazolo[1,5-a]pyridin-2-ylamino]-1,2,4,5-tetrahydro-3-benzazepine-3-carboxylic acid tert-butyl ester (0.744 g, 87%). ¹H NMR (400 MHz, (D₃C)₂SO, δ, ppm): 9.54 (s, 1H), 8.78 (d, 1H), 7.55 (m, 2H), 7.45 (m, 2H), 7.35 (s, 1H) 7.15 (m, 1H), 7.05 (m, 3H), 3.74 (s, 3H), 3.48 (m, 4H), 2.78 (m, 4H), 1.41 (s, 9H): MS=486 (MH)+.

Example 312

[8-(2-Methoxy-phenyl)-[1,2,4]triazolo[1,5-a]pyridin-2-yl]-2,3,4,5-tetrahydro-1H-3-benzazepin-7-yl)-amine

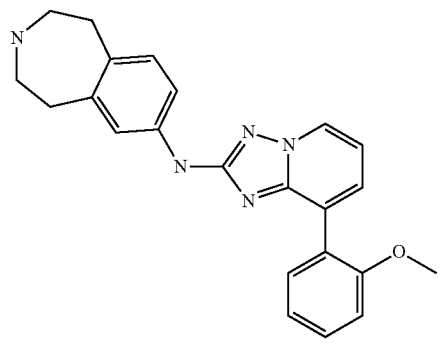 [SMILES: COc1ccccc1-c1cccn2nc(Nc3ccc4c(c3)CCNCC4)nc12]

To 7-[8-(2-methoxy-phenyl)[1,2,4]triazolo[1,5-a]pyridin-2-ylamino]-1,2,4,5-tetrahydro-3-benzazepine-3-carboxylic acid tert-butyl ester (0.740 g, 1.52 mmol) in dichloromethane (10.00 mL) was added trifluoroacetic acid (2 mL, 20 mmol) and the reaction was stirred at room temperature for 2 hours and concentrated. The reaction was partitioned between dichloromethane and 1N sodium carbonate, washed with water/brine, dried over sodium sulfate, and concentrated to give [8-(2-methoxy-phenyl)-[1,2,4]triazolo[1,5-a]pyridin-2-yl]-2,3,4,5-tetrahydro-1H-3-benzazepin-7-yl)-amine (0.562 g, 96%). ¹H NMR (400 MHz, (D₃C)₂SO, δ, ppm): 9.58 (s, 1H), 8.74 (d, 1H), 7.55 (m, 2H), 7.42 (m, 2H), 7.32 (s, 1H), 7.18 (m, 1H), 6.95-7.10 (m, 3H), 3.74 (s, 3H), 2.69-3.10 (br m, 9H): MS=386 (MH)+.

Example 313

2-{7-[8-(2-Methoxy-phenyl)-[1,2,4]triazolo[1,5-a]pyridine-2-ylamino]-1,2,4,5-tetrahydro-3-benzazepin-3-yl}-N,N-dimethyl-acetamide

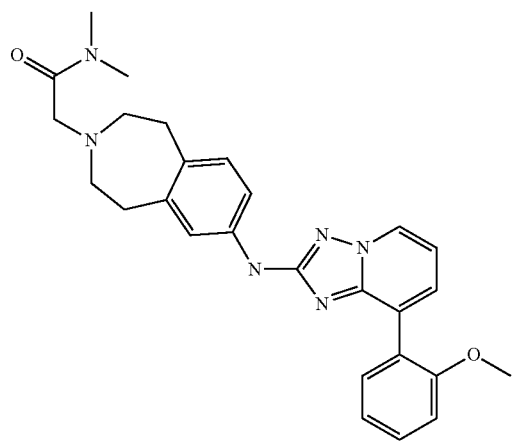 [SMILES: COc1ccccc1-c1cccn2nc(Nc3ccc4c(c3)CCN(CC(=O)N(C)C)CC4)nc12]

To [8-(2-methoxy-phenyl)-[1,2,4]triazolo[1,5-a]pyridin-2-yl]-2,3,4,5-tetrahydro-1H-3-benzazepin-7-yl)-amine (0.150 g, 0.389 mmol) in acetonitrile (7.00 mL, 100 mmol) under an atmosphere of nitrogen was added potassium carbonate (0.161 g, 1.17 mmol), 2-chloro-N,N-dimethyl-acetamide (0.071 g, 0.584 mmol), followed by sodium iodide (0.0583 g, 0.389 mmol) was heated at 70° C. for 1 hour and concentrated. The reaction was partitioned between dichloromethane/water, washed with brine, dried over sodium sulfate, and concentrated. The product was purified using Prep TLC plates (5% methanol in dichloromethane) and concentrated to give a solid (0.050 g, 27%). MP=102-105° C. $^1$H NMR (400 MHz, (D$_3$C)$_2$SO, δ, ppm): 9.52 (s, 1H), 8.75 (d, 1H), 7.55 (m, 2H), 7.42 (m, 2H), 7.32 (s, 1H), 7.18 (d, 1H), 6.95-7.10 (m, 3H), 3.74 (s, 3H), 3.28 (s, 2H), 3.05 (s, 3H), 2.81 (s, 3H), 2.75 (m, 4H), 2.60 (m, 4H): MS=471 (MH)+.

Example 314

[3-(2-Methanesulfonyl-ethyl)-2,3,4,5-tetrahydro-1H-3-benzazepin-7-yl]-[8-(2-methoxy-phenyl)-[1,2,4]triazolo[1,5-a]pyridine-2-yl]-amine

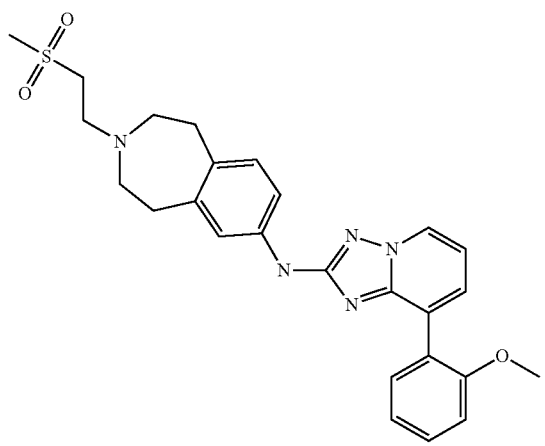

314a) To [8-(2-methoxy-phenyl)-[1,2,4]triazolo[1,5-a]pyridin-2-yl]-2,3,4,5-tetrahydro-1H-3-benzazepin-7-yl)-amine (0.256 g, 0.664 mmol) in N,N-dimethylformamide (10 mL) under an atmosphere of nitrogen was added potassium carbonate (0.275 g, 1.99 mmol), 2-chloroethyl methyl sulfide (0.0982 mL, 0.996 mmol), followed by sodium iodide (0.0996 g, 0.664 mmol) was heated at 70° C. overnight and cooled to room temperature. The reaction was diluted with ethyl acetate, washed with water several times, washed with brine, dried over sodium sulfate, and concentrated. The product was purified using Prep TLC plates (5% methanol in dichloromethane) and concentrated to give [8-(2-methoxy-phenyl)-[1,2,4]triazolo[1,5-a]pyridine-2-yl]-[3-(2-methylsulfanyl-ethyl)-2,3,4,5-tetrahydro-1H-3-benzazepin-7-yl]-amine (0.173 g, 57%). MS=460 (MH)+.
314b) To [8-(2-methoxy-phenyl)-[1,2,4]triazolo[1,5-a]pyridine-2-yl]-[3-(2-methylsulfanyl-ethyl)-2,3,4,5-tetrahydro-1H-3-benzazepin-7-yl]-amine (0.173 g, 0.376 mmol) in methanol (5 mL) was added oxone (0.694 g, 1.13 mmol) in water (2.5 mL) and was stirred at room temperature for 2 hours and concentrated. The reaction was partitioned between dichloromethane/1N sodium carbonate, washed with water/brine, dried over sodium sulfate, and concentrated. The product was purified using Prep TLC plates (5% methanol in dichloromethane) and concentrated to give [3-(2-methanesulfonyl-ethyl)-2,3,4,5-tetrahydro-1H-3-benzazepin-7-yl]-[8-(2-methoxy-phenyl)-[1,2,4]triazolo[1,5-a]pyridine-2-yl]-amine (0.025 g, 14%). MP=91-94° C. $^1$H NMR (400 MHz, (D$_3$C)$_2$SO, δ, ppm): 9.52 (s, 1H), 8.75 (d, 1H), 7.55 (m, 2H), 7.40 (m, 2H), 7.32 (s, 1H), 7.18 (d, 1H), 7.05 (m, 3H), 3.75 (s, 3H), 3.28 (m, 2H), 3.18 (s, 3H), 2.85 (m, 2H), 2.75 (m, 4H), 2.58 (m, 4H): MS=492 (MH)+.

Example 315

7-[8-(2-Methoxy-5-trifluoromethyl-phenyl)-[1,2,4]triazolo[1,5-a]pyridin-2-ylamino]-1,2,4,5-tetrahydro-3-benzazepine-3-carboxylic acid tert-butyl ester

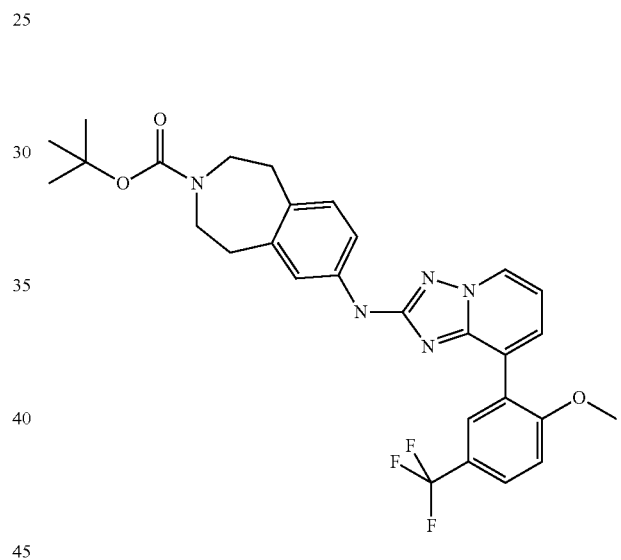

315a) 2-Chloro-8-(2-methoxy-5-trifluoromethyl-phenyl)-[1,2,4]triazolo[1,5-a]pyridine was prepared from 8-bromo-2-chloro-[1,2,4]triazolo[1,5-a]pyridine (0.500 g, 2.15 mmol) and 2-methoxy-5-trifluoromethylbenzeneboronic acid (0.710 g, 3.23 mmol) in a manner analogous to Example 311a to give product (0.636 g, 90%). MS=328 (MH)+.
315b) 7-[8-(2-Methoxy-5-trifluoromethyl-phenyl)-[1,2,4]triazolo[1,5-a]pyridin-2-ylamino]-1,2,4,5-tetrahydro-3-benzazepine-3-carboxylic acid tert-butyl ester was prepared from 2-chloro-8-(2-methoxy-5-trifluoromethyl-phenyl)-[1,2,4]triazolo[1,5-a]pyridine (0.630 g, 1.92 mmol) and 7-amino-1,2,4,5-tetrahydro-3-benzazepine-3-carboxylic acid tert-butyl ester (0.605 g, 2.31 mmol) in a manner analogous to Example 311b to give product (0.750 g, 71%). $^1$H NMR (400 MHz, (D$_3$C)$_2$SO, δ, ppm): 9.56 (s, 1H), 8.79 (d, 1H), 7.95 (s, 1H), 7.82 (d, 1H), 7.65 (d, 1H), 7.42 (m, 3H), 7.05 (m, 2H), 3.85 (s, 3H), 3.42 (m, 4H), 2.75 (m, 4H), 1.41 (s, 9H): MS=554 (MH)+.

Example 316

[8-(2-Methoxy-5-trifluoromethyl-phenyl)-[1,2,4]triazolo[1,5-a]pyridin-2-yl]-2,3,4,5-tetrahydro-1H-3-benzazepin-7-yl)-amine

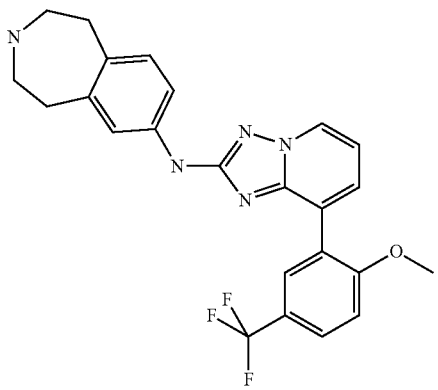 [SMILES: COc1ccc(C(F)(F)F)cc1-c1cccn2nc(Nc3ccc4c(c3)CCNCC4)nc12]

316) [8-(2-Methoxy-5-trifluoromethyl-phenyl)-[1,2,4]triazolo[1,5-a]pyridin-2-yl]-2,3,4,5-tetrahydro-1H-3-benzazepin-7-yl)-amine was prepared from 7-[8-(2-methoxy-5-trifluoromethyl-phenyl)-[1,2,4]triazolo[1,5-a]pyridin-2-ylamino]-1,2,4,5-tetrahydro-3-benzazepine-3-carboxylic acid tert-butyl ester (0.737 g, 1.33 mmol) and trifluoroacetic acid (2 mL) in a manner analogous to Example 312 to give product (0.579 g, 96%). $^1$H NMR (400 MHz, (D$_3$C)$_2$SO, δ, ppm): 9.49 (s, 1H), 8.79 (d, 1H), 7.95 (s, 1H), 7.82 (d, 1H), 7.62 (d, 1H), 7.38 (m, 3H), 7.05 (t, 1H), 6.98 (d, 1H), 3.85 (s, 3H), 2.62-3.00 (br m, 9H): MS=454 (MH)+.

Example 317

2-{7-[8-(2-Methoxy-5-trifluoromethyl-phenyl)-[1,2,4]triazolo[1,5-a]pyridin-2-ylamino]-1,2,4,5-tetrahydro-3-benzazepin-3-yl}-N,N-dimethyl-acetamide

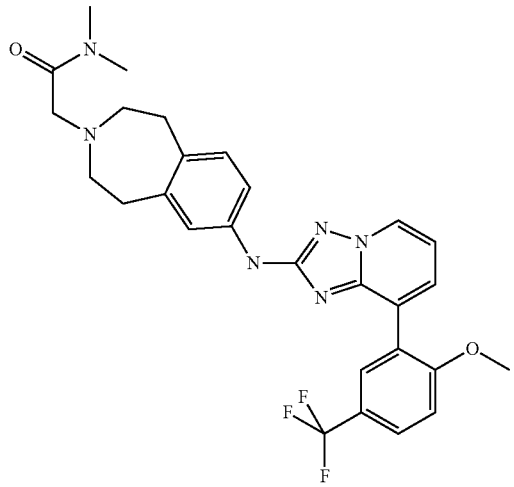 [SMILES: COc1ccc(C(F)(F)F)cc1-c1cccn2nc(Nc3ccc4c(c3)CCN(CC(=O)N(C)C)CC4)nc12]

317) 2-{7-[8-(2-Methoxy-5-trifluoromethyl-phenyl)-[1,2,4]triazolo[1,5-a]pyridin-2-ylamino]-1,2,4,5-tetrahydro-3-benzazepin-3-yl}-N,N-dimethyl-acetamide was prepared from [8-(2-methoxy-5-trifluoromethyl-phenyl)-[1,2,4]triazolo[1,5-a]pyridin-2-yl]-2,3,4,5-tetrahydro-1H-3-benzazepin-7-yl)-amine (0.200 g, 0.441 mmol) and 2-chloro-N,N-dimethyl-acetamide (0.068 mL, 0.662 mmol) in a manner analogous to Example 313 to give product (0.079 g, 33%). MP=113-116° C. $^1$H NMR (400 MHz, (D$_3$C)$_2$SO, δ, ppm): 9.52 (s, 1H), 8.79 (d, 1H), 7.95 (s, 1H), 7.82 (d, 1H), 7.62 (d, 1H), 7.38 (m, 3H), 7.05 (t, 1H), 6.98 (d, 1H), 3.85 (s, 3H), 3.18 (s, 2H), 3.05 (s, 3H), 2.80 (s, 3H), 2.75 (m, 4H), 2.55 (m, 4H): MS=539 (MH)+.

Example 318

7-[8-(2-Ethoxy-5-trifluoromethyl-phenyl)-[1,2,4]triazolo[1,5-a]pyridin-2-ylamino]-1,2,4,5-tetrahydro-3-benzazepine-3-carboxylic acid tert-butyl ester

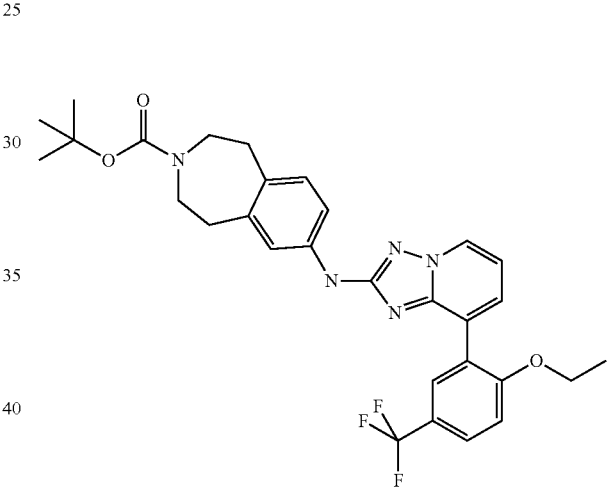

318a) 2-Chloro-8-(2-ethoxy-5-trifluoromethyl-phenyl)-[1,2,4]triazolo[1,5-a]pyridine was prepared from 8-bromo-2-chloro-[1,2,4]triazolo[1,5-a]pyridine (0.500 g, 2.15 mmol) and 2-ethoxy-5-trifluoromethylbenzeneboronic acid (0.755 g, 3.23 mmol) in a manner analogous to Example 311a to give product (0.645 g, 88%). MS=342 (MH)+.

318b) 7-[8-(2-Ethoxy-5-trifluoromethyl-phenyl)-[1,2,4]triazolo[1,5-a]pyridin-2-ylamino]-1,2,4,5-tetrahydro-3-benzazepine-3-carboxylic acid tert-butyl ester was prepared from 2-chloro-8-(2-ethoxy-5-trifluoromethyl-phenyl)-[1,2,4]triazolo[1,5-a]pyridine (0.640 g, 1.87 mmol) and 7-amino-1,2,4,5-tetrahydro-3-benzazepine-3-carboxylic acid tert-butyl ester (0.590 g, 2.25 mmol) in a manner analogous to Example 311b to give product (1.06 g, 99%). $^1$H NMR (400 MHz, (D$_3$C)$_2$SO, δ, ppm): 9.55 (s, 1H), 8.78 (d, 1H), 7.98 (s, 1H), 7.78 (d, 1H), 7.72 (d, 1H), 7.42 (m, 2H), 7.35 (d, 1H), 7.08 (t, 1H), 7.00 (d, 1H), 4.15 (q, 2H), 3.42 (m, 4H), 2.78 (m, 4H), 1.41 (s, 9H), 1.22 (t, 3H): MS=568 (MH)+.

Example 319

[8-(2-Ethoxy-5-trifluoromethyl-phenyl)-[1,2,4]triazolo[1,5-a]pyridin-2-yl]-2,3,4,5-tetrahydro-1H-3-benzazepin-7-yl)-amine

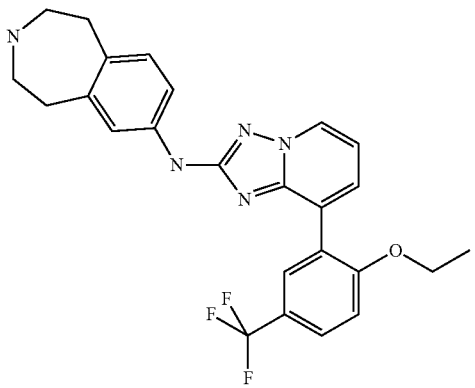 [SMILES: CCOc1ccc(C(F)(F)F)cc1-c1cccn2nc(Nc3ccc4c(c3)CCNCC4)nc12]

[8-(2-Ethoxy-5-trifluoromethyl-phenyl)-[1,2,4]triazolo[1,5-a]pyridin-2-yl]-2,3,4,5-tetrahydro-1H-3-benzazepin-7-yl)-amine was prepared from 7-[8-(2-ethoxy-5-trifluoromethyl-phenyl)-[1,2,4]triazolo[1,5-a]pyridin-2-ylamino]-1,2,4,5-tetrahydro-3-benzazepine-3-carboxylic acid tert-butyl ester (1.06 g, 1.87 mmol) and trifluoroacetic acid (3 mL) in a manner analogous to Example 312 to give product (0.800 g, 92%). MP=94-99° C. $^1$H NMR (400 MHz, (D$_3$C)$_2$SO, δ, ppm): 9.59 (s, 1H), 8.78 (d, 1H), 7.98 (s, 1H), 7.78 (d, 1H), 7.68 (d, 1H), 7.38 (m, 3H), 7.08 (t, 1H), 6.95 (d, 1H), 4.15 (q, 2H), 2.68-2.95 (br m, 9H), 1.22 (t, 3H): MS=468 (MH)+.

Example 320

[8-(2-Ethoxy-5-trifluoromethyl-phenyl)-[1,2,4]triazolo[1,5-a]pyridin-2-yl]-[3-(2-methanesulfonyl-ethyl)-2,3,4,5-tetrahydro-1H-3-benzazepin-7yl)-amine

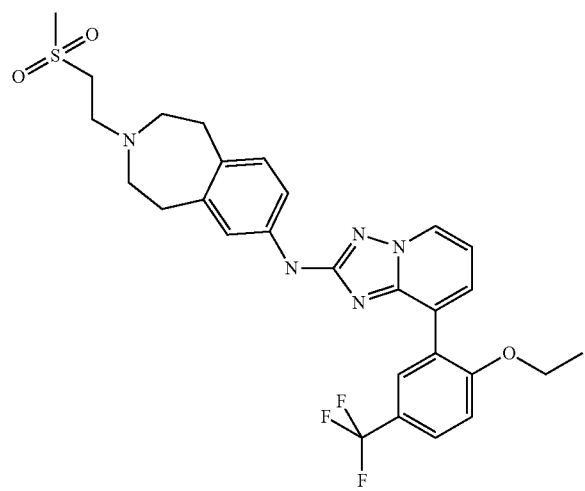 [SMILES: CCOc1ccc(C(F)(F)F)cc1-c1cccn2nc(Nc3ccc4c(c3)CCN(CCS(C)(=O)=O)CC4)nc12]

320a) To 2-chloroethyl methyl sulfide (0.891 mL, 9.04 mmol) in methanol (10 mL) was added oxone (11.12 g, 18.08 mmol) in water (5 mL) and the reaction was stirred at room temperature overnight and concentrated. The reaction was partitioned between dichloromethane/1N sodium carbonate, washed with water/brine, dried over sodium sulfate, and concentrated to give 1-chloro-2-methanesulfonyl-ethane (1.17 g, 91%).

320b) To [8-(2-ethoxy-5-trifluoromethyl-phenyl)-[1,2,4]triazolo[1,5-a]pyridine-2-yl]-(2,3,4,5-tetrahydro-1H-3-benzazepin-7-yl)-amine (0.200 g, 0.428 mmol) in N,N-dimethylformamide (5 mL) was added potassium carbonate (0.177 g, 1.28 mmol), 1-chloro-2-methanesulfonyl-ethane (0.122 g, 0.856 mmol), followed by sodium iodide (0.0641 g, 0.428 mmol) and was heated at 80° C. overnight and cooled at r.t. The reaction was diluted with ethyl acetate, washed with water several times, dried over sodium sulfate, and concentrated. The product was purified using Prep TLC plates (5% methanol in dichloromethane) and concentrated to give [8-(2-ethoxy-5-trifluoromethyl-phenyl)-[1,2,4]triazolo[1,5-a]pyridin-2-yl]-[3-(2-methanesulfonyl-ethyl)-2,3,4,5-tetrahydro-1H-3-benzazepin-7yl)-amine (0.140 g, 57%). MP=105-109° C. $^1$H NMR (400 MHz, (D$_3$C)$_2$SO, δ, ppm): 9.51 (s, 1H), 8.78 (d, 1H), 7.98 (s, 1H), 7.78 (d, 1H), 7.68 (d, 1H), 7.40 (m, 3H), 7.08 (t, 1H), 6.95 (d, 1H), 4.15 (q, 2H), 3.28 (m, 2H), 3.05 (s, 3H), 2.85 (m, 2H), 2.75 (m, 4H), 2.55 (m, 4H), 1.22 (t, 3H): MS=574 (MH)+.

Example 321

2-{7-[8-(2-Ethoxy-5-trifluoromethyl-phenyl)-[1,2,4]triazolo[1,5-a]pyridin-2-ylamino]-1,2,4,5-tetrahydro-3-benzazepin-3-yl}-N,N-dimethyl-acetamide

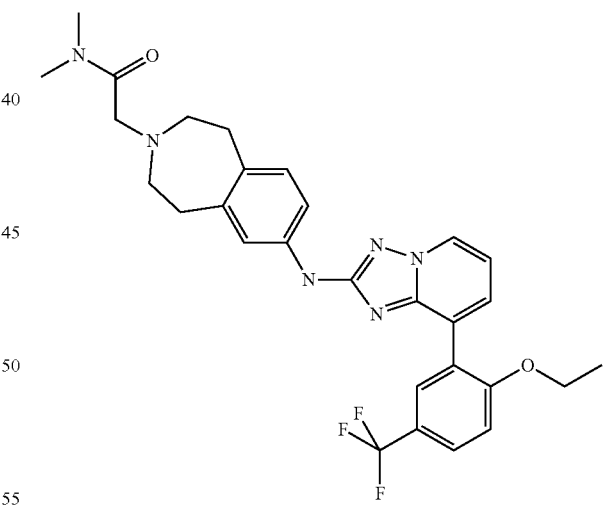

2-{7-[8-(2-Ethoxy-5-trifluoromethyl-phenyl)-[1,2,4]triazolo[1,5-a]pyridin-2-ylamino]-1,2,4,5-tetrahydro-3-benzazepin-3-yl}-N,N-dimethyl-acetamide was prepared from [8-(2-ethoxy-5-trifluoromethyl-phenyl)-[1,2,4]triazolo[1,5-a]pyridin-2-yl]-2,3,4,5-tetrahydro-1H-3-benzazepin-7-yl)-amine (0.200 g, 0.428 mmol) and 2-chloro-N,N-dimethyl-acetamide (0.066 mL, 0.642 mmol) in a manner analogous to Example 313 to give product (0.105 g, 44%). MP=197-200° C. $^1$H NMR (400 MHz, (D$_3$C)$_2$SO, δ, ppm): 9.51 (s, 1H), 8.78 (d, 1H), 7.98 (s, 1H), 7.78 (d, 1H), 7.68 (d, 1H), 7.38 (m, 3H), 7.08 (t, 1H), 6.95 (d, 1H), 4.15 (q, 2H), 3.28 (s, 2H), 3.05 (s, 3H), 2.80 (s, 3H), 2.75 (m, 4H), 2.55 (m, 4H), 1.22 (t, 3H): MS=553 (MH)+.

Example 322

[3-(2-Methanesulfonyl-ethyl)-2,3,4,5-tetrahydro-1H-3-benzazepin-7-yl]-[8-(2-methoxy-5-trifluoromethyl-phenyl)-[1,2,4]triazolo[1,5-a]pyridine-2-yl]-amine

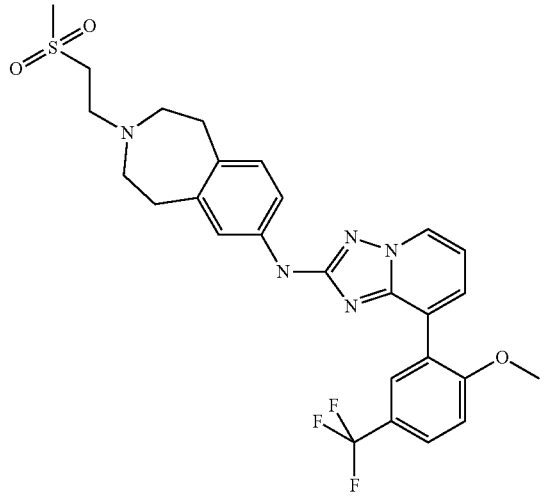 [SMILES: COc1ccc(C(F)(F)F)cc1-c1cccn2nc(Nc3ccc4c(c3)CCN(CCS(C)(=O)=O)CC4)nc12]

[3-(2-Methanesulfonyl-ethyl)-2,3,4,5-tetrahydro-1H-3-benzazepin-7-yl]-[8-(2-methoxy-5-trifluoromethyl-phenyl)-[1,2,4]triazolo[1,5-a]pyridine-2-yl]-amine was prepared from [8-(2-methoxy-5-trifluoromethyl-phenyl)-[1,2,4]triazolo[1,5-a]pyridine-2-yl]-(2,3,4,5-tetrahydro-1H-3-benzazepin-7-yl)-amine (0.200 g, 0.441 mmol) and 1-chloro-2-methanesulfonyl-ethane (0.126 g, 0.882 mmol) in a manner analogous to Example 320b to give product (0.150 g, 61%). MP=194-196° C. $^1$H NMR (400 MHz, (D$_3$C)$_2$SO, δ, ppm): 9.52 (s, 1H), 8.80 (d, 1H), 7.95 (s, 1H), 7.82 (d, 1H), 7.62 (d, 1H), 7.40 (m, 3H), 7.08 (t, 1H), 7.00 (d, 1H), 3.85 (s, 3H), 3.28 (m, 2H), 3.05 (s, 3H), 2.85 (m, 2H), 2.75 (m, 4H), 2.60 (m, 4H): MS=560 (MH)+.

Example 323

2-{7-[8-(5-Fluoro-2-methoxy-phenyl)-[1,2,4]triazolo[1,5-a]pyridin-2-ylamino]-1,2,4,5-tetrahydro-3-benzazepin-3-yl}-N,N-dimethyl-acetamide

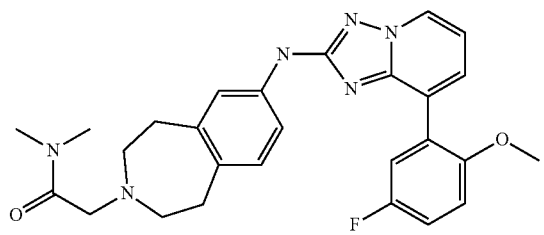 [SMILES: COc1ccc(F)cc1-c1cccn2nc(Nc3ccc4c(c3)CCN(CC(=O)N(C)C)CC4)nc12]

2-{7-[8-(5-Fluoro-2-methoxy-phenyl)-[1,2,4]triazolo[1,5-a]pyridin-2-ylamino]-1,2,4,5-tetrahydro-3-benzazepin-3-yl}-N,N-dimethyl-acetamide was prepared from [8-(5-fluoro-2-methoxy-phenyl)-[1,2,4]triazolo[1,5-a]pyridin-2-yl]-2,3,4,5-tetrahydro-1H-3-benzazepin-7-yl)-amine (0.150 g, 0.372 mmol) and 2-chloro-N,N-dimethyl-acetamide (0.0574 mL, 0.558 mmol) in a manner analogous to Example 313 to give product (0.035 g, 19%). MP=115-118° C. $^1$H NMR (400 MHz, (D$_3$C)$_2$SO, δ, ppm): 9.54 (s, 1H), 8.77 (d, 1H), 7.65 (d, 1H), 7.55 (m, 1H), 7.42 (m, 1H), 7.38 (s, 1H), 7.25 (m, 1H), 7.18 (m, 1H), 7.08 (t, 1H), 7.00 (d, 1H), 3.75 (s, 3H), 3.25 (s, 2H), 3.05 (s, 3H), 2.70-2.82 (br m, 7H), 2.55 (m, 4H): MS=489 (MH)+.

Example 324

2-{7-[8-(4-Fluoro-2-methoxy-phenyl)-[1,2,4]triazolo[1,5-a]pyridin-2-ylamino]-1,2,4,5-tetrahydro-3-benzazepin-3-yl}-N,N-dimethyl-acetamide

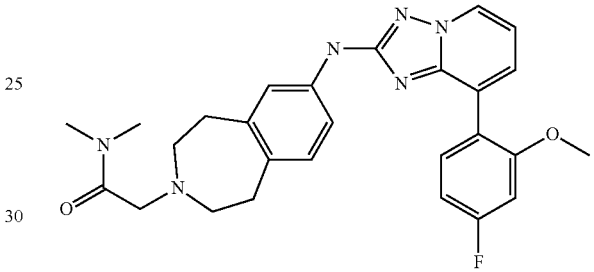

2-{7-[8-(4-Fluoro-2-methoxy-phenyl)-[1,2,4]triazolo[1,5-a]pyridin-2-ylamino]-1,2,4,5-tetrahydro-3-benzazepin-3-yl}-N,N-dimethyl-acetamide was prepared from [8-(4-fluoro-2-methoxy-phenyl)-[1,2,4]triazolo[1,5-a]pyridin-2-yl]-2,3,4,5-tetrahydro-1H-3-benzazepin-7-yl)-amine (0.066 g, 0.160 mmol) and 2-chloro-N,N-dimethyl-acetamide (0.025 mL, 0.240 mmol) in a manner analogous to Example 313 to give product (0.030 g, 38%). MP=101-105° C. $^1$H NMR (400 MHz, (D$_3$C)$_2$SO, δ, ppm): 9.52 (s, 1H), 8.75 (d, 1H), 7.60 (m, 1H), 7.55 (d, 1H), 7.42 (d, 1H), 7.32 (s, 1H), 7.05 (m, 3H), 6.88 (m, 1H), 3.77 (s, 3H), 3.25 (s, 2H), 3.05 (s, 3H), 2.82 (s, 3H), 2.75 (m, 4H), 2.60 (m, 4H): MS=489 (MH)+.

Example 325

2-{7-[8-(4-Chloro-2-methoxy-phenyl)-[1,2,4]triazolo[1,5-a]pyridin-2-ylamino]-1,2,4,5-tetrahydro-3-benzazepin-3-yl}-N,N-dimethyl-acetamide

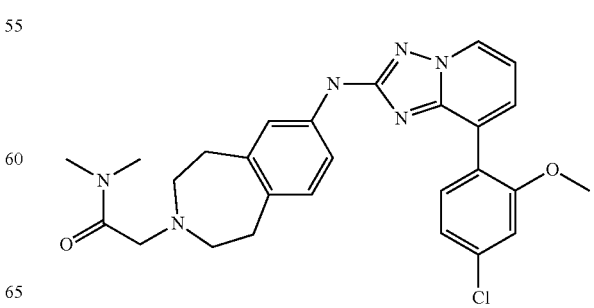

2-{7-[8-(4-Chloro-2-methoxy-phenyl)-[1,2,4]triazolo[1,5-a]pyridin-2-ylamino]-1,2,4,5-tetrahydro-3-benzazepin-3-yl}-N,N-dimethyl-acetamide was prepared from [8-(4-chloro-2-methoxy-phenyl)-[1,2,4]triazolo[1,5-a]pyridin-2-yl]-2,3,4,5-tetrahydro-1H-3-benzazepin-7-yl)-amine (0.044 g, 0.100 mmol) and 2-chloro-N,N-dimethyl-acetamide (.0162 mL, 0.157 mmol) in a manner analogous to Example 313 to give product (0.025 g, 47%). MP=105-109° C. ¹H NMR (400 MHz, (D₃C)₂SO, δ, ppm): 9.51 (s, 1H), 8.77 (d, 1H), 7.55 (m, 2H), 7.42 (d, 1H), 7.32 (s, 1H), 7.25 (s, 1H), 7.15 (m, 1H), 7.02 (m, 2H), 3.79 (s, 3H), 3.25 (s, 2H), 3.05 (s, 3H), 2.82 (s, 3H), 2.75 (m, 4H), 2.60 (m, 4H): MS=506 (MH)+.

Example 326

2-{7-[8-(2-Isopropoxy-5-trifluoromethyl-phenyl)-[1,2,4]triazolo[1,5-a]pyridin-2-ylamino]-1,2,4,5-tetrahydro-3-benzazepin-3-yl}-N,N-dimethyl-acetamide

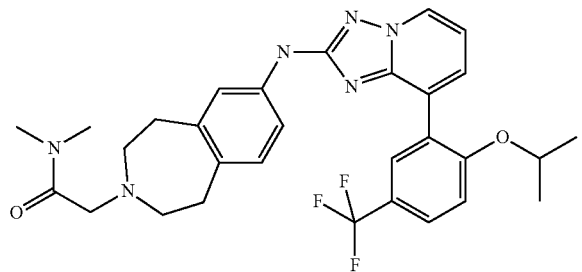 [SMILES: CC(C)Oc1ccc(C(F)(F)F)cc1-c1cccn2nc(Nc3ccc4c(c3)CCN(CC(=O)N(C)C)CC4)nc12]

2-{7-[8-(2-Isopropoxy-5-trifluoromethyl-phenyl)-[1,2,4]triazolo[1,5-a]pyridin-2-ylamino]-1,2,4,5-tetrahydro-3-benzazepin-3-yl}-N,N-dimethyl-acetamide was prepared from [8-(2-isopropoxy-5-trifluoromethyl-phenyl)-[1,2,4]triazolo[1,5-a]pyridin-2-yl]-2,3,4,5-tetrahydro-1H-3-benzazepin-7-yl)-amine (0.150 g, 0.312 mmol) and 2-chloro-N,N-dimethyl-acetamide (0.048 mL, 0.467 mmol) in a manner analogous to Example 313 to give product (0.050 g, 28%). MP=108-112° C. ¹H NMR (400 MHz, (D₃C)₂SO, δ, ppm): 9.49 (s, 1H), 8.77 (d, 1H), 8.00 (s, 1H), 7.75 (d, 1H), 7.65 (d, 1H), 7.40 (m, 3H), 7.05 (t, 1H), 6.98 (d, 1H), 4.75 (m, 1H), 3.25 (s, 2H), 3.05 (s, 3H), 2.82 (s, 3H), 2.75 (m, 4H), 2.55 (m, 4H), 1.22 (d, 6H): MS=567 (MH)+.

Example 327

2-[4-(4-{8-[2-(2,2-Difluoro-ethoxy)-5-trifluoromethyl-phenyl]-[1,2,4]-triazolo[1,5-a]pyridin-2-ylamino}-phenyl)-piperidin-1-yl]-N,N-dimethyl-acetamide

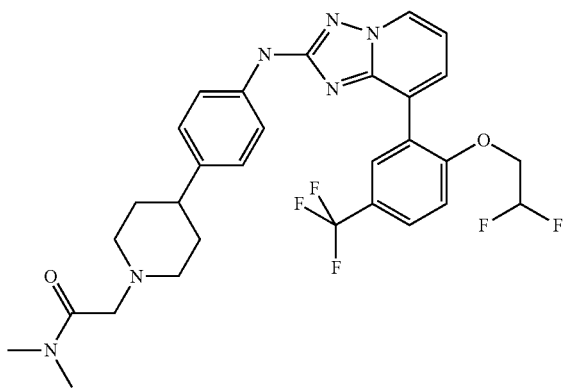 [SMILES: CN(C)C(=O)CN1CCC(c2ccc(Nc3nc4c(-c5cc(C(F)(F)F)ccc5OCC(F)F)cccn4n3)cc2)CC1]

2-[4-(4-{8-[2-(2,2-Difluoro-ethoxy)-5-trifluoromethyl-phenyl]-[1,2,4]-triazolo[1,5-a]pyridin-2-ylamino}-phenyl)-piperidin-1-yl]-N,N-dimethyl-acetamide was prepared from {8-[2-(2,2-difluoro-ethoxy)-5-trifluoromethyl-phenyl]-[1,2,4]-triazolo[1,5-a]pyridin-2-yl}-(4-piperidin-4-yl-phenyl)-amine (0.067 g, 0.130 mmol) and 2-chloro-N,N-dimethyl-acetamide (0.020 mL, 0.190 mmol) in a manner analogous to Example 313 to give product (0.020 g, 26%). MP=98-101° C. ¹H NMR (400 MHz, (D₃C)₂SO, δ, ppm): 9.54 (s, 1H), 8.80 (d, 1H), 8.08 (s, 1H), 7.82 (d, 1H), 7.68 (d, 1H), 7.58 (m, 2H), 7.45 (d, 1H), 7.10 (m, 3H), 6.30 (br m, 1H), 4.49 (m, 2H), 3.15 (s, 2H), 3.05 (s, 3H), 2.95 (m, 2H), 2.82 (s, 3H), 2.38 (m, 1H), 2.12 (m, 2H), 1.55-1.72 (br m, 4H): MS=603 (MH)+.

Example 328

{8-[2-(2,2-Difluoro-ethoxy)-5-trifluoromethyl-phenyl]-[1,2,4]triazolo[1,5-a]pyridin-2-yl}-2,3,4,5-tetrahydro-1H-3-benzazepin-7-yl)-amine

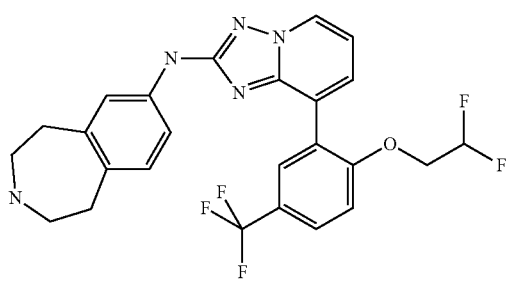 [SMILES: FC(F)COc1ccc(C(F)(F)F)cc1-c1cccn2nc(Nc3ccc4c(c3)CCNCC4)nc12]

{8-[2-(2,2-Difluoro-ethoxy)-5-trifluoromethyl-phenyl]-[1,2,4]triazolo[1,5-a]pyridin-2-yl}-2,3,4,5-tetrahydro-1H-3-benzazepin-7-yl)-amine was prepared from 7-{8-[2-(2,2-difluoroethoxy-ethoxy)-5-trifluoromethyl-phenyl]-[1,2,4]triazolo[1,5-a]pyridin-2-ylamino}-1,2,4,5-tetrahydro-3-benzazepine-3-carboxylic acid tert-butyl ester and trifluoroacetic acid (1 mL) in a manner analogous to Example 312 to give product (0.296 g). MP=104-108° C. ¹H NMR (400 MHz, (D₃C)₂SO, δ, ppm): 9.49 (s, 1H), 8.78 (d, 1H), 8.09 (s, 1H), 7.82 (d, 1H), 7.68 (d, 1H), 7.45 (m, 3H), 7.05 (t, 1H), 6.98 (d, 1H), 6.30 (br m, 1H), 4.45 (m, 2H), 2.80 (br m, 9H): MS=504 (MH)+.

Example 329

2-(7-{8-[2-(2,2-Difluoro-ethoxy)-5-trifluoromethyl-phenyl]-[1,2,4]triazolo[1,5-a]pyridin-2-ylamino}-1,2,4,5-tetrahydro-3-benzazepin-3-yl)-N,N-dimethyl-acetamide

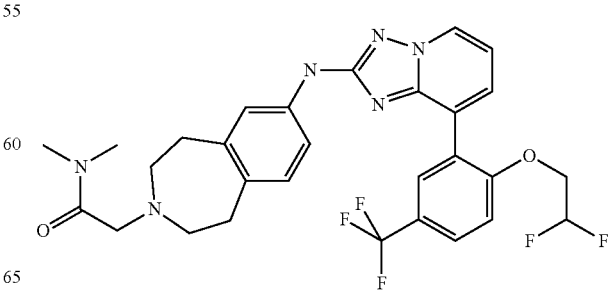

2-(7-{8-[2-(2,2-Difluoro-ethoxy)-5-trifluoromethyl-phenyl]-[1,2,4]triazolo[1,5-a]pyridin-2-ylamino}-1,2,4,5-tetrahydro-3-benzazepin-3-yl)-N,N-dimethyl-acetamide was prepared from {8-[2-(2,2-difluoro-ethoxy)-5-trifluoromethyl-phenyl]-[1,2,4]triazolo[1,5-a]pyridin-2-yl}-2,3,4,5-tetrahydro-1H-3-benzazepin-7-yl)-amine (0.150 g, 0.298 mmol) and 2-chloro-N,N-dimethyl-acetamide (0.046 mL, 0.447 mmol) in a maner analogous to Example 313 to give product (0.060 g, 34%). MP=107-110° C. $^1$H NMR (400 MHz, $(D_3C)_2SO$, δ, ppm): 9.49 (s, 1H), 8.79 (d, 1H), 8.09 (s, 1H), 7.82 (d, 1H), 7.68 (d, 1H), 7.45 (m, 3H), 7.05 (t, 1H), 6.98 (d, 1H), 6.30 (br m, 1H), 4.45 (m, 2H), 3.25 (s, 2H), 3.05 (s, 3H), 2.85 (s, 3H), 2.75 (m, 4H), 2.58 (m, 4H): MS=589 (MH)+.

Example 330

2-(4-{4-[8-(4-Chloro-2-methoxy-phenyl)-[1,2,4]-triazolo[1,5-a]pyridin-2-ylamino]-phenyl}-piperidin-1-yl)-N,N-dimethyl-acetamide

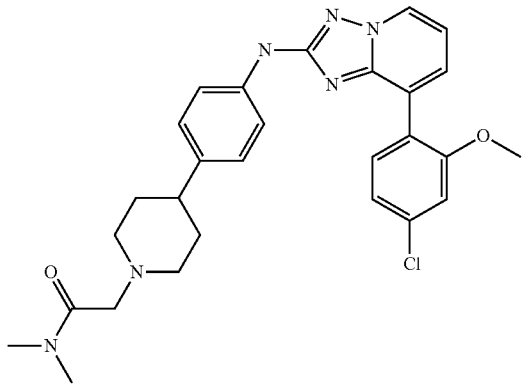

2-(4-{4-[8-(4-Chloro-2-methoxy-phenyl)-[1,2,4]-triazolo[1,5-a]pyridin-2-ylamino]-phenyl}-piperidin-1-yl)-N,N-dimethyl-acetamide was prepared from [8-(4-chloro-2-methoxy-phenyl)-[1,2,4]-triazolo[1,5-a]pyridin-2-yl]-(4-piperidin-4-yl-phenyl)-amine (0.046 g, 0.110 mmol) and 2-chloro-N,N-dimethyl-acetamide (0.016 mL, 0.159 mmol) in a manner analogous to Example 313 to give product (0.010 g, 18%). MP=104-107° C. $^1$H NMR (400 MHz, $(D_3C)_2SO$, δ, ppm): 9.49 (s, 1H), 8.79 (d, 1H), 7.58 (m, 4H), 7.25 (s, 1H), 7.15 (m, 3H), 7.05 (m, 1H), 3.78 (s, 3H), 3.15 (s, 2H), 3.05 (s, 3H), 2.92 (m, 2H), 2.85 (s, 3H), 2.35 (m, 1H), 2.12 (m, 2H), 1.65 (m, 4H): MS=520 (MH)+.

Example 331

2-{6-[8-(4-Chloro-2-methoxy-phenyl)-[1,2,4]-triazolo[1,5-a]pyridin-2-ylamino]-3,4-dihydro-1H-isoquinolin-2-yl}-N,N-dimethyl-acetamide

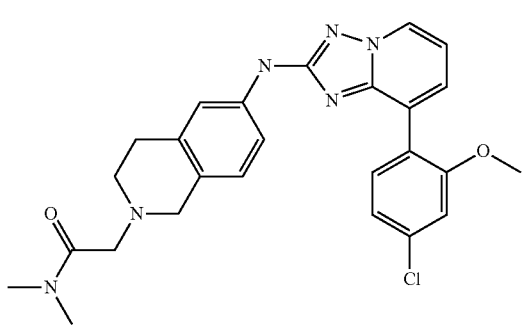

2-{6-[8-(4-Chloro-2-methoxy-phenyl)-[1,2,4]-triazolo[1,5-a]pyridin-2-ylamino]-3,4-dihydro-1H-isoquinolin-2-yl}-N,N-dimethyl-acetamide was prepared from [8-(4-chloro-2-methoxy-phenyl)-[1,2,4]-triazolo[1,5-a]pyridin-2-yl]-(1,2,3,4-tetrahydro-isoquinolin-6-yl)-amine (0.077 g, 0.190 mmol) and 2-chloro-N,N-dimethyl-acetamide (0.029 mL, 0.284 mmol) in a manner analogous to Example 313 to give product (0.015 g, 16%). MP=103-106° C. $^1$H NMR (400 MHz, $(D_3C)_2SO$, δ, ppm): 9.53 (s, 1H), 8.78 (d, 1H), 7.58 (m, 2H), 7.42 (m, 2H), 7.25 (s, 1H), 7.15 (d, 1H), 7.05 (t, 1H), 6.92 (d, 1H), 3.78 (s, 3H), 3.54 (s, 2H), 3.28 (s, 2H), 3.05 (s, 3H), 2.85 (s, 3H), 2.78 (m, 2H), 2.70 (m, 2H): MS=491 (MH)+.

Example 332

2-(4-{3-[8-(4-Chloro-2-methoxy-phenyl)-[1,2,4]-triazolo[1,5-a]pyridin-2-ylamino]-phenyl}-piperidin-1-yl)-N,N-dimethyl-acetamide

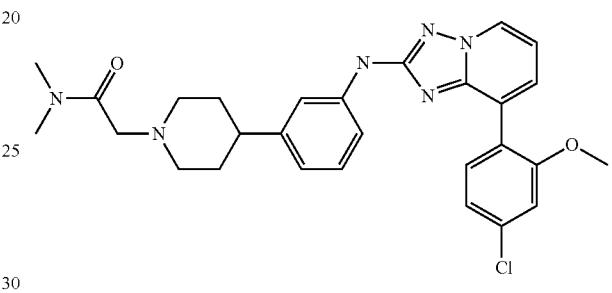

2-(4-{3-[8-(4-Chloro-2-methoxy-phenyl)-[1,2,4]-triazolo[1,5-a]pyridin-2-ylamino]-phenyl}-piperidin-1-yl)-N,N-dimethyl-acetamide was prepared from [8-(4-chloro-2-methoxy-phenyl)-[1,2,4]-triazolo[1,5-a]pyridin-2-yl]-(3-piperidin-4-yl-phenyl)-amine (0.047 g, 0.110 mmol) and 2-chloro-N,N-dimethyl-acetamide (0.017 mL, 0.160 mmol) in a manner analogous to Example 313 to give product (0.012 g, 21%). MP=79-82° C. $^1$H NMR (400 MHz, $(D_3C)_2SO$, δ, ppm): 9.59 (s, 1H), 8.77 (d, 1H), 7.60 (m, 3H), 7.45 (d, 1H), 7.25 (s, 1H), 7.15 (m, 2H), 7.05 (m, 1H), 6.75 (d, 1H), 3.78 (s, 3H), 3.15 (s, 2H), 3.05 (s, 3H), 2.95 (m, 2H), 2.80 (s, 3H), 2.35 (m, 1H), 2.15 (m, 2H), 1.65 (m, 4H): MS=520 (MH)+.

Example 333

4-{4-[8-(2-Methoxy-5-trifluoromethyl-phenyl)-[1,2,4]-triazolo[1,5-a]pyridin-2-ylamino]-phenyl}-piperidine-1-carboxylic acid tert-butyl ester

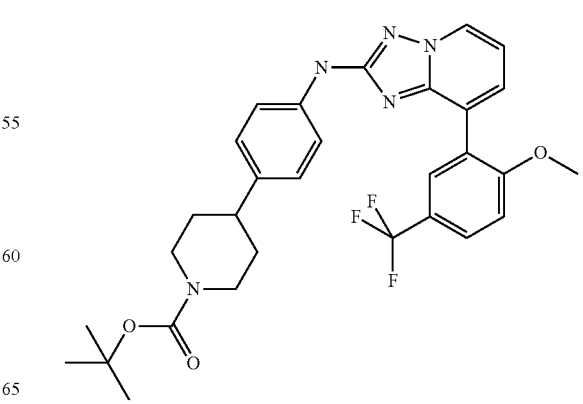

4-{4-[8-(2-Methoxy-5-trifluoromethyl-phenyl)-[1,2,4]-triazolo[1,5-a]pyridin-2-ylamino]-phenyl}-piperidine-1-carboxylic acid tert-butyl ester was prepared from 2-chloro-8-methoxy-5-trifluoromethyl-phenyl)-[1,2,4]-triazolo[1,5-a]pyridine (0.250 g, 0.763 mmol) and 4-(4-amino-phenyl)-piperidine-1-carboxylic acid tert-butyl ester (0.253 g, 0.916 mmol) in a manner analogous to Example 311a and 311b to give product (0.342 g, 79%). MP=100-103° C. $^1$H NMR (400 MHz, (D$_3$C)$_2$SO, δ, ppm): 9.57 (s, 1H), 8.79 (d, 1H), 7.95 (s, 1H), 7.82 (d, 1H), 7.62 (d, 1H), 7.55 (d, 2H), 7.35 (d, 1H) 7.05 (m, 3H), 4.05 (m, 2H), 3.85 (s, 3H), 2.80 (br m, 2H), 2.60 (m, 1H), 1.72 (m, 2H), 1.50 (m, 2H), 1.41 (s, 9H): MS=568 (MH)+.

Example 334

[8-(2-Methoxy-5-trifluoromethyl-phenyl)-[1,2,4]-triazolo[1,5-a]pyridin-2-yl]-(4-piperidin-4-yl-phenyl)-amine

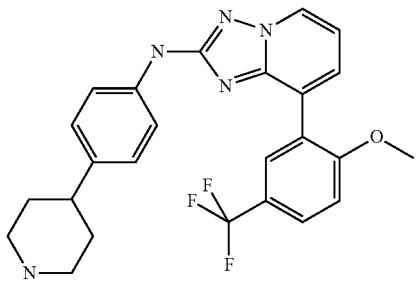 [SMILES: COc1ccc(C(F)(F)F)cc1-c1cccn2nc(Nc3ccc(C4CCNCC4)cc3)nc12]

[8-(2-Methoxy-5-trifluoromethyl-phenyl)-[1,2,4]-triazolo[1,5-a]pyridin-2-yl]-(4-piperidin-4-yl-phenyl)-amine was prepared from 4-{4-[8-(2-methoxy-5-trifluoromethyl-phenyl)-[1,2,4]-triazolo[1,5-a]pyridin-2-ylamino]-phenyl}-piperidine-1-carboxylic acid tert-butyl ester (0.342 g, 0.603 mmol) and trifluoroacetic acid (1 mL) in a manner analogous to Example 312 to give product (0.239 g, 85%). MP=104-108° C. $^1$H NMR (400 MHz, (D$_3$C)$_2$SO, δ, ppm): 9.54 (s, 1H), 8.79 (d, 1H), 7.95 (s, 1H), 7.82 (d, 1H), 7.62 (d, 1H), 7.55 (d, 2H), 7.35 (d, 1H), 7.05 (m, 3H), 3.85 (s, 3H), 3.00 (m, 2H), 2.55 (br m, 4H), 1.65 (m, 2H), 1.50 (m, 2H): MS=468 (MH)+.

Example 335

2-(4-{4-[8-(2-Methoxy-5-trifluoromethyl-phenyl)-[1,2,4]-triazolo[1,5-a]pyridin-2-ylamino]-phenyl}-piperidin-1-yl)-N,N-dimethyl-acetamide

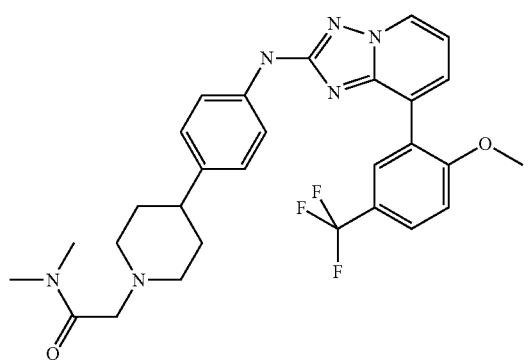

2-(4-{4-[8-(2-Methoxy-5-trifluoromethyl-phenyl)-[1,2,4]-triazolo[1,5-a]pyridin-2-ylamino]-phenyl}-piperidin-1-yl)-N,N-dimethyl-acetamide was prepared from [8-(2-methoxy-5-trifluoromethyl-phenyl)-[1,2,4]-triazolo[1,5-a]pyridin-2-yl]-(4-piperidin-4-yl-phenyl)-amine (0.150 g, 0.321 mmol) and 2-chloro-N,N-dimethyl-acetamide (0.049 mL, 0.481 mmol) in a manner analogous to Example 313 to give product (0.060 g, 34%). MP=109-112° C. $^1$H NMR (400 MHz, (D$_3$C)$_2$SO, δ, ppm): 9.55 (s, 1H), 8.79 (d, 1H), 7.95 (s, 1H), 7.82 (d, 1H), 7.62 (d, 1H), 7.55 (d, 2H), 7.35 (d, 1H), 7.05 (m, 3H), 3.85 (s, 3H), 3.15 (s, 2H), 3.05 (s, 3H), 2.95 (m, 2H), 2.82 (s, 3H), 2.40 (m, 1H), 2.10 (m, 2H), 1.65 (br m, 4H): MS=553 (MH)+.

Example 336

6-[8-(2-Methoxy-5-trifluoromethyl-phenyl)-[1,2,4]triazolo[1,5-a]pyridin-2-ylamino]-3,4-dihydro-1H-isoquinoline-2-carboxylic acid tert-butyl ester

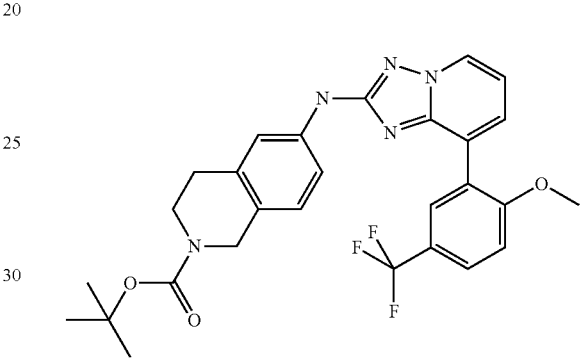

6-[8-(2-Methoxy-5-trifluoromethyl-phenyl)-[1,2,4]triazolo[1,5-a]pyridin-2-ylamino]-3,4-dihydro-1H-isoquinoline-2-carboxylic acid tert-butyl ester was prepared from 2-chloro-8-(2-methoxy-5-trifluoromethyl-phenyl)-[1,2,4]triazolo[1,5-a]pyridine (0.250 g, 0.763 mmol) and 6-amino-3,4-dihydro-1H-isoquinoline-2-carboxylic acid tert-butyl ester (0.284 g, 1.14 mmol) in a manner analogous to Example 311a and 311b to give product. MP=86-90° C. $^1$H NMR (400 MHz, (D$_3$C)$_2$SO, δ, ppm): 9.59 (s, 1H), 8.78 (d, 1H), 7.95 (s, 1H), 7.80 (d, 1H), 7.62 (d, 1H), 7.45 (m, 2H), 7.38 (d, 1H), 7.05 (m, 2H), 4.40 (m, 2H), 3.85 (s, 3H), 3.52 (m, 2H), 2.75 (m, 2H), 1.42 (s, 9H): MS=540 (MH)+.

Example 337

[8-(2-Methoxy-5-trifluoromethyl-phenyl)-[1,2,4]triazolo[1,5-a]pyridine-2-yl]-(1,2,3,4-tetrahydro-isoquinolin-6-yl)-amine

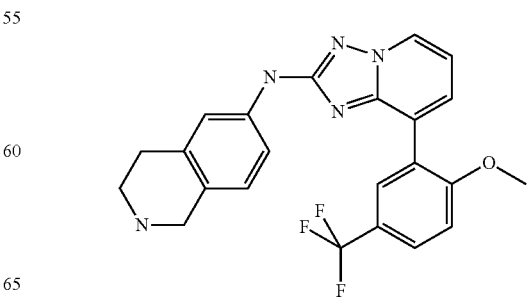

[8-(2-Methoxy-5-trifluoromethyl-phenyl)-[1,2,4]triazolo[1,5-a]pyridine-2-yl]-(1,2,3,4-tetrahydro-isoquinolin-6-yl)-amine was prepared from 6-[8-(2-methoxy-5-trifluoromethyl-phenyl)-[1,2,4]triazolo[1,5-a]pyridin-2-ylamino]-3,4-dihydro-1H-isoquinoline-2-carboxylic acid tert-butyl ester and trifluoroacetic acid (1 mL) in a manner analogous to Example 312 to give product (0.255 g). MP=99-103° C. $^1$H NMR (400 MHz, (D$_3$C)$_2$SO, δ, ppm): 9.47 (s, 1H), 8.79 (d, 1H), 7.95 (s, 1H), 7.80 (d, 1H), 7.62 (d, 1H), 7.38 (m, 3H), 7.05 (t, 1H), 6.85 (d, 1H), 3.85 (s, 3H), 3.75 (s, 2H), 2.92 (m, 2H), 2.63 (br m, 3H): MS=440 (MH)+.

Example 338

2-{6-[8-(2-Methoxy-5-trifluoromethyl-phenyl)-[1,2,4]-triazolo[1,5-a]pyridin-2-ylamino]-3,4-dihydro-1H-isoquinolin-2-yl}-N,N-dimethyl-acetamide

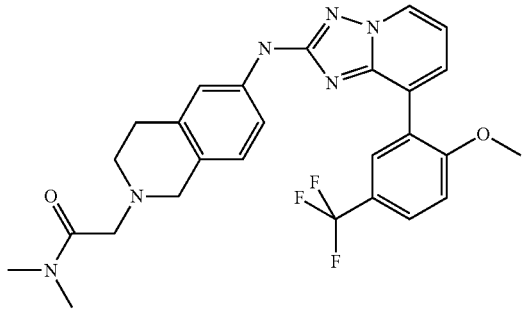

2-{6-[8-(2-Methoxy-5-trifluoromethyl-phenyl)-[1,2,4]-triazolo[1,5-a]pyridin-2-ylamino]-3,4-dihydro-1H-isoquinolin-2-yl}-N,N-dimethyl-acetamide was prepared from [8-(2-methoxy-5-trifluoromethyl-phenyl)-[1,2,4]-triazolo[1,5-a]pyridin-2-yl]-(1,2,3,4-tetrahydro-isoquinolin-6-yl)-amine (0.150 g, 0.341 mmol) and 2-chloro-N,N-dimethyl-acetamide (0.053 mL, 0.512 mmol) in a manner analogous to Example 313 to give product (0.060 g, 34%). MP=99-102° C. $^1$H NMR (400 MHz, (D$_3$C)$_2$SO, δ, ppm): 9.51 (s, 1H), 8.79 (d, 1H), 7.95 (s, 1H), 7.80 (d, 1H), 7.62 (d, 1H), 7.38 (m, 3H), 7.05 (t, 1H), 6.90 (d, 1H), 3.85 (s, 3H), 3.52 (s, 2H), 3.28 (s, 2H), 3.05 (s, 3H), 2.82 (s, 3H), 2.70 (br m, 4H): MS=525 (MH)+.

Example 339

4-{4-[8-(4-Difluoromethyl-2-methoxy-phenyl)-[1,2,4]-triazolo[1,5-a]pyridin-2-ylamino]-phenyl}-piperidine-1-carboxylic acid tert-butyl ester

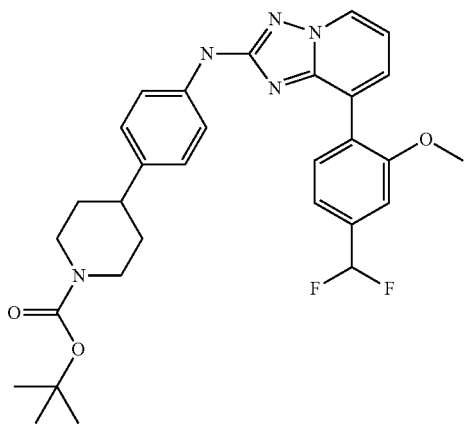 [SMILES: COc1cc(C(F)F)ccc1-c1cccn2nc(Nc3ccc(C4CCN(C(=O)OC(C)(C)C)CC4)cc3)nc12]

4-{4-[8-(4-Difluoromethyl-2-methoxy-phenyl)-[1,2,4]-triazolo[1,5-a]pyridin-2-ylamino]-phenyl}-piperidine-1-carboxylic acid tert-butyl ester was prepared from 2-chloro-8-(4-difluoromethyl-2-methoxy-phenyl)-[1,2,4]-triazolo[1,5-a]pyridine (0.150 g, 0.484 mmol) and 4-(4-amino-phenyl)-piperidine-1-carboxylic acid tert-butyl ester (0.161 g, 0.581 mmol) in a manner analogous to Example 311a and 311b to give product (0.191 g, 72%). MP=95-100° C. $^1$H NMR (400 MHz, (D$_3$C)$_2$SO, δ, ppm): 9.57 (s, 1H), 8.78 (d, 1H), 7.70 (d, 1H), 7.55 (m, 3H), 7.32 (s, 1H), 7.25 (m, 1H), 7.15 (d, 2H), 7.10 (br m, 1H), 7.05 (m, 1H), 4.10 (m, 2H), 3.78 (s, 3H), 2.78 (br m, 2H), 2.55 (m, 1H), 1.75 (m, 2H), 1.45 (m, 2H), 1.41 (s, 9H): MS=550 (MH)+.

Example 340

[8-(4-Difluoromethyl-2-methoxy-phenyl)-[1,2,4]-triazolo[1,5-a]pyridin-2-yl]-(4-piperidin-4-yl-phenyl)-amine

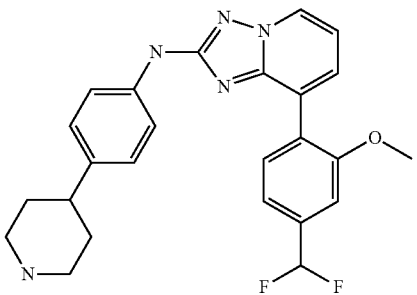 [SMILES: COc1cc(C(F)F)ccc1-c1cccn2nc(Nc3ccc(C4CCNCC4)cc3)nc12]

[8-(4-Difluoromethyl-2-methoxy-phenyl)-[1,2,4]-triazolo[1,5-a]pyridin-2-yl]-(4-piperidin-4-yl-phenyl)-amine was prepared from 4-{4-[8-(4-difluoromethyl-2-methoxy-phenyl)-[1,2,4]triazolo[1,5-a]pyridin-2-ylamino]-phenyl}-piperidine-1-carboxylic acid tert-butyl ester (0.191 g, 0.348 mmol) and trifluoroacetic acid (0.500 mL) in a manner analogous to Example 312 to give product (0.170 g, 99%). MP=208-212° C. $^1$H NMR (400 MHz, (D$_3$C)$_2$SO, δ, ppm): 9.57 (s, 1H), 8.78 (d, 1H), 7.70 (d, 1H), 7.55 (m, 3H), 7.32 (s, 1H), 7.25 (m, 1H), 7.15 (m, 3H), 7.10 (br m, 1H), 3.78 (s, 3H), 3.28 (br m, 3H), 2.92 (m, 2H), 2.65 (m, 1H), 1.83 (m, 2H), 1.65 (m, 2H): MS=450 (MH)+.

Example 341

2-(4-{4-[8-(4-difluoromethyl-2-methoxy-phenyl)-[1,2,4]-triazolo[1,5-a]pyridin-2-ylamino]-phenyl}-piperidin-1-yl)-N,N-dimethyl-acetamide

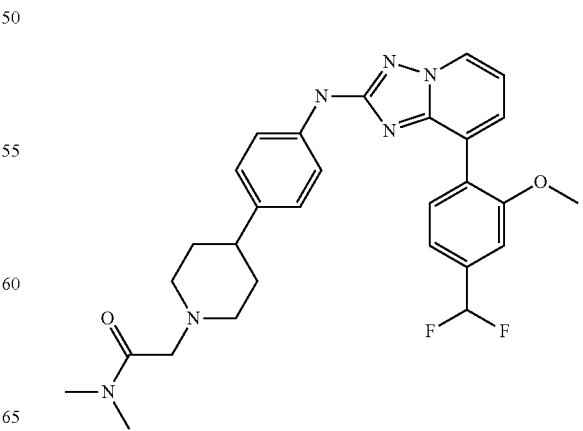

2-(4-{4-[8-(4-difluoromethyl-2-methoxy-phenyl)-[1,2,4]-triazolo[1,5-a]pyridin-2-ylamino]-phenyl}-piperidin-1-yl)-N,N-dimethyl-acetamide was prepared from [8-(4-difluoromethyl-2-methoxy-phenyl)-[1,2,4]-triazolo[1,5-a]pyridin-2-yl]-(4-piperidin-4-yl-phenyl)-amine (0.160 g, 0.356 mmol) and 2-chloro-N,N-dimethyl-acetamide (0.055 mL, 0.534 mmol) in a manner analogous to Example 313 to give product (0.035 g, 18%). MP=199-202° C. $^1$H NMR (400 MHz, (D$_3$C)$_2$SO, δ, ppm): 9.56 (s, 1H), 8.79 (d, 1H), 7.70 (d, 1H), 7.55 (m, 3H), 7.32 (s, 1H), 7.25 (d, 1H), 7.15 (d, 2H), 7.10 (br m, 1H), 7.05 (m, 1H), 3.81 (s, 3H), 3.12 (s, 2H), 3.05 (s, 3H), 2.90 (m, 2H), 2.82 (s, 3H), 2.38 (m, 1H), 2.10 (m, 2H), 1.65 (br m, 4H): MS=535 (MH)+.

Example 342

4-{4-[8-(4-Fluoro-phenyl)-[1,2,4]-triazolo[1,5-a]pyridin-2-ylamino]-phenyl}-piperidine-1-carboxylic acid tert-butyl ester

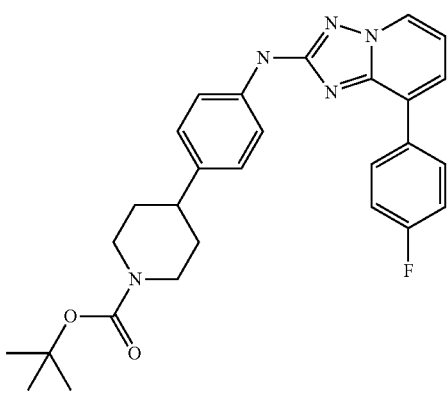 [SMILES: CC(C)(C)OC(=O)N1CCC(c2ccc(Nc3nc4c(-c5ccc(F)cc5)cccn4n3)cc2)CC1]

4-{4-[8-(4-Fluoro-phenyl)-[1,2,4]-triazolo[1,5-a]pyridin-2-ylamino]-phenyl}-piperidine-1-carboxylic acid tert-butyl ester was prepared from 2-chloro-8-(4-fluoro-phenyl)-[1,2,4]-triazolo[1,5-a]pyridine (0.190 g, 0.767 mmol) and 4-(4-amino-phenyl)-piperidine-1-carboxylic acid tert-butyl ester (0.254 g, 0.921 mmol) in a manner analogous to Example 311a and 311b to give product. MP=88-91° C. $^1$H NMR (400 MHz, (D$_3$C)$_2$SO, δ, ppm): 9.65 (s, 1H), 8.79 (d, 1H), 8.22 (m, 2H), 7.82 (d, 1H), 7.60 (d, 2H), 7.35 (m, 2H), 7.15 (d, 2H), 7.10 (m, 1H), 4.05 (m, 2H), 2.80 (m, 2H), 2.60 (m, 1H), 1.75 (m, 2H), 1.45 (m, 2H), 1.41 (s, 9H): MS=488 (MH)+.

Example 345

[8-(4-fluoro-phenyl)-[1,2,4]-triazolo[1,5-a]pyridin-2-yl]-(4-piperidin-4-yl-phenyl)-amine

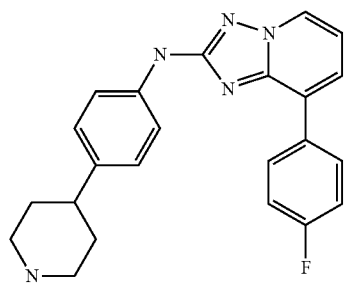 [SMILES: Fc1ccc(-c2cccn3nc(Nc4ccc(C5CCNCC5)cc4)nc23)cc1]

[8-(4-fluoro-phenyl)-[1,2,4]-triazolo[1,5-a]pyridin-2-yl]-(4-piperidin-4-yl-phenyl)-amine was prepared from 4-{4-[8-(4-fluoro-phenyl)-[1,2,4]-triazolo[1,5-a]pyridin-2-ylamino]-phenyl}-piperidine-1-carboxylic acid tert-butyl ester and trifluoroacetic acid (0.500 mL) in a manner analogous to Example 312 to give product (0.112 g). MP=244-247° C. $^1$H NMR (400 MHz, (D$_3$C)$_2$SO, δ, ppm): 9.62 (s, 1H), 8.79 (d, 1H), 8.22 (m, 2H), 7.82 (d, 1H), 7.60 (d, 2H), 7.35 (m, 2H), 7.12 (m, 3H), 3.00 (m, 2H), 2.55 (m, 3H), 2.20 br m, 1H), 1.65 (m, 2H), 1.45 (m, 2H). MS=388 (MH)+.

Example 346

(2,3-Dihydro-1H-isoindol-5-yl)-[8-(3-methoxy-phenyl)-[1,2,4]-triazolo[1,5-a]pyridin-2-yl]-amine

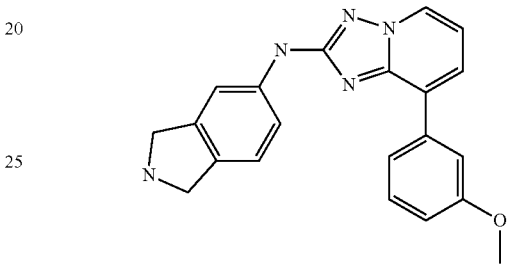

(2,3-Dihydro-1H-isoindol-5-yl)-[8-(3-methoxy-phenyl)-[1,2,4]-triazolo[1,5-a]pyridin-2-yl]-amine was prepared from 5-[8-(3-methoxy-phenyl)-[1,2,4]triazolo[1,5-a]pyridine-2-ylamino]-1,3-dihydro-isoindole-2-carboxylic acid tert-butyl ester and trifluoroacetic acid (0.500 mL) in a manner analogous to Example 312 to give product (0.025 g). MP=95-97° C. $^1$H NMR (400 MHz, (D$_3$C)$_2$SO, δ, ppm): 9.68 (s, 1H), 8.80 (d, 1H), 7.85 (d, 1H), 7.80 (s, 1H), 7.70 (m, 2H), 7.52 (m, 1H), 7.45 (m, 1H), 7.18 (d, 1H), 7.10 (t, 1H), 7.00 (d, 1H), 4.10 (br m, 4H), 3.86 (s, 3H), 3.40 (br m, 1H). MS=358 (MH)+.

Example 347

2-(4-{4-[8-(4-Fluoro-phenyl)-[1,2,4]-triazolo[1,5-a]pyridin-2-ylamino]-phenyl}-piperidin-1-yl)-N,N-dimethyl-acetamide

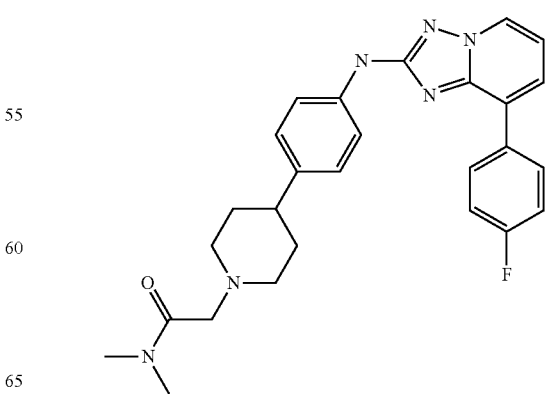

2-(4-{4-[8-(4-Fluoro-phenyl)-[1,2,4]-triazolo[1,5-a]pyridin-2-ylamino]-phenyl}-piperidin-1-yl)-N,N-dimethyl-acetamide was prepared from [8-(4-fluoro-phenyl)-[1,2,4]-triazolo[1,5-a]pyridin-2-yl]-(4-piperidin-4-yl-phenyl)-amine (0.092 g, 0.240 mmol) and 2-chloro-N,N-dimethyl-acetamide (0.037 mL, 0.360 mmol) in a manner analogous to Example 313 to give product (0.035 g, 31%). MP=209-212° C. $^1$H NMR (400 MHz, (D$_3$C)$_2$SO, δ, ppm): 9.64 (s, 1H), 8.79 (d, 1H), 8.22 (m, 2H), 7.82 (d, 1H), 7.60 (d, 2H), 7.35 (m, 2H), 7.12 (m, 3H), 3.13 (s, 2H), 3.05 (s, 3H), 2.92 (m, 2H), 2.82 (s, 3H), 2.40 (m, 1H), 2.12 (m, 2H), 1.64-1.70 (br m, 4H). MS=473 (MH)+.

Example 348

[8-(3-Methoxy-phenyl)-[1,2,4]-triazolo[1,5-a]pyridin-2-yl]-(4-piperidin-4-yl-phenyl)-amine

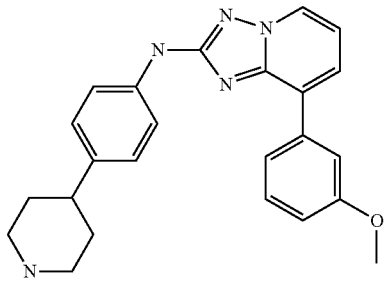 [SMILES: COc1cccc(-c2cccn3nc(Nc4ccc(C5CCNCC5)cc4)nc23)c1]

[8-(3-Methoxy-phenyl)-[1,2,4]-triazolo[1,5-a]pyridin-2-yl]-(4-piperidin-4-yl-phenyl)-amine was prepared from 4-{4-[8-(3-methoxy-phenyl)-[1,2,4]-triazolo[1,5-a]pyridin-2-ylamino]-phenyl}-piperidine-1-carboxylic acid tert-butyl ester (0.405 g, 0.812 mmol) and trifluoroacetic acid (2 mL) in a manner analogous to Example 312 to give product (0.150 g, 46%). MP=88-90° C. $^1$H NMR (400 MHz, (D$_3$C)$_2$SO, δ, ppm): 9.60 (s, 1H), 8.78 (d, 1H), 7.85 (m, 2H), 7.65 (m, 3H), 7.40 (m, 1H), 7.15 (m, 3H), 7.05 (m, 1H), 3.86 (s, 3H), 3.00 (m, 2H), 2.55 (m, 3H), 2.35 (br m, 1H), 1.65 (m, 2H), 1.45 (m, 2H). MS=400 (MH)+.

Example 349

2-(4-{4-[8-(3-Methoxy-phenyl)-[1,2,4]-triazolo[1,5-a]pyridin-2-ylamino]-phenyl}-piperidin-1-yl)-N,N-dimethyl-acetamide

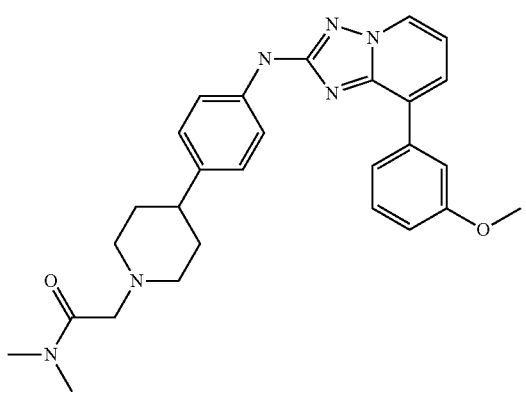

2-(4-{4-[8-(3-Methoxy-phenyl)-[1,2,4]-triazolo[1,5-a]pyridin-2-ylamino]-phenyl}-piperidin-1-yl)-N,N-dimethyl-acetamide was prepared from [8-(3-methoxy-phenyl)-[1,2,4]-triazolo[1,5-a]pyridin-2-yl]-(4-piperidin-4-yl-phenyl)-amine (0.150 g, 0.375 mmol) and 2-chloro-N,N-dimethyl-acetamide (0.057 mL, 0.563 mmol) in a manner analogous to Example 313 to give product (0.065 g, 36%). MP=178-179° C. $^1$H NMR (400 MHz, (D$_3$C)$_2$SO, δ, ppm): 9.61 (s, 1H), 8.78 (d, 1H), 7.85 (d, 1H), 7.80 (s, 1H), 7.65 (m, 3H), 7.40 (m, 1H), 7.15 (m, 3H), 7.05 (m, 1H), 3.86 (s, 3H), 3.15 (s, 2H), 3.05 (s, 3H), 2.92 (m, 2H), 2.85 (s, 3H), 2.40 (m, 1H), 2.10 (m, 2H), 1.65 (m, 4H). MS=485 (MH)+.

Example 350

4-{4-[8-(2-Fluoro-3-methoxy-phenyl)-[1,2,4]-triazolo[1,5-a]pyridin-2-ylamino]-phenyl}-piperidine-1-carboxylic acid tert-butyl ester

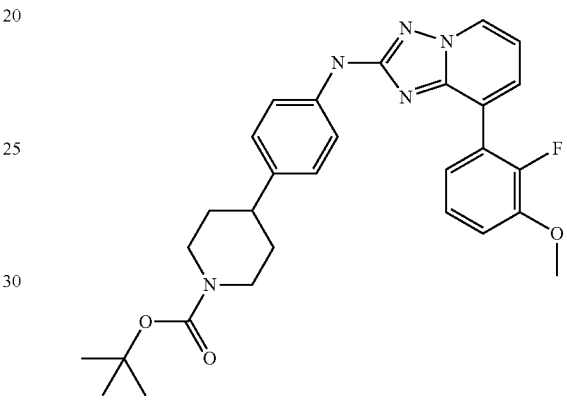

4-{4-[8-(2-Fluoro-3-methoxy-phenyl)-[1,2,4]-triazolo[1,5-a]pyridin-2-ylamino]-phenyl}-piperidine-1-carboxylic acid tert-butyl ester was prepared from 2-chloro-8-(2-fluoro-3-methoxy-phenyl)-[1,2,4]-triazolo[1,5-a]pyridine (0.248 g, 0.893 mmol) and 4-(4-amino-phenyl)-piperidine-1-carboxylic acid tert-butyl ester (0.296 g, 1.07 mmol) in a manner analogous to Example 311a and 311b to give product (0.312 g, 67%). MP=98-102° C. $^1$H NMR (400 MHz, (D$_3$C)$_2$SO, δ, ppm): 9.63 (s, 1H), 8.83 (d, 1H), 7.60 (m, 3H), 7.25 (m, 3H), 7.10 (m, 3H), 4.05 (m, 2H), 3.90 (s, 3H), 2.80 (br m, 2H), 2.60 (m, 1H), 1.45 (m, 2H), 1.75 (m, 2H), 1.41 (s, 9H). MS=518 (MH)+.

Example 351

[8-(2-Fluoro-3-methoxy-phenyl)-[1,2,4]-triazolo[1,5-a]pyridin-2-yl]-(4-piperidin-4-yl-phenyl)-amine

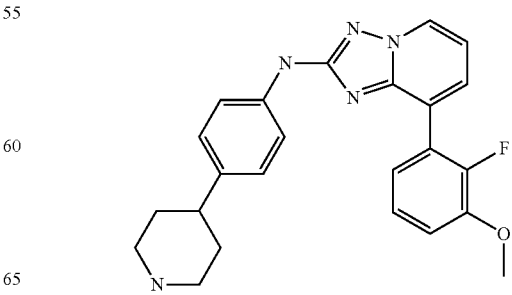

[8-(2-Fluoro-3-methoxy-phenyl)-[1,2,4]-triazolo[1,5-a]pyridin-2-yl]-(4-piperidin-4-yl-phenyl)-amine was prepared from 4-{4-[8-(2-fluoro-3-methoxy-phenyl)-[1,2,4]-triazolo[1,5-a]pyridin-2-ylamino]-phenyl}-piperidine-1-carboxylic acid tert-butyl ester (0.312 g, 0.603 mmol) and trifluoroacetic acid (1 mL) in a manner analogous to Example 312 to give product (0.248 g, 98%). MP=98-101° C. $^1$HNMR (400 MHz, (D$_3$C)$_2$SO, δ, ppm): 9.61 (s, 1H), 8.83 (d, 1H), 7.60 (m, 3H), 7.25 (m, 3H), 7.10 (m, 3H), 3.90 (s, 3H), 3.05 (m, 2H), 2.55 (br m, 4H), 1.65 (m, 2H), 1.45 (m, 2H). MS=418 (MH)+.

Example 352

2-(4-{4-[8-(2-Fluoro-3-methoxy-phenyl)-[1,2,4]-triazolo[1,5-a]pyridin-2-ylamino]-phenyl}-piperidin-1-yl)-N,N-dimethyl-acetamide

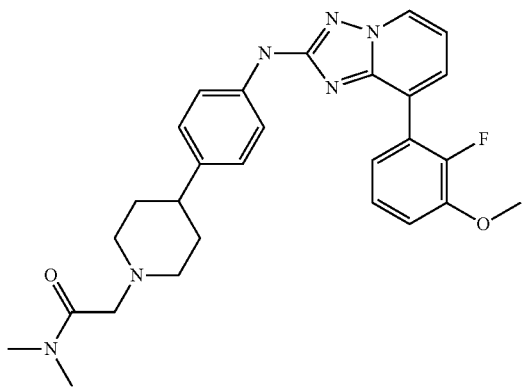

2-(4-{4-[8-(2-Fluoro-3-methoxy-phenyl)-[1,2,4]-triazolo[1,5-a]pyridin-2-ylamino]-phenyl}-piperidin-1-yl)-N,N-dimethyl-acetamide was prepared from [8-(2-fluoro-3-methoxy-phenyl)-[1,2,4]-triazolo[1,5-a]pyridin-2-yl]-(4-piperidin-4-yl-phenyl)-amine (0.150 g, 0.359 mmol) and 2-chloro-N,N-dimethyl-acetamide (0.055 mL, 0.539 mmol) in a manner analogous to Example 313 to give product (0.075 g, 42%). MP=237-240° C. $^1$H NMR (400 MHz, (D$_3$C)$_2$SO, δ, ppm): 9.62 (s, 1H), 8.82 (d, 1H), 7.60 (m, 3H), 7.25 (m, 3H), 7.10 (m, 3H), 3.90 (s, 3H), 3.15 (s, 2H), 3.05 (s, 3H), 2.95 (m, 2H), 2.85 (s, 3H), 2.35 (m, 1H), 2.10 (m, 2H), 1.65 (m, 4H). MS=503 (MH)+.

Example 353

4-{4-[8-(2,3-Dimethoxy-phenyl)-[1,2,4]-triazolo[1,5-a]pyridin-2-ylamino]-phenyl}-piperidine-1-carboxylic acid tert-butyl ester

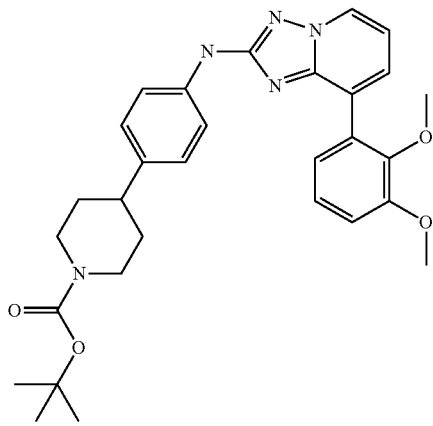 [SMILES: COc1cccc(-c2cccn3nc(Nc4ccc(C5CCN(C(=O)OC(C)(C)C)CC5)cc4)nc23)c1OC]

4-{4-[8-(2,3-Dimethoxy-phenyl)-[1,2,4]-triazolo[1,5-a]pyridin-2-ylamino]-phenyl}-piperidine-1-carboxylic acid tert-butyl ester was prepared from 2-chloro-8-(2,3-dimethoxy-phenyl)-[1,2,4]-triazolo[1,5-a]pyridine (0.200 g, 0.690 mmol) and 4-(4-amino-phenyl)-piperidine-1-carboxylic acid tert-butyl ester (0.229 g, 0.828 mmol) in a manner analogous to Example 311a and 311b to give product (0.264 g, 72%). MP=93-95° C. $^1$H NMR (400 MHz, (D$_3$C)$_2$SO, δ, ppm): 9.55 (s, 1H), 8.77 (d, 1H), 7.52 (m, 3H), 7.15 (m, 6H), 4.05 (m, 2H), 3.87 (s, 3H), 3.68 (s, 3H), 2.88 (br m, 2H), 2.60 (m, 1H), 1.75 (m, 2H), 1.45 (m, 2H), 1.41 (s, 9H). MS=530 (MH)+.

Example 354

[8-(2,3-Dimethoxy-phenyl)-[1,2,4]-triazolo[1,5-a]pyridin-2-yl]-(4-piperidin-4-yl-phenyl)-amine

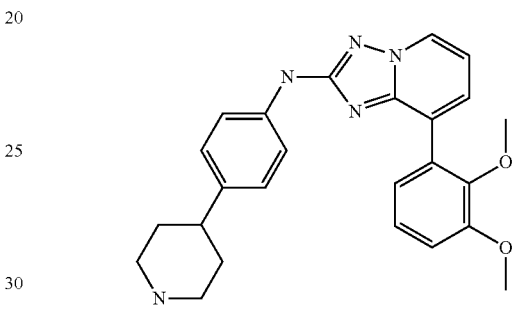

[8-(2,3-Dimethoxy-phenyl)-[1,2,4]-triazolo[1,5-a]pyridin-2-yl]-(4-piperidin-4-yl-phenyl)-amine was prepared from 4-{4-[8-(2,3-dimethoxy-phenyl)-[1,2,4]-triazolo[1,5-a]pyridin-2-ylamino]-phenyl}-piperidine-1-carboxylic acid tert-butyl ester (0.264 g, 0.499 mmol) and trifluoroacetic acid (1 mL) in a manner analogous to Example 312 to give product (0.203 g, 95%). MP=94-97° C. $^1$H NMR (400 MHz, (D$_3$C)$_2$SO, δ, ppm): 9.52 (s, 1H), 8.78 (d, 1H), 7.52 (m, 3H), 7.15 (m, 6H), 3.87 (s, 3H), 3.59 (s, 3H), 3.05 (m, 2H), 2.55 (m, 4H), 1.62 (m, 2H), 1.45 (m, 2H). MS=430 (MH)+.

Example 355

2-(4-{4-[8-(2,3-Dimethoxy-phenyl)-[1,2,4]-triazolo[1,5-a]pyridin-2-ylamino]-phenyl}-piperidin-1-yl)-N,N-dimethyl-acetamide

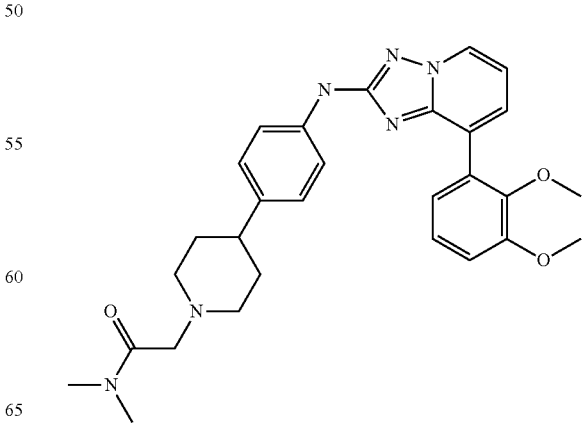

2-(4-{4-[8-(2,3-Dimethoxy-phenyl)-[1,2,4]-triazolo[1,5-a]pyridin-2-ylamino]-phenyl}-piperidin-1-yl)-N,N-dimethyl-acetamide was prepared from [8-(2,3-dimethoxy-phenyl)-[1,2,4]triazolo[1,5-a]pyridin-2-yl]-(4-piperidin-4-yl-phenyl)-amine (0.188 g, 0.438 mmol) and 2-chloro-N,N-dimethyl-acetamide (0.067 mL, 0.656 mmol) in a manner analogous to Example 313 to give product (0.050 g, 22%). MP=222-223° C. $^1$H NMR (400 MHz, (D$_3$C)$_2$SO, δ, ppm): 9.54 (s, 1H), 8.77 (d, 1H), 7.52 (m, 3H), 7.10 (m, 6H), 3.87 (s, 3H), 3.59 (s, 3H), 3.15 (s, 2H), 3.05 (s, 3H), 2.90 (m, 2H), 2.80 (s, 3H), 2.40 (m, 1H), 2.12 (m, 2H), 1.65 (m, 4H). MS=515 (MH)+.

Example 356

4-{4-[8-(4-Cyano-phenyl)-[1,2,4]-triazolo[1,5-a]pyridin-2-ylamino]-phenyl}-piperidine-1-carboxylic acid tert-butyl ester

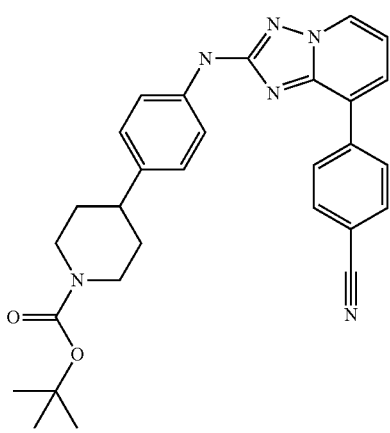 [SMILES: CC(C)(C)OC(=O)N1CCC(c2ccc(Nc3nc4c(-c5ccc(C#N)cc5)cccn4n3)cc2)CC1]

4-{4-[8-(4-Cyano-phenyl)-[1,2,4]-triazolo[1,5-a]pyridin-2-ylamino]-phenyl}-piperidine-1-carboxylic acid tert-butyl ester was prepared from 2-chloro-8-(4-cyano-phenyl)-[1,2,4]-triazolo[1,5-a]pyridine (0.164 g, 0.644 mmol) and 4-(4-amino-phenyl)-piperidine-1-carboxylic acid tert-butyl ester (0.214 g, 0.773 mmol) in a manner analogous to Example 311a and 311b to give product (0.181 g, 57%). MP=96-100° C. $^1$H NMR (400 MHz, (D$_3$C)$_2$SO, δ, ppm): 9.70 (s, 1H), 8.85 (d, 1H), 8.40 (d, 2H), 8.00 (m, 3H), 7.62 (d, 2H), 7.15 (m, 3H), 4.05 (m, 2H), 2.80 (br m, 2H), 2.60 (m, 1H), 1.75 (m, 2H), 1.45 (m, 2H), 1.41 (s, 9H). MS=495 (MH)+.

Example 357

4-[2-(4-Piperidin-4-yl-phenylamino)-[1,2,4]triazolo[1,5-a]pyridine-8-yl]benzonitrile

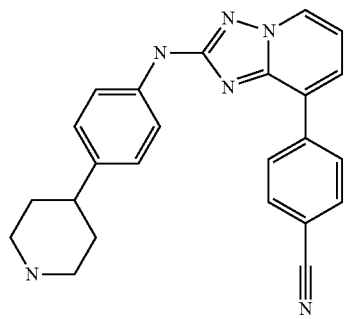 [SMILES: N#Cc1ccc(-c2cccn3nc(Nc4ccc(C5CCNCC5)cc4)nc23)cc1]

4-[2-(4-Piperidin-4-yl-phenylamino)-[1,2,4]triazolo[1,5-a]pyridine-8-yl]benzonitrile was prepared from 4-{4-[8-(4-cyano-phenyl)-[1,2,4]-triazolo[1,5-a]pyridin-2-ylamino]-phenyl}-piperidine-1-carboxylic acid tert-butyl ester (0.181 g, 0.366 mmol) and trifluoroacetic acid (0.500 mL) in a manner analogous to Example 312 to give prodct (0.130 g, 90%). MP=228-232° C. $^1$H NMR (400 MHz, (D$_3$C)$_2$SO, δ, ppm): 9.70 (s, 1H), 8.85 (d, 1H), 8.40 (d, 2H), 8.00 (m, 3H), 7.62 (d, 2H), 7.15 (m, 3H), 3.05 (m, 2H), 2.60 (br m, 4H), 1.65 (m, 2H), 1.45 (m, 2H). MS=395 (MH)+.

Example 358

2-(4-{4-[8-(4-Cyano-phenyl)-[1,2,4]-triazolo[1,5-a]pyridin-2-ylamino]-phenyl}-piperidin-1-yl)-N,N-dimethyl-acetamide

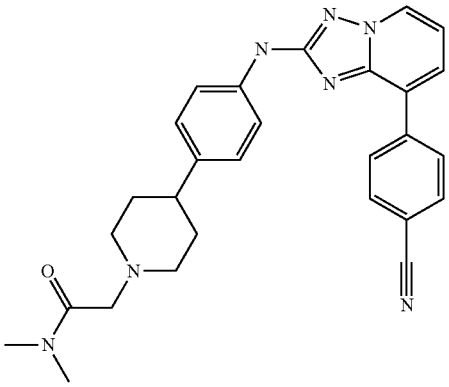 [SMILES: CN(C)C(=O)CN1CCC(c2ccc(Nc3nc4c(-c5ccc(C#N)cc5)cccn4n3)cc2)CC1]

2-(4-{4-[8-(4-Cyano-phenyl)-[1,2,4]-triazolo[1,5-a]pyridin-2-ylamino]-phenyl}-piperidin-1-yl)-N,N-dimethyl-acetamide was prepared from 4-[2-(4-piperidin-4-yl-phenylamino)-[1,2,4]triazolo[1,5-a]pyridine-8-yl]benzonitrile (0.111 g, 0.281 mmol) and 2-chloro-N,N-dimethyl-acetamide (0.043 mL, 0.422 mmol) in a manner analogous to Example 313 to give product (0.060 g, 44%). MP=245-246° C. $^1$H NMR (400 MHz, (D$_3$C)$_2$SO, δ, ppm): 9.71 (s, 1H), 8.87 (d, 1H), 8.40 (d, 2H), 8.00 (m, 3H), 7.62 (d, 2H), 7.15 (m, 3H), 3.12 (s, 2H), 3.05 (s, 3H), 2.95 (m, 2H), 2.80 (s, 3H), 2.40 (m, 1H), 2.12 (m, 2H), 1.65 (m, 4H). MS=480 (MH)+.

Example 359

4-{4-[8-(2-Fluoro-4-methoxy-phenyl)-[1,2,4]-triazolo[1,5-a]pyridin-2-ylamino]-phenyl}-piperidine-1-carboxylic acid tert-butyl ester

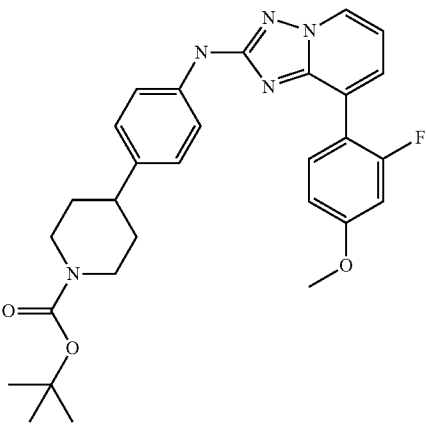 [SMILES: COc1ccc(-c2cccn3nc(Nc4ccc(C5CCN(C(=O)OC(C)(C)C)CC5)cc4)nc23)c(F)c1]

4-{4-[8-(2-Fluoro-4-methoxy-phenyl)-[1,2,4]-triazolo[1,5-a]pyridin-2-ylamino]-phenyl}-piperidine-1-carboxylic acid tert-butyl ester was prepared from 2-chloro-8-(2-fluoro-4-methoxy-phenyl)-[1,2,4]-triazolo[1,5-a]pyridine (0.250 g, 0.900 mmol) and 4-(4-amino-phenyl)-piperidine-1-carboxylic acid tert-butyl ester (0.298 g, 1.08 mmol) in a manner analogous to Example 311a and 311b to give product (0.253 g, 41%). MP=93-95° C. $^1$H NMR (400 MHz, (D$_3$C)$_2$SO, δ, ppm): 9.62 (s, 1H), 8.79 (d, 1H), 7.80 (m, 1H), 7.58 (m, 3H), 7.15 (m, 3H), 6.98 (m, 2H), 4.05 (m, 2H), 3.85 (s, 3H), 2.75 (br m, 2H), 2.55 (m, 1H) 1.75 (m, 2H), 1.45 (m, 2H), 1.41 (s, 9H). MS=518 (MH)+.

Example 360

[8-(2-Fluoro-4-methoxy-phenyl)-[1,2,4]-triazolo[1,5-a]pyridin-2-yl]-(4-piperidin-4-yl-phenyl)-amine

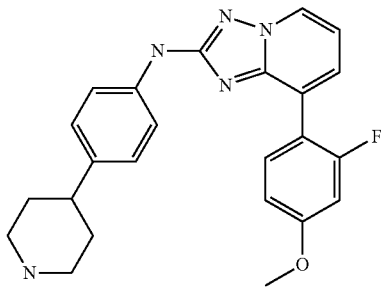 [SMILES: COc1ccc(-c2cccn3nc(Nc4ccc(C5CCNCC5)cc4)nc23)c(F)c1]

[8-(2-Fluoro-4-methoxy-phenyl)-[1,2,4]-triazolo[1,5-a]pyridin-2-yl]-(4-piperidin-4-yl-phenyl)-amine was prepared from 4-{4-[8-(2-fluoro-4-methoxy-phenyl)-[1,2,4]-triazolo[1,5-a]pyridin-2-ylamino]-phenyl}-piperidine-1-carboxylic acid tert-butyl ester (0.253 g, 0.488 mmol) and trifluoroacetic acid (1 mL) in a manner analogous to Example 312 to give product (0.179 g, 88%). MP=95-98° C. $^1$H NMR (400 MHz, (D$_3$C)$_2$SO, δ, ppm): 9.64 (s, 1H), 8.78 (d, 1H), 7.80 (m, 1H), 7.58 (m, 3H), 7.15 (m, 3H), 6.98 (m, 2H), 3.85 (s, 3H), 3.05 (m, 2H), 2.55 (br m, 3H), 2.25 (br m, 1H), 1.65 (m, 2H), 1.45 (m, 2H). MS=418 (MH)+.

Example 361

4-{4-[8-(3-Dimethylamino-phenyl)-[1,2,4]-triazolo[1,5-a]pyridin-2-ylamino]-phenyl}-piperidine-1-carboxylic acid tert-butyl ester

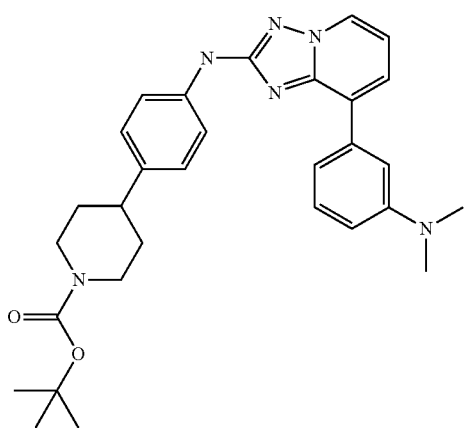 [SMILES: CN(C)c1cccc(-c2cccn3nc(Nc4ccc(C5CCN(C(=O)OC(C)(C)C)CC5)cc4)nc23)c1]

4-{4-[8-(3-Dimethylamino-phenyl)-[1,2,4]-triazolo[1,5-a]pyridin-2-ylamino]-phenyl}-piperidine-1-carboxylic acid tert-butyl ester was prepared from [3-(2-chloro-[1,2,4]-triazolo[1,5-a]pyridin-8-yl)-phenyl]-dimethyl-amine (0.250 g, 0.917 mmol) and 4-(4-amino-phenyl)-piperidine-1-carboxylic acid tert-butyl ester (0.304 g, 1.10 mmol) in a manner analogous to Example 311a and 311b to give product (0.288 g, 61%). MP=95-98° C. $^1$H NMR (400 MHz, (D$_3$C)$_2$SO, δ, ppm): 9.57 (s, 1H), 8.74 (d, 1H), 7.82 (d, 1H), 7.62 (d, 2H), 7.50 (s, 1H) 7.32 (m, 2H), 7.15 (m, 3H), 6.80 (d, 1H), 4.05 (m, 2H), 3.00 (s, 6H), 2.80 (br m, 2H), 2.60 (m, 1H), 1.75 (m, 2H), 1.45 (m, 2H), 1.41 (s, 9H). MS=513 (MH)+.

Example 362

2-(4-{4-[8-(2-Fluoro-4-methoxy-phenyl)-[1,2,4]-triazolo[1,5-a]pyridin-2-ylamino]-phenyl}-piperidin-1-yl)-N,N-dimethyl-acetamide

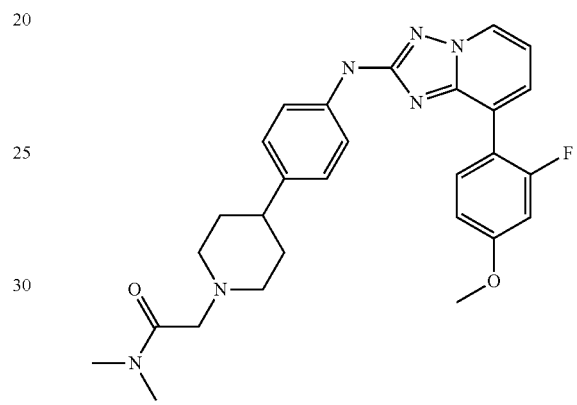

2-(4-{4-[8-(2-Fluoro-4-methoxy-phenyl)-[1,2,4]-triazolo[1,5-a]pyridin-2-ylamino]-phenyl}-piperidin-1-yl)-N,N-dimethyl-acetamide was prepared from [8-(2-fluoro-4-methoxy-phenyl)-[1,2,4]-triazolo[1,5-a]pyridin-2-yl]-(4-piperidin-4-yl-phenyl)-amine (0.179 g, 0.429 mmol) and 2-chloro-N,N-dimethyl-acetamide (0.066 mL, 0.643 mmol) in a manner analogous to Example 313 to give product (0.105 g, 49%). MP=192-195° C. $^1$H NMR (400 MHz, (D$_3$C)$_2$SO, δ, ppm): 9.61 (s, 1H), 8.79 (d, 1H), 7.80 (m, 1H), 7.58 (m, 3H), 7.15 (m, 3H), 6.98 (m, 2H), 3.85 (s, 3H), 3.15 (s, 2H), 3.05 (s, 3H), 2.92 (m, 2H), 2.85 (s, 3H), 2.40 (m, 1H), 2.10 (m, 2H), 1.65 (m, 4H). MS=503 (MH)+.

Example 363

[8-(3-Dimethylamino-phenyl)-[1,2,4]-triazolo[1,5-a]pyridin-2-yl]-(4-piperidin-4-yl-phenyl)-amine

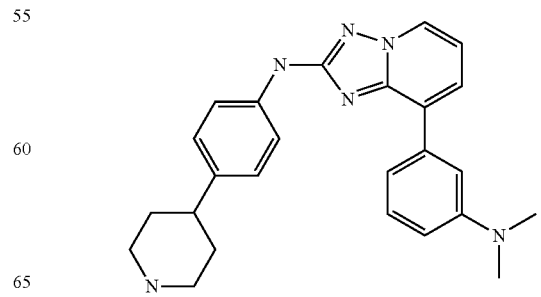

[8-(3-Dimethylamino-phenyl)-[1,2,4]-triazolo[1,5-a]pyridin-2-yl]-(4-piperidin-4-yl-phenyl)-amine was prepared from 4-{4-[8-(3-dimethylamino-phenyl)-[1,2,4]-triazolo[1,5-a]pyridin-2-ylamino]-phenyl}-piperidine-1-carboxylic acid tert-butyl ester (0.288 g, 0.563 mmol) and trifluoroacetic acid (1 mL) in a manner analogous to Example 312 to give product (0.218 g, 94%). MP=104-108° C. $^1$H NMR (400 MHz, (D$_3$C)$_2$SO, δ, ppm): 9.56 (s, 1H), 8.74 (d, 1H), 7.82 (d, 1H), 7.62 (d, 2H), 7.50 (s, 1H), 7.32 (m, 2H), 7.15 (m, 3H), 6.80 (d, 1H), 3.65 (br m, 1H), 3.15 (m, 2H), 3.00 (s, 6H), 2.60 (br m, 3H), 1.65 (m, 2H), 1.45 (m, 2H). MS=413 (MH)+.

Example 364

2-(4-{4-[8-(3-Dimethylamino-phenyl)-[1,2,4]-triazolo[1,5-a]pyridin-2-ylamino]-phenyl}-piperidin-1-yl)-N,N-dimethyl-acetamide

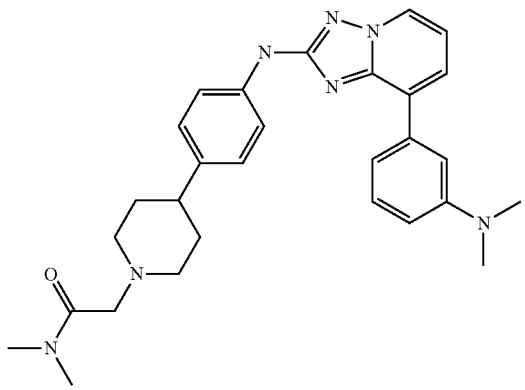

2-(4-{4-[8-(3-Dimethylamino-phenyl)-[1,2,4]-triazolo[1,5-a]pyridin-2-ylamino]-phenyl}-piperidin-1-yl)-N,N-dimethyl-acetamide was prepared from [8-(3-dimethylamino-phenyl)-[1,2,4]-triazolo[1,5-a]pyridin-2-yl]-(4-piperidin-4-yl-phenyl)-amine (0.100 g, 0.242 mmol) and 2-chloro-N,N-dimethyl-acetamide (0.037 mL, 0.364 mmol) in a manner analogous to Example 313 to give product (0.060 g, 50%). MP=100-104° C. $^1$H NMR (400 MHz, (D$_3$C)$_2$SO, δ, ppm): 9.56 (s, 1H), 8.75 (d, 1H), 7.82 (d, 1H), 7.62 (d, 2H), 7.50 (s, 1H), 7.32 (m, 2H), 7.15 (m, 3H), 6.80 (d, 1H), 3.15 (s, 2H), 3.05 (s, 3H), 3.00 (s, 6H), 2.95 (m, 2H), 2.82 (s, 3H), 2.45 (m, 1H), 2.15 (m, 2H), 1.65 (m, 4H). MS=498 (MH)+.

Example 365

[8-(4-Fluoro-phenyl)-[1,2,4]-triazolo[1,5-a]pyridin-2-yl]-[3-(4-methyl-piperazin-1-yl)-phenyl]-amine

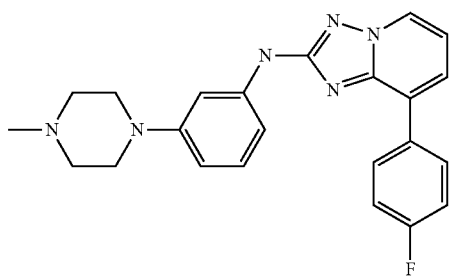 [SMILES: CN1CCN(c2cccc(Nc3nc4c(-c5ccc(F)cc5)cccn4n3)c2)CC1]

[8-(4-Fluoro-phenyl)-[1,2,4]-triazolo[1,5-a]pyridin-2-yl]-[3-(4-methyl-piperazin-1-yl)-phenyl]-amine was prepared from 2-chloro-8-(4-fluoro-phenyl)-[1,2,4]-triazolo[1,5-a]pyridine (0.185 g, 0.747 mmol) and 3-(4-methylpiperazin-1-yl)aniline (0.171 g, 0.896 mmol) in a manner analogous to Example 311a and 311b with purification method from 313 to give product (0.155 g, 52%): MP=194-196° C. $^1$H NMR (400 MHz, (D$_3$C)$_2$SO, δ, ppm): 9.56 (s, 1H), 8.78 (d, 1H), 8.20 (m, 2H), 7.85 (d, 1H), 7.50 (s, 1H), 7.35 (m, 2H), 7.10 (m, 3H), 6.45 (m, 1H), 3.12 (m, 4H), 2.46 (m, 4H), 2.23 (s, 3H). MS=403 (MH)+.

Example 366

7-{8-[2-(2,2-Difluoro-ethoxy)-phenyl]-[1,2,4]triazolo[1,5-a]pyridin-2-ylamino}-1,2,4,5-tetrahydro-3-benzazepine-3-carboxylic acid tert-butyl ester

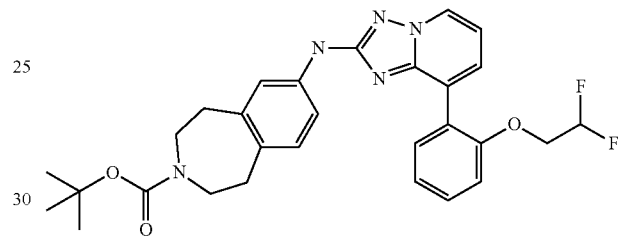

7-{8-[2-(2,2-Difluoro-ethoxy)-phenyl]-[1,2,4]triazolo[1,5-a]pyridin-2-ylamino}-1,2,4,5-tetrahydro-3-benzazepine-3-carboxylic acid tert-butyl ester was prepared from 2-chloro-8-[2-(2,2-difluoro-ethoxy)-phenyl]-[1,2,4]-triazolo[1,5-a]pyridine (0.371 g, 1.20 mmol) and 7-amino-1,2,4,5-tetrahydro-3-benzazepine-3-carboxylic acid tert-butyl ester (0.471 g, 1.80 mmol) in a manner analogous to Example 311a and 311b to give product (0.388 g, 60%). $^1$H NMR (400 MHz, (D$_3$C)$_2$SO, δ, ppm): 9.54 (s, 1H), 8.75 (d, 1H), 7.70 (m, 1H), 7.65 (m, 1H), 7.42 (m, 3H), 7.26 (m, 1H), 7.15 (m, 1H), 7.05 (m, 2H), 6.22 (br m, 1H), 4.39 (m, 2H), 3.45 (m, 4H), 2.76 (m, 4H), 1.41 (s, 9H). MS=536 (MH)+.

Example 367

{8-[2-(2,2-Difluoro-ethoxy)-phenyl]-[1,2,4]triazolo[1,5-a]pyridin-2-yl}-(2,3,4,5-tetrahydro-1H-3-benzazepin-7-yl)-amine

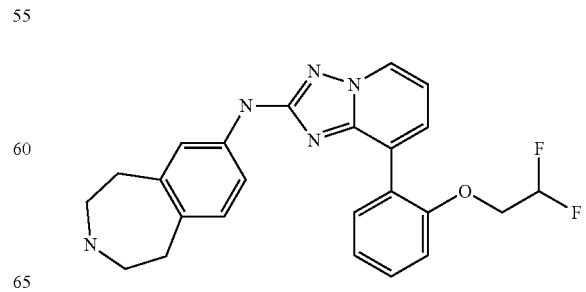

{8-[2-(2,2-Difluoro-ethoxy)-phenyl]-[1,2,4]triazolo[1,5-a]pyridin-2-yl}-(2,3,4,5-tetrahydro-1H-3-benzazepin-7-yl)-amine was prepared from 7-{8-[2-(2,2-difluoro-ethoxy)-phenyl]-[1,2,4]triazolo[1,5-a]pyridin-2-ylamino}-1,2,4,5-tetrahydro-3-benzazepine-3-carboxylic acid tert-butyl ester (0.388 g, 0.725 mmol) and trifluoroacetic acid (1 mL) in a manner analogous to Example 312 to give product (0.264 g, 84%). MP=87-90° C. $^1$H NMR (400 MHz, (D$_3$C)$_2$SO, δ, ppm): 9.46 (s, 1H), 8.75 (d, 1H), 7.65 (m, 2H), 7.42 (m, 2H), 7.35 (s, 1H), 7.25 (m, 1H), 7.15 (m, 1H), 7.05 (m, 1H), 6.98 (m, 1H), 6.22 (br m, 1H), 4.32 (m, 2H), 2.70 (br m, 9H). MS=436 (MH)+.

Example 368

2-(7-{8-[2-(2,2-Difluoro-ethoxy)-phenyl]-[1,2,4]triazolo[1,5-a]pyridin-2-ylamino}-1,2,4,5-tetrahydro-3-benzazepin-3-yl)-N,N-dimethyl-acetamide

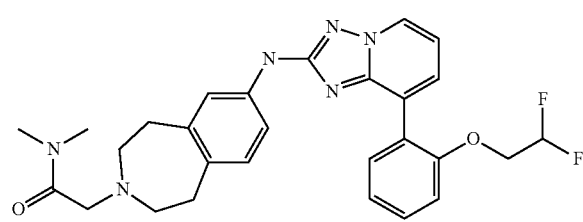 [SMILES: CN(C)C(=O)CN1CCc2ccc(Nc3nc4c(-c5ccccc5OCC(F)F)cccn4n3)cc2CC1]

2-(7-{8-[2-(2,2-Difluoro-ethoxy)-phenyl]-[1,2,4]triazolo[1,5-a]pyridin-2-ylamino}-1,2,4,5-tetrahydro-3-benzazepin-3-yl)-N,N-dimethyl-acetamide was prepared from {8-[2-(2,2-difluoro-ethoxy)-phenyl]-[1,2,4]triazolo[1,5-a]pyridin-2-yl}-(2,3,4,5-tetrahydro-1H-3-benzazepin-7-yl)-amine (0.100 g, 0.230 mmol) and 2-chloro-N,N-dimethyl-acetamide (0.035 mL, 0.344 mmol) in a manner analogous to Example 313 to give product (0.045 g, 38%). MP=213-215° C. $^1$H NMR (400 MHz, (D$_3$C)$_2$SO, δ, ppm): 9.49 (s, 1H), 8.77 (d, 1H), 7.65 (m, 2H), 7.40 (m, 2H), 7.35 (s, 1H), 7.25 (m, 1H), 7.15 (m, 1H), 7.05 (m, 1H), 6.98 (m, 1H), 6.22 (br m, 1H), 4.35 (m, 2H), 3.22 (s, 2H), 3.05 (s, 3H), 2.75 (m, 7H), 2.55 (m, 4H). MS=521 (MH)+.

Example 369

7-{8-[2-(2,2-Difluoro-ethoxy)-4-methanesulfonyl-phenyl]-[1,2,4]triazolo[1,5-a]pyridin-2-ylamino}-1,2,4,5-tetrahydro-3-benzazepine-3-carboxylic acid tert-butyl ester

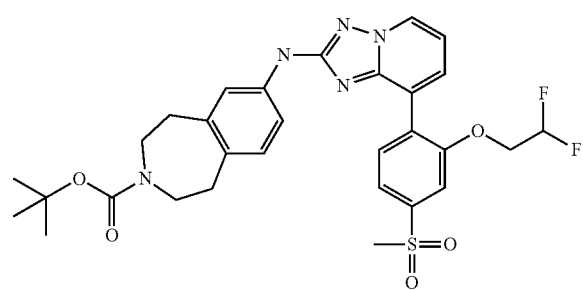 [SMILES: CC(C)(C)OC(=O)N1CCc2ccc(Nc3nc4c(-c5ccc(S(C)(=O)=O)cc5OCC(F)F)cccn4n3)cc2CC1]

7-{8-[2-(2,2-Difluoro-ethoxy)-4-methanesulfonyl-phenyl]-[1,2,4]triazolo[1,5-a]pyridin-2-ylamino}-1,2,4,5-tetrahydro-3-benzazepine-3-carboxylic acid tert-butyl ester was prepared from 2-chloro-8-[2-(2,2-difluoro-ethoxy)-4-methanesulfonyl-phenyl]-[1,2,4]-triazolo[1,5-a]pyridine (0.371 g, 1.20 mmol) and 7-amino-1,2,4,5-tetrahydro-3-benzazepine-3-carboxylic acid tert-butyl ester (0.253 g, 652 mmol) in a manner analogous to Example 311a and 311b to give product (0.285 g, 71%): $^1$H NMR (400 MHz, (D$_3$C)$_2$SO, δ, ppm): 9.58 (s, 1H), 8.82 (d, 1H), 7.94 (d, 1H), 7.74 (s, 1H), 7.68 (m, 2H), 7.48 (d, 1H), 7.37 (s, 1H), 7.05 (m, 2H), 6.27 (br m, 1H), 4.52 (m, 2H), 3.45 (m, 4H), 2.77 (m, 4H), 2.50 (s, 3H), 1.41 (s, 9H). MS=614 (MH)+.

Example 370

{8-[2-(2,2-Difluoro-ethoxy)-4-methanesulfonyl-phenyl]-[1,2,4]triazolo[1,5-a]pyridin-2-yl}-(2,3,4,5-tetrahydro-1H-3-benzazepin-7-yl)-amine

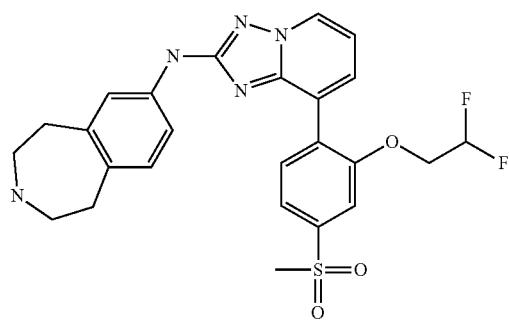 [SMILES: CS(=O)(=O)c1ccc(-c2cccn3nc(Nc4ccc5c(c4)CCNCC5)nc23)c(OCC(F)F)c1]

{8-[2-(2,2-Difluoro-ethoxy)-4-methanesulfonyl-phenyl]-[1,2,4]triazolo[1,5-a]pyridin-2-yl}-(2,3,4,5-tetrahydro-1H-3-benzazepin-7-yl)-amine was prepared from 7-{8-[2-(2,2-difluoro-ethoxy)-4-methanesulfonyl-phenyl]-[1,2,4]triazolo[1,5-a]pyridin-2-ylamino}-1,2,4,5-tetrahydro-3-benzazepine-3-carboxylic acid tert-butyl ester (0.285 g, 0.465 mmol) and trifluoroacetic acid (2 mL) in a manner analogous to Example 312 to give product (0.203 g, 85%). MP=128-131° C. $^1$H NMR (400 MHz, (D$_3$C)$_2$SO, δ, ppm): 9.56 (s, 1H), 8.82 (d, 1H), 7.95 (d, 1H), 7.72 (s, 1H), 7.65 (m, 2H), 7.40 (d, 1H), 7.32 (s, 1H), 7.09 (t, 1H), 7.01 (d, 1H), 6.22 (br m, 1H), 4.53 (m, 2H), 2.84 (br m, 8H), 2.67 (br m 1H), 2.50 (s, 3H). MS=514 (MH)+.

Example 371

7-{8-[2-(2,2-Difluoro-ethoxy)-5-methanesulfonyl-phenyl]-[1,2,4]triazolo[1,5-a]pyridin-2-ylamino}-1,2,4,5-tetrahydro-3-benzazepine-3-carboxylic acid tert-butyl ester

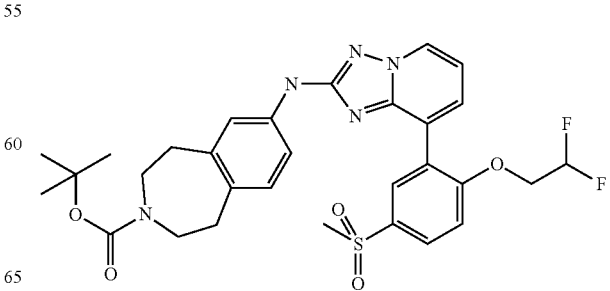

7-{8-[2-(2,2-Difluoro-ethoxy)-5-methanesulfonyl-phenyl]-[1,2,4]triazolo[1,5-a]pyridin-2-ylamino}-1,2,4,5-tetrahydro-3-benzazepine-3-carboxylic acid tert-butyl ester was prepared from 2-chloro-8-[2-(2,2-difluoro-ethoxy)-5-methanesulfonyl-phenyl]-[1,2,4]-triazolo[1,5-a]pyridine (0.282 g, 727 mmol) and 7-amino-1,2,4,5-tetrahydro-3-benzazepine-3-carboxylic acid tert-butyl ester (0.286 g, 1.09 mmol) in a manner analogous to Example 311a and 311b to give product (0.340 g, 76%): $^1$H NMR (400 MHz, (D$_3$C)$_2$SO, δ, ppm): 9.54 (s, 1H), 8.80 (d, 1H), 8.22 (s, 1H), 8.00 (d, 1H), 7.69 (d, 1H), 7.48 (m, 2H), 7.38 (s, 1H), 7.10 (t, 1H), 7.00 (d, 1H), 6.28 (br m, 1H), 4.54 (m, 2H), 3.44 (m, 4H), 3.23 (s, 3H), 2.76 (m, 4H), 1.41 (s, 9H). MS=614 (MH)+.

Example 372

{8-[2-(2,2-Difluoro-ethoxy)-5-methanesulfonyl-phenyl]-[1,2,4]triazolo[1,5-a]pyridin-2-yl}-(2,3,4,5-tetrahydro-1H-3-benzazepin-7-yl)-amine

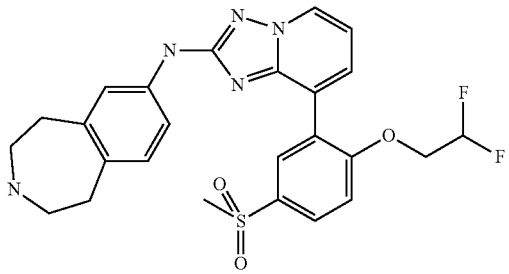 [SMILES: CS(=O)(=O)c1ccc(OCC(F)F)c(-c2cccn3nc(Nc4ccc5c(c4)CCNCC5)nc23)c1]

{8-[2-(2,2-Difluoro-ethoxy)-5-methanesulfonyl-phenyl]-[1,2,4]triazolo[1,5-a]pyridin-2-yl}-(2,3,4,5-tetrahydro-1H-3-benzazepin-7-yl)-amine was prepared from 7-{8-[2-(2,2-difluoro-ethoxy)-5-methanesulfonyl-phenyl]-[1,2,4]triazolo[1,5-a]pyridin-2-ylamino}-1,2,4,5-tetrahydro-3-benzazepine-3-carboxylic acid tert-butyl ester (0.340 g, 0.555 mmol) and trifluoroacetic acid (1 mL) in a manner analogous to Example 312 to give product (0.262 g, 92%). MP=122-125° C. $^1$H NMR (400 MHz, (D$_3$C)$_2$SO, δ, ppm): 9.48 (s, 1H), 8.80 (d, 1H), 8.20 (s, 1H), 8.00 (d, 1H), 7.65 (d, 1H), 7.50 (m, 2H), 7.32 (s, 1H), 7.10 (t, 1H), 6.98 (d, 1H), 6.28 (br m, 1H), 4.54 (m, 2H), 3.23 (s, 3H), 2.67-2.77 (br m, 9H). MS=514 (MH)+.

Example 373

2-(7-{8-[2-(2,2-Difluoro-ethoxy)-5-methanesulfonyl-phenyl]-[1,2,4]triazolo[1,5-a]pyridin-2-ylamino}-1,2,4,5-tetrahydro-3-benzazepin-3-yl)-N,N-dimethyl-acetamide

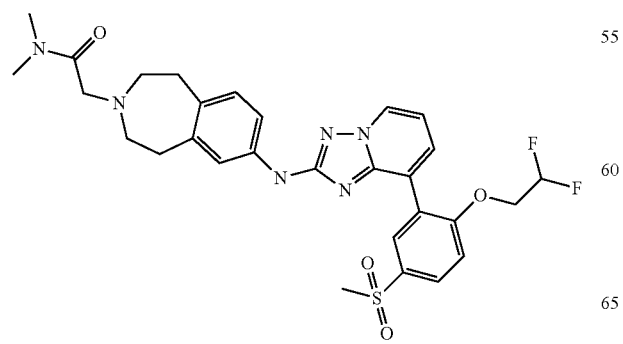

2-(7-{8-[2-(2,2-Difluoro-ethoxy)-5-methanesulfonyl-phenyl]-[1,2,4]triazolo[1,5-a]pyridin-2-ylamino}-1,2,4,5-tetrahydro-3-benzazepin-3-yl)-N,N-dimethyl-acetamide was prepared from {8-[2-(2,2-difluoro-ethoxy)-5-methanesulfonyl-phenyl]-[1,2,4]triazolo[1,5-a]pyridin-2-yl}-(2,3,4,5-tetrahydro-1H-3-benzazepin-7-yl)-amine (0.127 g, 0.247 mmol) and 2-chloro-N,N-dimethyl-acetamide (0.038 mL, 0.371 mmol) in a manner analogous to Example 313 to give product (0.060 g, 40%). MP=128-130° C. $^1$H NMR (400 MHz, (D$_3$C)$_2$SO, δ, ppm): 9.50 (s, 1H), 8.81 (d, 1H), 8.20 (s, 1H), 8.00 d, 1H), 7.65 (d, 1H), 7.50 (m, 2H), 7.32 (s, 1H), 7.10 (t, 1H), 6.98 (d, 1H), 6.28 (br m, 1H), 4.54 (m, 2H), 3.25 (m, 5H), 3.10 (s, 3H), 2.80 (m, 7H), 2.60 (m, 4H). MS=599 (MH)+.

Example 374

7-[8-(3-Trifluoromethyl-phenyl)-[1,2,4]triazolo[1,5-a]pyridin-2-ylamino]-1,2,4,5-tetrahydro-3-benzazepine-3-carboxylic acid tert-butyl ester

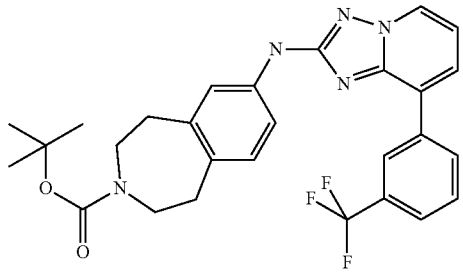 [SMILES: CC(C)(C)OC(=O)N1CCc2ccc(Nc3nc4c(-c5cccc(C(F)(F)F)c5)cccn4n3)cc2CC1]

7-[8-(3-Trifluoromethyl-phenyl)-[1,2,4]triazolo[1,5-a]pyridin-2-ylamino]-1,2,4,5-tetrahydro-3-benzazepine-3-carboxylic acid tert-butyl ester was prepared from 2-chloro-8-(3-trifluoromethyl-phenyl)-[1,2,4]-triazolo[1,5-a]pyridine (0.272 g, 914 mmol) and 7-amino-1,2,4,5-tetrahydro-3-benzazepine-3-carboxylic acid tert-butyl ester (0.360 g, 1.37 mmol) in a manner analogous to Example 311a and 311b to give product (0.203 g, 44%). $^1$H NMR (400 MHz, (D$_3$C)$_2$SO, δ, ppm): 9.62 (s, 1H), 8.83 (d, 1H), 8.65 (s, 1H), 8.40 (d, 1H), 7.95 (d, 1H), 7.82 (m, 2H), 7.50 (m, 2H), 7.15 (t, 1H), 7.05 (d, 1H), 3.45 (m, 4H), 2.75 (m, 4H), 1.41 (s, 9H). MS=524 (MH)+.

Example 375

(2,3,4,5-Tetrahydro-1H-3-benzazepin-7-yl)-[8-(3-trifluoromethyl-phenyl)-[1,2,4]triazolo[1,5-a]pyridin-2-yl]-amine

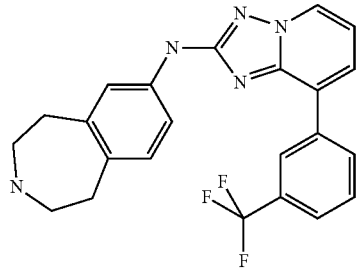 [SMILES: FC(F)(F)c1cccc(-c2cccn3nc(Nc4ccc5c(c4)CCNCC5)nc23)c1]

(2,3,4,5-Tetrahydro-1H-3-benzazepin-7-yl)-[8-(3-trifluoromethyl-phenyl)-[1,2,4]triazolo[1,5-a]pyridin-2-yl]-amine was prepared from 7-[8-(3-trifluoromethyl-phenyl)-[1,2,4]triazolo[1,5-a]pyridin-2-ylamino]-1,2,4,5-tetrahydro-3-benzazepine-3-carboxylic acid tert-butyl ester (0.203 g, 388 mmol) and trifluoroacetic acid (1 mL) in a manner analogous to Example 312 to give product (0.072 g, 44%). MP=88-91° C. $^1$H NMR (400 MHz, (D$_3$C)$_2$SO, δ, ppm): 9.55 (s, 1H), 8.83 (d, 1H), 8.65 (s, 1H), 8.40 (d, 1H), 7.95 (d, 1H), 7.82 (m, 2H), 7.50 (m, 2H), 7.15 (t, 1H), 7.05 (d, 1H), 2.75 (br m, 9H). MS=424 (MH)+.

Example 376

7-{8-[5-Chloro-2-(2,2-difluoro-ethoxy)-phenyl]-[1,2,4]triazolo[1,5-a]pyridin-2-ylamino}-1,2,4,5-tetrahydro-3-benzazepine-3-carboxylic acid tert-butyl ester

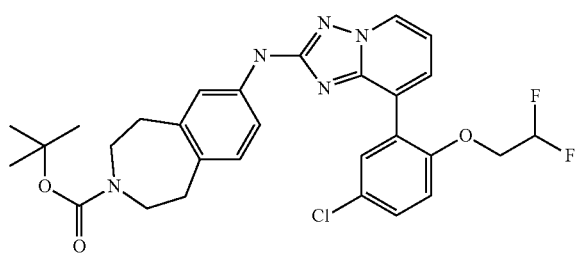 [SMILES: CC(C)(C)OC(=O)N1CCc2ccc(Nc3nc4c(-c5cc(Cl)ccc5OCC(F)F)cccn4n3)cc2CC1]

7-{8-[5-Chloro-2-(2,2-difluoro-ethoxy)-phenyl]-[1,2,4]triazolo[1,5-a]pyridin-2-ylamino}-1,2,4,5-tetrahydro-3-benzazepine-3-carboxylic acid tert-butyl ester was prepared from 2-chloro-8-[5-chloro-2-(2,2-difluoro-ethoxy)-phenyl]-[1,2,4]-triazolo[1,5-a]pyridine (0.215 g, 625 mmol) and 7-amino-1,2,4,5-tetrahydro-3-benzazepine-3-carboxylic acid tert-butyl ester (0.245 g, 937 mmol) in a manner analogous to Example 311a and 311b to give product (0.117 g, 33%). $^1$H NMR (400 MHz, (D$_3$C)$_2$SO, δ, ppm): 9.52 (s, 1H), 8.78 (d, 1H), 7.80 (s, 1H), 7.68 (d, 1H), 7.45 (m, 3H), 7.30 (m, 1H), 7.05 (m, 2H), 6.25 (br m, 1H), 4.35 (m, 2H), 3.45 (m, 4H), 2.82 (m, 4H), 1.41 (s, 9H). MS=571 (MH)+.

Example 377

{8-[5-Chloro-(2,2-difluoro-ethoxy)-phenyl]-[1,2,4]triazolo[1,5-a]pyridin-2-yl}-(2,3,4,5-tetrahydro-1H-3-benzazepin-7-yl)-amine

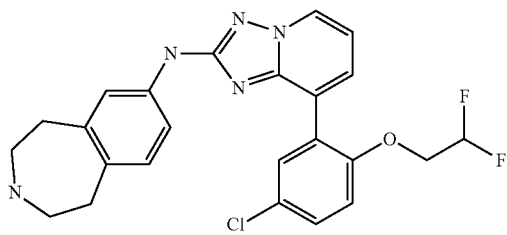 [SMILES: FC(F)COc1ccc(Cl)cc1-c1cccn2nc(Nc3ccc4c(c3)CCNCC4)nc12]

{8-[5-Chloro-(2,2-difluoro-ethoxy)-phenyl]-[1,2,4]triazolo[1,5-a]pyridin-2-yl}-(2,3,4,5-tetrahydro-1H-3-benzazepin-7-yl)-amine was prepared from 7-{8-[5-chloro-2-(2,2-difluoro-ethoxy)-phenyl]-[1,2,4]triazolo[1,5-a]pyridin-2-ylamino}-1,2,4,5-tetrahydro-3-benzazepine-3-carboxylic acid tert-butyl ester (0.117 g, 205 mmol) and trifluoroacetic acid (0.5 mL) in a manner analogous to Example 312 to give product (0.045 g, 47%). MP=102-105° C. $^1$H NMR (400 MHz, (D$_3$C)$_2$SO, δ, ppm): 9.52 (s, 1H), 8.78 (d, 1H), 7.80 (s, 1H), 7.65 (d, 1H), 7.50 (d, 1H), 7.40 (m, 2H), 7.30 (d, 1H), 7.05 (t, 1H), 7.00 (d, 1H), 6.25 (br m, 1H), 4.35 (m, 2H), 3.10 (br m, 1H), 2.79 (br m, 8H). MS=470 (MH)+.

Example 378

2-(7-{8-[2-(2,2-Difluoro-ethoxy)-5-fluoro-phenyl]-[1,2,4]triazolo[1,5-a]pyridin-2-ylamino}-1,2,4,5-tetrahydro-3-benzazepin-3-yl)-N,N-dimethyl-acetamide

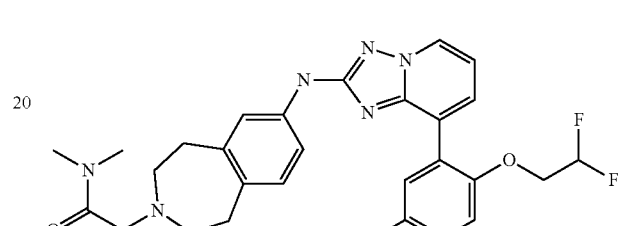

2-(7-{8-[2-(2,2-Difluoro-ethoxy)-5-fluoro-phenyl]-[1,2,4]triazolo[1,5-a]pyridin-2-ylamino}-1,2,4,5-tetrahydro-3-benzazepin-3-yl)-N,N-dimethyl-acetamide was prepared from {8-[2-(2,2-difluoro-ethoxy)-5-fluoro-phenyl]-[1,2,4]triazolo[1,5-a]pyridin-2-yl}-(2,3,4,5-tetrahydro-1H-3-benzazepin-7-yl)-amine (0.097 g, 0.210 mmol) and 2-chloro-N,N-dimethyl-acetamide (0.033 mL, 0.321 mmol) in a manner analogous to Example 313 to give product (0.045 g, 39%). MP=218° C. $^1$H NMR (400 MHz, (D$_3$C)$_2$SO, δ, ppm): 9.53 (s, 1H), 8.78 (d, 1H), 7.62 (m, 2H), 7.40 (m, 2H), 7.29 (m, 2H), 7.00 (m, 2H), 6.23 (br m, 1H), 4.35 (m, 2H), 3.22 (s, 2H), 3.05 (s, 3H), 2.80 (br m, 7H), 2.60 (m, 4H). MS=539 (MH)+.

Example 379

[8-(2-Isobutoxy-5-trifluoromethyl-phenyl)-[1,2,4]triazolo[1,5-a]pyridin-2-yl]-(2,3,4,5-tetrahydro-1H-3-benzazepin-7-yl)-amine

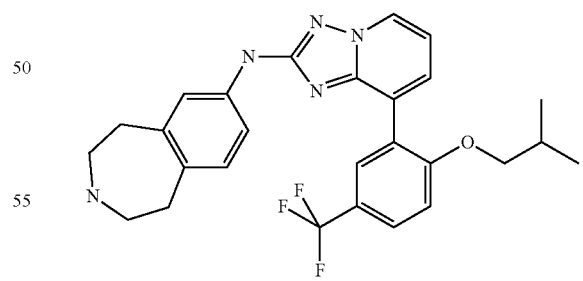

[8-(2-Isobutoxy-5-trifluoromethyl-phenyl)-[1,2,4]triazolo[1,5-a]pyridin-2-yl]-(2,3,4,5-tetrahydro-1H-3-benzazepin-7-yl)-amine was prepared from 7-[8-(2-isobutoxy-5-trifluoromethyl-phenyl)-[1,2,4]triazolo[1,5-a]pyridin-2-ylamino]-1,2,4,5-tetrahydro-3-benzazepine-3-carboxylic acid tert-butyl ester (0.263 g, 0.442 mmol) and trifluoroacetic acid (0.5 mL) in a manner analogous to Example 312 to give product (0.190 g, 87%). MP=102-103° C. $^1$H NMR (400

MHz, (D₃C)₂SO, δ, ppm): ¹H NMR (400 MHz, (D₃C)₂SO, δ, ppm): 9.47 (s, 1H), 8.78 (d, 1H), 7.98 (s, 1H), 7.75 (d, 1H), 7.62 (d, 1H), 7.35 (m, 3H), 7.05 (t, 1H), 6.98 (d, 1H), 3.87 (d, 2H), 2.62-2.75 (br m, 9H), 1.85 (m, 1H), 0.81 (d, 6H). MS=496 (MH)+.

Example 380

2-{7-[8-(2-Isobutoxy-5-trifluoromethyl-phenyl])-[1,2,4]triazolo[1,5-a]pyridin-2-ylamino]-1,2,4,5-tetrahydro-3-benzazepin-3-yl}-N,N-dimethyl-acetamide

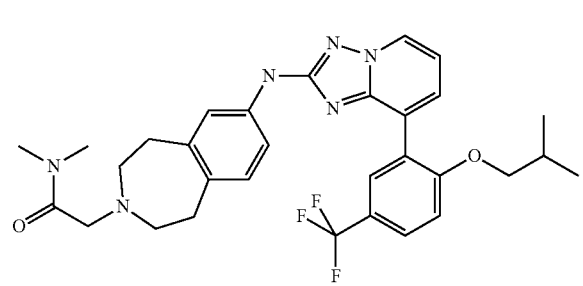 [SMILES: CC(C)COc1ccc(C(F)(F)F)cc1-c1cccn2nc(Nc3ccc4c(c3)CCN(CC(=O)N(C)C)CC4)nc12]

2-{7-[8-(2-Isobutoxy-5-trifluoromethyl-phenyl])-[1,2,4]triazolo[1,5-a]pyridin-2-ylamino]-1,2,4,5-tetrahydro-3-benzazepin-3-yl}-N,N-dimethyl-acetamide was prepared from [8-(2-isobutoxy-5-trifluoromethyl-phenyl)-[1,2,4]triazolo[1,5-a]pyridin-2-yl]-(2,3,4,5-tetrahydro-1H-3-benzazepin-7-yl)-amine (0.085 g, 0.170 mmol) and 2-chloro-N,N-dimethyl-acetamide (0.026 mL, 0.260 mmol) in a manner analogous to Example 313 to give product (0.055 g, 55%). MP=105-107° C. ¹H NMR (400 MHz, (D₃C)₂SO, δ, ppm): 9.50 (s, 1H), 8.78 (d, 1H), 7.98 (s, 1H), 7.75 (d, 1H), 7.62 (d, 1H), 7.35 (m, 3H), 7.05 (t, 1H), 6.98 (d, 1H), 3.87 (d, 2H), 3.25 (s, 2H), 3.05 (s, 3H), 2.75 (m, 7H), 2.55 (m, 4H), 1.90 (m, 1H), 0.80 (d, 6H). MS=581 (MH)+.

Example 381

2-(7-{8-[5-Chloro-2-(2,2-difluoro-ethoxy)-phenyl]-[1,2,4]triazolo[1,5-a]pyridin-2-ylamino}-1,2,4,5-tetrahydro-3-benzazepin-3-yl)-N,N-dimethyl-acetamide

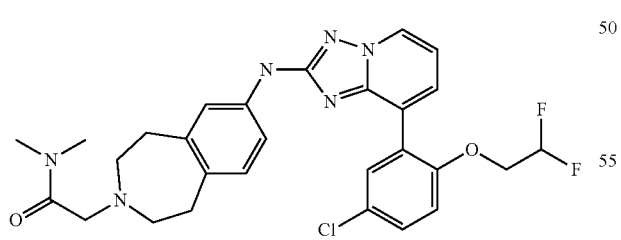

2-(7-{8-[5-Chloro-2-(2,2-difluoro-ethoxy)-phenyl]-[1,2,4]triazolo[1,5-a]pyridin-2-ylamino}-1,2,4,5-tetrahydro-3-benzazepin-3-yl)-N,N-dimethyl-acetamide was prepared from {8-[5-chloro-(2,2-difluoro-ethoxy)-phenyl]-[1,2,4]triazolo[1,5-a]pyridin-2-yl}-(2,3,4,5-tetrahydro-1H-3-benzazepin-7-yl)-amine (0.075 g, 0.160 mmol) and 2-chloro-N,N-dimethyl-acetamide (0.025 mL, 0.239 mmol) in a manner analogous to Example 313 to give product (0.030 g, 34%). MP=190-191° C. ¹H NMR (400 MHz, (D₃C)₂SO, δ, ppm): 9.54 (s, 1H), 8.78 (d, 1H), 7.80 (s, 1H), 7.65 (d, 1H), 7.50 (m, 3H), 7.30 (d, 1H), 7.05 (m, 2H), 6.25 (br m, 1H), 4.35 (m, 2H), 3.22 (s, 2H), 3.05 (s, 3H), 3.75 (m, 7H), 2.55 (m, 4H). MS=556 (MH)+.

Example 382

7-{8-[5-Chloro-2-(2,2-difluoro-ethoxy)-phenyl]-[1,2,4]triazolo[1,5-a]pyridin-2-ylamino}-1,2,4,5-tetrahydro-3-benzazepine-3-carboxylic acid dimethylamide

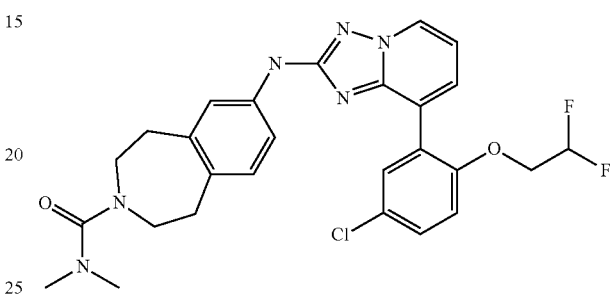

To {8-[5-chloro-(2,2-difluoro-ethoxy)-phenyl]-[1,2,4]triazolo[1,5-a]pyridin-2-yl}-(2,3,4,5-tetrahydro-1H-3-benzazepin-7-yl)-amine (0.054 g, 0.110 mmol) in dichloromethane (4 mL) under an atmosphere of nitrogen was added triethylamine (0.0349 g, 0.345 mmol), N,N-dimethyl-carbamoyl chloride (0.0159 mL, 0.172 mmol), followed by 4-dimethylaminopyridine (0.0014 g, 0.012 mmol) and was stirred at r.t. for 3 h and concentrated. The reaction was partitioned between dichloromethane/water, washed with brine, dried over sodium sulfate, and concentrated. The product was purified using Prep TLC plates (5% methanol in dichloromethane) and concentrated to give 7-{8-[5-chloro-2-(2,2-difluoro-ethoxy)-phenyl]-[1,2,4]triazolo[1,5-a]pyridin-2-ylamino}-1,2,4,5-tetrahydro-3-benzazepine-3-carboxylic acid dimethylamide (0.030 g, 48%). MP=98-99° C. ¹H NMR (400 MHz, (D₃C)₂SO, δ, ppm): 9.58 (s, 1H), 8.78 (d, 1H), 7.80 (s, 1H), 7.65 (d, 1H), 7.48 (m, 3H), 7.30 (d, 1H), 7.05 (m, 2H), 6.25 (br m, 1H), 4.38 (m, 2H), 3.28 (m, 4H), 2.84 (m, 4H), 2.74 (s, 6H). MS=541 (MH)+.

Example 383

7-{8-[2-(2,2-difluoro-ethoxy)-5-difluoromethyl-phenyl]-[1,2,4]triazolo[1,5-a]pyridin-2-ylamino}-1,2,4,5-tetrahydro-3-benzazepine-3-carboxylic acid tert-butyl ester

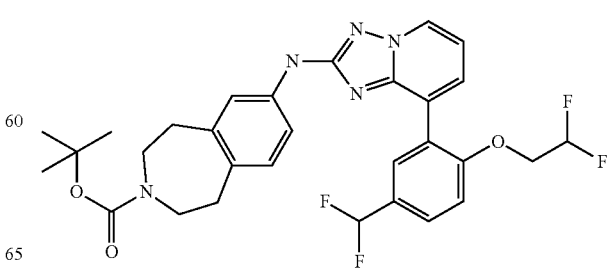

7-{8-[2-(2,2-difluoro-ethoxy)-5-difluoromethyl-phenyl]-[1,2,4]triazolo[1,5-a]pyridin-2-ylamino}-1,2,4,5-tetrahydro-3-benzazepine-3-carboxylic acid tert-butyl ester was prepared from 2-chloro-8-[2-(2,2-difluoro-ethoxy)-5-difluoromethyl-phenyl]-[1,2,4]-triazolo[1,5-a]pyridine (0.182 g, 506 mmol) and 7-amino-1,2,4,5-tetrahydro-3-benzazepine-3-carboxylic acid tert-butyl ester (0.199 g, 759 mmol) in a manner analogous to Example 311a and 311b to give product: $^1$H NMR (400 MHz, (D$_3$C)$_2$SO, δ, ppm): 9.54 (s, 1H), 8.78 (d, 1H), 7.90 (s, 1H), 7.65 (m, 2H), 7.42 (m, 3H), 7.10 (br m, 1H) 7.05 (m, 2H), 6.35 (br m, 1H), 4.43 (m, 2H), 3.40 (m, 4H), 2.75 (m, 4H), 1.41 (s, 9H). MS=586 (MH)+.

Example 384

{8-[2-(2,2-Difluoro-ethoxy)-5-difluoromethyl-phenyl]-[1,2,4]triazolo[1,5-a]pyridin-2-yl}-(2,3,4,5-tetrahydro-1H-3-benzazepin-7-yl)-amine

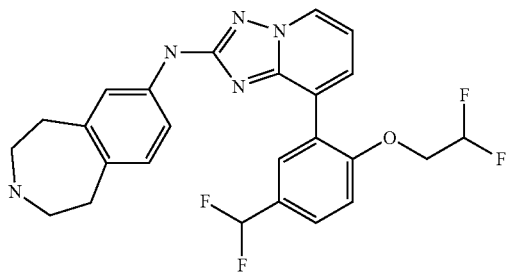 [SMILES: FC(F)COc1ccc(C(F)F)cc1-c1cccn2nc(Nc3ccc4c(c3)CCNCC4)nc12]

{8-[2-(2,2-Difluoro-ethoxy)-5-difluoromethyl-phenyl]-[1,2,4]triazolo[1,5-a]pyridin-2-yl}-(2,3,4,5-tetrahydro-1H-3-benzazepin-7-yl)-amine was prepared from 7-{8-[2-(2,2-difluoro-ethoxy)-5-difluoromethyl-phenyl]-[1,2,4]triazolo[1,5-a]pyridin-2-ylamino}-1,2,4,5-tetrahydro-3-benzazepine-3-carboxylic acid tert-butyl ester and trifluoroacetic acid (0.5 mL) in a manner analogous to Example 312 to give product (0.111 g). MP=92-93° C. $^1$H NMR (400 MHz, (D$_3$C)$_2$SO, δ, ppm): $^1$H NMR (400 MHz, (D$_3$C)$_2$SO, δ, ppm): 9.47 (s, 1H), 8.78 (d, 1H), 7.90 (s, 1H), 7.65 (m, 2H), 7.42 (m, 3H), 7.05 (m, 2H), 7.02 (br m, 1H), 6.30 (br m, 1H), 4.42 (m, 2H), 2.76 (br m, 9H). MS=486 (MH)+.

Example 385

2-(7-{8-[2-(2,2-difluoro-ethoxy)-5-difluoromethyl-phenyl]-[1,2,4]triazolo[1,5-a]pyridin-2-ylamino}-1,2,4,5-tetrahydro-3-benzazepin-3-yl)-N,N-dimethyl-acetamide

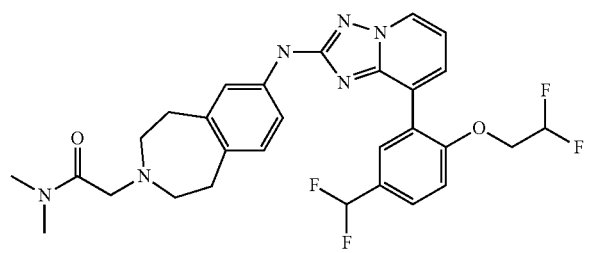 [SMILES: CN(C)C(=O)CN1CCc2ccc(Nc3nc4c(-c5cc(C(F)F)ccc5OCC(F)F)cccn4n3)cc2CC1]

2-(7-{8-[2-(2,2-difluoro-ethoxy)-5-difluoromethyl-phenyl]-[1,2,4]triazolo[1,5-a]pyridin-2-ylamino}-1,2,4,5-tetrahydro-3-benzazepin-3-yl)-N,N-dimethyl-acetamide was prepared from {8-[2-(2,2-difluoro-ethoxy)-5-difluoromethyl-phenyl]-[1,2,4]triazolo[1,5-a]pyridin-2-yl}-(2,3,4,5-tetrahydro-1H-3-benzazepin-7-yl)-amine (0.065 g, 0.130 mmol) and 2-chloro-N,N-dimethyl-acetamide (0.045 mL, 0.200 mmol) in a manner analogous to Example 313 to give product (0.045 g, 59%). MP=200-201° C. $^1$H NMR (400 MHz, (D$_3$C)$_2$SO, δ, ppm): 9.49 (s, 1H), 8.78 (d, 1H), 7.90 (s, 1H), 7.65 (m, 2H), 7.42 (m, 3H), 7.05 (m, 2H), 7.02 (br m, 1H), 6.30 (br m, 1H), 4.42 (m, 2H), 3.22 (s, 2H), 3.05 (s, 3H), 2.80 (m, 7H), 2.60 (m, 4H). MS=571 (MH)+.

Example 386

[8-(4-Methanesulfonyl-phenyl)-[1,2,4]trizolo[1,5-a]pyridin-2-yl]-(4-methyl-3,4,5,6-tetrahydro-2H-[1,2']bipyrazinyl-6'-yl)-amine

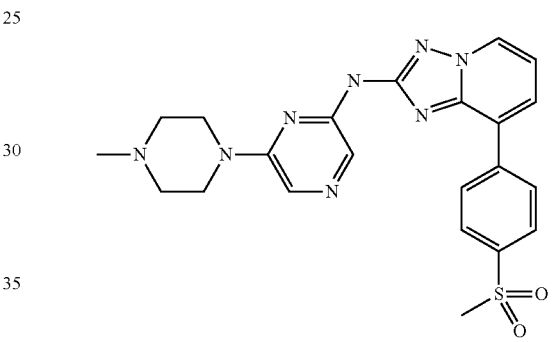

386a) 4-Methyl-3,4,5,6-tetrahydro-2H-[1,2']bipyrazinyl-6'-ylamine was prepared from 6-chloro-pyrazin-2-ylamine (1.00 g, 7.72 mmol) and 1-methylpiperazine (942 L, 8.49 mmol) combined in N,N-dimethylformamide (35 mL) and heated at 100° C. overnight. The reaction was poured into water and extracted with 3 portions of dichloromethane. The combined organic was dried over magnesium sulfate, filtered and evaporated to yield an off-white solid. This solid was purified via chromatography (silica gel 40 g methanol in dichloromethane). Product isolated as a tan oil that solidified upon standing. $^1$H NMR (400 MHz, (D$_3$C)$_2$SO, δ, ppm): 7.33 (s, 1H), 7.16 (s, 1H), 5.93 (s, 2H), 3.40 (s, 4H), 2.36 (s, 4H), 2.20 (s, 3H).

386b) [8-(4-Methanesulfonyl-phenyl)-[1,2,4]triazolo[1,5-a]pyridin-2-yl]-(4-methyl-3,4,5,6-tetrahydro-2H-[1,2']bipyrazinyl-6'-yl)-amine was prepared from 2-chloro-8-(4-methanesulfonyl-phenyl)-[1,2,4]triazolo[1,5-a]pyridine (133 mg, 0.434 mmol) and 4-methyl-3,4,5,6-tetrahydro-2H-[1,2']bipyrazinyl-6'-ylamine (92.159 mg, 0.47689 mmol) in a manner analogous to Example 2d. Product isolated as an off-white foam (28.64 mg, 14.2%). $^1$H NMR (400 MHz, (D$_3$C)$_2$SO, δ, ppm): 10.07 (s, 1H), 8.91 (d, J=6.6 Hz, 1H), 8.59 (s, 1H), 8.41 (d, J=8.5 Hz, 2H), 8.08 (d, J=8.3 Hz, 2H), 8.00 (d, J=7.6 Hz, 1H), 7.83 (s, 1H), 7.23 (t, J=14.5, 7.4 Hz, 1H), 3.32 (s, 3H), 3.56 (s, 4H), 2.40 (s, 4H), 2.23 (s, 3H). MS=465 (MH)+.

Example 387

N(8)-(2-Methoxy-benzyl)-N(2)-[4-(4-methyl-piper-azin-1-yl)-phenyl]-[1,2,4]triazolo[1,5-a]pyridine-2,8-diamine

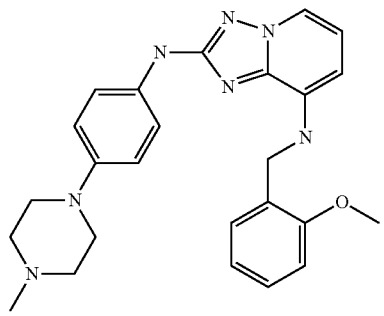 [SMILES: COc1ccccc1CNc1cccn2nc(Nc3ccc(N4CCN(C)CC4)cc3)nc12]

387a) (2-Chloro-[1,2,4]triazolo[1,5-a]pyridin-8-yl)-(2-methoxy-benzyl)-amine was prepared from 8-bromo-2-chloro-[1,2,4]triazolo[1,5-a]pyridine (2.00 g, 8.60 mmol) and 2-methoxy-benzylamine in a manner analogous to Example 2d. Product isolated as a tan oil that solidified upon standing (1.56 g. 63%). $^1$H NMR (400 MHz, (D$_3$C)$_2$SO, δ, ppm): 8.09 (d, J=6.7 Hz, 1H), 7.21 (m, 2H), 7.04-6.93 (m, 3H), 6.86 (t, J=14.5, 7.2 Hz, 1H), 6.35 (d, J=7.9 Hz, 1H), 4.43 (d, J=6.30 Hz, 2H), 3.86 (s, 3H).

387b) N(8)-(2-Methoxy-benzyl)-N(2)-[4-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(2-methoxy-benzyl)-amine (100.00 mg, 0.34634 mmol) and 4-(4-methyl-piperazin-1-yl)-phenylamine (74.2 mg, 0.388 mmol) in a manner analogous to Example 2d. Product isolated as a brown foam (23.79 mg, 15.5%). $^1$H NMR (400 MHz, (D$_3$C)$_2$SO, δ, ppm): 9.07 (s, 1H), 7.93 (d, J=6.2 Hz, 1H), 7.55 (d, J=8.4 Hz, 2H), 7.24 (m, 2H), 7.02 (d, J=8.4 Hz, 1H), 6.88 (m, 3H), 6.70 (t, J=13.70, 6.9 Hz, 1H), 6.29 (d, J=7.9 Hz, 1H), 6.09 (m, 1H), 4.46 (d, J=6.0 Hz, 2H), 3.87 (s, 3H), 3.02 (s, 4H), 2.45 (s, 4H), 2.22 (s, 3H). MS=444 (MH)+.

Example 388

N(8)-(2-Methoxy-benzyl)-N(2)-[3-(4-methyl-piperazin-1-yl)-phenyl]-[1,2,4]triazolo[1,5-a]pyridine-2,8-diamine

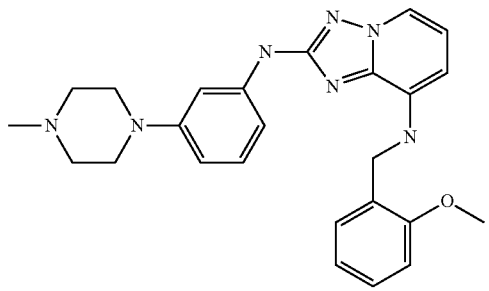

388a) N(8)-(2-Methoxy-benzyl)-N(2)-[3-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(2-methoxy-benzyl)-amine (100.00 mg, 0.34634 mmol) and 3-(4-methylpiperazin-1-yl)aniline (74.2 mg, 0.388 mmol) in a manner analogous to Example 2d. Product isolated as a brown foam (39.14 mg, 25.4%). $^1$H NMR (400 MHz, (D$_3$C)$_2$SO, δ, ppm): 9.12 (s, 1H), 7.96 (d, J=6.4 Hz, 1H), 7.25 (m, 4H), 7.09 (t, J=15.9, 7.8 Hz, 1H), 7.03 (d, J=8.6 Hz, 1H), 6.88 (t, J=15.0, 7.9 Hz, 1H), 6.73 (t, J=14.5, 7.4 Hz, 1H) 6.46 (d, J=8.6 Hz, 1H), 6.32 (d, J=8.1 Hz, 1H), 6.10 (m, 1H), 4.48 (d, J=5.2 Hz, 2H), 3.87 (s, 3H), 3.12 (s, 4H), 2.45 (s, 4H), 2.22 (s, 3H). MS=444 (MH)+.

Example 389

N-Methyl-N-(2-{[2-(4-methyl-3,4,5,6-tetrahydro-2H-[1,2']bipyrazinyl-6'-ylamino)-[1,2,4]triazolo[1,5-a]pyridin-8-ylamino]-methyl}-phenyl)-methanesulfonamide

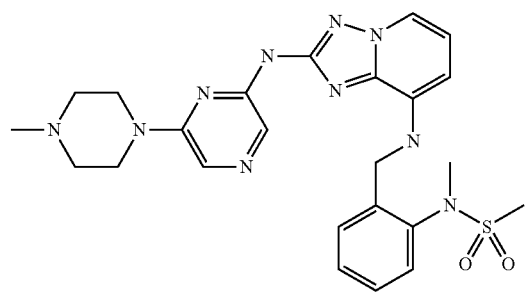

389a) N-Methyl-N-(2-{[2-(4-methyl-3,4,5,6-tetrahydro-2H-[1,2']bipyrazinyl-6'-ylamino)-[1,2,4]triazolo[1,5-a]pyridin-8-ylamino]-methyl}-phenyl)-methanesulfonamide was prepared from N-{2-[(2-chloro-[1,2,4]triazolo[1,5-a]pyridin-8-ylamino)-methyl]-phenyl}-N-methyl-methanesulfonamide (130 mg, 0.36 mmol) and 4-methyl-3,4,5,6-tetrahydro-2H-[1,2']bipyrazinyl-6'-ylamine (92.159 mg, 0.47689 mmol in a manner analogous to Example 2d. Product was isolated as an off-white foam (28.64 mg, 1.8%). $^1$H NMR (400 MHz, (D$_3$C)$_2$ SO, δ, ppm): 9.71 (s, 1H), 8.80 (s, 1H), 7.98 (d, J=6.7 Hz, 1H), 7.81 (s, 1H), 7.56 (d, J=7.5 Hz, 1H), 7.40-7.28 (m, 3H), 6.79-6.66 (m, 2H), 6.22 (d, J=8.6 Hz, 1H), 4.63 (s, 2H), 3.55 (s, 4H), 3.26 (s, 3H), 3.12 (s, 3H), 2.41 (s, 4H), 2.22 (s, 3H). MS=523 (MH)+.

Example 390

N(8)-(3-Methoxy-benzyl)-N(2)-[4-(4-methyl-piperazin-1-yl)-phenyl]-[1,2,4]triazolo[1,5-a]pyridine-2,8-diamine

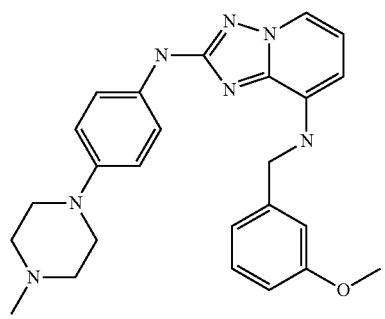 [SMILES: COc1cccc(CNc2cccn3nc(Nc4ccc(N5CCN(C)CC5)cc4)nc23)c1]

390a) (2-Chloro-[1,2,4]triazolo[1,5-a]pyridin-8-yl)-(3-methoxy-benzyl)-amine was prepared from 8-bromo-2-chloro-[1,2,4]triazolo[1,5-a]pyridine (2.00 g, 8.60 mmol), and 3-methoxy-benzylamine (1.26 mL, 9.72 mmol) in a manner analogous to Example 2d. Product was isolated as an off-white solid, (1.90 g. 77%). $^1$H NMR (400 MHz, (D$_3$C)$_2$SO, δ, ppm): 8.08 (d, J=6.4 Hz, 1H), 7.24 (m, 2H), 6.96 (s, 3H), 6.79 (d, J=8.0 Hz, 1H), 6.41 (d, J=8.0 Hz, 1H), 4.44 (d, J=5.9 Hz, 2H), 3.71 (s, 3H).

390b) N(8)-(3-Methoxy-benzyl)-N(2)-[4-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(2-methoxy-benzyl)-amine (100.00 mg, 0.34634 mmol) and 4-(4-methyl-piperazin-1-yl)-phenylamine (74.2 mg, 0.388 mmol), in a manner analogous to Example 2d. Product was isolated as a red foam (36.85 mg, 24%). $^1$H NMR (400 MHz, (D$_3$C)$_2$SO, δ, ppm): 9.03 (s, 1H), 7.92 (d, J=6.7 Hz, 1H), 7.57 (d, J=8.4 Hz, 2H), 7.23 (t, J=15.4, 8.1 Hz, 2H), 6.96 (s, 2H), 6.88 (d, J=8.1 Hz, 2H), 6.80 (d, J=8.6 Hz, 1H), 6.68 (t, J=14.6, 7.4 Hz, 1H), 6.40 (m, 1H), 6.29 (d, J=7.6 Hz, 1H), 4.48 (d, J=5.7 Hz, 2H), 3.72 (s, 3H), 3.03 (s, 4H), 2.46 (s, 4H), 2.20 (s, 3H). MS=444 (MH)+.

Example 391

N(8)-(4-Methoxy-benzyl)-N(2)-[4-(4-methyl-piperazin-1-yl)-phenyl]-[1,2,4]triazolo[1,5-a]pyridine-2,8-diamine

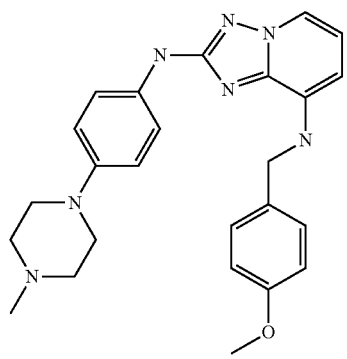 [SMILES: COc1ccc(CNc2cccn3nc(Nc4ccc(N5CCN(C)CC5)cc4)nc23)cc1]

391a) (2-Chloro-[1,2,4]triazolo[1,5-a]pyridin-8-yl)-(4-methoxy-benzyl)-amine was prepared from 8-bromo-2-chloro-[1,2,4]triazolo[1,5-a]pyridine (2.00 g, 8.60 mmol), and 4-methoxy-benzenemethanamine, (1.26 mL, 9.72 mmol) in a manner analogous to Example 2d. Product isolated as an off-white solid, (1.51 g. 61%). $^1$H NMR (400 MHz, (D$_3$C)$_2$SO, δ, ppm): 8.06 (d, J=6.90 Hz, 1H), 7.31 (d, J=8.2 Hz, 2H), 7.19 (m, 1H), 6.94 (t, J=14.4, 7.6 Hz, 1H), 6.87 (d, J=7.4 Hz, 2H), 6.42 (d, J=8.0 Hz, 1H), 4.40 (d, J=6.1 Hz, 2H), 3.71 (s, 3H). MS=289 (MH)+.

391b) N(8)-(4-Methoxy-benzyl)-N(2)-[4-(4-methyl-piperazin-1-yl)-phenyl]-[1,2,4]triazolo[1,5-a]pyridine-2,8-diamine was prepared from 4-(4-methyl-piperazin-1-yl)-phenylamine (74.2 mg, 0.388 mmol) and (2-chloro-[1,2,4]triazolo[1,5-a]pyridin-8-yl)-(4-methoxy-benzyl)-amine (99.9 mg, 0.346 mmol) in a manner analogous to Example 2d. Product was isolated as a red foam (10.64 mg, 7%). $^1$H NMR (400 MHz, (D$_3$C)$_2$SO, δ, ppm): 9.03 (s, 1H), 7.92 (d, J=6.2 Hz, 1H), 7.56 (d, J=8.3 Hz, 2H), 7.32 (d, J=7.8 Hz, 2H), 6.88 (d, J=8.3 Hz, 4H), 6.68 (t, J=13.9, 7.0 Hz, 1H), 6.29 (m, 2H), 4.42 (m, 2H), 3.72 (s, 3H), 3.03 (s, 4H), 2.47 (s, 4H), 2.22 (s, 3H). MS=444 (MH)+.

Example 392

N(8)-(3-Methoxy-benzyl)-N(2)-[3-(4-methyl-piperazin-1-yl)-phenyl]-[1,2,4]triazolo[1,5-a]pyridine-2,8-diamine

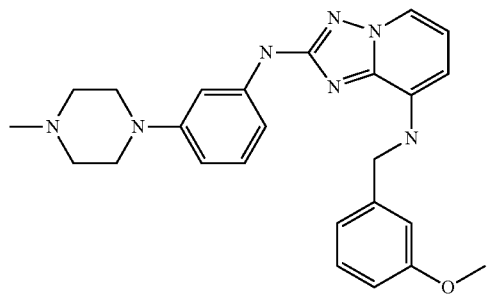

392a) N(8)-(3-Methoxy-benzyl)-N(2)-[3-(4-methyl-piperazin-1-yl)-phenyl]-[1,2,4]triazolo[1,5-a]pyridine-2,8-diamine was prepared from 3-(4-methylpiperazin-1-yl)aniline (74.2 mg, 0.388 mmol) and (2-chloro-[1,2,4]triazolo[1,5-a]pyridin-8-yl)-(3-methoxy-benzyl)-amine (99.9 mg, 0.346 mmol) in a manner analogous to Example 2d. Product isolated as a red foam (11.16 mg, 7%). $^1$H NMR (400 MHz, CD$_3$OD, δ, ppm): 7.85 (d, J=7.0 Hz, 1H), 7.32 (s, 1H), 7.24 (t, J=15.5, 7.8 Hz, 1H), 7.19-7.09 (m, 2H), 6.99 (s, 2H), 6.82 (d, J=8.0 Hz, 1H), 6.75 (t, J=14.2, 7.0 Hz, 1H), 6.57 (d, J=7.8 Hz, 1H), 6.41 (d, J=7.5 Hz, 1H), 4.48 (m, 2H), 3.77 (s, 3H), 3.24 (s, 4H), 2.65 (s, 4H), 2.37 (s, 3H). MS=444 (MH)+.

Example 393

N(8)-(4-Methoxy-benzyl)-N(2)-[3-(4-methyl-piperazin-1-yl)-phenyl]-[1,2,4]triazolo[1,5-a]pyridine-2,8-diamine

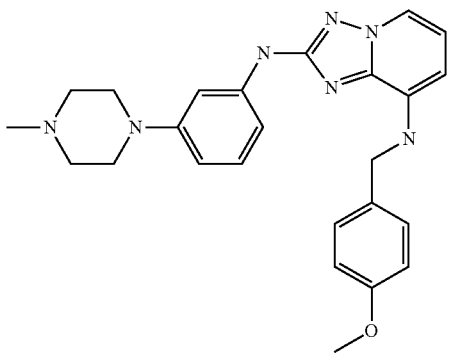 [SMILES: COc1ccc(CNc2cccn3nc(Nc4cccc(N5CCN(C)CC5)c4)nc23)cc1]

393a) N(8)-(4-Methoxy-benzyl)-N(2)-[3-(4-methyl-piperazin-1-yl)-phenyl]-[1,2,4]triazolo[1,5-a]pyridine-2,8-diamine was prepared from 3-(4-Methylpiperazin-1-yl)aniline (74.2 mg, 0.388 mmol) and (2-chloro-[1,2,4]triazolo[1,5-a]pyridin-8-yl)-(4-methoxy-benzyl)-amine (99.9 mg, 0.346 mmol) in a manner analogous to Example 2d. Product isolated as a red foam (9.16 mg, 6%). $^1$H NMR (400 MHz, CD₃OD, δ, ppm): 7.85 (d, J=5.9 Hz, 1H), 7.33 (m, 3H), 7.19-7.08 (m, 2H), 6.90 (d, J=8.0 Hz, 2H), 6.76 (t, J=14.4, 7.5 Hz, 1H), 6.57 (d, J=8.2 Hz, 1H), 6.44 (d, J=7.4 Hz, 1H), 4.42 (s, 2H), 3.78 (s, 3H), 3.23 (s, 4H), 2.64 (s, 4H), 2.37 (s, 3H). MS=444 (MH)+.

Example 394

N(8)-(3-Methoxy-benzyl)-N(2)-(6-methoxy-pyridin-3-yl)-[1,2,4]triazolo[1,5-a]pyridine-2,8-diamine

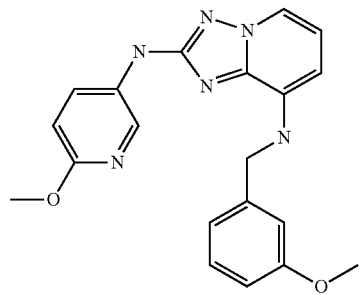

394a) N(8)-(3-Methoxy-benzyl)-N(2)-(6-methoxy-pyridin-3-yl)-[1,2,4]triazolo[1,5-a]pyridine-2,8-diamine was prepared from (2-chloro-[1,2,4]triazolo[1,5-a]pyridin-8-yl)-(3-methoxy-benzyl)-amine (99.9 mg, 0.346 mmol) and 5-amino-2-methoxypyridine (48.11 mg, 0.3875 mmol) in a manner analogous to Example 2d. Product was isolated as a red foam (41.48 mg, 32%). ¹H NMR (400 MHz, CD₃OD, δ, ppm): 8.42 (s, 1H), 8.04 (d, J=9 Hz, 1H), 7.83 (d, J=6.5 Hz, 1H), 7.24 (m, 1H), 6.98 (s, 2H), 6.83-6.71 (m, 3H), 6.40 (d, J=7.4 Hz, 1H), 4.48 (s, 2H), 3.88 (s, 3H), 3.76 (s, 3H). MS=377 (MH)+.

Example 395

N(8)-(2-Fluoro-benzyl)-N(2)-[3-(4-methyl-piperazin-1-yl)-phenyl]-[1,2,4]triazolo[1,5-a]pyridine-2,8-diamine

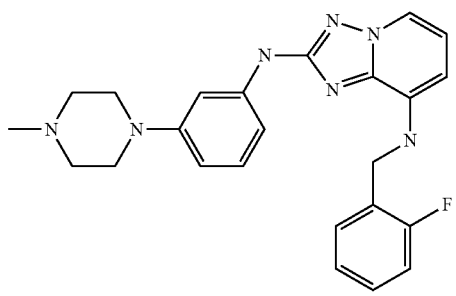 [SMILES: CN1CCN(c2cccc(Nc3nc4c(NCc5ccccc5F)cccn4n3)c2)CC1]

395a) (2-Chloro-[1,2,4]triazolo[1,5-a]pyridin-8-yl)-(2-fluoro-benzyl)-amine was prepared from 8-bromo-2-chloro-[1,2,4]triazolo[1,5-a]pyridine (2.00 g, 8.60 mmol), and 2-fluorobenzylamine (1.11 mL, 9.72 mmol) in a manner analogous to Example 2d. Product isolated as an off-white solid, (1.45 g. 61%). ¹H NMR (400 MHz, (D₃C)₂SO, δ, ppm): 8.11 (d, J=6.9 Hz, 1H), 7.39-7.26 (m, 2H), 7.23-7.10 (m, 3H), 6.98 (t, J=14.0, 7.3 Hz, 1H), 6.43 (d, J=8.0 Hz, 1H), 4.53 (d, J=6.1 Hz, 2H). 395b) N(8)-(2-Fluoro-benzyl)-N(2)-[3-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(2-fluoro-benzyl)-amine (0.3227 g, 1.166 mmol) and 3-(4-methylpiperazin-1-yl)aniline (223 mg, 1.17 mmol) in a manner analogous to Example 2d. Product isolated as a red foam (102.96 mg, 20.5%). ¹H NMR (400 MHz, (D₃C)₂SO, δ, ppm): 9.19 (s, 1H), 7.98 (d, J=7.3 Hz, 1H), 7.43-7.06 (m, 7H), 6.74 (t, J=14.3, 7.1 Hz, 1H), 6.46 (d, J=8.6 Hz, 1H), 6.35 (m, 2H), 4.59 (d, J=6.4 Hz, 2H), 3.11 (s, 4H), 2.45 (s, 4H), 2.22 (s, 3H). MS=432 (MH)+.

Example 396

N(8)-(4-Fluoro-benzyl)-N(2)-[3-(4-methyl-piperazin-1-yl)-phenyl]-[1,2,4]triazolo[1,5-a]pyridine-2,8-diamine

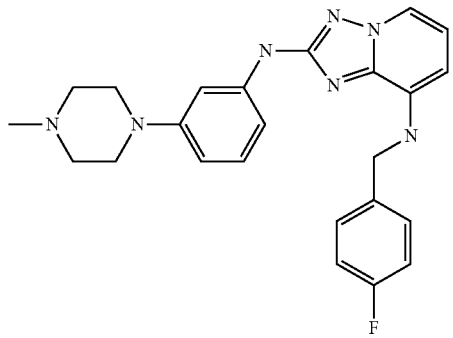 [SMILES: CN1CCN(c2cccc(Nc3nc4c(NCc5ccc(F)cc5)cccn4n3)c2)CC1]

396a) 2-Chloro-[1,2,4]triazolo[1,5-a]pyridin-8-yl)-(4-fluoro-benzyl)-amine was prepared from 8-bromo-2-chloro-[1,2,4]triazolo[1,5-a]pyridine (2.00 g, 8.60 mmol), and 4-fluorobenzylamine (1.11 mL, 9.72 mmol) in a manner analogous to Example 2d. Product isolated as an off-white solid, (1.94 g. 82%). ¹H NMR (400 MHz, (D₃C)₂SO, δ, ppm): 8.08 (d, J=6.5 Hz, 1H), 7.42 (m, 2H), 7.29 (m, 1H), 7.13 (t, J=17.1, 8.6 Hz, 2H), 6.95 (t, J=14.7, 7.3 Hz, 1H), 6.42 (d, J=7.8 Hz, 1H), 4.45 (d, J=6.0 Hz, 2H).

396b) N(8)-(4-Fluoro-benzyl)-N(2)-[3-(4-methyl-piperazin-1-yl)-phenyl]-[1,2,4]triazolo[1,5-a]pyridine-2,8-diamine was prepared from (2-chloro-[1,2,4]triazolo[1,5-a]pyridin-8-yl)-(4-fluoro-benzyl)-amine (0.288 g, 1.04 mol) and 3-(4-methylpiperazin-1-yl)aniline (223 mg, 1.17 mol) in a manner analogous to Example 2d. Product isolated as red foam (83.06 mg, 18.5%). ¹H NMR (400 MHz, (D₃C)₂SO, δ, pap): 9.16 (s, 1H), 7.96 (d, J=6.3 Hz, 1H), 7.43 (t, J=12.8, 6.7 Hz, 2H), 7.26 (m, 2H), 7.18-7.06 (m, 3H), 6.72 (t, J=14.3, 7.2 Hz, 1H), 6.45 (m, 2H), 6.32 (d, J=8.4 Hz, 1H), 4.50 (d, J=5.7 Hz, 2H), 3.11 (s, 4H), 2.45 (s, 4H), 2.22 (s, 3H). MS=432 (MH)+.

Example 397

N(8)-(3-Methoxy-benzyl)-N(2)-(2-methyl-pyridin-4-yl)-[1,2,4]triazolo[1,5-a]pyridine-2,8-diamine

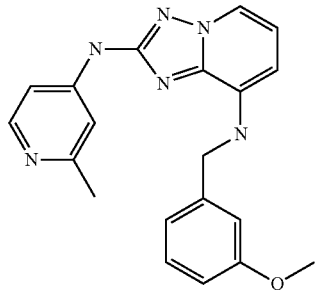 [SMILES: COc1cccc(CNc2cccn3nc(Nc4ccnc(C)c4)nc23)c1]

N(8)-(3-Methoxy-benzyl)-N(2)-(2-methyl-pyridin-4-yl)-[1,2,4]triazolo[1,5-a]pyridine-2,8-diamine was prepared from (2-chloro-[1,2,4]triazolo[1,5-a]pyridin-8-yl)-(3-methoxy-benzyl)-amine (99.9 mg, 0.346 mmol) and 6-methyl-pyridin-3-ylamine (41.91 mg, 0.3875 mmol) in a manner analogous to Example 2d. Product isolated as a tan foam (6.49 mg, 5%). $^1$H NMR (400 MHz, (D$_3$C)$_2$SO, δ, ppm): 9.90 (s, 1H), 8.19 (d, J=6.1 Hz, 1H), 8.00 (d, J=6.7 Hz, 1H), 7.55 (m, 1H), 7.48 (s, 1H), 7.24 (t, J=15.7, 8.0 Hz, 1H), 6.96 (s, 2H), 6.79 (m, 2H), 6.64 (m, 1H), 6.33 (d, J=8.0 Hz, 1H), 4.50 (d, J=6.1 Hz, 2H), 3.72 (s, 3H), 2.40 (s, 3H). MS=361 (MH)+.

Example 398

N(8)-(3-Methoxy-benzyl)-N(2)-pyridin-3-yl-[1,2,4]triazolo[1,5-a]pyridine-2,8-diamine

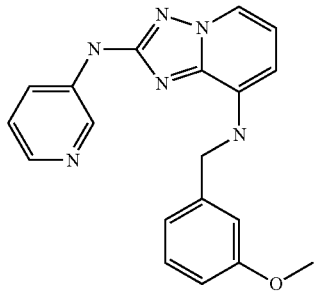 [SMILES: COc1cccc(CNc2cccn3nc(Nc4cccnc4)nc23)c1]

N(8)-(3-Methoxy-benzyl)-N(2)-pyridin-3-yl-[1,2,4]triazolo[1,5-a]pyridine-2,8-diamine was prepared from (2-chloro-[1,2,4]triazolo[1,5-a]pyridin-8-yl)-(3-methoxy-benzyl)-amine (99.9 mg, 0.346 mmol) and 3-aminopyridine (36.47 mg, 0.3875 mmol) in a manner analogous to Example 2d. Product isolated as an off-white foam (6.22 mg, 5%). $^1$H NMR (400 MHz, (D$_3$C)$_2$SO, δ, ppm): 9.65 (s, 1H), 8.89 (s, 1H), 8.22 (d, J=8.6 Hz, 1H), 8.08 (m, 1H), 7.97 (d, J=6.4 Hz, 1H), 7.32-7.20 (m, 2H), 6.97 (s, 2H), 6.82-6.72 (m, 2H), 6.62 (m, 1H), 6.32 (d, J=8.1 Hz, 1H), 4.50 (d, J=6.1 Hz, 2H), 3.72 (s, 3H). MS=347 (MH)+.

Example 399

N(8)-(3-Methoxy-benzyl)-N(2)-pyridin-4-yl-[1,2,4]triazolo[1,5-a]pyridine-2,8-diamine

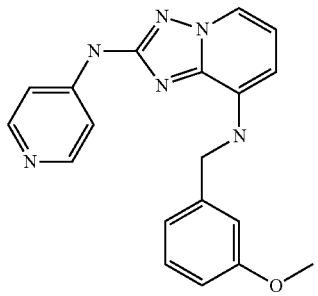 [SMILES: COc1cccc(CNc2cccn3nc(Nc4ccncc4)nc23)c1]

N(8)-(3-Methoxy-benzyl)-N(2)-pyridin-4-yl-[1,2,4]triazolo[1,5-a]pyridine-2,8-diamine was prepared from (2-chloro-[1,2,4]triazolo[1,5-a]pyridin-8-yl)-(3-methoxy-benzyl)-amine (99.9 mg, 0.346 mmol) and 4-aminopyridine (36.47 mg, 0.3875 mmol) in a manner analogous to Example 2d. Product was isolated as an off-white foam (3.63 mg, 3%). $^1$H NMR (400 MHz, (D$_3$C)$_2$SO, δ, ppm): 10.02 (s, 1H), 8.32 (m, 2H), 8.00 (d, J=6.7 Hz, 1H), 7.69 (m, 2H), 7.23 (t, J=16.4, 8.2 Hz, 1H), 6.97 (s, 2H), 6.79 (m, 2H), 6.67 (m, 1H), 6.34 (d, J=8.0 Hz, 1H), 4.50 (d, J=6.1 Hz, 2H), 3.72 (s, 3H). MS=347 (MH)+.

Example 400

N(8)-(2-Methoxy-benzyl)-N(2)-pyridin-3-yl-[1,2,4]triazolo[1,5-a]pyridine-2,8-diamine

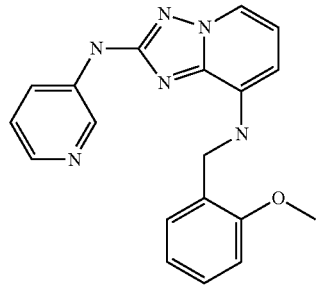 [SMILES: COc1ccccc1CNc1cccn2nc(Nc3cccnc3)nc12]

N(8)-(2-Methoxy-benzyl)-N(2)-pyridin-3-yl-[1,2,4]triazolo[1,5-a]pyridine-2,8-diamine was prepared from 3-aminopyridine (36.47 mg, 0.3875 mmol) and (2-chloro-[1,2,4]triazolo[1,5-a]pyridin-8-yl)-(2-methoxy-benzyl)-amine (99.9 mg, 0.346 mmol) in a manner analogous to Example 2d. Product isolated as an off-white foam (19.21 mg, 16%). $^1$H NMR (400 MHz, (D$_3$C)$_2$SO, δ, ppm): 9.68 (s, 1H), 8.88 (s, 1H), 8.21 (d, J=8.6 Hz, 1H), 8.09 (s, 1H), 7.99 (d, J=7.5 Hz, 1H), 7.33-7.20 (m, 3H), 7.03 (d, J=8.6 Hz, 1H), 6.87 (t, J=15.2, 8.1 Hz, 1H), 6.77 (t, J=13.5, 6.6 Hz, 1H), 6.31 (m, 2H), 4.47 (d, J=5.8 Hz, 2H), 3.87 (s, 3H). MS=347 (MH)+.

Example 401

N(8)-(2-Methoxy-benzyl)-N(2)-pyridin-4-yl-[1,2,4]triazolo[1,5-a]pyridine-2,8-diamine

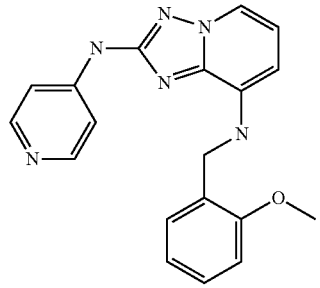 [SMILES: COc1ccccc1CNc1cccn2nc(Nc3ccncc3)nc12]

N(8)-(2-Methoxy-benzyl)-N(2)-pyridin-4-yl-[1,2,4]triazolo[1,5-a]pyridine-2,8-diamine was prepared from 4-aminopyridine (36.47 mg, 0.3875 mmol) and (2-chloro-[1,2,4]triazolo[1,5-a]pyridin-8-yl)-(2-methoxy-benzyl)-amine (99.9 mg, 0.346 mmol) in a manner analogous to Example 2d. Product isolated as a off-white foam (4.14 mg, 3.5%). $^1$H NMR (400 MHz, (D$_3$C)$_2$SO, δ, ppm): 10.04 (s, 1H), 8.32 (m, 2H), 8.01 (d, J=6.7 Hz, 1H), 7.68 (m, 2H), 7.24 (m, 2H), 7.03

(d, J=8.2 Hz, 1H), 6.87 (t, J=14.9, 7.6 Hz, 1H), 6.80 (t, J=14.3, 7.6 Hz, 1H), 6.40-6.31 (m, 2H), 4.47 (d, J=5.8 Hz, 2H), 3.87 (s, 3H). MS=347 (MH)+.

Example 402

N(8)-(2-Methoxy-benzyl)-N(2)-(6-methoxy-pyridin-3-yl)-[1,2,4]triazolo[1,5-a]pyridine-2,8-diamine

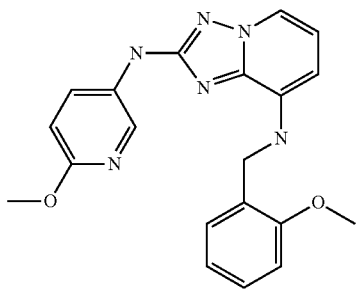

N(8)-(2-Methoxy-benzyl)-N(2)-(6-methoxy-pyridin-3-yl)-[1,2,4]triazolo[1,5-a]pyridine-2,8-diamine was prepared from 5-amino-2-methoxypyridine (96.31 mg, 0.7758 mmol) and (2-Chloro-[1,2,4]triazolo[1,5-a]pyridin-8-yl)-(2-methoxy-benzyl)-amine (200.00 mg, 0.69268 mmol) in a manner analogous to Example 2d. Product isolated as a red foam (41.05 mg, 16%). $^1$H NMR (400 MHz, $(D_3C)_2SO$, δ, ppm): 9.31 (s, 1H), 8.58 (s, 1H), 8.04 (d, J=9.3 Hz, 1H), 7.93 (d, J=6.8 Hz, 1H), 7.24 (m, 2H), 7.02 (d, J=8.4 Hz, 1H), 6.87 (t, J=14.9, 7.2 Hz, 1H), 6.78 (d, J=9.4 Hz, 1H), 6.72 (t, J=14.9, 7.2 Hz, 1H), 6.29 (m, 2H), 4.45 (d, J=6.0 Hz, 2H), 3.87 (s, 3H), 3.81 (s, 3H). MS=377 (MH)+.

Example 403

N(8)-(2-Methoxy-benzyl)-N(2)-(6-methyl-pyridin-3-yl)-[1,2,4]triazolo[1,5-a]pyridine-2,8-diamine

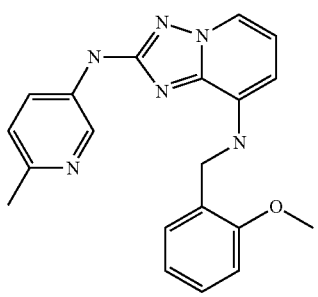 [SMILES: COc1ccccc1CNc1cccn2nc(Nc3ccc(C)nc3)nc12]

N(8)-(2-Methoxy-benzyl)-N(2)-(6-methyl-pyridin-3-yl)-[1,2,4]triazolo[1,5-a]pyridine-2,8-diamine was prepared from 6-Methyl-pyridin-3-ylamine (83.90 mg, 0.7758 mmol) and (2-chloro-[1,2,4]triazolo[1,5-a]pyridin-8-yl)-(2-methoxy-benzyl)-amine (200.00 mg, 0.69268 mmol) in a manner analogous to Example 2d. Product isolated as a red foam (23.23 mg, 9%). $^1$H NMR (400 MHz, $(D_3C)_2SO$, δ, ppm): 9.51 (s, 1H), 8.74 (s, 1H), 8.10 (d, J=8.8 Hz, 1H), 7.97 (d, J=6.7 Hz, 1H), 7.23 (m, 2H), 7.15 (d, J=8.8 Hz, 1H), 7.03 (d, J=8.8 Hz, 1H), 6.87 (t, J=15.1, 7.4 Hz, 1H), 6.75 (t, J=14.1, 7.1 Hz, 1H), 6.32-6.23 (m, 2H), 4.47 (d, J=5.9 Hz, 1H), 3.87 (s, 3H), 2.39 (s, 3H). MS=361. (MH)+.

Example 404

N(8)-(2-Methoxy-benzyl)-N(2)-(2-methyl-pyridin-4-yl)-[1,2,4]triazolo[1,5-a]pyridine-2,8-diamine

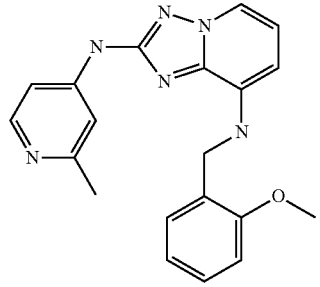 [SMILES: COc1ccccc1CNc1cccn2nc(Nc3ccnc(C)c3)nc12]

N(8)-(2-Methoxy-benzyl)-N(2)-(2-methyl-pyridin-4-yl)-[1,2,4]triazolo[1,5-a]pyridine-2,8-diamine was prepared from N(8)-(2-methoxy-benzyl)-N(2)-(2-methyl-pyridin-4-yl)-[1,2,4]triazolo[1,5-a]pyridine-2,8-diamine (200.00 mg, 0.69268 mmol) and 2-methyl-pyridin-4-ylamine (83.90 mg, 0.7758 mmol) in a manner analogous to Example 2d. Product isolated as a red foam (42.23 mg, 17%). $^1$H NMR (400 MHz, $(D_3C)_2SO$, δ, ppm): 9.92 (s, 1H), 8.19 (d, J=5.5 Hz, 1H), 8.04 (d, J=6.9 Hz, 1H), 7.53 (m, 1H), 7.48 (s, 1H), 7.24 (m, 2H), 7.03 (d, J=8.1 Hz, 1H), 6.88 (t, J=15.2, 7.3 Hz, 1H), 6.79 (t, J=14.6, 7.5 Hz, 1H), 6.34 (m, 2H), 4.48 (d, J=6.0 Hz, 2H), 3.87 (s, 3H), 2.40 (s, 3H). MS=361 (MH)+.

Example 405

N(8)-(3-Methoxy-benzyl)-N(2)-(6-methyl-pyridin-3-yl)-[1,2,4]triazolo[1,5-a]pyridine-2,8-diamine

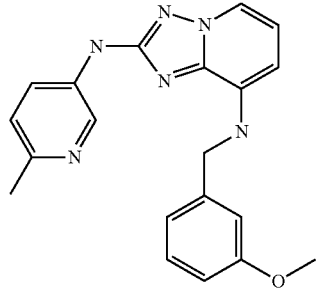 [SMILES: COc1cccc(CNc2cccn3nc(Nc4ccc(C)nc4)nc23)c1]

N(8)-(3-Methoxy-benzyl)-N(2)-(6-methyl-pyridin-3-yl)-[1,2,4]triazolo[1,5-a]pyridine-2,8-diamine was prepared from (2-chloro-[1,2,4]triazolo[1,5-a]pyridin-8-yl)-(3-methoxy-benzyl)-amine (99.9 mg, 0.346 mmol) and 6-methyl-pyridin-3-ylamine (41.91 mg, 0.3875 mmol) in a manner analogous to Example 2d. Product isolated as a red foam (8.55 mg, 7%). $^1$H NMR (400 MHz, $(D_3C)_2SO$, δ, ppm): 9.48 (s, 1H), 8.74 (s, 1H), 8.11 (d, J=8.2 Hz, 1H), 7.96 (d, J=6.7 Hz, 1H), 7.23 (t, J=15.8, 7.7 Hz, 1H), 7.15 (d, J=8.6 Hz, 1H), 6.96

(s, 2H), 6.82-6.70 (m, 2H), 6.57 (m, 1H), 6.31 (d, J=7.8 Hz, 1H), 4.48 (d, J=6.0 Hz, 2H), 3.71 (s, 3H), 2.40 (s, 3H). MS=361 (MH)+.

Example 406

[8-(4-Methanesulfonyl-phenyl)-[1,2,4]triazolo[1,5-a]pyridin-2-yl]-(2-pyridin-2-yl-ethyl)-amine

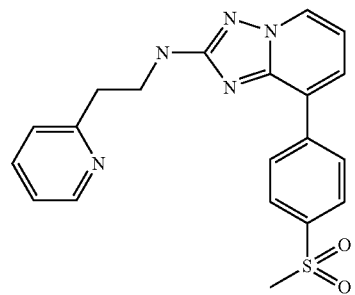 [SMILES: CS(=O)(=O)c1ccc(-c2cccn3nc(NCCc4ccccn4)nc23)cc1]

[8-(4-Methanesulfonyl-phenyl)-[1,2,4]triazolo[1,5-a]pyridin-2-yl]-(2-pyridin-2-yl-ethyl)-amine was prepared from 2-chloro-8-(4-methanesulfonyl-phenyl)-[1,2,4]triazolo[1,5-a]pyridine (250 mg, 0.81 mmol) and 2-pyridin-2-yl-ethylamine (0.97 mL, 8.1 mmol) combined in a microwave vial and heated to 200° C. for 2 hours. The reaction mixture was diluted with water, extracted with ethyl acetate, and the organic layer was dried, filtered, and concentrated. The residue was purified via reverse phase chromatography (Phenomenex Gemini-NX C18 AXIA column acetonitrile in water with trifluoroacetic acid modifier). Fractions containing product were neutralized by combining in saturated sodium bicarbonate and extracting with 3 portions of dichloromethane. The combined organic was dried over magnesium sulfate, filtered and evaporated to yield a light yellow powder (195 mg, 61%). $^1$H NMR (400 MHz, (D$_3$C)$_2$SO, δ, ppm): 8.70 (d, J=6.7 Hz, 1H), 8.49 (s, 1H), 8.42-8.35 (m, 3H), 8.04 (d, J=7.9 Hz, 2H), 7.87 (d, J=7.5 Hz, 1H), 7.70 (d, J=8.0 Hz, 1H), 7.31 (m, 1H), 7.04 (t, J=14.6, 7.4 Hz, 1H), 6.93 (m, 1H), 3.51 (m, 2H), 3.28 (s, 3H), 2.93 (t, J=14.1, 7.0 Hz, 2H). MS=394 (MH)+.

Example 407

[8-(4-Methanesulfonyl-phenyl)-[1,2,4]triazolo[1,5-a]pyridin-2-yl]-(2-pyridin-3-yl-ethyl)-amine

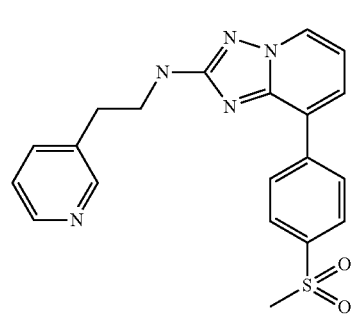 [SMILES: CS(=O)(=O)c1ccc(-c2cccn3nc(NCCc4cccnc4)nc23)cc1]

408a) [8-(4-Methanesulfonyl-phenyl)-[1,2,4]triazolo[1,5-a]pyridin-2-yl]-(2-pyridin-3-yl-ethyl)-amine was prepared from 2-chloro-8-(4-methanesulfonyl-phenyl)-[1,2,4]triazolo[1,5-a]pyridine (250 mg, 0.81 mmol) and 2-pyridin-3-yl-ethylamine (0.95 mL, 8.1 mmol) in a manner analogous to Example 406. Product isolated as a light yellow powder (98.5 mg, 31%). $^1$H NMR (400 MHz, (D$_3$C)$_2$SO, δ, ppm): 8.71 (d, J=6.4 Hz, 1H), 8.51 (m, 1H), 8.39 (d, J=7.8 Hz, 2H), 8.03 (d, J=7.4 Hz, 2H), 7.86 (d, J=7.4 Hz, 1H), 7.70 (t, J=15.1, 7.6 Hz, 1H), 7.30 (m, 1H), 7.22 (m, 1H), 7.04 (t, J=13.9, 7.3 Hz, 1H), 6.86 (m, 1H), 3.62 (m, 2H), 3.28 (s, 3H), 3.06 (m, 2H). MS=394 (MH)+.

Example 408

[8-(4-Methanesulfonyl-phenyl)-[1,2,4]triazolo[1,5-a]pyridin-2-yl]-pyridin-3-ylmethyl-amine

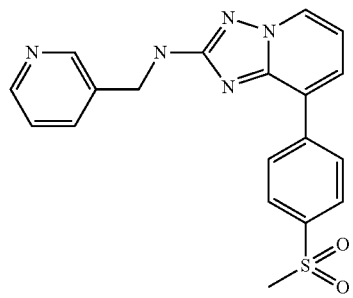 [SMILES: CS(=O)(=O)c1ccc(-c2cccn3nc(NCc4cccnc4)nc23)cc1]

[8-(4-Methanesulfonyl-phenyl)-[1,2,4]triazolo[1,5-a]pyridin-2-yl]-pyridin-3-ylmethyl-amine was prepared from 2-chloro-8-(4-methanesulfonyl-phenyl)-[1,2,4]triazolo[1,5-a]pyridine (250 mg, 0.81 mmol) and 3-(aminomethyl)-pyridine (0.82 mL, 8.1 mmol) in a manner analogous to Example 406. Product isolated as a light yellow powder (163 mg, 53%). $^1$H NMR (400 MHz, (D$_3$C)$_2$SO, δ, ppm): 8.64 (d, J=6.5 Hz, 1H), 8.62 (s, 1H), 8.44 (m, 1H), 8.38 (d, J=8.0 Hz, 2H), 8.04 (d, J=8.4 Hz, 2H), 7.86 (d, J=7.7 Hz, 1H), 7.79 (d, J=7.9 Hz, 1H), 7.47 (t, J=12.8, 6.4 Hz, 1H), 7.35 (m, 1H), 7.04 (t, J=14.2, 7.2 Hz, 1H), 4.50 (d, J=6.2 Hz, 2H), 3.28 (s, 3H). MS=380 (MH)+.

Example 409

[8-(4-Methanesulfonyl-phenyl)-[1,2,4]triazolo[1,5-a]pyridin-2-yl]-pyridin-2-ylmethyl-amine

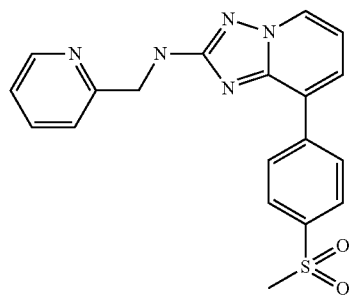 [SMILES: CS(=O)(=O)c1ccc(-c2cccn3nc(NCc4ccccn4)nc23)cc1]

[8-(4-Methanesulfonyl-phenyl)-[1,2,4]triazolo[1,5-a]pyridin-2-yl]-pyridin-2-ylmethyl-amine was prepared from 2-chloro-8-(4-methanesulfonyl-phenyl)-[1,2,4]triazolo[1,5-a]pyridine (250 mg, 0.81 mmol) and C-pyridin-2-yl-methylamine (0.84 mL, 8.1 mmol) in a manner analogous to Example 406. Product isolated as a light yellow powder (207 mg, 67%). $^1$H NMR (400 MHz, (D$_3$C)$_2$SO, δ, ppm): 8.68 (d, J=6.5 Hz, 1H), 8.51 (m, 1H), 8.38 (d, J=7.7 Hz, 2H), 8.04 (d, J=7.9 Hz, 2H), 7.87 (d, J=7.7 Hz, 1H), 7.73 (t, J=15.5, 7.9 Hz, 1H), 7.46-7.37 (m, 2H), 7.24 (m, 1H), 7.04 (t, J=14.2, 6.9 Hz, 1H), 4.59 (d, J=5.8 Hz, 2H), 3.28 (s, 3H). MS=380 (MH)+.

Example 410

2-(4-3-[8-(2-Methoxy-5-trifluoromethyl-phenyl)-[1,2,4]triazolo[1,5-a]pyridin-2-ylamino]-phenyl)-piperidin-1-yl)-N,N-dimethyl-acetamide

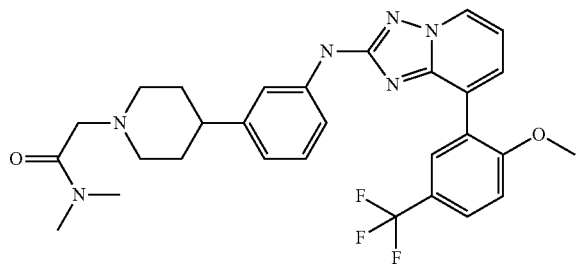 [SMILES: COc1ccc(C(F)(F)F)cc1-c1cccn2nc(Nc3cccc(C4CCN(CC(=O)N(C)C)CC4)c3)nc12]

2-(4-(-[8-(2-Methoxy-5-trifluoromethyl-phenyl)-[1,2,4]triazolo[1,5-a]pyridin-2-yl-amino]-phenyl)-piperidin-1-yl)-N,N-dimethyl-acetamide was prepared from [8-(2-methoxy-5-trifluoromethyl-phenyl)-[1,2,4]triazolo[1,5-a]pyridin-2-yl]-(3-piperidin-4-yl-phenyl)-amine (0.12 g, 0.26 mmol) and 2-chloro-N,N-dimethyl-acetamide (0.06 g, 0.5 mmol), in a manner analogous to Example 235a. Product was isolated as a foam (0.034 g, 24%). $^1$H NMR (400 MHz, CDCl$_3$, δ, ppm): 8.48 (d, J=6.4 Hz, 1H), 7.93 (s, 1H), 7.69 (d, J=7.5 Hz, 1H), 7.54 (d, J=6.4 Hz, 1H), 7.47-7.40 (m, 2H), 7.31-7.28 (m, 1H), 7.12 (d, J=7.5 Hz, 1H), 6.96 (t, J=6.4 Hz, 1H), 6.89-6.85 (m, 2H), 3.88 (s, 3H), 3.24 (s, 2H), 3.17-3.12 (m, 2H), 3.08-3.03 (m, 2H), 2.98 (s, 3H), 2.59-2.48 (m, 1H), 2.30-2.16 (m, 2H), 1.87 (s, 3H). MS=553 (MH)+.

Example 411

N-[4-(1-ethyl-4-oxido-1,4-azaphosphinan-4-yl)phenyl]-8-[4-(methylsulfonyl)phenyl][1,2,4]triazolo[1,5-a]pyridin-2-amine

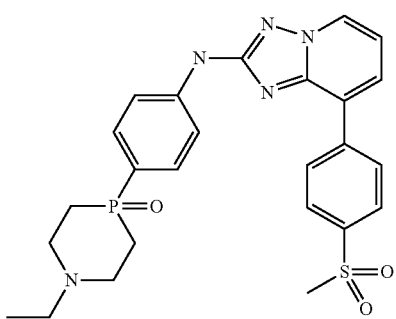 [SMILES: CCN1CCP(=O)(c2ccc(Nc3nc4c(-c5ccc(S(C)(=O)=O)cc5)cccn4n3)cc2)CC1]

411a) A mixture of 1-bromo-4-nitrobenzene (400 mg, 2.00 mmol), tetrakis(triphenylphosphine)palladium(0) (120 mg, 0.20 mmol) and cesium carbonate (734 mg, 2.2 mmol) in a 30 mL microwave vial was purged and backfilled with nitrogen. Tetrahydrofuran (20 mL) was added followed by diethyl phosphite (0.360 mL, 2.8 mmol). The mixture was vortexed, then microwaved for 45 minutes at 120° C. Reaction was repeated three times to achieve total scale then the combined reaction mixtures were purified via chromatography (120 g silica gel 5%→75% ethyl acetate in hexane). (4-Nitro-phenyl)-phosphonic acid diethyl ester isolated as a light yellow oil (969 mg, 47%). $^1$H NMR (400 MHz, (D$_3$C)$_2$SO, δ, ppm): 8.35 (d, J=8.0 Hz, 2H), 7.16 (s, 1H), 5.93 (s, 2H), 3.40 (s, 4H), 2.36 (s, 4H), 2.20 (s, 3H), 8.05-7.95 (m, 2H), 4.09 (m, 4H), 1.25 (t, J=13.8, 7.4 Hz, 6H).

411b) To a solution of (4-Nitro-phenyl)-phosphonic acid diethyl ester (2.31 g, 8.91 mmol) in N,N-dimethylformamide (1 mL) was added thionyl chloride (3.25 mL, 44.6 mmol). The reaction mixture was heated to reflux for 2 hours, cooled to room temperature and concentrated in vacuo. The residue was azeotroped with carbon tetrachloride several times to remove excess thionyl chloride. 4-Nitrophenylphosphonic dichloride was carried on crude to the next reaction.

411c) To a solution of 4-Nitrophenylphosphonic dichloride (2.14 g, 8.91 mmol) in tetrahydrofuran at −78° C. was added vinylmagnesium bromide (2.34 g, 17.8 mmol). The solution was stirred at −78° C. for one hour then quenched by the addition of ammonium chloride solution. The mixture was extracted with dichloromethane. The combined organic layers were dried and concentrated. 4-(Divinyl-phosphinoyl)nitro benzene was isolated as a brown-yellow oil (1.69 g, 85%). MS=224 (MH)+.

411d) A mixture of 4-(Divinyl-phosphinoyl)nitro benzene (1.69 g, 7.56 mmol), water (10 mL), 1.0 M of sodium hydroxide in water (7.56 mL, 7.56 mmol) and tetrahydrofuran (10.0 mL, 123 mmol) was treated with ethylamine hydrochloride (678 mg, 8.32 mmol) then heated at 105° C. for one hour. An additional portion of ethylamine hydrochloride was added and the reaction was heated for an additional 2 hours. The reaction was cooled, poured into saturated sodium bicarbonate solution and extracted with dichloromethane. The aqueous layer was treated with solid sodium chloride and extracted and additional 4 times to isolate all the product. The combined organic layers were dried over magnesium sulfate, filtered and evaporated. The residue was purified via chromatography (40 g silica gel and 0%→10% methanol in dichloromethane). 1-Ethyl-4-(4-nitro-phenyl)-perhydro-1,4-azaphosphorine 4-oxide was isolated as yellow oil (300 mg, 10%). $^1$H NMR (400 MHz, (D$_3$C)$_2$SO, δ, ppm): 8.34 (d, J=8.4 Hz, 2H), 8.11 (t, J=18.46, 9.15 Hz, 2H), 2.91-2.75 (m, 4H), 2.51-2.46 (m, 2H), 2.29 (m, 2H), 1.96 (m, 2H), 1.01 (t, J=14.4, 7.5 Hz, 3H). MS=269 (MH)+.

411e) 1-Ethyl-4-(4-nitro-phenyl)-perhydro-1,4-azaphosphorine 4-oxide (269.80 mg, 1.0058 mmol) dissolved in Ethanol (50 mL) and treated with palladium on carbon 10% (90:10, carbon black:Palladium, 30 mg, 2 mmol), 2.5 M of hydrogen chloride in ethanol (1.21 mL, 3.02 mmol) and 50 PSI of hydrogen gas. The mixture was shaken on a Parr apparatus for 5 hours. The mixture was degassed and backflushed with nitrogen. The mixture was filtered through a plug of diatomaceous earth and washed with ethanol. The filtrate was evaporated. 4-(1-ethyl-4-oxido-1,4-azaphosphinan-4-yl)aniline hydrochloride was isolated (401 mg, 145%). MS=238 (MH)+.

411f) N-[4-(1-ethyl-4-oxido-1,4-azaphosphinan-4-yl)phenyl]-8-[4-(methylsulfonyl)phenyl][1,2,4]triazolo[1,5-a]pyridin-2-amine was prepared from 2-Chloro-8-(4-methanesulfonyl-phenyl)-[1,2,4]triazolo[1,5-a]pyridine (133 mg, 0.434 mmol) and 4-(1-ethyl-4-oxido-1,4-azaphosphinan-4-yl)aniline hydrochloride (131.01 mg, 0.47689 mmol) in a manner analogous to Example 2d. Product isolated as an off-white solid (31.56 mg, 14%). $^1$H NMR (400 MHz, CDCl$_3$, δ, ppm): 8.54 (d, J=8.3 Hz, 1H), 8.23 (d, J=8.0 Hz, 2H), 8.01 (d, J=8.0 Hz, 2H), 7.80-7.67 (m, 5H), 7.08 (t, J=13.6, 7.0 Hz, 1H), 3.13-2.90 (m, 7H), 2.61 (m, 2H), 2.27-2.02 (m, 4H), 1.13 (t, J=13.6, 6.4 Hz, 3H). MS=510 (MH)+.

The invention claimed is:

1. A compound of Formula V:

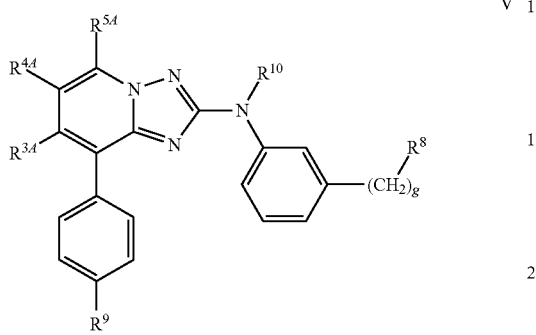

or a salt thereof, wherein:

$R^{3A}$, $R^{4A}$, and $R^{5A}$ are each independently selected from H, OH, CN, NO$_2$, halogen, (C$_1$-C$_8$)alkyl, (C$_1$-C$_8$)alkoxy, halo(C$_1$-C$_4$)alkyl, and halo(C$_1$-C$_4$)alkoxy;

$R^{7A}$ is selected from H and (C$_1$-C$_8$)alkyl;

$R^8$ is selected from SO$_2$R$^{7A}$, (C$_2$-C$_8$)alkyl, (C$_1$-C$_8$)alkoxy, halo(C$_2$-C$_4$)alkyl, halo(C$_1$-C$_4$)alkoxy, (C$_3$-C$_{14}$)cycloalkyl, (C$_3$-C$_{14}$)cycloalkyloxy, (C$_3$-C$_{14}$)cycloalkyl(C$_1$-C$_4$)alkyl, (C$_3$-C$_{14}$)cycloalkyl(C$_1$-C$_4$)alkoxy, (C$_6$-C$_{10}$)aryl, (C$_6$-C$_{10}$)aryloxy, (C$_6$-C$_{10}$)aryl(C$_1$-C$_4$)alkyl, (C$_6$-C$_{10}$)aryl(C$_1$-C$_4$)alkoxy, (C$_2$-C$_{14}$)heterocycloalkyl, (C$_2$-C$_{14}$)heterocycloalkyloxy, (C$_2$-C$_{14}$)heterocycloalkyl(C$_1$-C$_4$)alkyl, (C$_2$-C$_{14}$)heterocycloalkyl(C$_1$-C$_4$)alkoxy, (C$_2$-C$_9$)heteroaryl, (C$_2$-C$_9$)heteroaryloxy, (C$_2$-C$_9$)heteroaryl(C$_1$-C$_4$)alkyl, and (C$_2$-C$_9$)heteroaryl(C$_1$-C$_4$)alkoxy, wherein each of the aforementioned groups may be optionally substituted with between one to four substituents;

$R^9$ is selected from SO$_2$R$^{7A}$, POR$^{7A}$R$^{7A}$, NR$^{7A}$SO$_2$R$^{7A}$, halo(C$_1$-C$_4$)alkyl, halogen, or (C$_2$-C$_{14}$)heterocycloalkyl optionally substituted with between one to four substituents;

$R^{10}$ is selected from H and (C$_1$-C$_4$)alkyl optionally substituted with SO$_2$(C$_1$-C$_4$)alkyl;

g is selected from 0, 1, 2, or 3; and wherein said optional substituents are each independently selected from OH, CN, oxo, NO$_2$, halogen, (C$_1$-C$_8$)alkyl, (C$_1$-C$_8$)alkoxy, hydroxy(C$_1$-C$_4$)alkyl, halo(C$_1$-C$_4$)alkyl, halo(C$_1$-C$_4$)alkoxy, (C$_3$-C$_{14}$)cycloalkyl, (C$_3$-C$_{14}$)cycloalkyl(C$_1$-C$_4$)alkyl, (C$_3$-C$_{14}$)cycloalkyloxy, (C$_3$-C$_{14}$)cycloalkyl(C$_1$-C$_4$)alkoxy, NR$^{7A}$R$^{7A}$, (C$_1$-C$_4$)alkyl-NR$^{7A}$R$^{7A}$, (C$_6$-C$_{10}$)aryl, (C$_6$-C$_{10}$)aryl(C$_1$-C$_4$)alkyl, (C$_6$-C$_{10}$)aryloxy, (C$_6$-C$_{10}$)aryl(C$_1$-C$_4$)alkoxy, SO$_2$R$^{7A}$, (C$_1$-C$_4$)alkyl-SO$_2$R$^{7A}$, (C$_1$-C$_{14}$)alkyl-C(O)NR$^{7A}$R$^{7A}$, C(O)NR$^{7A}$R$^{7A}$, (C$_1$-C$_4$)alkyl-SO$_2$NR$^{7A}$R$^{7A}$, SO$_2$NR$^{7A}$R$^{7A}$, (C$_2$-C$_{14}$)heterocycloalkyl, (C$_2$-C$_{14}$)heterocycloalkyloxy, (C$_2$-C$_{14}$)heterocycloalkyl(C$_1$-C$_4$)alkyl, (C$_2$-C$_{14}$)heterocycloalkyl(C$_1$-C$_4$)alkoxy, (C$_2$-C$_9$)heteroaryl, (C$_2$-C$_9$)heteroaryloxy, (C$_2$-C$_9$)heteroaryl(C$_1$-C$_4$)alkyl, (C$_2$-C$_9$)heteroaryl(C$_1$-C$_4$)alkoxy, COR$^{7A}$, (C$_1$-C$_4$)alkyl-COR$^{7A}$, NR$^{7A}$COR$^{7A}$, (C$_1$-C$_4$)alkyl-NR$^{7A}$COR$^{7A}$, NR$^{7A}$SO$_2$R$^{7A}$, (C$_1$-C$_4$)alkyl-NR$^{7A}$SO$_2$R$^{7A}$, OSO$_2$R$^{7A}$, (C$_1$-C$_4$)alkyl-OSO$_2$R$^{7A}$, POR$^{7A}$R$^{7A}$, (C$_1$-C$_4$)alkyl-POR$^{7A}$R$^{7A}$, CO$_2$R$^{7A}$ or (C$_1$-C$_4$)alkyl-CO$_2$R$^{7A}$.

2. A compound according to claim 1, or a salt thereof, selected from the following:

| Structure | Name |
|---|---|
| 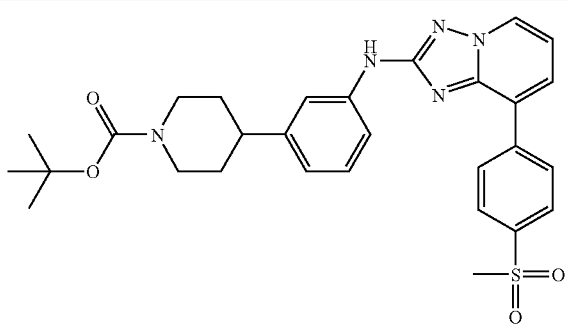 | 4-{3-[8-(4-Methanesulfonyl-phenyl)-[1,2,4]triazolo[1,5-a]pyridin-2-ylamino]-phenyl}-piperidine-1-carboxylic acid tert butyl ester |
| 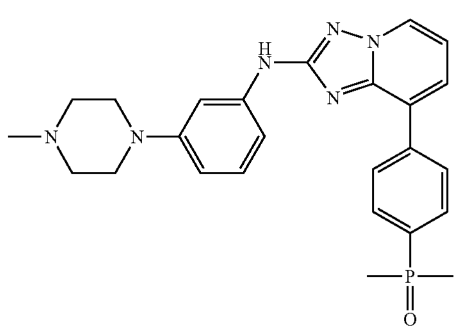 | {8-[4-(Dimethyl-phosphinoyl)-phenyl]-[1,2,4]triazolo[1,5-a]pyridin-2-yl}-[3-(4-methyl-piperazin-1-yl)-phenyl]-amine |

-continued

| Structure | Name |
|---|---|
| 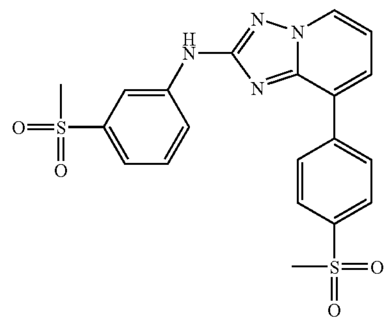 [SMILES: CS(=O)(=O)c1ccc(-c2cccn3nc(Nc4cccc(S(C)(=O)=O)c4)nc23)cc1] | (3-Methanesulfonyl-phenyl)-[8-(4-methanesulfonyl-phenyl)-1,2,4]triazolo[1,5-a]pyridin-2-yl]-amine |
| 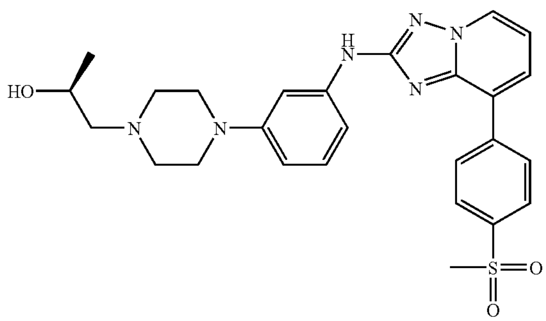 [SMILES: C[C@H](O)CN1CCN(c2cccc(Nc3nc4c(-c5ccc(S(C)(=O)=O)cc5)cccn4n3)c2)CC1] | (S)-1-(4-{3-[8-(4-Methanesulfonyl-phenyl)-[1,2,4]triazolo[1,5-a]pyridin-2-ylamino]-phenyl}-piperazin-1-yl)-propan-2-ol |
| 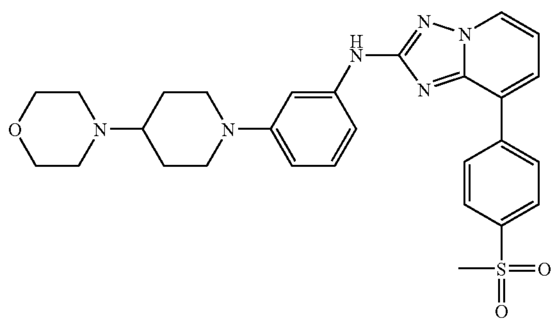 [SMILES: CS(=O)(=O)c1ccc(-c2cccn3nc(Nc4cccc(N5CCC(N6CCOCC6)CC5)c4)nc23)cc1] | [8-(4-Methanesulfonyl-phenyl)-[1,2,4]triazolo[1,5-a]pyridin-2-yl]-[3-(4-morpholin-4-yl-piperidin-1-yl)-phenyl]-amine |
| 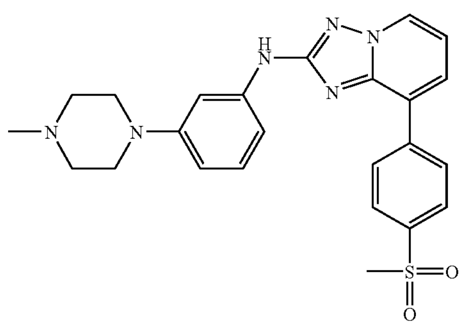 | [8-(4-Methanesulfonyl-phenyl)-[1,2,4]triazolo[1,5-a]pyridin-2-yl]-[3-(4-methyl-piperazin-1-yl)-phenyl]-amine |
| 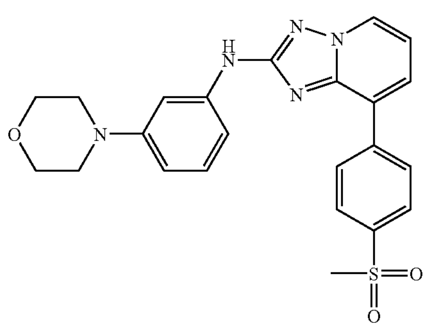 | [8-(4-Methanesulfonyl-phenyl)-[1,2,4]triazolo[1,5-a]pyridin-2-yl]-(3-morpholin-4-yl-phenyl)-amine |

| Structure | Name |
|---|---|
| 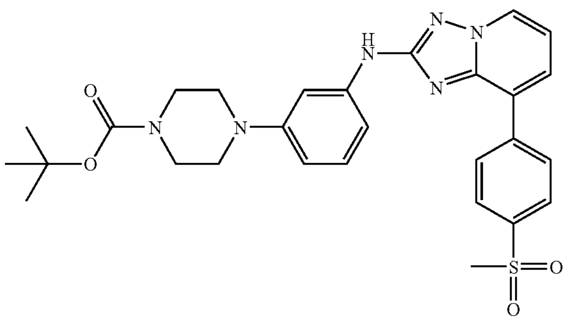 [SMILES: CC(C)(C)OC(=O)N1CCN(c2cccc(Nc3nc4c(-c5ccc(S(C)(=O)=O)cc5)cccn4n3)c2)CC1] | 4-{3-[8-(4-Methanesulfonyl-phenyl)-[1,2,4]triazolo[1,5-a]pyridin-2-ylamino]-phenyl}-piperazine-1-carboxylic acid tert-butyl ester |
| 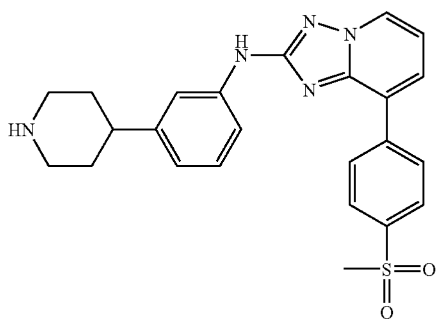 [SMILES: CS(=O)(=O)c1ccc(-c2cccn3nc(Nc4cccc(C5CCNCC5)c4)nc23)cc1] | [8-(4-Methanesulfonyl-phenyl)-[1,2,4]triazolo[1,5-a]pyridin-2-yl]-(3-piperidin-4-yl-phenyl)-amine |
| 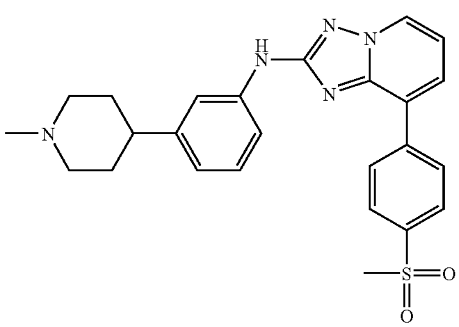 | [8-(4-Methanesulfonyl-phenyl)-[1,2,4]triazolo[1,5-a]pyridin-2-yl]-[3-(1-methyl-piperidin-4-yl)-phenyl]-amine |
| 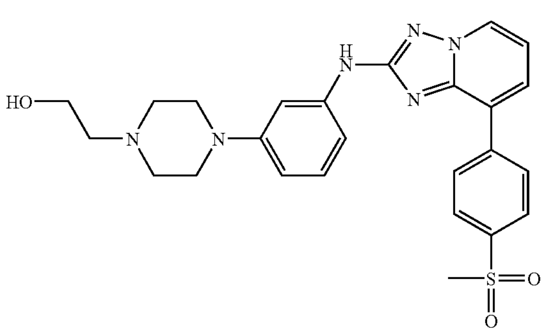 [SMILES: CS(=O)(=O)c1ccc(-c2cccn3nc(Nc4cccc(N5CCN(CCO)CC5)c4)nc23)cc1] | 2-(4-{3-[8-(4-Methanesulfonyl-phenyl)-[1,2,4]triazolo[1,5-a]pyridin-2-ylamino]-phenyl}-piperazin-1-yl)-ethanol |

-continued

| Structure | Name |
|---|---|
| 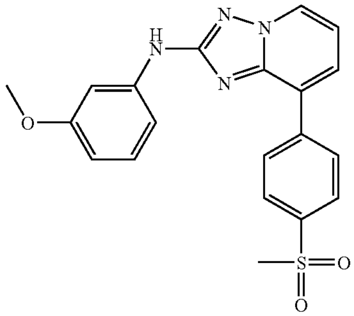 [SMILES: COc1cccc(Nc2nc3c(-c4ccc(S(C)(=O)=O)cc4)cccn3n2)c1] | [8-(4-Methanesulfonyl-phenyl)-[1,2,4]triazolo[1,5-a]pyridin-2-yl]-(3-methoxy-phenyl)-amine |
| 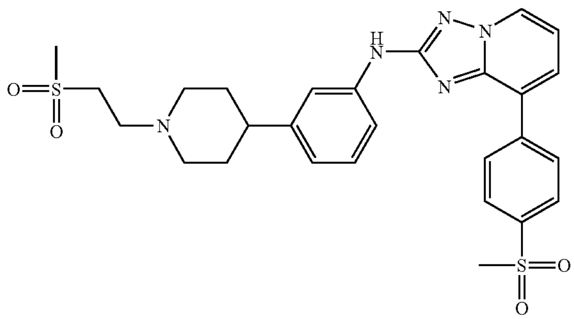 [SMILES: CS(=O)(=O)CCN1CCC(c2cccc(Nc3nc4c(-c5ccc(S(C)(=O)=O)cc5)cccn4n3)c2)CC1] | {3-[1-(2-Methanesulfonyl-ethyl)-piperidin-4-yl]-phenyl}-[8-(4-methanesulfonyl-phenyl)-[1,2,4]triazolo[1,5-a]pyridin-2-yl]-amine |
| 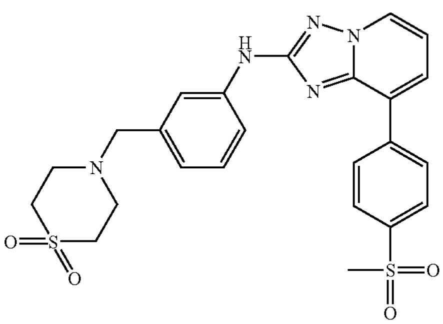 [SMILES: CS(=O)(=O)c1ccc(-c2cccn3nc(Nc4cccc(CN5CCS(=O)(=O)CC5)c4)nc23)cc1] | N-{3-[(1,1-dioxidothiomorpholin-4-yl)methyl]phenyl}-8-[4-(methylsulfonyl)phenyl][1,2,4]triazolo[1,5-a]pyridin-2-amine |
| 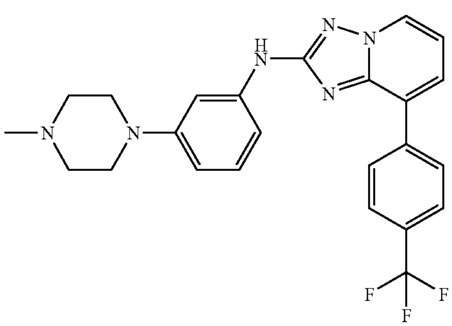 [SMILES: CN1CCN(c2cccc(Nc3nc4c(-c5ccc(C(F)(F)F)cc5)cccn4n3)c2)CC1] | [3-(4-Methyl-piperazin-1-yl)-phenyl]-[8-(4-trifluoromethyl-phenyl)-[1,2,4]triazolo[1,5-a]pyridin-2-yl]-amine |
| | [8-(4-Methanesulfonyl-phenyl)-[1,2,4]triazolo[1,5-a]pyridin-2-yl]-{3-[4-(4-methyl-piperazin-1-yl)-piperidin-1-yl]-phenyl}-amine |

| Structure | Name |
|---|---|
| 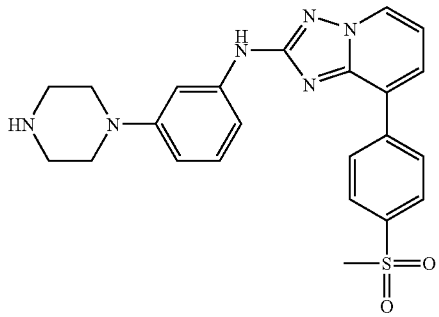 | [8-(4-Methanesulfonyl-phenyl)-[1,2,4]triazolo[1,5-a]pyridin-2-yl]-(3-piperazin-1-yl-phenyl)-amine |
| 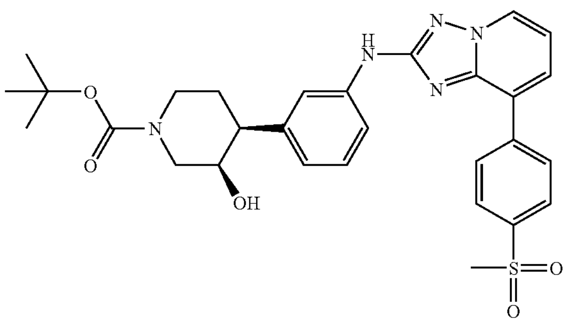 [SMILES: CC(C)(C)OC(=O)N1CC[C@@H](c2cccc(Nc3nc4c(-c5ccc(S(C)(=O)=O)cc5)cccn4n3)c2)[C@@H](O)C1] | (±)-cis-3-Hydroxy-4-{3-[8-(4-methanesulfonyl-phenyl)[1,2,4]triazolo[1,5-a]pyridin-2-ylamino]-phenyl}-piperidine-1-carboxylic acid tert-butyl ester |
| 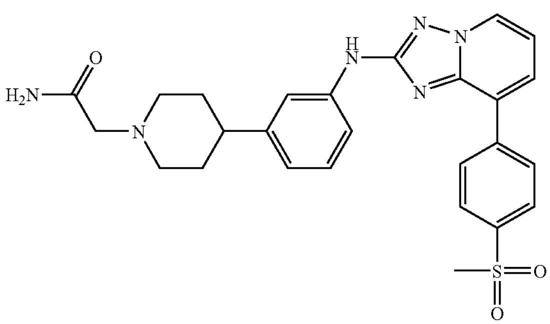 [SMILES: CS(=O)(=O)c1ccc(-c2cccn3nc(Nc4cccc(C5CCN(CC(N)=O)CC5)c4)nc23)cc1] | 2-(4-{3-[8-(4-Methanesulfonyl-phenyl)-[1,2,4]triazolo[1,5-a]pyridin-2-ylamino]-phenyl}-piperidin-1-yl)-acetamide |
| 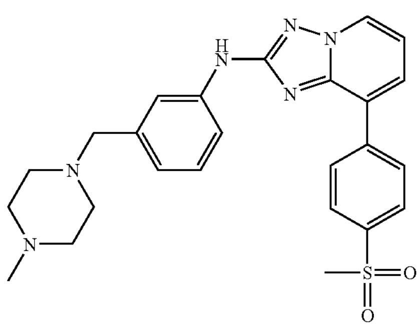 [SMILES: CN1CCN(Cc2cccc(Nc3nc4c(-c5ccc(S(C)(=O)=O)cc5)cccn4n3)c2)CC1] | [8-(4-Methanesulfonyl-phenyl)-[1,2,4]triazolo[1,5-a]pyridin-2-yl]-[3-(4-methyl-piperazin-1-ylmethyl)-phenyl]-amine |

| Structure | Name |
|---|---|
| 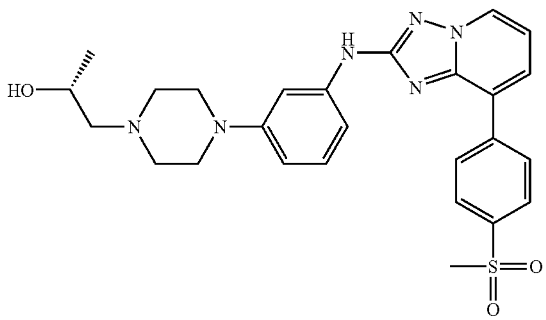 [SMILES: C[C@@H](O)CN1CCN(c2cccc(Nc3nc4c(-c5ccc(S(C)(=O)=O)cc5)cccn4n3)c2)CC1] | (R)-1-(4-{3-[8-(4-Methanesulfonyl-phenyl)-[1,2,4]triazolo[1,5-a]pyridin-2-ylamino]-phenyl}-piperazin-1-yl)-propan-2-ol |
| 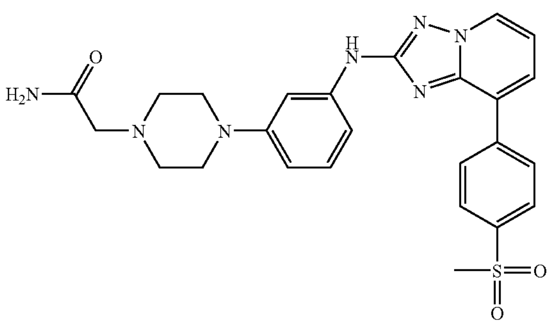 [SMILES: CS(=O)(=O)c1ccc(-c2cccn3nc(Nc4cccc(N5CCN(CC(N)=O)CC5)c4)nc23)cc1] | 2-(4-{3-[8-(4-Methanesulfonyl-phenyl)-[1,2,4]triazolo[1,5-a]pyridin-2-ylamino]-phenyl}-piperazin-1-yl)-acetamide |
| 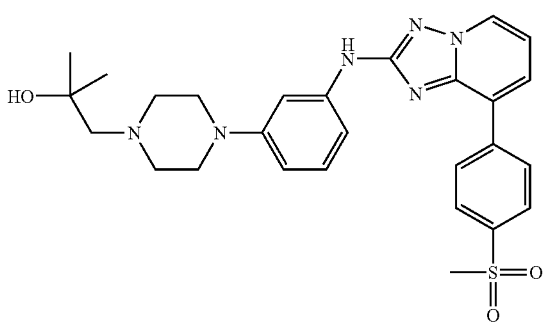 | 1-(4-{3-[8-(4-Methanesulfonyl-phenyl)-[1,2,4]triazolo[1,5-a]pyridin-2-ylamino]-phenyl}-piperazin-1-yl)-2-methyl-propan-2-ol |
| 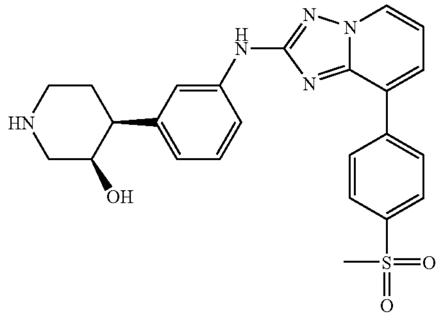 [SMILES: CS(=O)(=O)c1ccc(-c2cccn3nc(Nc4cccc([C@@H]5CCNC[C@@H]5O)c4)nc23)cc1] | (±)-(cis)-4-{3-[8-(4-Methanesulfonyl-phenyl)-[1,2,4]triazolo[1,5-a]pyridin-2-ylamino]-phenyl}-piperidin-3-ol |

| Structure | Name |
|---|---|
| 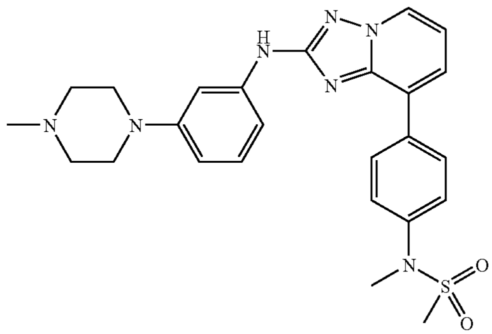 [SMILES: CN1CCN(c2cccc(Nc3nc4c(-c5ccc(N(C)S(C)(=O)=O)cc5)cccn4n3)c2)CC1] | N-Methyl-N-(4-{2-[3-(4-methyl-piperazin-1-yl)-phenylamino]-[1,2,4]triazolo[1,5-a]pyridin-8-yl}-phenyl)methanesulfonamide |
| | {3-[4-(3-Fluoro-propyl)-piperazin-1-yl]-phenyl}-[8-(4-methanesulfonyl-phenyl)-[1,2,4]triazolo[1,5-a]pyridin-2-yl]-amine |
| 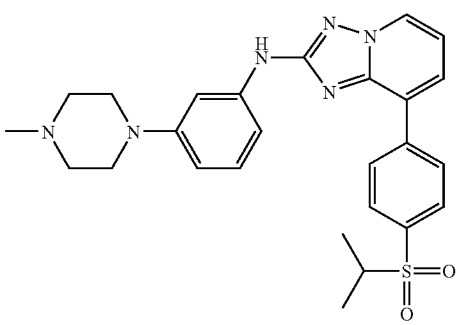 [SMILES: CC(C)S(=O)(=O)c1ccc(-c2cccn3nc(Nc4cccc(N5CCN(C)CC5)c4)nc23)cc1] | [3-(4-Methyl-piperazin-1-yl)-phenyl]-{8-[4-(propane-2-sulfonyl)-phenyl]-[1,2,4]triazolo[1,5-a]pyridin-2-yl}-amine |
| 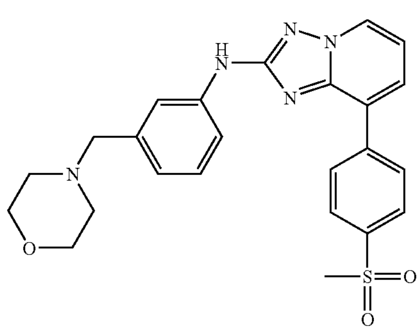 [SMILES: CS(=O)(=O)c1ccc(-c2cccn3nc(Nc4cccc(CN5CCOCC5)c4)nc23)cc1] | [8-(4-Methanesulfonyl-phenyl)-[1,2,4]triazolo[1,5-a]pyridin-2-yl]-(3-morpholin-4-ylmethyl-phenyl)-amine |

-continued

| Structure | Name |
|---|---|
| 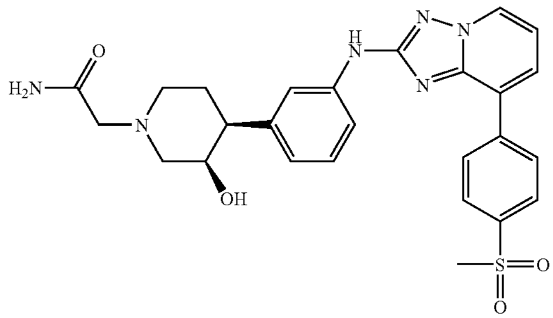 [SMILES: CS(=O)(=O)c1ccc(-c2cccn3nc(Nc4cccc([C@@H]5CCN(CC(N)=O)C[C@@H]5O)c4)nc23)cc1] | (±)2-(cis)-3-Hydroxy-4-{3-[8-(4-methanesulfonyl-phenyl)[1,2,4]triazolo[1,5-a]pyridin-2-ylamino]-phenyl}-piperidin-1-yl)-acetamide |
| 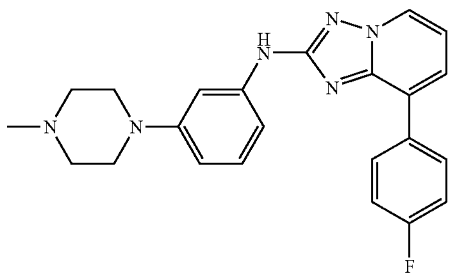 [SMILES: CN1CCN(c2cccc(Nc3nc4c(-c5ccc(F)cc5)cccn4n3)c2)CC1] | [8-(4-Fluoro-phenyl)-[1,2,4]triazolo[1,5-a]pyridin-2-yl]-[3-(4-methyl-piperazin-1-yl)-phenyl]-amine |
| 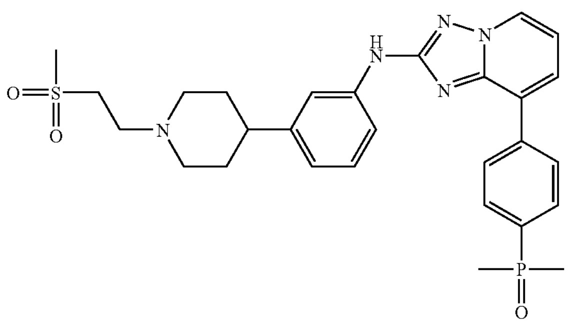 [SMILES: CP(C)(=O)c1ccc(-c2cccn3nc(Nc4cccc(C5CCN(CCS(C)(=O)=O)CC5)c4)nc23)cc1] | {8-[4-(Dimethyl-phosphinoyl)-phenyl]-[1,2,4]triazolo[1,5-a]pyridin-2-yl}-{3-[1-(2-methanesulfonyl-ethyl)-piperidin-4-yl]-phenyl}-amine |
| 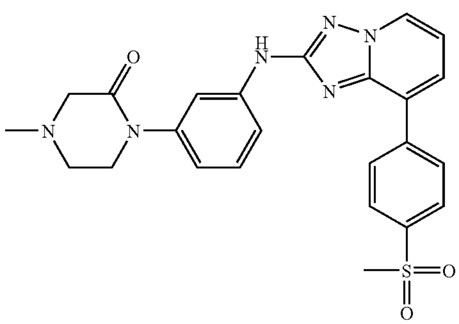 [SMILES: CN1CCN(c2cccc(Nc3nc4c(-c5ccc(S(C)(=O)=O)cc5)cccn4n3)c2)C(=O)C1] | 1-{3-[8-(4-Methanesulfonyl-phenyl)-[1,2,4]triazolo[1,5-a]pyridin-2-ylamino]-phenyl}-4-methyl-piperazin-2-one |
| 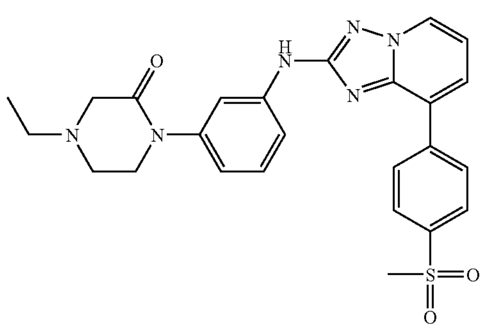 [SMILES: CCN1CCN(c2cccc(Nc3nc4c(-c5ccc(S(C)(=O)=O)cc5)cccn4n3)c2)C(=O)C1] | 4-Ethyl-1-{3-[8-(4-methanesulfonyl-phenyl)-[1,2,4]triazolo[1,5-a]pyridin-2-ylamino]-phenyl}-piperazin-2-one |

-continued

| Structure | Name |
|---|---|
| 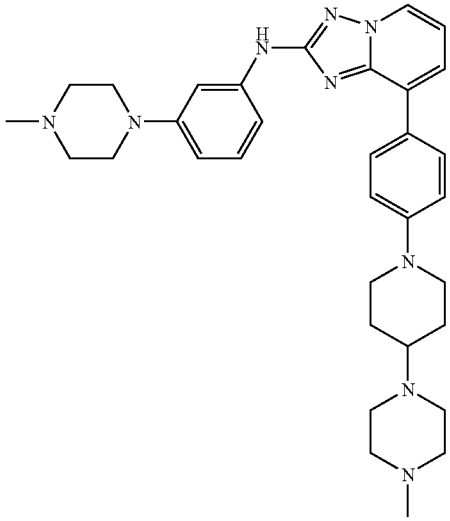 [SMILES: CN1CCN(c2cccc(Nc3nc4c(-c5ccc(N6CCC(N7CCN(C)CC7)CC6)cc5)cccn4n3)c2)CC1] | [3-(4-Methyl-piperazin-1-yl)-phenyl]-(8-{4-[4-(4-methyl-piperazin-1-yl)-piperidin-1-yl]-phenyl}-[1,2,4]triazolo[1,5-a]pyridin-2-yl)-amine |
| 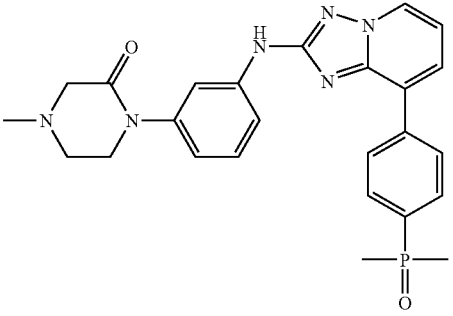 | 1-(3-{8-[4-(Dimethyl-phosphinoyl)-phenyl]-[1,2,4]triazolo[1,5-a]pyridin-2-ylamino}-phenyl)-4-methyl-piperazin-2-one |
| 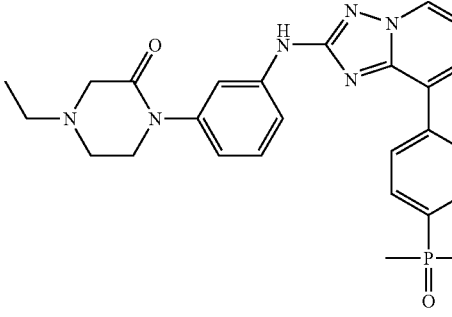 | 1-(3-{8-[4-(Dimethyl-phosphinoyl)-phenyl]-[1,2,4]triazolo[1,5-a]pyridin-2-ylamino}-phenyl)-4-ethyl-piperazin-2-one |

3. A compound according to claim 1, that is {8-[4-(Dimethyl-phosphinoyl)-phenyl]-[1,2,4]triazolo[1,5-a]pyridin-2-yl}-(2-methanesulfonyl-ethyl)-{3-[1-(2-methanesulfonyl-ethyl)-piperidin-4-yl]-phenyl}-amine, or a salt thereof.

4. A compound according to claim 1, that is [8-(4-Methanesulfonyl-phenyl)-6-trifluoromethyl-[1,2,4]triazolo[1,5-a]pyridin-2-yl]-[3-(4-methyl-piperazin-1-yl)-phenyl]-amine, or a salt thereof.

5. A compound according to claim 1, or a salt thereof, wherein $R^{3A}$, $R^{4A}$, $R^{5A}$, and $R^{10}$ are each H and $R^9$ is $SO_2R^{7A}$.

6. A compound according to claim 5, or a salt thereof, selected from the following:

| Structure | Name |
|---|---|
| 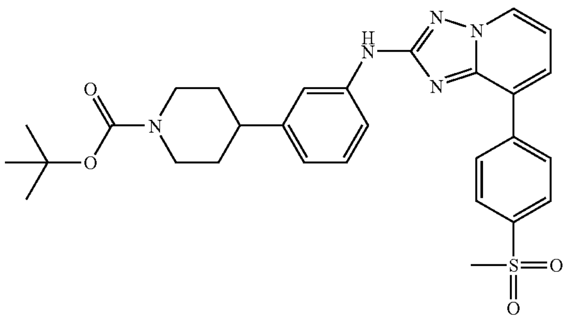 | 4-{3-[8-(4-Methanesulfonyl-phenyl)-[1,2,4]triazolo[1,5-a]pyridin-2-ylamino]-phenyl}-piperidine-1-carboxylic acid tert-butyl ester |
| 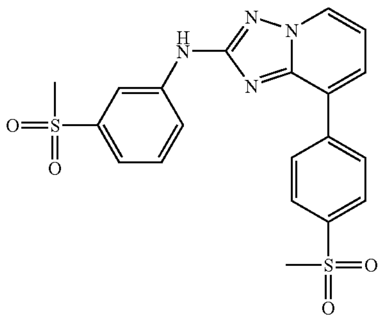 [SMILES: CS(=O)(=O)c1ccc(-c2cccn3nc(Nc4cccc(S(C)(=O)=O)c4)nc23)cc1] | (3-Methanesulfonyl-phenyl)-[8-(4-methanesulfonyl-phenyl)[1,2,4]triazolo[1,5-a]pyridin-2-yl]-amine |
| 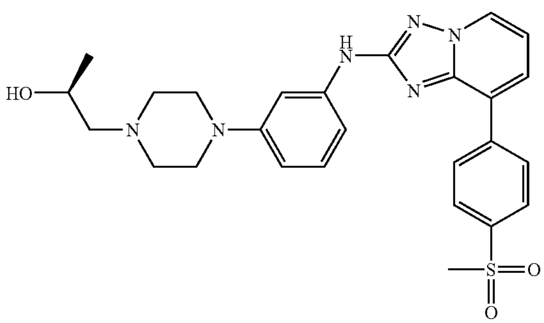 [SMILES: C[C@H](O)CN1CCN(c2cccc(Nc3nc4c(-c5ccc(S(C)(=O)=O)cc5)cccn4n3)c2)CC1] | (S)-1-(4-{3-[8-(4-Methanesulfonyl-phenyl)-[1,2,4]triazolo[1,5-a]pyridin-2-ylamino]-phenyl}-piperazin-1-yl)-propan-2-ol |
| 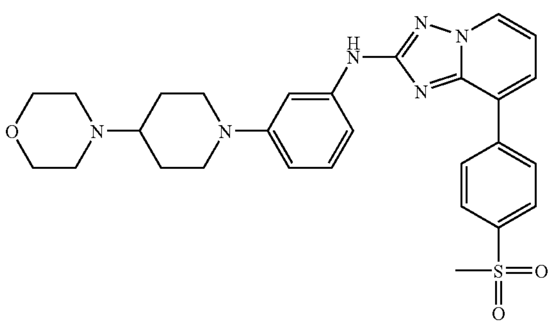 [SMILES: CS(=O)(=O)c1ccc(-c2cccn3nc(Nc4cccc(N5CCC(N6CCOCC6)CC5)c4)nc23)cc1] | [8-(4-Methanesulfonyl-phenyl)-[1,2,4]triazolo[1,5-a]pyridin-2-yl]-[3-(4-morpholin-4-yl-piperidin-1-yl)-phenyl]-amine |
| 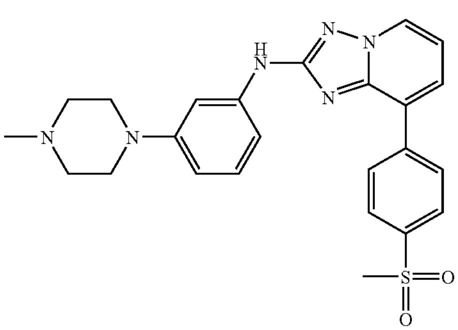 | [8-(4-Methanesulfonyl-phenyl)-[1,2,4]triazolo[1,5-a]pyridin-2-yl]-[3-(4-methyl-piperazin-1-yl)-phenyl]-amine |

-continued

| Structure | Name |
|---|---|
| 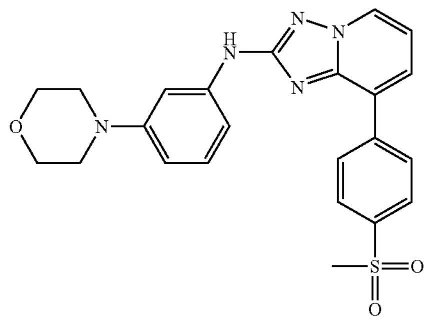 [SMILES: CS(=O)(=O)c1ccc(-c2cccn3nc(Nc4cccc(N5CCOCC5)c4)nc23)cc1] | [8-(4-Methanesulfonyl-phenyl)-[1,2,4]triazolo[1,5-a]pyridin-2-yl]-(3-morpholin-4-yl-phenyl)-aine |
| 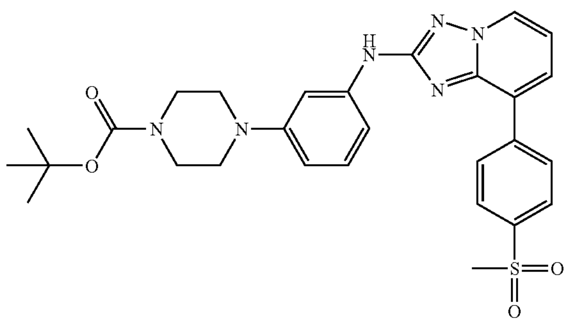 [SMILES: CC(C)(C)OC(=O)N1CCN(c2cccc(Nc3nc4c(-c5ccc(S(C)(=O)=O)cc5)cccn4n3)c2)CC1] | 4-{3-[8-(4-Methanesulfonyl-phenyl)-[1,2,4]triazolo[1,5-a]pyridin-2-ylamino]-phenyl}-piperazine-1-carboxylic acid tert-butyl ester |
| 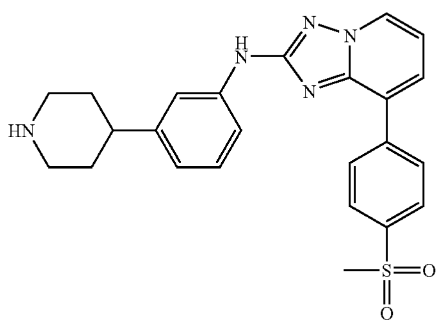 [SMILES: CS(=O)(=O)c1ccc(-c2cccn3nc(Nc4cccc(C5CCNCC5)c4)nc23)cc1] | [8-(4-Methanesulfonyl-phenyl)-[1,2,4]triazolo[1,5-a]pyridin-2-yl]-(3-piperidin-4-yl-phenyl)-amine |
| 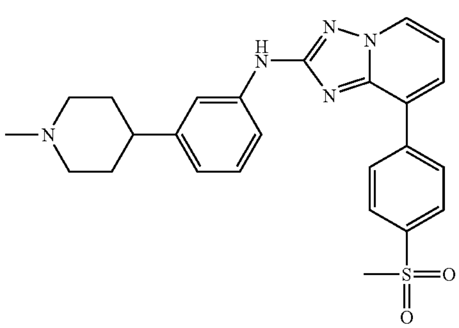 [SMILES: CN1CCC(c2cccc(Nc3nc4c(-c5ccc(S(C)(=O)=O)cc5)cccn4n3)c2)CC1] | [8-(4-Methanesulfonyl-phenyl)-[1,2,4]triazolo[1,5-a]pyridin-2-yl]-[3-(1-methyl-piperidin-4-yl)-phenyl]-amine |

-continued

| Structure | Name |
|---|---|
| 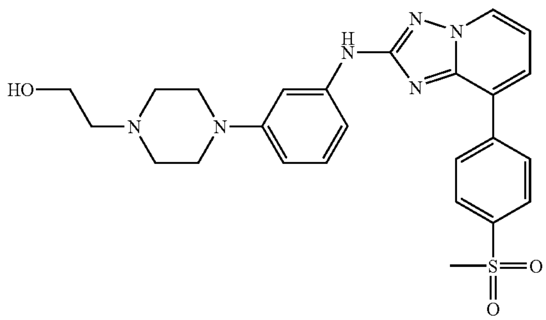 [SMILES: CS(=O)(=O)c1ccc(-c2cccn3nc(Nc4cccc(N5CCN(CCO)CC5)c4)nc23)cc1] | 2-(4-{3-[8-(4-Methanesulfonyl-phenyl)-[1,2,4]triazolo[1,5-a]pyridin-2-ylamino]-phenyl}-piperazin-1-yl)-ethanol |
| 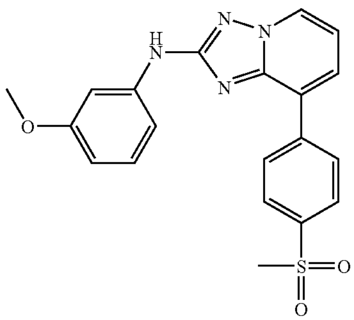 [SMILES: COc1cccc(Nc2nc3c(-c4ccc(S(C)(=O)=O)cc4)cccn3n2)c1] | [8-(4-Methanesulfonyl-phenyl)-[1,2,4]triazolo[1,5-a]pyridin-2-yl]-(3-methoxy-phenyl)-amine |
| | {3-[1-(2-Methanesulfonyl-ethyl)-piperidin-4-yl]-phenyl}-[8-(4-methanesulfonyl-phenyl)-[1,2,4]triazolo[1,5-a]pyridin-2-yl]-amine |
| 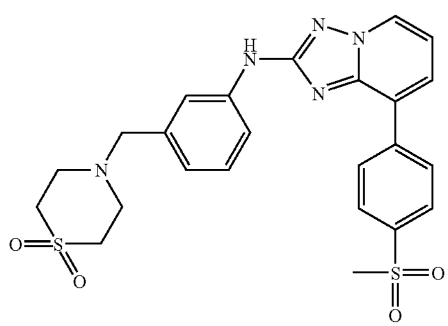 [SMILES: CS(=O)(=O)c1ccc(-c2cccn3nc(Nc4cccc(CN5CCS(=O)(=O)CC5)c4)nc23)cc1] | N-{3-[(1,1-dioxidothiomorpholin-4-yl)methyl]phenyl}-8-[4-(methylsulfonyl)phenyl][1,2,4]triazolo[1,5-a]pyridin-2-amine |
| | [8-(4-Methanesulfonyl-phenyl)-[1,2,4]triazolo[1,5-a]pyridin-2-yl]-{3-[4-(4-methyl-piperazin-1-yl)-piperidin-1-yl]-phenyl}-amine |

| Structure | Name |
|---|---|
| 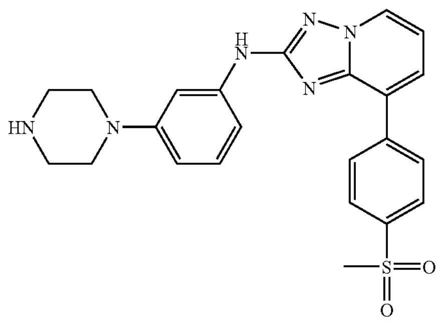 | [8-(4-Methanesulfonyl-phenyl)-[1,2,4]triazolo[1,5-a]pyridin-2-yl]-(3-piperazin-1-yl-phenyl)-amine |
| 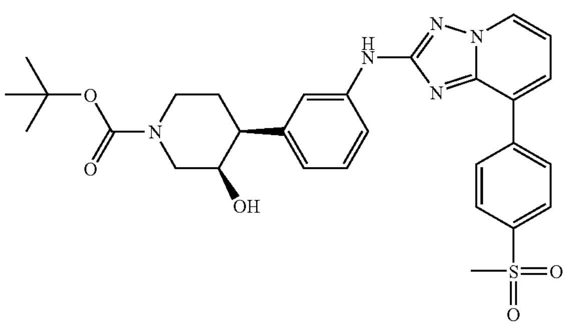 [SMILES: CC(C)(C)OC(=O)N1CC[C@@H](c2cccc(Nc3nc4c(-c5ccc(S(C)(=O)=O)cc5)cccn4n3)c2)[C@@H](O)C1] | (±)-cis-3-Hydroxy-4-{3-[8-(4-methanesulfonyl-phenyl)[1,2,4]triazolo[1,5-a]pyridin-2-ylamino]-phenyl}-piperidine-1-carboxylic acid tert-butyl ester |
| 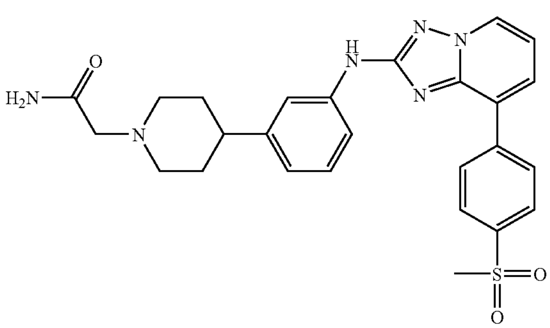 | 2-(4-{3-[8-(4-Methanesulfonyl-phenyl)-[1,2,4]triazolo[,5-a]pyridin-2-ylamino]-phenyl}-piperidin-1-yl)-acetamide |
| 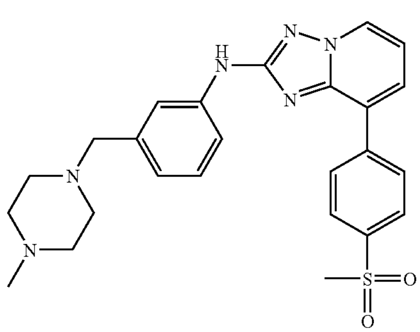 [SMILES: CN1CCN(Cc2cccc(Nc3nc4c(-c5ccc(S(C)(=O)=O)cc5)cccn4n3)c2)CC1] | [8-(4-Methanesulfonyl-phenyl)-[1,2,4]triazolo[1,5-a]pyridin-2-yl]-[3-(4-methyl-piperazin-1-ylmethyl)-phenyl]-amine |

-continued

| Structure | Name |
|---|---|
| 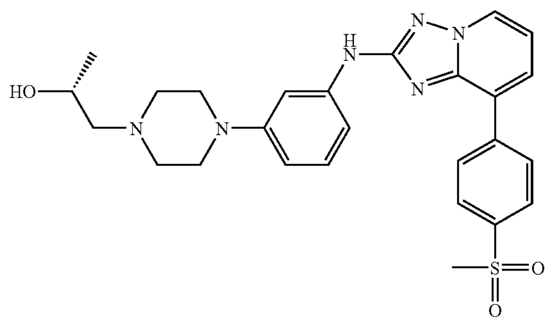 | (R)-1-(4-{3-[8-(4-Methanesulfonyl-phenyl)-[1,2,4]triazolo[1,5-a]pyridin-2-ylamino]-phenyl}-piperazin-1-yl)-propan-2-ol |
| 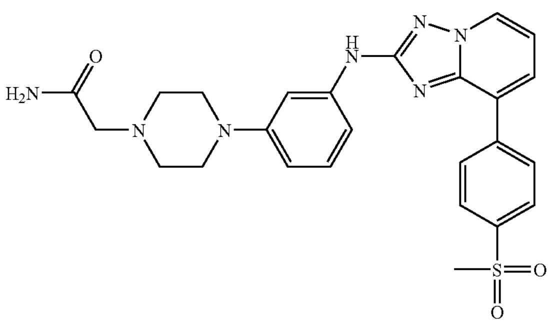 | 2-(4-{3-[8-(4-Methanesulfonyl-phenyl)-[1,2,4]triazolo[1,5-a]pyridin-2-ylamino]-phenyl}-piperazin-1-yl)-acetamide |
| 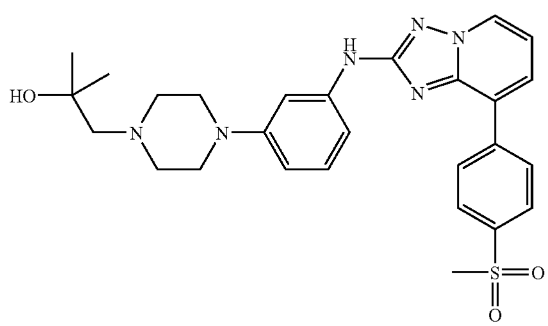 [SMILES: CC(C)(O)CN1CCN(c2cccc(Nc3nc4c(-c5ccc(S(C)(=O)=O)cc5)cccn4n3)c2)CC1] | 1-(4-{3-[8-(4-Methanesulfonyl-phenyl)-[1,2,4]triazolo[1,5-a]pyridin-2-ylamino]-phenyl}-piperazin-1-yl)-2-methyl-propan-2-ol |
| 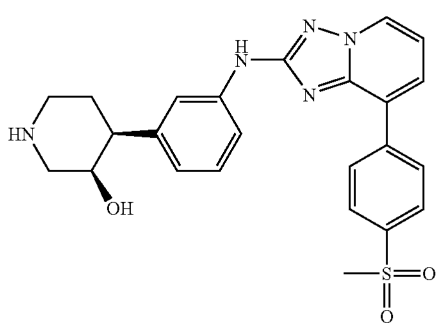 [SMILES: CS(=O)(=O)c1ccc(-c2cccn3nc(Nc4cccc([C@@H]5CCNC[C@@H]5O)c4)nc23)cc1] | (±)-(cis)-4-{3-[8-(4-Methanesulfonyl-phenyl)-[1,2,4]triazolo[1,5-a]pyridin-2-ylamino]-phenyl}-piperidin-3-ol |
| 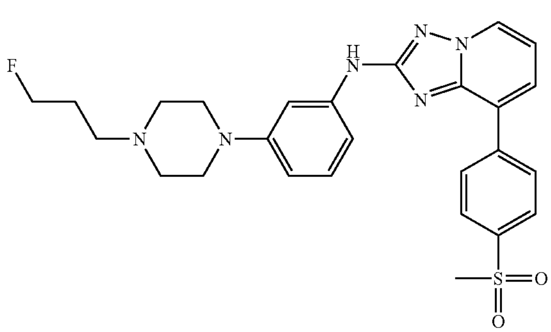 [SMILES: CS(=O)(=O)c1ccc(-c2cccn3nc(Nc4cccc(N5CCN(CCCF)CC5)c4)nc23)cc1] | {3-[4-(3-Fluoro-propyl)-piperazin-1-yl]-phenyl}-[8-(4-methanesulfonyl-phenyl)-[1,2,4]triazolo[1,5-a]pyridin-2-yl]-amine |

| Structure | Name |
|---|---|
| 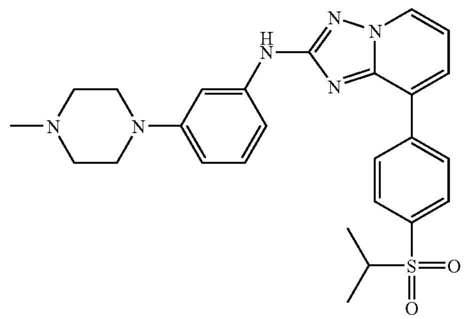 [SMILES: CC(C)S(=O)(=O)c1ccc(-c2cccn3nc(Nc4cccc(N5CCN(C)CC5)c4)nc23)cc1] | [3-(4-Methyl-piperazin-1-yl)-phenyl]-{8-[4-(propane-2-sulfonyl)-phenyl]-[1,2,4]triazolo[1,5-a]pyridin-2-yl}-amine |
| 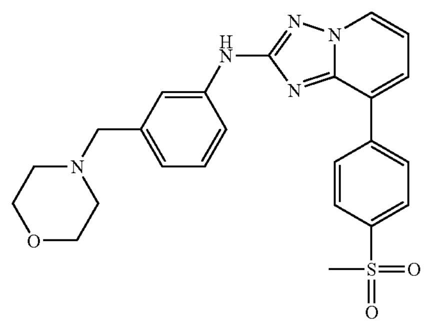 [SMILES: CS(=O)(=O)c1ccc(-c2cccn3nc(Nc4cccc(CN5CCOCC5)c4)nc23)cc1] | [8-(4-Methanesulfonyl-phenyl)-[1,2,4]triazolo[1,5-a]pyridin-2-yl]-(3-morpholin-4-ylmethyl-phenyl)-amine |
| | (±)2-(cis-3-Hydroxy-4-{3-[8-(4-methanesulfonyl-phenyl)-[1,2,4]triazolo[1,5-a]pyridin-2-ylamino]-phenyl}-piperidin-1-yl)-acetamide |
| 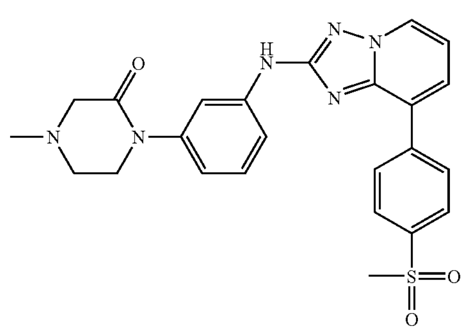 [SMILES: CN1CCN(c2cccc(Nc3nc4c(-c5ccc(S(C)(=O)=O)cc5)cccn4n3)c2)C(=O)C1] | 1-{3-[8-(4-Methanesulfonyl-phenyl)-[1,2,4]triazolo[1,5-a]pyridin-2-ylamino]-phenyl}-4-methyl-piperazin-2-one |

| Structure | Name |
|---|---|
| 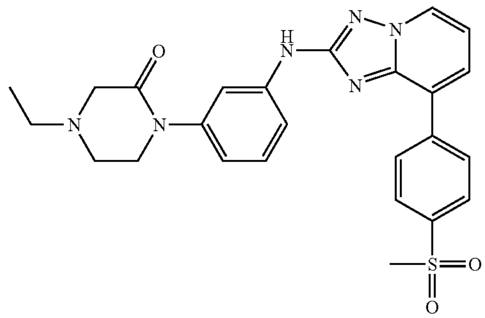 [SMILES: CCN1CCN(c2cccc(Nc3nc4c(-c5ccc(S(C)(=O)=O)cc5)cccn4n3)c2)C(=O)C1] | 4-Ethyl-1-{3-[8-(4-methanesulfonyl-phenyl)- [1,2,4]triazolo [1,5-a] pyridin-2-ylamino]-phenyl}-piperazin-2-one |

7. A compound, or a salt thereof, selected from the group consisting of:
- 4-{3-[8-(4-Methanesulfonyl-phenyl)-[1,2,4]triazolo[1,5-a]pyridin-2-ylamino]-phenyl}-piperidine-1-carboxylic acid tert-butyl ester;
- {8-[4-(Dimethyl-phosphinoyl)-phenyl]-[1,2,4]triazolo[1,5-a]pyridin-2-yl}-[3-(4-methyl-piperazin-1-yl)-phenyl]-amine;
- (3-Methanesulfonyl-phenyl)-[8-(4-methanesulfonyl-phenyl)-[1,2,4]triazolo[1,5-a]pyridin-2-yl]-amine;
- (S)-1-(4-{3-[8-(4-Methanesulfonyl-phenyl)-[1,2,4]triazolo[1,5-a]pyridin-2-ylamino]-phenyl}-piperazin-1-yl)-propan-2-ol;
- [8-(4-Methanesulfonyl-phenyl)-[1,2,4]triazolo[1,5-a]pyridin-2-yl]-[3-(4-morpholin-4-yl-piperidin-1-yl)-phenyl]-amine;
- [8-(4-Methanesulfonyl-phenyl)-[1,2,4]triazolo[1,5-a]pyridin-2-yl]-[3-(4-methyl-piperazin-1-yl)-phenyl]-amine;
- [8-(4-Methanesulfonyl-phenyl)-[1,2,4]triazolo[1,5-a]pyridin-2-yl]-(3-morpholin-4-yl-phenyl)-amine;
- 4-{3-[8-(4-Methanesulfonyl-phenyl)-[1,2,4]triazolo[1,5-a]pyridin-2-ylamino]-phenyl}-piperazine-1-carboxylic acid tert-butyl ester;
- [8-(4-Methanesulfonyl-phenyl)-[1,2,4]triazolo[1,5-a]pyridin-2-yl]-(3-piperidin-4-yl-phenyl)-amine;
- [8-(4-Methanesulfonyl-phenyl)-[1,2,4]triazolo[1,5-a]pyridin-2-yl]-[3-(1-methyl-piperidin-4-yl)-phenyl]-amine;
- 2-(4-{3-[8-(4-Methanesulfonyl-phenyl)-[1,2,4]triazolo[1,5-a]pyridin-2-ylamino]-phenyl}-piperazin-1-yl)-ethanol;
- 2-{2-[3-(4-Methyl-piperazin-1-yl)-phenylamino]-[1,2,4]triazolo[1,5-a]pyridin-8-yloxymethyl}-benzonitrile;
- [8-(4-Methanesulfonyl-phenyl)-[1,2,4]triazolo[1,5-a]pyridin-2-yl]-(3-methoxy-phenyl)-amine;
- {3-[1-(2-Methanesulfonyl-ethyl)-piperidin-4-yl]-phenyl}-[8-(4-methanesulfonyl-phenyl)-[1,2,4]triazolo[1,5-a]pyridin-2-yl]-amine;
- N-{3-[(1,1-dioxidothiomorpholin-4-yl)methyl]phenyl}-8-[4-(methylsulfonyl)phenyl][1,2,4]triazolo[1,5-a]pyridin-2-amine;
- [3-(4-Methyl-piperazin-1-yl)-phenyl]-[8-(4-trifluoromethyl-phenyl)-[1,2,4]triazolo[1,5-a]pyridin-2-yl]-amine;
- [8-(4-Methanesulfonyl-phenyl)-[1,2,4]triazolo[1,5-a]pyridin-2-yl]-{3-[4-(4-methyl-piperazin-1-yl)-piperidin-1-yl]-phenyl}-amine;
- [8-(4-Methanesulfonyl-phenyl)-[1,2,4]triazolo[1,5-a]pyridin-2-yl]-(3-piperazin-1-yl-phenyl)-amine;
- (±)-cis-3-Hydroxy-4-{3-[8-(4-methanesulfonyl-phenyl)-[1,2,4]triazolo[1,5-a]pyridin-2-ylamino]-phenyl}-piperidine-1-carboxylic acid tert-butyl ester;
- 2-(4-{3-[8-(4-Methanesulfonyl-phenyl)-[1,2,4]triazolo[1,5-a]pyridin-2-ylamino]-phenyl}-piperidin-1-yl)-acetamide;
- [8-(4-Methanesulfonyl-phenyl)-[1,2,4]triazolo[1,5-a]pyridin-2-yl]-[3-(4-methyl-piperazin-1-ylmethyl)-phenyl]-amine;
- (R)-1-(4-{3-[8-(4-Methanesulfonyl-phenyl)-[1,2,4]triazolo[1,5-a]pyridin-2-ylamino]-phenyl}-piperazin-1-yl)-propan-2-ol;
- 2-(4-{3-[8-(4-Methanesulfonyl-phenyl)-[1,2,4]triazolo[1,5-a]pyridin-2-ylamino]-phenyl}-piperazin-1-yl)-acetamide;
- 1-(4-{3-[8-(4-Methanesulfonyl-phenyl)-[1,2,4]triazolo[1,5-a]pyridin-2-ylamino]-phenyl}-piperazin-1-yl)-2-methyl-propan-2-ol;
- (±)-(cis)-4-{3-[8-(4-Methanesulfonyl-phenyl)-[1,2,4]triazolo[1,5-a]pyridin-2-ylamino]-phenyl}-piperidin-3-ol;
- N-Methyl-N-(3-{2-[3-(4-methyl-piperazin-1-yl)-phenylamino]-[1,2,4]triazolo[1,5-a]pyridin-8-yl}-benzyl)-methanesulfonamide;
- N-Methyl-N-(4-{2-[3-(4-methyl-piperazin-1-yl)-phenylamino]-[1,2,4]triazolo[1,5-a]pyridin-8-yl}-phenyl)-methanesulfonamide;
- {3-[4-(3-Fluoro-propyl)-piperazin-1-yl]-phenyl}-[8-(4-methanesulfonyl-phenyl)-[1,2,4]triazolo[1,5-a]pyridin-2-yl]-amine;
- [8-(3-Methanesulfonyl-phenyl)-[1,2,4]triazolo[1,5-a]pyridin-2-yl]-(3-morpholin-4-yl-phenyl)-amine;
- [8-(3-Methanesulfonyl-phenyl)-[1,2,4]triazolo[1,5-a]pyridin-2-yl]-[3-(4-methyl-piperazin-1-yl)-phenyl]-amine;
- [3-(4-Methyl-piperazin-1-yl)-phenyl]-{8-[4-(propane-2-sulfonyl)-phenyl]-[1,2,4]triazolo[1,5-a]pyridin-2-yl}-amine;
- {8-[1-(4-Fluoro-phenyl)-1H-pyrazol-4-yl]-[1,2,4]triazolo[1,5-a]pyridin-2-yl}-[3-(4-methyl-piperazin-1-yl)-phenyl]-amine;
- [8-(4-Methanesulfonyl-phenyl)-[1,2,4]triazolo[1,5-a]pyridin-2-yl]-(3-morpholin-4-ylmethyl-phenyl)-amine;
- [8-(2-Methoxy-5-trifluoromethyl-phenyl)-[1,2,4]triazolo[1,5-a]pyridin-2-yl]-(3-piperidin-4-yl-phenyl)-amine;
- (±)-2-(cis-3-Hydroxy-4-{3-[8-(4-methanesulfonyl-phenyl)-[1,2,4]triazolo[1,5-a]pyridin-2-ylamino]-phenyl}-piperidin-1-yl)-acetamide;

N-Methyl-N-(3-{2-[3-(1-methyl-piperidin-4-yl)-phenylamino]-[1,2,4]triazolo[1,5-a]pyridin-8-yl}-phenyl)-methanesulfonamide;

N-Methyl-N-(2-{2-[3-(4-methyl-piperazin-1-yl)-phenylamino]-[1,2,4]triazolo[1,5-a]pyridin-8-ylethynyl}-phenyl)-methanesulfonamide;

N(8)-(2-Methanesulfonyl-phenyl)-N(2)-[3-(4-methyl-piperazin-1-yl)-phenyl]-[1,2,4]triazolo[1,5-a]pyridine-2,8-diamine;

[8-(2-Methoxy-5-trifluoromethyl-phenyl)-[1,2,4]triazolo[1,5-a]pyridin-2-yl]-[3-(4-methyl-piperazin-1-yl)-phenyl]-amine;

N-Methyl-N-(3-{2-[3-(4-methyl-piperazin-1-yl)-phenylamino]-[1,2,4]triazolo[1,5-a]pyridin-8-ylamino}-pyridin-2-yl)-methanesulfonamide;

[8-(4-Fluoro-phenyl)-[1,2,4]triazolo[1,5-a]pyridin-2-yl)-3-(4-methyl-piperazin-1-yl)-phenyl]-amine;

[8-(3-Chloro-benzyloxy)-[1,2,4]triazolo[1,5-a]pyridin-2-yl]-[3-(4-methyl-piperazin-1-yl)-phenyl]-amine;

2-{2-[3-(4-Methyl-piperazin-1-yl)-phenylamino]-[1,2,4]triazolo[1,5-a]pyridin-8-yloxymethyl}-benzamide;

N(8)-(3-Methanesulfonyl-benzyl)-N(2)-[4-(1-methyl-piperidin-4-yl)-phenyl]-[1,2,4]triazolo[1,5-a]pyridine-2,8-diamine;

2-(4-{3-[8-(2-Methoxy-5-trifluoromethyl-phenyl)-[1,2,4]triazolo[1,5-a]pyridin-2-ylamino]-phenyl}-piperidin-1-yl)-N,N-dimethyl-acetamide;

N-(3-{[2-(3-Methanesulfonyl-phenylamino)-[1,2,4]triazolo[1,5-a]pyridin-8-ylamino]-methyl}-pyridin-2-yl)-N-methyl-methanesulfonamide;

N-Methyl-N-[2-({2-[3-(4-methyl-piperazin-1-yl)-phenylamino]-[1,2,4]triazolo[1,5-a]pyridin-8-ylamino}-methyl)-benzyl]-methanesulfonamide;

2-(4-{3-[8-(4-Chloro-2-methoxy-phenyl)-[1,2,4]triazolo[1,5-a]pyridin-2-ylamino]-phenyl}-piperidin-1-yl)-N,N-dimethyl-acetamide;

N-Methyl-N-[3-({2-[3-(4-methyl-piperazin-1-yl)-phenylamino]-[1,2,4]triazolo[1,5-a]pyridin-8-ylamino}-methyl)-pyridin-2-yl]-methanesulfonamide;

[8-(2-Methoxy-phenyl)-[1,2,4]triazolo[1,5-a]pyridin-2-yl]-[3-(4-methyl-piperazin-1-yl)-phenyl]-amine;

N-Methyl-N-[2-({2-[3-(4-methyl-piperazin-1-yl)-phenylamino]-[1,2,4]triazolo[1,5-a]pyridin-8-ylamino}-methyl)-phenyl]-methanesulfonamide;

N(8)-(2-Methanesulfonyl-benzyl)-N(2)-[3-(4-methyl-piperazin-1-yl)-phenyl]-[1,2,4]triazolo[1,5-a]pyridine-2,8-diamine;

N-Methyl-N-(2-{2-[3-(4-methyl-piperazin-1-yl)-phenylamino]-[1,2,4]triazolo[1,5-a]pyridin-8-ylamino}-benzyl)-methanesulfonamide;

[6-Fluoro-8-(4-methanesulfonyl-phenyl)-[1,2,4]triazolo[1,5-a]pyridin-2-yl]-bis-[3-(4-methyl-piperazin-1-yl)-phenyl]-amine;

N(8)-(3-Methanesulfonyl-phenyl)-N(2)-[3-(4-methyl-piperazin-1-yl)-phenyl]-[1,2,4]triazolo[1,5-a]pyridine-2,8-diamine;

[8-(4-Methanesulfonyl-phenoxy)-[1,2,4]triazolo[1,5-a]pyridin-2-yl]-[3-(4-methyl-piperazin-1-yl)-phenyl]-amine;

N(2)-[3-(4-Methyl-piperazin-1-yl)-phenyl]-N(8)-pyridin-3-ylmethyl-[1,2,4]triazolo[1,5-a]pyridine-2,8-diamine;

[8-(2-Methanesulfonyl-phenyl)-[1,2,4]triazolo[1,5-a]pyridin-2-yl]-[3-(4-methyl-piperazin-1-yl)-phenyl]-amine;

N*8*-(2-Methoxy-5-trifluoromethyl-phenyl)-N*2*-[3-(4-methyl-piperazin-1-yl)-phenyl]-[1,2,4]triazolo[1,5-a]pyridine-2,8-diamine;

[8-(4-Methanesulfonyl-phenyl)-6-trifluoromethyl-[1,2,4]triazolo[1,5-a]pyridin-2-yl]-[3-(4-methyl-piperazin-1-yl)-phenyl]-amine;

4-{3-[8-(2-Methoxy-5-trifluoromethyl-phenyl)-[1,2,4]triazolo[1,5-a]pyridin-2-ylamino]-phenyl}-piperidine-1-carboxylic acid tert-butyl ester;

N-Methyl-N-(2-{2-[3-(1-methyl-piperidin-4-yl)-phenylamino]-[1,2,4]triazolo[1,5-a]pyridin-8-yl}-phenyl)-methanesulfonamide;

{8-(4-(Dimethyl-phosphinoyl)-phenyl)-[1,2,4]triazolo[1,5-a]pyridin-2-yl}-(2-methanesulfonyl-ethyl)-{3-[1-(2-methanesulfonyl-ethyl)-piperidin-4-yl]-phenyl}-amine;

N(8)-(2-Methoxy-benzyl)-N(2)-[3-(4-methyl-piperazin-1-yl)-phenyl]-[1,2,4]triazolo[1,5-a]pyridine-2,8-diamine;

{8-[4-(Dimethyl-phosphinoyl)-phenyl]-[1,2,4]triazolo[1,5-a]pyridin-2-yl}-{3-[1-(2-methanesulfonyl-ethyl)-piperidin-4-yl]-phenyl}-amine;

N(8)-(3-Methoxy-benzyl)-N(2)-[3-(4-methyl-piperazin-1-yl)-phenyl]-[1,2,4]triazolo[1,5-a]pyridine-2,8-diamine;

N(8)-(4-Methoxy-benzyl)-N(2)-[3-(4-methyl-piperazin-1-yl)-phenyl]-[1,2,4]triazolo[1,5-a]pyridine-2,8-diamine;

N(8)-(2-Fluoro-benzyl)-N(2)-[3-(4-methyl-piperazin-1-yl)-phenyl]-[1,2,4]triazolo[1,5-a]pyridine-2,8-diamine;

N(8)-(4-Fluoro-benzyl)-N(2)-[3-(4-methyl-piperazin-1-yl)-phenyl]-[1,2,4]triazolo[1,5-a]pyridine-2,8-diamine;

1-{3-[8-(4-Methanesulfonyl-phenyl)-[1,2,4]triazolo[1,5-a]pyridin-2-ylamino]-phenyl}-4-methyl-piperazin-2-one;

4-Ethyl-1-{3-[8-(4-methanesulfonyl-phenyl)-[1,2,4]triazolo[1,5-a]pyridin-2-ylamino]-phenyl}-piperazin-2-one; or

[3-(4-Methyl-piperazin-1-yl)-phenyl]-(8-{4-[4-(4-methyl-piperazin-1-yl)-piperidin-1-yl]-phenyl}-[1,2,4]triazolo[1,5-a]pyridin-2-yl)-amine.

8. A composition comprising a compound according to claim 1 or a salt thereof and at least one excipient.

9. A composition comprising a compound according to claim 6 or a salt thereof and at least one excipient.

* * * * *